US010961202B2

(12) United States Patent
Disney et al.

(10) Patent No.: US 10,961,202 B2
(45) Date of Patent: Mar. 30, 2021

(54) BIS-BENZIMIDAZOLE COMPOUNDS AND METHODS OF USING THE SAME

(71) Applicants: THE SCRIPPS RESEARCH INSTITUTE, La Jolla, CA (US); EXPANSION THERAPEUTICS, INC., San Diego, CA (US)

(72) Inventors: Matthew Disney, Jupiter, FL (US); Timothy Allen Blizzard, Princeton, NJ (US); Suzanne Rzuczek, Jupiter, FL (US); John Ndungu, West Palm Beach, FL (US); Joseph Vacca, Telford, PA (US); Andy Jennings, San Diego, CA (US); Alexei Pushechnikov, San Diego, CA (US)

(73) Assignees: THE SCRIPPS RESEARCH INSTITUTE, La Jolla, CA (US); EXPANSION THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/193,486

(22) Filed: Nov. 16, 2018

(65) Prior Publication Data
US 2019/0152924 A1 May 23, 2019

Related U.S. Application Data

(60) Provisional application No. 62/587,606, filed on Nov. 17, 2017.

(51) Int. Cl.
| | |
|---|---|
| *C07D 235/20* | (2006.01) |
| *C07D 403/10* | (2006.01) |
| *C07D 401/14* | (2006.01) |
| *C07D 487/04* | (2006.01) |
| *A61P 25/00* | (2006.01) |
| *C07D 403/14* | (2006.01) |
| *C07D 403/04* | (2006.01) |
| *A61P 25/28* | (2006.01) |
| *C07D 407/14* | (2006.01) |

(52) U.S. Cl.
CPC ............ *C07D 235/20* (2013.01); *A61P 25/00* (2018.01); *A61P 25/28* (2018.01); *C07D 401/14* (2013.01); *C07D 403/04* (2013.01); *C07D 403/10* (2013.01); *C07D 403/14* (2013.01); *C07D 407/14* (2013.01); *C07D 487/04* (2013.01)

(58) Field of Classification Search
CPC ............................... C07D 235/20; A61P 25/14
See application file for complete search history.

(56) References Cited

U.S. PATENT DOCUMENTS

| 2,488,094 A | 11/1949 | Graenacher et al. |
| 5,466,468 A | 11/1995 | Schneider et al. |
| 2014/0128352 A1 | 5/2014 | Brand et al. |

FOREIGN PATENT DOCUMENTS

| EP | 009163 A2 | 4/1980 |
| WO | WO-1993/015712 A1 | 8/1993 |
| WO | WO-2003/094861 A2 | 11/2003 |
| WO | WO-2006/094235 A1 | 9/2006 |
| WO | WO-2015/031819 A1 | 3/2015 |
| WO | WO-2017/049165 A1 | 3/2017 |

OTHER PUBLICATIONS

Alamgir, Synthesis and Reactivity of some Activated Heterocyclic Compounds, The School of Chemistry Faculty of Science, The University of New South Wales (2007).
Arandel et al., Immortalized human myotonic dystrophy muscle cell lines to assess therapeutic compounds, *Dis. Model. Mech.* 10:487-97 (2017).
Ausubel, Current Protocols in Molecular Biology, John Wiley & Sons (1994).
Berge et al., Pharmaceutical salts, *J. Pharm. Sci.* 66:1-19 (1977).
Brouwer et al., Elevated Fmr1 mRNA levels and reduced protein expression in a mouse model with an unmethylated Fragile X full mutation, *Exp. Cell. Res.* 313:244-53 (2007).
Chen et al., Two high-throughput screening assays for aberrant RNA-protein interactions in myotonic dystrophy type 1, *Anal. Bioanal. Chem.* 402:1889-98 (2012).
Database Accession No. 904034-83-9, 6,6- [1,4-phenylenebis(1H-benzimidazole-2, 6-diylimino)]bis-1-hexanol, Aug. 24, 2006.
Davis et al., Preparation and characterization of antibodies with specificity for the amino-terminal tetrapeptide sequence of the platelet-derived connective tissue activating peptide-III, *Biochem. Intl.* 10:395-404 (1985).
De Haro et al., MBNL1 and CUGBP1 modify expanded CUG-induced toxicity in a *Drosophila* model of myotonic dystrophy type 1, *Hum. Mol. Gen.* 15:2138-45 (2006).
Del Poeta et al., Structure—in vitro activity relationships of pentamidine analogues and dication-substituted bis-benzimidazoles as new antifungal agents, *Antimicrob. Agents. Chemother.* 42:2495-502 (1998).
DeLuca et al., Parenteral Drug-Delivery Systems, Pharmaceutics and Pharmacy Practice, J. B. Lippincott Company, Philadelphia, pp. 238-50 (1982).
Erickson et al., Solid-Phase Peptide Synthesis, The Proteins, vol. 2, pp. 257-527 (3rd ed. 1976).
Fairley et al., Structure, DNA minor groove binding, and base pair specificity of alkyl- and aryl-linked bis(amidinobenzimidazoles) and bis(amidinoindoles), *J. Med. Chem.* 36:1746-53 (1993).

(Continued)

*Primary Examiner* — Golam M Shameem
(74) *Attorney, Agent, or Firm* — Marshall, Gerstein & Borun LLP

(57) ABSTRACT

Provided herein are compounds and methods for modulating abnormal repeat expansions of gene sequences. More particularly, provided are inhibitors of RNA and the uses of such inhibitors in regulating nucleotide repeat expansions, e.g., to treat Myotonic Dystrophy Type 1 (DM1), Myotonic Dystrophy Type 2 (DM2), Fuchs dystrophy, Huntington Disease, Amyotrophic Lateral Sclerosis, or Frontotemporal Dementia.

12 Claims, No Drawings

(56) References Cited

OTHER PUBLICATIONS

Finn et al., The Synthesis of Peptides by Solution Methods with Emphasis on Peptide Hormones, The Proteins, vol. 2, pp. 105-253 (3rd ed. 1976).

Gallant et al., Mild and selective reduction of imines: formation of an unsymmetrical macrocycle, *J. Org. Chem.* 69:8739-44 (2004).

Gillingwater et al., In vitro activity and preliminary toxicity of various diamidine compounds against Trypanosoma evansi, *Vet. Parasitol.* 169:264-72 (2010).

Greene et al., Protective Groups in Organic Synthesis, John Wiley & Sons, New York (3rd ed. 1999).

Hall et al., RNA—Protein Interaction Protocols, Methods in Molecular Biology, Humana Press, vol. 118 (1999).

Jin et al., RNA—mediated neurodegeneration caused by the fragile X premutation rCGG repeats in *Drosophila, Neuron.* 39:739-47 (2003).

Larsen et al., The merrifield peptide synthesis studied by near-infrared fourier-transform raman spectroscopy, *J. Am. Chem. Soc.* 115:6247-53 (1993).

Mankodi et al., Myotonic dystrophy in transgenic mice expressing an expanded CUG repeat, *Science.* 289:1769-73 (2000).

Merrifield, Solid Phase Peptide Synthesis. I. The Synthesis of a Tetrapeptide. *J. Am. Chem. Soc.* 85:2149 (1963).

Moseley et al., Bidirectional expression of CUG and CAG expansion transcripts and intranuclear polyglutamine inclusions in spinocerebellar ataxia type 8, *Nat. Genet.* 38:758-69 (2006).

Mutsuddi et al., The spinocerebellar ataxia 8 noncoding RNA causes neurodegeneration and associates with staufen in *Drosophila, Curr. Biol.*14:302-8 (2004).

O'Donnell et al., Solid-Phase Unnatural Peptide Synthesis, *J. Am. Chem. Soc.* 118:6070-1 (1996).

Osborne et al., RNA—dominant diseases, *Hum. Mol. Genet.* 15:R162-9 (2006).

Ozcubukcu et al., A highly active catalyst for Huisgen 1,3-dipolar cycloadditions based on the tris(triazolyl)methanol-Cu(I) structure, *Org. Lett.* 11:4680-3 (2009).

Prieto et al., Application of linear discriminant analysis in the virtual screening of antichagasic drugs through trypanothione reductase inhibition, *Mol. Divers.* 10:361-75 (2006).

Remington's Pharmaceutical Sciences, Mack Publishing Co., Easton, PA, pp. 1435-1712 (18th ed. 1990).

Sambrook et al., A Laboratory Manual, Cold Spring Harbor Laboratory (2001).

Sibertsev et al., Comparative study of DNA—specific dyes of the indole and benzimidazole derivates, *Bioorg. Khim.* 27:57-65 (2001).

Sibirtsev et al., Mechanisms of variation in fluorescent properties of bis-benzimidazole dyes, *Bioorg. Khim.* 21:731-6 (1995).

Sibirtsev et al., Spectral properties of bisbenzimidazole dyes upon interaction with DNA, *Bioorg. Khim.* 23:969-78 (1997).

Sibirtsev, Fluorescent DNA probes: study of mechanisms of changes in spectral properties and features of practical application, *Biochemistry (Mosc).* 72:887-900 (2007).

Smith et al., Solid-phase peptide synthesis and biological activity of bovine thymopoietin (bTP-II), *Int. J. Peptide Protein Res.* 44:183-91 (1994).

Stewart et al., Solid Phase Peptide Synthesis, Freeman (1969).

Toissel, ASHP Handbook on Injectable Drugs, pp. 622-630 (4th ed. 1986).

BIS-BENZIMIDAZOLE COMPOUNDS AND METHODS OF USING THE SAME

STATEMENT OF U.S. GOVERNMENT SUPPORT

This invention was made with government support under DP1NS096898 and R01-GM079235, each awarded by the National Institutes of Health. The government has certain rights in this invention.

STATEMENT OF GOVERNMENT LICENSE RIGHTS

This invention was made with government support under grant number NS096898 awarded by The National Institutes of Health. The government has certain rights in the invention.

BACKGROUND

Nucleotide repeat expansion disorders are caused by an inherited expansion of unstable repetitive elements in a gene or intron. The precise genetic nature of these diseases has only been recognized relatively recently, and as such, the development of drugs targeting these toxic nucleotide repeats is becoming an important strategy in addressing the need for additional therapies for the treatment of these disorders.

SUMMARY

Provided herein are compounds and methods for modulating abnormal repeat expansions of gene sequences. More particularly, provided are binders of RNA and the uses of such binders in regulating nucleotide repeat expansions, e.g., to treat Myotonic Dystrophy Type 1 (DM1), Myotonic Dystrophy Type 2 (DM2), Fuchs dystrophy, Huntington Disease, Amyotrophic Lateral Sclerosis, or Frontotemporal Dementia.

In one aspect, the disclosure provides compounds of Formula I:

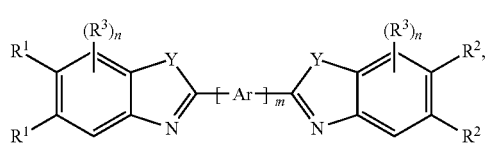

wherein Ar is $C_{6-10}$ aryl or 5-10 membered heteroaryl having 1-4 heteroatoms selected from N, O, and S, wherein Ar is optionally substituted with 1 to 4 $R^3$;

each $R^1$ and $R^2$ is independently selected from the group consisting of H, $C_{0-3}$ alkylene-halo, $C_{0-3}$ alkylene-CN, $C_{0-3}$ alkylene-NO$_2$, $C_{0-6}$ alkylene-CO$_2$R$^4$, $C_{0-6}$ alkylene-COR$^4$, $C_{0-6}$ alkylene-CON(R$^4$)$_2$, $C_{0-6}$ alkylene-OR$^4$, $C_{0-6}$ alkylene-N(R$^4$)$_2$, $C_{0-6}$ alkylene-SR$^4$, $C_{0-6}$ alkylene-NH(C=NH)NHR$^4$, $C_{0-6}$ alkylene-NHCONHR$^4$, $C_{0-6}$ alkylene-(C=NR$^4$)NHR$^4$, $C_{0-6}$ alkylene-NHCOR$^4$, $C_{0-6}$ alkylene-R$^4$, $C_{0-6}$ alkylene-NHR$^5$, $C_{0-6}$ alkylene-R$^5$, and $C_{0-6}$ alkylene-Z, and at least one $R^1$ and at least one $R^2$ is other than H;

each $R^3$ is independently selected from the group consisting of H, $C_{0-3}$ alkylene-halo, $C_{0-3}$ alkylene-CN, $C_{0-3}$ alkylene-NH$_2$, $C_{0-6}$ alkylene-NH(C=NH)NHR$^8$, $C_{0-3}$ alkylene-OH, and $C_{0-3}$ alkylene-O—$C_{1-6}$alkyl;

each $R^4$ is independently selected from the group consisting of H, $C_{1-6}$ alkyl, $C_{0-6}$alkylene-N(R$^6$)$_2$, $C_{0-6}$alkylene-N(R$^6$)$_3^+$, $C_{0-6}$alkylene-NR$^7$—$C_{0-6}$alkylene-N(R$^6$)$_2$, CH(OR$^6$)$_2$, $C_{0-6}$alkylene-OR$^6$, $C_{0-6}$alkylene-O—$C_{0-6}$alkylene-N(R$^6$)$_2$, $C_{0-6}$alkylene-NR$^6$(C=NR$^6$)N(R$^6$)$_2$, $C_{0-6}$alkylene-NR$^6$CO$_2$R$^6$, $C_{0-6}$alkylene-NR$^6$COR$^6$, CH(R$^7$)—$C_{0-6}$alkylene-NR$^6$(C=NR$^6$)N(R$^6$)$_2$, $C_{0-6}$alkylene-NR$^6$ $C_{0-6}$alkylene-NHCO—$C_{0-6}$alkylene-CO$_2$R$^6$, $C_{0-6}$alkylene-NHR$^5$, and $C_{0-6}$alkylene-Z, or two $R^4$ together with the nitrogen atom to which they are attached form a 4-7 membered heterocycloalkyl ring optionally further including one additional ring heteroatom selected from O and NR$^7$;

$R^5$ is selected from the group consisting of 5-10 membered heteroaryl having 1-4 heteroatoms selected from N, O, and S,

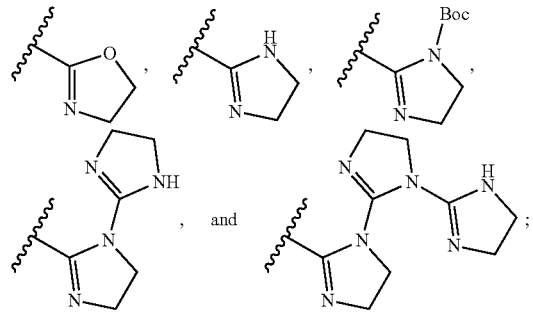

each $R^6$ is independently selected from the group consisting of H, $C_{1-6}$ alkyl, $C_{2-6}$ alkenyl, and $C_{2-6}$ alkynyl, or two $R^6$s taken together with the heteroatom(s) to which they are attached form a 4-10 membered heterocycloalkyl ring, optionally having 1 to 3 additional heteroatom ring atom(s) selected from 0 and N, and said heterocycloalkyl ring is optionally substituted with one or more $R^7$;

$R^7$ is H, $C_{1-6}$ alkyl, $C_{0-6}$ alkyl-OH, or CO$_2$R$^5$;

$R^8$ is H or $C_{1-6}$ alkyl;

each Y is independently NH or N—$C_{1-3}$alkyl, and said $C_{1-3}$alkyl is optionally substituted with 1, 2, or 3 groups independently selected from OH, NH$_2$, F. CO$_2$H, CO$_2$C$_{1-3}$alkyl, CO$_2$NH$_2$, C(=NH)NH$_2$, NHC(=NH)NH$_2$, and CN;

Z is a bond to a linking moiety;

each n is independently 0-2; and m is 1 or 2, with the proviso that the compound is not
2,2'-(1,4-phenylene)bis(1H-benzo[d]imidazol-6-amine),
N,N'''-[1,4-phenylenebis(1H-benzimidazole-2,6-diyl)]bis-guanidine,
N,N'''-[1,4-phenylenebis(1H-benzimidazole-2,5-diyl)]bis-guanidine,
2,2'-(1,4-phenylene)bis[6-chloro-5-methyl]-1H-benzimidazole,
2,2'-(1,4-phenylene)bis[5,7-dimethoxy]-1H-benzimidazole,
2,2'-[1,1'-biphenyl]-4,4'-diylbis[N-(1-methylethyl)]-1H-benzimidazole-6-carboximidamide,
6,6'-[1,4-phenylenebis(1H-benzimidazole-2,6-diylimino)]bis-1-hexanol,
2,2'-(1,4-phenylene)bis[N-ethyl]-1H-benzimidazole-5-carboximidamide,
2,2'-(1,4-phenylene)bis[N-(1,1-dimethylethyl)]-1H-benzimidazole-5-carboximidamide,
2,2'-(1,4-phenylene)bis[N-(2-methoxyethyl)]-1H-benzimidazole-5-carboximidamide, 2,2'-(1,4-phenylene)bis[N-methyl]-1H-benzimidazole-5-carboximidamide,
2,2'-(1,4-phenylene)bis[N-[3-(dimethylamino)propyl]]-1H-benzimidazole-5-carboximidamide,
2,2'-(1,4-phenylene)bis[N-pentyl]-1H-benzimidazole-5-carboximidamide,
2,2'-(1,4-phenylene)bis[N-(2-methylpropyl)]-1H-benzimidazole-5-carboximidamide,
2,2'-(1,4-phenylene)bis[N-propyl]-1H-benzimidazole-5-carboximidamide,
2,2'-(1,4-phenylene)bis[N-[2-(4-morpholinyl)ethyl]]-1H-benzimidazole-5-carboximidamide,
2,2'-(1,4-phenylene)bis[N-hexyl]-1H-benzimidazole-5-carboximidamide,
N,N'-[1,4-phenylenebis(1H-benzimidazole-2,5-diyl)]bis-acetamide,
N,N'-[1,4-phenylenebis(1H-benzimidazole-2,5-diyl)]bis[2,2,2-trifluoro]-acetamide,
N,N'[[1,1'-biphenyl]-4,4'-diylbis(1H-benzimidazole-2,5-diyl)]bis-acetamide,
2,2'-(1,4-phenylene)bis[N-[3-(dimethylamino)propyl]-1H-benzimidazole-6-carboxamide,
2,2'-(1,4-phenylene)bis[N-(1-methylethyl)-1H-benzimidazole-5-carboximidamide,
2,2'-(1,4-phenylene)bis[N-butyl-1H-benzimidazole-5-carboximidamide;
2,2'-(pyridine-2,6-diyl)bis(1H-benzo[d]imidazol-5-amine),
2,2'-(1,4-phenylene)bis(1H-benzo[d]imidazol-5-amine),
N,N'-(pyridine-2,6-diylbis(1H-benzo[d]imidazole-2,6-diyl))bis(2-(piperidin-1-yl)acetamide), or
1,1'-(2,6-pyridinediylbis(1H-benz[d]imidazole-2,6-diyl)imino(2-oxo-2,1-ethanediyl)))bis(1-methyl-piperidinium).

In some cases, the compounds are compounds of Formulae Ia-If:

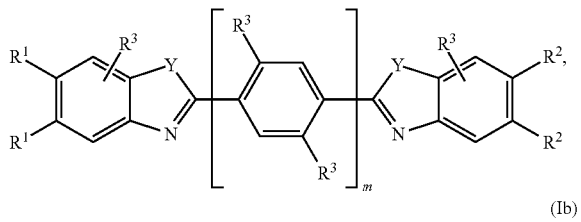
(Ia)

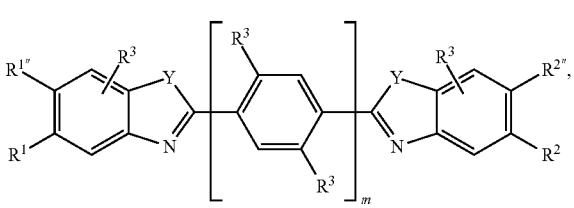
(Ib)

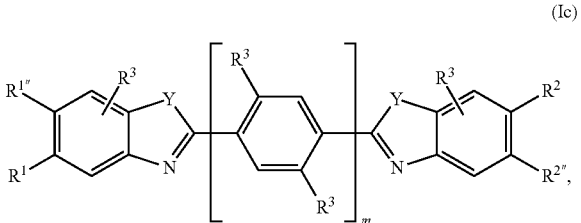
(Ic)

-continued

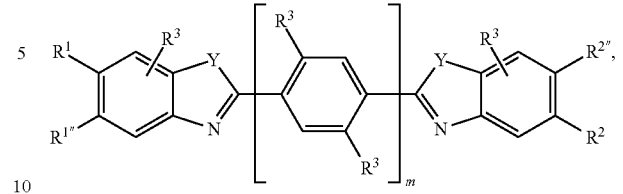
(Id)

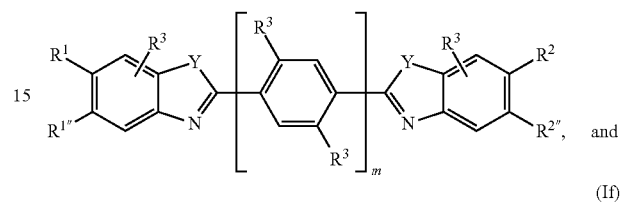
(Ie), and

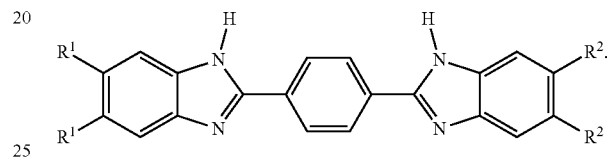
(If)

Also provided herein are compounds of Formula II:

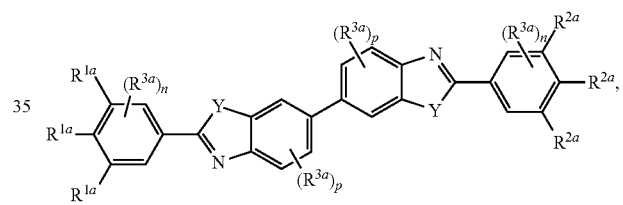
(II)

wherein each $R^{1a}$ and $R^{2a}$ is independently selected from the group consisting of H, $C_{1-3}$alkyl, $C_{0-3}$ alkylene-halo, $C_{0-3}$ alkylene-CN, $C_{0-3}$ alkylene-NO$_2$, $C_{0-6}$ alkylene-CO$_2R^{4a}$, $C_{0-6}$ alkylene-CON($R^{4a}$)$_2$, $C_{0-6}$ alkylene-OR$^{4a}$, $C_{0-6}$alkylene-N($R^{4a}$)$_2$, $C_{0-6}$ alkylene-SR$^{4a}$, $C_{0-6}$alkylene-NH(C=NH)NHR$^{4a}$, $C_{0-6}$ alkylene-NHCONHR$^{4a}$, $C_{0-6}$ alkylene-(C=NR$^{4a}$)N(R$^{4a}$)$_2$, $C_{0-6}$ alkylene-NHCOR$^{4a}$, $C_{0-6}$ alkylene-R$^{4a}$, $C_{0-6}$alkylene-NHR$^{5a}$, $C_{0-6}$alkylene-R$^{5a}$, and $C_{0-6}$alkylene-Z, with the proviso that at least one $R^{1a}$ and at least one $R^{2a}$ is other than H;

each $R^{3a}$ is independently selected from the group consisting of H, $C_{0-3}$ alkylene-halo, $C_{0-3}$ alkylene-CN, $C_{0-3}$ alkylene-NH$_2$, $C_{0-6}$ alkylene-NH(C=NH)NHR$^{7a}$, $C_{0-3}$ alkylene-OH, and $C_{0-3}$ alkylene-O—$C_{1-3}$alkyl;

each $R^{4a}$ is independently selected from the group consisting of H, $C_{1-6}$ alkyl, $C_{0-6}$ alkylene-N(R$^{6a}$)$_2$, $C_{0-6}$alkylene-N(R$^{6a}$)$_3^+$, $C_{0-6}$alkylene-NR$^{7a}$—C$_{0-6}$alkylene-N(R$^{6a}$)$_2$, $C_{0-6}$alkylene-OR$^{6a}$, $C_{0-6}$alkylene-O—$C_{0-6}$alkylene-N(R$^{6a}$)$_2$, $C_{0-6}$alkylene-NR$^{6a}$(C=N$^{6a}$)N(R$^{6a}$)$_2$, $C_{0-6}$alkylene-NR$^{6a}$CO$_2$R$^{6a}$, $C_{0-6}$alkylene-NR$^{6a}$COR$^{6a}$, CH(R$^{7a}$)—$C_{0-6}$alkylene-NR$^{6a}$(C=N$^{6a}$)N(R$^{6a}$)$_2$, $C_{0-6}$alkylene-NR$^{6a}$—$C_{0-6}$alkylene-NHCO—$C_{0-6}$alkylene-CO$_2$R$^{6a}$, $C_{0-6}$alkylene-NHR$^{5a}$, and $C_{0-6}$alkylene-Z;

$R^{5a}$ is selected from the group consisting of 5-10 membered heteroaryl having 1-4 ring heteroatoms selected from N, O, and S,

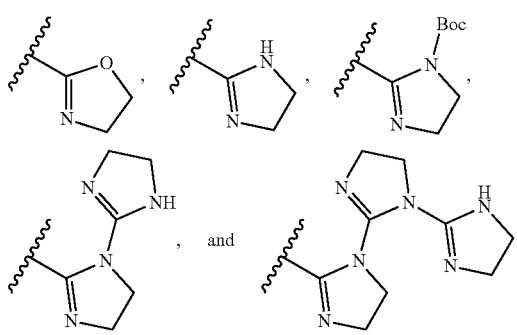

each $R^{6a}$ is independently selected from the group consisting of H, $C_{1-6}$ alkyl, $C_{2-6}$ alkenyl, and $C_{2-6}$ alkynyl, or two $R^{6a}$s taken together with the heteroatom(s) to which they are attached form a 4-7 membered heterocycloalkyl ring, optionally having 1 additional heteroatom ring atom selected from O and N, and said heterocycloalkyl ring is optionally substituted with one or more $R^{7a}$;

$R^{7a}$ is H or $C_{1-6}$ alkyl;

each Y is independently NH or N—$C_{1-3}$alkyl, and said $C_{1-3}$alkyl is optionally substituted with 1, 2, or 3 groups independently selected from OH, $NH_2$, F. $CO_2H$, $CO_2C_{1-3}$alkyl, $CO_2NH_2$, C(=NH)$NH_2$, NHC(=NH)$NH_2$, and CN;

Z is a bond to a linking moiety;

each n is independently 0-3; and each p is independently 0-3.

In various embodiments, the compound is a compound of Formulae II', IIa', or IIa-IIe:

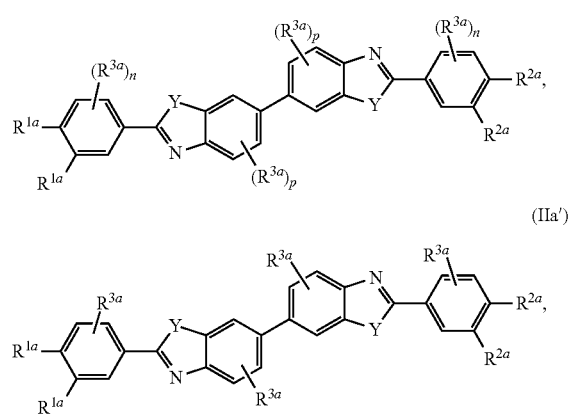

Further provided are compounds of structure $B^1$-$(L-B^x)_n$-$L$-$B^2$, wherein each of $B^1$, $B^x$, and $B^2$ independently has a structure of any one of Formulae I, Ia-Ie, II, II', IIa', or IIa-IIe, or a compound as disclosed in any of Tables A, A1, A2, B, C, C1, and D, and comprising (or further comprising) a Z moiety, said Z moiety forming a covalent bond to L; each L is a linking moiety; and n is 0-2. In some embodiments, the compound is as disclosed in any of Tables A, A1, B, C, and D, and comprising (or further comprising) a Z moiety, said Z moiety forming a covalent bond to L; each L is a linking moiety; and n is 0-2.

In some embodiments, each L independently has a structure of Formula $A^1$ or $A^2$:

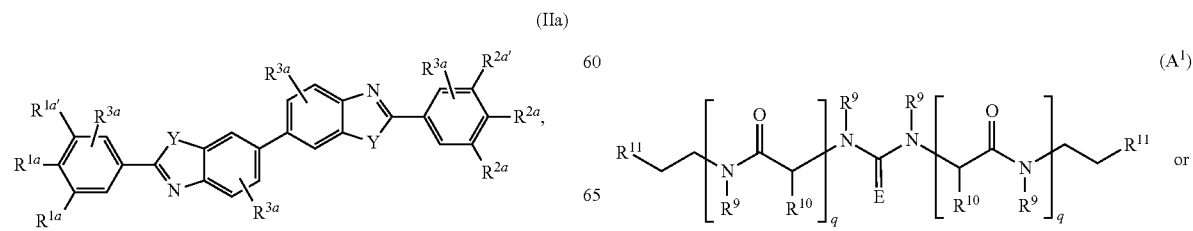

-continued

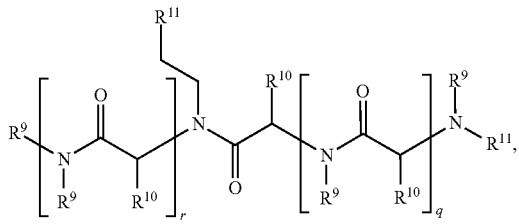

(A²)

wherein each R⁹ is independently H or $C_{1-6}$ alkyl;

each $R^{10}$ is independently H, $C_{1-6}$ alkyl, or $C_{0-6}$alkylene-$R^{12}$, and $R^{10}$ is optionally substituted with one to three substituents selected from the group consisting of halo, OH, CN, $NO_2$, $N_3$, $NH_2$, SH, $SCH_3$, COOH, $CONH_2$, $NH(C=NH)NH_2$, $C_{6-10}$ aryl, 5 to 10-membered heteroaryl having 1-4 ring heteroatoms selected from N, O, and S, $C_{6-10}$ cycloalkyl, and 5 to 12-membered heterocycloalkyl having 1-3 ring heteroatoms selected from N, O, and S;

each $R^{11}$ is independently selected from the group consisting of $C_{0-6}$alkylene-(Het)$_s$-$C_{0-6}$alkylene-QZ, CO—$C_{0-6}$alkylene-(Het)$_s$-$C_{0-6}$alkylene-QZ, $C_{0-6}$alkylene-(Het)$_s$-$C_{0-6}$alkylene-(C=O)-QZ, CO—$C_{0-6}$alkylene-(Het)$_s$-$C_{0-6}$alkylene-CO-QZ, $(OCH_2CH_2)_q$-Het-$(CH_2CH_2O)_q$-QZ, $(OCH_2CH_2)_q$-Het-$(CH_2CH_2O)_q$—CO-QZ, $(NR^9CH_2CH_2)_q$-Het-$(CH_2CH_2NR^9)_q$-QZ, and $(NR^9CH_2CH_2)_q$-Het-$(CH_2CH_2NR^9)_q$—CO-QZ;

$R^{12}$ is selected from the group consisting of $CO_2H$, $CO_2C_{1-6}$alkyl, SH, $SC_{1-6}$alkyl, OH, $OC_{1-6}$alkyl, $NH_2$, $NHC_{1-6}$alkyl, $N(C_{1-6}$alkyl$)_2$, $NH(C=NH)NH_2$, $CONH_2$, $C_{6-10}$aryl, 5 to 10-membered heteroaryl having 1-4 ring heteroatoms selected from N, O, and S, 5 to 12-membered heterocycloalkyl having 1-3 ring heteroatoms selected from N, O, and S;

E is O or $NR^9$;

Het is 5 to 10-membered heteroaryl having 1-4 ring heteroatoms selected from N, O, and S or 5 to 12-membered heterocycloalkyl having 1-3 ring heteroatoms selected from N, O, and S;

Q is selected from the group consisting of O, $NR^9$, S, $C_{6-10}$ aryl, 5 to 10-membered heteroaryl having 1-4 ring heteroatoms selected from N, O, and S, $C_{6-10}$ cycloalkyl, and 5 to 12-membered heterocycloalkyl having 1-3 ring heteroatoms selected from N, O, and S;

Z is a bond to the B1, B$^x$, or B2 moiety;

each q is independently 1-13;

each r is independently 0 or 1; and each s is independently 0 or 1.

Further provided herein are methods of using the compounds disclosed to treat or prevent a nucleotide repeat disorder in a subject.

Other aspects of the disclosure include a compound as disclosed herein for use in the preparation of a medicament for treating or preventing a nucleotide repeat disorder in a subject, and the use of a compound as disclosed herein in a method of treating or preventing a nucleotide repeat disorder in a subject.

DETAILED DESCRIPTION

Provided herein are nucleic acid-binding compounds that can treat or prevent a nucleotide repeat disorder in a subject. These compounds are useful in the treatment of a variety of diseases and disorders, including but not limited to, Myotonic Dystrophy Type 1, Myotonic Dystrophy Type 2, Fuchs dystrophy, Huntington Disease, Amyotrophic Lateral Sclerosis, or Frontotemporal Dementia.

Compounds of the Disclosure

The disclosure provides compounds of Formula I:

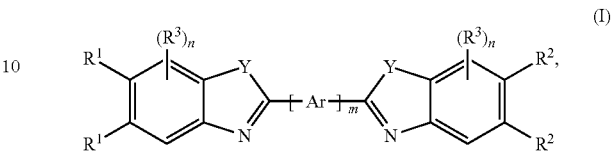

(I)

wherein Ar is $C_{b-10}$aryl or 5-10 membered heteroaryl having 1-4 heteroatoms selected from N, O, and S, wherein Ar is optionally substituted with 1 to 4 $R^3$;

each $R^1$ and $R^2$ is independently selected from the group consisting of H, $C_{0-3}$ alkylene-halo, $C_{0-3}$ alkylene-CN, $C_{0-3}$ alkylene-$NO_2$, $C_{0-6}$alkylene-$CO_2R^4$, $C_{0-6}$ alkylene-$COR^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-$SR^4$, $C_{0-6}$ alkylene-$NH(C=NH)NHR^4$, $C_{0-6}$ alkylene-$NHCONHR^4$, $C_{0-6}$ alkylene-$(C=NR^4)NHR^4$, $C_{0-6}$ alkylene-$NHCOR^4$, $C_{0-6}$ alkylene-$R^4$, $C_{0-6}$ alkylene-$NHR^5$, $C_{0-6}$ alkylene-$R^5$, and $C_{0-6}$ alkylene-Z, and at least one $R^1$ and at least one $R^2$ is other than H;

each $R^3$ is independently selected from the group consisting of H, $C_{0-3}$ alkylene-halo, $C_{0-3}$ alkylene-CN, $C_{0-3}$ alkylene-$NH_2$, $C_{0-6}$ alkylene-$NH(C=NH)NHR^8$, $C_{0-3}$ alkylene-OH, and $C_{0-3}$ alkylene-O—$C_{1-6}$alkyl;

each $R^4$ is independently selected from the group consisting of H, $C_{1-6}$ alkyl, $C_{0-6}$alkylene-$N(R^6)_2$, $C_{0-6}$alkylene-$N(R^6)_3^+$, $C_{0-6}$alkylene-$NR^7$—$C_{0-6}$alkylene-$N(R^6)_2$, $CH(OR^6)_2$, $C_{0-6}$alkylene-$OR^6$, $C_{0-6}$alkylene-O—$C_{0-6}$alkylene-$N(R^6)_2$, $C_{0-6}$alkylene-$NR^6(C=NR^6)N(R^6)_2$, $C_{0-6}$alkylene-$NR^6CO_2R^6$, $C_{0-6}$alkylene-$NR^6COR^6$, $CH(R^7)$—$C_{0-6}$alkylene-$NR^6(C=NR^6)N(R^6)_2$, $C_{0-6}$alkylene-$NR^6$ $C_{0-6}$alkylene-NHCO—$C_{0-6}$alkylene-$CO_2R^6$, $C_{0-6}$alkylene-$NHR^5$, and $C_{0-6}$alkylene-Z, or two $R^4$ together with the atom to which they are attached form a 4-7 membered heterocycloalkyl ring optionally further including one additional ring heteroatom selected from O and $NR^7$;

$R^5$ is selected from the group consisting of 5-10 membered heteroaryl having 1-4 heteroatoms selected from N, O, and S,

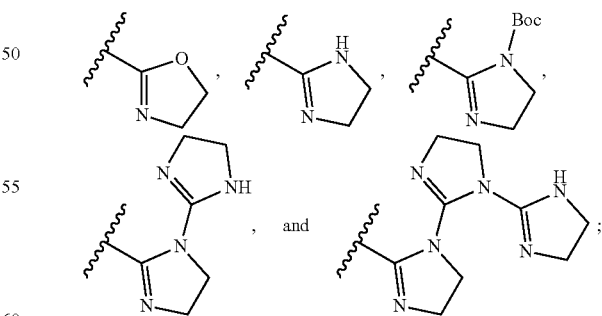

each $R^6$ is independently selected from the group consisting of H, $C_{1-6}$ alkyl, $C_{2-6}$ alkenyl, and $C_{2-6}$ alkynyl, or two $R^6$s taken together with the heteroatom(s) to which they are attached form a 4-10 membered heterocycloalkyl ring, optionally having 1 to 3 (e.g., 1-2, 1, 2, or 3) additional heteroatom ring atom(s) selected from 0 and N, and said heterocycloalkyl ring is optionally substituted with one or more (e.g., 1-3, 1-2, 1, 2, or 3) $R^7$;

$R^7$ is H, $C_{1-6}$ alkyl, $C_{0-6}$ alkyl-OH, or $CO_2R^5$;

$R^8$ is H or $C_{1-6}$ alkyl;

each Y is independently NH or N—$C_{1-3}$alkyl, and said $C_{1-3}$alkyl is optionally substituted with 1, 2, or 3 groups selected from OH, $NH_2$, F. $CO_2H$, $CO_2C_{1-3}$alkyl, $CO_2NH_2$, C(=NH)$NH_2$, NHC(=NH)$NH_2$, or CN;

Z is a bond to a linking moiety;

each n is independently 0-2; and m is 1 or 2, with the proviso that the compound is not 2,2'-(1,4-phenylene)bis(1H-benzo[d]imidazol-6-amine), N,N'''-[1,4-phenylenebis(1H-benzimidazole-2,6-diyl)]bis-guanidine, N,N'''-[1,4-phenylenebis(1H-benzimidazole-2,5-diyl)]bis-guanidine, 2,2'-(1,4-phenylene)bis[6-chloro-5-methyl]-1H-benzimidazole, 2,2'-(1,4-phenylene)bis[5,7-dimethoxy]-1H-benzimidazole, 2,2'-[1,1'-biphenyl]-4,4'-diylbis[N-(1-methylethyl)]-1H-benzimidazole-6-carboximidamide, 6,6'-[1,4-phenylenebis(1H-benzimidazole-2,6-diylimino)]bis-1-hexanol, 2,2'-(1,4-phenylene)bis[N-ethyl]-1H-benzimidazole-5-carboximidamide, 2,2'-(1,4-phenylene)bis[N-(1,1-dimethylethyl)]-1H-benzimidazole-5-carboximidamide, 2,2'-(1,4-phenylene)bis[N-(2-methoxyethyl)]-1H-benzimidazole-5-carboximidamide, 2,2'-(1,4-phenylene)bis[N-methyl]-1H-benzimidazole-5-carboximidamide, 2,2'-(1,4-phenylene)bis[N-[3-(dimethylamino)propyl]]-1H-benzimidazole-5-carboximidamide, 2,2'-(1,4-phenylene)bis[N-pentyl]-1H-benzimidazole-5-carboximidamide, 2,2'-(1,4-phenylene)bis[N-(2-methylpropyl)]-1H-benzimidazole-5-carboximidamide, 2,2'-(1,4-phenylene)bis[N-propyl]-1H-benzimidazole-5-carboximidamide, 2,2'-(1,4-phenylene)bis[N-[2-(4-morpholinyl)ethyl]]-1H-benzimidazole-5-carboximidamide, 2,2'-(1,4-phenylene)bis[N-hexyl]-1H-benzimidazole-5-carboximidamide, N,N'-[1,4-phenylenebis(1H-benzimidazole-2,5-diyl)]bis-acetamide, N,N'-[1,4-phenylenebis(1H-benzimidazole-2,5-diyl)]bis[2,2,2-trifluoro]-acetamide, N,N'-[[1,1'-biphenyl]-4,4'-diylbis(1H-benzimidazole-2,5-diyl)]bis-acetamide, 2,2'-(1,4-phenylene)bis[N-[3-(dimethylamino)propyl]]-1H-benzimidazole-6-carboxamide, 2,2'-(1,4-phenylene)bis[N-(1-methylethyl)-1H-benzimidazole-5-carboximidamide, 2,2'-(1,4-phenylene)bis[N-butyl-1H-benzimidazole-5-carboximidamide;

2,2'-(pyridine-2,6-diyl)bis(1H-benzo[d]imidazol-5-amine), 2,2'-(1,4-phenylene)bis(1H-benzo[d]imidazol-5-amine), N,N'-(pyridine-2,6-diylbis(1H-benzo[d]imidazole-2,6-diyl))bis(2-(piperidin-1-yl)acetamide), or 1,1'-(2,6-pyridinediylbis(1H-benz[d]imidazole-2,6-diyl) imino(2-oxo-2,1-ethanediyl)))bis(1-methyl-piperidinium).

The compounds of Table A1 are explicitly provisoed out from the scope of compounds of Formula (I).

In various embodiments, Ar is a monocyclic $C_6$ aryl or monocyclic 5-6 membered heteroaryl. In various embodiments, Ar is a monocyclic 5-6 membered heteroaryl having 1-4 heteroatoms selected from N, O, and S and is optionally substituted with 1 to 4 $R^3$, and in some cases is unsubstituted, or substituted with 1 or 2 $R^3$. In another embodiment, Ar is a monocyclic $C_6$ aryl and is optionally substituted with 1 to 4 $R^3$, and in some cases is unsubstituted, or substituted with 1 or 2 $R^3$. In some cases, the $R^3$ substitution on Ar is halo or $C_{1-3}$alkyl.

In some embodiments, the compound of Formula I has the structure of Formula Ia:

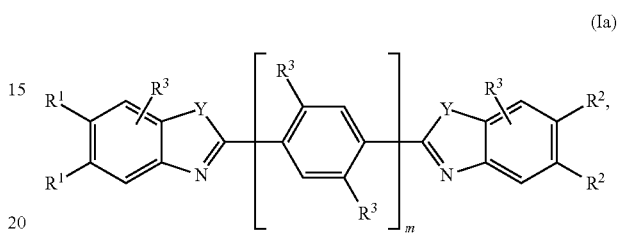

(Ia)

wherein each $R^1$ and $R^2$ is independently selected from the group consisting of H, $C_{0-3}$ alkylene-halo, $C_{0-3}$ alkylene-$NO_2$, $C_{0-6}$ alkylene-$CO_2R^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-NH(C=NH)$NHR^4$, $C_{0-6}$ alkylene-NH(C=O)$NHR^4$, $C_{0-6}$ alkylene-(C=NH)$NHR^4$, $C_{0-6}$ alkylene-NH(C=O)$R^4$, $C_{0-6}$ alkylene-$R^4$, $C_{0-6}$ alkylene-$NHR^5$, $C_{0-6}$ alkylene-$R^5$, and $C_{0-6}$ alkylene-Z;

each $R^3$ is independently selected from the group consisting of H, F, $NH_2$, NH(C=NH)$NH_2$, OH, and $OCH_3$;

each $R^4$ is independently selected from the group consisting of H, $C_{0-6}$alkylene-$N(R^6)_2$, $C_{0-6}$alkylene-$NR^7$—$C_{0-6}$alkylene-$N(R^6)_2$, $C_{0-6}$alkylene-O—$C_{0-6}$alkylene-$N(R^6)_2$, $C_{0-6}$alkylene-$NR^6$(C=NH)$N(R^6)_2$, $C_{0-6}$alkylene-$NHR^5$, and $C_{0-6}$alkylene-Z;

$R^5$ is

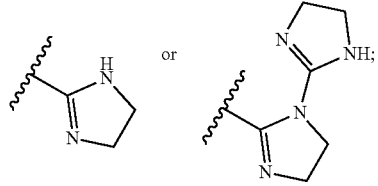 [SMILES: *C1=NCCN1 ; "or" ; *C1=NCCN1C1=NCCN1]

$R^7$ is H or $C_{1-6}$ alkyl;

each Y is independently NH or N—$C_{1-3}$alkyl, and said $C_{1-3}$alkyl is optionally substituted with 1, 2, or 3 groups selected from OH, $NH_2$, F. $CO_2H$, $CO_2C_{1-3}$alkyl, $CO_2NH_2$, C(=NH)$NH_2$, NHC(=NH)$NH_2$, or CN; and each n is independently 0-2.

In various embodiments, the compound of Formula I has the structure of Formula Ib, Ic, Id, or Ie:

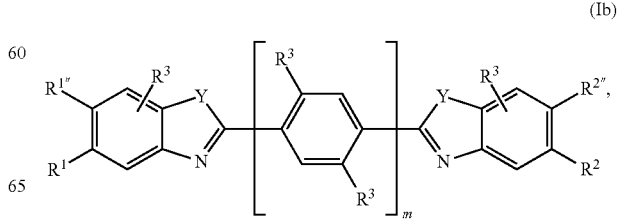

(Ib)

-continued (Ic)

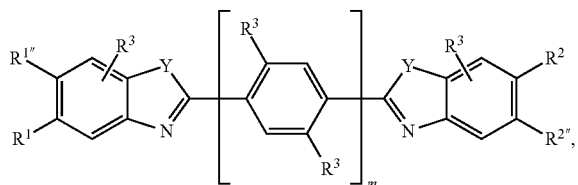

(Id)

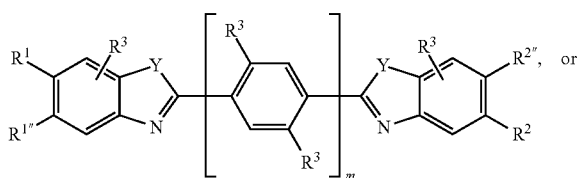

(Ie)

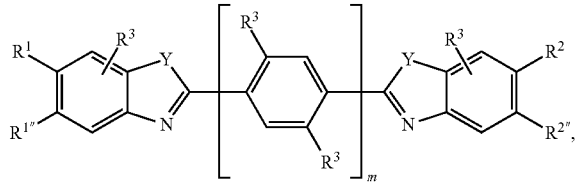

wherein $R^1$ and $R^2$ are each independently selected from the group consisting of $C_{0-6}$ alkylene-$CO_2R^4$, $C_{0-6}$ alkylene-$COR^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-$SR^4$, $C_{0-6}$ alkylene-NH(C=NH)$NHR^4$, $C_{0-6}$ alkylene-$NHCONHR^4$, $C_{0-6}$ alkylene-(C=$NR^4$)$NHR^4$, $C_{0-6}$ alkylene-$NHCOR^4$, $C_{0-6}$ alkylene-$R^4$, $C_{0-6}$ alkylene-$NHR^5$, $C_{0-6}$ alkylene-$R^5$, and $C_{0-6}$ alkylene-Z; and $R^{1'''}$ and $R^{2'''}$ are each independently selected from the group consisting of H, $C_{0-3}$ alkylene-halo, $C_{0-3}$ alkylene-CN, $C_{0-3}$ alkylene-$NO_2$, $C_{0-6}$ alkylene-$OR^4$, $C_{0-6}$ alkylene-$SR^4$, and $C_{0-6}$ alkylene-Z.

In some embodiments, the compound of Formula I has the structure of Formula If:

(If)

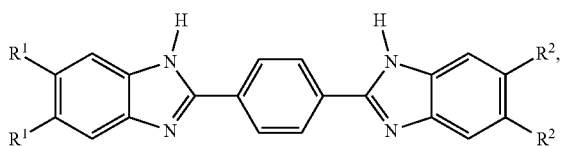

wherein each $R^1$ and $R^2$ is independently selected from the group consisting of H, F, $C_{0-6}$ alkylene-$CO_2R^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-NH(C=NH)$NHR^4$, $C_{0-6}$ alkylene-NH(C=O)$NHR^4$, $C_{0-6}$ alkylene-(C=NH)$NHR^4$, $C_{0-6}$ alkylene-NH(C=O)$R^4$, $C_{0-6}$ alkylene-$R^4$, $NHR^5$, $C_{0-6}$ alkylene-$R^5$, and $C_{0-6}$ alkylene-Z;

each $R^4$ is independently selected from the group consisting of H, $C_{0-6}$alkylene-$N(R^6)_2$, $C_{0-6}$alkylene-$NR^7$—$C_{0-6}$alkylene-$N(R^6)_2$, $C_{0-6}$alkylene-O—$C_{0-6}$alkylene-$N(R^6)_2$, $C_{0-6}$alkylene-$NR^6$(C=NH)$N(R^6)_2$, $C_{0-6}$alkylene-$NHR^5$, and $C_{0-6}$alkylene-Z;

$R^5$ is

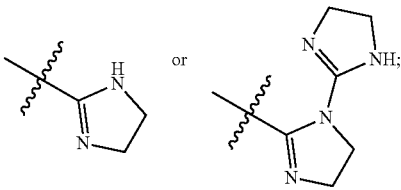 [SMILES: *C1=NCCN1 ; "or" ; *C1=NCCN1C1=NCCN1]

and $R^7$ is H or $C_{1-6}$ alkyl.

In various embodiments, m is 1. In another embodiment, m is 2.

In various embodiments, each Y NH or unsubstituted N—$C_{1-3}$alkyl.

In some embodiments, at least one Y is N—$C_{1-3}$alkyl, and said $C_{1-3}$alkyl is optionally substituted with 1, 2, or 3 groups independently selected from OH, $NH_2$, F, $CO_2H$, $CO_2C_{1-3}$alkyl, $CO_2NH_2$, C(=NH)$NH_2$, NHC(=NH)$NH_2$, and CN. In some cases, the $C_{1-3}$alkyl is substituted with 1 or 2 groups independently selected from OH, $NH_2$, F, $CO_2H$, $CO_2C_{1-3}$alkyl, $CO_2NH_2$, C(=NH)$NH_2$, NHC(=NH)$NH_2$, and CN. In various embodiments, each Y is NH or $NCH_3$.

In various embodiments, one $R^1$ is selected from the group consisting of $C_{0-6}$ alkylene-$CO_2R^4$, $C_{0-6}$ alkylene-$COR^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-$SR^4$, $C_{0-6}$ alkylene-NH(C=NH)$NHR^4$, $C_{0-6}$ alkylene-$NHCONHR^4$, $C_{0-6}$ alkylene-(C=$NR^4$)$NHR^4$, $C_{0-6}$ alkylene-$NHCOR^4$, $C_{0-6}$ alkylene-$R^4$, $C_{0-6}$ alkylene-$NHR^5$, $C_{0-6}$ alkylene-$R^5$, and $C_{0-6}$ alkylene-Z, and the other $R^1$ is selected from the group consisting of H, $C_{0-3}$ alkylene-halo, $C_{0-3}$ alkylene-CN, $C_{0-3}$ alkylene-$NO_2$, $C_{0-6}$ alkylene-$OR^4$, and $C_{0-6}$ alkylene-$SR^4$, and $C_{0-6}$ alkylene-Z.

In some embodiments, one $R^2$ is selected from the group consisting of $C_{0-6}$ alkylene-$CO_2R^4$, $C_{0-6}$ alkylene-$COR^4$, $C_{0-6}$ alkylene-$CON(R^4)_2$, $C_{0-6}$ alkylene-$OR^4$, $C_{0-6}$ alkylene-$N(R^4)_2$, $C_{0-6}$ alkylene-$SR^4$, $C_{0-6}$ alkylene-NH(C=NH)$NHR^4$, $C_{0-6}$ alkylene-$NHCONHR^4$, $C_{0-6}$ alkylene-(C=$NR^4$)$NHR^4$, $C_{0-6}$ alkylene-$NHCOR^4$, $C_{0-6}$ alkylene-$R^4$, $C_{0-6}$ alkylene-$NHR^5$, $C_{0-6}$ alkylene-$R^5$, and $C_{0-6}$ alkylene-Z, and the other $R^2$ is selected from the group consisting of H, $C_{0-3}$ alkylene-halo, $C_{0-3}$alkylene-CN, $C_{0-3}$ alkylene-$NO_2$, $C_{0-6}$ alkyl-$OR^4$, $C_{0-6}$ alkyl-$SR^4$, and $C_{0-6}$ alkyl-Z.

In some embodiments, each $R^1$ and $R^2$ is independently selected from the group consisting of H, $C_{0-3}$ alkylene-$NH_2$, $C_{0-6}$ alkylene-$CON(R^4)_2$, $C_{0-6}$ alkylene-$N(R^4)_2$, and $C_{0-6}$ alkylene-NH(C=NH)$NHR^4$.

In some embodiments, each $R^3$ is independently selected from the group consisting of H, $C_{0-3}$ alkylene-halo, $C_{0-3}$ alkylene-CN, $C_{0-3}$ alkylene-$NH_2$, $C_{0-6}$ alkylene-NH(C=NH)$NHR_8$, $C_{0-3}$ alkylene-OH, and $C_{0-3}$ alkylene-O—$C_{1-3}$alkyl.

In some embodiments, $R^4$ is selected from the group consisting of $C_{0-6}$alkylene-$N(R^6)_2$, $C_{0-6}$alkylene-$N(R^6)_3^+$, $C_{0-6}$alkylene-$NR^7$—$C_{0-6}$alkylene-$N(R^6)_2$, $C_{0-6}$alkylene-O—$C_{0-6}$alkylene-$N(R^6)_2$, and $C_{0-6}$alkylene-$NHR^5$.

In some embodiments, each $R^4$ is independently selected from the group consisting of H, $C_{1-6}$ alkyl, $C_{2-6}$alkylene-$N(R^6)_2$, $C_{2-6}$alkylene-$N(R^6)_3^+$, $C_{2-6}$alkylene-$NR^{1'}$—$C_{2-6}$alkylene-$N(R^6)_2$, $CH(OR^6)_2$, $C_{2-6}$alkylene-$OR^6$, $C_{2-6}$alkylene-O—$C_{2-6}$alkylene-$N(R^6)_2$, $C_{2-6}$alkylene-$NR^6$(C=NH)$N(R^6)_2$, $C_{2-6}$alkylene-$NR^6CO_2R^6$, $C_{2-6}$alkylene-$NR^6COR^6$, $CH(R^7)$—$C_{2-6}$alkylene-$NR^6$(C=NH)$N(R^6)_2$, $C_{2-6}$alkylene-$NR^6$ $C_{2-6}$alkylene-NHCO—$C_{2-6}$alkylene-$CO_2R^6$, $C_{2-6}$alkylene-$NHR^5$, and $C_{2-6}$alkylene-Z.

In some embodiment, $R^5$ is

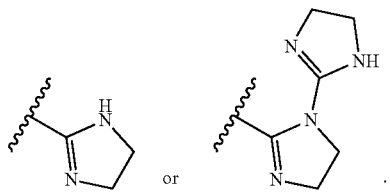 [SMILES: *C1=NCCN1 ; *C1=NCCN1C1=NCCN1]

In various cases, at least one $R^1$ or $R^2$ comprises $C_{0-6}$ alkylene-CON($R^4$)$_2$, $C_{0-6}$ alkylene-OR$^4$, $C_{0-6}$ alkylene-N($R^4$)$_2$, $C_{0-6}$ alkylene-SR$^4$, $C_{0-6}$ alkylene-NHCOR$^4$, $C_{0-6}$ alkylene-R$^4$, and $R^4$ comprises $C_{0-6}$alkylene-N($R^6$)$_2$, $C_{0-6}$alkylene-N($R^6$)$_3^+$, $C_{0-6}$alkylene-NR$^7$—$C_{0-6}$alkylene-N($R^6$)$_2$, or $C_{0-6}$alkylene-O—$C_{0-6}$alkylene-N($R^6$)$_2$. In some cases, one $R^1$ and one $R^2$ each comprise $C_{0-6}$ alkylene-CON($R^4$)$_2$, $C_{0-6}$ alkylene-OR$^4$, $C_{0-6}$ alkylene-N($R^4$)$_2$, $C_{0-6}$ alkylene-SR$^4$, $C_{0-6}$ alkylene-NHCOR$^4$, $C_{0-6}$ alkylene-R$^4$, and $R^4$ comprises $C_{0-6}$alkylene-N($R^6$)$_2$, $C_{0-6}$alkylene-N($R^6$)$_3^+$, $C_{0-6}$alkylene-NR$^7$—$C_{0-6}$alkylene-N($R^6$)$_2$, or $C_{0-6}$alkylene-O—$C_{0-6}$alkylene-N($R^6$)$_2$. In some cases, $R^6$ comprises H or $C_{1-6}$alkyl, or two $R^6$s taken together with the heteroatom(s) to which they are attached form a 4-10 membered heterocycloalkyl ring, optionally having 1 to 3 (e.g., 1-2, 1, 2, or 3) additional heteroatom ring atom(s) selected from O and N, and said heterocycloalkyl is optionally substituted with 1 or 2 $R^7$. In some cases, $R^7$ is $C_{1-6}$ alkyl, $C_{0-6}$ alkyl-OH, $CO_2H$, or $CO_2C_{1-6}$alkyl;

Further provided herein are compounds of Formula II:

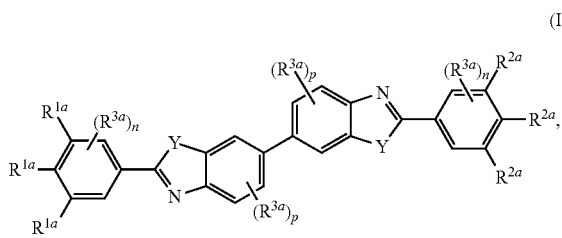

(II)

wherein each $R^{1a}$ and $R^{2a}$ is independently selected from the group consisting of H, $C_{1-3}$alkyl, $C_{0-3}$ alkylene-halo, $C_{0-3}$ alkylene-CN, $C_{0-3}$ alkylene-NO$_2$, $C_{0-6}$ alkylene-CO$_2$R$^{4a}$, $C_{0-6}$ alkylene-CON(R$^{4a}$)$_2$, $C_{0-6}$ alkylene-OR$^{4a}$, $C_{0-6}$ alkylene-N(R$^{4a}$)$_2$, $C_{0-6}$ alkylene-SR$^{4a}$, $C_{0-6}$ alkylene-NH(C=NH)NHR$^{4a}$, $C_{0-6}$ alkylene-NHCONHR$^{4a}$, $C_{0-6}$ alkylene-(C=NR$^{4a}$)N(R$^{4a}$)$_2$, $C_{0-6}$ alkylene-NHCOR$^{4a}$, $C_{0-6}$ alkylene-R$^{4a}$, $C_{0-6}$alkylene-NHR$^{5a}$, $C_{0-6}$alkylene-R$^{5a}$, and $C_{0-6}$alkylene-Z, with the proviso that at least one $R^{1a}$ and at least one $R^{2a}$ is other than H;

each $R^{3a}$ is independently selected from the group consisting of H, $C_{0-3}$ alkylene-halo, $C_{0-3}$ alkylene-CN, $C_{0-3}$ alkylene-NH$_2$, $C_{0-6}$ alkylene-NH(C=NH)NHR$^{7a}$, $C_{0-3}$ alkylene-OH, and $C_{0-3}$ alkylene-O—$C_{1-3}$alkyl;

each $R^{4a}$ is independently selected from the group consisting of H, $C_{1-6}$ alkyl, $C_{0-6}$alkylene-N(R$^{6a}$)$_2$, $C_{0-6}$alkylene-N(R$^{6a}$)$_3^+$, $C_{0-6}$alkylene-NR$^{7a}$—$C_{0-6}$alkylene-N(R$^{6a}$)$_2$, $C_{0-6}$alkylene-OR$^{6a}$, $C_{0-6}$alkylene-O—$C_{0-6}$alkylene-N(R$^{6a}$)$_2$, $C_{0-6}$alkylene-NR$^{6a}$(C=N$^{6a}$)N(R$^{6a}$)$_2$, $C_{0-6}$alkylene-NR$^{6a}$CO$_2$R$^{6a}$, $C_{0-6}$alkylene-NR$^{6a}$COR$^{6a}$, CH(R$^7$)—$C_{0-6}$alkylene-NR$^{6a}$(C=N$^{6a}$)N(R$^{6a}$)$_2$, $C_{0-6}$alkylene-NR$^{6a}$—$C_{0-6}$alkylene-NHCO—$C_{0-6}$alkylene-CO$_2$R$^{6a}$, $C_{0-6}$alkylene-NHR$^{5a}$, and $C_{0-6}$alkylene-Z;

$R^{5a}$ is selected from the group consisting of 5-10 membered heteroaryl having 1-4 ring heteroatoms selected from N, O, and S,

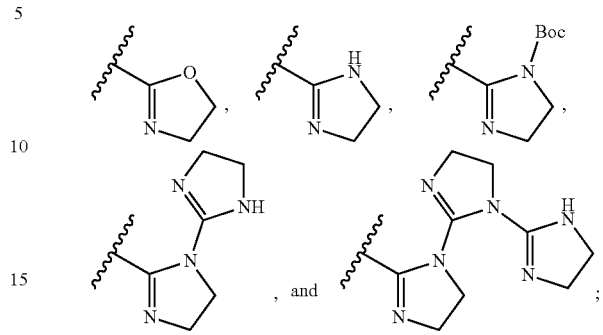

each $R^{6a}$ is independently selected from the group consisting of H, $C_{1-6}$ alkyl, $C_{2-6}$ alkenyl, and $C_{2-6}$ alkynyl, or two $R^6$ as taken together with the heteroatom(s) to which they are attached form a 4-7 membered heterocycloalkyl ring, optionally having 1 additional heteroatom ring atom selected from O and N, and said heterocycloalkyl ring is optionally substituted with one or more $R^{7a}$;

$R^{7a}$ is H or $C_{1-6}$ alkyl;

each Y is independently NH or N—$C_{1-3}$alkyl, and said $C_{1-3}$alkyl is optionally substituted with 1, 2, or 3 groups independently selected from OH, NH$_2$, F, CO$_2$H, CO$_2$C$_{1-3}$alkyl, CO$_2$NH$_2$, C(=NH)NH$_2$, NHC(=NH)NH$_2$, and CN;

Z is a bond to a linking moiety;

each n is independently 0-3; and each p is independently 0-3, with the proviso that the compound is not di-tert-butyl (1H,1'H-[5,5'-bibenzo[d]imidazole]-2,2'-diylbis(4,1-phenylene))dicarbamate.

In various embodiments, the compound of Formula II has the structure of Formula II':

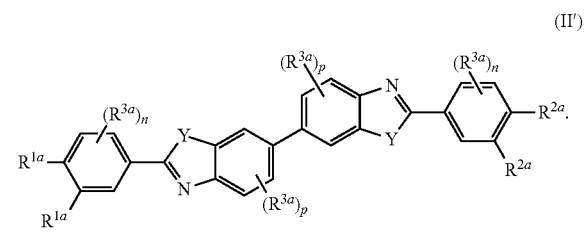

(II')

In various embodiments, the compound of Formula II has the structure of Formula IIa:

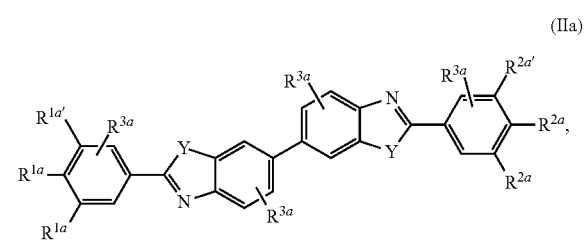

(IIa)

wherein each $R^{1a}$ and $R^{2a}$ is independently selected from the group consisting of H, $C_{1-3}$alkyl, $C_{0-3}$ alkylene-halo, $C_{0-3}$ alkylene-CN, $C_{0-3}$ alkylene-NO$_2$, $C_{0-6}$ alkylene-CO$_2$R$^{4a}$, $C_{0-6}$ alkylene-CON(R$^{4a}$)$_2$, $C_{0-6}$ alkylene-OR$^{4a}$, $C_{0-6}$alkylene-N(R$^{4a}$)$_2$, $C_{0-6}$ alkylene-NH(C=NH)NHR$^{4a}$, $C_{0-6}$alkylene-NHCONHR$^{4a}$, $C_{0-6}$alkylene-(C=NH)NHR$^{4a}$, $C_{0-6}$alkylene-NHCOR$^{4a}$, $C_{0-6}$alkylene-R$^{4a}$, $C_{0-6}$ alkylene-NHR$^{5a}$, $C_{0-6}$alkylene-R$^{5a}$, and $C_{0-6}$alkylene-Z;

each R$^{1a}$, R$^{2a}$, and R$^{3a}$ is independently selected from the group consisting of H, F, CN, NH$_2$, NH(C=NH)NH$_2$, OH, and OCH$_3$;

each R$^{4a}$ is independently selected from the group consisting of H, $C_{0-6}$alkylene-N(R$^{6a}$)$_2$, $C_{0-6}$alkylene-NR$^{7a}$—$C_{0-6}$alkylene-N(R$^{6a}$)$_2$, $C_{0-6}$alkylene-O—$C_{0-6}$alkylene-N(R$^{6a}$)$_2$, $C_{0-6}$alkylene-NR$^{6a}$(C=NH)N(R$^{6a}$)$_2$, or $C_{0-6}$alkylene-NHR$^{5a}$, and $C_{0-6}$alkylene-Z;

R$^{5a}$ is

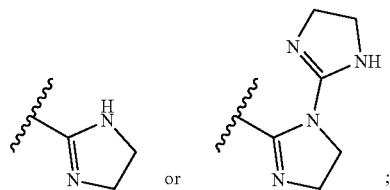 [SMILES: *C1=NCCN1 ; *C1=NCCN1C1=NCCN1]

and each Y is independently NH or N—$C_{1-3}$alkyl, and said $C_{1-3}$alkyl is optionally substituted with 1, 2, or 3 groups independently selected from OH, NH$_2$, F. CO$_2$H, CO$_2$C$_{1-3}$alkyl, CO$_2$NH$_2$, C(=NH)NH$_2$, NHC(=NH)NH$_2$, and CN.

In some embodiments, the compound of Formula II has the structure of Formula IIa':

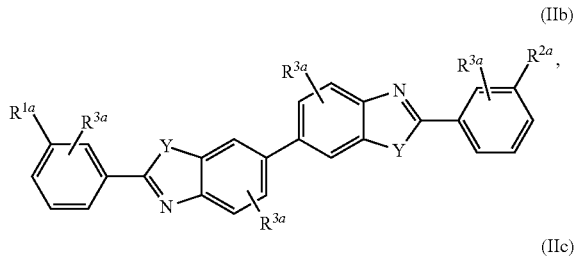

(IIa')

In some embodiments, the compound of Formula II has the structure of any one of Formulae IIb-IIe:

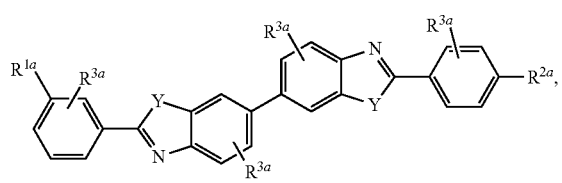

(IIb)

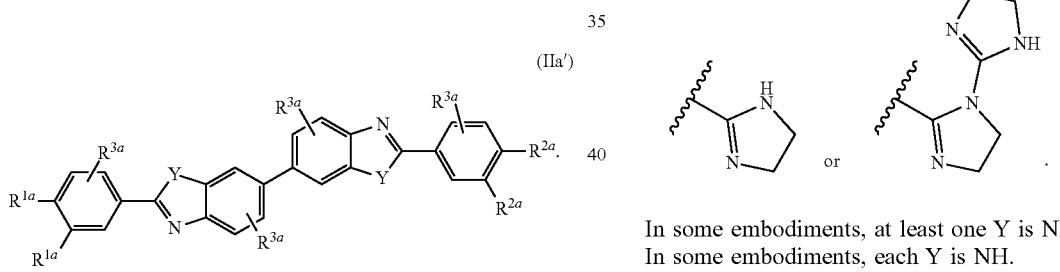

(IIc)

(IId)

(IIe)

In some embodiment, each R$^{1a}$ and R$^{2a}$ is independently selected from the group consisting of H, F, CN, NO$_2$, CO$_2$R$^{4a}$, CON(R$^{4a}$)$_2$, OR$^{4a}$, N(R$^{4a}$)$_2$, NH(C=NH)NHR$^{4a}$, NH(C=O)NHR$^{4a}$, (C=NH)NHR$^{4a}$, NH(C=O)R$^{4a}$, R$^{4a}$, NHR$^{5a}$, R$^{5a}$, and Z;

each R$^{3a}$ is H;

each R$^{4a}$ is independently selected from the group consisting of H, $C_{0-6}$alkylene-N(R$^{6a}$)$_2$, $C_{0-6}$alkylene-NR$^{7a}$—$C_{0-6}$alkylene-N(R$^{6a}$)$_2$, $C_{0-6}$alkylene-O—$C_{0-6}$alkylene-N(R$^{6a}$)$_2$, $C_{0-6}$alkylene-NR$^{6a}$(C=NH)N(R$^{6a}$)$_2$, $C_{0-6}$alkylene-NHR$^{5a}$, and $C_{0-6}$alkylene-Z; and R$^{5a}$ is

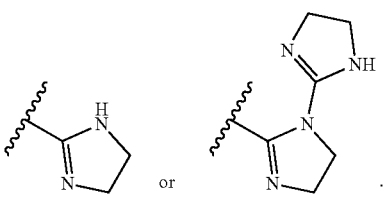 [SMILES: *C1=NCCN1 ; *C1=NCCN1C1=NCCN1]

In some embodiments, at least one Y is NH or NCH$_3$.

In some embodiments, each Y is NH.

In various embodiments, at least one R$^{1a}$ and one R$^{2a}$ is selected from the group consisting of $C_{0-6}$ alkylene-CO$_2$R$^{4a}$, $C_{0-6}$ alkylene-COR$^{4a}$, $C_{0-6}$ alkylene-CON(R$^{4a}$)$_2$, $C_{0-6}$ alkylene-OR$^{4a}$, $C_{0-6}$ alkylene-N(R$^{4a}$)$_2$, $C_{0-6}$ alkylene-SR$^{4a}$, $C_{0-6}$ alkylene-NH(C=NH)NHR$^{4a}$, $C_{0-6}$ alkylene-NHCONHR$^{4a}$, $C_{0-6}$ alkylene-(C=NR$^4$a)NHR$^{4a}$, $C_{0-6}$ alkylene-NHCOR$^{4a}$, $C_{0-6}$ alkylene-R$^{4a}$, $C_{0-6}$ alkylene-NHR$^{5a}$, $C_{0-6}$ alkylene-R$^{5a}$, and $C_{0-6}$ alkylene-Z.

In some embodiments, each R$^{1a}$ and R$^{2a}$ is independently selected from the group consisting of H, NH$_2$, CN, NO$_2$, $C_{0-6}$ alkylene-CON(R$^{4a}$)$_2$, $C_{0-6}$ alkylene-N(R$^{4a}$)$_2$, and $C_{0-6}$ alkylene-NH(C=NH)NHR$^{4a}$.

In some embodiments, R$^{4a}$ is selected from the group consisting of $C_{0-6}$alkylene-N(R$^{6a}$)$_2$, $C_{0-6}$alkylene-N(R$^{6a}$)$_3^+$, $C_{0-6}$alkylene-NR$^{7a}$—$C_{0-6}$alkylene-N(R$^{6a}$)$_2$, $C_{0-6}$alkylene-O—$C_{0-6}$alkylene-N(R$^{6a}$)$_2$, and $C_{0-6}$alkylene-NHR$^{5a}$.

In various embodiments, each R$^{4a}$ is independently selected from the group consisting of H, $C_{1-6}$ alkyl, $C_{2-6}$alkylene-N(R$^{6a}$)$_2$, $C_{2-6}$alkylene-N(R$^{6a}$)$_3^+$, $C_{2-6}$alkylene-NR$^{7a}$—$C_{2-6}$alkylene-N(R$^{6a}$)$_2$, $C_{2-6}$alkylene-OR$^{6a}$, $C_{2-6}$alkylene-O—$C_{2-6}$alkylene-N(R$^{6a}$)$_2$, $C_{2-6}$alkylene-NR$^{6a}$(C=NH)N(R$^{6a}$)$_2$, $C_{2-6}$alkylene-NR$^{6a}$CO$_2$R$^{6a}$, $C_{2-6}$alkylene-NR$^{6a}$COR$^{6a}$, CH(R$^{7a}$)—$C_{2-6}$alkylene-NR$^{6a}$ (C=NH)N($R^{6a}$)$_2$, $C_{2-6}$alkylene-NR$^{6a}$, $C_{2-6}$alkylene-NHCO—$C_{2-6}$alkylene-CO$_2$R$^{6a}$, $C_{2-6}$alkylene-NHR$^{9a}$, and $C_{2-6}$alkylene-Z.

In one embodiment, R$^{5a}$ is

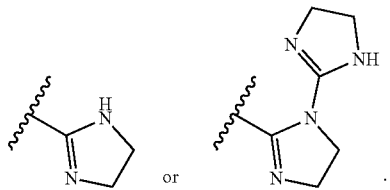 [SMILES: *C1=NCCN1 ; *C1=NCCN1C1=NCCN1]

or

The disclosure further provides oligomers of the compounds described herein, e.g., compounds of structure B$^1$-(L-B$^x$)$_n$-L-B$^2$, wherein each of B$^1$, B$^x$, and B$^2$ independently has a structure of any one of Formulae I, Ia-Ie, II, II', IIa', or IIa-IIe or a compound as reported in any of Tables A, A1, A2, B, C, C1, or D, comprising (or further comprising) a Z moiety, said Z moiety comprising a covalent bond to L; each L is a linking moiety; and n is 0-2. Z is a moiety by which the compounds of Formulae I, Ia-Ie, II, II', IIa', or IIa-IIe or the compound of Table A, A1, A2, B, C, or C1 are connected to the linking moiety, L, and thereby linked to another compound of Formulae I, Ia-Ie, II, II', IIa', or IIa-IIe, or a compound of Table A, A1, A2, B, C, C1, or D. For example, the Z moiety and the L moiety together comprise an aryl, a heteroaryl, a cycloalkyl, a heterocycloalkyl, an amide, an ester, a urea, a carbamate, a ketone, or the like. More specifically, for example, a Z moiety and an L moiety can be connected using click chemistry, e.g., whereby one of Z and L (or precursor of Z or L) comprises an alkyne and the other an azide, whereupon reaction in the presence of a catalyst, e.g., copper, form a triazole ring to connect the two moieties together thereby linking two compounds of any of Formulae I, Ia-Ie, II, II', IIa', or IIa-IIe, or as shown in Table A, A1, A2, B, C, C1, or D together. Z can be the attached to any unsubstituted position on a compound as disclosed herein, or generally a compound of Formulae I, Ia-Ie, II, II', IIa', or IIa-IIe. In various cases, Z is a bond indicating the point of attachment of the L group. In some of the embodiments above, the compound is as shown in Table A, A1, B, C, or D.

In some embodiments, each L independently has a structure of Formula A$^1$ or A$^2$:

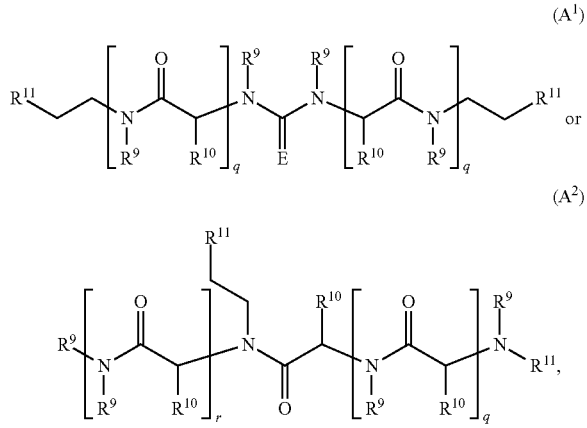

wherein each R$^9$ is independently H or C$_{1-6}$ alkyl;

each R$^{10}$ is independently H, C$_{1-6}$ alkyl, or C$_{0-6}$alkylene-R$^{12}$, and R$^{10}$ is optionally substituted with one to three substituents selected from the group consisting of halo, OH, CN, NO$_2$, N$_3$, NH$_2$, SH, SCH$_3$, COOH, CONH$_2$, NH(C=NH)NH$_2$, C$_{6-10}$ aryl, 5 to 10-membered heteroaryl having 1-4 ring heteroatoms selected from N, O, and S, C$_{6-10}$ cycloalkyl, and 5 to 12-membered heterocycloalkyl having 1-3 ring heteroatoms selected from N, O, and S;

each R$^{11}$ is independently selected from the group consisting of C$_{0-6}$alkylene-(Het)$_s$—C$_{0-6}$alkylene-QZ, CO—C$_{0-6}$alkylene-(Het)$_s$—C$_{0-6}$alkylene-QZ, C$_{0-6}$alkylene-(Het)$_s$—C$_{0-6}$alkylene-(C=O)-QZ, CO—C$_{0-6}$alkylene-(Het)$_s$—C$_{0-6}$alkylene-CO-QZ, (OCH$_2$CH$_2$)$_q$-Het-(CH$_2$CH$_2$O)$_q$-QZ, (OCH$_2$CH$_2$)$_q$-Het-(CH$_2$CH$_2$O)$_q$—CO-QZ, (NR$^9$CH$_2$CH$_2$)$_q$-Het-(CH$_2$CH$_2$NR$^9$)$_q$-QZ, and (NR$^9$CH$_2$CH$_2$)$_q$-Het-(CH$_2$CH$_2$NR$^9$)$_q$—CO-QZ;

R$^{12}$ is selected from the group consisting of CO$_2$H, CO$_2$C$_{1-6}$alkyl, SH, SC$_{1-6}$alkyl, OH, OC$_{1-6}$alkyl, NH$_2$, NHC$_{1-6}$alkyl, N(C$_{1-6}$alkyl)$_2$, NH(C=NH)NH$_2$, CONH$_2$, C$_{6-10}$aryl, 5 to 10-membered heteroaryl having 1-4 ring heteroatoms selected from N, O, and S, 5 to 12-membered heterocycloalkyl having 1-3 ring heteroatoms selected from N, O, and S;

E is O or NR$^9$;

Het is 5 to 10-membered heteroaryl having 1-4 ring heteroatoms selected from N, O, and S or 5 to 12-membered heterocycloalkyl having 1-3 ring heteroatoms selected from N, O, and S;

Q is selected from the group consisting of O, NR$^9$, S, C$_{6-10}$ aryl, 5 to 10-membered heteroaryl having 1-4 ring heteroatoms selected from N, O, and S, C$_{6-10}$ cycloalkyl, and 5 to 12-membered heterocycloalkyl having 1-3 ring heteroatoms selected from N, O, and S;

Z is a bond to the B1, B$^x$, or B2 moiety;

each q is independently 1-13;

each r is independently 0 or 1; and each s is independently 0 or 1.

In some embodiments, the compound has the structure B$^1$-L-B$^2$.

In various embodiments, the compound has the structure B$^1$-L-B$^x$-L-B$^2$.

In various embodiments, the compound has the structure B$^1$-L-B$^x$-L-B$^x$-L-B$^2$.

In various embodiment, E is O.

In some embodiments, R$^{10}$ is H, C$_{1-6}$alkyl, or C$_{0-6}$alkylene-R$^{12}$; and R$^{12}$ is selected from the group consisting of CO$_2$H, CO$_2$C$_{1-6}$alkyl, SH, SC$_{1-6}$alkyl, OH, OC$_{1-6}$alkyl, NH$_2$, NHC$_{1-6}$alkyl, N(C$_{1-6}$alkyl)$_2$, NH(C=NH)NH$_2$, CONH$_2$, C$_{6-10}$aryl, 5 to 10-membered heteroaryl having 1-4 ring heteroatoms selected from N, O, and S, 5 to 12-membered heterocycloalkyl having 1-3 ring heteroatoms selected from N, O, and S.

In various embodiments, R$^{10}$ is selected from the group consisting of H, CH$_3$, CH(CH$_3$)$_2$, CH(CH$_3$)(C$_2$H$_5$), CH$_2$(CH(CH$_3$)$_2$), (CH$_2$)$_2$SCH$_3$, CH$_2$Ph, CH$_2$(p-C$_6$H$_4$OH), CH$_2$(3-indole), CH$_2$OH, CH(OH)(CH$_3$), CH$_2$CONH$_2$, (CH$_2$)$_2$CONH$_2$, CH$_2$SH, 2-pyrrolidinyl, CH$_2$CO$_2$H, (CH$_2$)$_2$CO$_2$H, (CH$_2$)$_4$NH$_2$, CH$_2$(3-imidazolyl), and (CH$_2$)$_3$-guanidinyl.

In various embodiments, Het comprises triazolyl, imidazolyl, or piperazinyl.

In some embodiments, Q is O or NR$^9$. In another embodiment, Q comprises 5 to 10-membered heteroaryl having 1-4 ring heteroatoms selected from N, O, and S.

In some embodiments, $R^9$ is H or $CH_3$.

In various embodiments, $R^{10}$ is H or $CH_3$.

In various embodiments, at least one of $B^1$ and $B^2$ has a structure of Formula I, Ia, Ib, Ic, Id, Ie, or If. In some embodiments, at least one of $B^1$ and $B^2$ has a structure of Formula II, IIa, IIb, IIc, IId, or IIe.

In various embodiments, $B^1$ and $B^2$ are the same. In another embodiment, $B^1$ and $B^2$ are different.

In some embodiments, $B^x$ is the same as $B^1$ or $B^2$. In another embodiment, each of B1, B2, and $B^x$ is the same.

In various embodiments, at least one L has the structure of Formula $A^1$. In another embodiment, at least one L has the structure of Formula $A^2$.

Further provided are compounds as recited in Tables A, A2, B, C, C1, D, E, F, G, H, I, J, or K, or a pharmaceutically acceptable salt thereof. Also provided are use of compounds recited in Table A1, or a pharmaceutically acceptable salt thereof.

Specific compounds contemplated include those listed in Table A, or a pharmaceutically acceptable salt thereof:

TABLE A

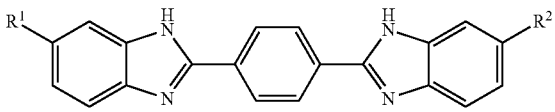

| Compound # | $R^1$ | $R^2$ |
|---|---|---|
| 1 | $NO_2$ | $NO_2$ |
| 5 | $NH_2$ | 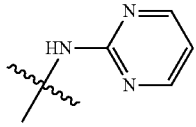 [SMILES: *Nc1ncccn1] |
| 7 | NHAc | 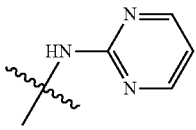 [SMILES: *Nc1ncccn1] |
| 8 | 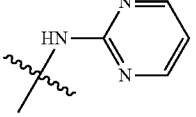 | 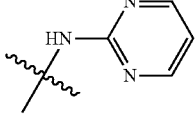 |
| 9 | CN | CN |
| 10 | $CO_2Me$ | $CO_2Me$ |
| 11 | $CO_2H$ | $CO_2H$ |
| 13 | CN | 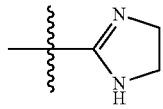 |
| 14 | 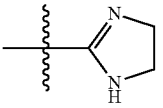 | 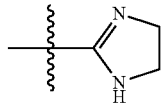 |
| 15 | CN | 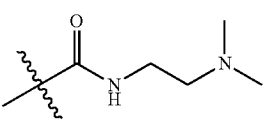 [SMILES: *C(=O)NCCN(C)C] |
| 16 | 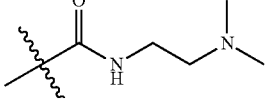 | 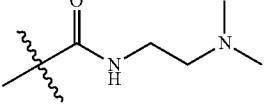 |
| 17 | $NH_2$ | 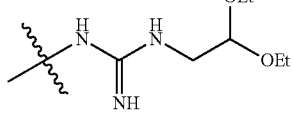 |

TABLE A-continued
| Compound # | R¹ | R² |
|---|---|---|
| 18 | 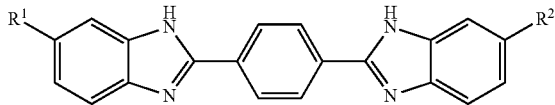 | 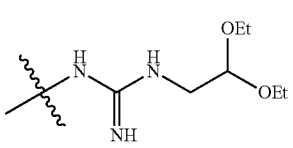 [SMILES: *NC(=N)NCC(OCC)OCC] |
| 19 | NH₂ | 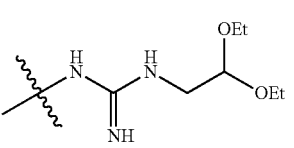 [SMILES: *NC(=N)NCC(OCC)OCC] |
| 20 | 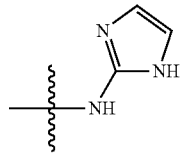 [SMILES: *Nc1ncc[nH]1] | 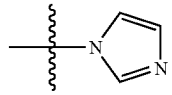 [SMILES: *n1ccnc1] |
| 21 | NH₂ | 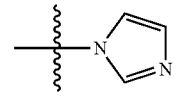 |
| 22 | 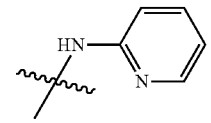 [SMILES: *Nc1ccccn1] | 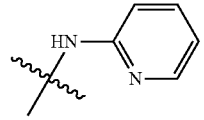 |
| 23 | NH₂ | 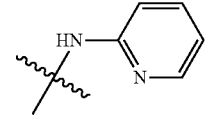 [SMILES: *Nc1ccccn1] |
| 24 | NH₂ | 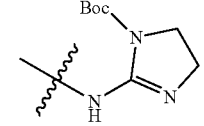 [SMILES: *NC1=NCCN1C(=O)OC(C)(C)C] |
| 25 | 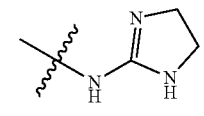 [SMILES: *NC1=NCCN1] | 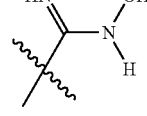 |
| 27 | 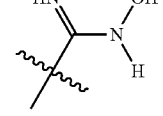 | 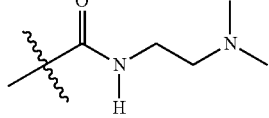 |
| 28 | 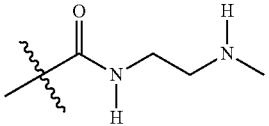 [SMILES: *C(=O)NCCNC] | 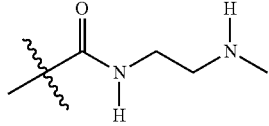 [SMILES: *C(=O)NCCNC] |

TABLE A-continued
| Compound # | R¹ | R² |
|---|---|---|
| 29 | 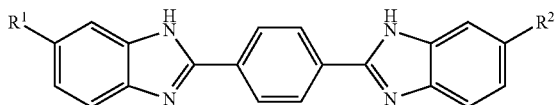 | 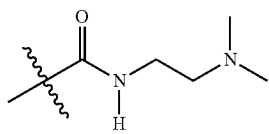 |
| 30 | 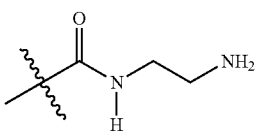 [SMILES: *C(=O)NCCN] | 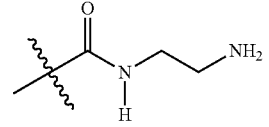 [SMILES: *C(=O)NCCN] |
| 31 | 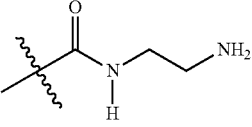 [SMILES: *C(=O)NCCN] | 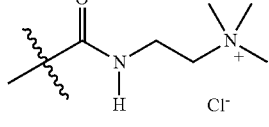 |
| 32 | 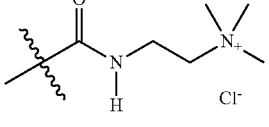 | 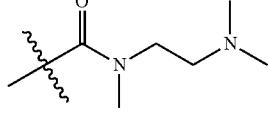 |
| 33 | 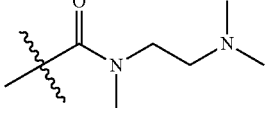 | 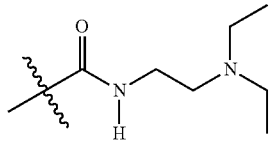 [SMILES: *C(=O)NCCN(CC)CC] |
| 34 | 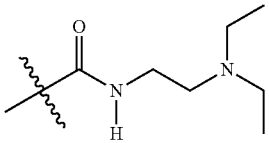 [SMILES: *C(=O)NCCN(CC)CC] | 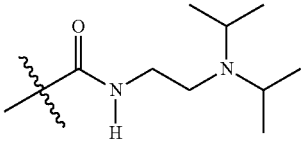 [SMILES: *C(=O)NCCN(C(C)C)C(C)C] |
| 35 | 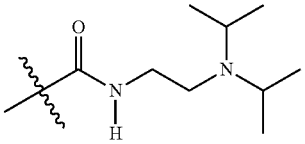 [SMILES: *C(=O)NCCN(C(C)C)C(C)C] | 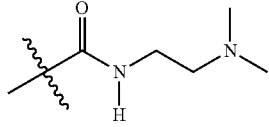 |
| 36 | 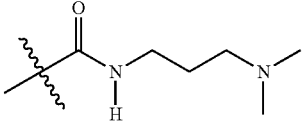 [SMILES: *C(=O)NCCCN(C)C] | 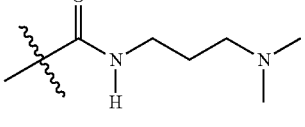 |
| 37 | 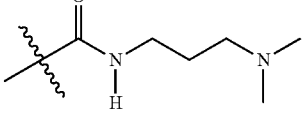 | 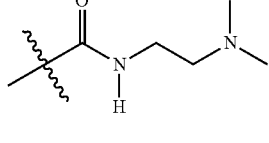 |
| 38 | 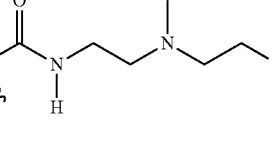 | 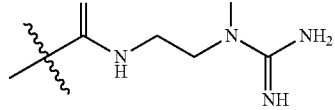 |

TABLE A-continued

| Compound # | R¹ | R² |
|---|---|---|
| 39 | -C(O)-NH-CH(CO₂Me)-CH₂CH₂CH₂-NH-C(=NH)NH₂ | -C(O)-NH-CH(CO₂Me)-CH₂CH₂CH₂-NH-C(=NH)NH₂ |
| 40 | -C(O)-NH-CH₂CH₂-(pyrrolidin-1-yl) | -C(O)-NH-CH₂CH₂-(pyrrolidin-1-yl) |
| 41 | -C(O)-NH-CH₂CH₂-(piperidin-1-yl) | -C(O)-NH-CH₂CH₂-(piperidin-1-yl) |
| 42 | -C(O)-NH-CH₂CH₂-(morpholin-4-yl) | -C(O)-NH-CH₂CH₂-(morpholin-4-yl) |
| 43 | -C(O)-NH-CH₂CH₂-(piperidin-1-yl) | CO₂H |
| 44 | -C(O)-NH-CH₂CH₂-(piperidin-1-yl) | -C(O)-NH-CH₂CH₂-(4-methylpiperazin-1-yl) |
| 45 | -C(O)-NH-CH₂CH₂-(4-methylpiperazin-1-yl) | -C(O)-NH-CH₂CH₂-(4-methylpiperazin-1-yl) |
| 46 | -C(O)-NH-CH₂CH₂-(4-Boc-piperazin-1-yl) | -C(O)-NH-CH₂CH₂-(4-Boc-piperazin-1-yl) |
| 47 | -C(O)-NH-CH₂CH₂-(piperazin-1-yl) | -C(O)-NH-CH₂CH₂-(piperazin-1-yl) |

TABLE A-continued
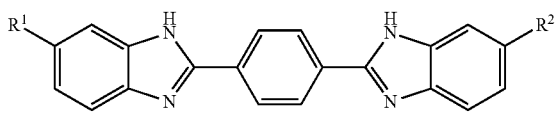
| Compound # | R[1] | R[2] |
|---|---|---|
| 48 | 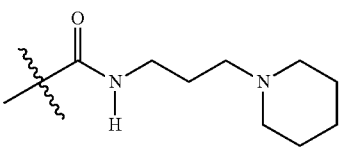 [SMILES: *C(=O)NCCCN1CCCCC1] | 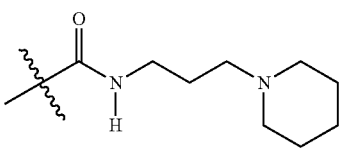 [SMILES: *C(=O)NCCCN1CCCCC1] |
| 49 | 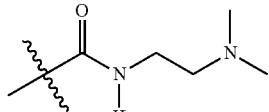 | 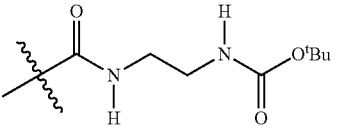 [SMILES: *C(=O)NCCNC(=O)OC(C)(C)C] |
| 50 | 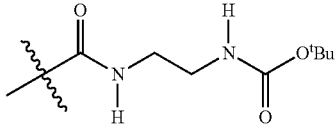 | 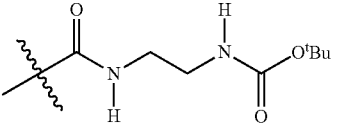 [SMILES: *C(=O)NCCNC(=O)OC(C)(C)C] |
| 51 | 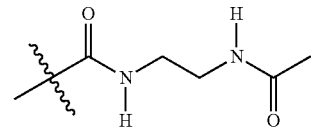 [SMILES: *C(=O)NCCNC(C)=O] | 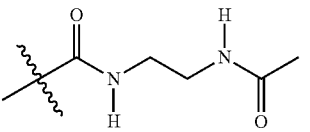 [SMILES: *C(=O)NCCNC(C)=O] |
| 52 | 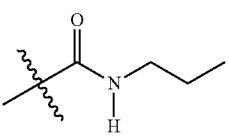 [SMILES: *C(=O)NCCC] | 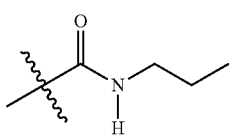 [SMILES: *C(=O)NCCC] |
| 53 | 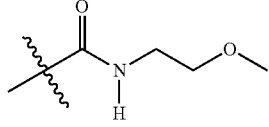 [SMILES: *C(=O)NCCOC] | 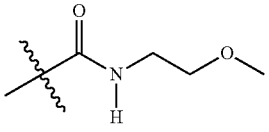 [SMILES: *C(=O)NCCOC] |
| 54 | 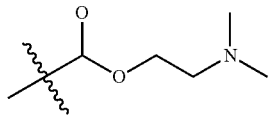 [SMILES: *C(O)OCCN(C)C] | 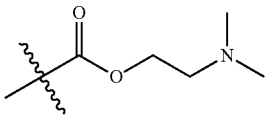 [SMILES: *C(=O)OCCN(C)C] |
| 55 | 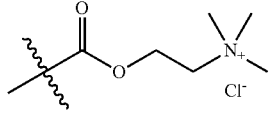 | 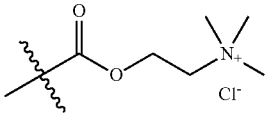 |
| 56 | 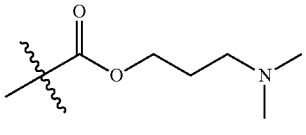 [SMILES: *C(=O)OCCCN(C)C] | 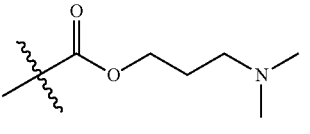 [SMILES: *C(=O)OCCCN(C)C] |
| 57 | 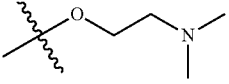 [SMILES: *OCCN(C)C] | 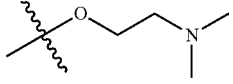 |

TABLE A-continued
| Compound # | R¹ | R² |
|---|---|---|
| 58 | 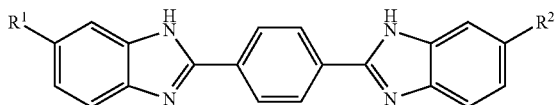 | 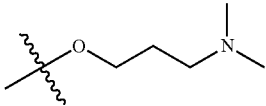 |
| 59 | 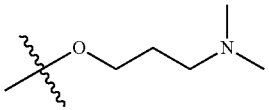 [SMILES: *OCCCN(C)C] | 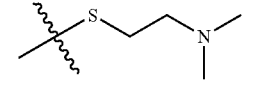 |
| 60 | 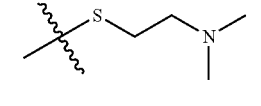 [SMILES: *SCCN(C)C] | 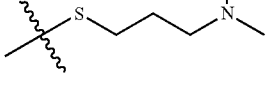 |
| 61 | 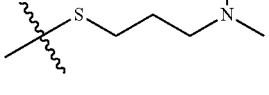 | 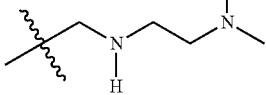 |
| 62 | 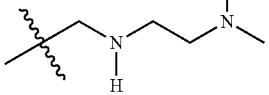 | 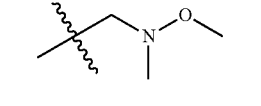 [SMILES: *CN(C)OC] |
| 63 | 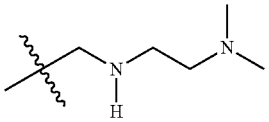 [SMILES: *CNCCN(C)C] | 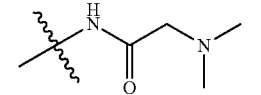 [SMILES: *NC(=O)CN(C)C] |
| 64 | 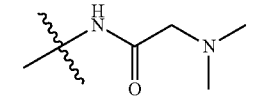 [SMILES: *NC(=O)CN(C)C] | 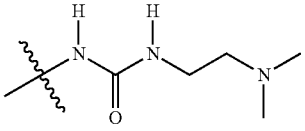 [SMILES: *NC(=O)NCCN(C)C] |
| 65 | 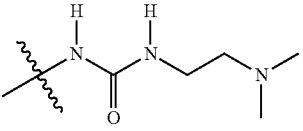 [SMILES: *NC(=O)NCCN(C)C] | 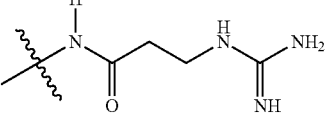 |
| 66 | 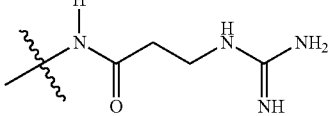 | 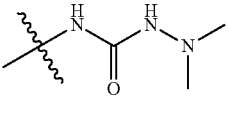 [SMILES: *NC(=O)NN(C)C] |
| 67 | 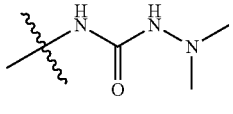 [SMILES: *NC(=O)NN(C)C] | 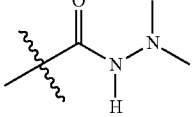 |
| 68 | 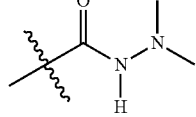 | 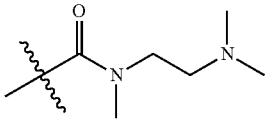 [SMILES: *C(=O)N(C)CCN(C)C] |

TABLE A-continued
| Compound # | R¹ | R² |
|---|---|---|
| 70 | 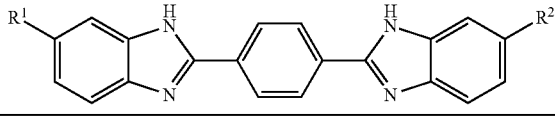 | 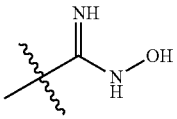 [SMILES: *C(=N)NO] |
| 72 | 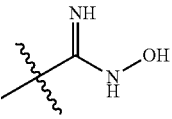 | 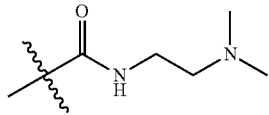 [SMILES: *C(=O)NCCN(C)C] |
| 73 | 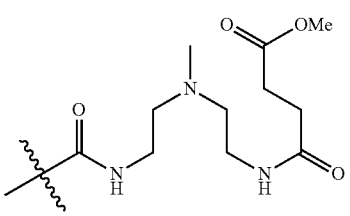 [SMILES: *C(=O)NCCN(C)CCNC(=O)CCC(=O)OC] | 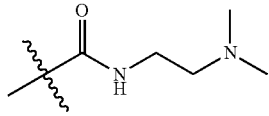 [SMILES: *C(=O)NCCN(C)C] |
| 74 | 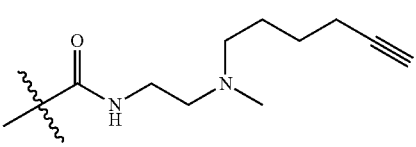 [SMILES: *C(=O)NCCN(C)CCCCC#C] | 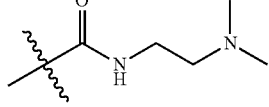 |
| 75 | NH₂ | 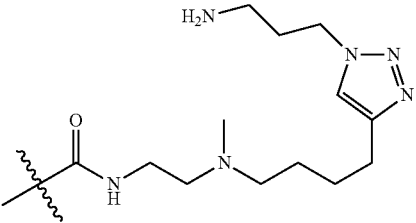 [SMILES: *C(=O)NCCN(C)CCCCc1cn(CCCN)nn1] |
| 76 | 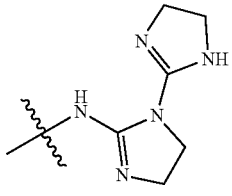 [SMILES: *NC1=NCCN1C1=NCCN1] | 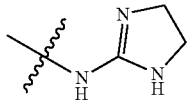 |
| 77 | 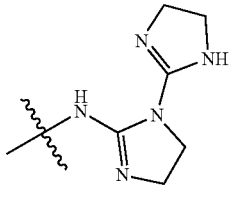 [SMILES: *NC1=NCCN1C1=NCCN1] | 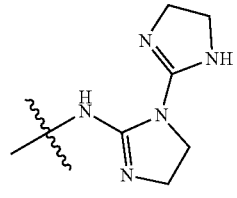 |

Additional compounds contemplated for use in the disclosed methods include those listed in Table A1, or a pharmaceutically acceptable salt thereof:

TABLE A1

| Compound # | R¹ | R² |
|---|---|---|
| 2 | NH$_2$ | NH$_2$ |
| 3 | NH(C=NH)NH$_2$ | NH(C=NH)NH$_2$ |
| 4 | NH$_2$ | NHAc |
| 6 | NHAc | NHAc |
| 12 | CONH$_2$ | CONH$_2$ |

TABLE A1-continued

| Compound # | R¹ | R² |
|---|---|---|
| 26 | H$_2$N−C(=NH)− | H$_2$N−C(=NH)− |

Additional compounds contemplated for use in the disclosed methods include those listed in Table A2, or a pharmaceutically acceptable salt thereof:

TABLE A2

| Compound # | Structure |
|---|---|
| 171 | 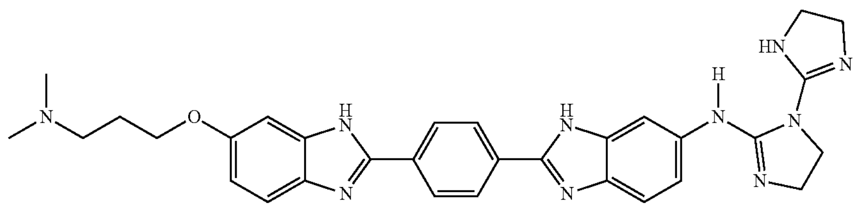 [SMILES: CN(C)CCCOc1ccc2nc(-c3ccc(-c4nc5ccc(NC6=NCCN6C6=NCCN6)cc5[nH]4)cc3)[nH]c2c1] |
| 172 | 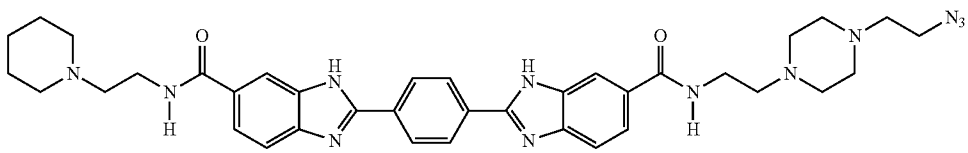 [SMILES: [N-]=[N+]=NCCN1CCN(CCNC(=O)c2ccc3nc(-c4ccc(-c5nc6ccc(C(=O)NCCN7CCCCC7)cc6[nH]5)cc4)[nH]c3c2)CC1] |
| 179 | 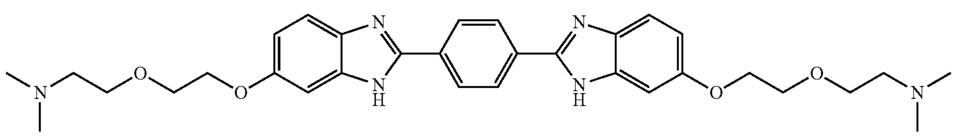 |
| 180 | 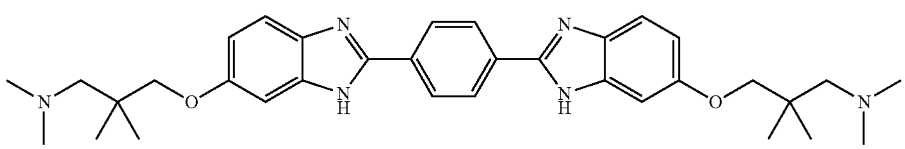 |
| 181 | 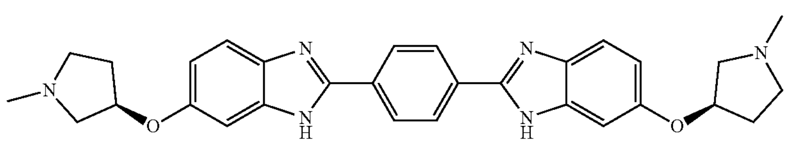 |
| 182 | 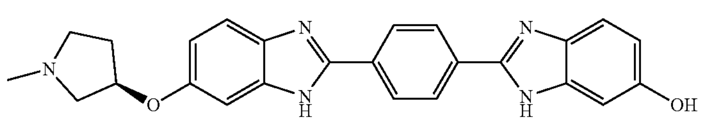 [SMILES: CN1CC[C@@H](Oc2ccc3nc(-c4ccc(-c5nc6ccc(O)cc6[nH]5)cc4)[nH]c3c2)C1] |
| 183 | 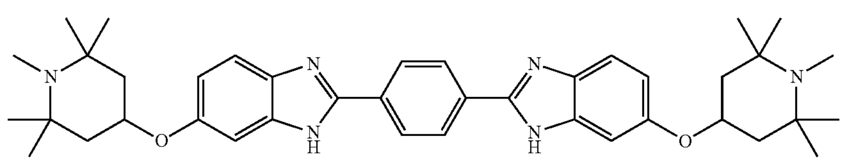 |

TABLE A2-continued
| Compound # | Structure |
| --- | --- |
| 184 | 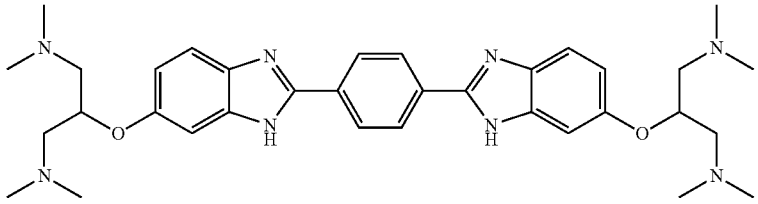 |
| 186 | 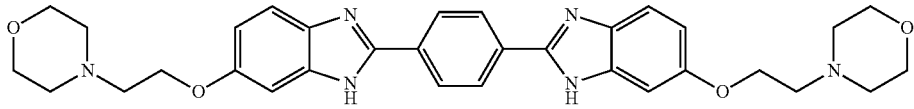 [SMILES: c1cc2nc(-c3ccc(-c4nc5ccc(OCCN6CCOCC6)cc5[nH]4)cc3)[nH]c2cc1OCCN1CCOCC1] |
| 187 | 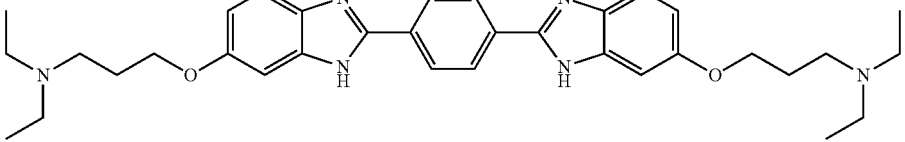 |
| 188 | 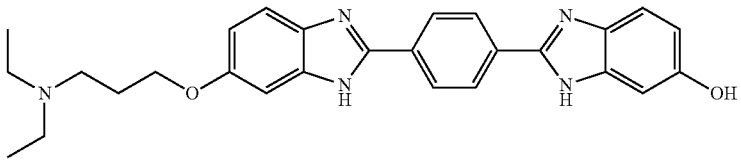 [SMILES: CCN(CC)CCCOc1ccc2nc(-c3ccc(-c4nc5ccc(O)cc5[nH]4)cc3)[nH]c2c1] |
| 189 | 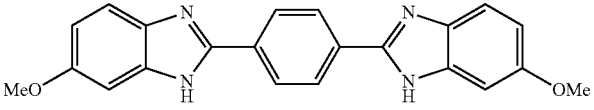 [SMILES: COc1ccc2nc(-c3ccc(-c4nc5ccc(OC)cc5[nH]4)cc3)[nH]c2c1] |
| 190 | 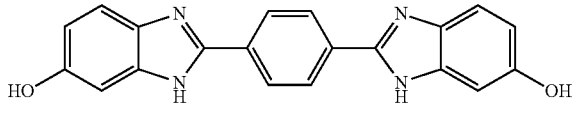 |
| 191 | 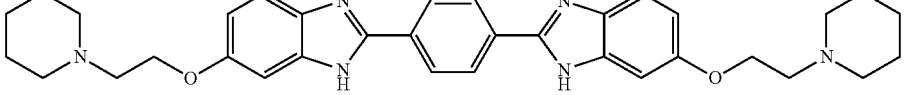 |
| 192 | 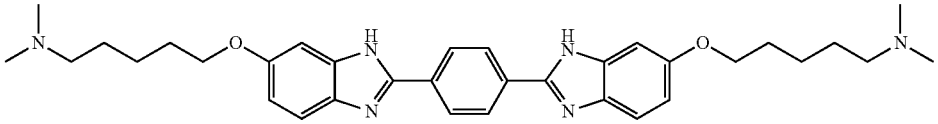 |
| 193 | 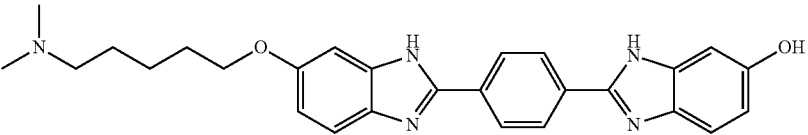 [SMILES: CN(C)CCCCCOc1ccc2nc(-c3ccc(-c4nc5ccc(O)cc5[nH]4)cc3)[nH]c2c1] |
| 194 | 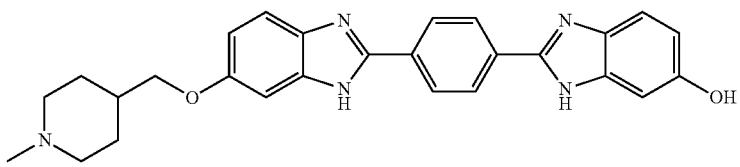 [SMILES: CN1CCC(COc2ccc3nc(-c4ccc(-c5nc6ccc(O)cc6[nH]5)cc4)[nH]c3c2)CC1] |

TABLE A2-continued

| Compound # | Structure |
|---|---|
| 195 | 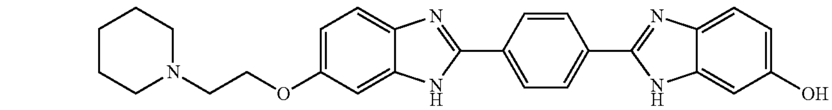 [SMILES: Oc1ccc2nc(-c3ccc(-c4nc5ccc(OCCN6CCCCC6)cc5[nH]4)cc3)[nH]c2c1] |
| 196 | 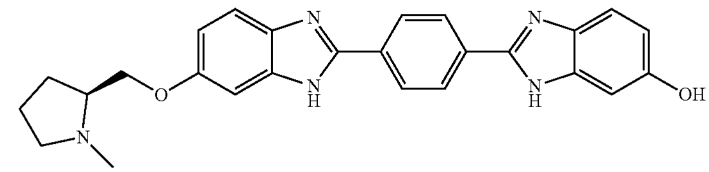 [SMILES: CN1CCC[C@H]1COc1ccc2nc(-c3ccc(-c4nc5ccc(O)cc5[nH]4)cc3)[nH]c2c1] |
| 197 | 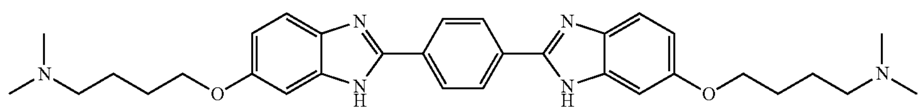 |
| 198 | 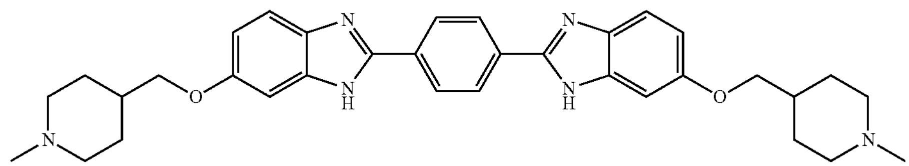 |
| 199 | 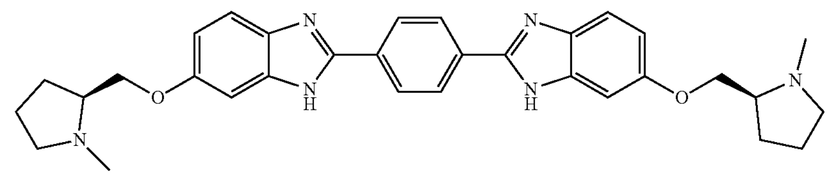 [SMILES: CN1CCC[C@H]1COc1ccc2nc(-c3ccc(-c4nc5ccc(OC[C@@H]6CCCN6C)cc5[nH]4)cc3)[nH]c2c1] |
| 200 | 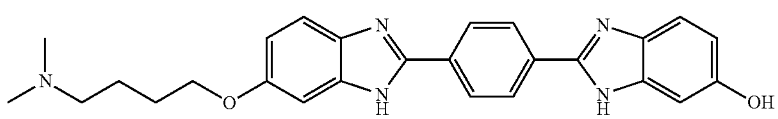 [SMILES: CN(C)CCCCOc1ccc2nc(-c3ccc(-c4nc5ccc(O)cc5[nH]4)cc3)[nH]c2c1] |
| 201 | 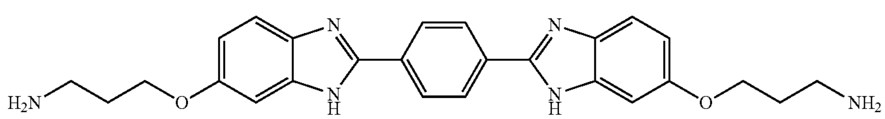 [SMILES: NCCCOc1ccc2nc(-c3ccc(-c4nc5ccc(OCCCN)cc5[nH]4)cc3)[nH]c2c1] |
| 202 | 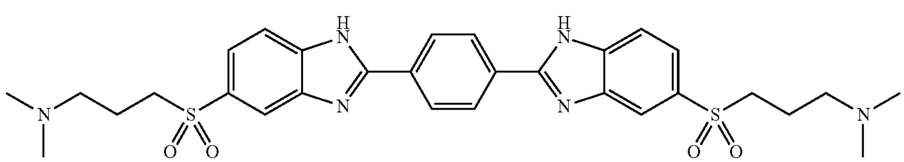 |
| 203 | 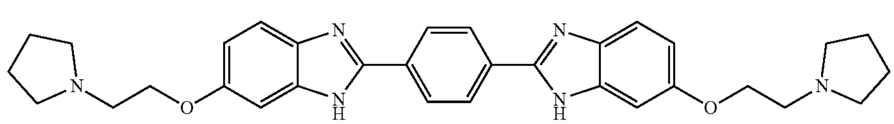 [SMILES: c1cc2nc(-c3ccc(-c4nc5ccc(OCCN6CCCC6)cc5[nH]4)cc3)[nH]c2cc1OCCN1CCCC1] |
| 204 | 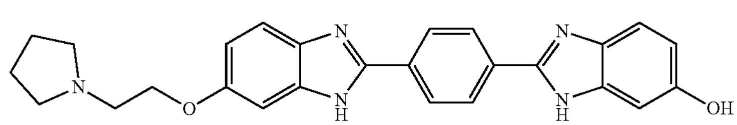 [SMILES: Oc1ccc2nc(-c3ccc(-c4nc5ccc(OCCN6CCCC6)cc5[nH]4)cc3)[nH]c2c1] |
| 205 | 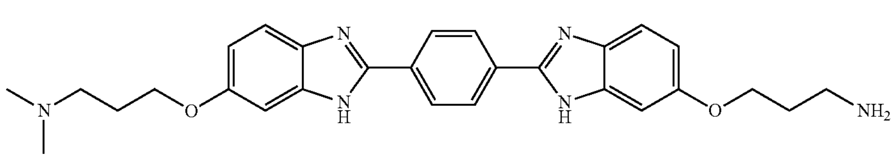 [SMILES: CN(C)CCCOc1ccc2nc(-c3ccc(-c4nc5ccc(OCCCN)cc5[nH]4)cc3)[nH]c2c1] |

TABLE A2-continued

| Compound # | Structure |
|---|---|
| 206 | (structure) |
| 207 | (structure) |
| 208 | (structure) |
| 209 | (structure) |
| 210 | (structure) |
| 211 | (structure) |
| 212 | (structure) |
| 213 | (structure) |
| 214 | (structure) |
| 215 | (structure) |

TABLE A2-continued
| Compound # | Structure |
|---|---|
| 216 | 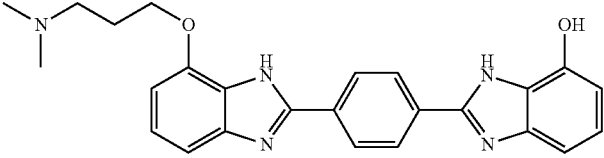 [SMILES: CN(C)CCCOc1cccc2nc(-c3ccc(-c4nc5cccc(O)c5[nH]4)cc3)[nH]c12] |
| 217 | 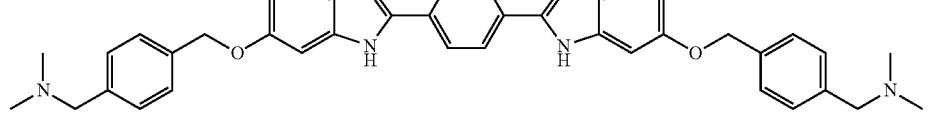 |
| 218 | 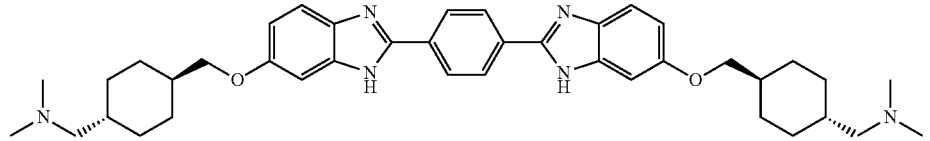 |
| 219 | 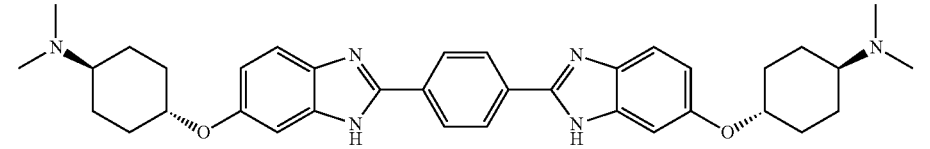 |
| 220 | 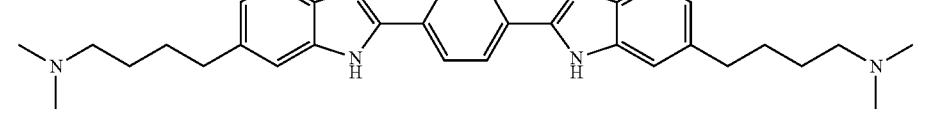 |
| 221 | 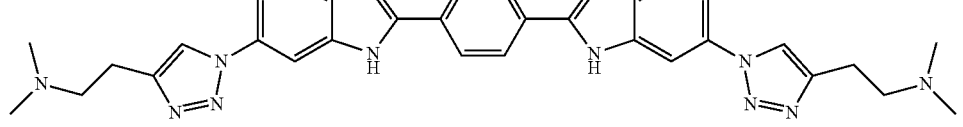 |
| 222 | 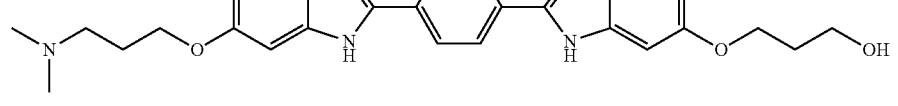 |
| 223 | 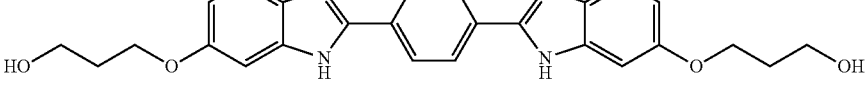 |
| 224 | 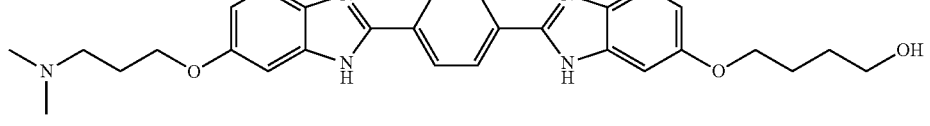 |
| 225 | 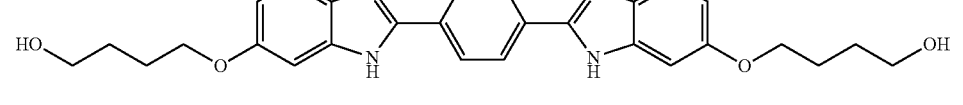 |

TABLE A2-continued

| Compound # | Structure |
|---|---|
| 226 | 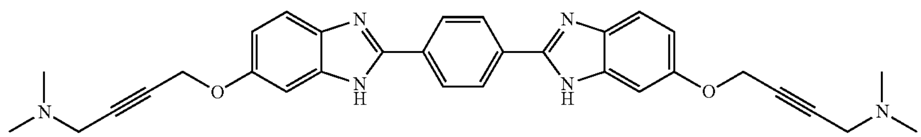 |
| 227 | 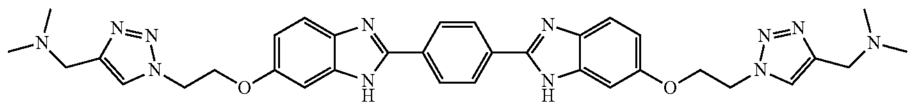 |
| 228 | 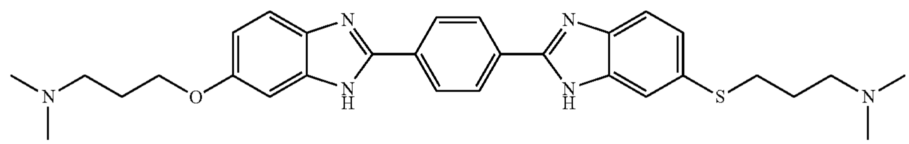 |
| 229 | 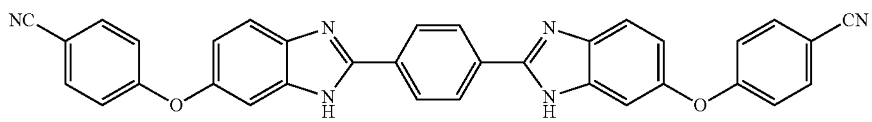 [SMILES: N#Cc1ccc(Oc2ccc3nc(-c4ccc(-c5nc6ccc(Oc7ccc(C#N)cc7)cc6[nH]5)cc4)[nH]c3c2)cc1] |
| 230 | 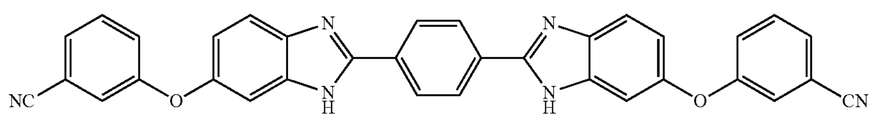 [SMILES: N#Cc1cccc(Oc2ccc3nc(-c4ccc(-c5nc6ccc(Oc7cccc(C#N)c7)cc6[nH]5)cc4)[nH]c3c2)c1] |
| 231 | 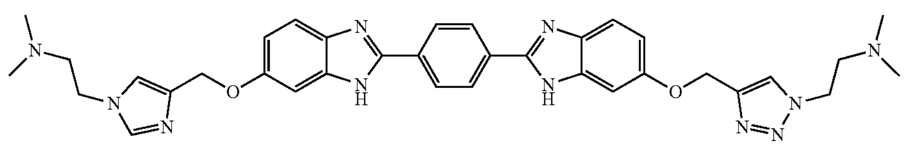 |
| 232 | 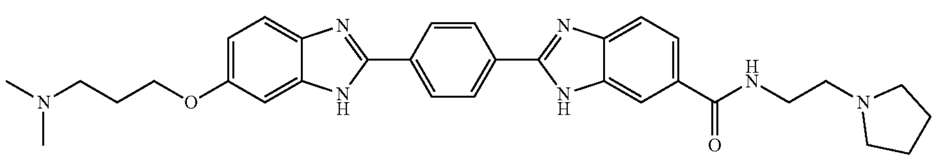 [SMILES: CN(C)CCCOc1ccc2nc(-c3ccc(-c4nc5ccc(C(=O)NCCN6CCCC6)cc5[nH]4)cc3)[nH]c2c1] |
| 233 | 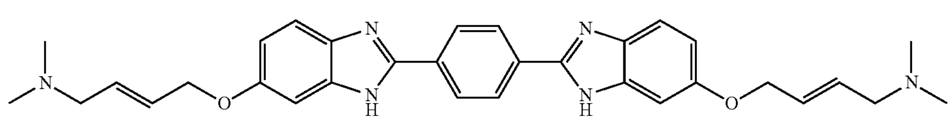 |
| 234 | 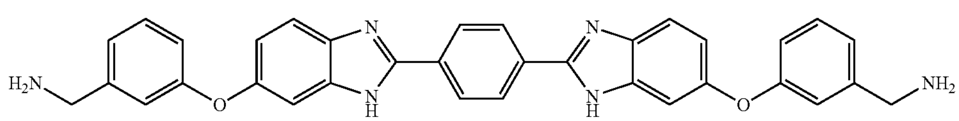 [SMILES: NCc1cccc(Oc2ccc3nc(-c4ccc(-c5nc6ccc(Oc7cccc(CN)c7)cc6[nH]5)cc4)[nH]c3c2)c1] |
| 235 | 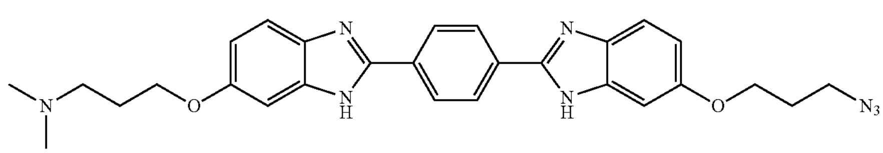 [SMILES: CN(C)CCCOc1ccc2nc(-c3ccc(-c4nc5ccc(OCCCN=[N+]=[N-])cc5[nH]4)cc3)[nH]c2c1] |
| 236 | 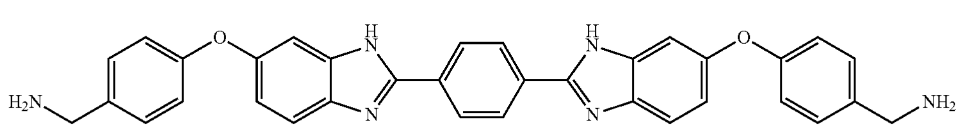 [SMILES: NCc1ccc(Oc2ccc3nc(-c4ccc(-c5nc6ccc(Oc7ccc(CN)cc7)cc6[nH]5)cc4)[nH]c3c2)cc1] |

TABLE A2-continued

| Compound # | Structure |
|---|---|
| 237 | 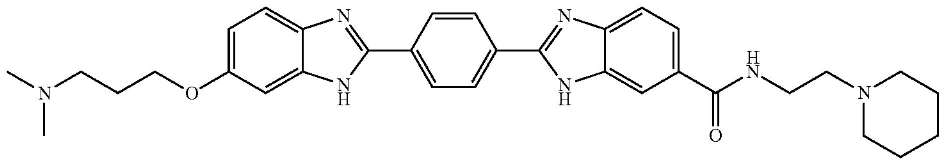 [SMILES: CN(C)CCCOc1ccc2nc(-c3ccc(-c4nc5ccc(C(=O)NCCN6CCCCC6)cc5[nH]4)cc3)[nH]c2c1] |
| 238 | 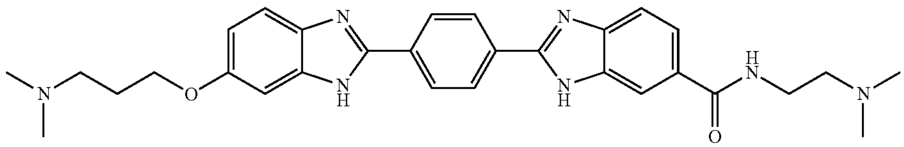 |
| 239 | 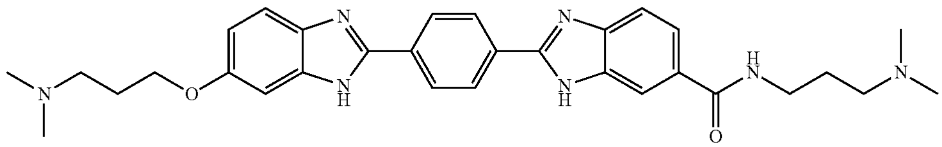 |
| 240 | 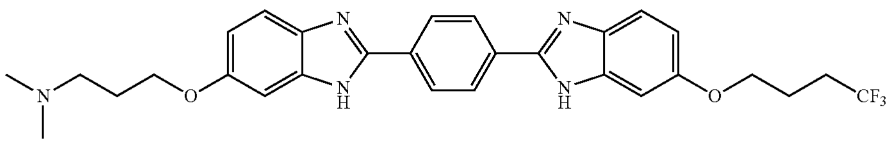 [SMILES: CN(C)CCCOc1ccc2nc(-c3ccc(-c4nc5ccc(OCCCC(F)(F)F)cc5[nH]4)cc3)[nH]c2c1] |
| 241 | 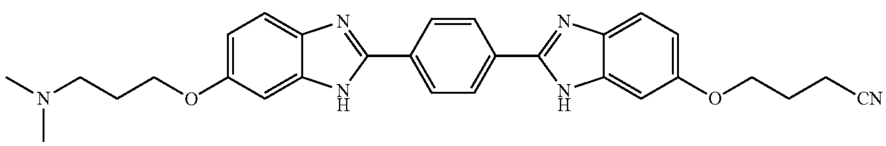 [SMILES: CN(C)CCCOc1ccc2nc(-c3ccc(-c4nc5ccc(OCCCC#N)cc5[nH]4)cc3)[nH]c2c1] |
| 242 | 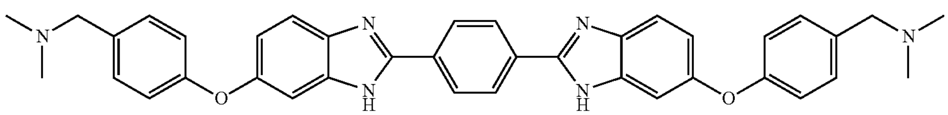 |
| 243 | 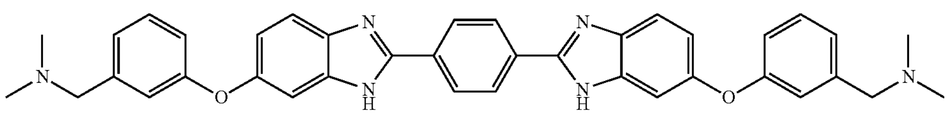 |
| 244 | 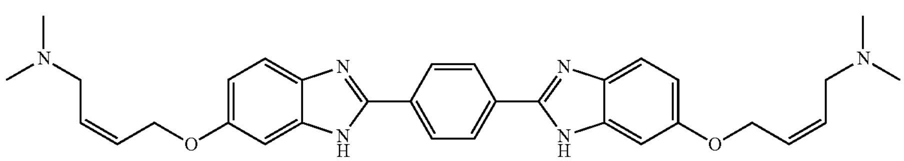 |
| 245 | 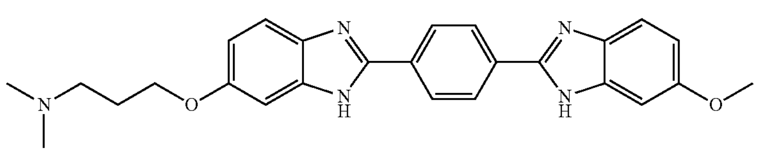 |
| 246 | 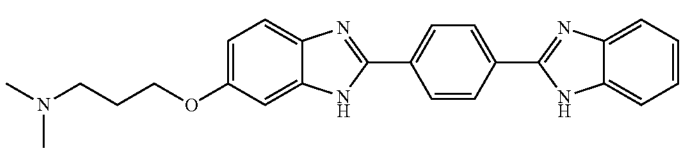 [SMILES: CN(C)CCCOc1ccc2nc(-c3ccc(-c4nc5ccccc5[nH]4)cc3)[nH]c2c1] |

TABLE A2-continued

| Compound # | Structure |
|---|---|
| 247 | 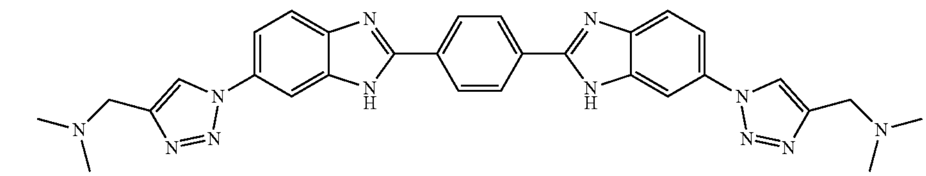 |
| 248 | 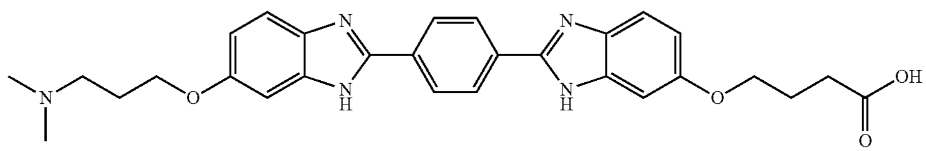 [SMILES: CN(C)CCCOc1ccc2nc(-c3ccc(-c4nc5ccc(OCCCC(=O)O)cc5[nH]4)cc3)[nH]c2c1] |
| 249 | 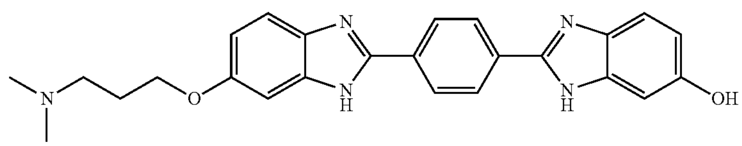 [SMILES: CN(C)CCCOc1ccc2nc(-c3ccc(-c4nc5ccc(O)cc5[nH]4)cc3)[nH]c2c1] |
| 250 | 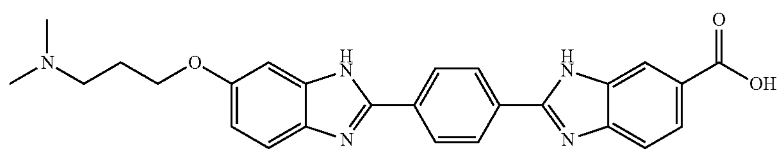 [SMILES: CN(C)CCCOc1ccc2nc(-c3ccc(-c4nc5ccc(C(=O)O)cc5[nH]4)cc3)[nH]c2c1] |
| 251 | 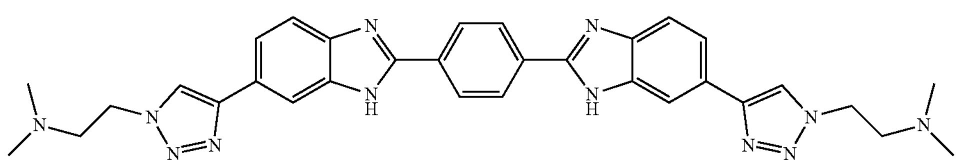 |
| 252 | 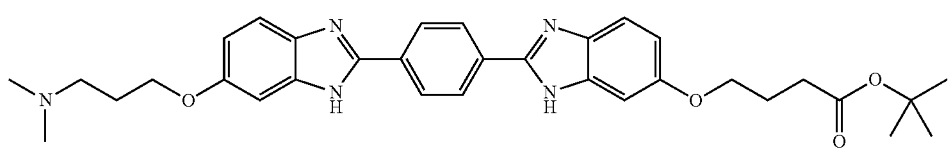 [SMILES: CN(C)CCCOc1ccc2nc(-c3ccc(-c4nc5ccc(OCCCC(=O)OC(C)(C)C)cc5[nH]4)cc3)[nH]c2c1] |
| 254 | 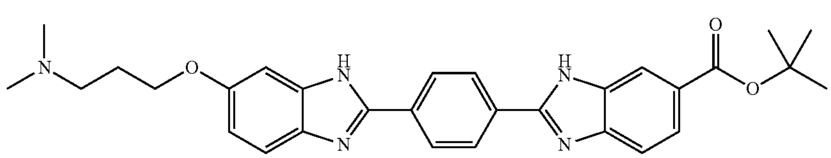 [SMILES: CN(C)CCCOc1ccc2nc(-c3ccc(-c4nc5ccc(C(=O)OC(C)(C)C)cc5[nH]4)cc3)[nH]c2c1] |
| 264 | 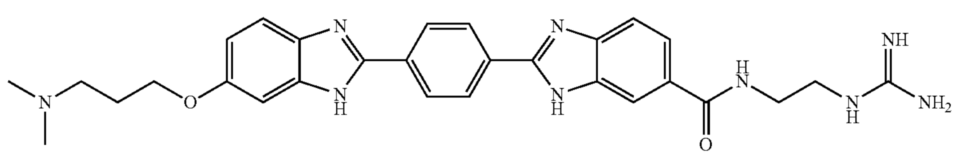 [SMILES: CN(C)CCCOc1ccc2nc(-c3ccc(-c4nc5ccc(C(=O)NCCNC(=N)N)cc5[nH]4)cc3)[nH]c2c1] |
| 266 | 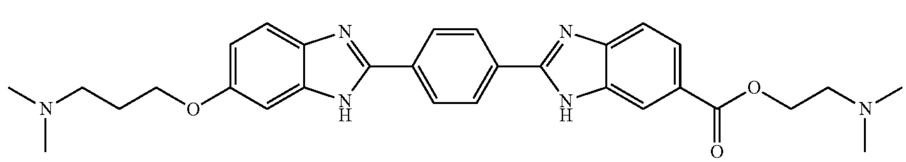 |

TABLE A2-continued

| Compound # | Structure |
|---|---|
| 273 | 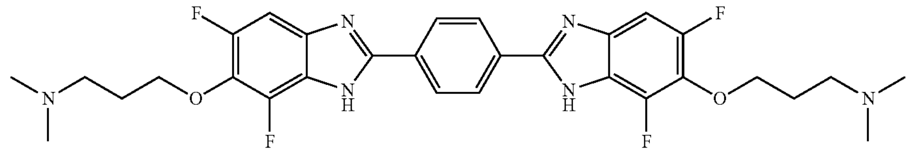 |
| 275 | 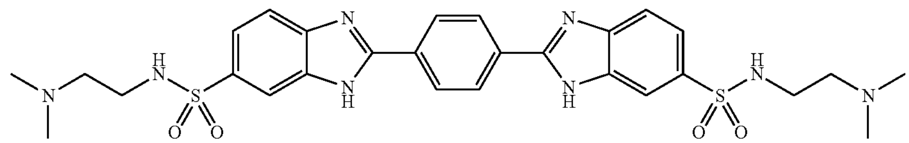 |
| 281 | 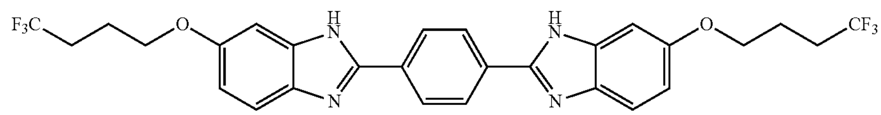 [SMILES: FC(F)(F)CCCOc1ccc2nc(-c3ccc(-c4nc5ccc(OCCCC(F)(F)F)cc5[nH]4)cc3)[nH]c2c1] |
| 282 | 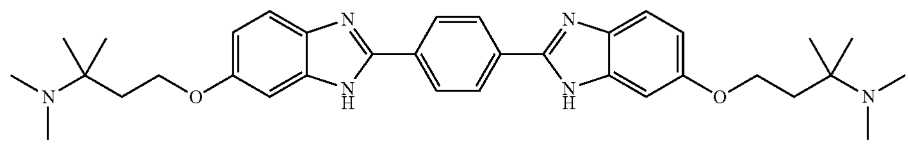 |
| 284 | 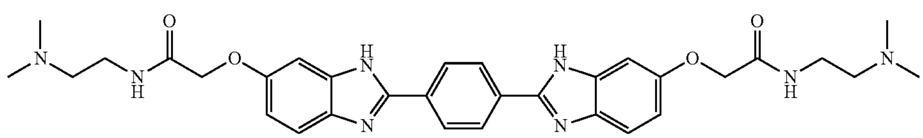 |
| 285 | 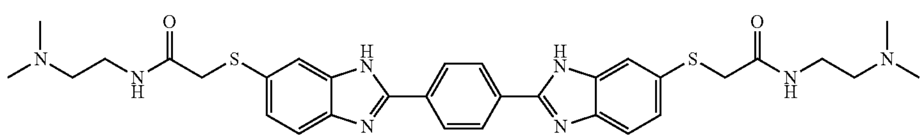 |
| 289 | 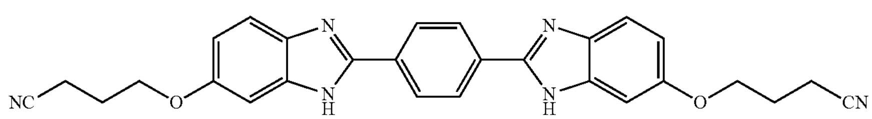 [SMILES: N#CCCCOc1ccc2nc(-c3ccc(-c4nc5ccc(OCCCC#N)cc5[nH]4)cc3)[nH]c2c1] |
| 295 | 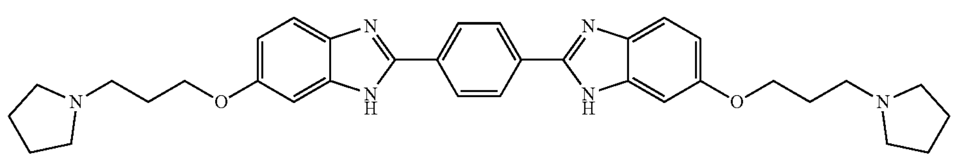 [SMILES: c1cc2nc(-c3ccc(-c4nc5ccc(OCCCN6CCCC6)cc5[nH]4)cc3)[nH]c2cc1OCCCN1CCCC1] |
| 297 | 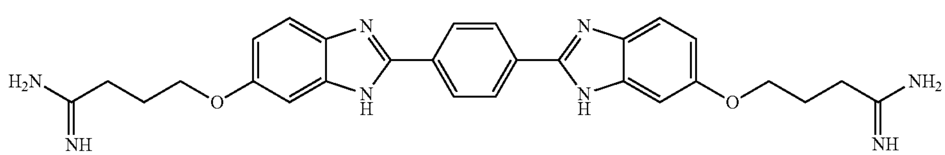 [SMILES: N=C(N)CCCOc1ccc2nc(-c3ccc(-c4nc5ccc(OCCCC(=N)N)cc5[nH]4)cc3)[nH]c2c1] |
| 318 | 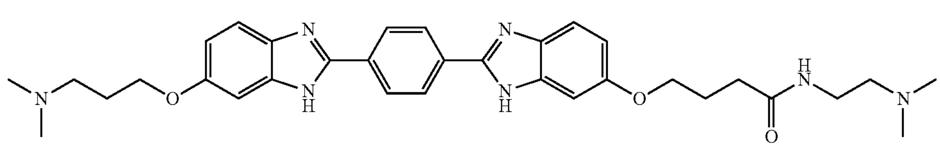 |

TABLE A2-continued
| Compound # | Structure |
|---|---|
| 319 | 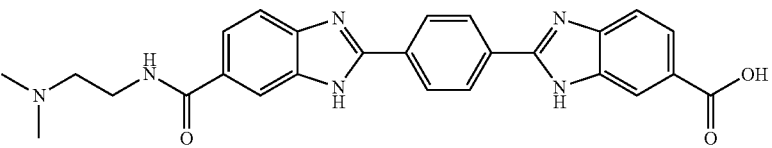 [SMILES: CN(C)CCNC(=O)c1ccc2nc(-c3ccc(-c4nc5ccc(C(=O)O)cc5[nH]4)cc3)[nH]c2c1] |
| 321 | 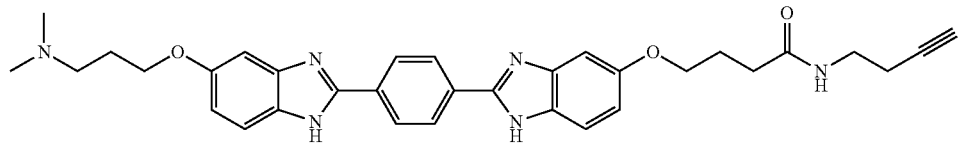 [SMILES: C#CCCNC(=O)CCCOc1ccc2[nH]c(-c3ccc(-c4nc5cc(OCCCN(C)C)ccc5[nH]4)cc3)nc2c1] |
| 322 | 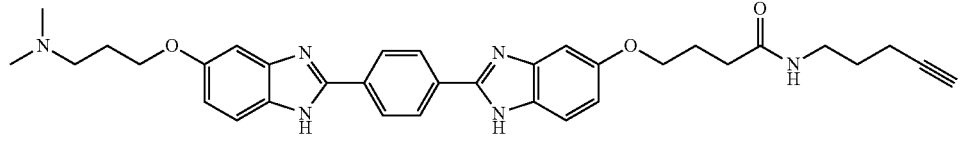 [SMILES: C#CCCCNC(=O)CCCOc1ccc2[nH]c(-c3ccc(-c4nc5cc(OCCCN(C)C)ccc5[nH]4)cc3)nc2c1] |
| 323 | 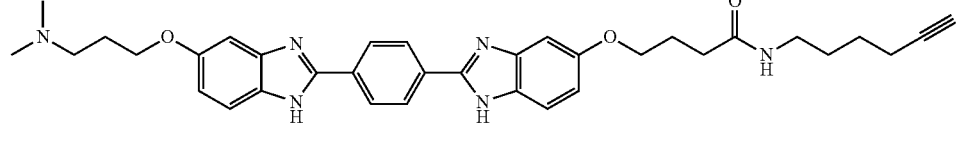 |
| 325 | 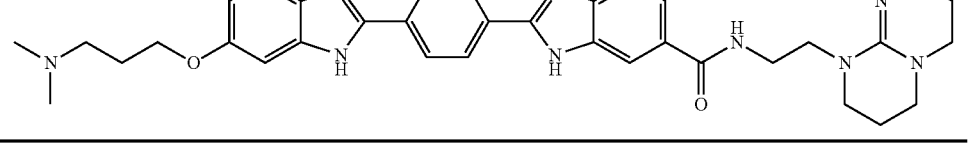 |
Additional compounds contemplated include those listed in Table B, or a pharmaceutically acceptable salt thereof:

TABLE B

| Compound # | Structure |
|---|---|
| 78 | (structure) |
| 79 | (structure) |
| 80 | (structure) |
| 81 | (structure) |
| 82 | (structure) |
| 83 | (structure) |
| 84 | (structure) |

TABLE B-continued
| Compound # | Structure |
|---|---|
| 85 | 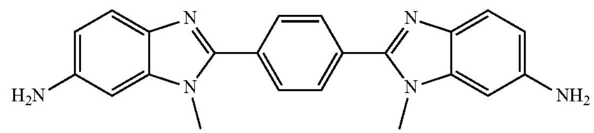 [SMILES: Cn1c(-c2ccc(-c3nc4ccc(N)cc4n3C)cc2)nc2ccc(N)cc21] |
| 86 | 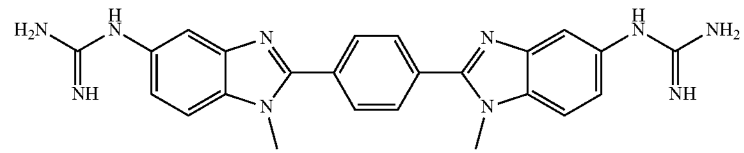 [SMILES: Cn1c(-c2ccc(-c3nc4cc(NC(=N)N)ccc4n3C)cc2)nc2cc(NC(=N)N)ccc21] |
| 87 | 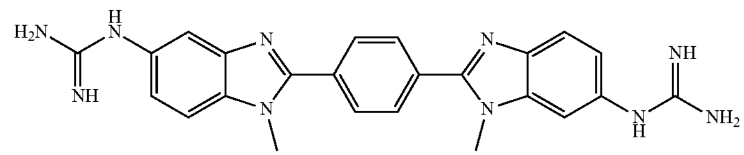 [SMILES: Cn1c(-c2ccc(-c3nc4ccc(NC(=N)N)cc4n3C)cc2)nc2cc(NC(=N)N)ccc21] |
| 88 | 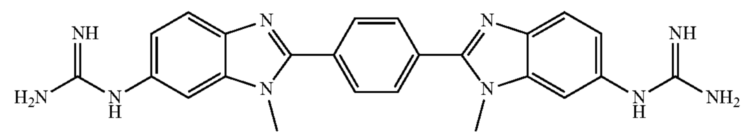 [SMILES: Cn1c(-c2ccc(-c3nc4ccc(NC(=N)N)cc4n3C)cc2)nc2ccc(NC(=N)N)cc21] |
| 89 | 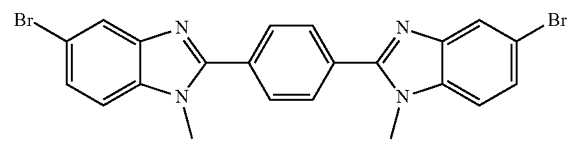 [SMILES: Cn1c(-c2ccc(-c3nc4cc(Br)ccc4n3C)cc2)nc2cc(Br)ccc21] |
| 90 | 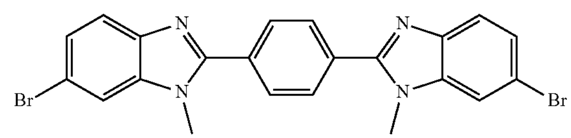 [SMILES: Cn1c(-c2ccc(-c3nc4ccc(Br)cc4n3C)cc2)nc2ccc(Br)cc21] |
| 170 | 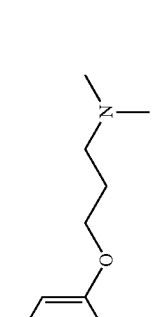 |

TABLE B-continued

| Compound # | Structure |
|---|---|
| 173 | (structure with NO2 substituent) |
| 174 | (structure with F substituent) |
| 175 | (structure with polyhydroxy chains) |
| 176 | (structure with NH2 substituent) |

TABLE B-continued

| Compound # | Structure |
|---|---|
| 253 | 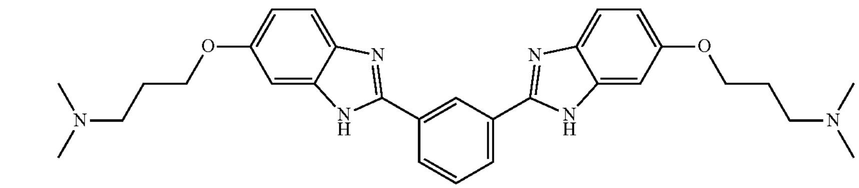 |
| 255 | 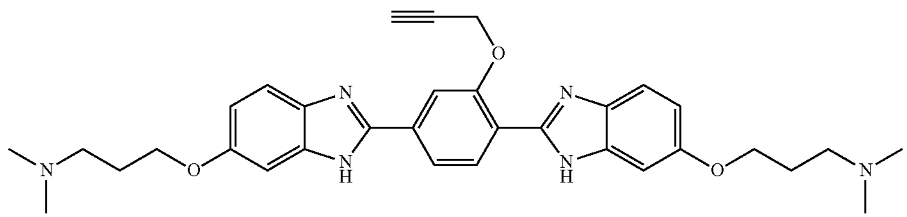 |
| 256 | 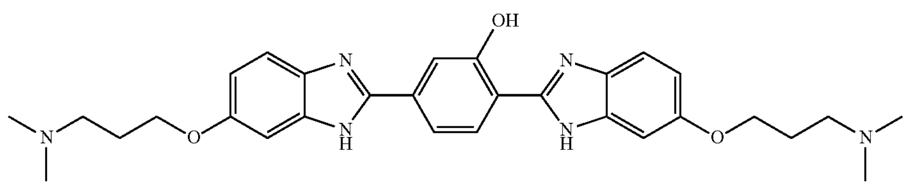 |
| 257 | 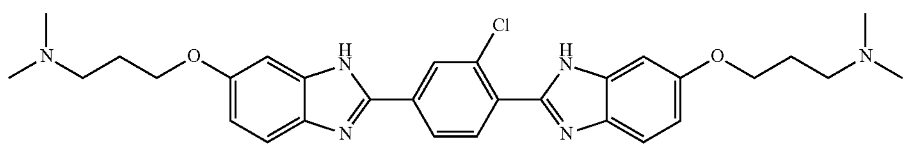 |
| 258 | 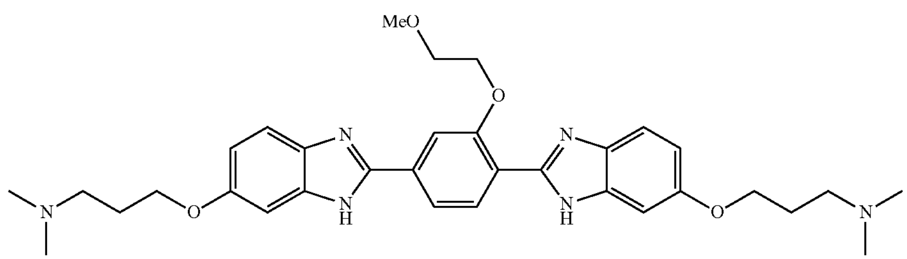 |

TABLE B-continued

| Compound # | Structure |
|---|---|
| 259 | 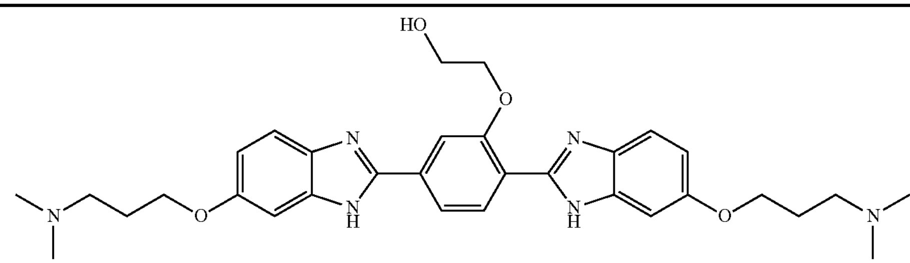 |
| 260 | 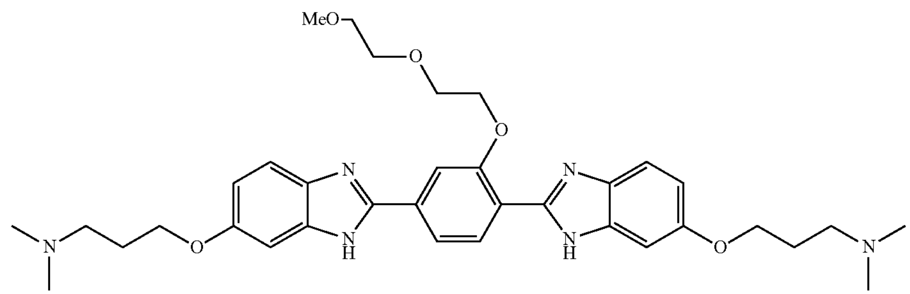 |
| 261 | 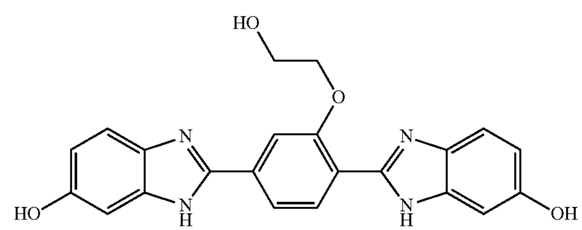 [SMILES: OCCOc1cc(-c2nc3ccc(O)cc3[nH]2)ccc1-c1nc2ccc(O)cc2[nH]1] |
| 262 | 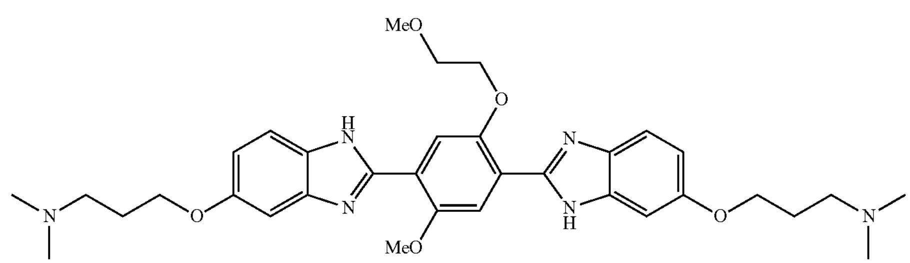 |

TABLE B-continued

| Compound # | Structure |
|---|---|
| 263 | 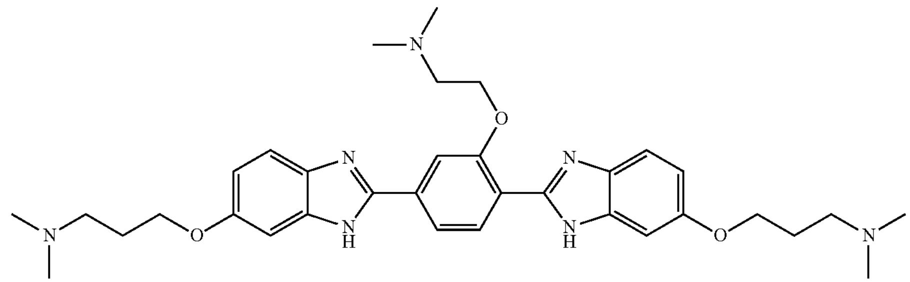 |
| 265 | 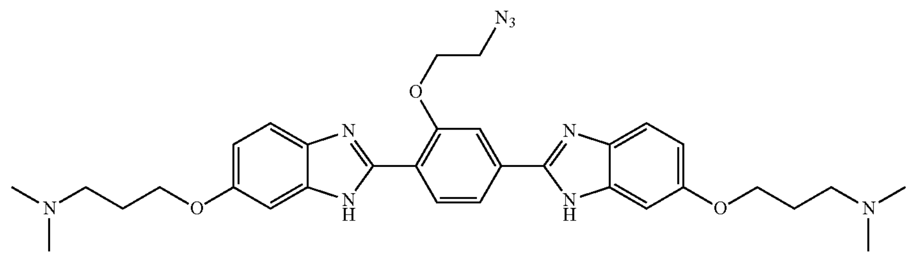 |
| 267 | 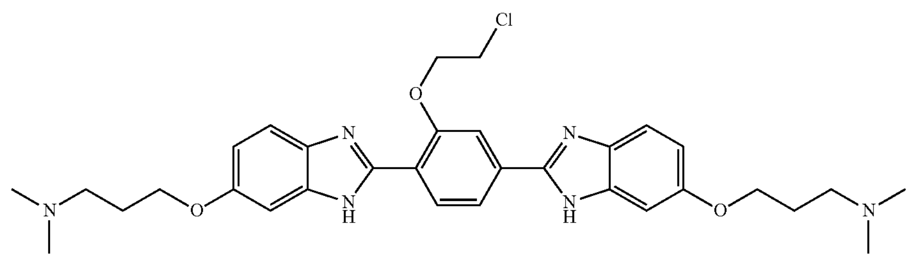 |
| 268 | 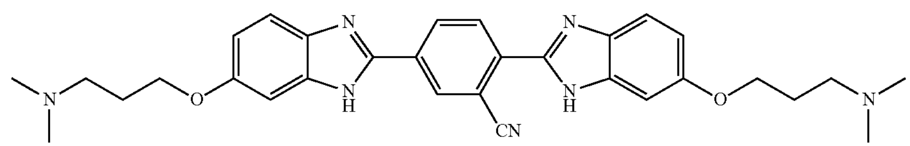 |

TABLE B-continued

| Compound # | Structure |
|---|---|
| 269 | 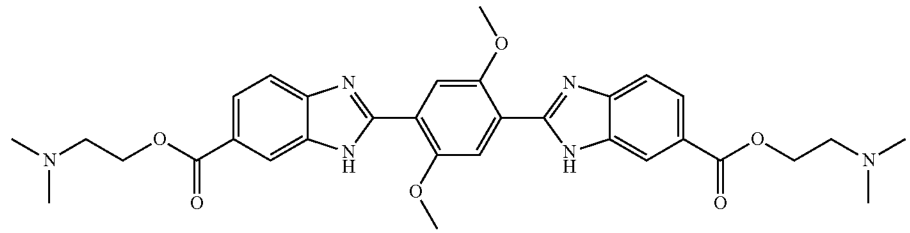 |
| 270 | 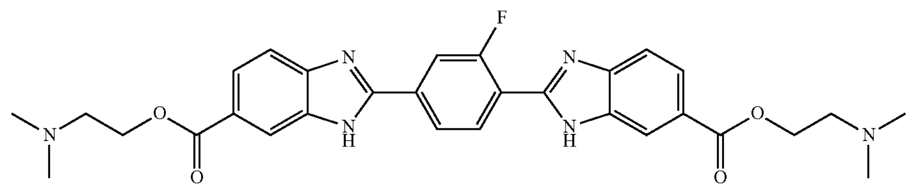 |
| 271 | 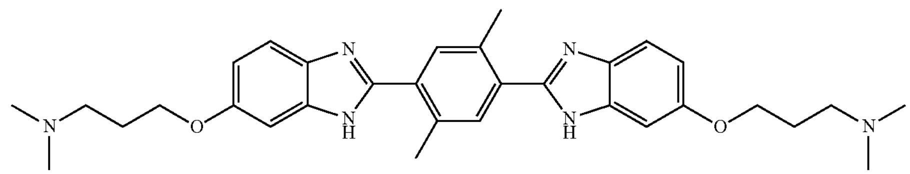 |
| 272 | 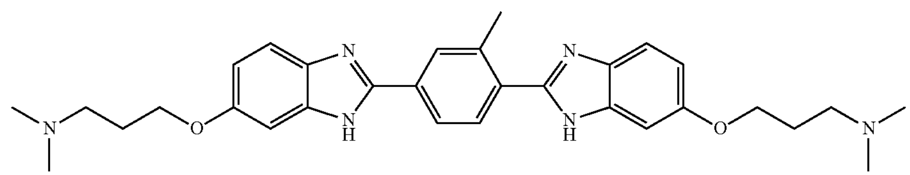 |
| 274 | 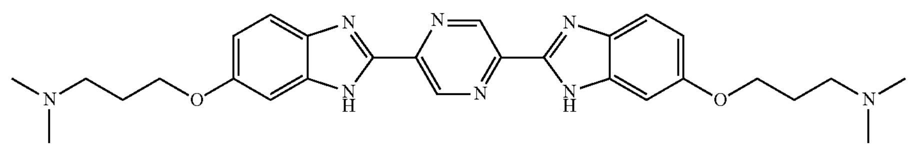 |

TABLE B-continued
| Compound # | Structure |
|---|---|
| 276 | 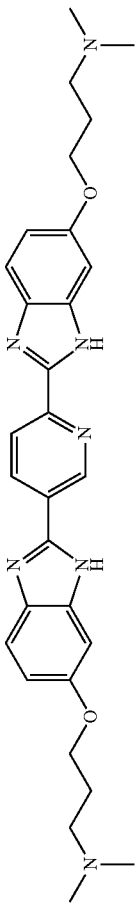 |
| 286 | 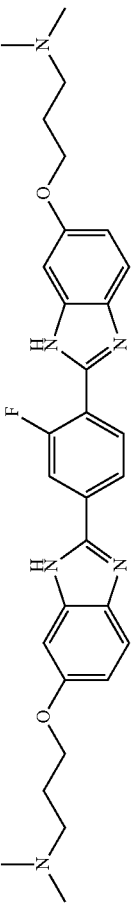 |
| 288 | 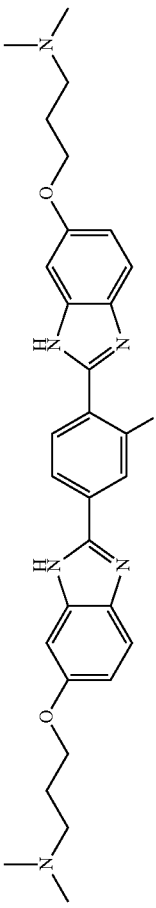 |
| 290 | 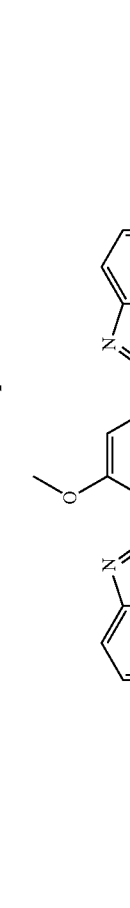 |
| 291 | 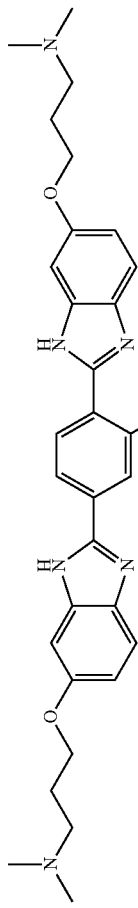 |

TABLE B-continued

| Compound # | Structure |
|---|---|
| 292 | 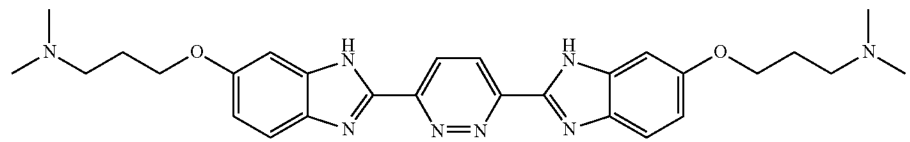 |
| 293 | 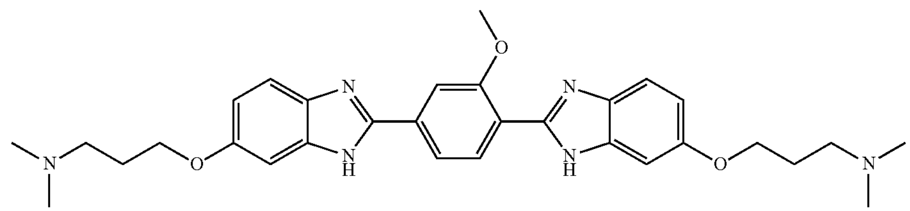 |
| 294 | 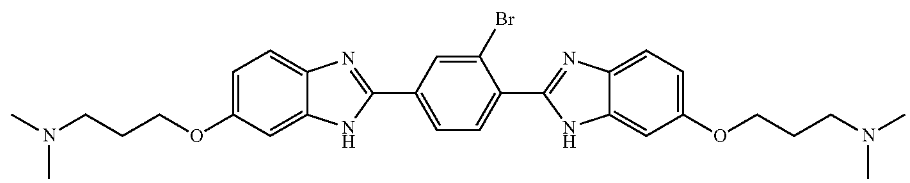 |
| 296 | 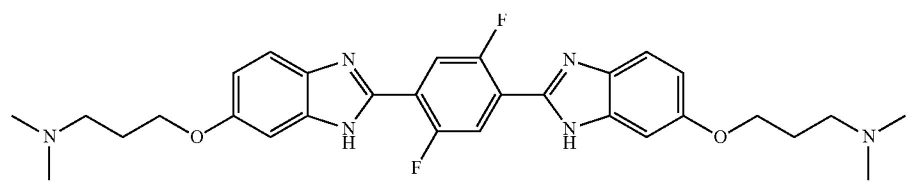 |
| 298 | 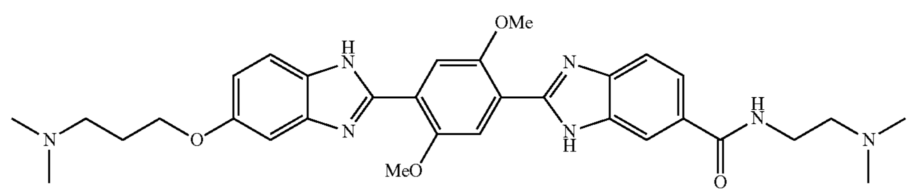 |

TABLE B-continued

| Compound # | Structure |
|---|---|
| 299 | 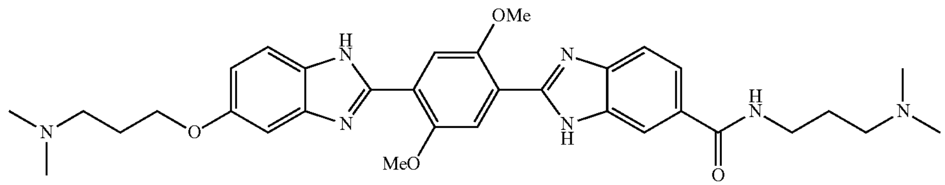 |
| 300 | 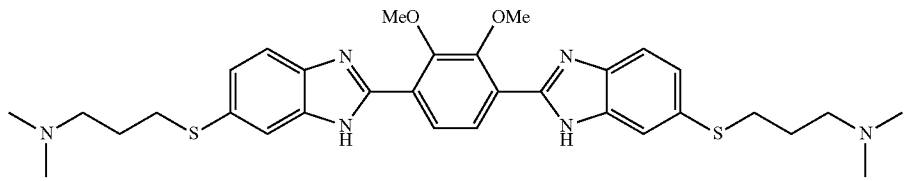 |
| 301 | 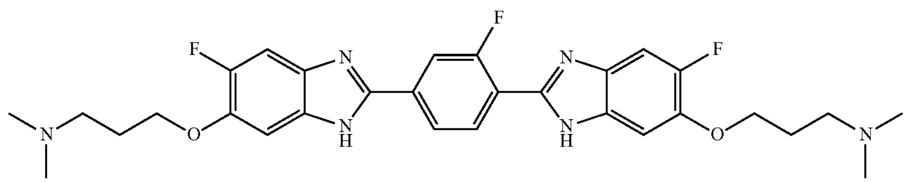 |
| 302 | 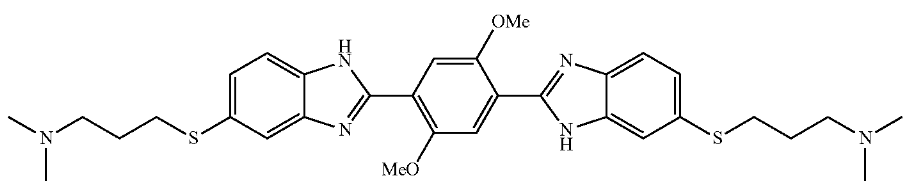 |
| 303 | 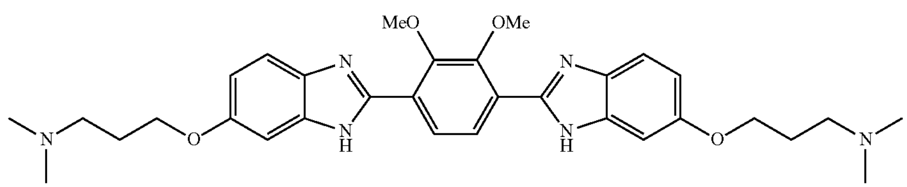 |

TABLE B-continued

| Compound # | Structure |
|---|---|
| 305 | 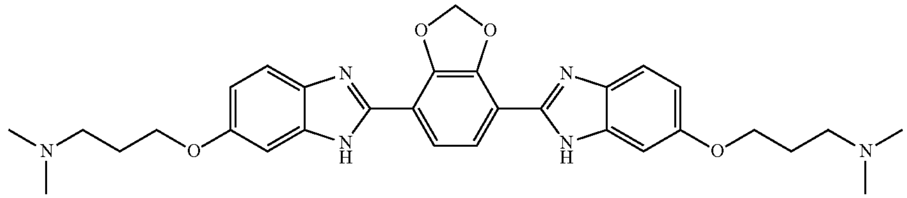 |
| 306 | 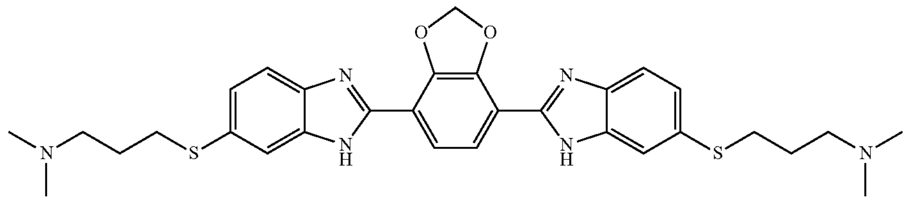 |
| 307 | 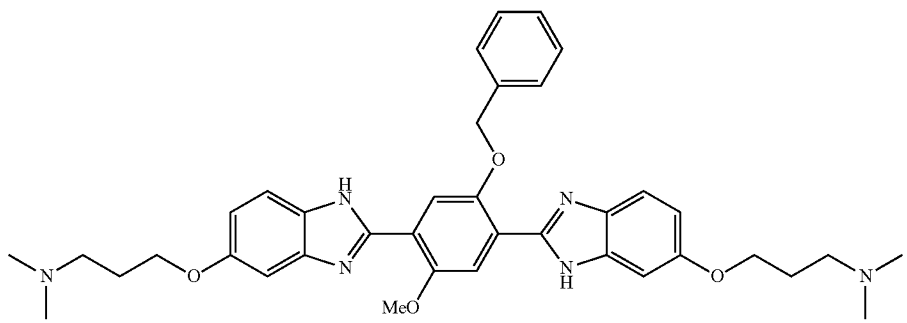 |
| 308 | 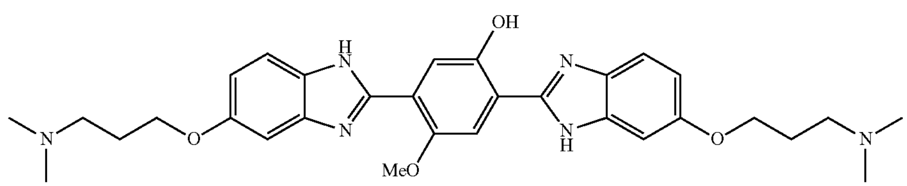 |

TABLE B-continued

| Compound # | Structure |
|---|---|
| 314 | (structure) |
| 315 | (structure) |
| 316 | (structure) |
| 317 | (structure) |
| 324 | (structure) |

TABLE B-continued
| Compound # | Structure |
|---|---|
| 326 | 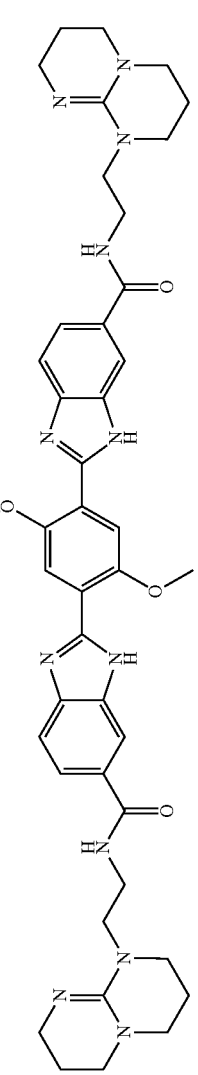 |
| 327 | 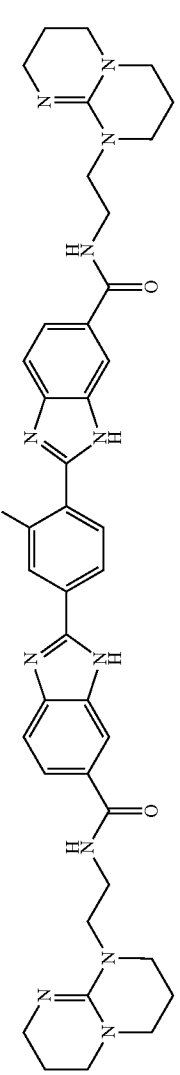 |
| 328 | 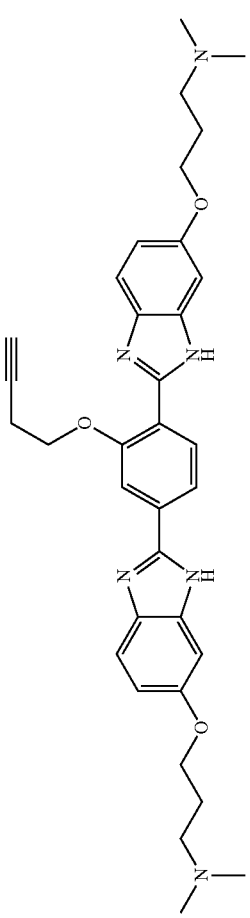 |
| 332 | 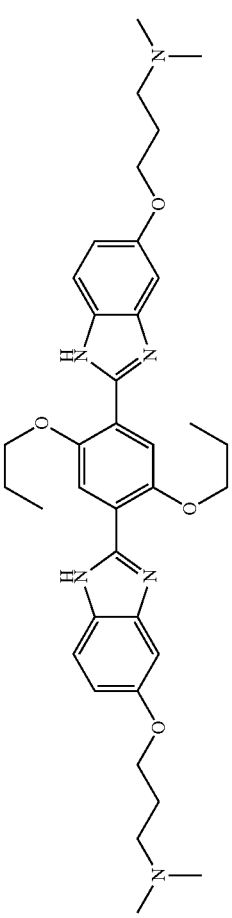 |

TABLE B-continued

| Compound # | Structure |
|---|---|
| 333 | 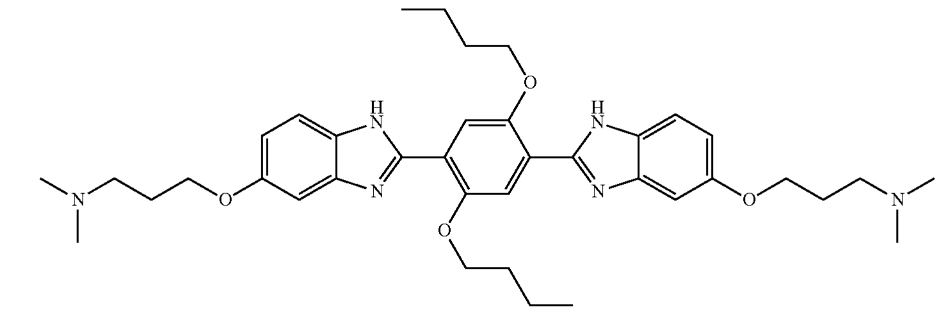 |
| 462 | 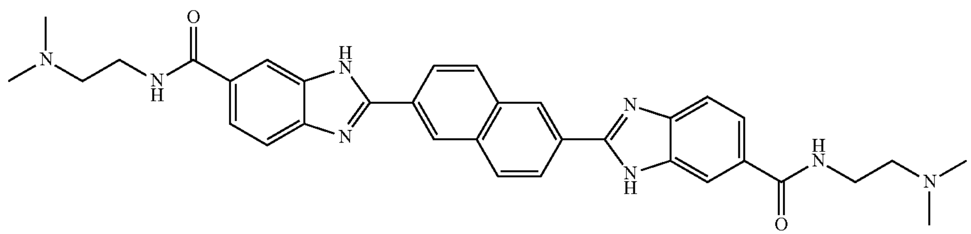 |
| 463 | 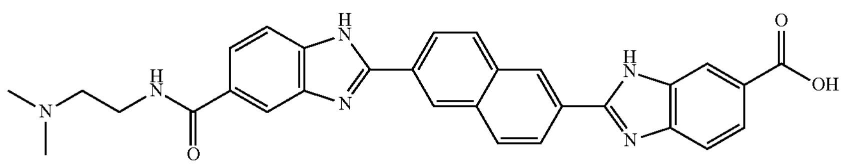 [SMILES: CN(C)CCNC(=O)c1ccc2[nH]c(-c3ccc4cc(-c5nc6ccc(C(=O)O)cc6[nH]5)ccc4c3)nc2c1] |
| 464 | 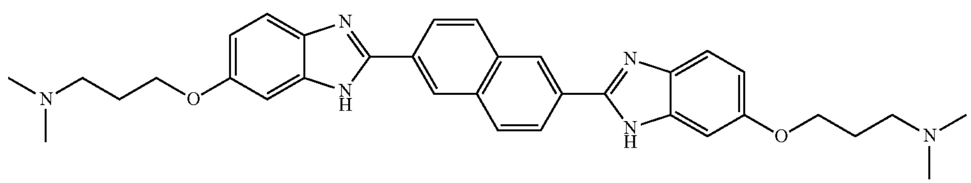 |

TABLE B-continued

| Compound # | Structure |
|---|---|
| 465 | (structure) |
| 466 | (structure) |
| 467 | (structure) xHCl |

TABLE B-continued
| Compound # | Structure |
|---|---|
| 468 | 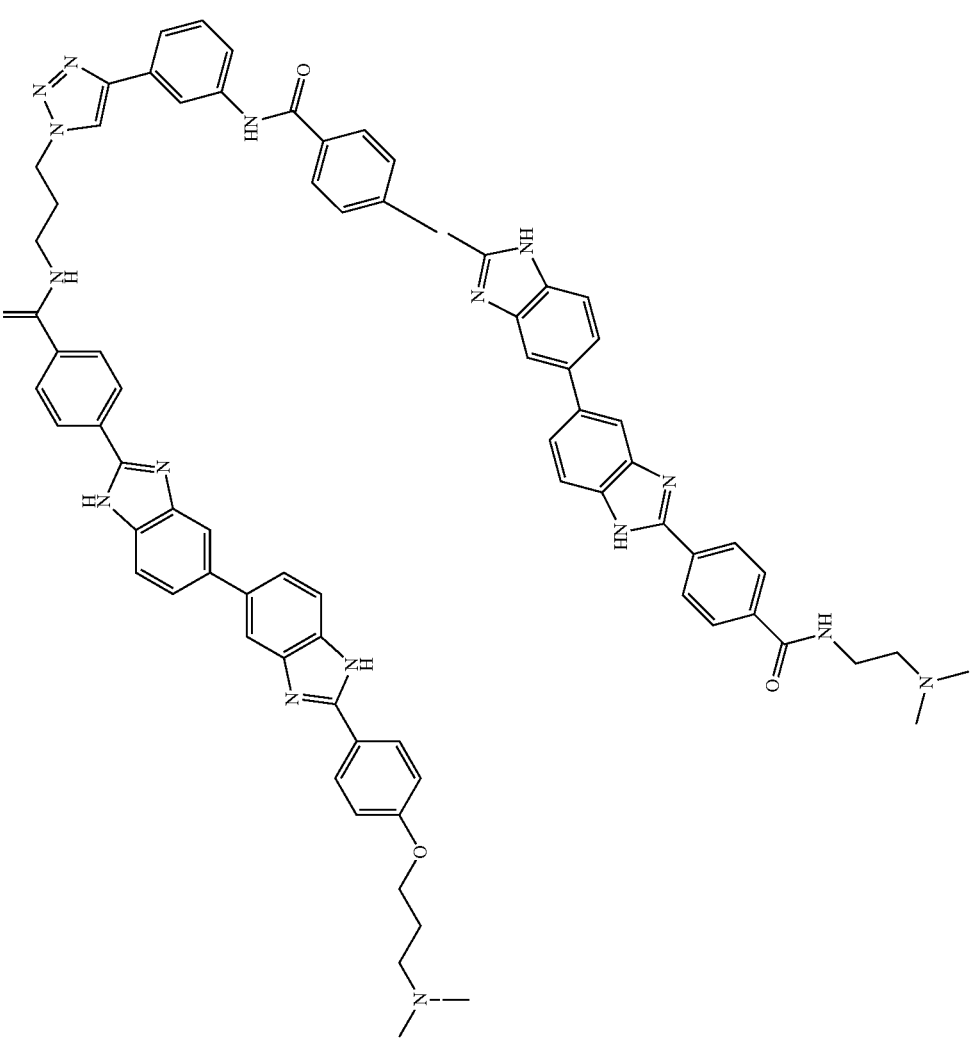 |

TABLE B-continued
| Compound # | Structure |
|---|---|
| 469 | 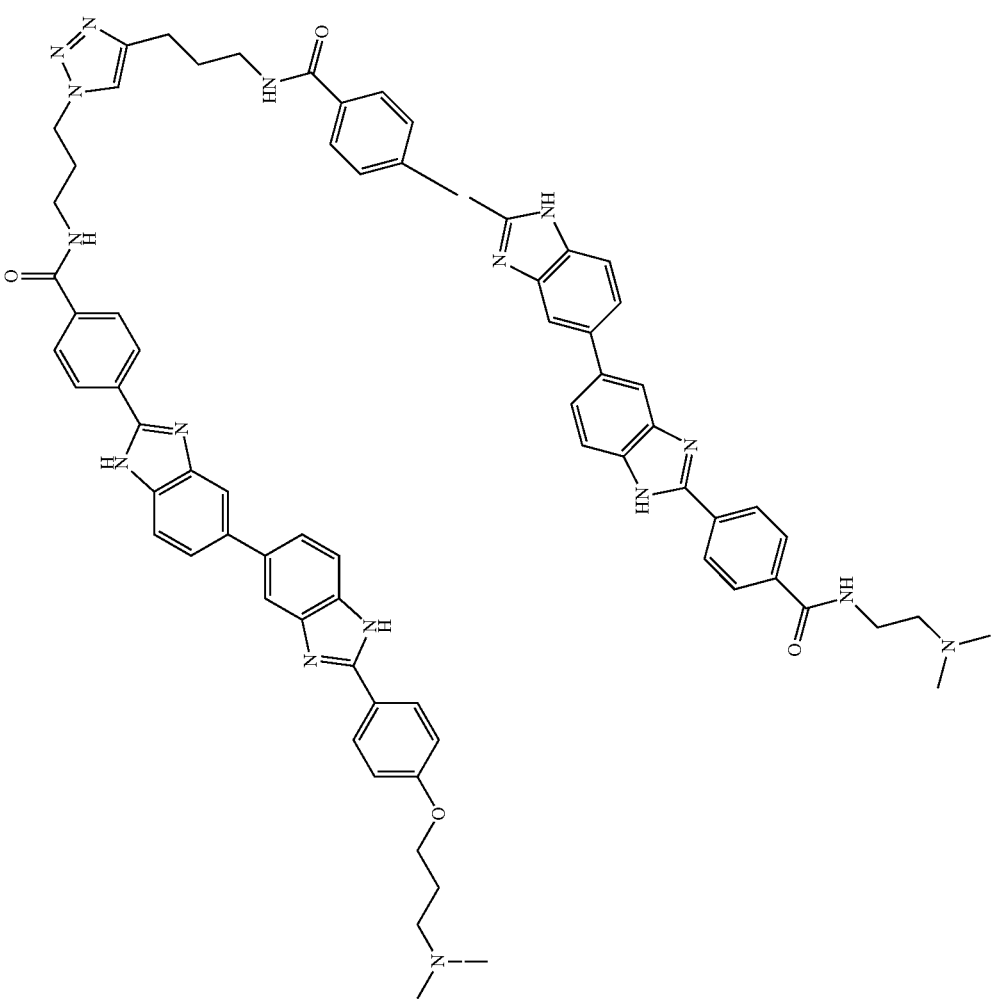 |

TABLE B-continued
| Compound # | Structure |
|---|---|
| 470 | 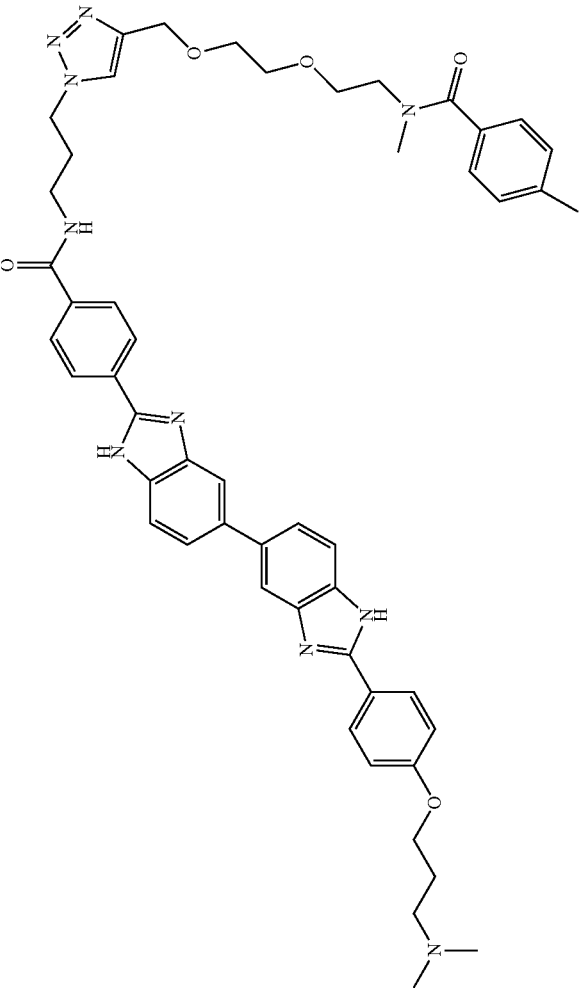 |

TABLE B-continued
| Compound # | Structure |
|---|---|
| | 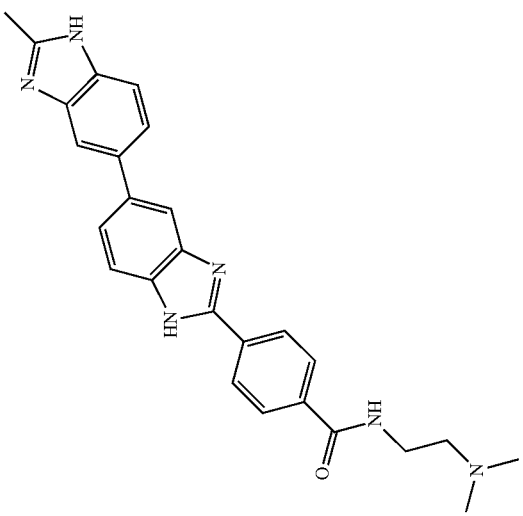 |
| 471 | 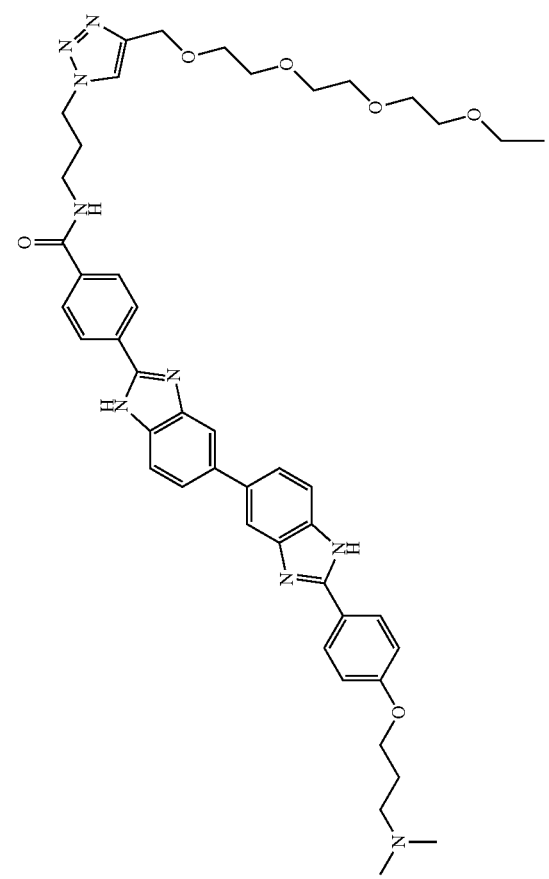 |

TABLE B-continued

| Compound # | Structure |
|---|---|
| | (structure image) |

TABLE B-continued

| Compound # | Structure |
|---|---|
| 472 | 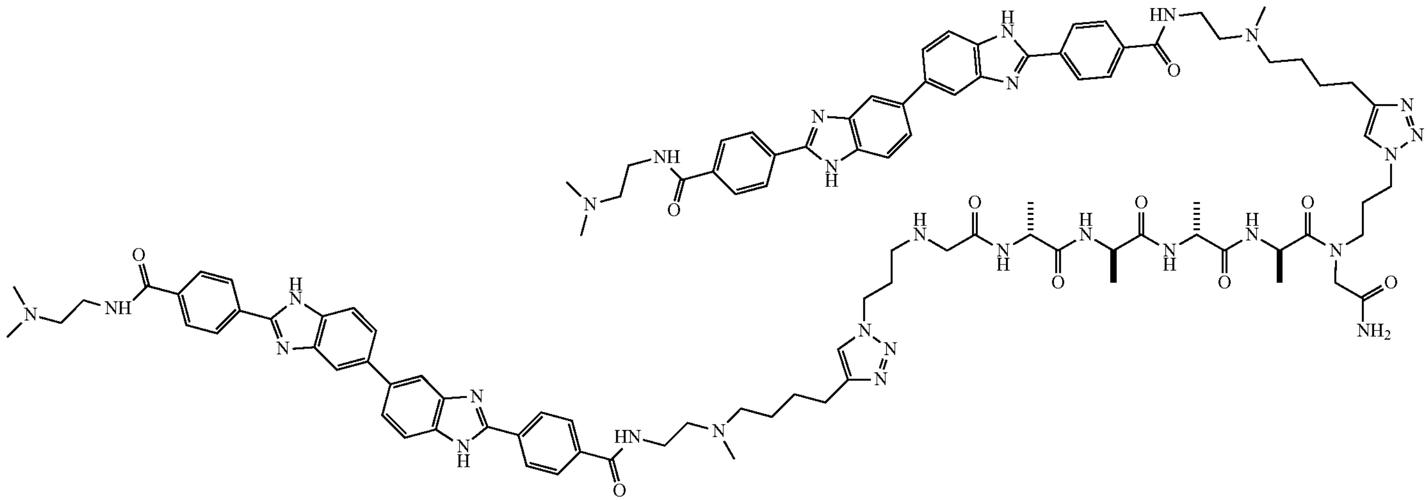 [SMILES: C[C@@H](NC(=O)CNCCCn1cc(CCCCN(C)CCNC(=O)c2ccc(-c3nc4cc(-c5ccc6[nH]c(-c7ccc(C(=O)NCCN(C)C)cc7)nc6c5)ccc4[nH]3)cc2)nn1)C(=O)N[C@H](C)C(=O)N[C@H](C)C(=O)N[C@H](C)C(=O)N(CCCn1cc(CCCCN(C)CCNC(=O)c2ccc(-c3nc4cc(-c5ccc6[nH]c(-c7ccc(C(=O)NCCN(C)C)cc7)nc6c5)ccc4[nH]3)cc2)nn1)CC(N)=O] |
| 473 | 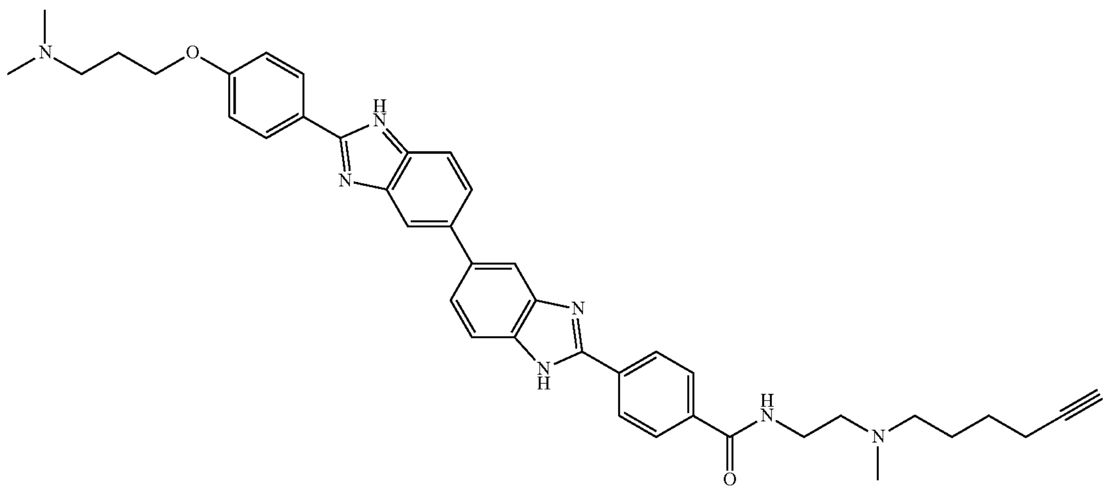 |

TABLE B-continued
| Compound # | Structure |
|---|---|
| 474 | 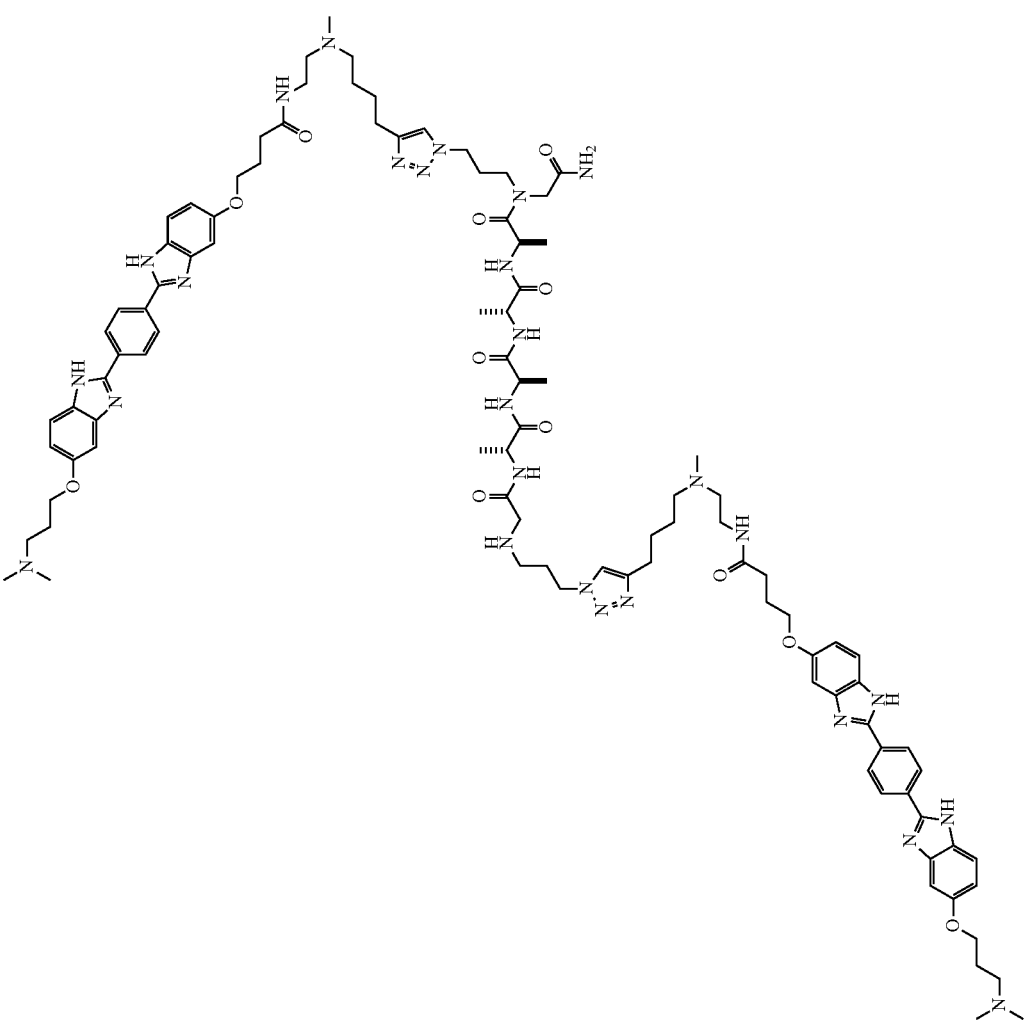 |

TABLE B-continued

| Compound # | Structure |
|---|---|
| 475 | 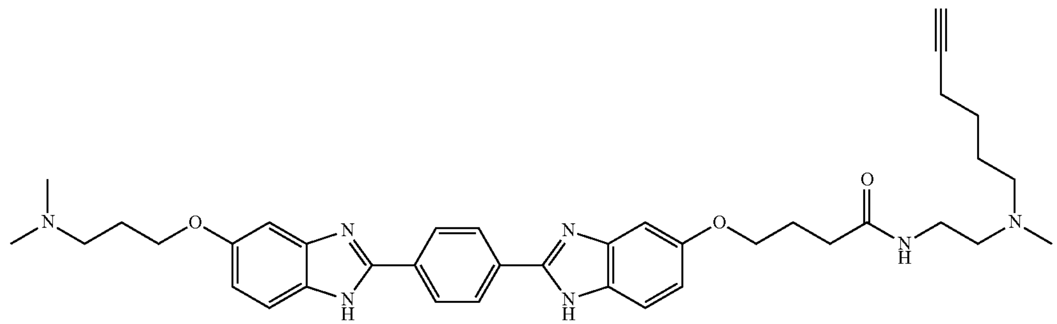 |
| 476 | 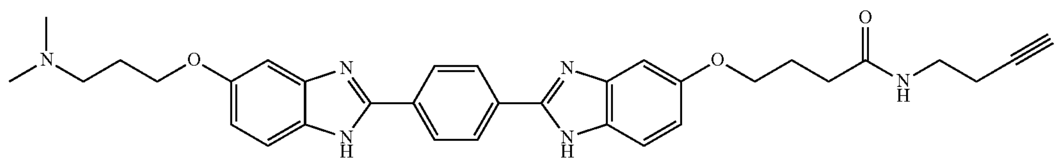 [SMILES: C#CCCNC(=O)CCCOc1ccc2[nH]c(-c3ccc(-c4nc5cc(OCCCN(C)C)ccc5[nH]4)cc3)nc2c1] |
| 477 | 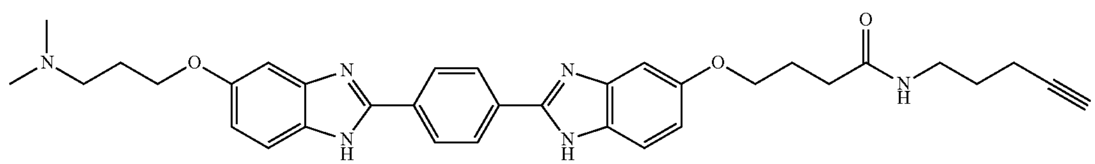 [SMILES: C#CCCCNC(=O)CCCOc1ccc2[nH]c(-c3ccc(-c4nc5cc(OCCCN(C)C)ccc5[nH]4)cc3)nc2c1] |
| 478 | 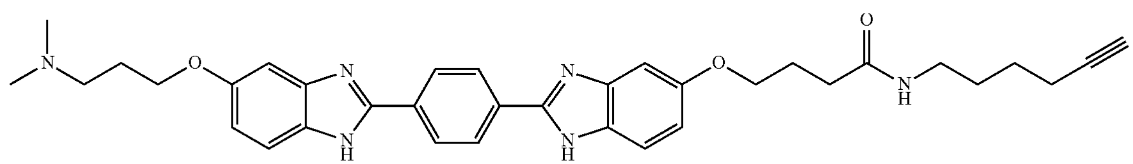 [SMILES: C#CCCCCNC(=O)CCCOc1ccc2[nH]c(-c3ccc(-c4nc5cc(OCCCN(C)C)ccc5[nH]4)cc3)nc2c1] |
| 479 | 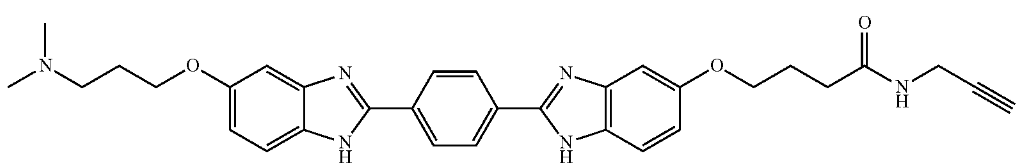 [SMILES: C#CCNC(=O)CCCOc1ccc2[nH]c(-c3ccc(-c4nc5cc(OCCCN(C)C)ccc5[nH]4)cc3)nc2c1] |

In some embodiments, the compound is selected from compounds 78-90 in Table B, above.

Further compounds contemplated include those listed in Table C:

TABLE C

[Structure: R$^1$-phenyl-benzimidazole-benzimidazole-phenyl-R$^2$]

| Compound # | R$^1$ | R$^2$ |
|---|---|---|
| 94 | NO$_2$ | NO$_2$ |
| 95 | NH$_2$ | NH$_2$ |
| 96 | NH(C=NH)NH$_2$ | NH(C=NH)NH$_2$ |
| 97 | NH(C=O)NH$_2$ | NH(C=O)NH$_2$ |
| 98 | (C=NH)NHOH | (C=NH)NHOH |
| 99 | (C=NH)NH$_2$ | (C=NH)NH$_2$ |
| 100 | CN | CN |
| 101 | CONH$_2$ | CONH$_2$ |
| 102 | CO$_2$CH$_3$ | CO$_2$CH$_3$ |
| 103 | CO$_2$H | CO$_2$H |
| 104 | Br | Br |
| 105 | OH | OH |
| 106 | OCH$_3$ | OCH$_3$ |
| 107 | [imidazolyl] | [imidazolyl] |
| 108 | [C(=O)NH-CH$_2$CH$_2$-N(CH$_3$)$_2$] | [C(=O)NH-CH$_2$CH$_2$-N(CH$_3$)$_2$] |
| 109 | CN | [C(=O)NH-CH$_2$CH$_2$-N(CH$_3$)$_2$] |
| 110 | [C(=O)NH-CH$_2$CH$_2$-N(CH$_3$)$_2$] | [C(=O)NH-CH$_2$CH$_2$-NH-CH$_3$] |
| 111 | [C(=O)NH-CH$_2$CH$_2$-NH-CH$_3$] | [C(=O)NH-CH$_2$CH$_2$-NH-CH$_3$] |
| 112 | [C(=O)NH-CH$_2$CH$_2$-N(CH$_2$CH$_3$)$_2$] | [C(=O)NH-CH$_2$CH$_2$-N(CH$_2$CH$_3$)$_2$] |
| 113 | [C(=O)NH-CH$_2$CH$_2$-N(iPr)$_2$] | [C(=O)NH-CH$_2$CH$_2$-N(iPr)$_2$] |

TABLE C-continued

[Structure: R¹-phenyl-benzimidazole-benzimidazole-phenyl-R²]

| Compound # | R¹ | R² |
|---|---|---|
| 114 | -C(O)NH-CH₂CH₂-N(CH₃)₂ | -C(O)NH-CH₂CH₂-N(CH₃)-CH₂CH₂CH₂C≡CH |
| 115 | -C(O)NH-CH₂CH₂-(pyrrolidin-1-yl) | -C(O)NH-CH₂CH₂-(pyrrolidin-1-yl) |
| 116 | -C(O)NH-CH₂CH₂-(piperidin-1-yl) | -C(O)NH-CH₂CH₂-(piperidin-1-yl) |
| 117 | -C(O)NH-CH₂CH₂-(4-methylpiperazin-1-yl) | -C(O)NH-CH₂CH₂-(4-methylpiperazin-1-yl) |
| 167 | NH(C=NH)NH₂ | NH₂ |

Additional compounds contemplated include those listed in Table C1:

TABLE C1

| Compound # | Structure |
|---|---|
| 334 | 4-methylpiperazin-1-yl-phenyl-benzimidazole-benzimidazole-phenyl-4-methylpiperazin-1-yl |
| 335 | (1-methylpiperidin-4-yl)oxy-phenyl-benzimidazole-benzimidazole-phenyl-O-(1-methylpiperidin-4-yl) |

TABLE C1-continued

| Compound # | Structure |
|---|---|
| 336 | 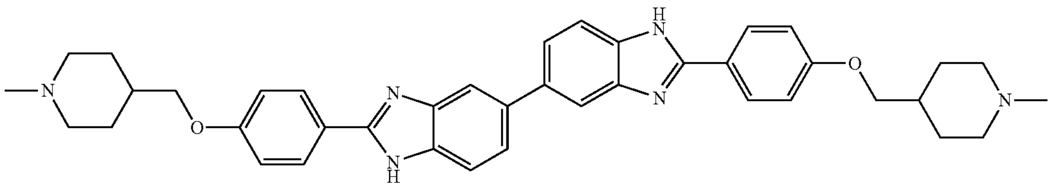 |
| 337 | 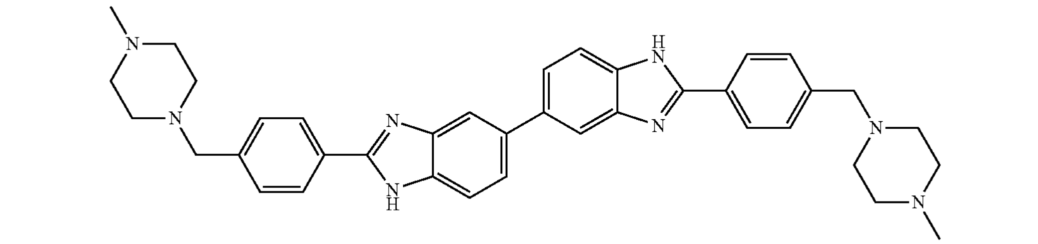 [SMILES: CN1CCN(Cc2ccc(-c3nc4cc(-c5ccc6[nH]c(-c7ccc(CN8CCN(C)CC8)cc7)nc6c5)ccc4[nH]3)cc2)CC1] |
| 338 | 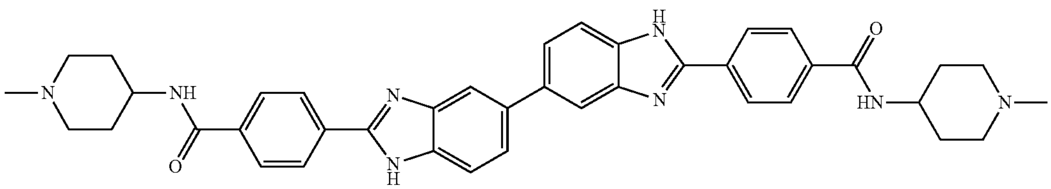 |
| 339 | 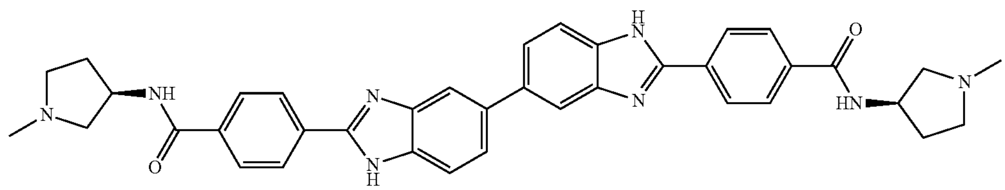 |
| 340 | 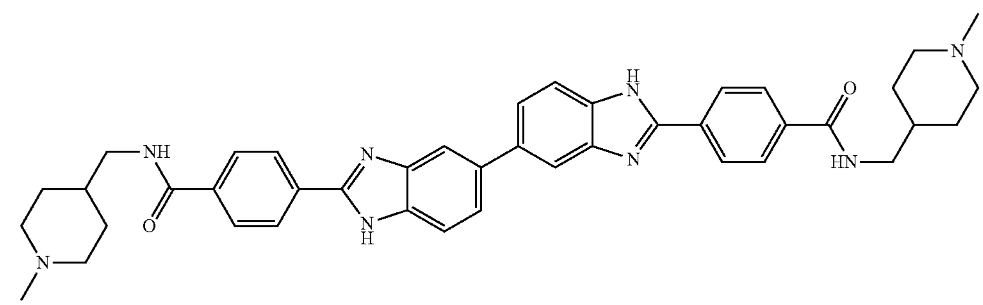 [SMILES: CN1CCC(CNC(=O)c2ccc(-c3nc4cc(-c5ccc6[nH]c(-c7ccc(C(=O)NCC8CCN(C)CC8)cc7)nc6c5)ccc4[nH]3)cc2)CC1] |
| 341 | 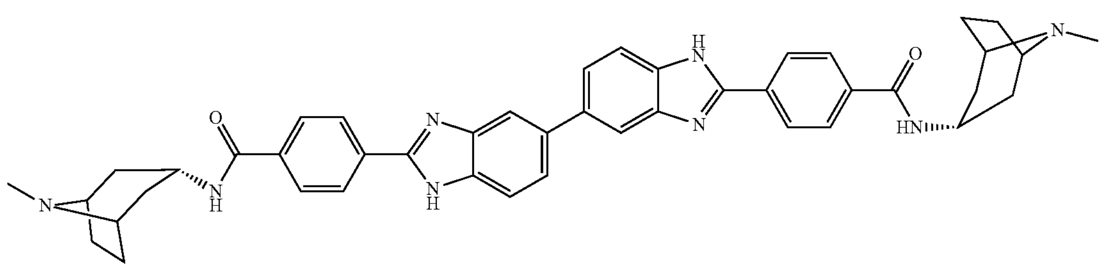 |
| 342 | 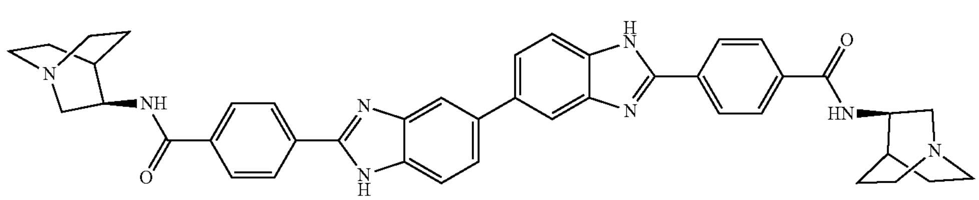 [SMILES: O=C(N[C@H]1CN2CCC1CC2)c1ccc(-c2nc3cc(-c4ccc5[nH]c(-c6ccc(C(=O)N[C@H]7CN8CCC7CC8)cc6)nc5c4)ccc3[nH]2)cc1] |

TABLE C1-continued

| Compound # | Structure |
|---|---|
| 343 | 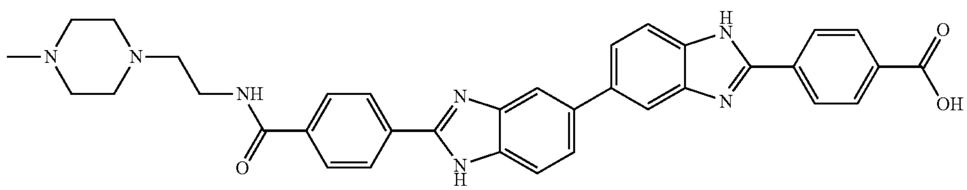 [SMILES: CN1CCN(CCNC(=O)c2ccc(-c3nc4cc(-c5ccc6[nH]c(-c7ccc(C(=O)O)cc7)nc6c5)ccc4[nH]3)cc2)CC1] |
| 344 | 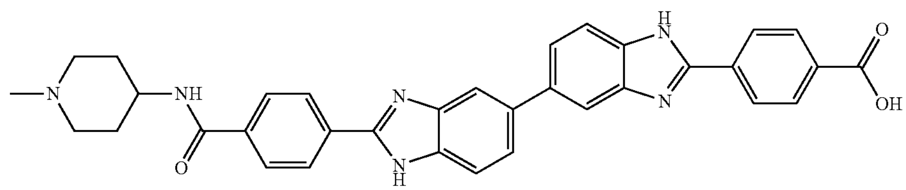 [SMILES: CN1CCC(NC(=O)c2ccc(-c3nc4cc(-c5ccc6[nH]c(-c7ccc(C(=O)O)cc7)nc6c5)ccc4[nH]3)cc2)CC1] |
| 346 | 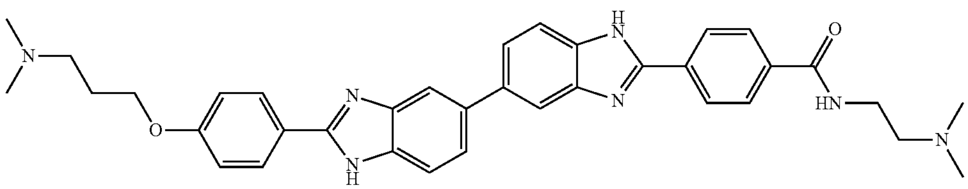 |
| 347 | 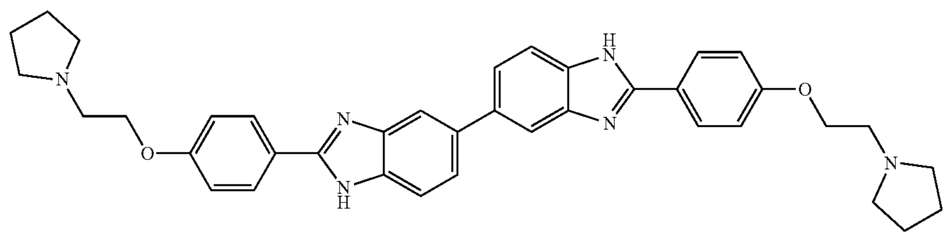 [SMILES: c1cc(-c2nc3cc(-c4ccc5[nH]c(-c6ccc(OCCN7CCCC7)cc6)nc5c4)ccc3[nH]2)ccc1OCCN1CCCC1] |
| 348 | 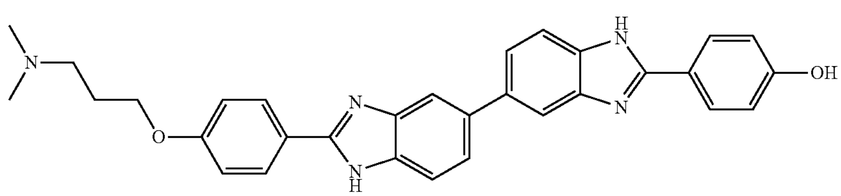 [SMILES: CN(C)CCCOc1ccc(-c2nc3cc(-c4ccc5[nH]c(-c6ccc(O)cc6)nc5c4)ccc3[nH]2)cc1] |
| 349 | 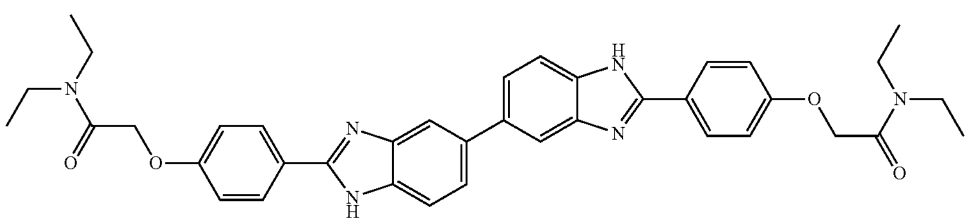 [SMILES: CCN(CC)C(=O)COc1ccc(-c2nc3cc(-c4ccc5[nH]c(-c6ccc(OCC(=O)N(CC)CC)cc6)nc5c4)ccc3[nH]2)cc1] |
| 350 | 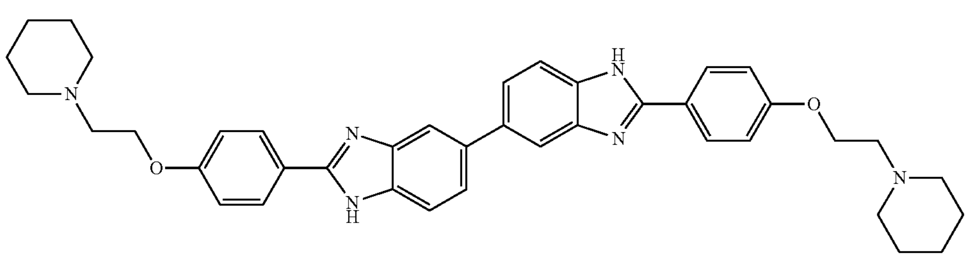 [SMILES: c1cc(-c2nc3cc(-c4ccc5[nH]c(-c6ccc(OCCN7CCCCC7)cc6)nc5c4)ccc3[nH]2)ccc1OCCN1CCCCC1] |

TABLE C1-continued

| Compound # | Structure |
|---|---|
| 351 | 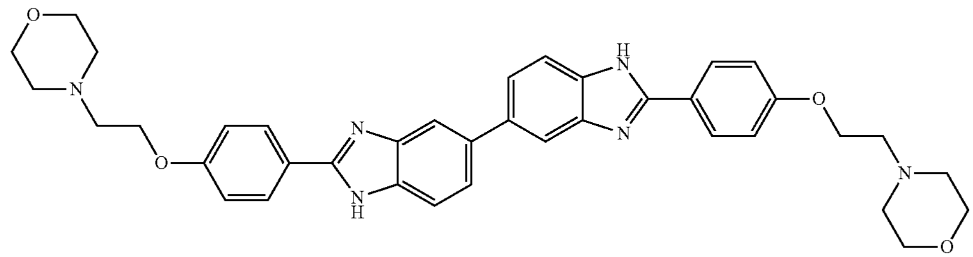 [SMILES: c1cc(-c2nc3cc(-c4ccc5[nH]c(-c6ccc(OCCN7CCOCC7)cc6)nc5c4)ccc3[nH]2)ccc1OCCN1CCOCC1] |
| 352 | 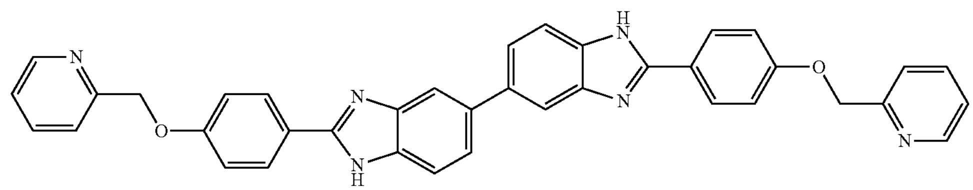 [SMILES: c1ccc(COc2ccc(-c3nc4cc(-c5ccc6[nH]c(-c7ccc(OCc8ccccn8)cc7)nc6c5)ccc4[nH]3)cc2)nc1] |
| 353 | 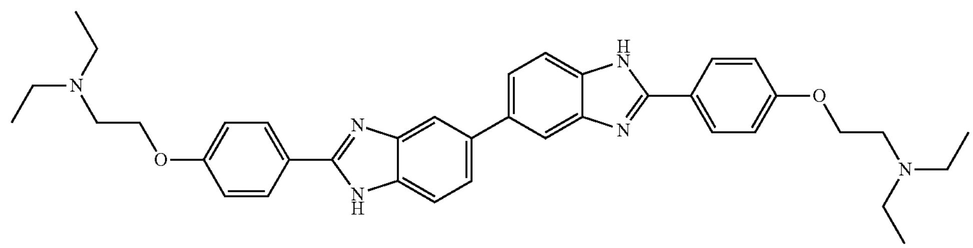 [SMILES: CCN(CC)CCOc1ccc(-c2nc3cc(-c4ccc5[nH]c(-c6ccc(OCCN(CC)CC)cc6)nc5c4)ccc3[nH]2)cc1] |
| 354 | 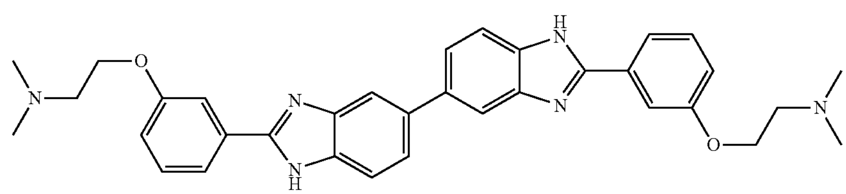 |
| 355 | 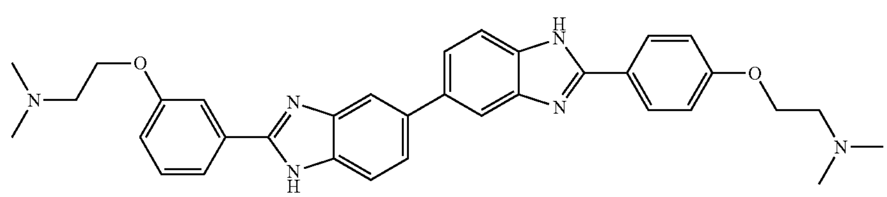 |
| 356 | 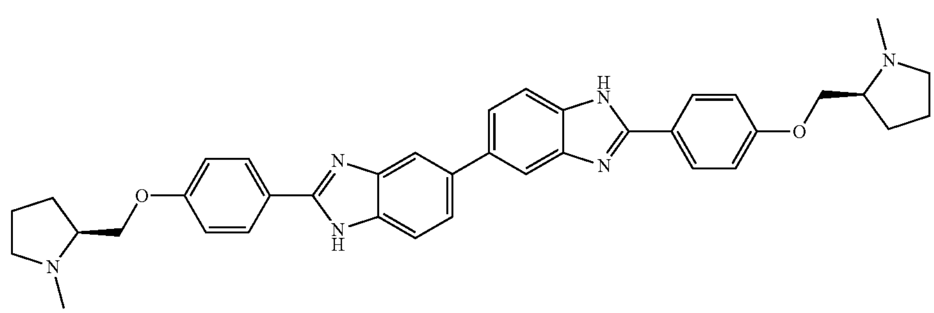 [SMILES: CN1CCC[C@H]1COc1ccc(-c2nc3cc(-c4ccc5[nH]c(-c6ccc(OC[C@@H]7CCCN7C)cc6)nc5c4)ccc3[nH]2)cc1] |

TABLE C1-continued

| Compound # | Structure |
|---|---|
| 357 | 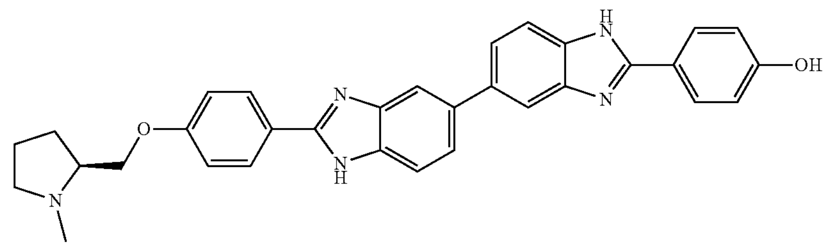 [SMILES: CN1CCC[C@H]1COc1ccc(-c2nc3cc(-c4ccc5[nH]c(-c6ccc(O)cc6)nc5c4)ccc3[nH]2)cc1] |
| 358 | 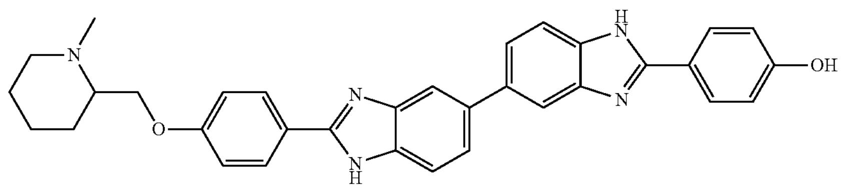 [SMILES: CN1CCCCC1COc1ccc(-c2nc3cc(-c4ccc5[nH]c(-c6ccc(O)cc6)nc5c4)ccc3[nH]2)cc1] |
| 359 | 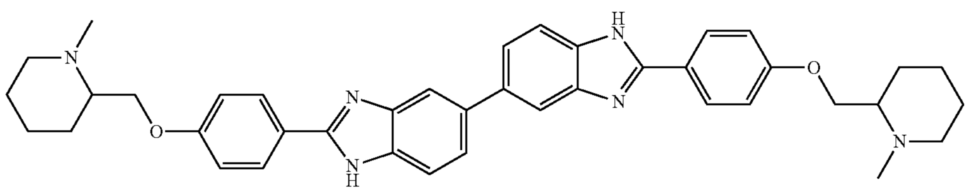 [SMILES: CN1CCCCC1COc1ccc(-c2nc3cc(-c4ccc5[nH]c(-c6ccc(OCC7CCCCN7C)cc6)nc5c4)ccc3[nH]2)cc1] |
| 362 | 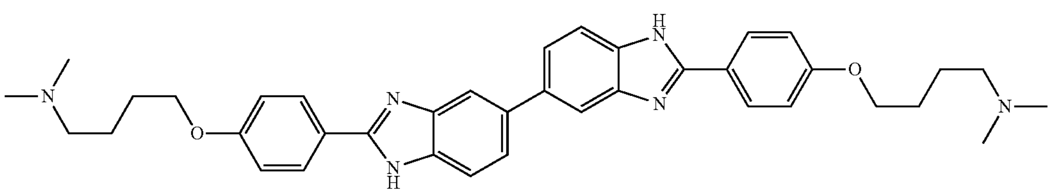 |
| 363 | 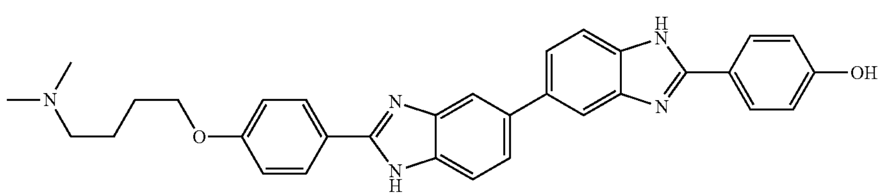 [SMILES: CN(C)CCCCOc1ccc(-c2nc3cc(-c4ccc5[nH]c(-c6ccc(O)cc6)nc5c4)ccc3[nH]2)cc1] |
| 366 | 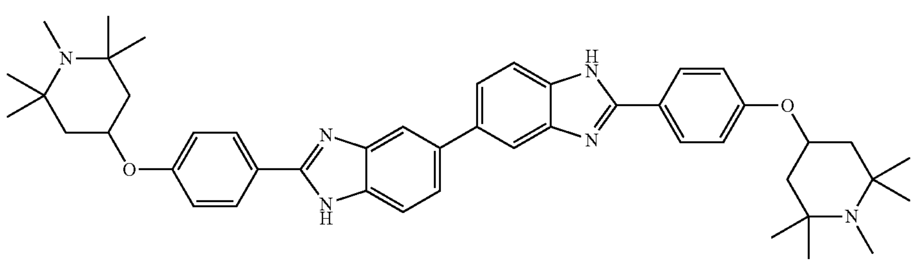 |
| 367 | 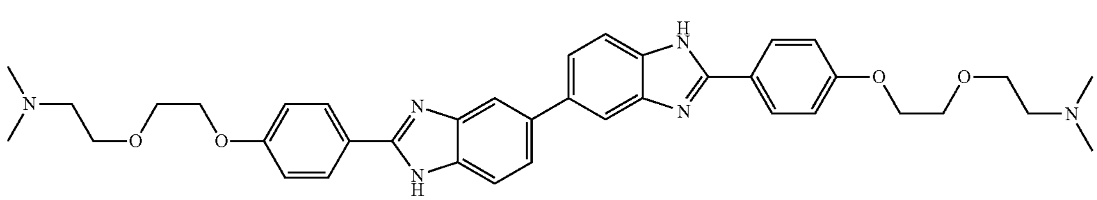 |

TABLE C1-continued

| Compound # | Structure |
|---|---|
| 368 | 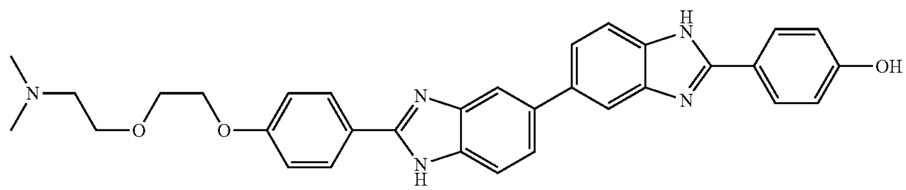 [SMILES: CN(C)CCOCCOc1ccc(-c2nc3cc(-c4ccc5[nH]c(-c6ccc(O)cc6)nc5c4)ccc3[nH]2)cc1] |
| 369 | 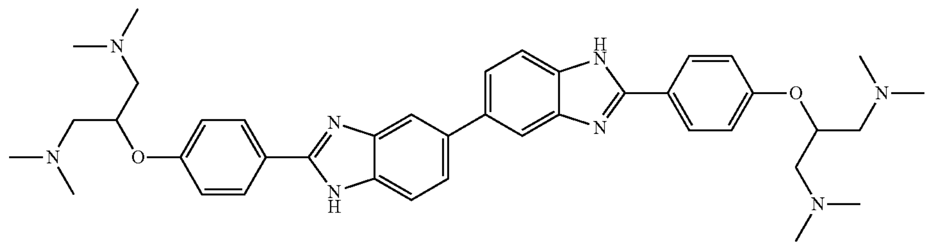 |
| 370 | 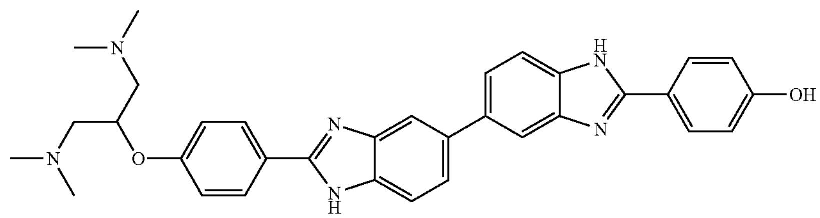 [SMILES: CN(C)CC(CN(C)C)Oc1ccc(-c2nc3cc(-c4ccc5[nH]c(-c6ccc(O)cc6)nc5c4)ccc3[nH]2)cc1] |
| 371 | 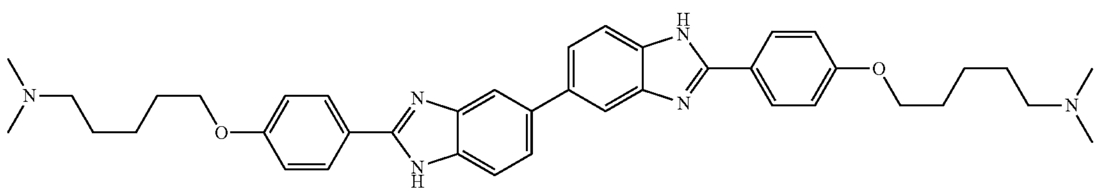 |
| 373 | 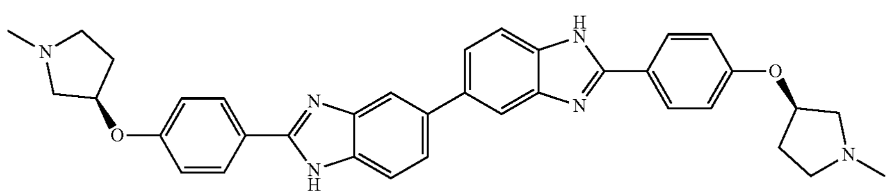 |
| 374 | 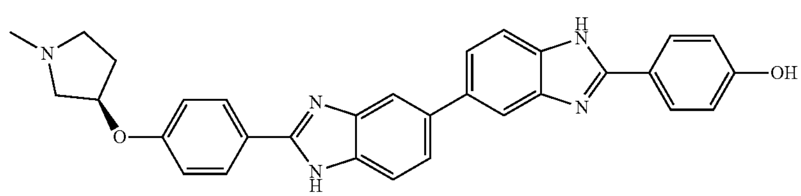 [SMILES: CN1CC[C@@H](Oc2ccc(-c3nc4cc(-c5ccc6[nH]c(-c7ccc(O)cc7)nc6c5)ccc4[nH]3)cc2)C1] |
| 376 | 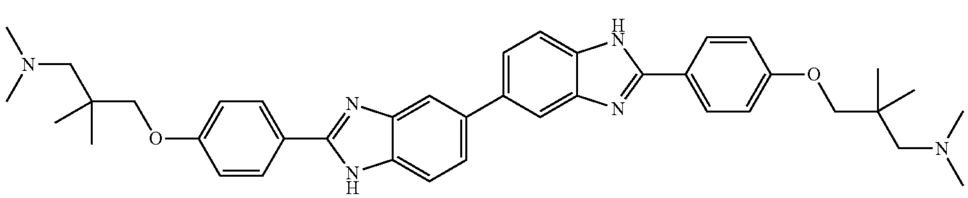 |

TABLE C1-continued

| Compound # | Structure |
|---|---|
| 378 | 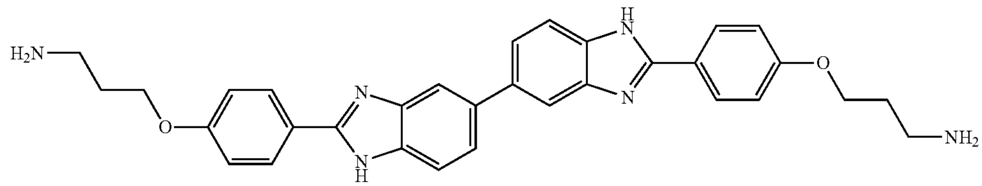 [SMILES: NCCCOc1ccc(-c2nc3cc(-c4ccc5[nH]c(-c6ccc(OCCCN)cc6)nc5c4)ccc3[nH]2)cc1] |
| 379 | 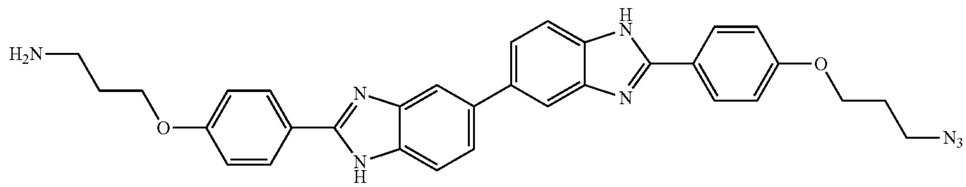 [SMILES: [N-]=[N+]=NCCCOc1ccc(-c2nc3cc(-c4ccc5[nH]c(-c6ccc(OCCCN)cc6)nc5c4)ccc3[nH]2)cc1] |
| 380 | 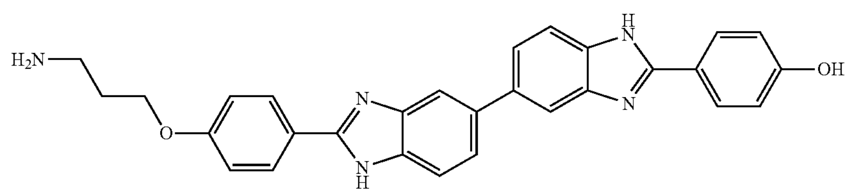 [SMILES: NCCCOc1ccc(-c2nc3cc(-c4ccc5[nH]c(-c6ccc(O)cc6)nc5c4)ccc3[nH]2)cc1] |
| 381 | 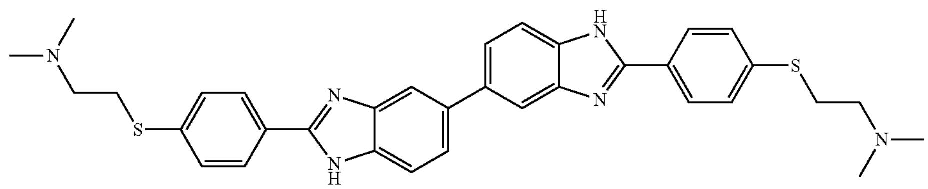 |
| 382 | 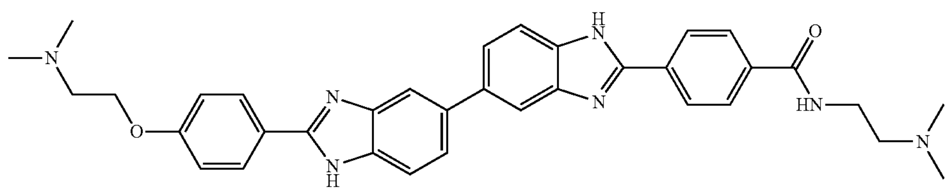 |
| 383 | 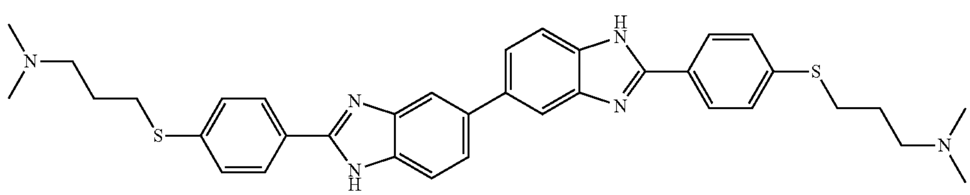 |
| 384 | 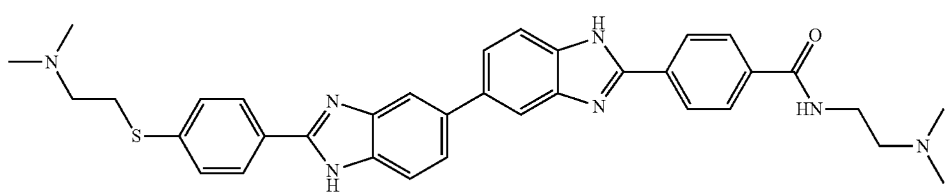 |
| 385 | 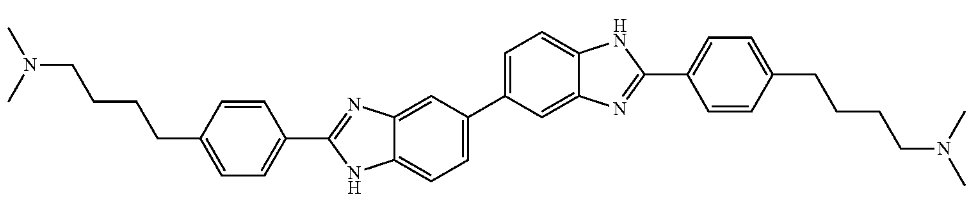 |

TABLE C1-continued

| Compound # | Structure |
|---|---|
| 386 | 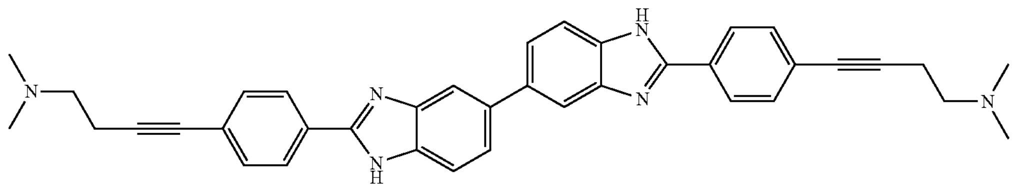 |
| 387 | 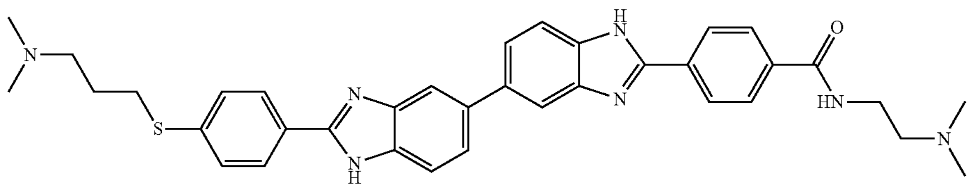 |
| 388 | 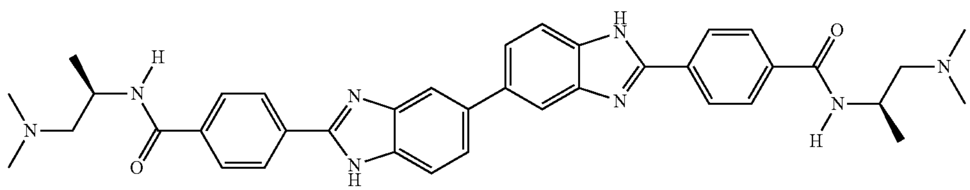 |
| 389 | 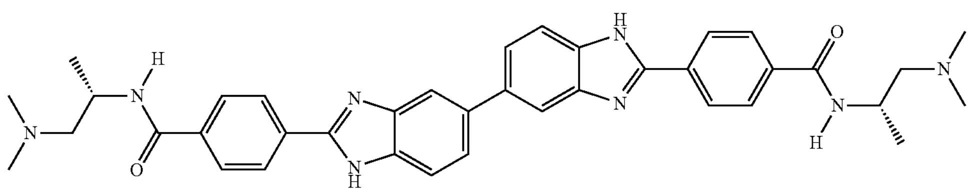 |
| 390 | 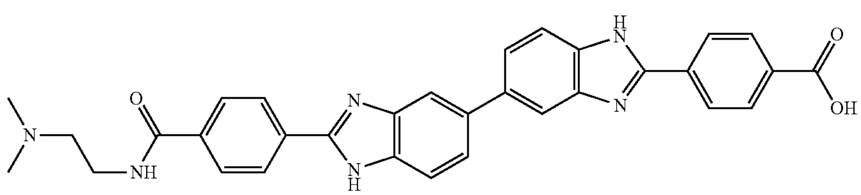 [SMILES: CN(C)CCNC(=O)c1ccc(-c2nc3cc(-c4ccc5[nH]c(-c6ccc(C(=O)O)cc6)nc5c4)ccc3[nH]2)cc1] |
| 391 | 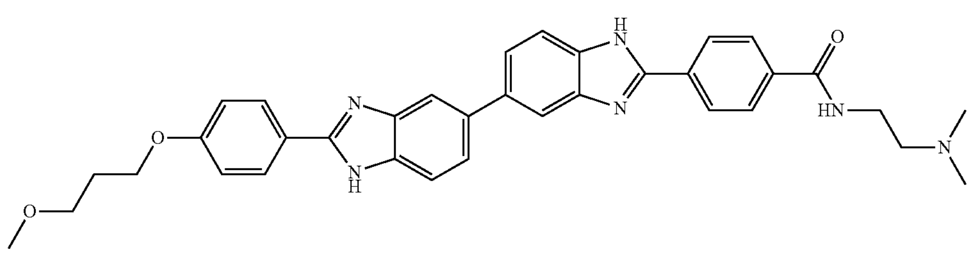 |
| 392 | 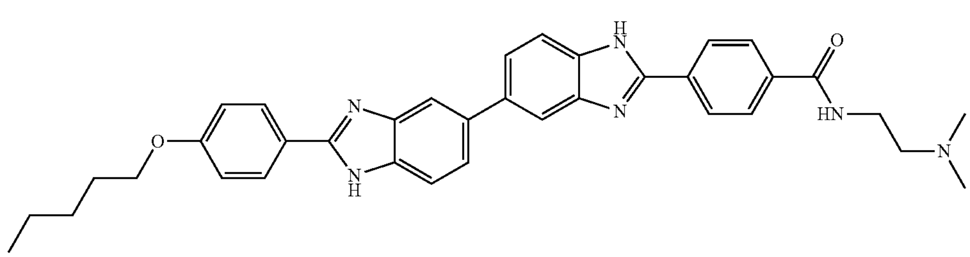 |

TABLE C1-continued

| Compound # | Structure |
|---|---|
| 393 | 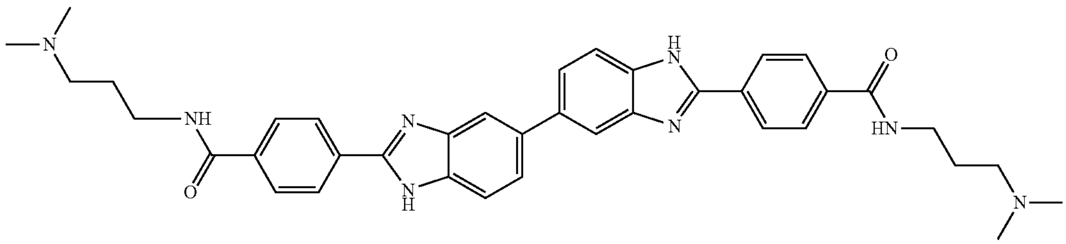 |
| 394 | 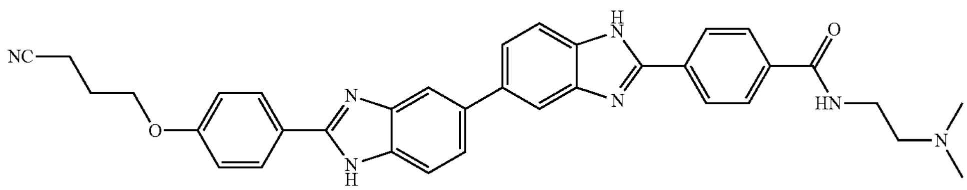 [SMILES: CN(C)CCNC(=O)c1ccc(-c2nc3cc(-c4ccc5[nH]c(-c6ccc(OCCCC#N)cc6)nc5c4)ccc3[nH]2)cc1] |
| 395 | 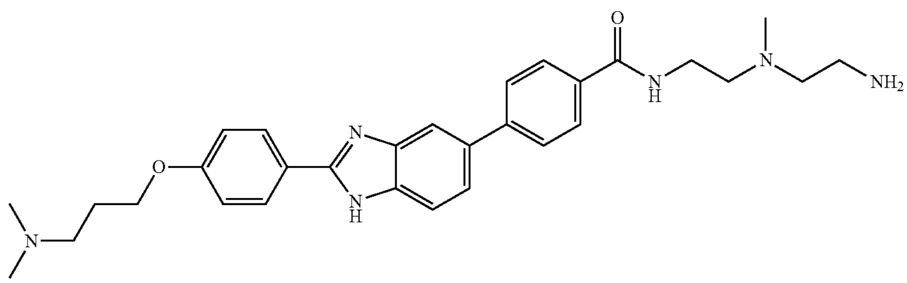 [SMILES: CN(C)CCCOc1ccc(-c2nc3cc(-c4ccc(C(=O)NCCN(C)CCN)cc4)ccc3[nH]2)cc1] |
| 397 | 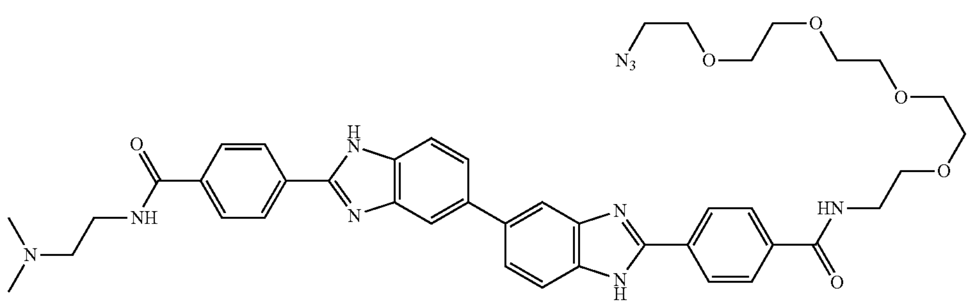 [SMILES: CN(C)CCNC(=O)c1ccc(-c2nc3cc(-c4ccc5[nH]c(-c6ccc(C(=O)NCCOCCOCCOCCOCCN=[N+]=[N-])cc6)nc5c4)ccc3[nH]2)cc1] |
| 398 | 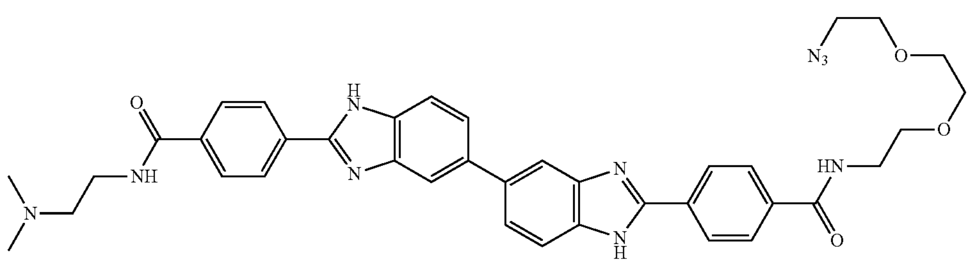 [SMILES: CN(C)CCNC(=O)c1ccc(-c2nc3cc(-c4ccc5[nH]c(-c6ccc(C(=O)NCCOCCOCCN=[N+]=[N-])cc6)nc5c4)ccc3[nH]2)cc1] |
| 399 | 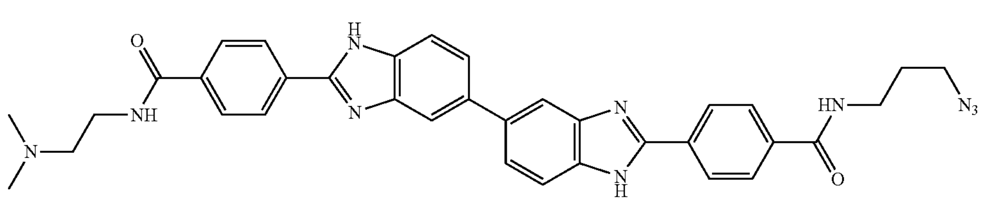 [SMILES: CN(C)CCNC(=O)c1ccc(-c2nc3cc(-c4ccc5[nH]c(-c6ccc(C(=O)NCCCN=[N+]=[N-])cc6)nc5c4)ccc3[nH]2)cc1] |

TABLE C1-continued

| Compound # | Structure |
|---|---|
| 400 | 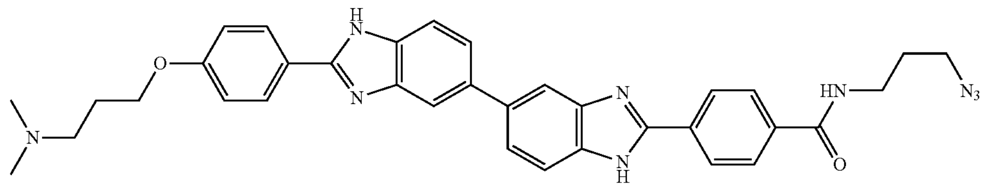 [SMILES: CN(C)CCCOc1ccc(-c2nc3cc(-c4ccc5[nH]c(-c6ccc(C(=O)NCCCN=[N+]=[N-])cc6)nc5c4)ccc3[nH]2)cc1] |
| 401 | 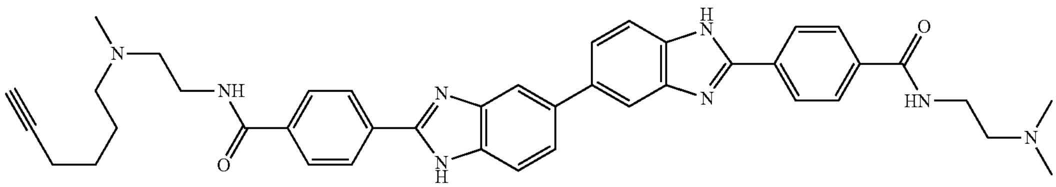 [SMILES: C#CCCCCN(C)CCNC(=O)c1ccc(-c2nc3cc(-c4ccc5[nH]c(-c6ccc(C(=O)NCCN(C)C)cc6)nc5c4)ccc3[nH]2)cc1] |
| 403 | 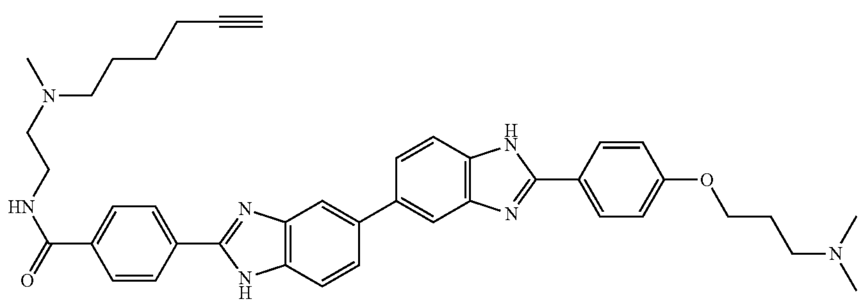 [SMILES: C#CCCCCN(C)CCNC(=O)c1ccc(-c2nc3cc(-c4ccc5[nH]c(-c6ccc(OCCCN(C)C)cc6)nc5c4)ccc3[nH]2)cc1] |

Additional compounds contemplated include those listed in Table D:

TABLE D

| Compound # | Structure |
|---|---|
| 120 | 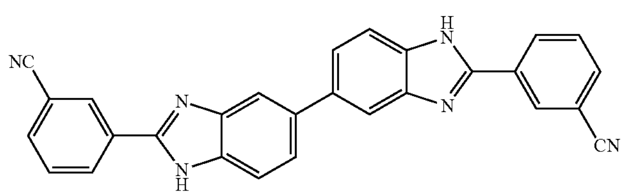 [SMILES: N#Cc1cccc(-c2nc3cc(-c4ccc5[nH]c(-c6cccc(C#N)c6)nc5c4)ccc3[nH]2)c1] |
| 121 | 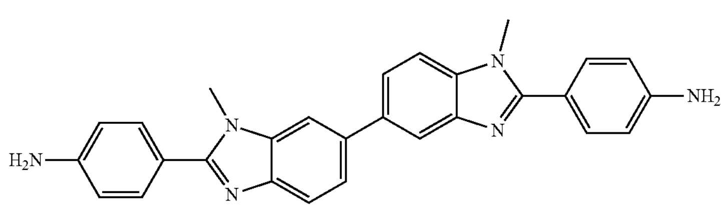 [SMILES: Cn1c(-c2ccc(N)cc2)nc2cc(-c3ccc4nc(-c5ccc(N)cc5)n(C)c4c3)ccc21] |

TABLE D-continued

| Compound # | Structure |
|---|---|
| 122 | 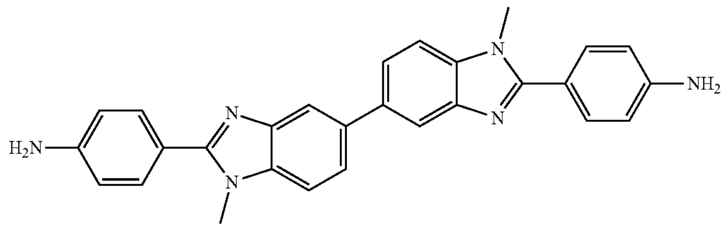 [SMILES: Cn1c(-c2ccc(N)cc2)nc2cc(-c3ccc4c(c3)nc(-c3ccc(N)cc3)n4C)ccc21] |
| 124 | 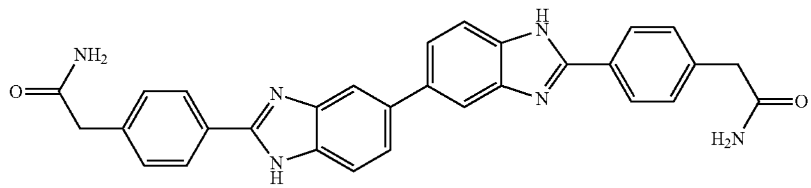 [SMILES: NC(=O)Cc1ccc(-c2nc3cc(-c4ccc5[nH]c(-c6ccc(CC(N)=O)cc6)nc5c4)ccc3[nH]2)cc1] |
| 125 | 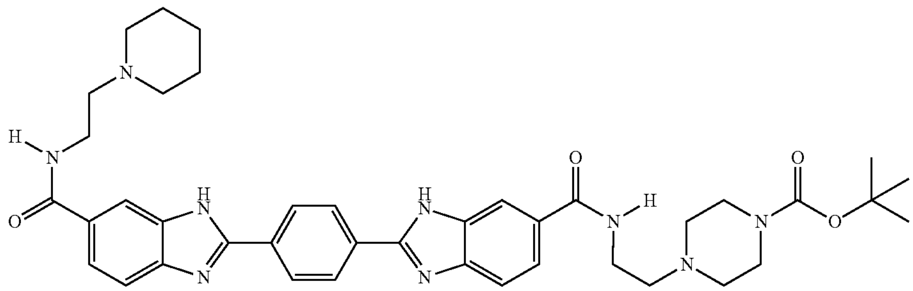 [SMILES: CC(C)(C)OC(=O)N1CCN(CCNC(=O)c2ccc3nc(-c4ccc(-c5nc6ccc(C(=O)NCCN7CCCCC7)cc6[nH]5)cc4)[nH]c3c2)CC1] |
| 126 | 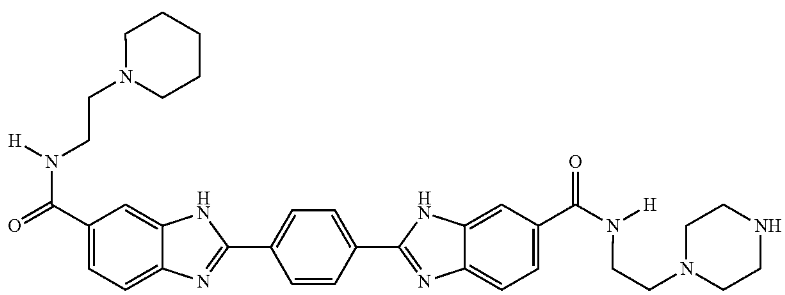 [SMILES: O=C(NCCN1CCCCC1)c1ccc2nc(-c3ccc(-c4nc5ccc(C(=O)NCCN6CCNCC6)cc5[nH]4)cc3)[nH]c2c1] |
| 127 | 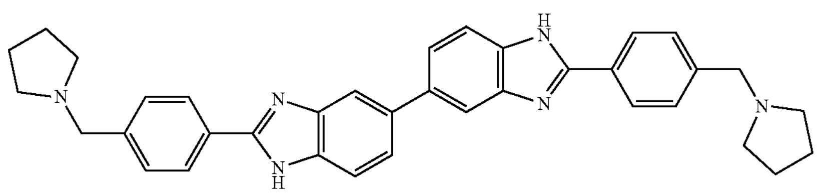 [SMILES: c1cc(-c2nc3cc(-c4ccc5[nH]c(-c6ccc(CN7CCCC7)cc6)nc5c4)ccc3[nH]2)ccc1CN1CCCC1] |
| 145 | 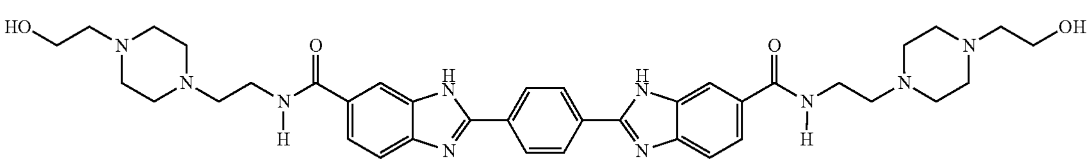 [SMILES: O=C(NCCN1CCN(CCO)CC1)c1ccc2nc(-c3ccc(-c4nc5ccc(C(=O)NCCN6CCN(CCO)CC6)cc5[nH]4)cc3)[nH]c2c1] |
| 146 | 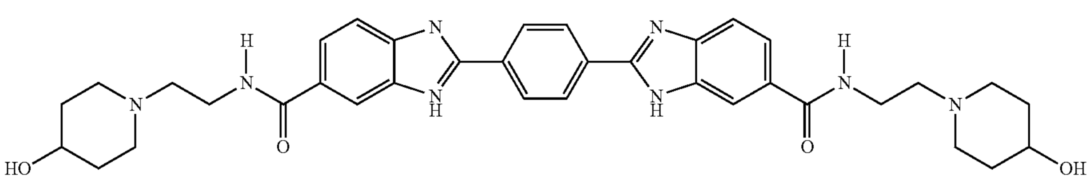 [SMILES: O=C(NCCN1CCC(O)CC1)c1ccc2[nH]c(-c3ccc(-c4nc5ccc(C(=O)NCCN6CCC(O)CC6)cc5[nH]4)cc3)nc2c1] |

TABLE D-continued

| Compound # | Structure |
|---|---|
| 147 | 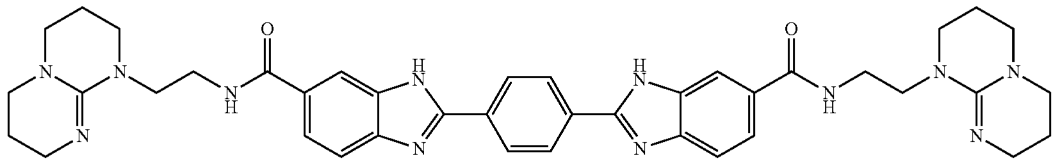 [SMILES: O=C(NCCN1CCCN2CCCN=C21)c1ccc2nc(-c3ccc(-c4nc5ccc(C(=O)NCCN6CCCN7CCCN=C76)cc5[nH]4)cc3)[nH]c2c1] |
| 148 | 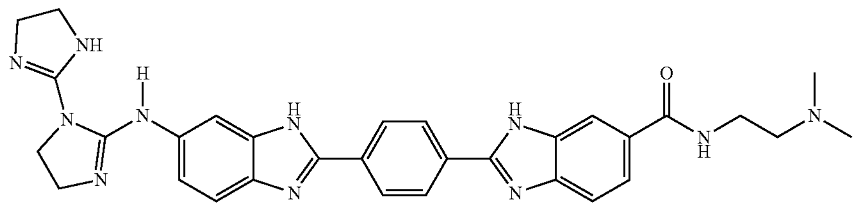 [SMILES: CN(C)CCNC(=O)c1ccc2nc(-c3ccc(-c4nc5ccc(NC6=NCCN6C6=NCCN6)cc5[nH]4)cc3)[nH]c2c1] |
| 149 | 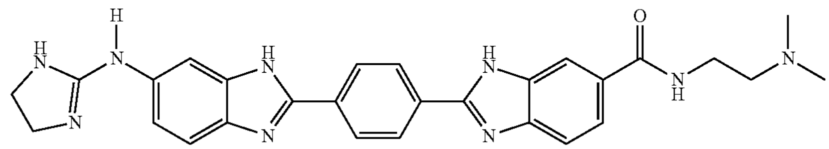 [SMILES: CN(C)CCNC(=O)c1ccc2nc(-c3ccc(-c4nc5ccc(NC6=NCCN6)cc5[nH]4)cc3)[nH]c2c1] |
| 150 | 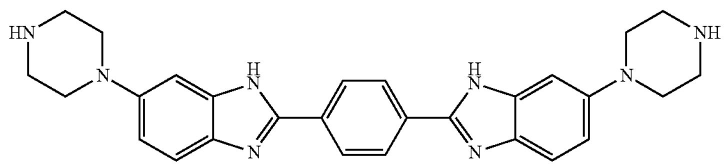 [SMILES: c1cc(-c2nc3ccc(N4CCNCC4)cc3[nH]2)ccc1-c1nc2ccc(N3CCNCC3)cc2[nH]1] |
| 151 | 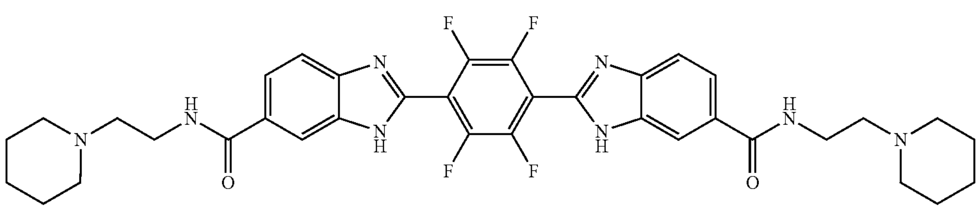 [SMILES: O=C(NCCN1CCCCC1)c1ccc2nc(-c3c(F)c(F)c(-c4nc5ccc(C(=O)NCCN6CCCCC6)cc5[nH]4)c(F)c3F)[nH]c2c1] |
| 152 | 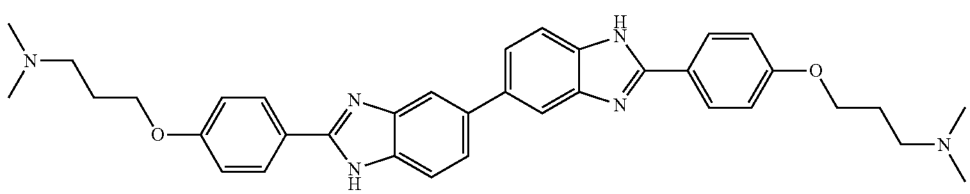 |
| 153 | 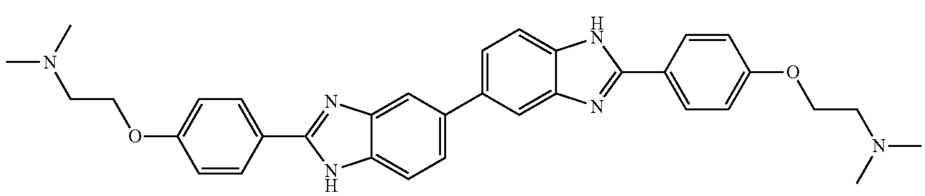 |
| 154 | 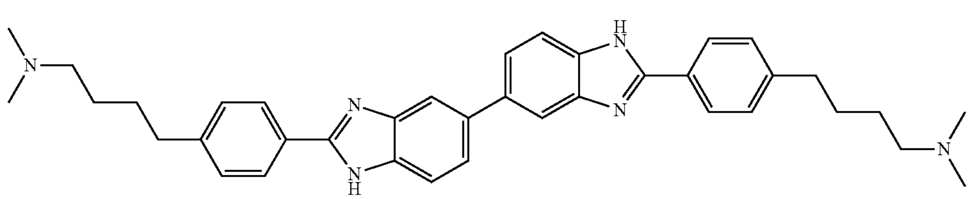 |

TABLE D-continued

| Compound # | Structure |
|---|---|
| 155 | 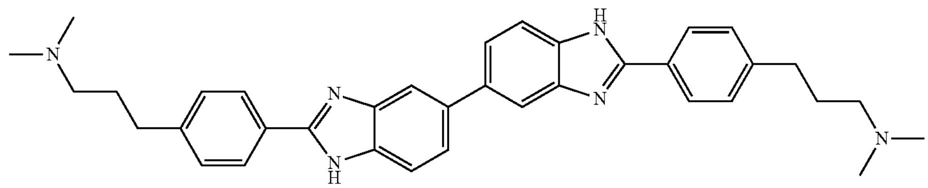 |
| 156 | 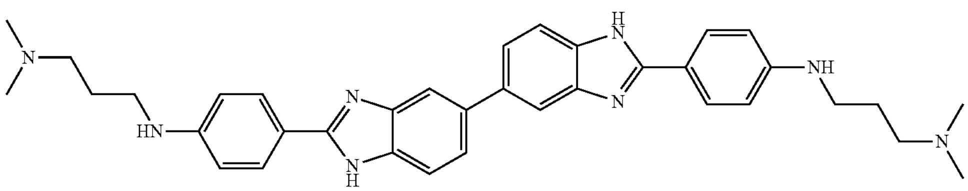 |
| 157 | 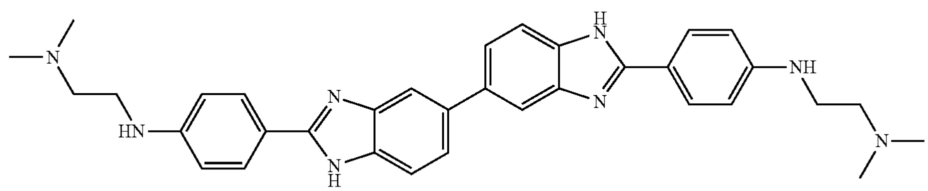 |
| 158 | 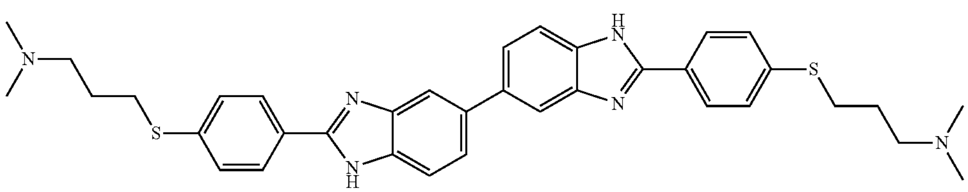 |
| 159 | 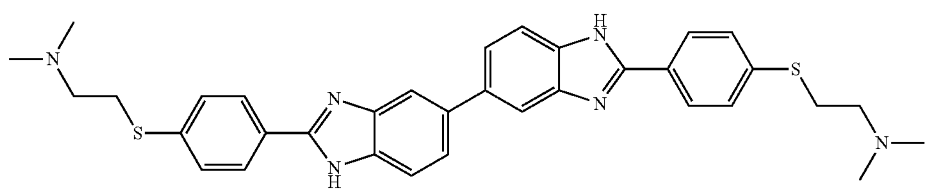 |
| 160 | 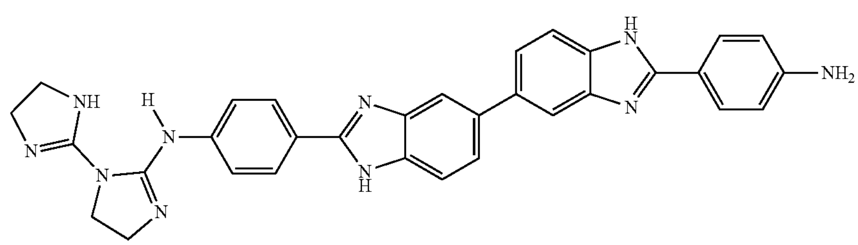 [SMILES: Nc1ccc(-c2nc3cc(-c4ccc5[nH]c(-c6ccc(NC7=NCCN7C7=NCCN7)cc6)nc5c4)ccc3[nH]2)cc1] |
| 161 | 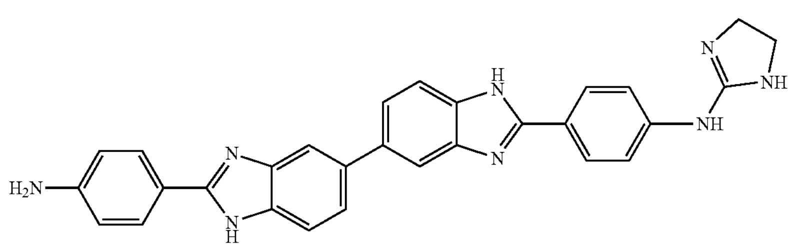 [SMILES: Nc1ccc(-c2nc3cc(-c4ccc5[nH]c(-c6ccc(NC7=NCCN7)cc6)nc5c4)ccc3[nH]2)cc1] |

TABLE D-continued

| Compound # | Structure |
|---|---|
| 166 | 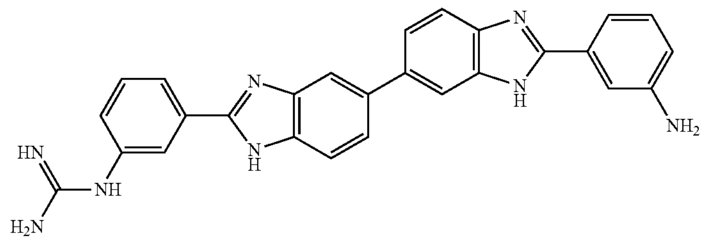 [SMILES: N=C(N)Nc1cccc(-c2nc3cc(-c4ccc5nc(-c6cccc(N)c6)[nH]c5c4)ccc3[nH]2)c1] |
| 177 | 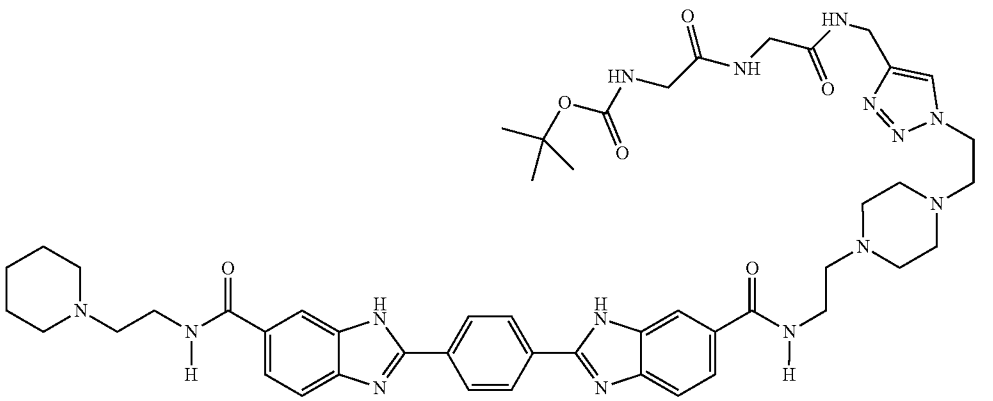 [SMILES: CC(C)(C)OC(=O)NCC(=O)NCC(=O)NCc1cn(CCN2CCN(CCNC(=O)c3ccc4nc(-c5ccc(-c6nc7ccc(C(=O)NCCN8CCCCC8)cc7[nH]6)cc5)[nH]c4c3)CC2)nn1] |
| 178 | 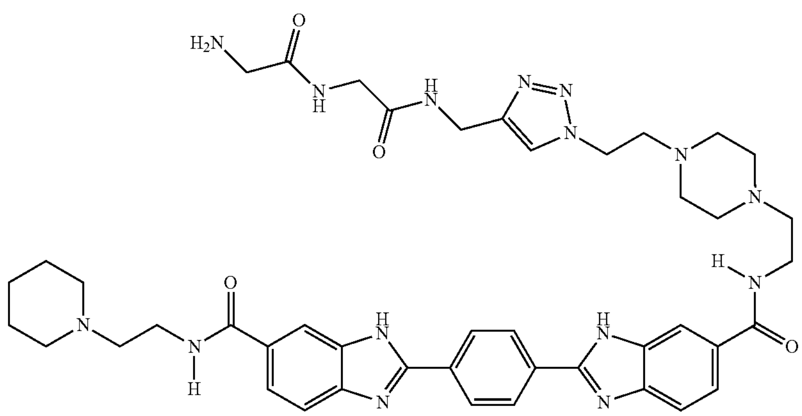 [SMILES: NCC(=O)NCC(=O)NCc1cn(CCN2CCN(CCNC(=O)c3ccc4nc(-c5ccc(-c6nc7ccc(C(=O)NCCN8CCCCC8)cc7[nH]6)cc5)[nH]c4c3)CC2)nn1] |
| 185 | 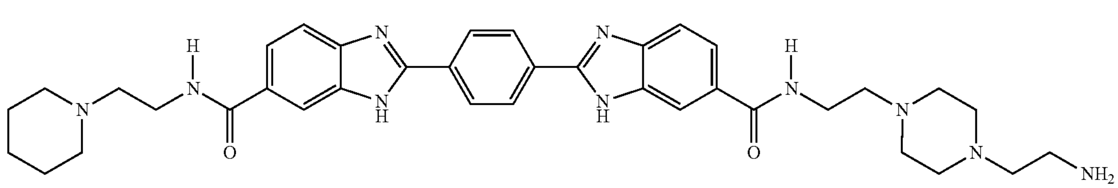 [SMILES: NCCN1CCN(CCNC(=O)c2ccc3nc(-c4ccc(-c5nc6ccc(C(=O)NCCN7CCCCC7)cc6[nH]5)cc4)[nH]c3c2)CC1] |
| 277 | 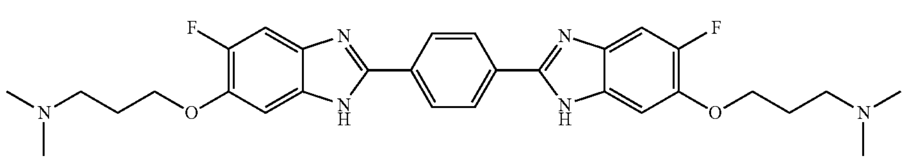 |
| 278 | 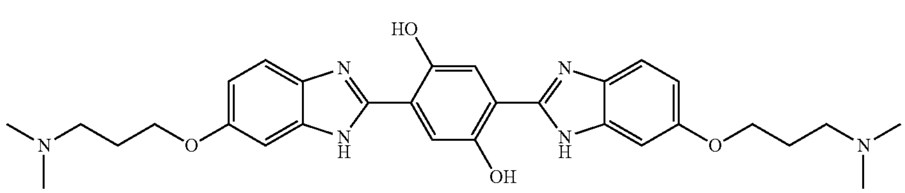 |

TABLE D-continued

| Compound # | Structure |
|---|---|
| 279 | 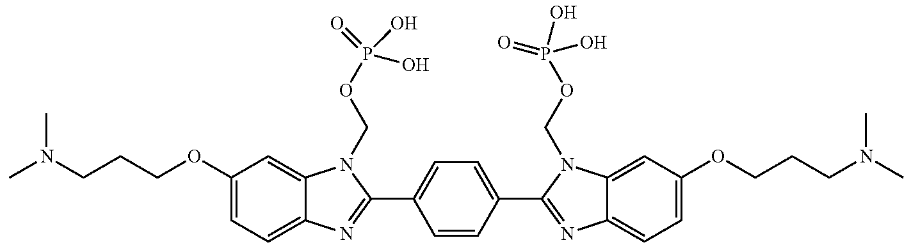 |
| 280 | 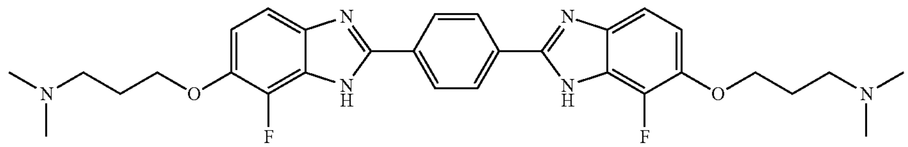 |
| 283 | 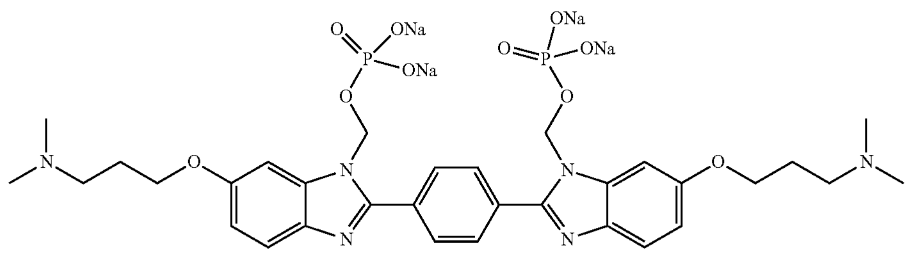 |
| 287 | 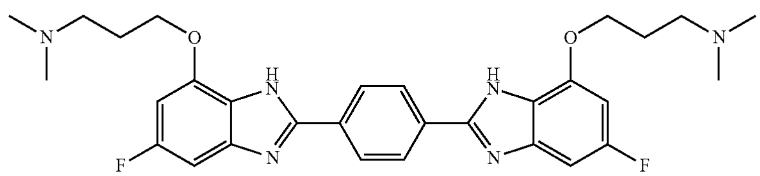 |
| 304 | 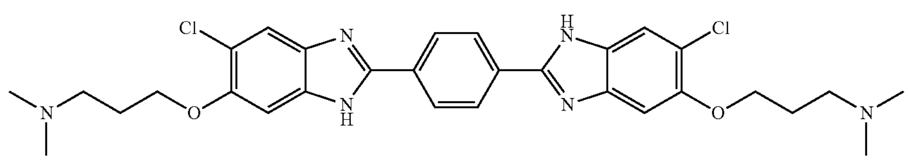 |
| 309 | 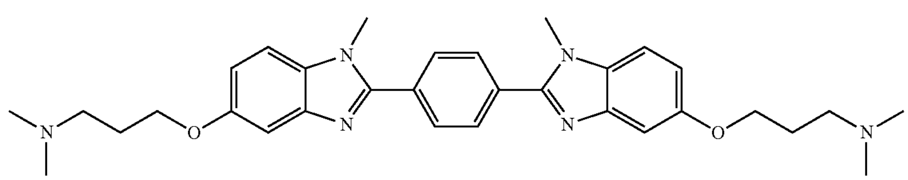 |
| 310 | 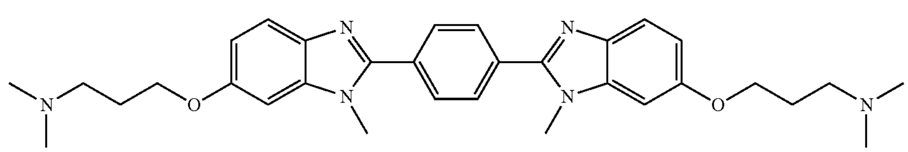 |
| 311 | 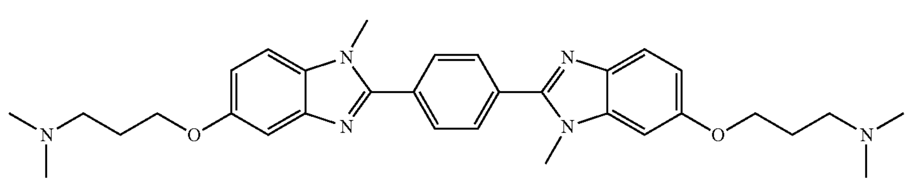 |

TABLE D-continued

| Compound # | Structure |
|---|---|
| 312 | 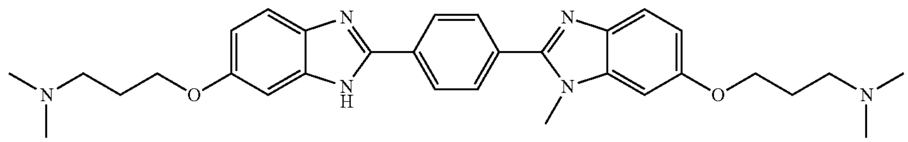 |
| 313 | 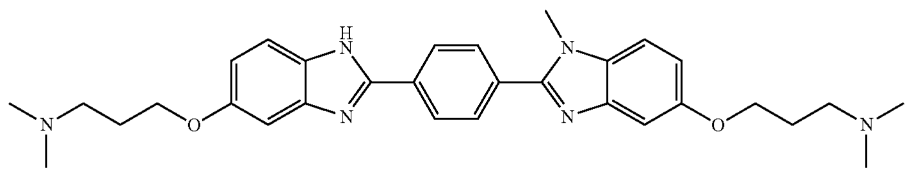 |
| 320 | 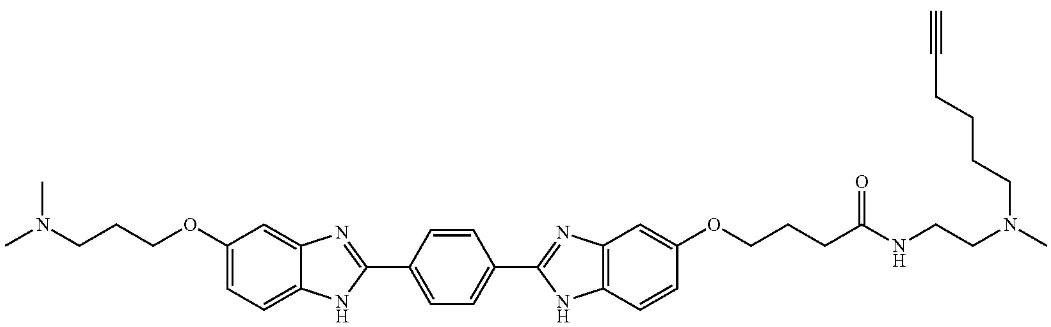 |
| 329 | 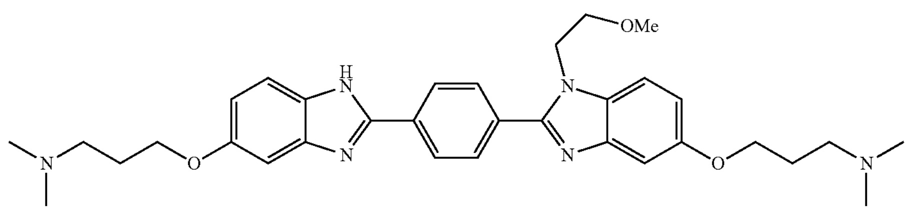 |
| 330 | 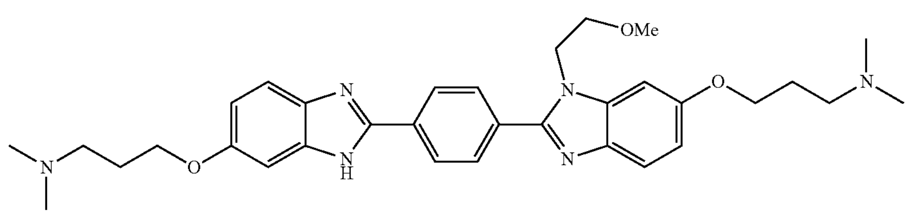 |
| 331 | 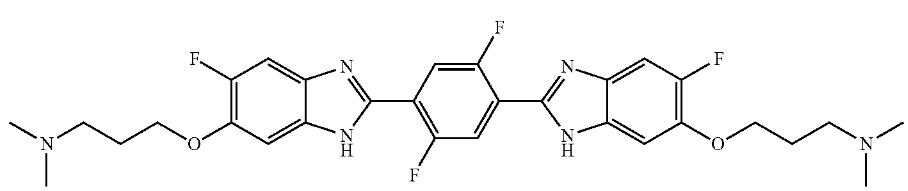 |

TABLE D-continued

| Compound # | Structure |
|---|---|
| 345 | 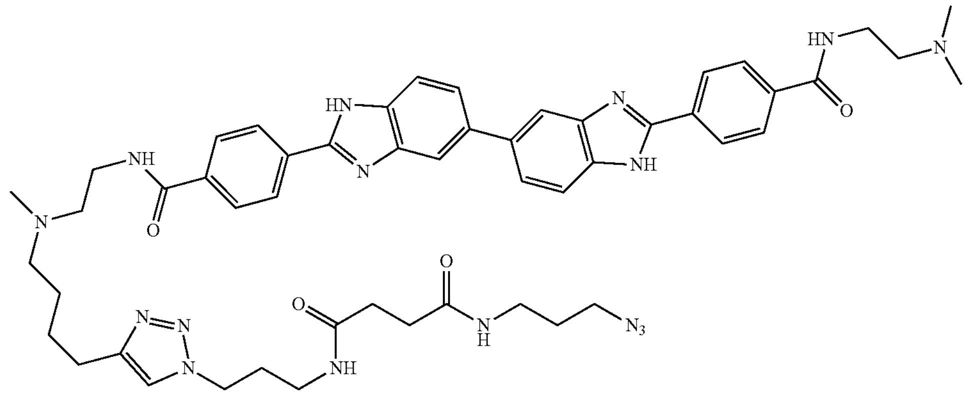 |
| 360 | 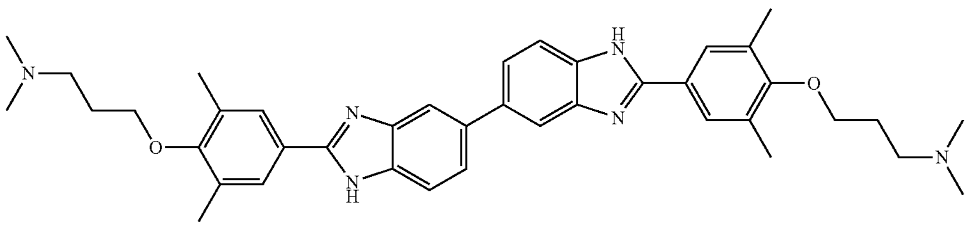 |
| 361 | 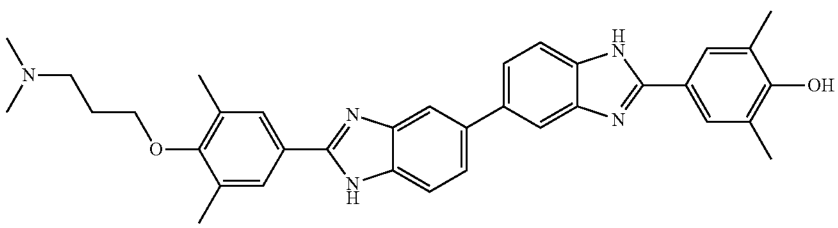 [SMILES: Cc1cc(-c2nc3cc(-c4ccc5[nH]c(-c6cc(C)c(OCCCN(C)C)c(C)c6)nc5c4)ccc3[nH]2)cc(C)c1O] |
| 364 | 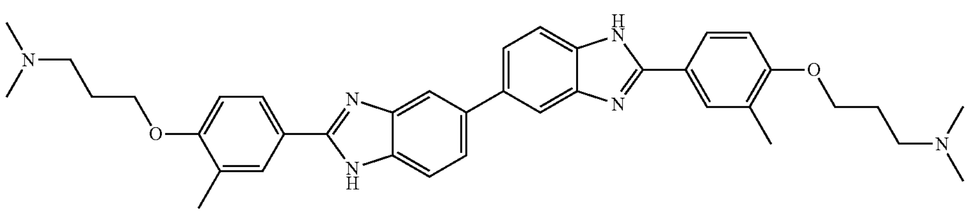 |
| 365 | 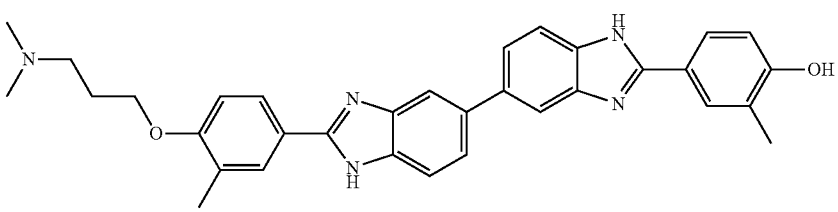 [SMILES: Cc1cc(-c2nc3cc(-c4ccc5[nH]c(-c6ccc(OCCCN(C)C)c(C)c6)nc5c4)ccc3[nH]2)ccc1O] |
| 372 | 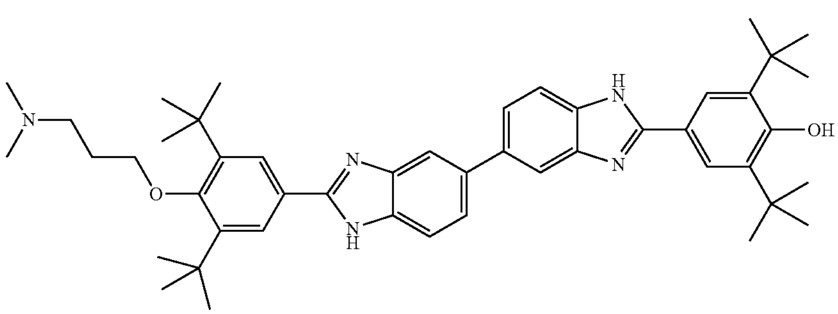 [SMILES: CN(C)CCCOc1c(C(C)(C)C)cc(-c2nc3cc(-c4ccc5[nH]c(-c6cc(C(C)(C)C)c(O)c(C(C)(C)C)c6)nc5c4)ccc3[nH]2)cc1C(C)(C)C] |

TABLE D-continued

| Compound # | Structure |
|---|---|
| 375 | 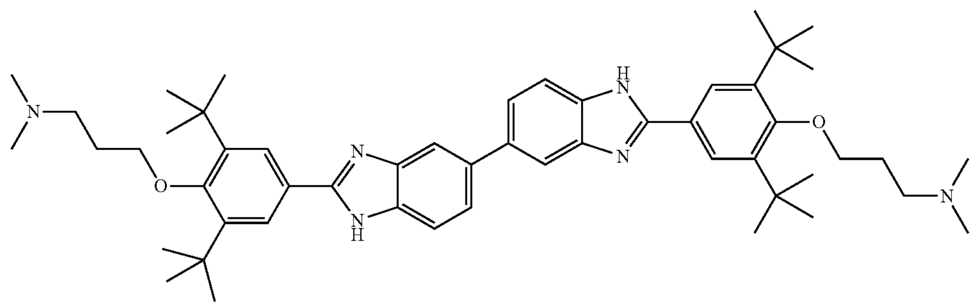 |
| 396 | 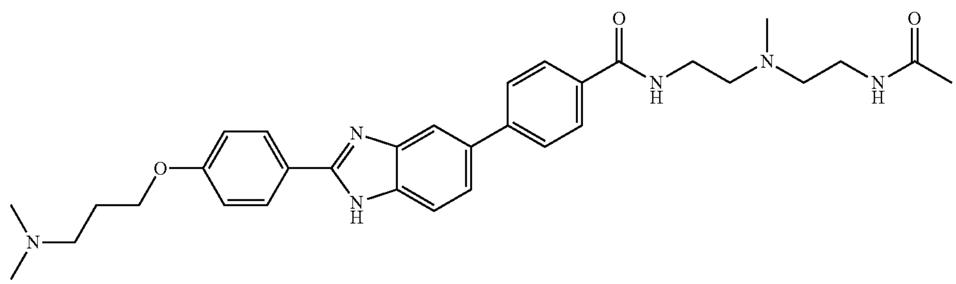 [SMILES: CC(=O)NCCN(C)CCNC(=O)c1ccc(-c2ccc3[nH]c(-c4ccc(OCCCN(C)C)cc4)nc3c2)cc1] |
| 402 | 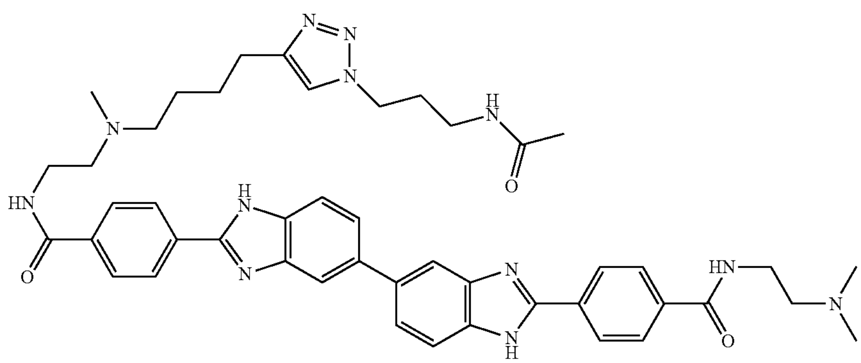 [SMILES: CC(=O)NCCCn1cc(CCCCN(C)CCNC(=O)c2ccc(-c3nc4cc(-c5ccc6[nH]c(-c7ccc(C(=O)NCCN(C)C)cc7)nc6c5)ccc4[nH]3)cc2)nn1] |
| 404 | 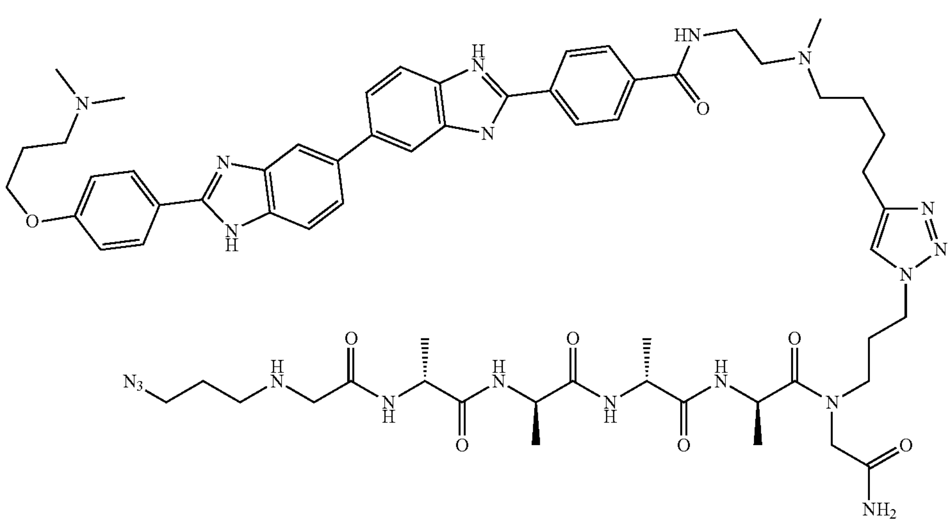 |

In some embodiments, the compound is selected from compounds 120-166 in Table D, above.
Further compounds contemplated include those listed in Table E:
TABLE E
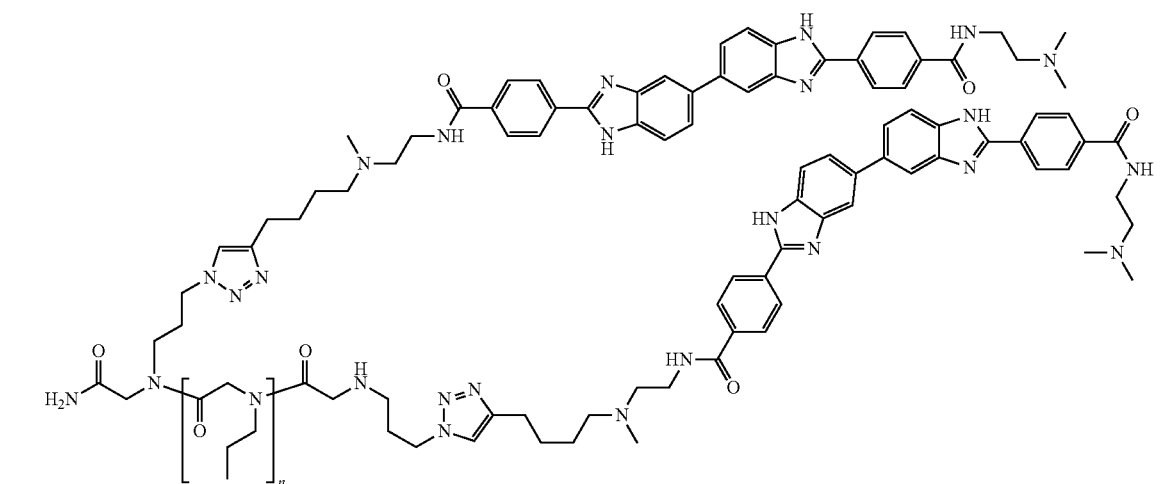
| Compound # | n |
|---|---|
| 128 | 2 |
| 129 | 3 |
| 130 | 4 |
| 131 | 5 |
| 132 | 6 |
Further compounds contemplated include those listed in Table F:
TABLE F
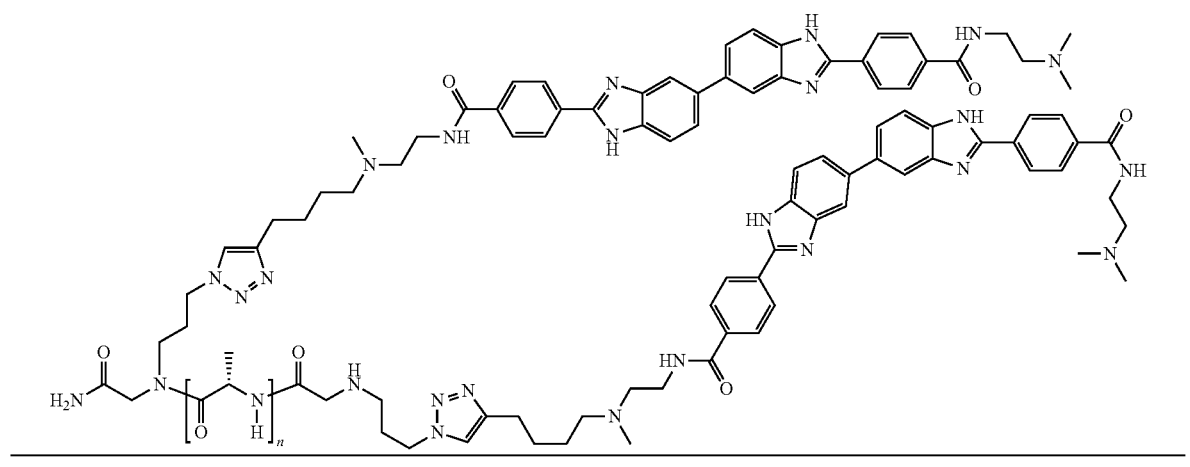
| Compound # | n |
|---|---|
| 133 | 2 |
| 134 | 3 |
| 135 | 4 |
| 136 | 5 |

Further compounds contemplated include those listed in Table G:

TABLE G

| Compound # | n |
|---|---|
| 137 | 2 |
| 138 | 3 |
| 139 | 4 |
| 140 | 5 |

Further compounds contemplated include those listed in Table H:

TABLE H

| Compound # | n |
|---|---|
| 141 | 2 |
| 142 | 3 |
| 143 | 4 |
| 144 | 5 |

Further compounds contemplated include those listed in Table I:
TABLE I
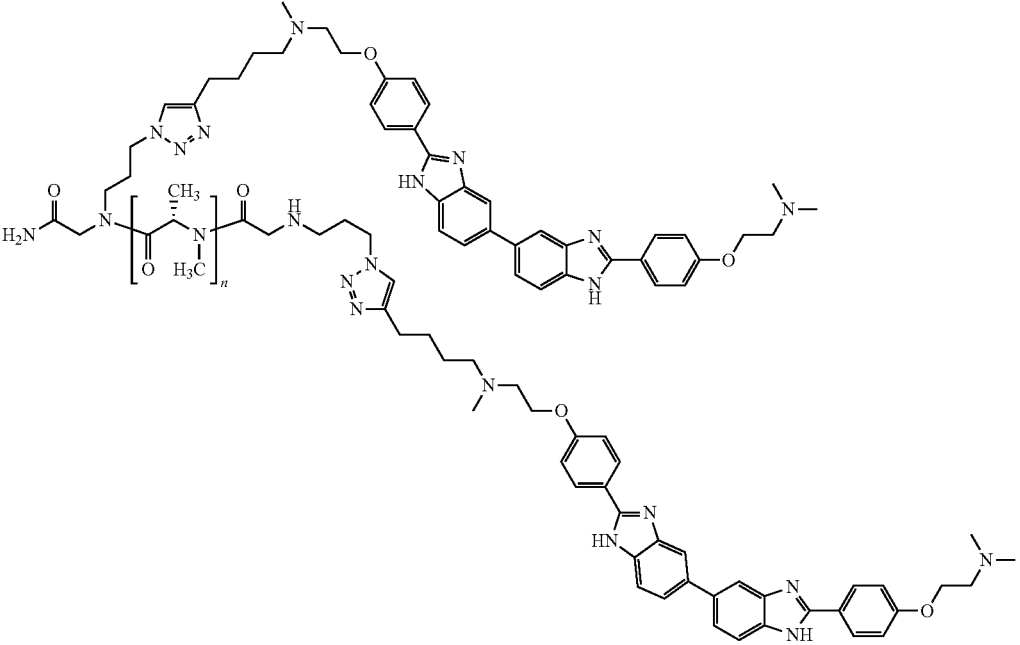
| Compound # | n |
|---|---|
| 162 | 2 |
| 163 | 3 |
| 164 | 4 |
| 165 | 5 |
Further compounds contemplated include those listed in Table J:
TABLE J
| Compound # | Structure |
|---|---|
| 405 | 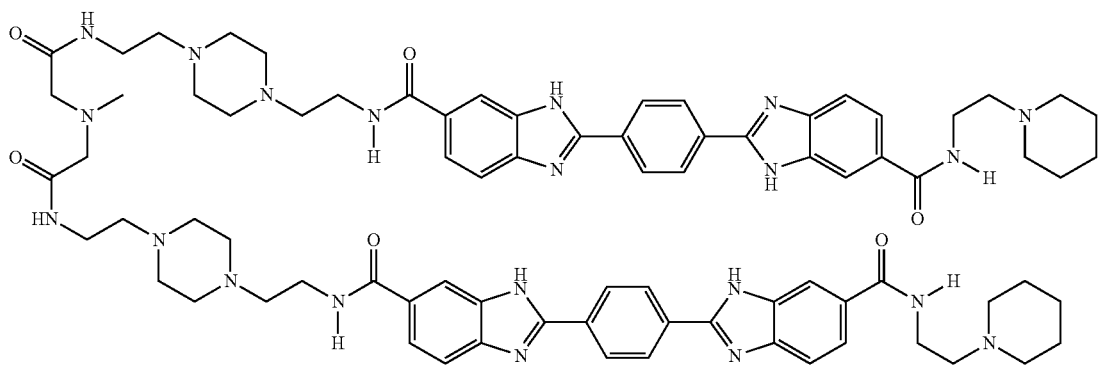 [SMILES: CN(CC(=O)NCCN1CCN(CCNC(=O)c2ccc3nc(-c4ccc(-c5nc6ccc(C(=O)NCCN7CCCCC7)cc6[nH]5)cc4)[nH]c3c2)CC1)CC(=O)NCCN1CCN(CCNC(=O)c2ccc3nc(-c4ccc(-c5nc6ccc(C(=O)NCCN7CCCCC7)cc6[nH]5)cc4)[nH]c3c2)CC1] |

TABLE J-continued

| Compound # | Structure |
|---|---|
| 406 | 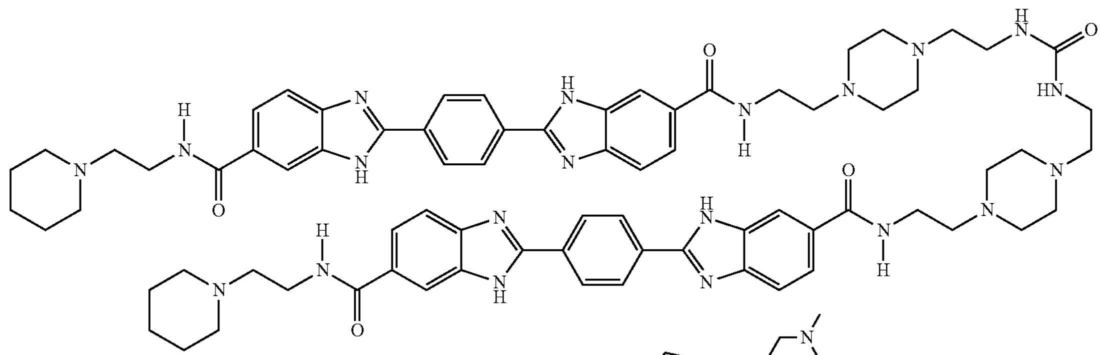 [SMILES: O=C(NCCN1CCN(CCNC(=O)c2ccc3nc(-c4ccc(-c5nc6ccc(C(=O)NCCN7CCCCC7)cc6[nH]5)cc4)[nH]c3c2)CC1)NCCN1CCN(CCNC(=O)c2ccc3nc(-c4ccc(-c5nc6ccc(C(=O)NCCN7CCCCC7)cc6[nH]5)cc4)[nH]c3c2)CC1] |
| 407 | 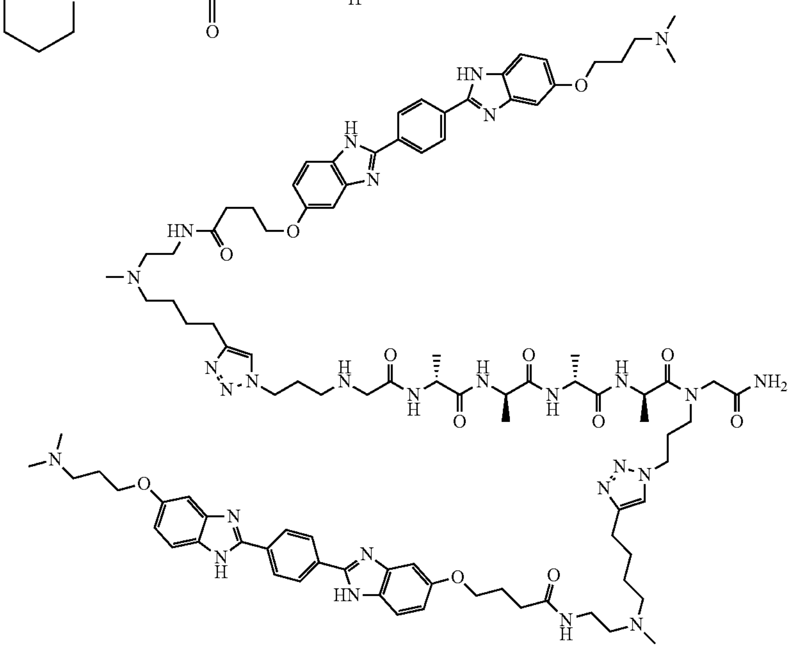 |

Further compounds contemplated include those listed in Table K:

TABLE K

| Compound # | Structure |
|---|---|
| 408 | 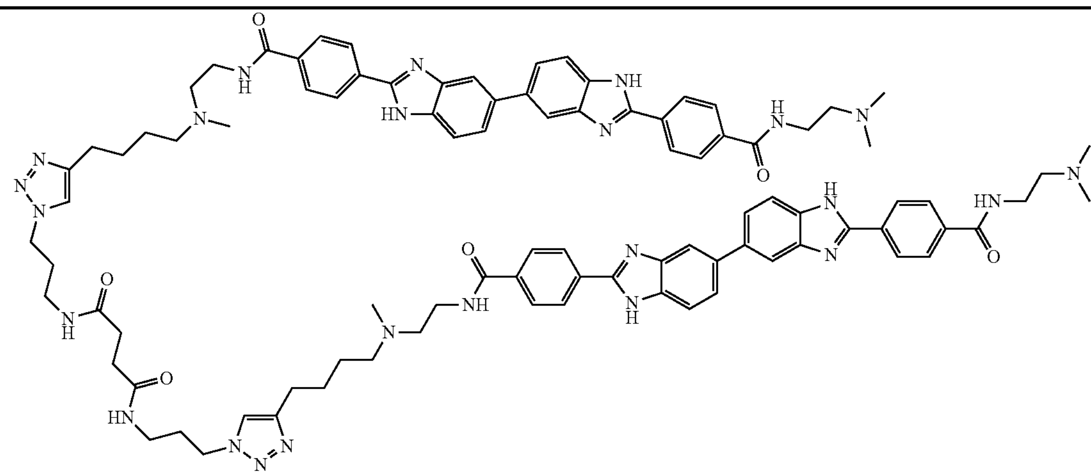 |

TABLE K-continued
| Compound # | Structure |
|---|---|
| 409 | 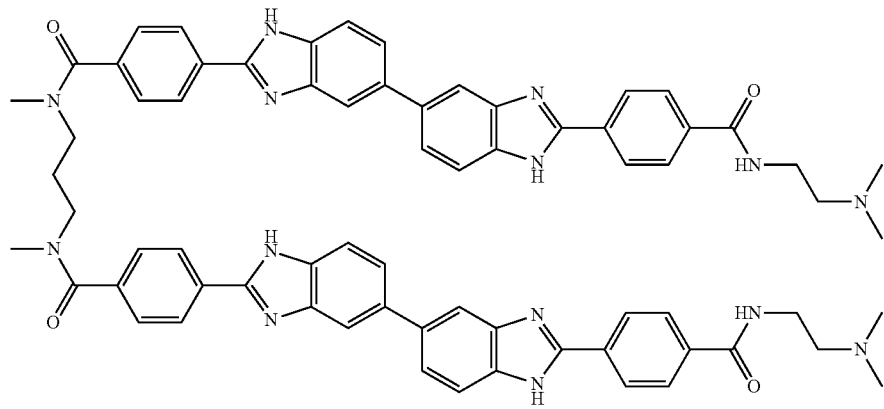 |
| 410 | 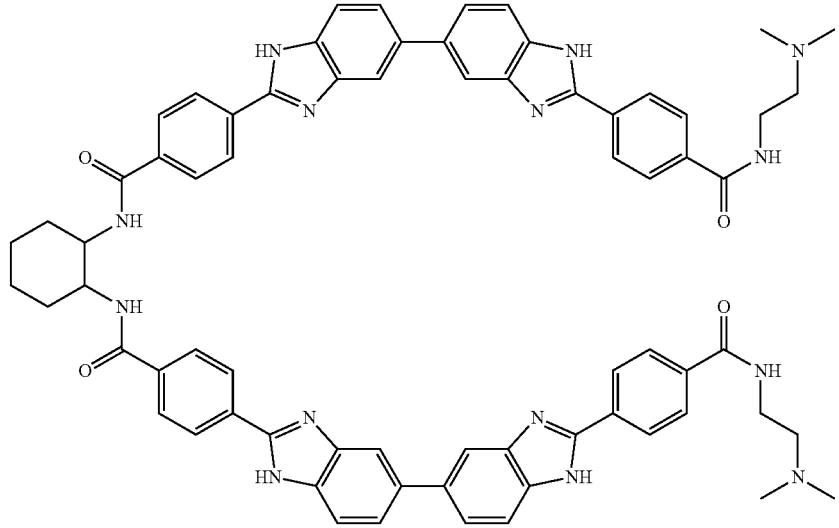 [SMILES: CN(C)CCNC(=O)c1ccc(-c2nc3cc(-c4ccc5[nH]c(-c6ccc(C(=O)NC7CCCCC7NC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 411 | 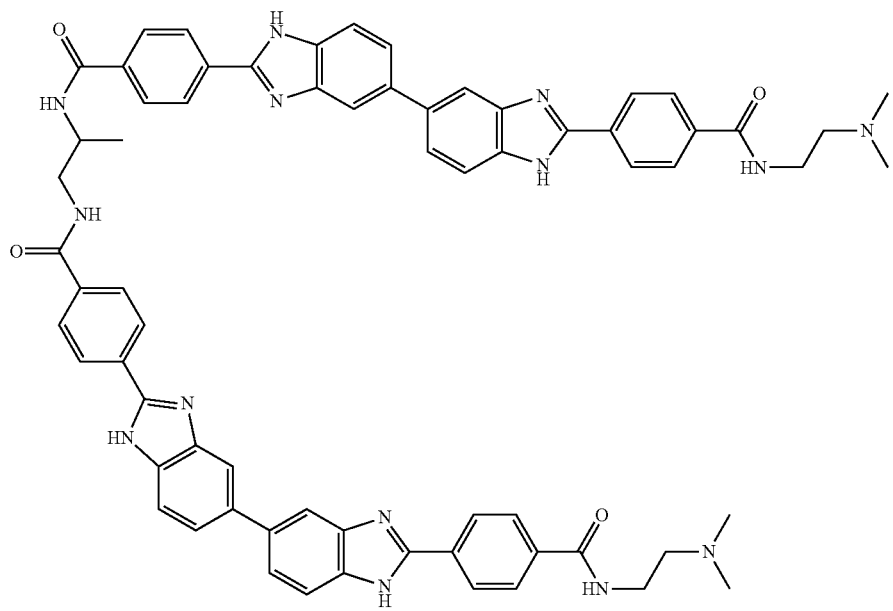 [SMILES: CC(CNC(=O)c1ccc(-c2nc3cc(-c4ccc5[nH]c(-c6ccc(C(=O)NCCN(C)C)cc6)nc5c4)ccc3[nH]2)cc1)NC(=O)c1ccc(-c2nc3cc(-c4ccc5[nH]c(-c6ccc(C(=O)NCCN(C)C)cc6)nc5c4)ccc3[nH]2)cc1] |

TABLE K-continued

| Compound # | Structure |
|---|---|
| 412 | 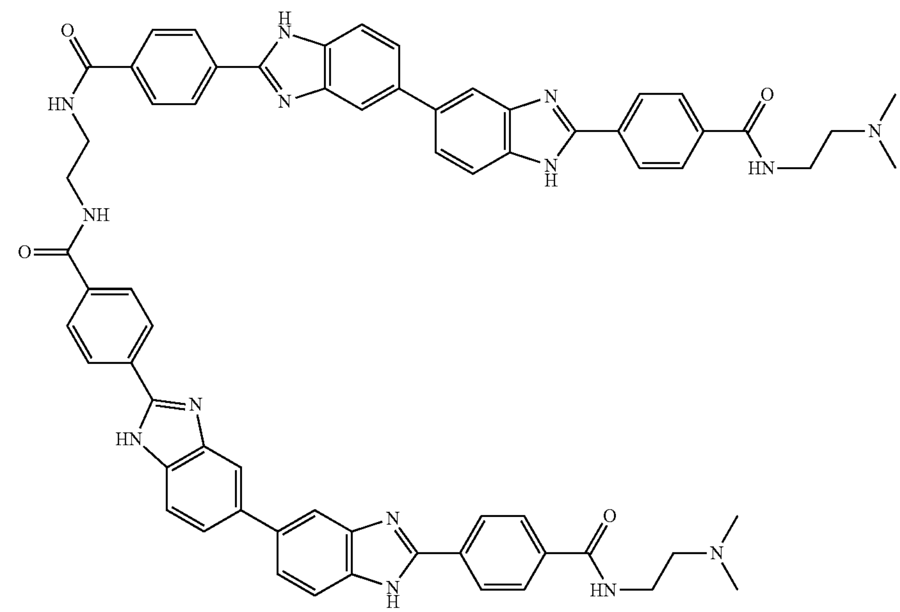 [SMILES: CN(C)CCNC(=O)c1ccc(-c2nc3cc(-c4ccc5[nH]c(-c6ccc(C(=O)NCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 413 | 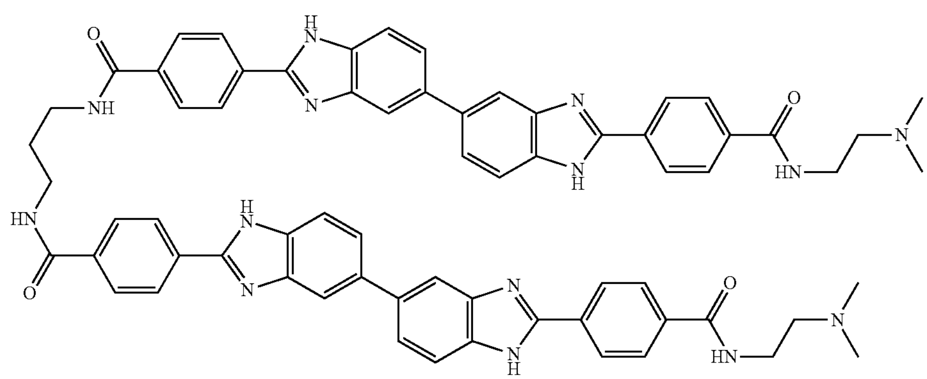 [SMILES: CN(C)CCNC(=O)c1ccc(-c2nc3cc(-c4ccc5[nH]c(-c6ccc(C(=O)NCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 414 | 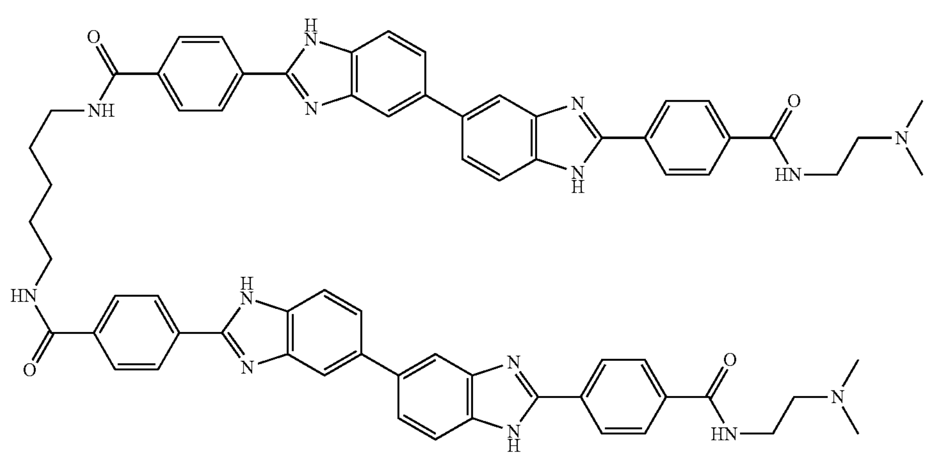 [SMILES: CN(C)CCNC(=O)c1ccc(-c2nc3cc(-c4ccc5[nH]c(-c6ccc(C(=O)NCCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |

TABLE K-continued
| Compound # | Structure |
|---|---|
| 415 | 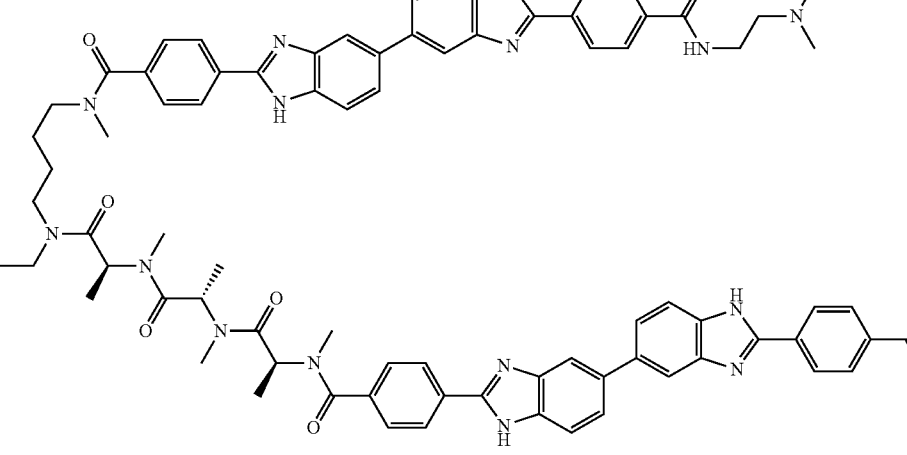 |
| 416 | 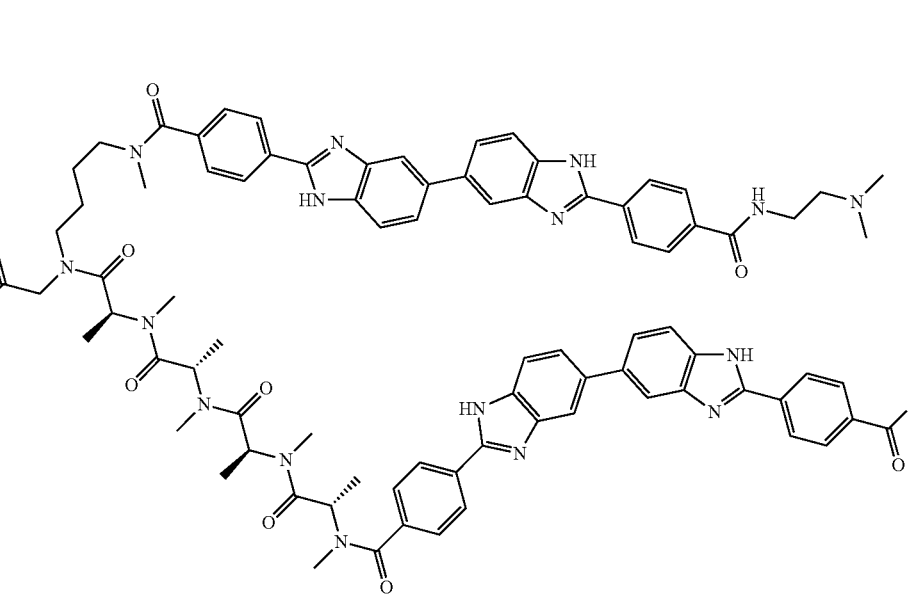 |
| 417 | 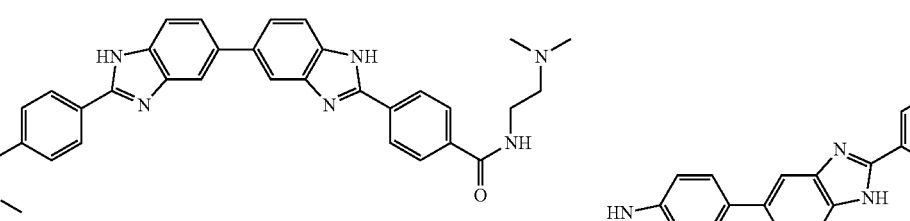 |

TABLE K-continued
| Compound # | Structure |
|---|---|
| 418 | 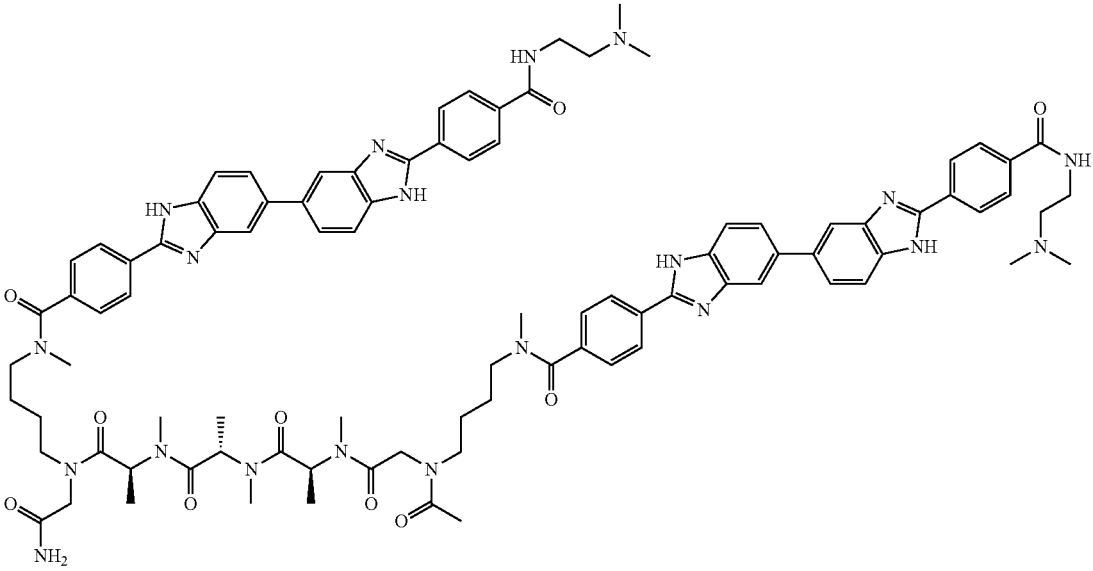 [SMILES: CC(=O)N(CCCCN(C)C(=O)c1ccc(-c2nc3cc(-c4ccc5[nH]c(-c6ccc(C(=O)NCCN(C)C)cc6)nc5c4)ccc3[nH]2)cc1)CC(=O)N(C)[C@@H](C)C(=O)N(C)[C@@H](C)C(=O)N(C)[C@@H](C)C(=O)N(CCCCN(C)C(=O)c1ccc(-c2nc3cc(-c4ccc5[nH]c(-c6ccc(C(=O)NCCN(C)C)cc6)nc5c4)ccc3[nH]2)cc1)CC(N)=O] |
| 419 | 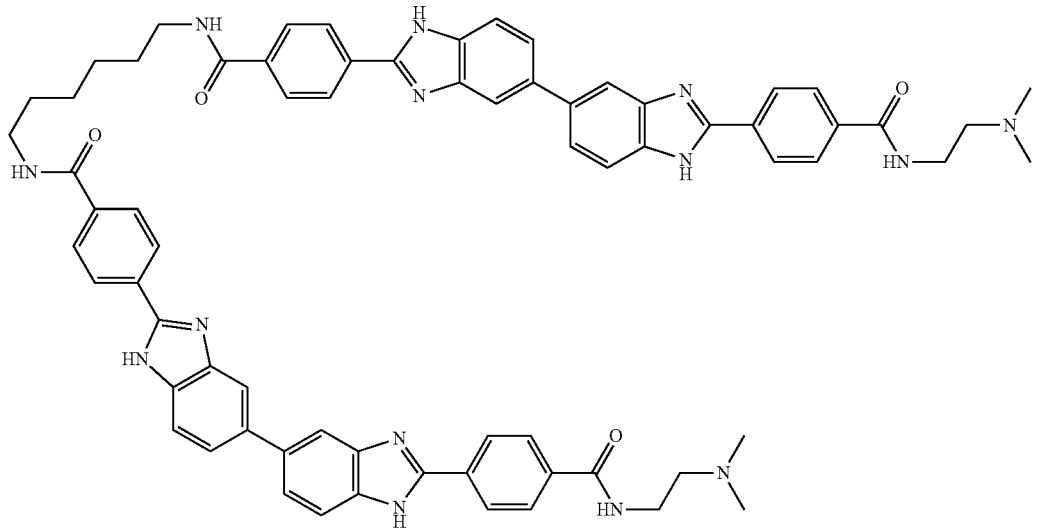 [SMILES: CN(C)CCNC(=O)c1ccc(-c2nc3cc(-c4ccc5[nH]c(-c6ccc(C(=O)NCCCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |

TABLE K-continued

| Compound # | Structure |
|---|---|
| 420 | 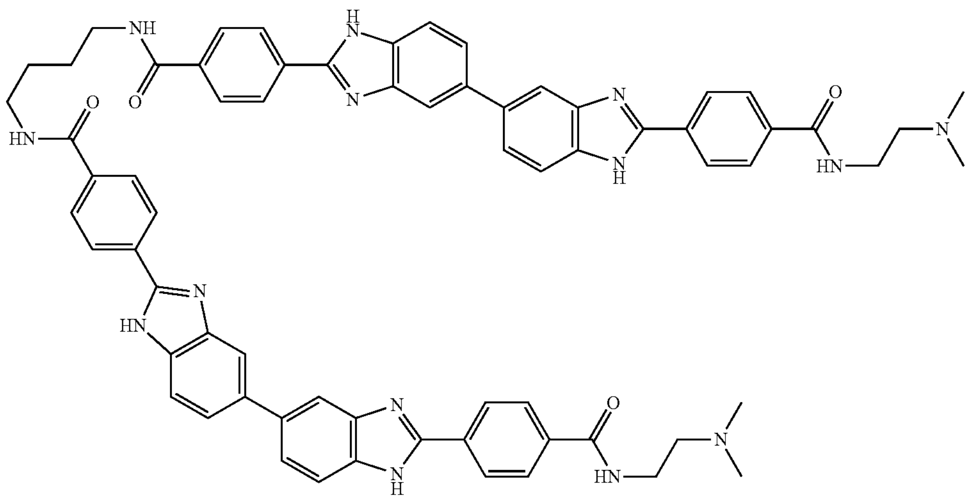 [SMILES: CN(C)CCNC(=O)c1ccc(-c2nc3cc(-c4ccc5[nH]c(-c6ccc(C(=O)NCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 421 | 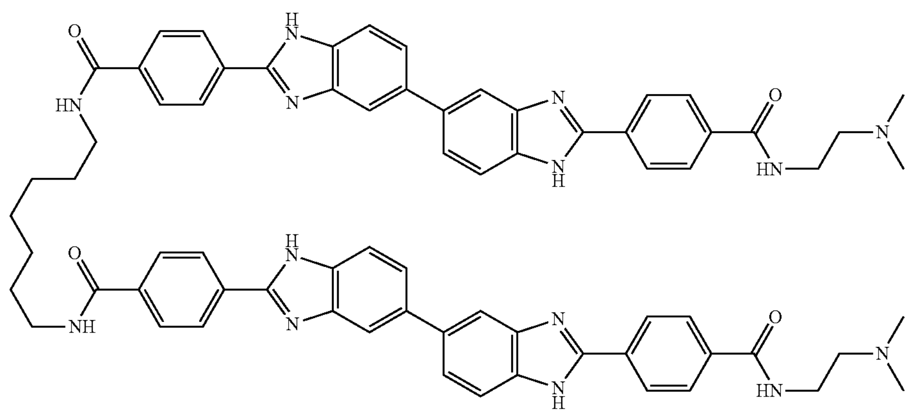 [SMILES: CN(C)CCNC(=O)c1ccc(-c2nc3cc(-c4ccc5[nH]c(-c6ccc(C(=O)NCCCCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 422 | 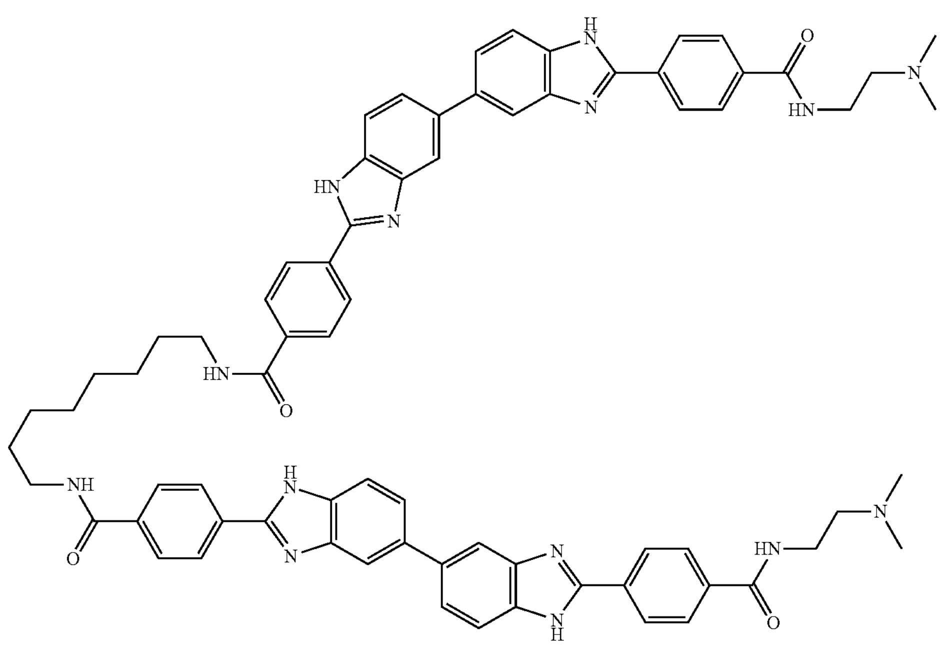 [SMILES: CN(C)CCNC(=O)c1ccc(-c2nc3cc(-c4ccc5[nH]c(-c6ccc(C(=O)NCCCCCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |

TABLE K-continued
| Compound # | Structure |
|---|---|
| 423 | 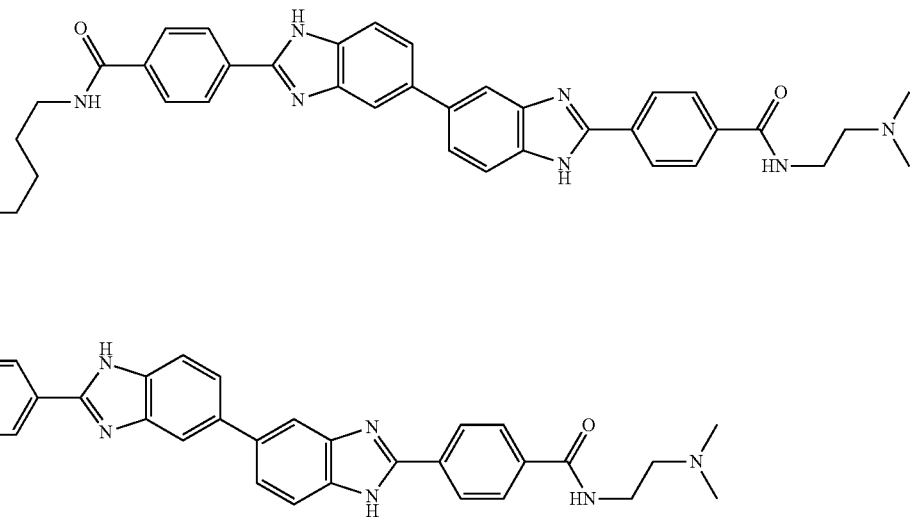 |
| 424 | 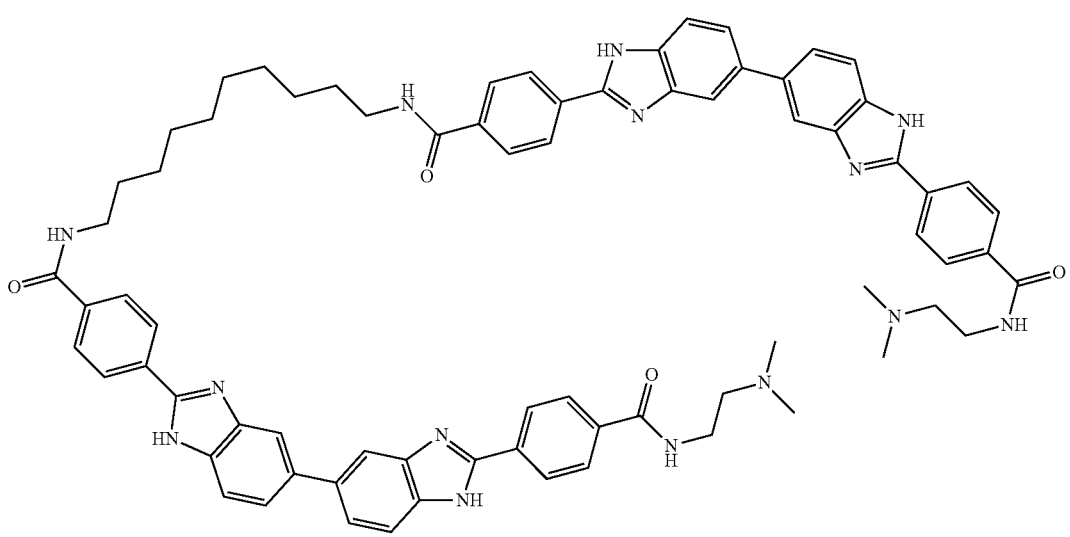 [SMILES: CN(C)CCNC(=O)c1ccc(-c2nc3cc(-c4ccc5[nH]c(-c6ccc(C(=O)NCCCCCCCCCCNC(=O)c7ccc(-c8nc9cc(-c%10ccc%11[nH]c(-c%12ccc(C(=O)NCCN(C)C)cc%12)nc%11c%10)ccc9[nH]8)cc7)cc6)nc5c4)ccc3[nH]2)cc1] |
| 425 | 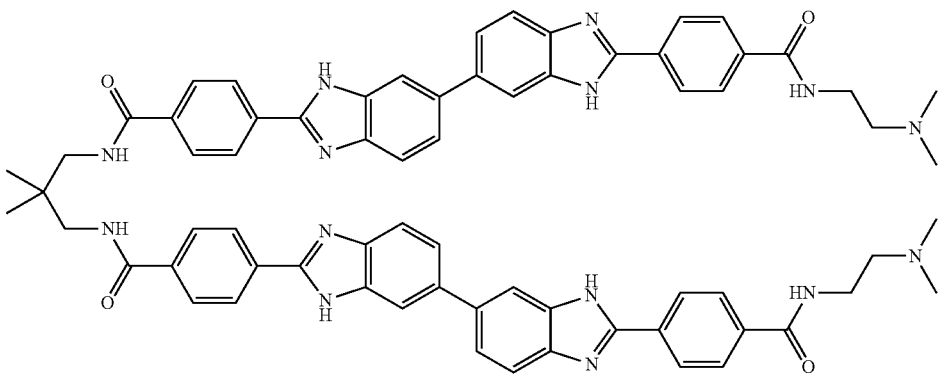 [SMILES: CN(C)CCNC(=O)c1ccc(-c2nc3ccc(-c4ccc5nc(-c6ccc(C(=O)NCC(C)(C)CNC(=O)c7ccc(-c8nc9ccc(-c%10ccc%11nc(-c%12ccc(C(=O)NCCN(C)C)cc%12)[nH]c%11c%10)cc9[nH]8)cc7)cc6)[nH]c5c4)cc3[nH]2)cc1] |

US 10,961,202 B2
157 158
TABLE K-continued
| Compound # | Structure |
|---|---|
| 426 | 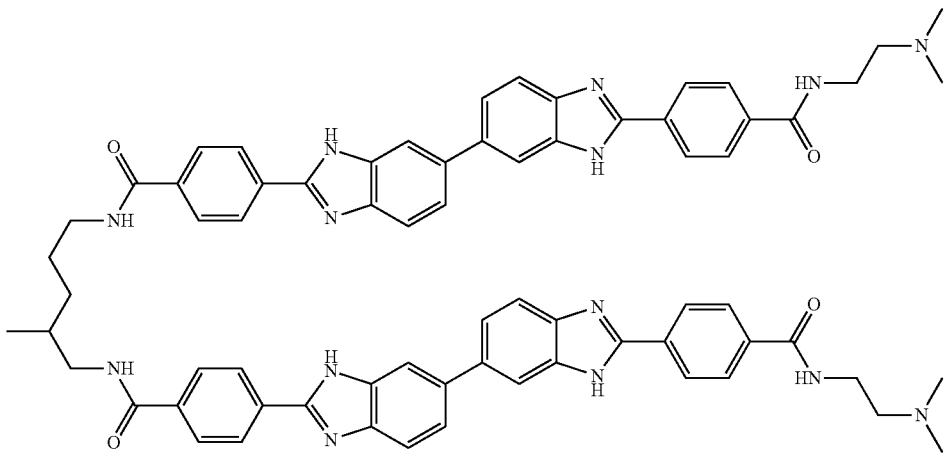 [SMILES: CC(CCCNC(=O)c1ccc(-c2nc3ccc(-c4ccc5nc(-c6ccc(C(=O)NCCN(C)C)cc6)[nH]c5c4)cc3[nH]2)cc1)CNC(=O)c1ccc(-c2nc3ccc(-c4ccc5nc(-c6ccc(C(=O)NCCN(C)C)cc6)[nH]c5c4)cc3[nH]2)cc1] |
| 427 | 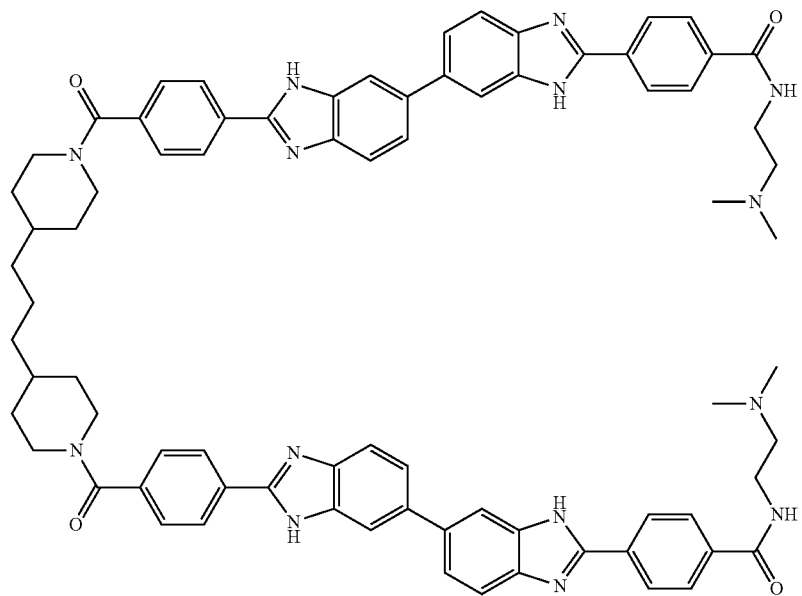 [SMILES: CN(C)CCNC(=O)c1ccc(-c2nc3ccc(-c4ccc5nc(-c6ccc(C(=O)N7CCC(CCCC8CCN(C(=O)c9ccc(-c%10nc%11ccc(-c%12ccc%13nc(-c%14ccc(C(=O)NCCN(C)C)cc%14)[nH]c%13c%12)cc%11[nH]%10)cc9)CC8)CC7)cc6)[nH]c5c4)cc3[nH]2)cc1] |
| 428 | 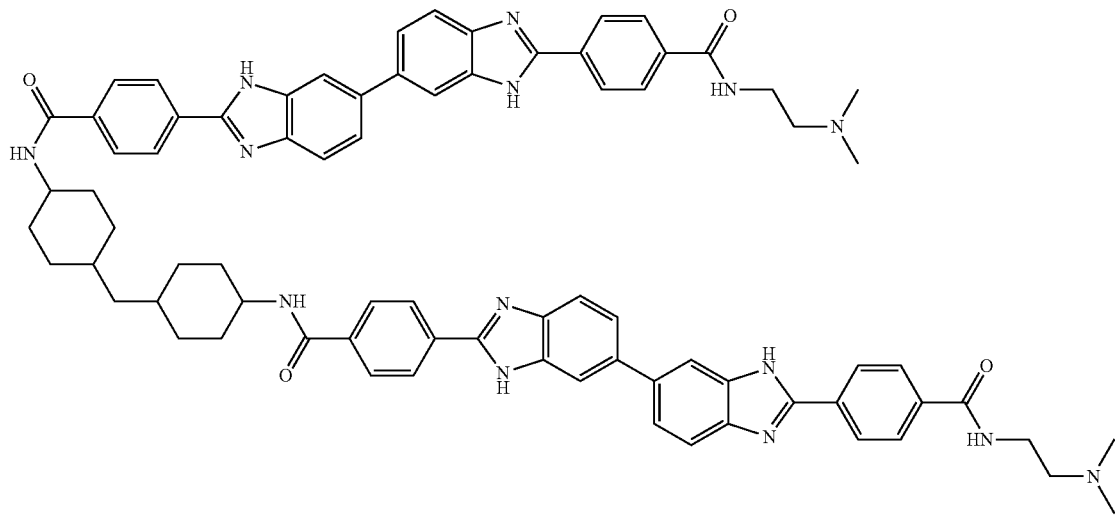 [SMILES: CN(C)CCNC(=O)c1ccc(-c2nc3ccc(-c4ccc5nc(-c6ccc(C(=O)NC7CCC(CC8CCC(NC(=O)c9ccc(-c%10nc%11ccc(-c%12ccc%13nc(-c%14ccc(C(=O)NCCN(C)C)cc%14)[nH]c%13c%12)cc%11[nH]%10)cc9)CC8)CC7)cc6)[nH]c5c4)cc3[nH]2)cc1] |

| Compound # | Structure |
|---|---|
| 429 | 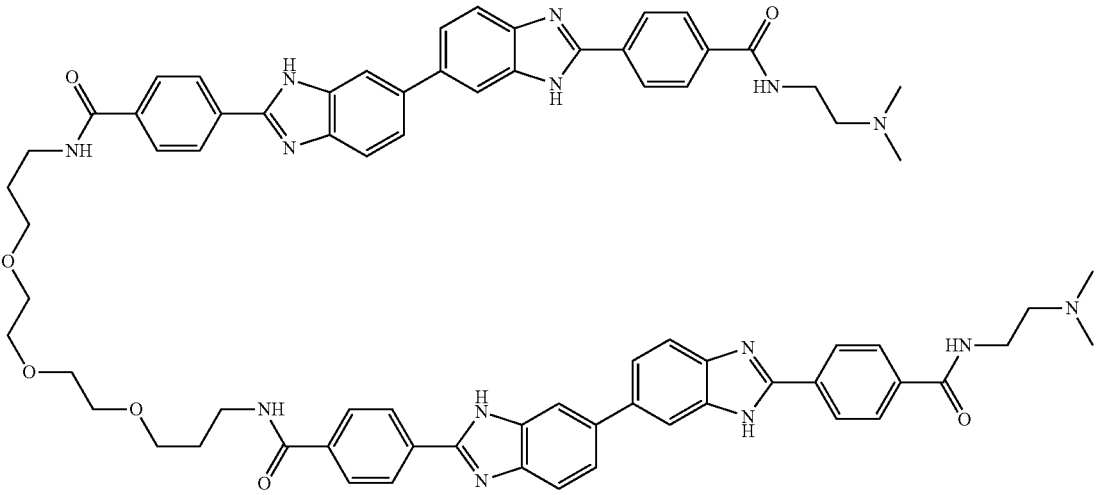 [SMILES: CN(C)CCNC(=O)c1ccc(-c2nc3ccc(-c4ccc5nc(-c6ccc(C(=O)NCCCOCCOCCOCCCNC(=O)c7ccc(-c8nc9ccc(-c%10ccc%11nc(-c%12ccc(C(=O)NCCN(C)C)cc%12)[nH]c%11c%10)cc9[nH]8)cc7)cc6)[nH]c5c4)cc3[nH]2)cc1] |
| 430 | 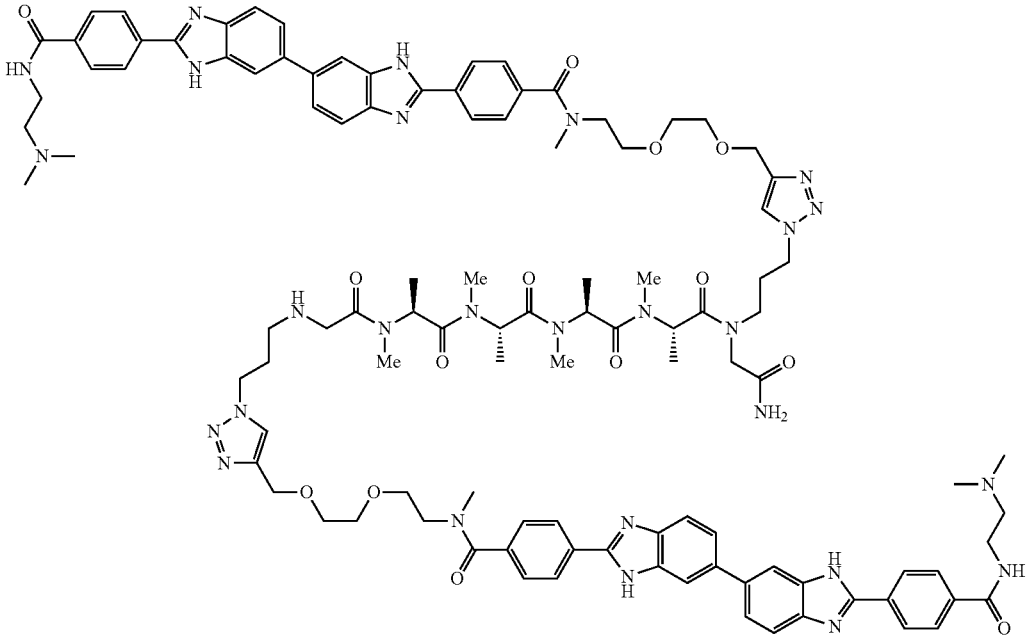 [SMILES: C[C@@H](C(=O)N(C)[C@@H](C)C(=O)N(C)[C@@H](C)C(=O)N(C)[C@@H](C)C(=O)N(CCCn1cc(COCCOCCN(C)C(=O)c2ccc(-c3nc4ccc(-c5ccc6nc(-c7ccc(C(=O)NCCN(C)C)cc7)[nH]c6c5)cc4[nH]3)cc2)nn1)CC(N)=O)N(C)C(=O)CNCCCn1cc(COCCOCCN(C)C(=O)c2ccc(-c3nc4ccc(-c5ccc6nc(-c7ccc(C(=O)NCCN(C)C)cc7)[nH]c6c5)cc4[nH]3)cc2)nn1] |

TABLE K-continued
| Compound # | Structure |
|---|---|
| 431 | 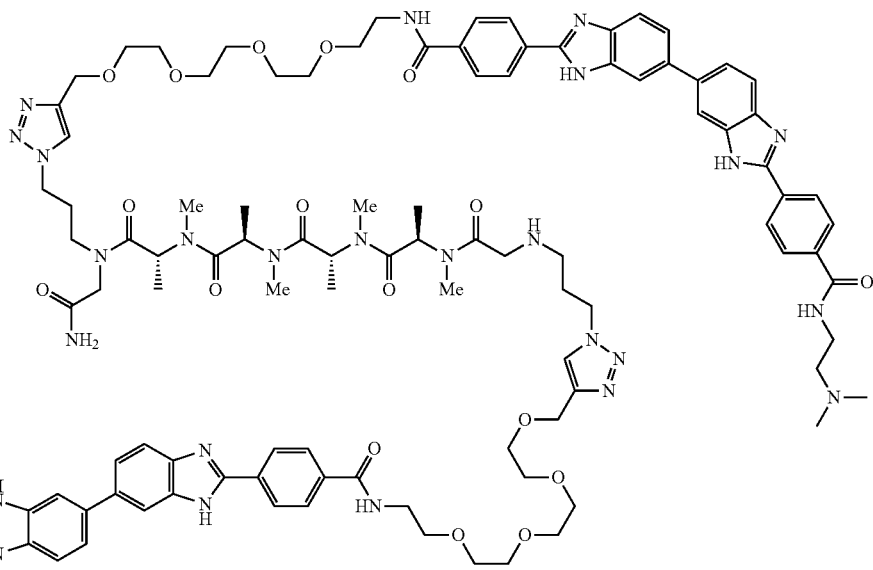 |
| 432 | 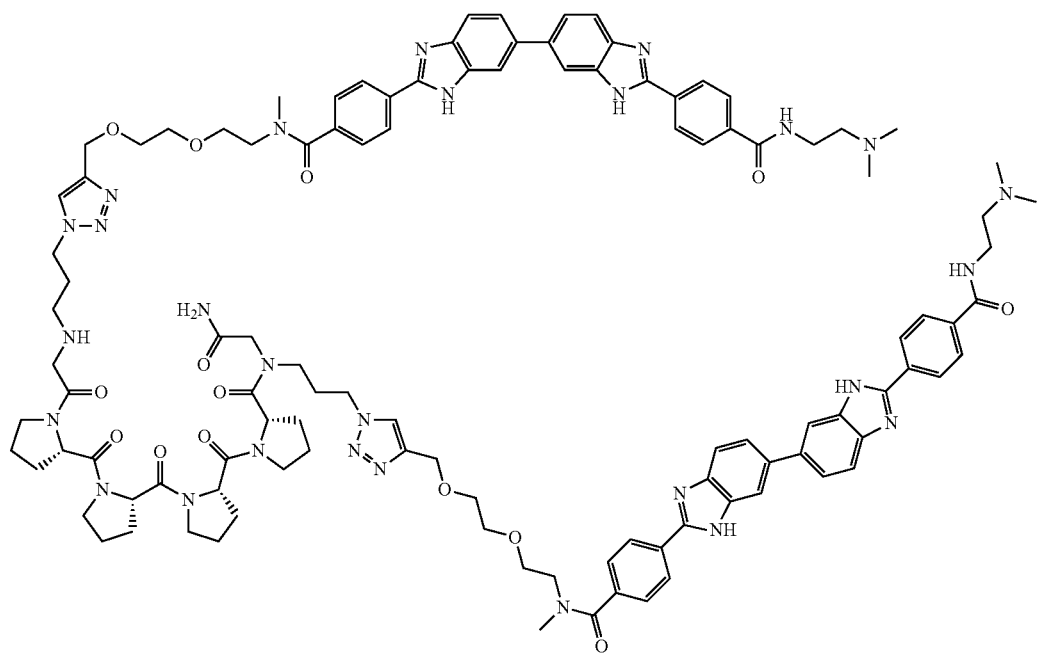 [SMILES: CN(C)CCNC(=O)c1ccc(-c2nc3ccc(-c4ccc5nc(-c6ccc(C(=O)N(C)CCOCCOCc7cn(CCCNCC(=O)N8CCC[C@H]8C(=O)N8CCC[C@H]8C(=O)N8CCC[C@H]8C(=O)N8CCC[C@H]8C(=O)N(CCCn8cc(COCCOCCN(C)C(=O)c9ccc(-c%10nc%11ccc(-c%12ccc%13nc(-c%14ccc(C(=O)NCCN(C)C)cc%14)[nH]c%13c%12)cc%11[nH]%10)cc9)nn8)CC(N)=O)nn7)cc6)[nH]c5c4)cc3[nH]2)cc1] |

163 164
TABLE K-continued
| Compound # | Structure |
|---|---|
| 433 | 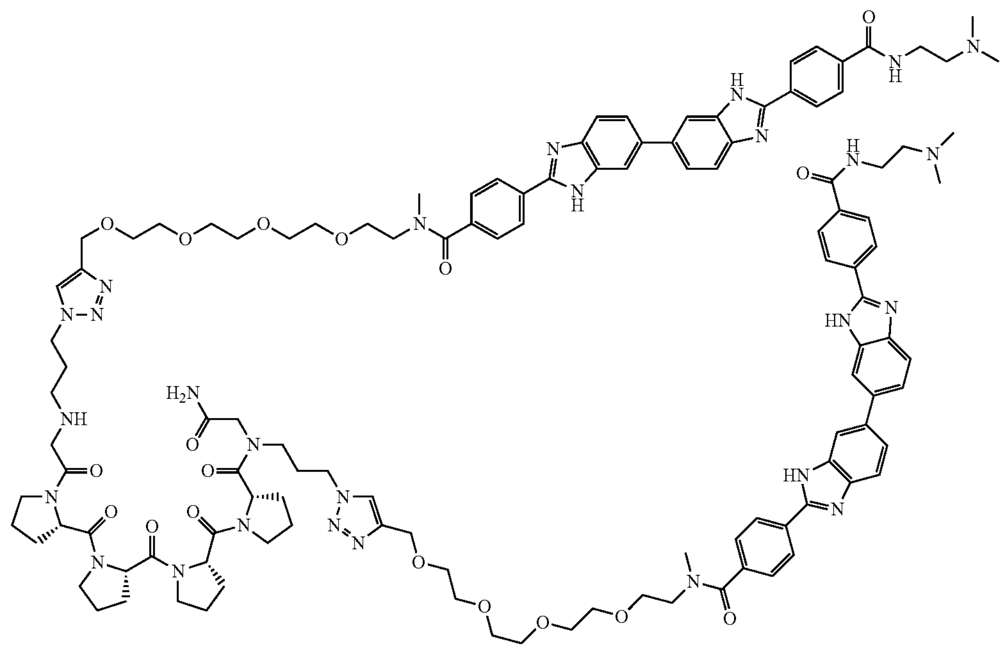 [SMILES: CN(C)CCNC(=O)c1ccc(-c2nc3ccc(-c4ccc5nc(-c6ccc(C(=O)N(C)CCOCCOCCOCCOCc7cn(CCCNCC(=O)N8CCC[C@H]8C(=O)N8CCC[C@H]8C(=O)N8CCC[C@H]8C(=O)N8CCC[C@H]8C(=O)N(CCCn8cc(COCCOCCOCCOCCN(C)C(=O)c9ccc(-c%10nc%11ccc(-c%12ccc%13nc(-c%14ccc(C(=O)NCCN(C)C)cc%14)[nH]c%13c%12)cc%11[nH]%10)cc9)nn8)CC(N)=O)nn7)cc6)[nH]c5c4)cc3[nH]2)cc1] |
| 434 | 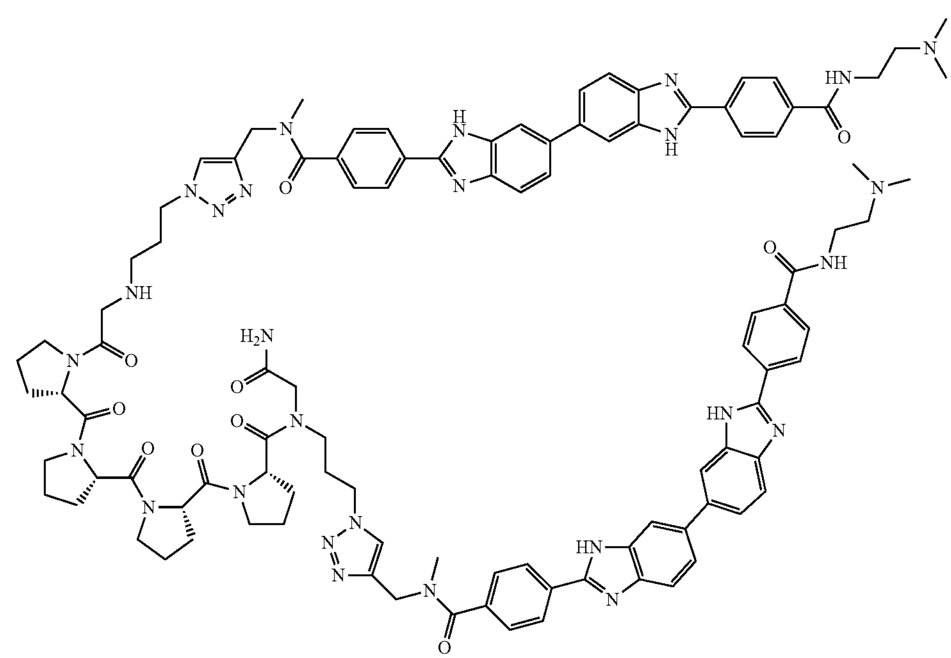 [SMILES: CN(C)CCNC(=O)c1ccc(-c2nc3ccc(-c4ccc5nc(-c6ccc(C(=O)N(C)Cc7cn(CCCNCC(=O)N8CCC[C@H]8C(=O)N8CCC[C@H]8C(=O)N8CCC[C@H]8C(=O)N8CCC[C@H]8C(=O)N(CCCn8cc(CN(C)C(=O)c9ccc(-c%10nc%11ccc(-c%12ccc%13nc(-c%14ccc(C(=O)NCCN(C)C)cc%14)[nH]c%13c%12)cc%11[nH]%10)cc9)nn8)CC(N)=O)nn7)cc6)[nH]c5c4)cc3[nH]2)cc1] |
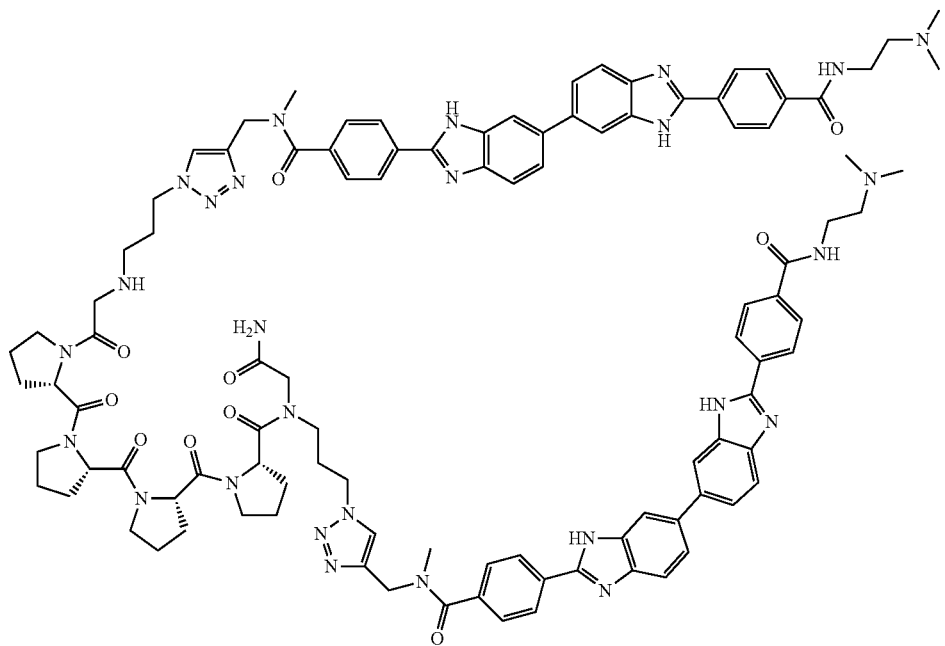

| Compound # | Structure |
|---|---|
| 435 | 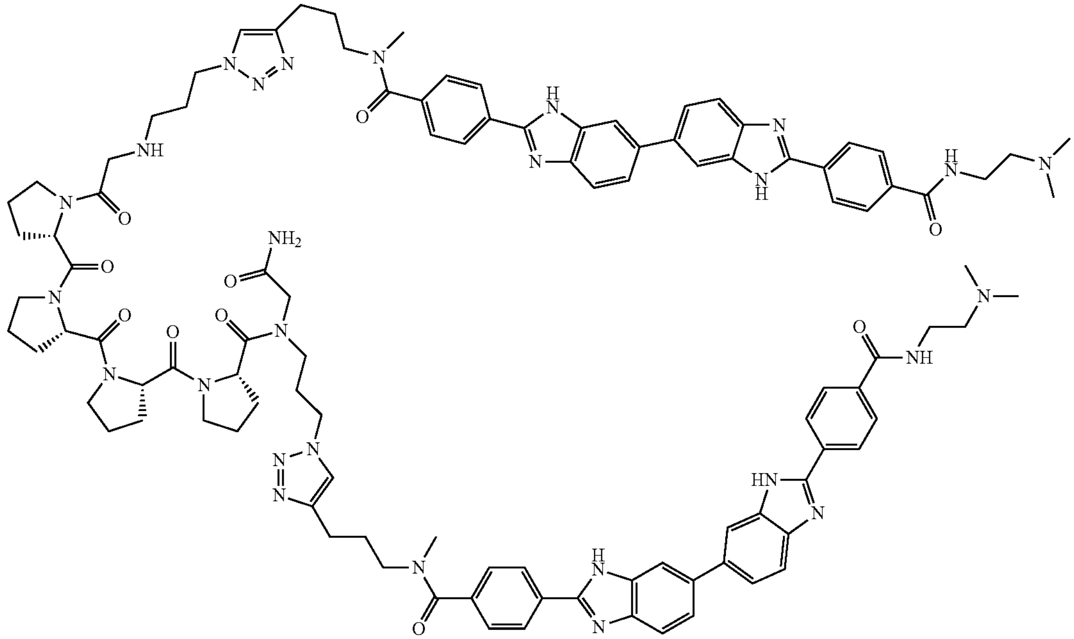 [SMILES: CN(C)CCNC(=O)c1ccc(-c2nc3ccc(-c4ccc5nc(-c6ccc(C(=O)N(C)CCCc7cn(CCCNCC(=O)N8CCC[C@H]8C(=O)N8CCC[C@H]8C(=O)N8CCC[C@H]8C(=O)N8CCC[C@H]8C(=O)N(CCCn8cc(CCCN(C)C(=O)c9ccc(-c%10nc%11ccc(-c%12ccc%13nc(-c%14ccc(C(=O)NCCN(C)C)cc%14)[nH]c%13c%12)cc%11[nH]%10)cc9)nn8)CC(N)=O)nn7)cc6)[nH]c5c4)cc3[nH]2)cc1] |
| 436 | 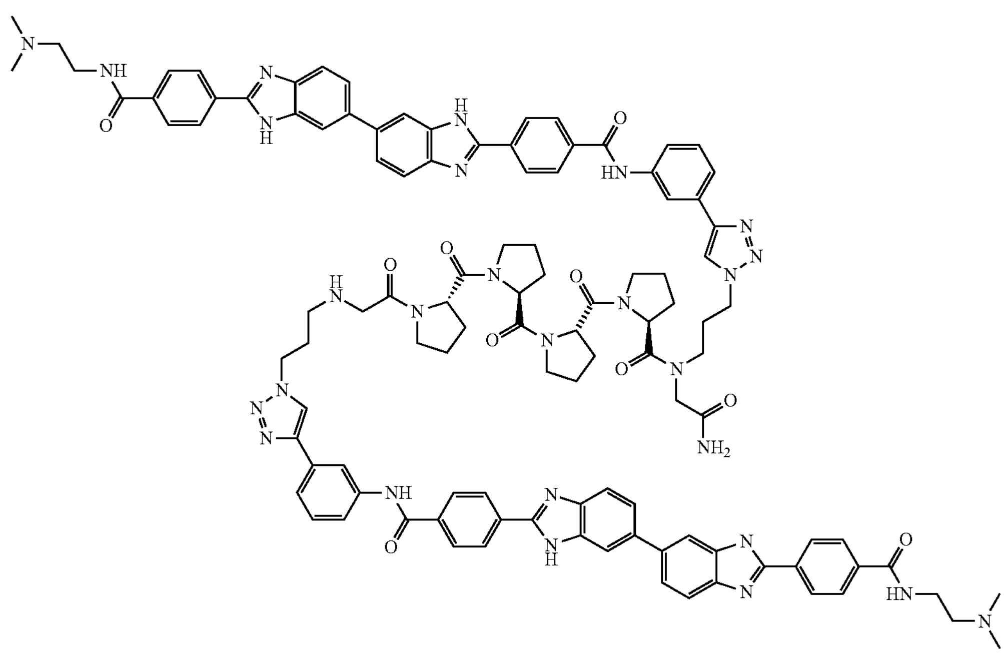 |

TABLE K-continued

| Compound # | Structure |
|---|---|
| 437 | 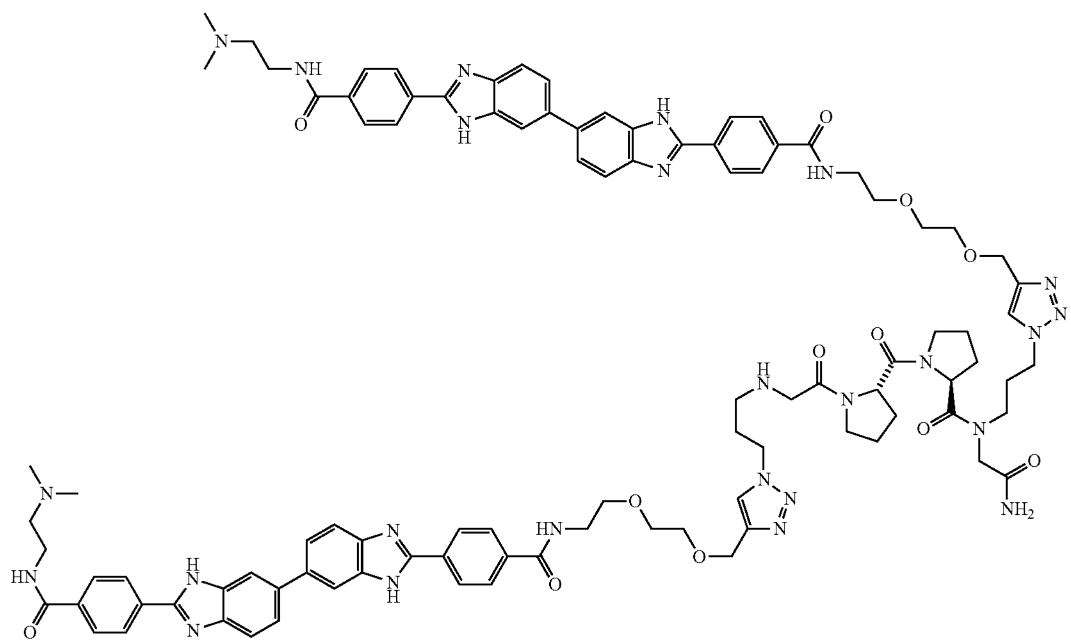 |
| 438 | 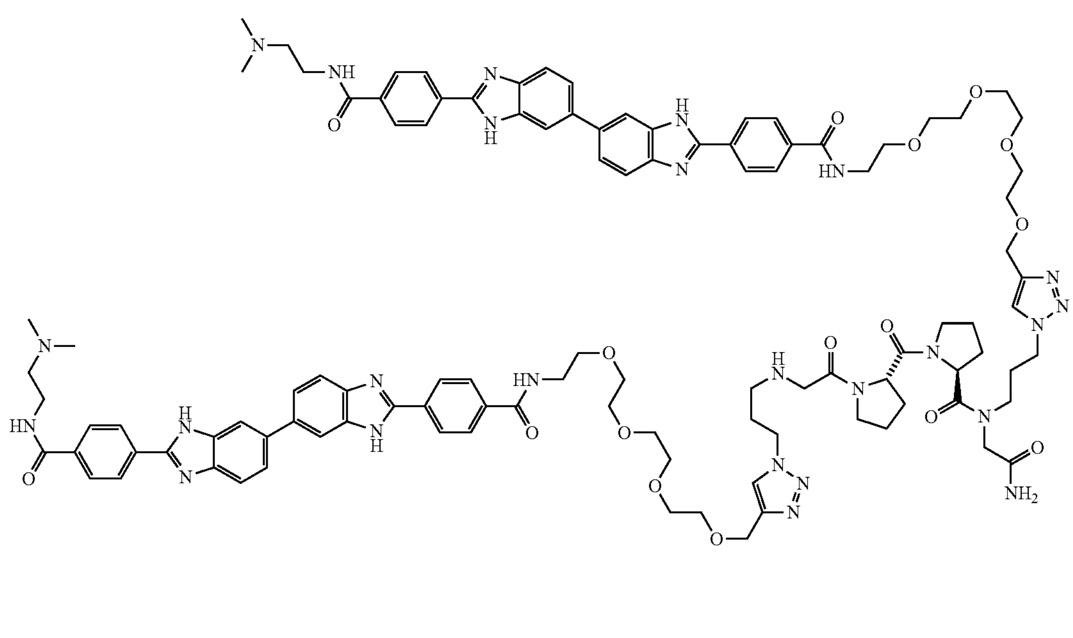 |

TABLE K-continued
| Compound # | Structure |
|---|---|
| 439 | 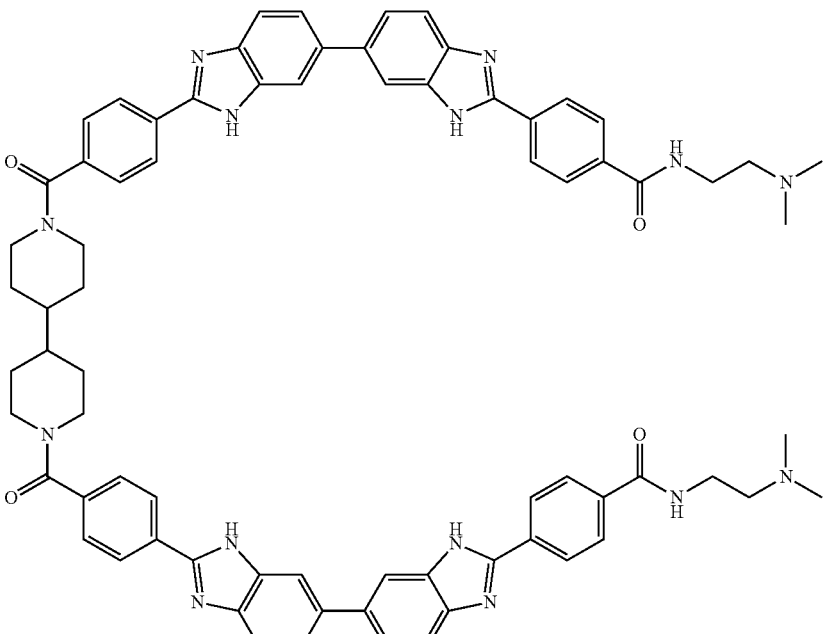 |
| 440 | 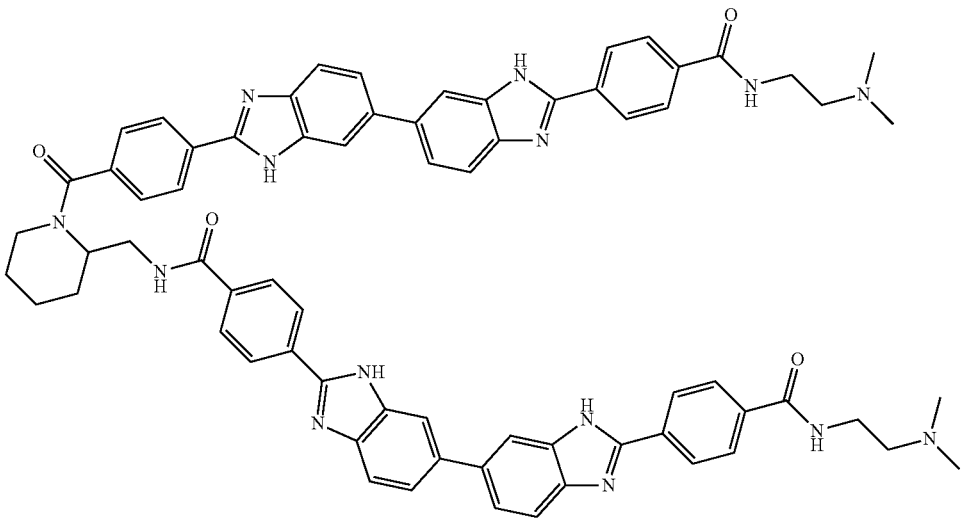 [SMILES: CN(C)CCNC(=O)c1ccc(-c2nc3ccc(-c4ccc5nc(-c6ccc(C(=O)NCC7CCCCN7C(=O)c7ccc(-c8nc9ccc(-c%10ccc%11nc(-c%12ccc(C(=O)NCCN(C)C)cc%12)[nH]c%11c%10)cc9[nH]8)cc7)cc6)[nH]c5c4)cc3[nH]2)cc1] |

TABLE K-continued
| Compound # | Structure |
|---|---|
| 441 | 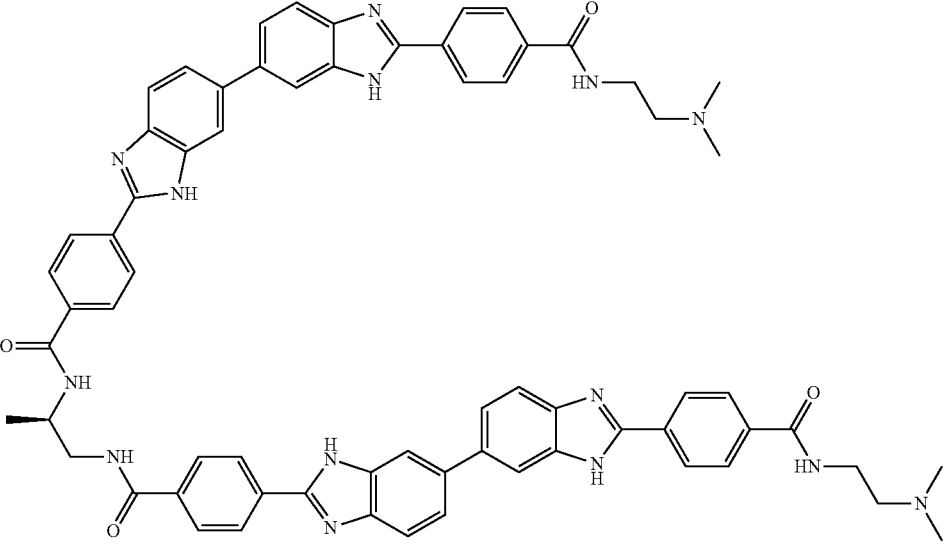 [SMILES: C[C@H](CNC(=O)c1ccc(-c2nc3ccc(-c4ccc5nc(-c6ccc(C(=O)NCCN(C)C)cc6)[nH]c5c4)cc3[nH]2)cc1)NC(=O)c1ccc(-c2nc3ccc(-c4ccc5nc(-c6ccc(C(=O)NCCN(C)C)cc6)[nH]c5c4)cc3[nH]2)cc1] |
| 442 | 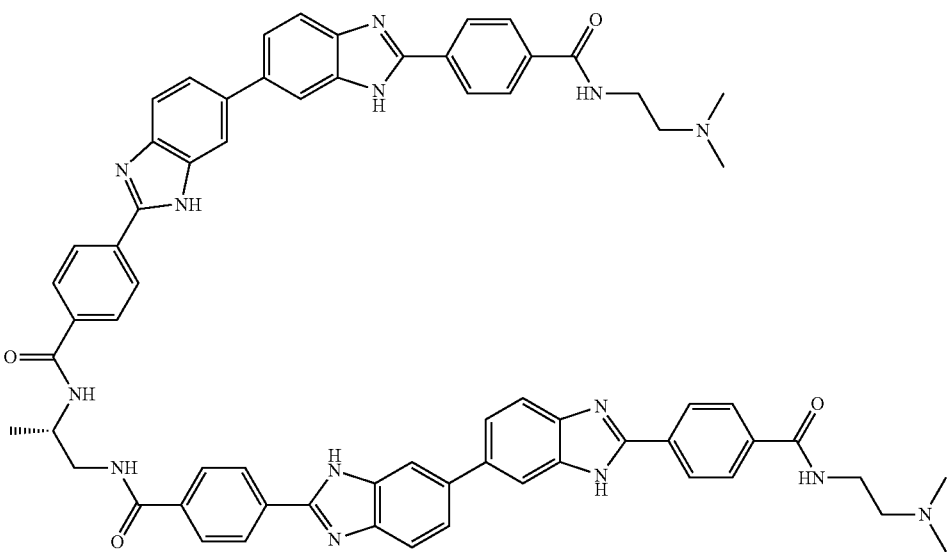 [SMILES: C[C@@H](CNC(=O)c1ccc(-c2nc3ccc(-c4ccc5nc(-c6ccc(C(=O)NCCN(C)C)cc6)[nH]c5c4)cc3[nH]2)cc1)NC(=O)c1ccc(-c2nc3ccc(-c4ccc5nc(-c6ccc(C(=O)NCCN(C)C)cc6)[nH]c5c4)cc3[nH]2)cc1] |

TABLE K-continued
| Compound # | Structure |
|---|---|
| 443 | 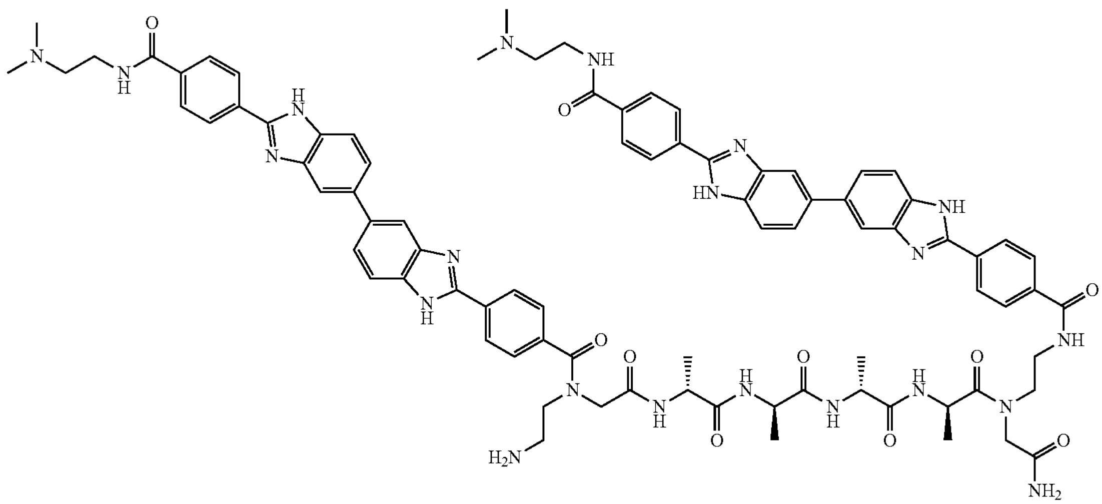 [SMILES: C[C@@H](NC(=O)CN(CCN)C(=O)c1ccc(-c2nc3cc(-c4ccc5[nH]c(-c6ccc(C(=O)NCCN(C)C)cc6)nc5c4)ccc3[nH]2)cc1)C(=O)N[C@H](C)C(=O)N[C@H](C)C(=O)N[C@H](C)C(=O)N(CCNC(=O)c1ccc(-c2nc3cc(-c4ccc5[nH]c(-c6ccc(C(=O)NCCN(C)C)cc6)nc5c4)ccc3[nH]2)cc1)CC(N)=O] |
| 444 | 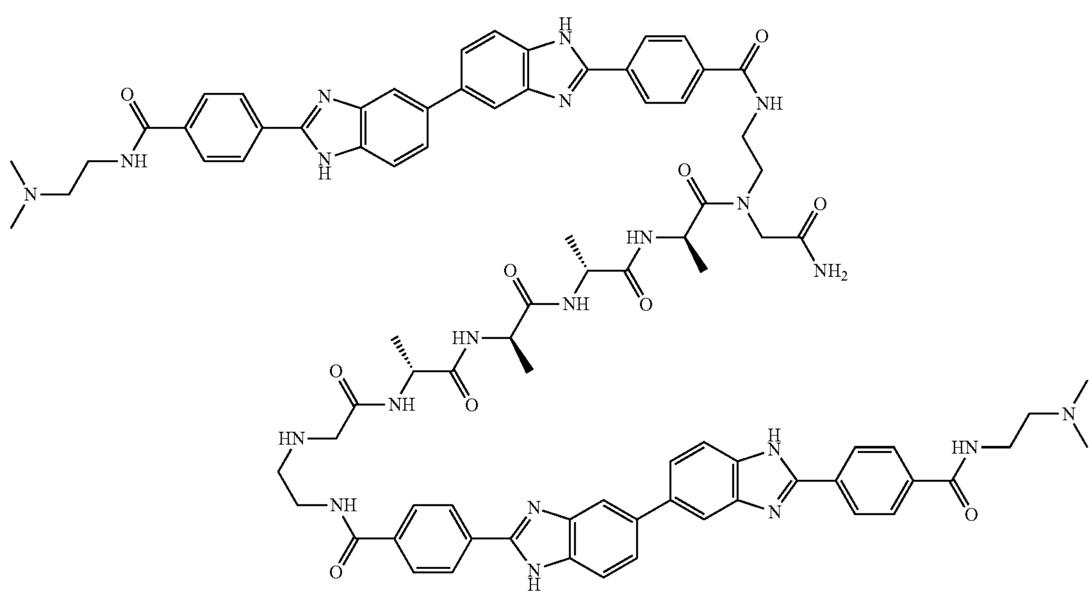 |
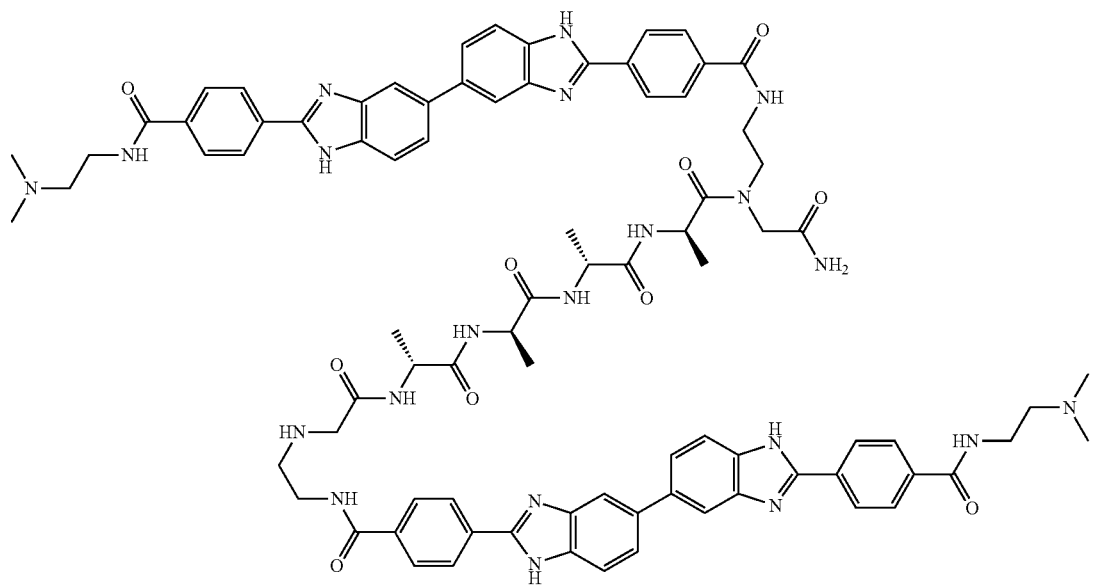

TABLE K-continued
| Compound # | Structure |
|---|---|
| 445 | 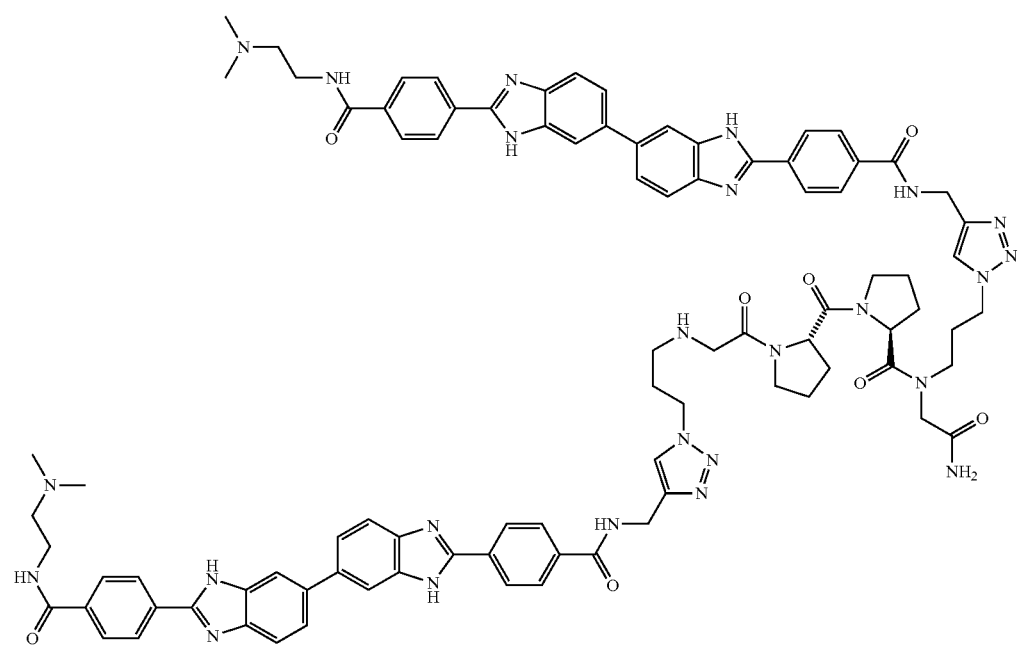 |
| 446 | 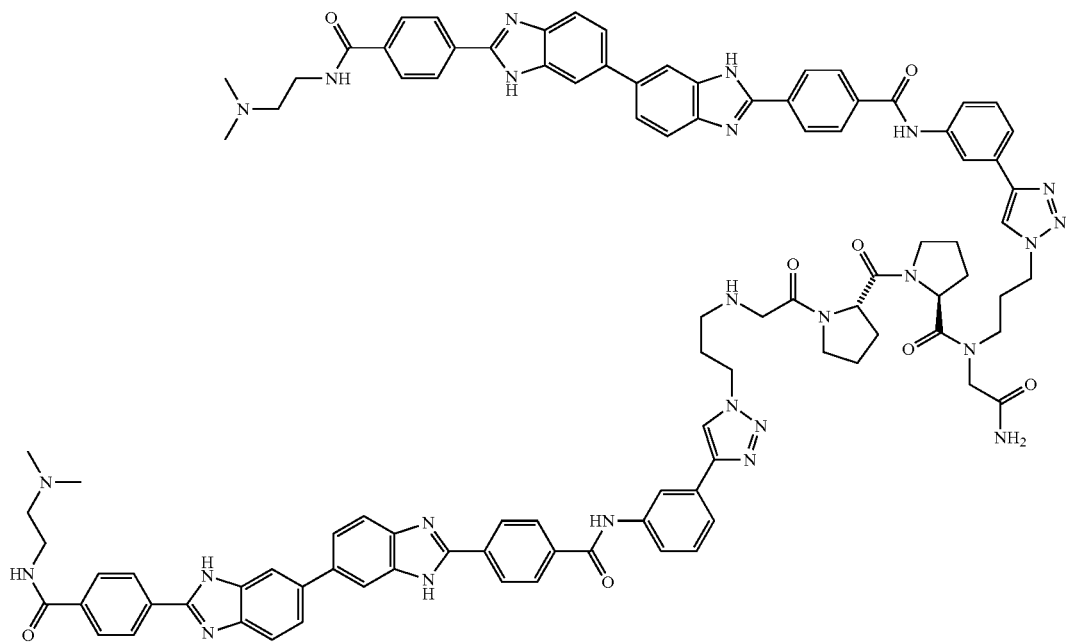 |

TABLE K-continued
| Compound # | Structure |
|---|---|
| 447 | 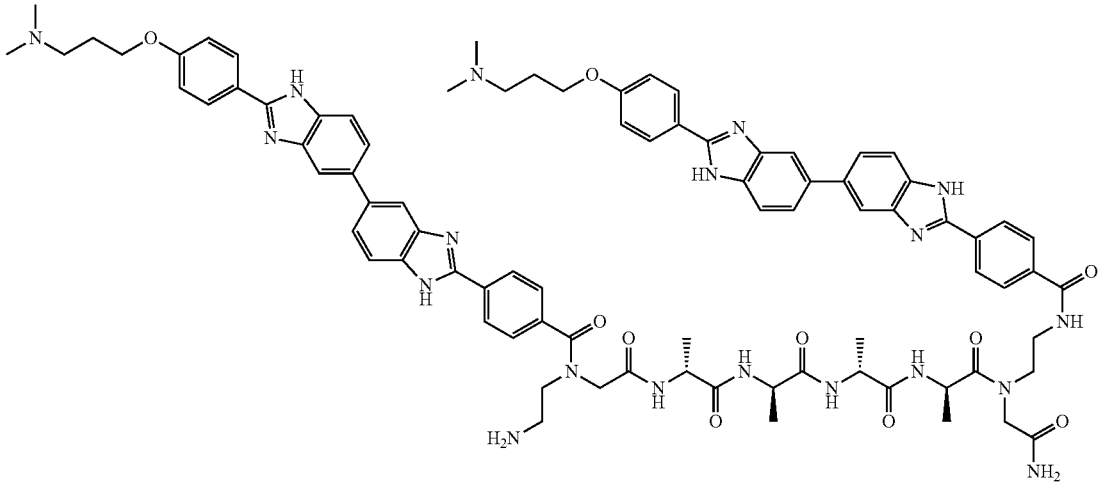 [SMILES: C[C@@H](NC(=O)CN(CCN)C(=O)c1ccc(-c2nc3cc(-c4ccc5[nH]c(-c6ccc(OCCCN(C)C)cc6)nc5c4)ccc3[nH]2)cc1)C(=O)N[C@H](C)C(=O)N[C@H](C)C(=O)N[C@H](C)C(=O)N(CCNC(=O)c1ccc(-c2nc3cc(-c4ccc5[nH]c(-c6ccc(OCCCN(C)C)cc6)nc5c4)ccc3[nH]2)cc1)CC(N)=O] |
| 448 | 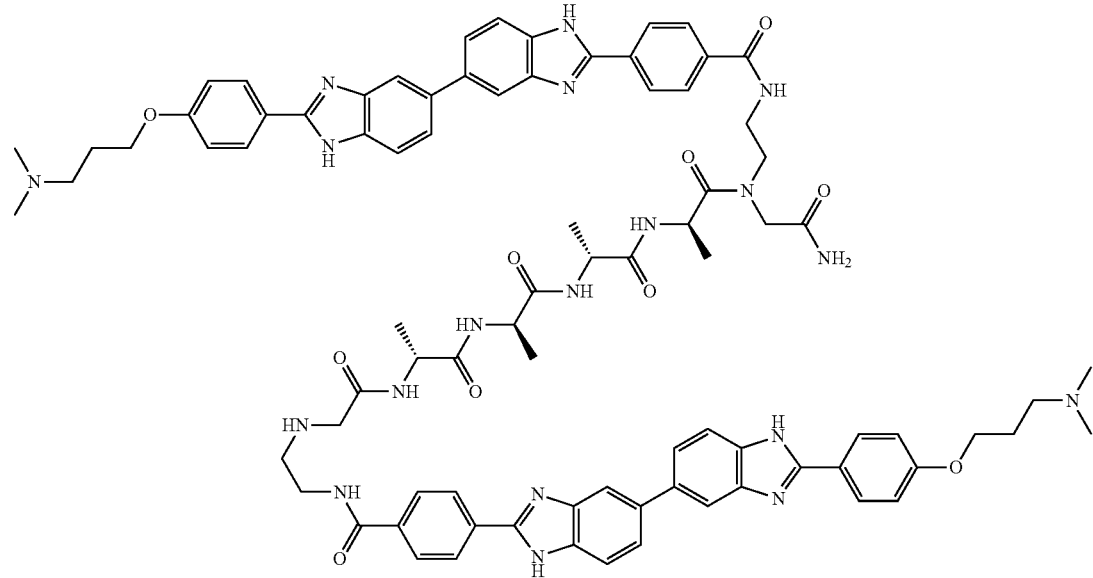 |
| 449 | 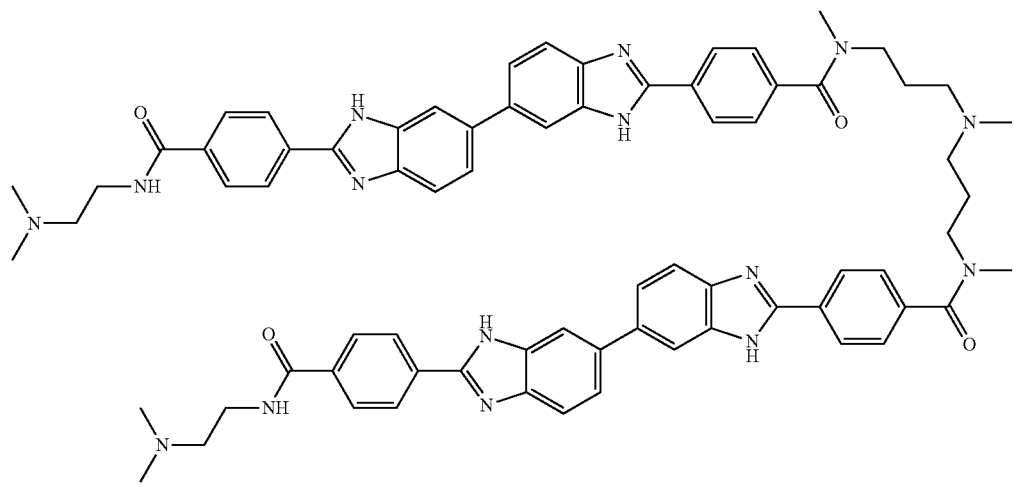 |

TABLE K-continued
| Compound # | Structure |
|---|---|
| 450 | 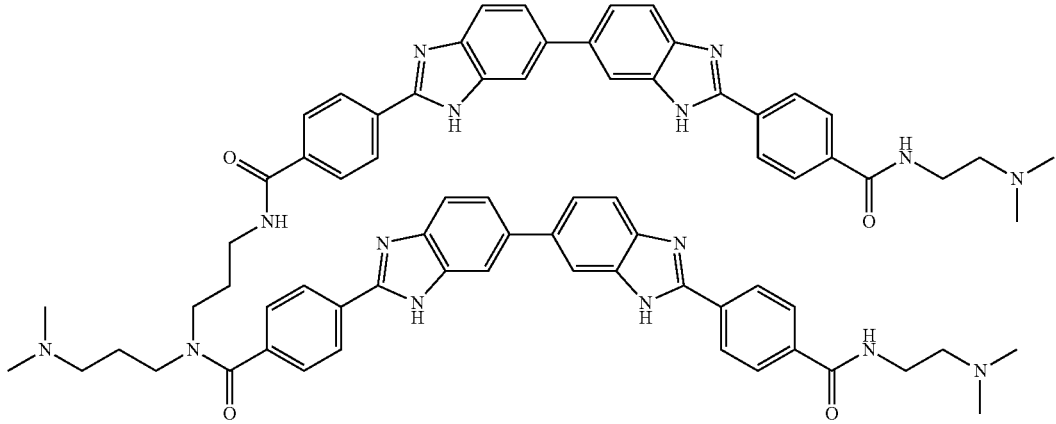 |
| 451 | 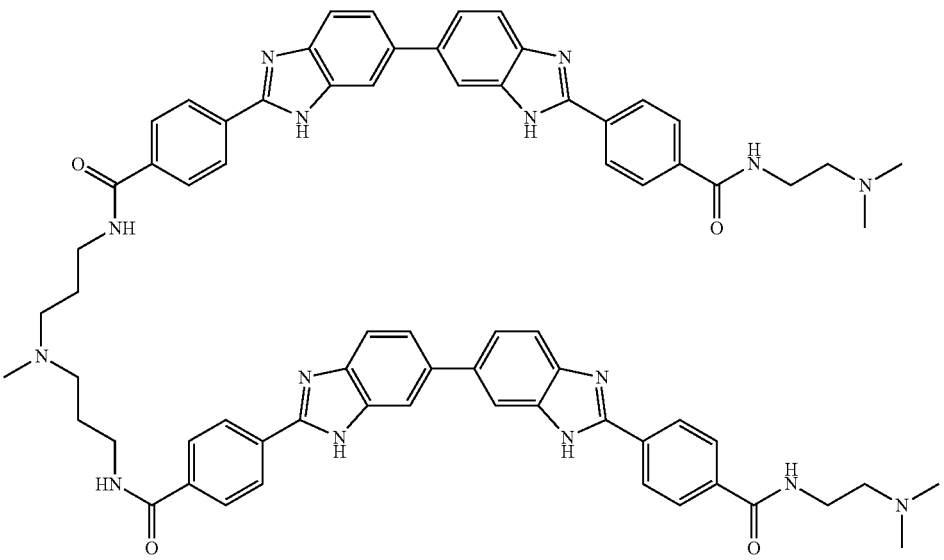 |
| 452 | 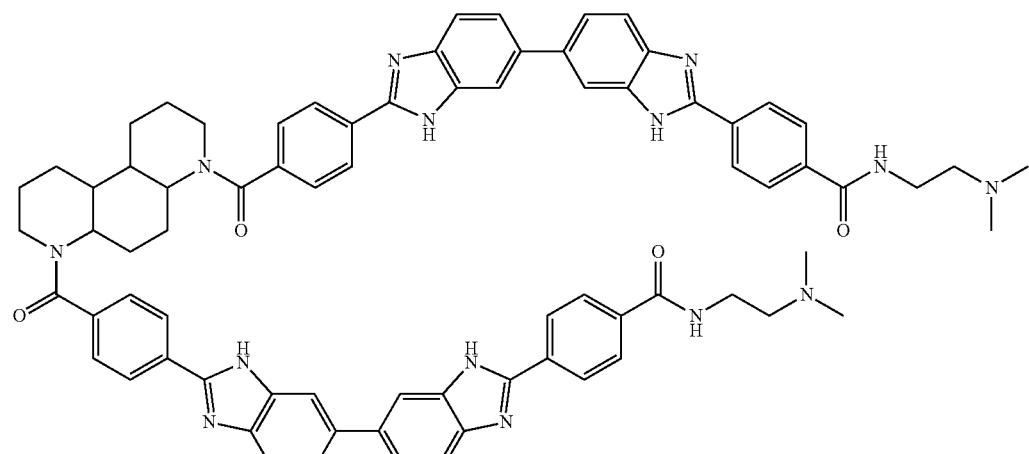 |

TABLE K-continued
| Compound # | Structure |
|---|---|
| 453 | 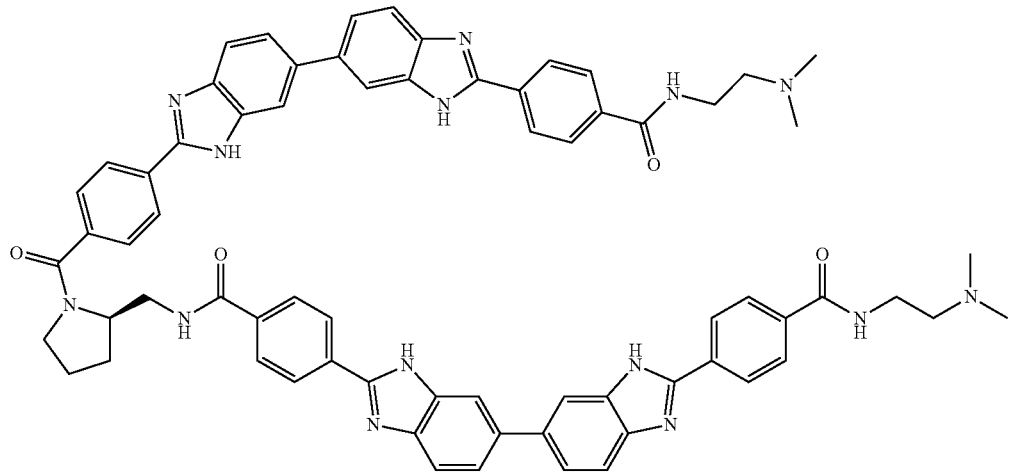 [SMILES: CN(C)CCNC(=O)c1ccc(-c2nc3ccc(-c4ccc5nc(-c6ccc(C(=O)NC[C@H]7CCCN7C(=O)c7ccc(-c8nc9ccc(-c%10ccc%11nc(-c%12ccc(C(=O)NCCN(C)C)cc%12)[nH]c%11c%10)cc9[nH]8)cc7)cc6)[nH]c5c4)cc3[nH]2)cc1] |
| 454 | 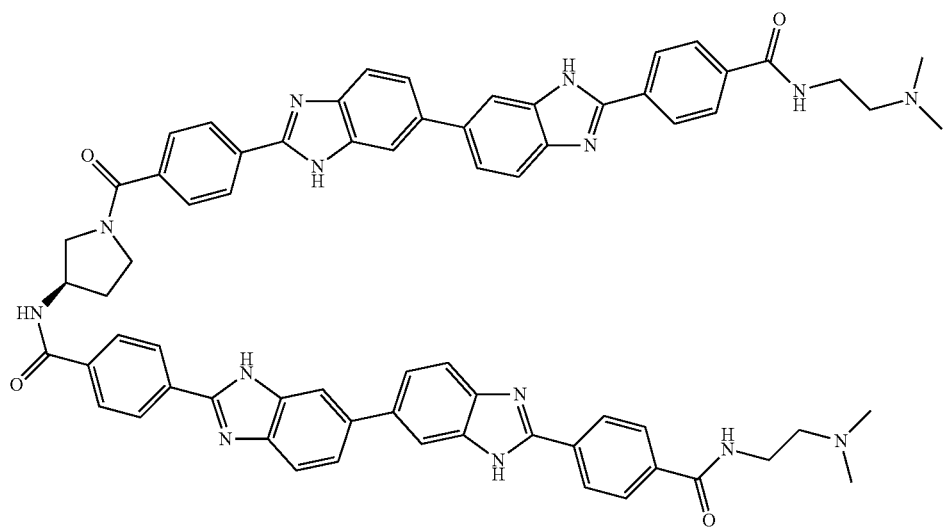 [SMILES: CN(C)CCNC(=O)c1ccc(-c2nc3ccc(-c4ccc5nc(-c6ccc(C(=O)N[C@@H]7CCN(C(=O)c8ccc(-c9nc%10ccc(-c%11ccc%12nc(-c%13ccc(C(=O)NCCN(C)C)cc%13)[nH]c%12c%11)cc%10[nH]9)cc8)C7)cc6)[nH]c5c4)cc3[nH]2)cc1] |
| 455 | 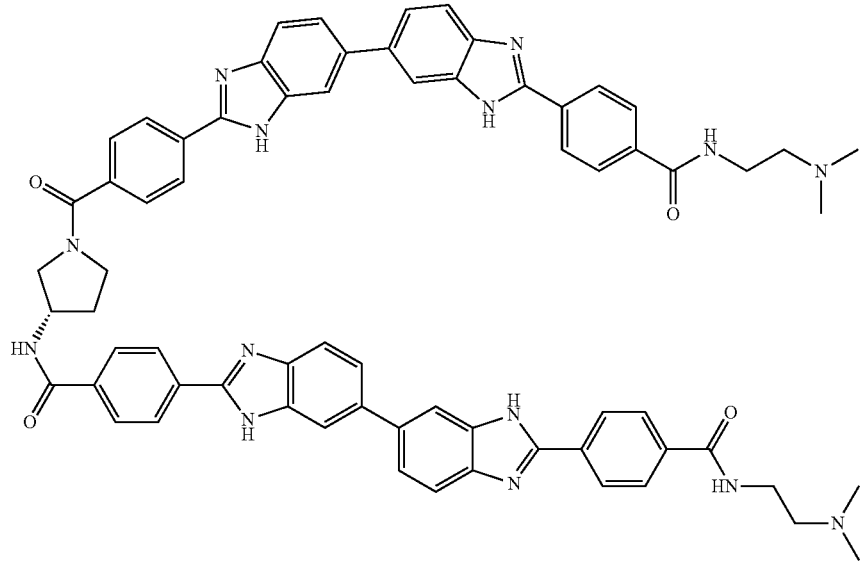 [SMILES: CN(C)CCNC(=O)c1ccc(-c2nc3ccc(-c4ccc5nc(-c6ccc(C(=O)N[C@H]7CCN(C(=O)c8ccc(-c9nc%10ccc(-c%11ccc%12nc(-c%13ccc(C(=O)NCCN(C)C)cc%13)[nH]c%12c%11)cc%10[nH]9)cc8)C7)cc6)[nH]c5c4)cc3[nH]2)cc1] |

TABLE K-continued
| Compound # | Structure |
|---|---|
| 456 | 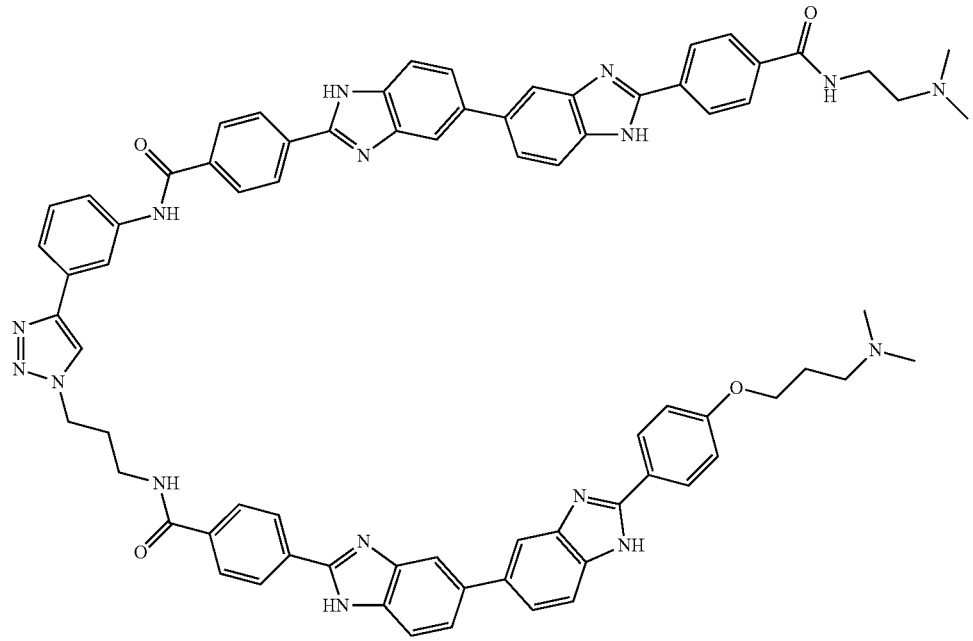 [SMILES: CN(C)CCCOc1ccc(-c2nc3cc(-c4ccc5[nH]c(-c6ccc(C(=O)NCCCn7cc(-c8cccc(NC(=O)c9ccc(-c%10nc%11cc(-c%12ccc%13[nH]c(-c%14ccc(C(=O)NCCN(C)C)cc%14)nc%13c%12)ccc%11[nH]%10)cc9)c8)nn7)cc6)nc5c4)ccc3[nH]2)cc1] |
| 457 | 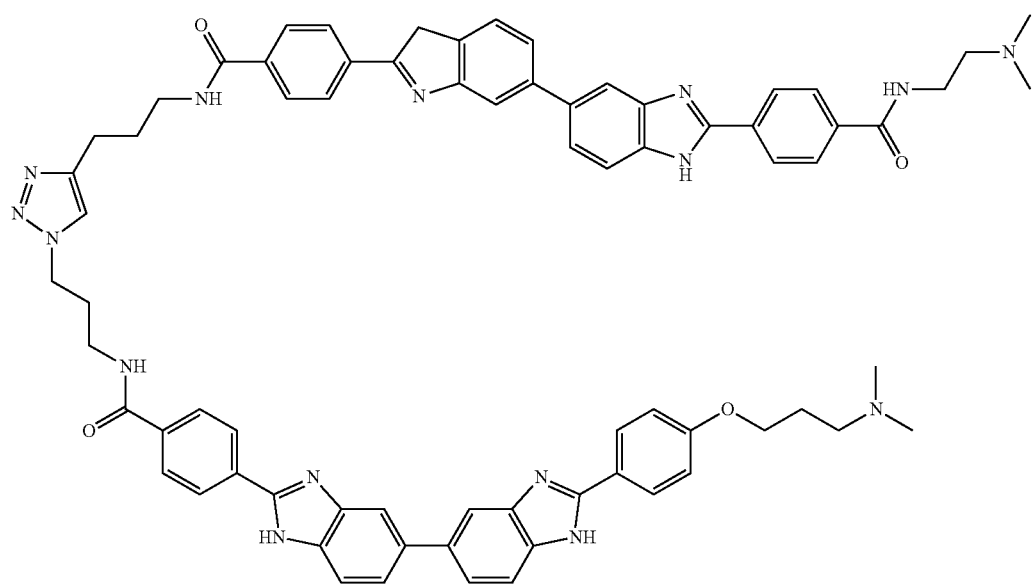 [SMILES: CN(C)CCCOc1ccc(-c2nc3cc(-c4ccc5[nH]c(-c6ccc(C(=O)NCCCn7cc(CCCNC(=O)c8ccc(C9=Nc%10cc(-c%11ccc%12[nH]c(-c%13ccc(C(=O)NCCN(C)C)cc%13)nc%12c%11)ccc%10C9)cc8)nn7)cc6)nc5c4)ccc3[nH]2)cc1] |

TABLE K-continued
| Compound # | Structure |
| --- | --- |
| 458 | 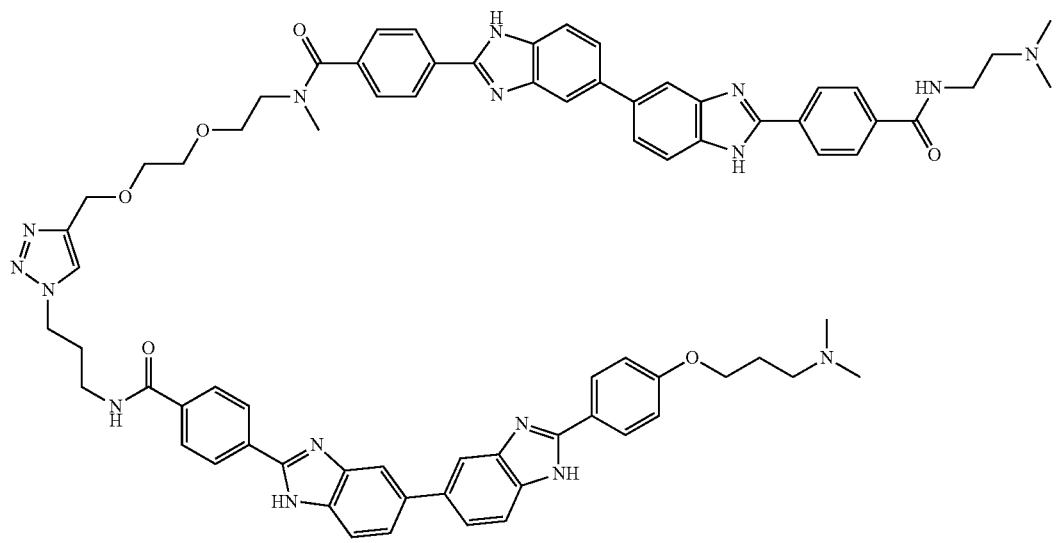 [SMILES: CN(C)CCCOc1ccc(-c2nc3cc(-c4ccc5[nH]c(-c6ccc(C(=O)NCCCn7cc(COCCOCCN(C)C(=O)c8ccc(-c9nc%10cc(-c%11ccc%12[nH]c(-c%13ccc(C(=O)NCCN(C)C)cc%13)nc%12c%11)ccc%10[nH]9)cc8)nn7)cc6)nc5c4)ccc3[nH]2)cc1] |
| 459 | 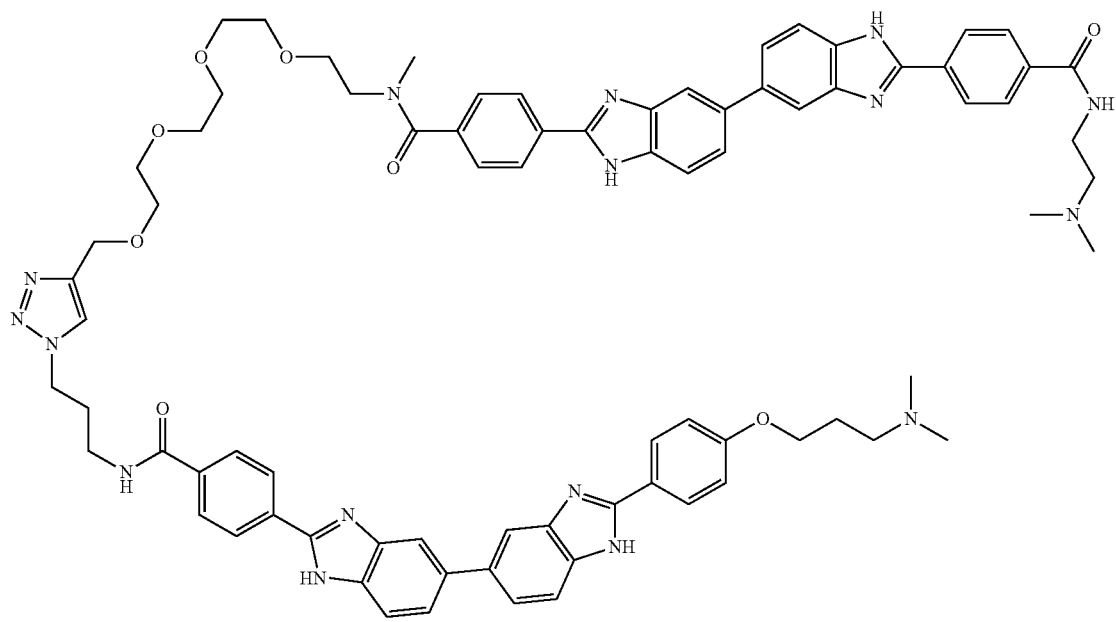 [SMILES: CN(C)CCCOc1ccc(-c2nc3cc(-c4ccc5[nH]c(-c6ccc(C(=O)NCCCn7cc(COCCOCCOCCOCCN(C)C(=O)c8ccc(-c9nc%10cc(-c%11ccc%12[nH]c(-c%13ccc(C(=O)NCCN(C)C)cc%13)nc%12c%11)ccc%10[nH]9)cc8)nn7)cc6)nc5c4)ccc3[nH]2)cc1] |

TABLE K-continued

| Compound # | Structure |
|---|---|
| 460 | 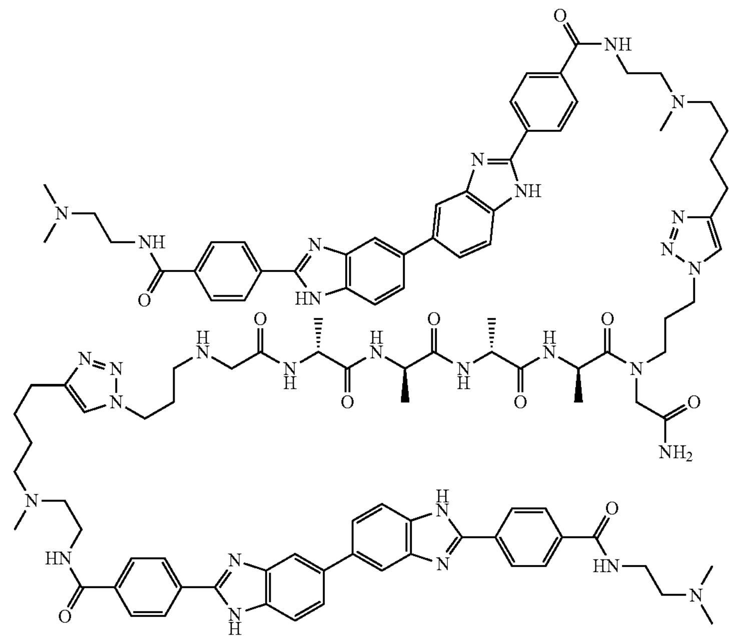 [SMILES: C[C@@H](NC(=O)CNCCCn1cc(CCCCN(C)CCNC(=O)c2ccc(-c3nc4cc(-c5ccc6[nH]c(-c7ccc(C(=O)NCCN(C)C)cc7)nc6c5)ccc4[nH]3)cc2)nn1)C(=O)N[C@H](C)C(=O)N[C@H](C)C(=O)N[C@H](C)C(=O)N(CCCn1cc(CCCCN(C)CCNC(=O)c2ccc(-c3nc4cc(-c5ccc6[nH]c(-c7ccc(C(=O)NCCN(C)C)cc7)nc6c5)ccc4[nH]3)cc2)nn1)CC(N)=O] |
| 461 | 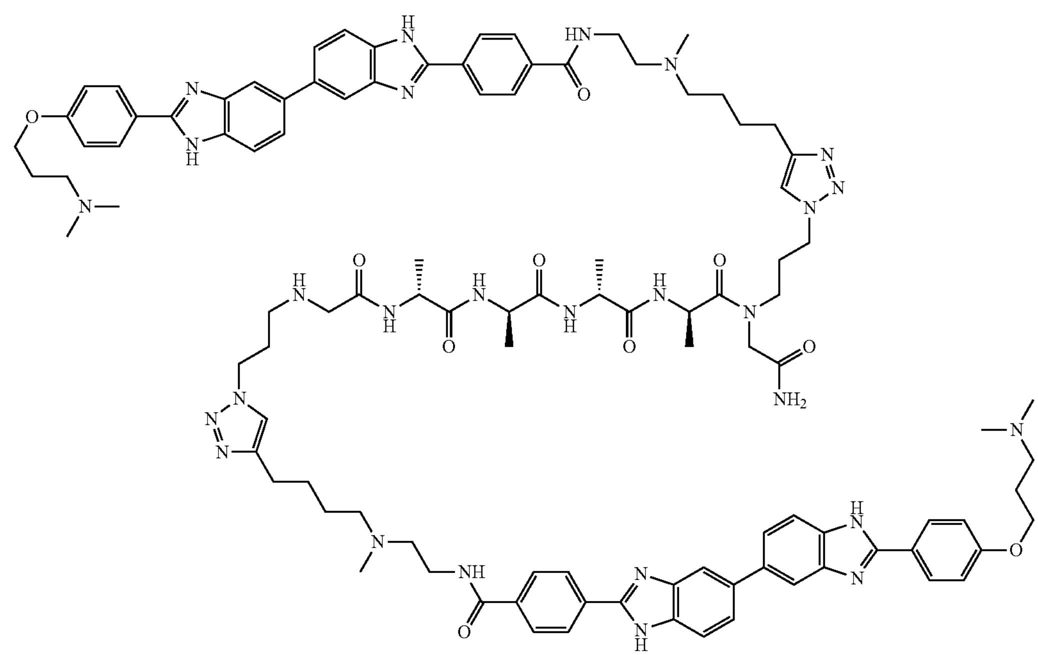 [SMILES: C[C@@H](NC(=O)CNCCCn1cc(CCCCN(C)CCNC(=O)c2ccc(-c3nc4cc(-c5ccc6[nH]c(-c7ccc(OCCCN(C)C)cc7)nc6c5)ccc4[nH]3)cc2)nn1)C(=O)N[C@H](C)C(=O)N[C@H](C)C(=O)N[C@H](C)C(=O)N(CCCn1cc(CCCCN(C)CCNC(=O)c2ccc(-c3nc4cc(-c5ccc6[nH]c(-c7ccc(OCCCN(C)C)cc7)nc6c5)ccc4[nH]3)cc2)nn1)CC(N)=O] |

Definitions

As used herein, the term "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (e.g., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "alkylene" used herein refers to an alkyl group having a substituent. For example, the term "alkylenehalo" refers to an alkyl group substituted with a halo group. For example, an alkylene group can be —$CH_2CH_2$— or —$CH_2$—. The term $C_n$ means the alkylene group has "n"

carbon atoms. For example, $C_{1-6}$ alkylene refers to an alkylene group having a number of carbon atoms encompassing the entire range, as well as all subgroups, as previously described for "alkyl" groups. Unless otherwise indicated, an alkylene group can be an unsubstituted alkylene group or a substituted alkylene group.

The term "alkenyl" used herein refers to an unsaturated aliphatic group analogous in length and possible substitution to an alkyl group described above, but that contains at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. For example, a straight chain or branched alkenyl group can have six or fewer carbon atoms in its backbone (e.g., $C_2$-$C_6$ for straight chain, $C_3$-$C_6$ for branched chain). The term "$C_2$-$C_6$" includes chains having a number of carbon atoms encompassing the entire range (e.g., 2 to 6 carbon atoms), as well as all subgroups (e.g., 2-6, 2-5, 2-4, 3-6, 2, 3, 4, 5, and 6 carbon atoms). The term "$C_3$-$C_6$" includes chains having a number of carbon atoms encompassing the entire range (e.g., 3 to 6 carbon atoms), as well as all subgroups (e.g., 3-6, 3-5, 3-4, 3, 4, 5, and 6 carbon atoms). Unless otherwise indicated, an alkenyl group can be an unsubstituted alkenyl group or a substituted alkenyl group.

The term "alkynyl" used herein refers to an unsaturated aliphatic group analogous in length and possible substitution to an alkyl group described above, but that contains at least one triple bond. For example, the term "alkynyl" includes straight chain alkynyl groups (e.g., ethynyl, propynyl, butynyl, pentynyl, hexynyl, heptynyl, octynyl, nonynyl, decynyl), and branched alkynyl groups. For example, a straight chain or branched alkynyl group can have six or fewer carbon atoms in its backbone (e.g., $C_2$-$C_6$ for straight chain, $C_4$-$C_6$ for branched chain). The term "$C_2$-$C_6$" includes chains having a number of carbon atoms encompassing the entire range (e.g., 2 to 6 carbon atoms), as well as all subgroups (e.g., 2-6, 2-5, 2-4, 3-6, 2, 3, 4, 5, and 6 carbon atoms). The term "$C_4$-$C_6$" includes chains having a number of carbon atoms encompassing the entire range (e.g., 4 to 6 carbon atoms), as well as all subgroups (e.g., 4-6, 4-5, 4, 5, and 6 carbon atoms). Unless otherwise indicated, an alkynyl group can be an unsubstituted alkynyl group or a substituted alkynyl group.

As used herein, the term "cycloalkyl" refers to an aliphatic cyclic hydrocarbon group containing three to ten carbon atoms (e.g., 3, 4, 5, 6, 7, 8, 9, or 10 carbon atoms). The term $C_n$ means the cycloalkyl group has "n" carbon atoms. For example, $C_5$ cycloalkyl refers to a cycloalkyl group that has 5 carbon atoms in the ring. $C_6$-$C_{10}$ cycloalkyl refers to cycloalkyl groups having a number of carbon atoms encompassing the entire range (e.g., 6 to 10 carbon atoms), as well as all subgroups (e.g., 6-7, 6-8, 7-8, 6-9, 6, 7, 8, 9, and 10 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group. The cycloalkyl groups described herein can be isolated or fused to another cycloalkyl group, a heterocycloalkyl group, an aryl group and/or a heteroaryl group. When a cycloalkyl group is fused to another cycloalkyl group, then each of the cycloalkyl groups can contain three to ten carbon atoms unless specified otherwise. Unless otherwise indicated, a cycloalkyl group can be unsubstituted or substituted.

As used herein, the term "heterocycloalkyl" is defined similarly as cycloalkyl, except the ring contains one to three heteroatoms independently selected from oxygen, nitrogen, and sulfur. In particular, the term "heterocycloalkyl" refers to a ring containing a total of three to ten atoms (e.g., five to ten), of which 1, 2, 3 or three of those atoms are heteroatoms independently selected from the group consisting of oxygen, nitrogen, and sulfur, and the remaining atoms in the ring are carbon atoms. Nonlimiting examples of heterocycloalkyl groups include piperdine, pyrazolidine, tetrahydrofuran, tetrahydropyran, dihydrofuran, morpholine, and the like. Cycloalkyl and heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, alkylenehalo, halo, and OH. Other substitutents are also contemplated, including $C_{0-3}$ alkylene-halo, $C_{0-3}$ alkylene-CN, $C_{0-3}$ alkylene-NH$_2$, $C_{0-3}$ alkylene-OH, and $C_{0-3}$ alkylene-O—$C_{1-3}$alkyl. Heterocycloalkyl groups optionally can be further N-substituted with alkyl, alkyleneOH, alkylenearyl, and alkyleneheteroaryl. The heterocycloalkyl groups described herein can be isolated or fused to another heterocycloalkyl group, a cycloalkyl group, an aryl group, and/or a heteroaryl group. When a heterocycloalkyl group is fused to another heterocycloalkyl group, then each of the heterocycloalkyl groups can contain three to ten total ring atoms, and one to three heteroatoms. Unless otherwise indicated, a heterocycloalkyl group can be unsubstituted or substituted.

As used herein, the term "aryl" refers to an aromatic group, such as phenyl. Aryl groups can be e.g., monocyclic or polycyclic. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Other substituents are also contemplated, including $C_{0-3}$ alkylene-halo, $C_{0-3}$ alkylene-CN, $C_{0-3}$ alkylene-NH$_2$, $C_{0-3}$ alkylene-OH, and $C_{0-3}$ alkylene-O—$C_{1-3}$alkyl. Aryl groups can be isolated (e.g., phenyl) or fused to another aryl group (e.g., naphthyl, anthracenyl), a cycloalkyl group (e.g. tetraydronaphthyl), a heterocycloalkyl group, and/or a heteroaryl group. Exemplary aryl groups include, but are not limited to, phenyl, chlorophenyl, methylphenyl, methoxyphenyl, trifluoromethylphenyl, nitrophenyl, 2,4-methoxychlorophenyl, and the like. Throughout, the abbreviation "Ph" refers to phenyl and "Bn" refers to benzyl (i.e., CH$_2$phenyl).

As used herein, the term "heteroaryl" refers to an aromatic ring having 5 to 10 total ring atoms, and containing one to four heteroatoms selected from nitrogen, oxygen, and sulfur atom in the aromatic ring. A heteroaryl can have 5 to 10 total ring atoms, e.g., 5 or 6 total ring atoms. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. Other substituents are also contemplated, including $C_{0-3}$ alkylene-halo, $C_{0-3}$ alkylene-CN, $C_{0-3}$ alkylene-NH$_2$, $C_{0-3}$ alkylene-OH, and $C_{0-3}$ alkylene-O—$C_{1-3}$alkyl. In some cases, the heteroaryl group is substituted with one or more of alkyl and alkoxy groups. Examples of heteroaryl groups include, but are not limited to, thienyl, furyl, pyridyl, pyrrolyl, oxazolyl, triazinyl, triazolyl, isothiazolyl, isoxazolyl, imidazolyl, pyrazinyl, pyrimidinyl, thiazolyl, and thiadiazolyl.

As used herein, the term "alkoxy" or "alkoxyl" as used herein refers to a "—O-alkyl" group. The alkoxy or alkoxyl group can be unsubstituted or substituted.

As used herein, the term "substituted," when used to modify a chemical functional group, refers to the replacement of at least one hydrogen radical on the functional group with a substituent. Substituents can include, but are not limited to, alkyl, cycloalkyl, alkenyl, cycloalkenyl, alkynyl, heterocycloalkyl, aryl, heteroaryl, hydroxyl, oxy, alkoxy, heteroalkoxy, ester, thioester, carboxy, cyano, nitro, amino, amido, acetamide, and halo (e.g., fluoro, chloro, bromo, or iodo). When a chemical functional group includes more than one substituent, the substituents can be bound to the same carbon atom or to two or more different carbon atoms.

As used herein, the term "linking moiety" refers to a bond, or a straight or branched chain group comprising saturated hydrocarbon groups containing one to one hundred carbon atoms, for example, one to ninety, one to eighty, one to seventy, one to sixty, one to fifty, one to forty carbon atoms, one to thirty carbon atoms, one to twenty carbon atoms, or one to ten carbon atoms, and optionally interrupted with one or more (e.g., 1-15, 1-10, 1-5, 1, 2, 3, 4, 5, 6, 7, 8, 9, or 10) heteroatoms (e.g., selected from O, N, S, P, Se, and B, or selected from N, O, and S). Unless otherwise indicated, the chain may be optionally substituted. Substituents can include but are not limited to alkyl, cycloalkyl, alkenyl, cycloalkenyl, alkynyl, heterocycloalkyl, aryl, heteroaryl, hydroxyl, oxo, alkoxy, heteroalkoxy, ester, thioester, carboxy, cyano, nitro, amino, amido, azido, acetamide, and halo (e.g., fluoro, chloro, bromo, or iodo). Linking moieties can be polymer chains, but are not required to be polymeric. Nonlimiting examples of linking moieties include polyalkylene chains (such as polyethylene or polypropylene chains), polyalkylene glycol chains (such as polyethylene glycol and polypropylene glycol), polyamide chains (such as polypeptide chains), and the like. The linking moiety can be attached to the rest of the compound via an amide functional group, an ester functional group, a thiol functional group, an ether functional group, a carbamate functional group, a carbonate functional group, a urea functional group, an alkene functional group, an alkyne functional group, a heteroaryl ring (e.g., as formed via a Click chemistry reaction between an alkyne and an azide).

As used herein, the term "therapeutically effective amount" means an amount of a compound or combination of therapeutically active compounds (e.g., an opioid receptor modulator or combination of opioid receptor modulators) that ameliorates, attenuates or eliminates one or more symptoms of a particular disease or condition (e.g., heart disease), or prevents or delays the onset of one of more symptoms of a particular disease or condition.

As used herein, the terms "patient" and "subject" may be used interchangeably and mean animals, such as dogs, cats, cows, horses, and sheep (e.g., non-human animals) and humans. Particular patients or subjects are mammals (e.g., humans). The terms patient and subject includes males and females.

As used herein, the term "pharmaceutically acceptable" means that the referenced substance, such as a compound of the present disclosure, or a formulation containing the compound, or a particular excipient, are safe and suitable for administration to a patient or subject. The term "pharmaceutically acceptable excipient" refers to a medium that does not interfere with the effectiveness of the biological activity of the active ingredient(s) and is not toxic to the host to which it is administered.

The compounds disclosed herein can be as a pharmaceutically acceptable salt. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66, 1-19, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, trifluoroacetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, glutamate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts of compounds containing a carboxylic acid or other acidic functional group can be prepared by reacting with a suitable base. Such salts include, but are not limited to, alkali metal, alkaline earth metal, aluminum salts, ammonium, $N^+(C_{1-4}alkyl)_4$ salts, and salts of organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bis-dehydroabietylamine, glucamine, N-methylglucamine, collidine, quinine, quinoline, and basic amino acids such as lysine and arginine. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein the terms "treating", "treat" or "treatment" and the like include preventative (e.g., prophylactic) and palliative treatment.

As used herein, the term "excipient" means any pharmaceutically acceptable additive, carrier, diluent, adjuvant, or other ingredient, other than the active pharmaceutical ingredient (API).

Synthesis of Compounds of the Disclosure

The compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, 5$^{th}$ edition, John Wiley & Sons: New York, 2001; and Greene, T. W., Wuts, P. G. M., Protective Groups in Organic Synthesis, 3$^{rd}$ edition, John Wiley & Sons: New York, 1999, are useful and recognized reference textbooks of organic synthesis known to those in the art. For example, the compounds disclosed herein can be synthesized by solid phase synthesis techniques including those described in Merrifield, J. Am. Chem. Soc. 1963; 85:2149; Davis et al., Biochem. Intl. 1985; 10:394-414; Larsen et al., J. Am. Chem. Soc. 1993; 115:6247; Smith et al., J. Peptide Protein Res. 1994; 44: 183; O'Donnell et al., J. Am. Chem. Soc. 1996; 118:6070; Stewart and Young, Solid Phase Peptide Synthesis, Freeman (1969); Finn et al., The Proteins, 3rd ed., vol. 2, pp. 105-253 (1976); and Erickson et al., The Proteins, 3rd ed., vol. 2, pp. 257-527 (1976). The following descriptions of synthetic methods are designed to illustrate, but not to limit, general procedures for the preparation of compounds of the present disclosure.

The synthetic processes disclosed herein can tolerate a wide variety of functional groups; therefore, various substituted starting materials can be used. The processes generally provide the desired final compound at or near the end of the overall process, although it may be desirable in certain instances to further convert the compound to a pharmaceutically acceptable salt, ester or prodrug thereof.

In general, compounds of Formula (I) can be synthesized according to Scheme 1.

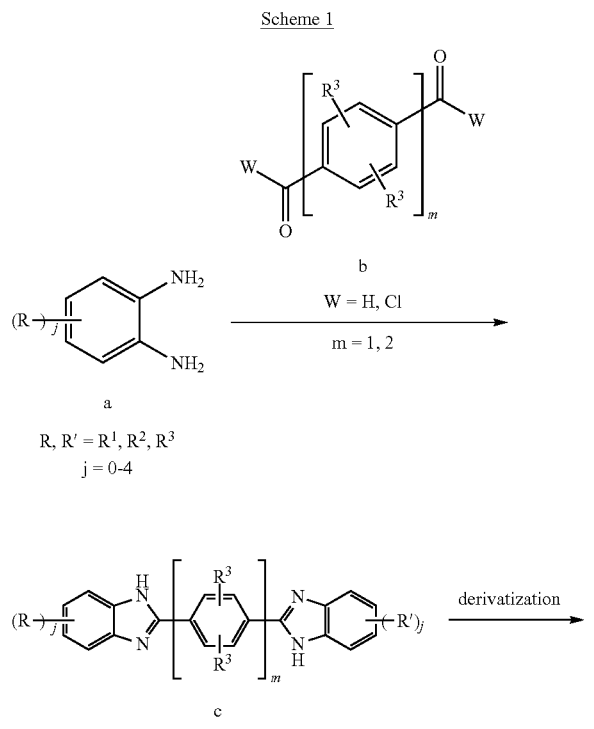

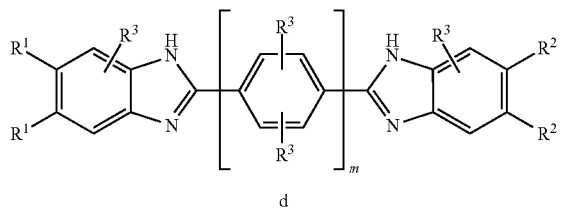

d

Compounds having structure d can be synthesized using the procedure shown in Scheme 1. Reaction of an optionally substituted o-phenylenediamine a with an optionally substituted dicarbonyl compound b produces bis-benzimidazoles having structure c. Subsequent derivatization gives compounds as described herein, i.e., compounds of Formula I having structure d. Appropriate derivatization reactions can be selected based on the nature of substituents R and R'.

The coupling of compounds a and b can be catalyzed by appropriate reagents selected based on the precise nature of compounds a and b. For example, when compound b is a dialdehyde compound (i.e., when each W is H), the coupling of compounds a and b can be catalyzed by e.g., sodium bisulfite or sodium metabisulfite. Occasionally, the coupling reaction may not require a catalyst, e.g., when compound b is a diacyl chloride (i.e., when each W is Cl).

Compounds a and b can be purchased commercially or prepared by a variety of methods from commercially-available starting materials. For example, diamines such as compounds having structure a can be prepared by the reduction (e.g., palladium-catalyzed reduction) of appropriate compounds bearing nitro functional groups. Dialdehyde compounds having structure b can be prepared by the oxidation (e.g., Dess-Martin oxidation) of appropriate compounds bearing alcohol functional groups.

Derivatization reactions to transform compounds having structure c into compounds having structure d can be selected based on the nature of the substituents R and R' in compound c and the functionality desired in compound d. For example, R and/or R' can be nitro groups, which can be reduced (e.g., via palladium-catalyzed reduction) to amino groups, which can be further derivatized by methods known in the art to form a variety of functional groups. Alternately, R and/or R' can be nitrile groups, which can be hydrolyzed (e.g., by treatment with concentrated sulfuric acid) to amide or carboxylic acid groups. Derivatization of amino and amide groups can be effected via known methods such as carbodiimide chemistry, or through the use of catalytic reagents such as HATU and the like, according to the nature of the derivatization reaction as disclosed herein.

In general, compounds of Formula (II) can be synthesized according to Scheme 2.

Scheme 2

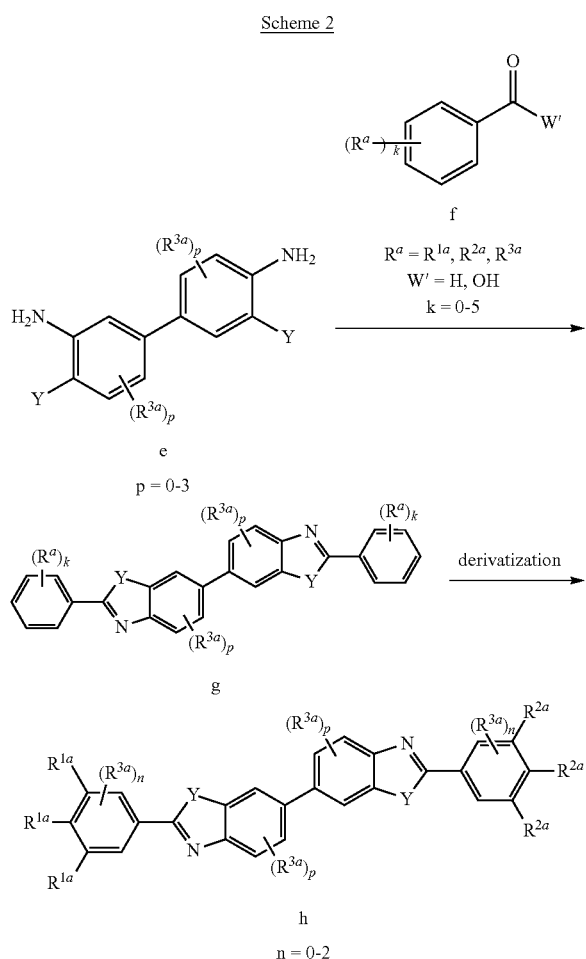

Compounds having structure h can be synthesized using the procedure shown in Scheme 2. For example, reaction of an optionally substituted tetraaminobiphenyl compound having structure e with an optionally substituted carbonyl compound f produces bis-benzimidazoles having structure g. Subsequent derivatization gives compounds as described herein, i.e., compounds of Formula II having structure h. Appropriate derivatization reactions can be selected based on the nature of substituent(s) $R^a$.

The coupling of compounds e and f can be catalyzed by appropriate reagents selected based on the precise nature of compounds e and f. For example, when compound f is an aldehyde compound (i.e., when W' is H), the coupling of compounds e and f can be catalyzed by e.g., sodium bisulfite or sodium metabisulfite, or when compound f is a carboxylic acid (i.e., when W' is OH), the coupling can be catalyzed by polyphosphoric acid (PPA).

Compounds e and f can be purchased commercially or prepared by a variety of methods from commercially-available starting materials. For example, tetraaminobiphenyl or diamino-biphenyl-diol compounds having structure e can be prepared by the reduction (e.g., palladium-catalyzed reduction) of appropriate compounds bearing nitro functional groups. Aldehyde compounds having structure f can be prepared by the oxidation (e.g., Dess-Martin oxidation) of appropriate compounds bearing alcohol functional groups.

Derivatization reactions to transform compounds having structure g into compounds having structure h can be selected based on the nature of the substituent(s) $R^a$ in compound g and the functionality desired in compound h. For example, $R^a$ can be a nitro group, which can be reduced (e.g., via palladium-catalyzed reduction) to an amino group, which can be further derivatized by methods known in the art to form a variety of functional groups. Alternately, $R^a$ can be a nitrile group, which can be hydrolyzed (e.g., by treatment with concentrated sulfuric acid) to an amide or a carboxylic acid. Derivatization of amino or amide groups can be effected via known methods such as carbodiimide chemistry, or through the use of catalytic reagents such as HATU and the like, according to the nature of the derivatization reaction as disclosed herein.

Additional synthetic procedures for preparing the compounds disclosed herein can be found in the Examples section.

Pharmaceutical Formulations, Dosing, and Routes of Administration

Further provided are pharmaceutical formulations comprising a compound as described herein (e.g., compounds of Formula I, Formula II, dimers thereof, or pharmaceutically acceptable salts of the salts and/or dimers) and a pharmaceutically acceptable excipient.

The compounds described herein can be administered to a subject in a therapeutically effective amount (e.g., in an amount sufficient to prevent or relieve the symptoms of a nucleotide repeat disorder). The compounds can be administered alone or as part of a pharmaceutically acceptable composition or formulation. In addition, the compounds can be administered all at once, multiple times, or delivered substantially uniformly over a period of time. It is also noted that the dose of the compound can be varied over time.

A particular administration regimen for a particular subject will depend, in part, upon the compound, the amount of compound administered, the route of administration, and the cause and extent of any side effects. The amount of compound administered to a subject (e.g., a mammal, such as a human) in accordance with the disclosure should be sufficient to effect the desired response over a reasonable time frame. Dosage typically depends upon the route, timing, and frequency of administration. Accordingly, the clinician titers the dosage and modifies the route of administration to obtain the optimal therapeutic effect, and conventional range-finding techniques are known to those of ordinary skill in the art.

Purely by way of illustration, the method comprises administering, e.g., from about 0.1 mg/kg up to about 100 mg/kg of compound or more, depending on the factors mentioned above. In other embodiments, the dosage ranges from 1 mg/kg up to about 100 mg/kg; or 5 mg/kg up to about 100 mg/kg; or 10 mg/kg up to about 100 mg/kg. Some conditions require prolonged treatment, which may or may not entail administering lower doses of compound over multiple administrations. If desired, a dose of the compound is administered as two, three, four, five, six or more subdoses administered separately at appropriate intervals throughout the day, optionally, in unit dosage forms. The treatment period will depend on the particular condition and type of pain, and may last one day to several months.

Suitable methods of administering a physiologically-acceptable composition, such as a pharmaceutical composition comprising the compounds disclosed herein (e.g., compounds of Formula (I)), are well known in the art. Although more than one route can be used to administer a compound, a particular route can provide a more immediate and more effective reaction than another route. Depending on the circumstances, a pharmaceutical composition comprising the compound is applied or instilled into body cavities, absorbed through the skin or mucous membranes, ingested, inhaled, and/or introduced into circulation. For example, in certain circumstances, it will be desirable to deliver a pharmaceutical composition comprising the agent orally, through injection by intravenous, intraperitoneal, intracerebral (intra-parenchymal), intracerebroventricular, intramuscular, intra-ocular, intraarterial, intraportal, intralesional, intramedullary, intrathecal, intraventricular, transdermal, subcutaneous, intraperitoneal, intranasal, enteral, topical, sublingual, urethral, vaginal, or rectal means, by sustained release systems, or by implantation devices. If desired, the compound is administered regionally via intrathecal administration, intracerebral (intra-parenchymal) administration, intracerebroventricular administration, or intraarterial or intravenous administration feeding the region of interest. Alternatively, the composition is administered locally via implantation of a membrane, sponge, or another appropriate material onto which the desired compound has been absorbed or encapsulated. Where an implantation device is used, the device is, in one aspect, implanted into any suitable tissue or organ, and delivery of the desired compound is, for example, via diffusion, timed-release bolus, or continuous administration.

To facilitate administration, the compound is, in various aspects, formulated into a physiologically-acceptable composition comprising a carrier (e.g., vehicle, adjuvant, or diluent). The particular carrier employed is limited only by chemico-physical considerations, such as solubility and lack of reactivity with the compound, and by the route of administration. Physiologically-acceptable carriers are well known in the art. Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). Injectable formulations are further described in, e.g., Pharmaceutics and Pharmacy Practice, J. B. Lippincott Co., Philadelphia. Pa., Banker and Chalmers, eds., pages 238-250 (1982), and ASHP Handbook on Injectable Drugs, Toissel, 4th ed., pages 622-630 (1986)). A pharmaceutical composition comprising the compound is, in one aspect, placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents (e.g., water, saline or PBS) that may be necessary to reconstitute the pharmaceutical composition.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

The compositions used in the methods of the invention may be formulated in micelles or liposomes. Such formulations include sterically stabilized micelles or liposomes and sterically stabilized mixed micelles or liposomes. Such formulations can facilitate intracellular delivery, since lipid bilayers of liposomes and micelles are known to fuse with the plasma membrane of cells and deliver entrapped contents into the intracellular compartment.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

The frequency of dosing will depend on the pharmacokinetic parameters of the agents and the routes of administration. The optimal pharmaceutical formulation will be determined by one of skill in the art depending on the route of administration and the desired dosage. See, for example, Remington's Pharmaceutical Sciences, 18th Ed. (1990) Mack Publishing Co., Easton, Pa., pages 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

The precise dosage to be employed depends upon several factors including the host, whether in veterinary medicine or human medicine, the nature and severity of the condition, e.g., disease or disorder, being treated, the mode of administration and the particular active substance employed. The compounds may be administered by any conventional route, in particular enterally, and, in one aspect, orally in the form of tablets or capsules. Administered compounds can be in the free form or pharmaceutically acceptable salt form as appropriate, for use as a pharmaceutical, particularly for use in the prophylactic or curative treatment of a disease of interest. These measures will slow the rate of progress of the disease state and assist the body in reversing the process direction in a natural manner.

It will be appreciated that the pharmaceutical compositions and treatment methods of the invention are useful in fields of human medicine and veterinary medicine. Thus the subject to be treated is in one aspect a mammal. In another aspect, the mammal is a human.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

Methods of Use

The compounds described herein (e.g., the compounds of Formulae I or II, compounds of Tables A, A1, A2, B, C, C1, D, E, F, G, H, I, J, or K, or dimers thereof) can bind nucleic acids. In some embodiments, the compounds bind RNA, e.g., the compounds trigger or inhibit RNA-mediated biological activity, such as gene expression. In various embodiments, the compounds are RNA modulators, e.g., the compounds change, inhibit, or prevent one or more of RNA's biological activities.

The compounds disclosed herein are particularly advantageous for the treatment of diseases or disorders caused by abnormal nucleotide repeats or toxic RNA repeats. The incidence and/or intensity of diseases or disorders associated with expansion of nucleotide repeats in certain genes or introns is reduced.

Toxic RNA is RNA which contains a non-coding nucleotide repeat expansion and which results in cellular damage or disease. In some instances, toxic RNA may accumulate in the nucleus, sequester binding proteins, and result in abnormal splicing for some pre-mRNAs (Osborne et al. Mol. Genet. 15:R162-R169, 2006).

CUG repeat expansions, such as in DM1, lead to sequestration of muscleblind-like proteins in ribonuclear foci and depletion in other parts of the nucleoplasm. However, not all toxic RNA diseases are expected to be caused by an identical mechanism. Myotonic dystrophy is the prototypical toxic RNA disease. Spinocerebellar ataxia type 8 (SCA8) and fragile X tremor ataxia syndrome (FXTAS) are representative additional diseases. SCA8 is caused by CUG repeat expansions in a non-coding RNA (ATXN8OS/SCA8), while in FXTAS there is an expansion of about 70-120 CGG repeats in the 5' UTR of the FMRI gene. Another toxic RNA disease is Huntington disease-like 2 (HDL2), which is caused by a CUG repeat expansion in an intron or the 3' UTR of the junctophilin 3 gene.

The disclosed methods include methods for treating an expansion repeat disorder, e.g., myotonic dystrophy, comprising administering to a subject a compound that binds a nucleotide repeat expansion in RNA. In some examples, the compound disrupts binding of a protein to the nucleotide repeat expansion. In one example, the method includes use of a compound that disrupts binding of a protein to CUG repeats of DMPK. In a particular example, the compound disrupts binding of a muscleblind-like protein (such as MBNL, MBLL, or MBXL) to CUG repeats of DMPK. In another example, the method includes use of a compound that disrupts binding of a protein to CCUG repeats of ZNF9. In a particular example, the compound disrupts binding of a muscleblind-like protein (such as MBNL, MBLL, or MBXL) to CCUG repeats of ZNF9. The compound may disrupt binding of additional proteins to RNA nucleotide repeat expansions, such as heterogeneous nuclear ribonucleoprotein H (hnRNP H) or other proteins.

Methods for determining whether a compound disrupts RNA binding activity of a protein to a particular sequence are well known to those of skill in the art. See e.g., Current Protocols in Molecular Biology, Ausubel, John Wiley & Sons, 1994; Molecular Cloning, A Laboratory Manual, Sambrook et ah, Cold Spring Harbor Laboratory, 2001. In one example, binding of a protein to a nucleic acid may be determined by EMSA. A nucleic acid sequence (such as a CUG repeat sequence or a CCUG repeat sequence) is incubated in the presence or absence of a protein or mixture of proteins (such as a muscleblind-like protein). The nucleic acid sequence is linked to a detectable label, for example a radioactive, fluorescent, chemiluminescent, or biotin label. The samples are separated by polyacrylamide gel electrophoresis and the labeled nucleic acid is detected, with a shift to slower mobility (higher molecular weight) in the presence of protein compared to nucleic acid in the absence of protein indicating that a protein in the sample binds to the nucleic acid sequence. To determine whether a compound disrupts the protein-nucleic acid binding, samples containing nucleic acid (such as a CUG repeat expansion or a CCUG repeat expansion) and a binding protein (such as a muscleblind-like protein) are incubated in the presence or absence of a candidate compound. If the compound disrupts the protein-nucleic acid interaction, the shift to slower mobility that is observed in the absence of the compound will not occur or will be reduced compared to the shift in the absence of the compound. In another example, RNA-protein interaction may be determined using a filter binding assay. Such assays are well known in the art (see, e.g., Hall and Kranz, in RNA-Protein Interaction Protocols (Methods in Molecular Biology, volume 118), Humana Press, 1999). Briefly, an RNA (such as a CUG repeat sequence or a CCUG repeat sequence) which is labeled (such as with a radioactive label) is incubated in the presence or absence of a protein or mixture of proteins (such as a muscleblind-like protein). The mixture is then passed over a filter (such as a nitrocellulose filter) and RNA-protein complexes are retained and detected.

RNA-protein interaction may also be assessed utilizing fluorescence resonance energy transfer (FRET). Methods for FRET are well known to those of skill in the art. Briefly, a donor fluorophore is coupled to one molecule (such as an RNA binding protein) and an acceptor fluorophore is coupled to another molecule (such as an RNA, for example a CUG or CCUG nucleotide repeat sequence). If the molecules interact, the fluorophores are brought into proximity, such that an excited donor fluorophore can transfer energy to an acceptor fluorophore, which then emits a particular wavelength. Detection of fluorescence emissions may be made utilizing techniques such as fluorescence microscopy or fluorimetry. One of skill in the art will appreciate that the donor and acceptor fluorophores may be coupled to either the protein or RNA binding partners. The disclosed methods include use of compounds that disrupt binding of a protein to an RNA nucleotide repeat expansion. In some cases, the compounds described herein show binding to RNA with an $IC_{50}$ in a range of about 0.1 to 3000 nM, 0.1 to 1000 nM, 0.1 to 500 nM, 0.1 to 100 nM, 0.1 to 50 nM, 0.1 to 25 nM, 0.1 to 10 nM, 0.1 to 5 nM, 0.1 to 1 nM, 0.1 to 0.5 nM, 1000 to 2000 nM, 100 to 1000 nM, 10 or 100 nM, 5 to 50 nM, or 1 to 10 nM.

Thus, provided herein is a method of modulating RNA in a cell, comprising contacting the cell with a compound or a composition as disclosed herein (e.g., the compounds of formula (I) in an amount sufficient to bind to and modulate RNA. The contacting of the cell can occur in vitro or in vivo. In some cases, contacting of the cell occurs in vitro. In other cases, contacting of the cell occurs in vivo. Therefore, the disclosure includes administering one or more of a compound described herein to a subject, such as a human, in need thereof. In some embodiments, the subject suffers from a nucleotide repeat disorder. Disorders associated with nucleotide repeat expansion include, but are not limited to, Myotonic Dystrophy Type 1, Myotonic Dystrophy Type 2, Fuchs dystrophy, Huntington Disease, Amyotrophic Lateral Sclerosis, or Frontotemporal Dementia. In some cases, the compounds are useful for treating Myotonic Dystrophy Type 1, Myotonic Dystrophy Type 2, or Fuchs dystrophy.

The disclosed methods utilize compounds that bind to RNA nucleotide repeat expansions, such as CUG or CCUG repeats, for treating, e.g., DM. Methods for assessing the usefulness of a compound for treating DM are known to those of skill in the art. For example, compounds may be assessed using models of DM, including cells (such as DM1 or DM2 cells), animal models (such as *Drosophila* or mouse models of DM), or in human subjects having DM1 or DM2.

A *Drosophila* model of DM (DM *Drosophila*) was created by overexpressing a non-coding mRNA containing 480 interrupted CUG repeats of the sequence [(CUG)2OCUCGA]24 (de Haro et al, Hum. Mol. Gen. 15:2138-2145, 2006). DM *Drosophila* expressing the 480 interrupted CUG repeats exhibit progressive muscle degeneration and nuclear foci containing CUG repeat RNA, unlike flies expressing a (CUG)2O repeat. DM *Drosophila* expressing the 480 interrupted CUG repeat sequence in the eye also exhibit smaller eyes, disorganization and fusion of the ommatidia, and loss and duplication of the inter-ommatidial bristles. Compounds may be assessed for their ability to decrease or prevent DM-like phenotypes in a *Drosophila* model of DM. In a particular example, a test compound or mixture is administered orally, such as by mixing with the fly food. Treatment with test compounds may continue for about 1-10 weeks (such as about 1 week to about 4 weeks), or may continue throughout the life of the fly. In one example, a test compound is administered beginning at the larval stage, and continuing throughout the life of the fly. Doses of test compound included in the fly food are from about 1 µM to about 500 µM, such as about 5 µM to about 250 µM, such as about 25 µM to 125 µM.

The phenotype of the DM *Drosophila* is assessed in the presence and absence of treatment with test compound. In one example, skeletal muscle (for example, indirect flight muscles) of *Drosophila* may be sectioned for histological examination. The indirect flight muscles of *Drosophila* expressing the 480 interrupted CUG repeats show vacuolization, loss of muscle fiber organization, and dispersal of nuclei (de Haro et al, 2006). Sections of skeletal muscle from DM *Drosophila* treated with test compounds are compared to untreated DM *Drosophila* to determine whether treatment prevents or decreases the muscle degeneration phenotype. In a particular example, muscle degeneration is measured by assessing the size of vacuoles compared to cell size. DM *Drosophila* are also unable to fly (de Haro et al, 2006), therefore in another example, flies treated with or without test compounds are assessed for their ability to fly and quality or duration of flight. In a further example, *Drosophila* expressing the 480 interrupted CUG repeat sequence in the eye are treated with test compounds to determine whether treatment prevents or decreases the eye disorganization phenotype.

*Drosophila* treated with a test compound or compounds are compared to control flies which are not treated with the compound. Control samples are assigned a relative value of 100%. Treatment with the test compound decreases the DM phenotype when the phenotype relative to the control is about 90%, about 80%, about 70%, about 60%, about 50%, about 25%, or about 10%.

A mouse model of DM has been developed by generating mice that express an expanded CUG repeat (250 repeats) in the 3'UTR of a human skeletal actin transgene (Mankodi et al, Science 289:1769-1772, 2000). These mice exhibit myotonia and muscle histopathology consistent with DM (including increases in central nuclei and ring fibers and variability in fiber size), and oxidative muscle fibers. Compounds may be assessed for their ability to decrease or prevent DM-like phenotypes in a mouse model of DM. In a particular example, a test compound or mixture is administered orally, such as by mixing with distilled water. In another example, a test compound or mixture is administered intraperitoneally, intravenously, such as in saline, distilled water, or other appropriate vehicle. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for about 1 day to about 10 weeks, such as about 2 days, about 3 days, about 4 days, about 5 days, about 6 days, about 1 week, about 2 weeks, about 4 weeks, about six weeks, about 8 weeks, or about 10 weeks. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 40 mg/kg. In one example, myotonic discharges of skeletal muscle (such as forelimb muscles or paraspinal muscles) are assessed by electromyography (EMG). EMG recordings are made from DM mice treated with or without test compounds and the number of mice exhibiting myotonic discharges in each group is compared to determine if the test compound inhibits or decreases myotonia in a mouse model of DM. In another example, skeletal muscle histology may be compared between DM mice treated with or without test compound to assess if the test compound inhibits or decreases the muscle pathology of the DM mouse model. In a further example, features of oxidative muscle fibers, such as upregulation of succinate dehydrogenase and cytochrome oxidase are compared between DM mice treated with or without test compounds. In another example, rescue of mis-splicing of RNA (such as cTNT, IR, Clc-I or Sercal) in mice treated with the test compound is assessed.

Mice treated with a test compound or compounds are compared to control mice which are not treated with the compound. Control samples are assigned a relative value of 100%. Treatment with the test compound decreases the DM phenotype when the phenotype relative to the control is about 90%, about 80%, about 70%, about 60%, about 50%, about 25%, or about 10%.

The compounds described herein can be used to decrease or prevent DM phenotypes in human subjects with DM1 or DM2. In a particular example, a compound or mixture is administered orally, such as by mixing with distilled water. In another example, a test compound or mixture is administered intravenously, such as in saline or distilled water. In some examples, treatment with test compound may be a single dose or repeated doses. The test compound may be administered about every 6 hours, about every 12 hours, about every 24 hours (daily), about every 48 hours, about every 72 hours, or about weekly. Treatment with repeated doses may continue for a period of time, for example for about 1 week to 12 months, such as about 1 week to about 6 months, or about 2 weeks to about 3 months, or about 1 to 2 months. Administration of a compound may also continue indefinitely. Doses of test compound are from about 0.1 mg/kg to about 400 mg/kg, such as about 1 mg/kg to about 300 mg/kg, about 2 mg/kg to 200 mg/kg, about 10 mg/kg to about 100 mg/kg, about 20 mg/kg to about 75 mg/kg, or about 25 mg/kg to about 50 mg/kg.

Methods of assessing DM phenotypes are well known to those of skill in the art. DM phenotypes in affected individuals include muscle weakness (which may lead to foot drop and gait disturbance, as well as difficulty in performing tasks requiring hand dexterity), myotonia (sustained muscle contraction), which often manifests as the inability to quickly release a hand grip (grip myotonia) and which can be demonstrated by tapping a muscle with a reflex hammer (percussion myotonia), and myotonic discharges observed by EMG recording. Pathologic features may be observed by muscle biopsy, including rows of internal nuclei, ring fibers, sarcoplasmic masses, type I fiber atrophy, and increased number of intrafusal muscle fibers.

Changes in DM phenotypes may be monitored in DM subjects following administration of one or more compounds disclosed herein. DM phenotypes may be compared to DM subjects who have not received the compounds or comparison may be made to the subject's phenotype prior to administration of the compound in order to assess effectiveness of the compound for treatment of DM.

It will be understood that the methods and compositions described herein for treating DM, comprising administering a compound that binds an RNA nucleotide repeat expansion, are applicable to methods of treating toxic RNA diseases, such as those described above. The methods for assessing the effectiveness of test compounds for treating such diseases in cells, appropriate animal models, or affected subjects are known to one of skill in the art. For example, animal models of FXTAS (Jin et al, Neuron 39:739-747, 2003; Brouwer et al, Exp. Cell Res. 313:244-253, 2007) and SCA8 (Mutsuddi et al., Curr. Biol. 14:302-308, 2004; Moseley et al., Nature Genet. 38:758-769, 2006) are known to those in the art.

Uses of the compounds disclosed herein in the preparation of a medicament for treating nucleotide repeat disorders also are provided herein.

The disclosure herein will be understood more readily by reference to the following examples, below.

EXAMPLES

The following examples are provided for illustration and are not intended to limit the scope of the disclosure.

Synthetic Procedures for Compounds of Formula (I)

General Experimental Procedures. All reagents and solvents were obtained from commercial sources and used without additional purification. The synthesis of certain precursors is detailed in the Preparations, below. The syntheses of compounds of Formula I and Formula II are detailed in the Examples, below.

Preparation 1

Synthesis of 5-(1H-imidazol-1-yl)-2-nitroaniline

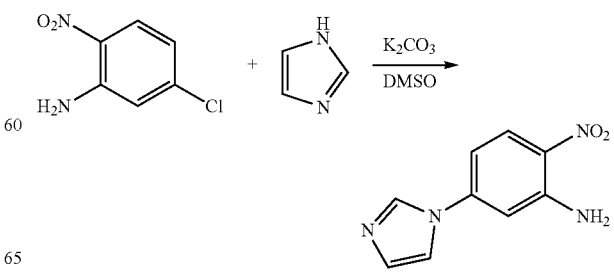

5-chloro-2-nitro aniline (3.0 g, 17.4 mmol), imidazole (1.2 g, 17.6 mmol) and potassium carbonate (7.2 g, 52.1 mmol) were mixed in DMSO and heated at 150° C. overnight. The reaction mixture was poured into water (330 ml) and stirred for 1 hour, filtered and the residue washed with water. The resultant crude material was purified on the biotage using dichloromethane/MeOH to give 892 mg. 1H NMR (CD3OD, 400 MHz) δ: 8.26-8.21 (m, 2H), 7.64 (t, J=1.4 Hz, 1H), 7.20-7.19 (m, 1H), 7.15 (d, J=2.4 Hz, 1H), 6.90 (dd, J=2.4, 9.3 Hz, 1H), MS (MALDI): m/z=205 [M+H]+.

Preparation 2

Synthesis of 4-(1H-imidazol-1-yl)benzene-1,2-diamine

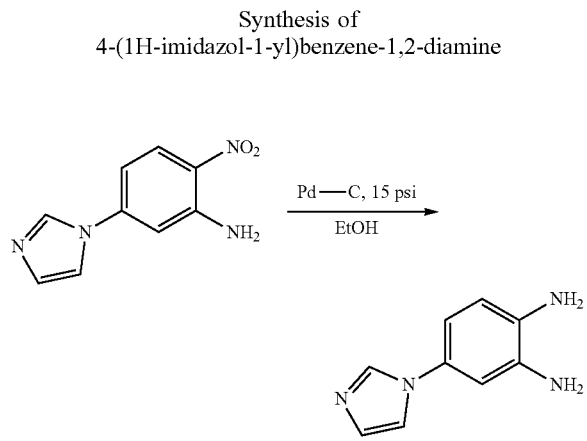

To a solution of 5-(1H-imidazol-1-yl)-2-nitroaniline (300 mg, 1.47 mmol) in EtOH (50 ml) was added 10% Pd on carbon (100 mg) and the mixture exposed to hydrogen at 15 Psi for 3 hours. The solution was filtered through celite and the filtrate concentrated to give the product that was used in the next step without further purification. 1H NMR (CD3OD, 400 MHz) δ: 7.89 (t, J=1.1 Hz, 1H), 7.37 (t, J=1.3 Hz, 1H), 7.08 (t, J=1.2 Hz, 1H), 6.83 (d, J=2.4 Hz, 1H), 6.78 (d, J=8.2 Hz, 1H), 6.70 (dd, J=2.4, 8.8 Hz, 1H), MS (MALDI): m/z=174 [M+H]+.

Preparation 3

Synthesis of (2-bromo-1,4-phenylene)dimethanol

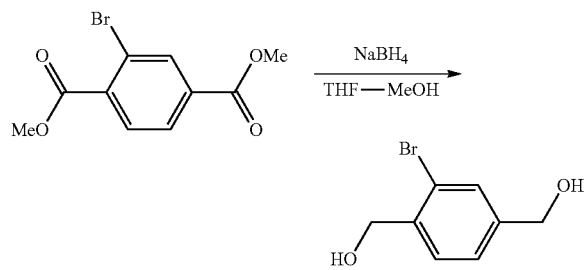

Dimethyl bromoterephthalate was reduced using a literature procedure. To a solution of dimethyl bromoterephthalate (2.0 g, 7.34 mmol) in THF (50 ml) was added powdered sodium borohydride (1.7 g, 44.8 mmol) and the mixture heated at reflux for 1 hour. Methanol (20 ml) was then added dropwise (effervescence observed) and heating continued for another 1 hour. The mixture was allowed to cool to room temperature and aqueous concentrated ammonium chloride (30 ml) added and stirring continued overnight. To the reaction mixture was added ethyl acetate and the organic phase washed with brine, dried over sodium sulfate, filtered and concentrated. The crude product was dissolved in a minimal amount of ethyl acetate and trituration with hexanes and dried under vacuum. 1H NMR (CD3OD, 400 MHz) δ: 7.57 (br s, 1H), 7.52 (d, J=7.8 Hz, 1H), 7.35 (d, J=7.8 Hz, 1H), 4.67 (s, 2H), 4.60 (s, 2H).

Preparation 4

Synthesis of 2-bromoterephthalaldehyde

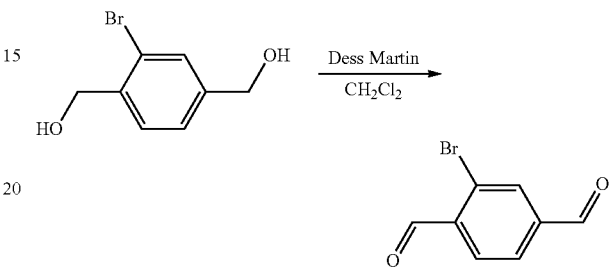

To a suspension of (2-bromo-1,4-phenylene)dimethanol (740 mg, 3.42 mmol) in dichloromethane (100 ml) was added sodium bicarbonate (2.3 g, 27.4 mmol) and Dess-Martin periodinane (4.4 g, 10.4 mmol). The mixture was stirred for 2 hours and a saturated solution of sodium thiosulfate added and stirring continued for 1 hour. The mixture was filtered and the organic layer separated. The aqueous phase was extracted with dichloromethane and the combined organic phase washed with brine, dried over sodium sulfate, filtered and concentrated. To the resultant material was added methanol, the mixture filtered and the filtrate concentrated. The crude product was purified on a silica column using dichloromethane and methanol. 1H NMR (CDCl3, 400 MHz) δ: 10.44 (s, 1H), 10.06 (s, 1H), 8.16 (d, J=1.4 Hz), 8.07 (d, J=7.9 Hz, 1H), 7.93 (d, J=7.9 Hz, 1H).

Preparation 5

Synthesis of 4-(6-nitro-1H-benzo[d]imidazol-2-yl)benzoic Acid

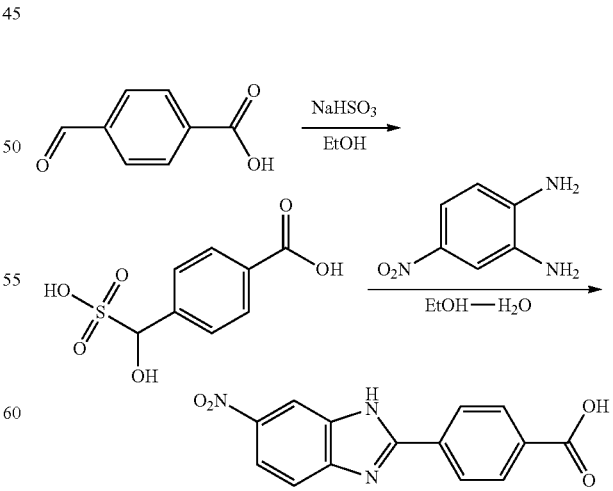

To a solution of 4-carboxybenzaldehyde (2.25 g, 15 mmol) in EtOH (80 ml) at 0° C. was added a solution of sodium bisulfite (1.6 g, 15.4 mmol) in water (30 ml)

dropwise. After addition of sodium bisulfite, 4-nitro-o-phenelenediamine (2.3 g, 15 mmol) and water (50 ml) were added and the mixture stirred for 3 hours at reflux. The reaction mixture was allowed to cool down and then filtered. The residue was washed with water and dried under vacuum. 1H NMR (DMSO-d6, 400 MHz) δ: 14.02-13.61 (br s, 1H), 8.65-8.43 (br s, 1H), 8.34 (d, J=8.3 Hz, 2H), 8.20-8.12 (m, 3H), 7.91-7.70 (br s, 1H), MS (MALDI): m/z=284 [M+H]+.

Preparation 6

Synthesis of 3,3'-dinitro-[1,1'-biphenyl]-4,4'-diol

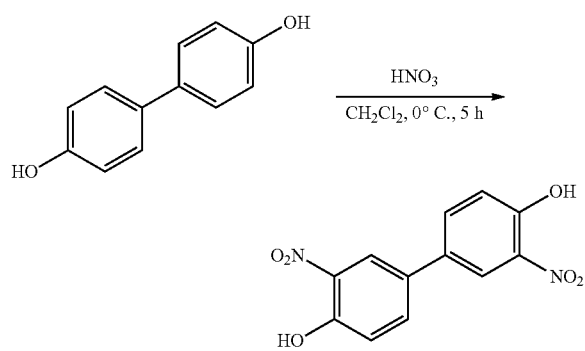

Fuming nitric acid (2.0 mL) was added over 10 minutes to a solution of [1,1'-biphenyl]-4,4'-diol (4.0 g, 21.50 mmol) in CH2Cl2 (40.0 mL) at 0° C. The reaction mixture was stirred at 0° C. for 5 hours, poured onto ice and neutralized with aqueous saturated sodium bicarbonate solution. The product was collected by filtration under vacuum and dried to obtain 3,3'-dinitro-[1,1'-biphenyl]-4,4'-diol. 1H NMR (DMSO-d6, 400 MHz) δ: 11.14 (s, 2H), 8.15 (d, J=2.4 Hz, 2H), 7.87 (dd, J=8.8 Hz, 2.4 Hz, 2H), 7.20 (d, J=8.4 Hz, 2H).

Preparation 7

Synthesis of 3,3'-diamino-[1,1'-biphenyl]-4,4'-diol

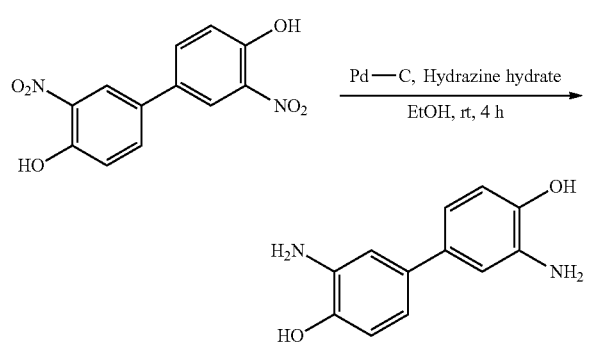

To a solution of 3,3'-dinitro-[1,1'-biphenyl]-4,4'-diol (2.0 g, 7.24 mmol), hydrazine monohydrate (9.2 mL, 289 mmol), and Pd/C (0.50 g), dissolved in ethanol (10.0 mL). The reaction mixture was stirred at room temperature for 4 hours, the crude products were filtered. The obtained material was dissolved in hot DMF and filtered through celite. The filtrate was poured onto ice cold water to obtain the product. The product was collected by filtration under vacuum and dried to obtain 3,3'-diamino-[1,1'-biphenyl]-4,4'-diol. 1H NMR (DMSO-d6, 400 MHz): 8.90 (s, 2H), 6.74 (d, J=1.6 Hz, 2H), 6.62 (d, J=8.0 Hz, 2H), 6.52 (dd, J=8.0 Hz, 1.2 Hz, 2H), 4.50 (s, 4H). MS (MM): m/z=215 [M+H]−.

Preparation 8

Synthesis of 4-(cyanomethyl)benzoic acid 2

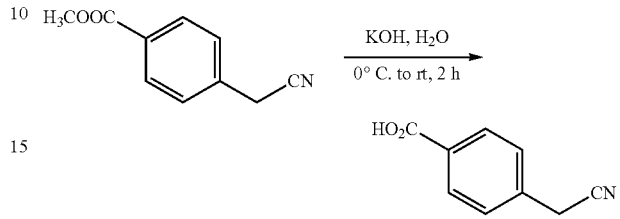

A solution of KOH (0.19 g, 3.42 mmol) in H2O (5.0 mL) was added to methyl 4-(cyanomethyl)benzoate (0.3 g, 1.71 mmol) in H2O (10 mL) slowly at 0° C. and stirred at room temperature for 2 h. The reaction mixture was poured into crushed ice, acidified with aqueous 2N HCl solution to pH~2, and the resulting precipitate was collected by filtration under vacuum to obtain the crude product. The crude product was purified by silica gel chromatography (5% CH3OH in CH2Cl2). The fractions containing the product were combined and concentrated under vacuum to obtain 4-(cyanomethyl)benzoic acid 2 (0.15 g, 26%) as a light yellow solid. 1H NMR (400 MHz, DMSO-d6): δ 13.03 (brs, 1H), 7.96 (d, J=8.0 Hz, 1H), 7.47 (d, J=8.4 Hz, 2H), 4.16 (s, 2H). MS (ESI+APCl) m/z 160 [M−H]−.

Preparation 9

Synthesis of alanine-Based Peptide Linkers

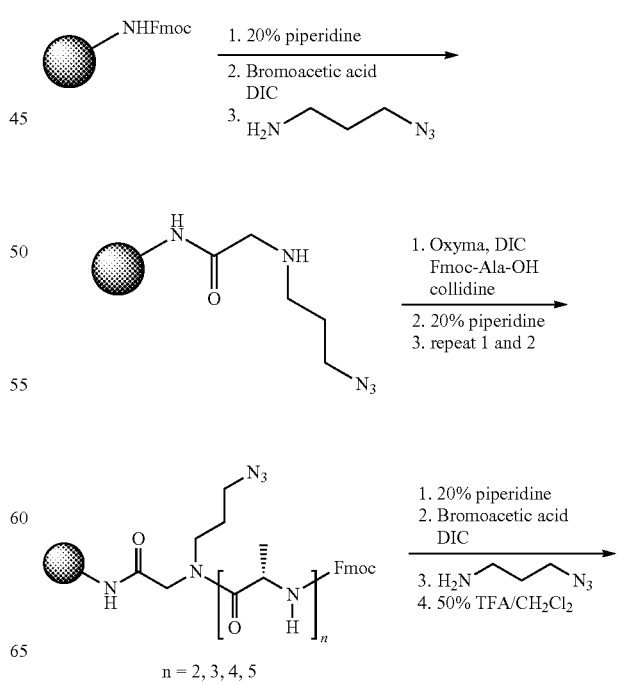

n = 2, 3, 4, 5

-continued

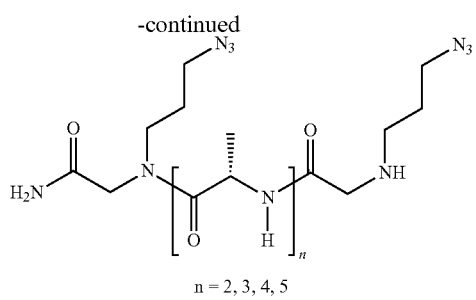

n = 2, 3, 4, 5

Rink Amide beads (1.0 g, 0.57 mmol) were swelled in DMF for 1 h then treated with 20% piperidine in DMF (6 ml) for 15 min. The piperidine solution was removed and a fresh 20% piperidine in DMF added and the beads mixed for 15 min. The beads were then washed with DMF (×5) and bromoacetic acid (2M in DMF, 4 ml) and DIC (3.2 M in DMF, 4 ml) added. The beads were heated in a microwave for 5 sec at 10% power and mixed for 10 min then washed with DMF (×5). 3-azidopropylamine (0.5 M, 6 ml) was added and the beads heated in a microwave for 5 sec at 10% power, mixed for 10 min before heating again and mixing for 20 min at RT. The beads were washed with DMF (×5), and treated with a solution of Fmoc-Ala-OH (3.0 equiv.), collidine (3.0 equiv.), DIC (4.5 equiv.) and Oxyma (3.0 equiv.) that had been premixed for 5 min in DMF (6 ml). The beads were mixed at RT for 1 h and washed with DMF (×3) followed by cleavage of the Fmoc group using 20% piperidine in DMF. The beads were split into 4 equal parts and Fmoc-Ala-OH coupled as described above to give the requisite length of the linker. The terminal 3-azidopropylamine was coupled by first treating the beads with bromoacetic acid and DIC. The linkers were cleaved from the beads by treating the beads with 50% TFA in CH2Cl2 containing 2.5% triisopropylsilane (4 ml for 250 mg of beads) at RT for 30 min. The cleavage cocktail was transferred to a falcon tube and the beads washed with minimal amounts of CH2CL2. To the cleavage cocktail in a falcon tube was added cold ether (−20° C., 8 mL) leading to the precipitation of the peptide. Centrifugation afforded a pellet that was washed ether dissolved in 20% MeOH in water and purified by reverse phase HPLC using a gradient of 20-100% MeOH in water containing 0.1% TFA.

Preparation 10

Synthesis of glycine-Based Peptide Linkers

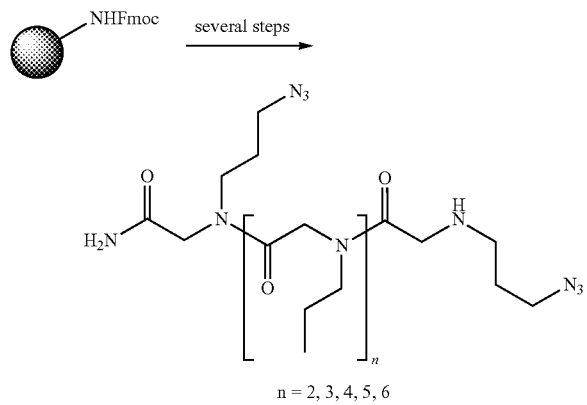

n = 2, 3, 4, 5, 6

The glycine-based peptide linkers were prepared by a procedure analogous to the one described in Preparation 9 for the alanine-based linkers.

Example 1

Synthesis of 1,4-bis(6-nitro-1H-benzo[d]imidazol-2-yl)benzene

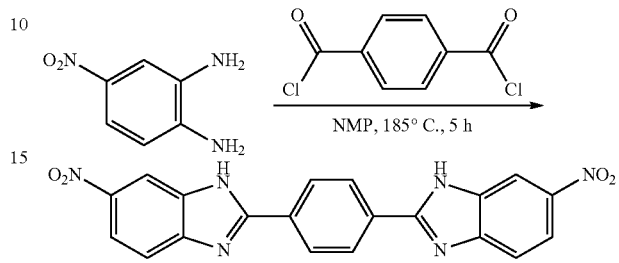

To a solution of 4-nitro-1,2-phenylene diamine (0.50 g, 3.26 mmol) in anhydrous NMP (5.0 mL), under $N_2$ atmosphere, was added terephthaloyl chloride (0.33 g, 1.63 mmol) at room temperature, and the reaction mixture was heated at 185° C. for 5 hours. The reaction mixture was cooled to 60° C., and the contents were slowly poured into ice-cold water and stirred for 10 minutes, whereupon a precipitate was formed. The precipitate was collected by filtration under vacuum and washed with water (50 mL). The obtained material was suspended in ethanol and the mixture was refluxed for 15 min. The material was filtered under vacuum while the contents were still hot, washed with ethanol (30 mL), and dried under vacuum to obtain 1,4-bis (6-nitro-1H-benzo[d]imidazol-2-yl)benzene. 1H NMR (DMSO-d6, 400 MHz) δ: 8.50 (d, J=2.4 Hz, 2H), 8.45 (s, 4H), 8.16 (dd, J=8.8 Hz, 2.4 Hz, 2H), 7.82 (d, J=9.26 Hz, 2H). MS (ESI): m/z=399 [M+H]+.

Example 2

Synthesis of 2,2'-(1,4-phenylene)bis(1H-benzo[d]imidazol-6-amine)

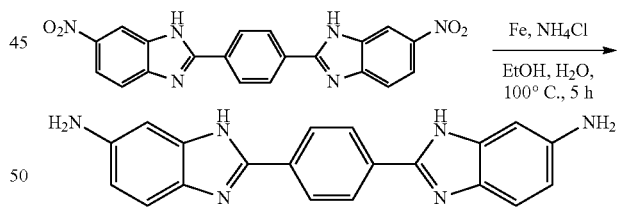

To a solution of 1,4-bis(6-nitro-1H-benzo[d]imidazol-2-yl)benzene (0.20 g, 0.5 mmol) in ethanol (10.0 mL) and water (5.0 mL) at room temperature, was added iron powder (0.27 g, 5.0 mmol) followed with ammonium chloride (0.27 g, 5.0 mmol), and the reaction mixture was heated at reflux for 5 hours. The reaction mixture was cooled to room temperature and the contents were filtered through a celite pad and the pad was washed with ethanol (50 mL). The filtrate was concentrated under vacuum and the obtained material was suspended in water. The mixture was stirred at 60° C. for 30 minutes and the material was collected by filtration under vacuum and dried for 16 hours to obtain 2,2'-(1,4-phenylene)bis(1H)benzo[d]imidazol-6-amine. 1H NMR (DMSO-d6, 400 MHz) δ 8.23 (s, 4H), 7.37 (d, J=8.4 Hz, 2H), 6.81 (s, 2H), 6.66 (dd, J=8.4 Hz, 2.0 Hz, 2H). MS (ESI+APCl): m/z=341 [M+H]+.

Example 3

Synthesis of 1,1'-(2,2'-(1,4-phenylene)bis(1H-benzo[d]imidazole-6,2-diyl))diguanidine Step 1: synthesis of compound 3A: To a solution of 2,2'-(1,4-phenylene)bis(1H-benzo[d]imidazol-6-amine) (0.40 g, 1.17 mmol) in dichloromethane (15.0 mL) and Et3N (0.95 mL) at 0° C., was added 1,3-bis(tert-butoxycarbonyl)-2-methyl-2-thiopseudourea (0.85 g, 2.94 mmol) followed with mercury (II) chloride (0.63 g, 2.35 mmol), and the reaction mixture was stirred at room temperature for 24 hours. The reaction mixture was poured upon ice, whereupon the product precipitated. The crude product was triturated with methanol:dichloromethane (1:9, 30 mL), filtered under vacuum, washed with methanol:dichloromethane (1:9, 10 mL) and dried to obtain compound 3A. 1H NMR (DMSO-d6, 300 MHz) δ: 13.12 (brs, 2H), 11.53 (s, 1H), 11.48 (s, 1H), 10.15 (s, 1H), 10.07 (s, 1H), 8.33 (s, 4H), 8.05 (s, 1H), 8.03 (s, 1H), 7.64 (d, J=8.7 Hz, 1H), 7.52 (d, J=5.4 Hz, 1H), 7.24 (d, J=8.4 Hz, 1H), 7.15 (d, J=8.7 Hz, 1H), 1.53-1.41 (m, 36H).

Step 2: synthesis of 1,1'-(2,2'-(1,4-phenylene)bis(1H-benzo[d]imidazole-6,2-diyl))diguanidine: To a solution of compound 3A (0.52 g, 1.23 mmol) in dichloromethane (15.0 mL) at 0° C. was added HCl (4.0 M in dioxane, 2.50 mL, 9.90 mmol), and the reaction mixture was stirred at room temperature for 8 hours. The product precipitated in the reaction mixture, which was collected by filtration under vacuum and washed with dichloromethane (50 mL). The crude product was triturated with methanol (20 mL), filtered under vacuum, washed with methanol (10 mL), and dried under vacuum to obtain 1,1'-(2,2'-(1,4-phenylene)bis(1H-benzo[d]imidazole-6,2-diyl))diguanidine hydrochloride. 1H NMR (CD3OD, 300 MHz) δ: 8.42 (s, 4H), 7.85 (d, J=8.4 Hz, 2H), 7.72 (s, 1H), 7.72 (s, 1H), 7.44 (dd, J=8.8 Hz, 2.0 Hz, 2H). MS (ESI+APCl): m/z=425 [M+H]+.

Example 4

Synthesis of Compounds 4, 5, 6, 7, and 8

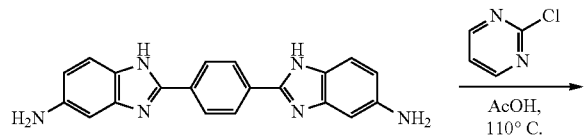

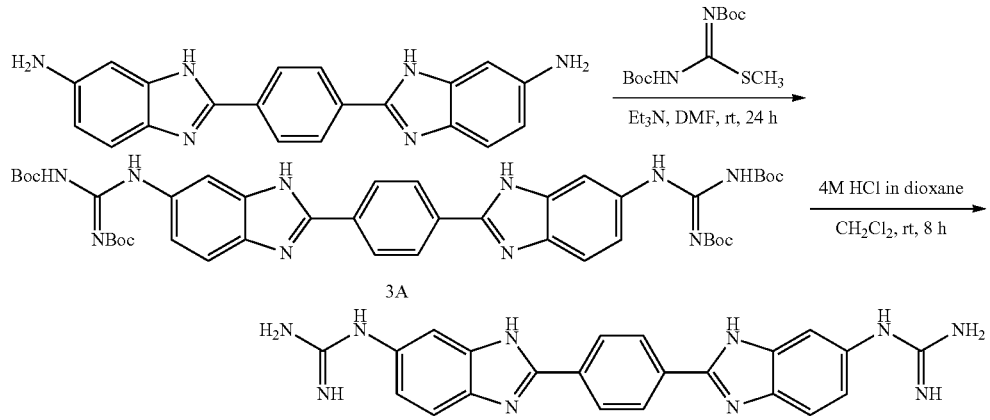

Procedure: 1,1'-(2,2'-(1,4-phenylene)bis(1H-benzo[d]imidazole-6,2-diyl))diguanidine (100 mg, 0.29 mmol) and 2-chloropyrimidine (67 mg, 0.59 mmol, 2 eq) were dissolved in acetic acid (3 mL) and heated to 110° C. via microwave for 1 hour to give a mixture of products. The reaction mixture was concentrated in vacuo and purified using a 20 g C18 column with a gradient of 0-100% MeOH/water+0.1% TFA. The title compounds were further purified using reverse phase HPLC with a gradient of 0-100% MeOH/water+0.1% TFA over 1 hour.

Compound 4 (N-(2-(4-(5-amino-1H-benzo[d]imidazol-2-yl)phenyl)-1H-benzo[d]imidazol-5-yl)acetamide): 1H NMR (DMSO-d6): δ 10.09 (s, 1H), 8.37 (d, 2H, J=9), 8.32 (d, 2H, J=9), 8.20 (s, 1H), 7.62 (d, 2H, J=9), 7.33 (d, 1H, J¬=8), 7.04 (d, 1H, J=9), 2.09 (s, 3H) ppm. Compound 4 (C22H19N6O) calculated mass 383.1620 (M+H+); mass found 383.1574 (M+H+).

Compound 5 (2-(4-(5-amino-1H-benzo[d]imidazol-2-yl)phenyl)-N-(pyrimidin-2-yl)-1H-benzo[d]imidazol-5-amine): 1H NMR (DMSO-d6): δ 10.00 (s, 1H), 8.56 (d, 2H, J=5), 8.54 (s, 1H), 8.39 (m, 4H), 8.23 (m, 1H), 7.7 (m, 3H), 7.35 (br s, 1H), 7.11 (d, 1H, J=9), 6.92 (t, 1H, J=5) ppm. Compound 5 (C24H19N8) calculated mass 419.1733 (M+H+); mass found 419.1663 (M+H+).

Compound 6 (N,N'-(2,2'-(1,4-phenylene)bis(1H-benzo[d]imidazole-5,2-diyl))diacetamide): 1H NMR (DMSO-d6): δ 10.19 (s, 2H), 8.37 (s, 4H), 8.27 (d, 2H, J=1.4), 7.69 (d, 2H, J=9), 7.41 (dd, 2H, J=1.6, 9), 2.10 (s, 6H) ppm. Compound 6 (C24H21N6O2) calculated mass 425.1726 (M+H+); mass found 425.1608 (M+H+).

Compound 7 (N-(2-(4-(5-(pyrimidin-2-ylamino)-1H-benzo[d]imidazol-2-yl)phenyl)-1H-benzo[d]imidazol-5-yl)acetamide): 1H NMR (DMSO-d6): δ 10.26 (s, 1H), 10.07 (s, 1H), 8.59 (d, 1H, J=1.2), 8.57 (d, 1H, J=5), 8.41 (m, 4H), 8.31 (d, 1H, J=1.3), 8.28 (m, 1H), 8.21 (m, 1H), 8.05 (m, 1H), 7.74 (m, 3H), 7.56 (m, 1H), 7.45 (dd, 1H, J=1.8, 9), 6.94 (t, 1H, J=5), 2.10 (s, 3H) ppm. Compound 7 (C26H21N8O) calculated mass 461.1838 (M+H+); mass found 461.1752 (M+H+).

Compound 8 (2,2'-(1,4-phenylene)bis(N-(pyrimidin-2-yl)-1H-benzo[d]imidazol-5-amine)): 1H NMR (DMSO-d6): δ 10.11 (s, 2H), 8.56 (d, 2H, J=5), 8.52 (d, 2H, J=5), 8.38 (s, 4H), 8.26 (d, 2H, J=9), 7.68 (d, 2H, J=9), 7.34 (dd, 2H, J=1.8, 9), 6.91 (t, 2H, J=5) ppm. Compound 8 (C28H21N10) calculated mass 497.1951 (M+H+); mass found 497.1978 (M+H+).

Example 5

Synthesis of 2,2'-(1,4-phenylene)bis(1H-benzo[d]imidazole-6-carbonitrile)

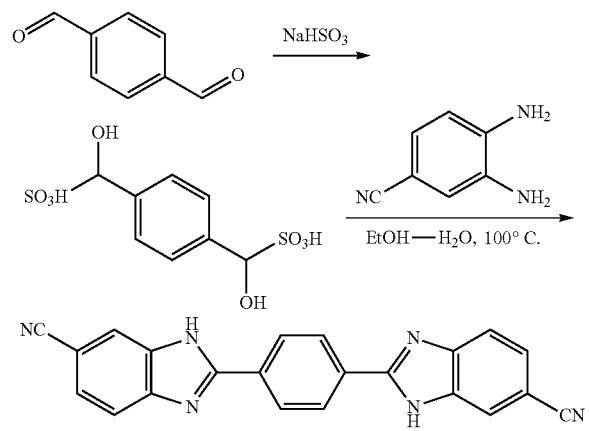

A solution of terephthaldehyde (1.0 g, 7.46 mmol) in ethanol (50 ml) was cooled to 0° C. and a solution of sodium bisulfite (1.55 g, 14.9 mmol) in water (20 ml) added dropwise. The cold-bath was removed and the mixture stirred for 1 hour before adding 3,4-diaminobenzonitrile (1.8 g, 13.5 mmol) and water (30 ml). The mixture was heated at reflux for 3 h and after cooling filtered. The filtrate was washed with water and methanol then dried under vacuum to give the title compound. 1H NMR (DMSO-d6, 400 MHz) δ: 8.45 (s, 4H), 8.23-8.21 (m, 2H), 7.82 (d, J=8.4 Hz, 2H), 7.67 (dd, J=1.5, 8.4 Hz, 2H), MS (MALDI): m/z=361 [M+H]+.

Example 6

Synthesis of dimethyl 2,2'-(1,4-phenylene)bis(1H-benzo[d]imidazole-6-carboxylate)

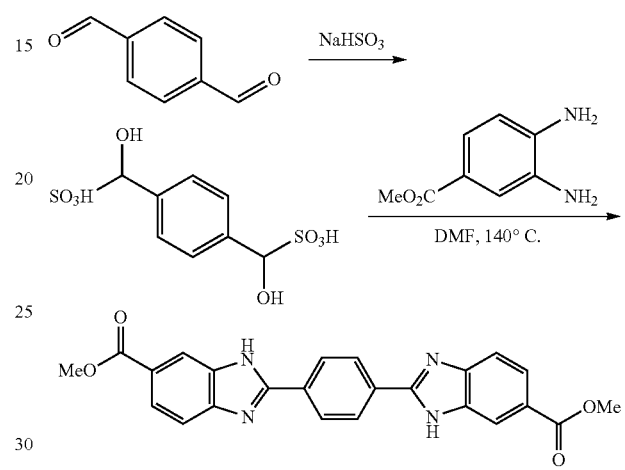

A solution of terephthaldehyde (1.0 g, 7.46 mmol) in ethanol (50 ml) was cooled to 0° C. and a solution of sodium bisulfite (1.55 g, 14.9 mmol) in water (15 ml) added dropwise. The cold-bath was removed and the mixture stirred for 1 hour then cooled to 0° C. and filtered. The compound was dried under vacuum to give 2.5 g of a bisulfite adduct. The product was mixed with Methyl-3,4-diaminobenzoate (2.5 g, 15.0 mmol) in DMF (60 ml) and heated at 140° C. for 3 h. The solvent was removed under vacuum and water (100 ml) added. After mixing for 1 hour the mixture was filtered and the residue washed with water and methanol then dried under vacuum to afford 2,2'-(1,4-phenylene)bis(1H-benzo[d]imidazole-6-carboxylate). 1H NMR (DMSO-d6, 400 MHz) δ: 8.40 (s, 4H), 8.24 (br s, 2H), 7.89 (dd, J=1.4, 8.4 Hz, 2H), 7.73 (d, J=8.4 Hz, 2H), 3.90 (s, 6H).

Example 7

Synthesis of 2,2'-(1,4-phenylene)bis(1H-benzo[d]imidazole-6-carboxylic acid)

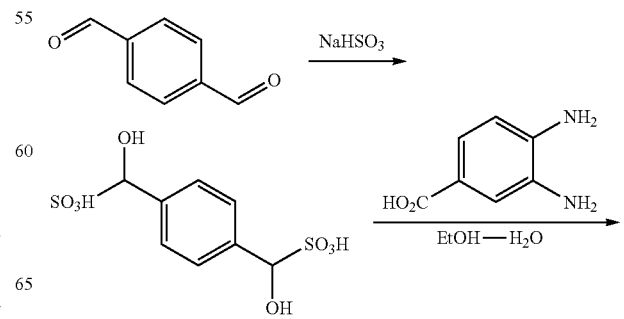

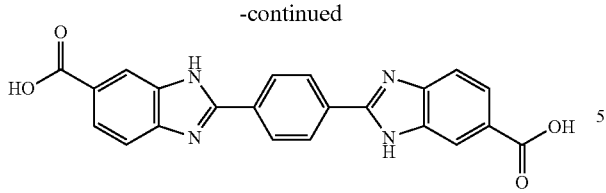

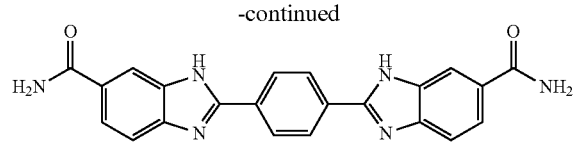

A solution of terephthaldehyde (2.0 g, 14.9 mmol) in ethanol (80 ml) was cooled to 0° C. and a solution of sodium bisulfite (3.1 g, 30 mmol) in water (30 ml) added dropwise. The cold-bath was removed and the mixture stirred for 1 hour before adding 3,4-diaminobenzoic acid (4.5 g, 29.6 mmol) and water (50 ml). The mixture was refluxed for 4 hours and allowed to cool to RT, filtered and the residue washed with water (×3) and methanol (×3) then dried under vacuum to give 2,2'-(1,4-phenylene)bis(1H-benzo[d]imidazole-6-carboxylic acid). 1H NMR (DMSO-d6, 400 MHz) δ: 8.41 (s, 4H), 8.22 (br s, 2H), 7.88 (dd, J=1.3, 8.5 Hz, 2H), 7.71 (d, J=8.5 Hz, 2H), MS (ESI): m/z=399 [M+H]+.

A mixture of 2,2'-(1,4-phenylene)bis(1H-benzo[d]imidazole-6-carbonitrile) (0.20 g, 0.55 mmol) and conc.H₂SO₄ (3.00 mL) was stirred at 60° C. for 2 hours. The reaction mixture was poured into ice and neutralized with aqueous saturated potassium carbonate solution, whereupon the product precipitated. The precipitated product was collected by filtration under vacuum and dried. The crude product was triturated with hot methanol, filtered under vacuum, washed with MTBE (25.0 mL) and dried to obtain 2,2'-(1,4-phenylene)bis(1H-benzo[d]imidazole-6-carboxamide). 1H NMR (DMSO-d6, 400 MHz): 13.27 (d, J=10 Hz, 2H), 8.39 (brs, 4H), 8.28 (s, 1H), 8.09 (s, 1H), 8.03 (d, J=19.2 Hz, 2H), 7.84 (d, J=9.2 Hz, 1H), 7.79 (d, J=8.4 Hz, 1H), 7.71 (d, J=8.4 Hz, 1H), 7.59 (d, J=8.4 Hz, 1H), 7.31 (d, J=17.2 Hz, 2H). MS (ESI+APCI) m/z 397 [M+H]+.

Example 8

Synthesis of 2,2'-(1,4-phenylene)bis(1H-benzo[d]imidazole-6-carboxamide)

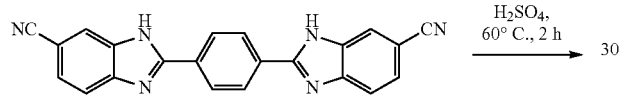

Example 9

Synthesis of 1,4-bis(6-(4,5-dihydro-1H-imidazol-2-yl)-1H-benzo[d]imidazol-2-yl)benzene (Compound 14) and 2-(4-(6-(4,5-dihydro-1H-imidazol-2-yl)-1H-benzo[d]imidazol-2-yl)phenyl)-1H-benzo[d]imidazole-6-carbonitrile (Compound 13)

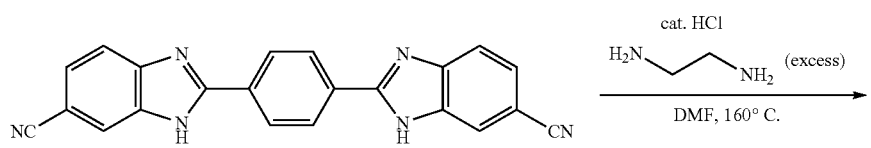

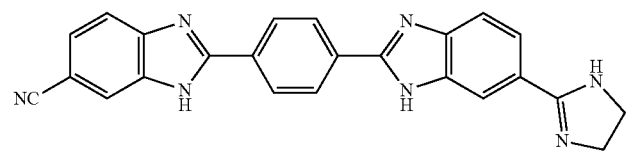

Compound 13

+

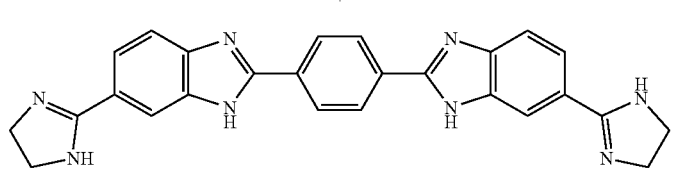

Compound 14

To a solution of 2,2'-(1,4-phenylene)bis(1H-benzo[d]imidazole-6-carbonitrile) (100.0 mg, 0.28 mmol) in DMF (3 ml) was added ethylene diamine (120 µL, 1.8 mmol) and 4N HCl in dioxane (50 µL) and the mixture stirred overnight at 160° C. The solvent was removed under vacuum and the resultant compound washed with ether then purified using a C-18 column and a gradient of 0-100% MeOH in water containing 0.1% TFA. Compound 13; 1H NMR (DMSO-d6, 400 MHz) δ: 10.48 (s, 2H, NH), 8.44 (s, 4H), 8.32 (s, 1H), 8.20 (s, 1H), 7.88 (d, J=8.4 Hz, 1H), 7.85-7.77 (m, 2H), 7.65 (dd, J=1.4, 9.0 Hz, 1H), 4.05 (s, 4H). Compound 14; 1H NMR (CD3OD, 400 MHz) □: 8.39 (s, 4H), 8.27-8.25 (m, 2H), 7.87 (d, J=8.5 Hz, 2H), 7.79 (dd, J=1.8, 8.5 Hz, 2H), 4.15 (s, 8H), MS (MALDI): m/z=447 [M+H]+.

Example 10

Synthesis of 2-(4-(6-cyano-1H-benzo[d]imidazol-2-yl)phenyl)-N-isopentyl-1H-benzo[d]imidazole-6-carboxamide (Compound 15)

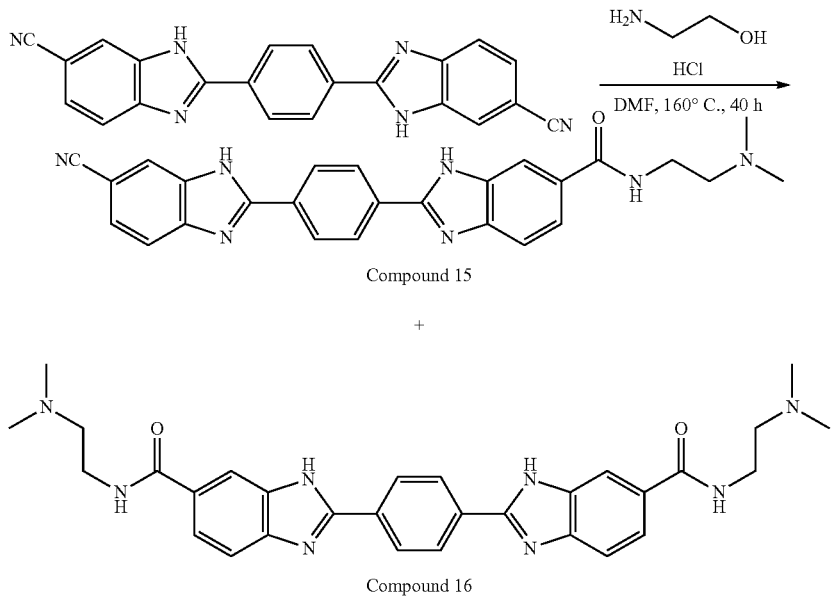

To a solution of 2,2'-(1,4-phenylene)bis(1H-benzo[d]imidazole-6-carbonitrile) (Compound 9, 100 mg, 0.28 mmol) in DMF (3 ml) was added ethanolamine (200 µL) and 4N HCl in dioxane (50 µL) and the mixture stirred overnight at 160° C. The solvent was removed under vacuum and the residue washed with ether before purification using a C-18 column and a gradient of 0-100% MeOH in water containing 0.1% TFA to afford Compounds 15 and 16 (see separate procedure for preparation of Compound 16). Compound 15; 1H NMR (CD3OD, 400 MHz) δ: 8.39 (s, 4H), 8.27-8.24 (m, 2H), 7.86 (dd, J=0.6, 8.5 Hz, 2H), 7.79 (dd, J=1.8, 8.5 Hz, 2H), 4.15 (s, 8H), MS (ESI): m/z=450 [M+H]+.

Example 11

Synthesis of 2,2'-(1,4-phenylene)bis(N-(2-(dimethylamino)ethyl)-1H-benzo[d]imidazole-6-carboxamide) (Compound 16)

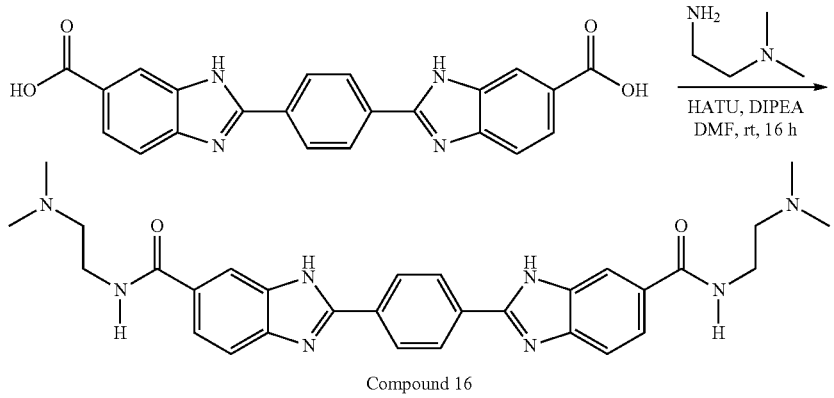

To a suspension of 2,2'-(1,4-phenylene)bis(1H-benzo[d]imidazole-6-carboxylic acid) (0.10 g, 0.25 mmol) in DMF (5.00 mL) at 0° C., was added HATU (0.21 g, 0.55 mmol), DIPEA (0.27 mL, 1.50 mmol) and the reaction mixture was stirred for 15 minutes. N,N'-Dimethylethane-1,2-diamine (50 mg, 0.55 mmol) was added to the above mixture at 0° C. and the reaction mixture was allowed to warm to room temperature and stirred for 16 hours. The reaction mixture was concentrated under vacuum and the crude product was diluted with ice-cold water (10 mL), and stirred for 15 minutes, whereupon the product precipitated. The product was collected by filtration under vacuum, washed with methanol (10 mL), and dried under vacuum. The product was purified by silica gel chromatography (1:4 methanol: dichloromethane). The fractions containing the pure product were combined and concentrated under vacuum to obtain 2,2'-(1,4-phenylene)bis(N-(2-(dimethylamino)ethyl)-1H-benzo[d]imidazole-6-carboxamide). 1H NMR (DMSO-d6, 400 MHz) δ: 13.27 (brs, 1H), 8.52-8.39 (m, 6H), 8.23 (s, 1H), 8.05 (s, 1H), 7.87-7.61 (m, 4H), 3.42-3.37 (m, 4H), 2.45 (t, J=7.2 Hz, 4H), 2.20 (s, 12H), MS (ESI+APCl): m/z=539 [M+H]+.

Example 12

Synthesis of Compounds 17, 18, and 19

N-(2,2-diethoxyethyl)carbodiimide (110 mg, 0.7 mmol, 2.4 eq) and 1,1'-(2,2'-(1,4-phenylene)bis(1H-benzo[d]imidazole-6,2-diyl))diguanidine (100 mg, 0.29 mmol, 1 eq) were suspended in ethanol (20 mL) and methanesulfonic acid (45 μL, 0.7 mmol, 2.4 eq) was added. The reaction was heated to reflux overnight. Added additional carbodiimide (110 mg, 0.7 mmol, 2.4 eq) and methanesulfonic acid (45 μL, 0.7 mmol, 2.4 eq) and heated to reflux again overnight. All starting material was consumed. The reaction mixture was concentrated in vacuo and purified using a 20 g C18 flash column (0-100% MeOH/water+0.1% TFA). The fractions containing single and double addition compound were concentrated and then purified using reverse phase HPLC (30-70% MeOH (no TFA)/water (0.1% TFA) over 60 min.

Compound 17 (1-(2-(4-(5-amino-1H-benzo[d]imidazol-2-yl)phenyl)-1H-benzo[d]imidazol-5-yl)-3-(2,2-diethoxyethyl)guanidine): 1H NMR (DMSO-d6): δ 10.43 (s, 1H), 9.81 (s, 1H), 8.44 (dd, 2H, J=2, 9), 8.37 (dd, 2H, J=2, 12), 7.75 (d, 1H, J=9), 7.68 (m, 2H), 7.57 (dd, 1H, J=2, 13), 7.33 (s, 1H), 7.16 (dd, 1H, J=2, 9), 7.12 (s, 1H), 7.10 (s, 1H), 4.66 (t, 1H, J=5), 3.70 (m, 2H), 3.57 (m, 2H), 3.42 (m, 2H), 1.18 (t, 6H, J=7) ppm. calculated mass 499.2570 (M+H+); mass found 499.2547 (M+H+).

Compound 18 (1,1'-(2,2'-(1,4-phenylene)bis(1H-benzo[d]imidazole-5,2-diyl))bis(3-(2,2-diethoxyethyl)guanidine)). 1H NMR (DMSO-d6): δ 9.61 (s, 2H), 8.38 (s, 4H), 7.71 (d, 2H, J=9), 7.51 (s, 4H), 7.24 (s, 1H), 7.12 (dd, 2H, J=2, 8), 6.98 (s, 1H), 4.65 (t, 2H, J=5), 3.69 (m, 4H), 3.57 (m, 4H), 3.42 (m, 2H), 1.18 (t, 12H, J=7) ppm. calculated mass 657.3625 (M+H+); mass found 657.3862 (M+H+).

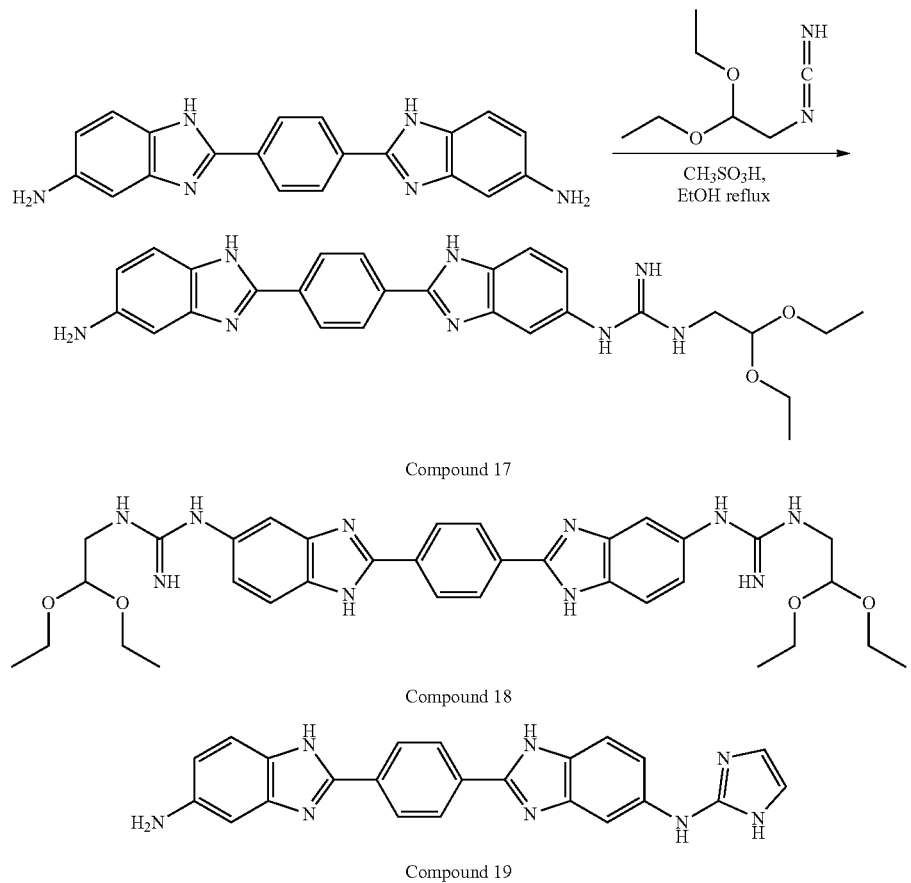

Compound 19 (2-(4-(5-amino-1H-benzo[d]imidazol-2-yl)phenyl)-N-(1H-imidazol-2-yl)-1H-benzo[d]imidazol-5-amine). 1H NMR (DMSO-d6): δ 10.29 (s, 1H), 8.43 (d, 2H, J=9), 8.35 (d, 2H, J=9), 7.73 (d, 1H, J=9), 7.67 (d, 1H, J=9), 7.56 (d, 1H, J=2), 7.20 (dd, 1H, J=2, 9), 7.10 (m, 2H), 7.07 (s, 1H) ppm. calculated mass 407.1733 (M+H+); mass found 407.1679 (M+H+).

Example 13

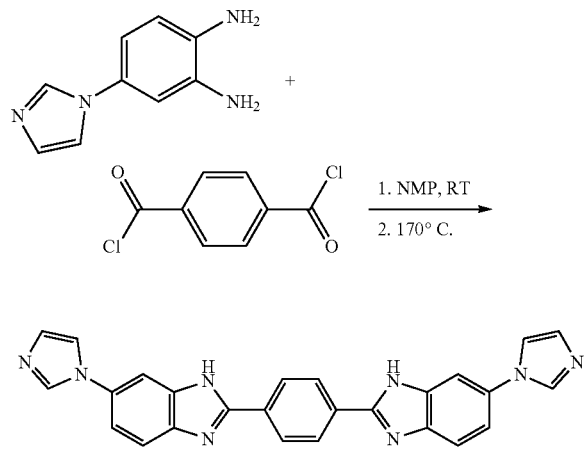

Synthesis of 1,4-bis(6-(1H-imidazol-1-yl)-1H-benzo[d]imidazol-2-yl)benzene 4-(1H-imidazol-1-yl)benzene-1,2-diamine (200 mg, 1.15 mmol) was dissolved in anhydrous NMP (3 ml) and the mixture cooled to 0° C. Terephthloyl chloride (118 mg, 0.58 mmol) was added and stirring continued overnight while allowing the reaction to warm to RT. The mixture was then heated at 170° C. for 8 hours and the solvent removed under vacuum. The crude product was washed with ether then purified using a C-18 column and a gradient of 0-100% MeOH in water containing 0.1% TFA. 1H NMR (DMSO-d6, 400 MHz) δ: 9.71 (s, 2H), 8.44 (s, 4H), 8.35 (t, J=1.7 Hz, 2H), 8.11 (d, J=1.9 Hz, 2H), 7.96 (t, J=1.6 Hz, 2H), 7.88 (d, J=8.6 Hz, 2H), 7.65 (dd, J=2.2, 8.6 Hz, 2H), MS (MALDI): m/z=443 [M+H]+.

Example 14

Synthesis of (2-(4-(5-amino-1H-benzo[d]imidazol-2-yl)phenyl)-N-(pyridin-2-yl)-1H-benzo[d]imidazol-5-amine) (Compound 21) and (2,2'-(1,4-phenylene)bis(N-(pyridin-2-yl)-1H-benzo[d]imidazol-5-amine)) (Compound 22)

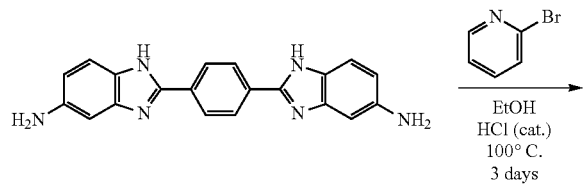

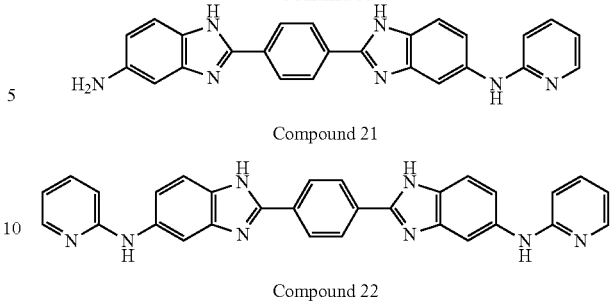

Compound 21

Compound 22

1,1'-(2,2'-(1,4-phenylene)bis(1H-benzo[d]imidazole-6,2-diyl))diguanidine (100 mg, 0.29 mmol) was dissolved in ethanol (3 mL) and 2-bromopyridine (3 mL, 31.3 mmol, 108 eq) and one drop of HCl was added. The reaction was heated to reflux for 48 hours. The reaction mixture was then cooled and concentrated in vacuo. The reaction mixture was dissolved in water and excess 2-bromopyridine was removed by washing with DCM using a separatory funnel. The water layer was concentrated down to ~5 mL and left at room temperature overnight. A compound precipitated and was filtered. This was a mixture of single and double addition products. Purified crude reaction mixture using a 20 g C18 flash column (0-100% MeOH/water+0.1% TFA). Initial purification did not separate two products. Fractions were concentrated and purified using reverse phase HPLC (10-60% MeOH (no TFA)/water (0.1% TFA)) over 60 min.

Compound 21 (2-(4-(5-amino-1H-benzo[d]imidazol-2-yl)phenyl)-N-(pyridin-2-yl)-1H-benzo[d]imidazol-5-amine). 1H NMR (DMSO-d6): δ 10.00 (s, 1H), 8.41 (m, 5H), 8.15 (d, 1H, J=5), 7.78 (m, 2H), 7.70 (d, 1H, J=8.7), 7.46 (dd, 1H, J=1.7, 9), 7.40 (s, 1H), 7.14 (dd, 1H, J=1.7, 9), 7.03 (d, 1H, J=9), 6.91 (t, 1H, J=6) ppm. calculated mass 418.1780 (M+H+); mass found 418.1810 (M+H+).

Compound 22 (2,2'-(1,4-phenylene)bis(N-(pyridin-2-yl)-1H-benzo[d]imidazol-5-amine)). 1H NMR (DMSO-d6): δ 10.01 (s, 2H), 8.44 (s, 4H), 8.37 (s, 2H), 8.14 (d, 2H, J=5), 7.80 (m, 4H), 7.45 (dd, 2H, J=1.6, 9), 7.04 (d, 2H, J=9), 6.91 (t, 2H, J=6) ppm. calculated mass 495.2046 (M+H+); mass found 495.2182 (M+H+).

Example 15

Synthesis of (tert-butyl 2-((2-(4-(5-amino-1H-benzo[d]imidazol-2-yl)phenyl)-1H-benzo[d]imidazol-5-yl)amino)-4,5-dihydro-1H-imidazole-1-carboxylate)

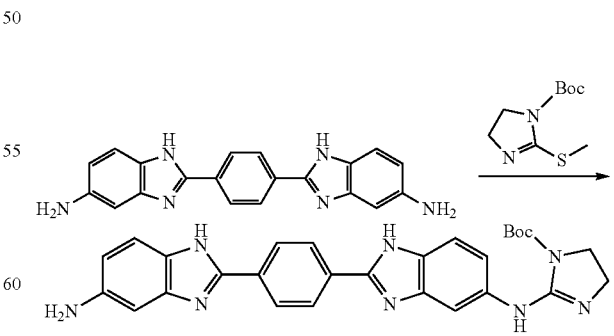

1,1'-(2,2'-(1,4-phenylene)bis(1H-benzo[d]imidazole-6,2-diyl))diguanidine (100 mg, 0.29 mmol) and tert-butyl 2-(methylthio)-4,5-dihydro-1H-imidazole-1-carboxylate (69 mg, 0.32 mmol, 1.1 eq) were dissolved in ethanol (3 mL)

and stirred at room temperature overnight. The reaction mixture was concentrated in vacuo and purified using a 20 g C18 flash column (0-100% MeOH/water+0.1% TFA). 1H NMR (DMSO-d6): δ 10.40 (s, 1H), 9.52 (s, 1H), 8.39 (d, 2H, J=9), 8.32 (d, 2H, J=9), 8.26 (s, 2H), 7.93 (s, 1H), 7.70 (d, 1H, J=8), 7.60 (d, 1H, J=9), 7.56 (s, 1H), 7.37 (d, 1H, J=9), 7.15 (dd, 1H, J=2, 9), 3.67 (s, 4H), 1.51 (s, 9H) ppm. MS: (C28H29N8O2) calculated mass 509.2413 (M+H+); mass found 509.2351 (M+H+).

Example 16

Synthesis of (2-(4-(5-amino-1H-benzo[d]imidazol-2-yl)phenyl)-N-(4,5-dihydro-1H-imidazol-2-yl)-1H-benzo[d]imidazol-5-amine)

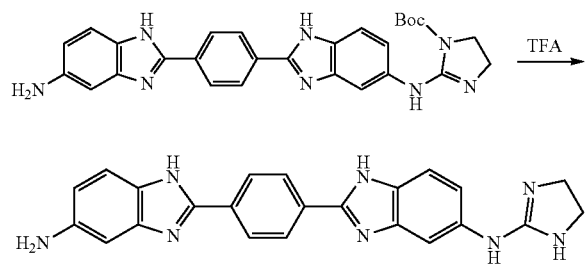

(tert-butyl 2-((2-(4-(5-amino-1H-benzo[d]imidazol-2-yl)phenyl)-1H-benzo[d]imidazol-5-yl)amino)-4,5-dihydro-1H-imidazole-1-carboxylate) (5 mg, 10 μmop was dissolved in dichloromethane (1 mL) and cooled to 0° C. Then TFA (1 mL) was added and the reaction stirred at 0° C. for 1 hour. Then the reaction mixture was concentrated in vacuo and then resuspended in water and purified using reverse phase HPLC with a gradient of 0-100% MeOH/water+0.1% TFA over 1 hour. 1H NMR (DMSO-d6): δ 10.38 (s, 1H), 8.41 (d, 2H, J=9), 8.32 (d, 2H, J=9), 8.25 (s, 2H), 7.70 (d, 1H, J=8), 7.62 (d, 1H, J=9), 7.56 (s, 1H), 7.15 (dd, 1H, J=1.9, 9), 3.67 (s, 4H) ppm. MS: (C23H21N8) calculated mass 409.1889 (M+H+); mass found 409.1988 (M+H+).

Example 17

Synthesis of 2,2'-(1,4-phenylene)bis(N-hydroxy-1H-benzo[d]imidazole-6-carboximidamide)

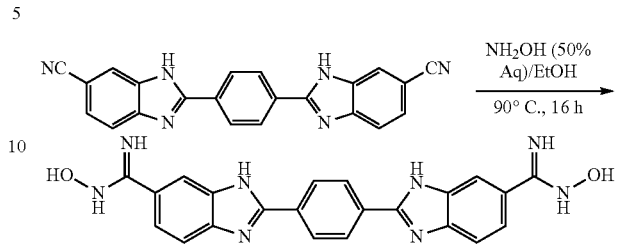

To a suspension of 2,2'-(1,4-phenylene)bis(1H-benzo[d]imidazole-6-carbonitrile) (0.15 g, 0.42 mmol) in ethanol (5.0 mL) was added hydroxylamine (50% in water, 0.33 mL, 5.0 mmol) in a sealed tube and stirred at 90° C. for 16 hours. The reaction mixture was cooled to room temperature and the product was collected by filtration under vacuum, washed with methanol (5 mL), and dried under vacuum. The product was triturated with hot methanol (10 mL) and dried under vacuum to obtain 2,2'-(1,4-phenylene)bis(N-hydroxy-1H-benzo[d]imidazole-6-carboximidamide). 1H NMR (DMSO-d6, 400 MHz) δ: 13.22 (brs, 2H), 9.65 (brs, 2H), 8.36 (brs, 4H), 8.01 (s, 1H), 7.83 (s, 1H), 7.62-7.60 (m, 4H), 5.98 (brs, 3H), MS (ESI+APCl): m/z=427 [M+H]+.

Example 18

Synthesis of 2,2'-(1,4-phenylene)bis(1H-benzo[d]imidazole-6-carboximidamide) acetate

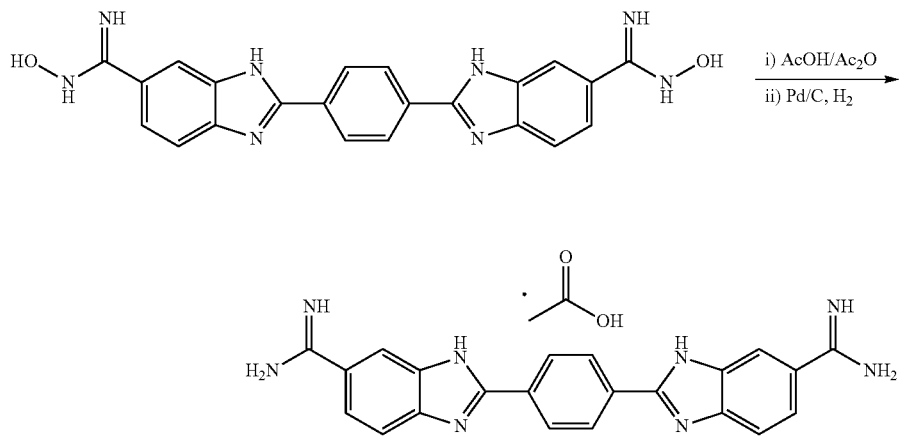

To a suspension of 2,2'-(1,4-phenylene)bis(N-hydroxy-1H-benzo[d]imidazole-6-carboximidamide) (50 mg, 0.12 mmol) in glacial acetic acid (2.00 mL) was slowly added acetic anhydride (0.1 mL) and stirred at room temperature for 16 hours. 10% Pd/C (10 mg) was added in one lot and the reaction mixture was hydrogenated (~1 atmospheric pressure; balloon pressure) at room temperature for 6 h. The reaction mixture was filtered through a celite bed and washed with methanol (10.0 mL). The filtrate was concentrated under vacuum and the residue was triturated with methanol (10.0 mL), filtered under vacuum, washed with methanol (5.00 mL) and dried to obtain 2,2'-(1,4-phenylene)bis(1H-benzo[d]imidazole-6-carboximidamide) acetate. 1H NMR (DMSO-d6, 400 MHz) δ: 11.7-10.0 (m, 2H), 8.39 (brs, 4H), 8.12 (s, 2H), 7.74-7.72 (m, 2H), 7.65-7.58 (m, 2H), 1.77 (s, 6H), MS (ESI+APCl): m/z=395 [M+H]+.

Example 19
Synthesis of N-(2-(dimethylamino)ethyl)-2-(4-(6-((2-(methylamino)ethyl)carbamoyl)-1H-benzo[d]imidazol-2-yl)phenyl)-1H-benzo[d]imidazole-6-carboxamide (Compound 27) and 2,2'-(1,4-phenylene)bis(N-(2-(methylamino)ethyl)-1H-benzo[d]imidazole-6-carboxamide) (Compound 28)
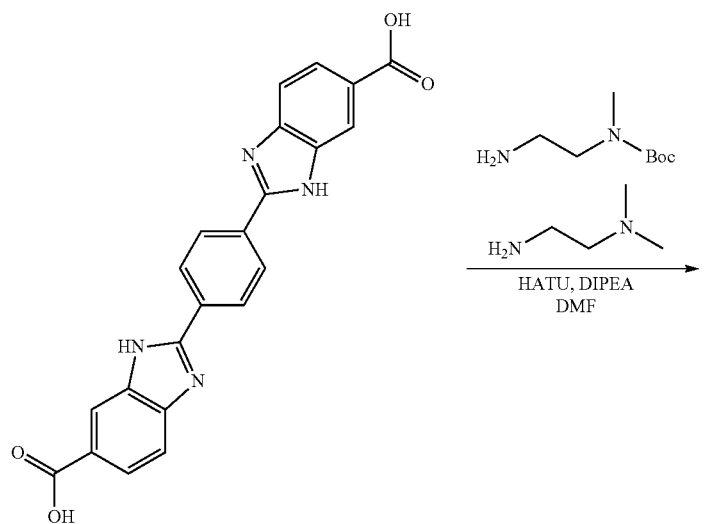
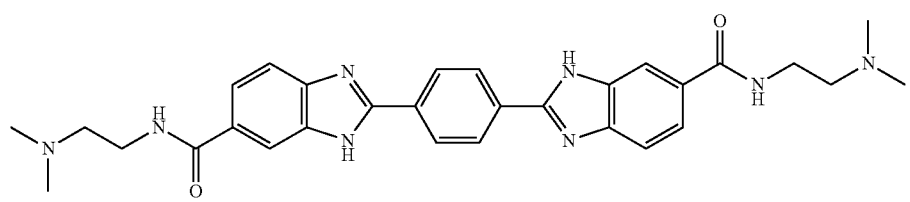
Compound 16
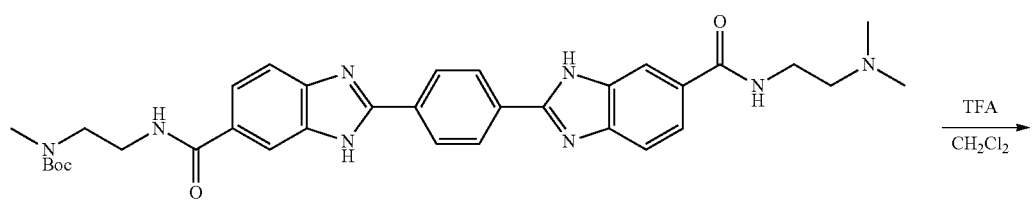
Compound 27-a
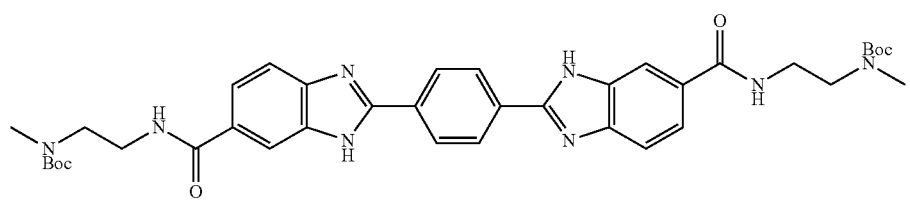
Compound 28-b

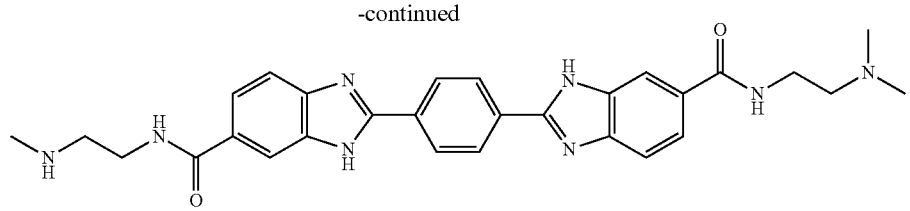

Compound 27

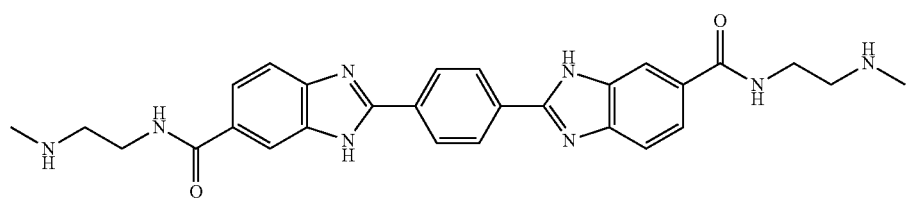

Compound 28

To a solution of 2,2'-(1,4-phenylene)bis(1H-benzo[d]imidazole-6-carboxylic acid) (200 mg, 0.52 mmol) in DMF (5 ml) was added HATU (400 mg, 1.06 mmol) and DIPEA (600 μL, 3.4 mmol). The mixture was stirred for 5 minutes before adding 2-(Dimethylamino)ethylamine (46 mg, 0.52 mmol) and Boc-N-Methyl ethylenediamine (95 mg, 0.54 mmol) and stirring overnight. The solvent was removed under vacuum and the crude material washed with ether and ethyl acetate. The resultant residue was purified on a C-18 column using a gradient of 0-100% MeOH in water containing 0.1% TFA to afford Compound 16, Compound 27-a and Compound 28-a Concentration of fractions containing Compound 27-a and Compound 28-a led to partial cleavage of the Boc-group. Consequently, the Boc-group was cleaved using 30% TFA in dichloromethane to afford Compounds 27 and 28. Compound 27; 1H NMR (DMSO-d6, 400 MHz) δ: 9.49 (br s, 1H, —NH), 8.79-8.70 (m, 2H, —NH), 8.52 (br s, 2H, —NH), 8.42 (s, 4H), 8.21 (s, 2H), 7.87-7.81 (m, 2H), 7.73 (d, J=8.4 Hz, 2H), 3.70-3.55 (m, 4H), 3.34-3.28 (m, 2H), 3.19-3.10 (m, 2H), 2.89 (d, J=4.7 Hz, 6H), 2.64 (t, J=5.3 Hz, 3H), MS (ESI): m/z=525 [M+H]+. Compound 28; 1H NMR (DMSO-d6, 400 MHz) δ: 8.75 (t, J=5.2 Hz, 2H, —NH), 8.49 (br s, 4H, —NH), 8.42 (s, 4H), 8.21 (br s, 2H), 7.83 (d, J=8.4 Hz, 2H), 7.72 (d, J=8.4 Hz, 2H), 3.64-3.54 (m, 4H), 3.18-3.10 (m, 4H), 2.64 (t, J=5.2 Hz, 6H), MS (ESI): m/z=511 [M+H]+.

Example 20

Synthesis of N-(2-aminoethyl)-2-(4-(6-((2-(dimethylamino)ethyl)carbamoyl)-1H-benzo[d]imidazol-2-yl)phenyl)-1H-benzo[d]imidazole-6-carboxamide

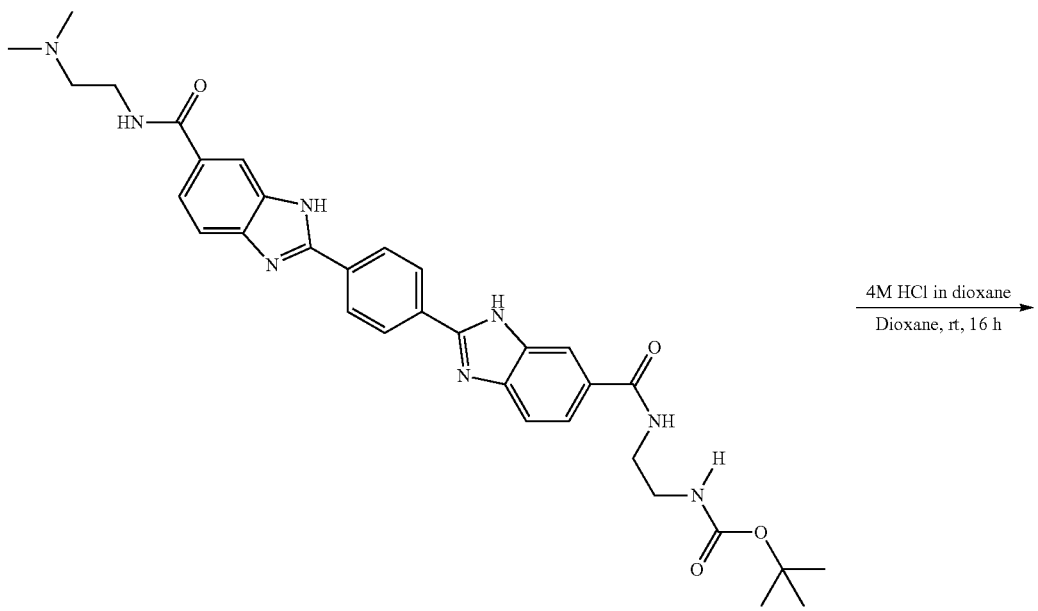

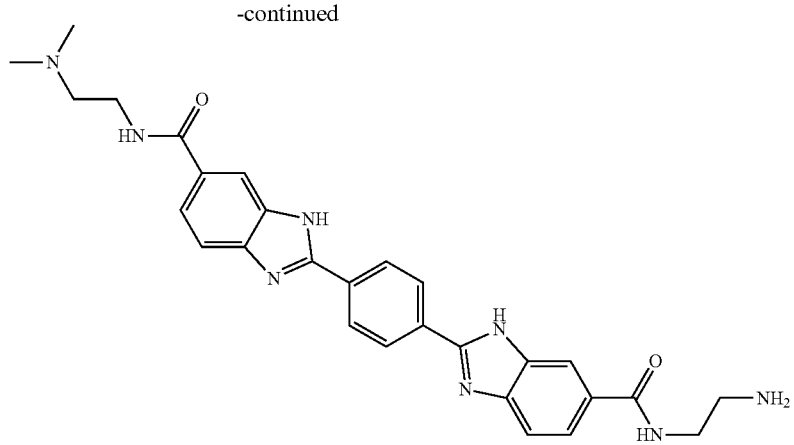

To a solution of tert-butyl (2-(2-(4-(6-((2-(dimethylamino)ethyl)carbamoyl)-1H-benzo[d]imidazol-2-yl)phenyl)-1H-benzo[d]imidazole-6-carboxamido)ethyl)carbamate (43 mg, 0.07 mmol) in 1,4-dioxane (3.0 mL) at 0° C. was added 4M HCl in 1,4-dioxane (2.00 mL) and the reaction mixture was stirred at room temperature for 16 hours. The reaction mixture was concentrated under reduced pressure to obtain the crude product. The product was triturated with methanol (10 mL), filtered under vacuum, washed with methanol (5.00 mL), and dried to obtain N-(2-aminoethyl)-2-(4-(6-((2-(dimethylamino)ethyl)carbamoyl)-1H-benzo[d]imidazol-2-yl)phenyl)-1H-benzo[d]imidazole-6-carboxamide as hydrochloride salt.

1H NMR (DMSO-d6, 400 MHz) δ: 10.03 (brs, 1H), 8.97 (t, J=5.2 Hz, 1H), 8.88-8.87 (m, 1H), 8.53 (brs, 4H), 8.31 (d, J=3.2 Hz, 2H), 8.01 (brs, 3H), 7.94 (d, J=8.8 Hz, 2H), 7.78 (d, J=8.8 Hz, 2H), 3.69-3.67 (m, 2H), 3.60-3.57 (m, 2H), 3.33-3.30 (m, 2H), 3.06-3.01 (m, 2H), 2.86 (d, J=5.2 Hz, 6H). MS (ESI+APCI): m/z=511 [M+H]+.

Example 21

Synthesis of 2,2'-(1,4-phenylene)bis(N-(2-aminoethyl)-1H-benzo[d]imidazole-6-carboxamide)

A solution of 2,2'-(1,4-phenylene)bis(1H-benzo[d]imidazole-6-carboxylic acid) (Compound 11, 50 mg, 0.126 mmol) in DMF (3 ml) was treated with HATU (100 mg, 0.26 mmol) and DIPEA (130 μL, 0.75 mmol) for 5 minutes before adding Boc-ethylenediamine (44 mg, 0.27 mmol). After stirring overnight, the solvent was removed in vacuo and to the crude material added water (5 ml). Centrifugation gave a material that was dried under vacuum and a solution of 30% TFA in dichloromethane (3 ml) cooled to 0° C. added. After stirring for 2 hours, ether (6 ml) was added followed by centrifugation to afford a material that was purified using a C-18 column and a gradient of 0-100% MeOH in water containing 0.1% TFA to afford 2,2'-(1,4-phenylene)bis(N-(2-aminoethyl)-1H-benzo[d]imidazole-6-carboxamide). 1H NMR (CD3OD, 400 MHz) δ: 8.43 (s, 4H), 8.33 (br s, 2H), 7.99 (dd, J=1.5, 8.5 Hz, 2H), 7.83 (d, J=8.5 Hz, 2H), 3.76 (t, J=5.9, 12 Hz, 4H), 3.26 (t, J=5.9, 12 Hz, 4H), MS (ESI): m/z=483 [M+H]+.

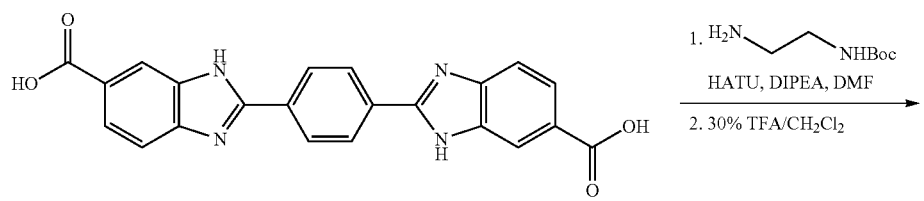

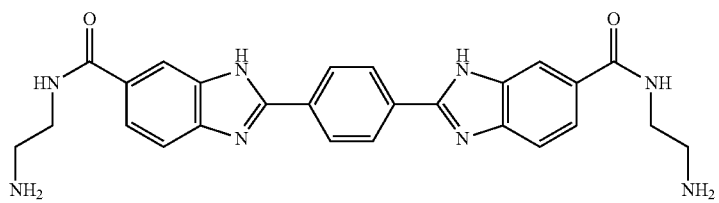

Compound 30

Example 22

Synthesis of 2,2'-((2,2'-(1,4-phenylene)bis(1H-benzo[d]imidazole-6,6'-carbonyl))bis(azanediyl))bis(N,N,N-trimethylethanaminium) chloride

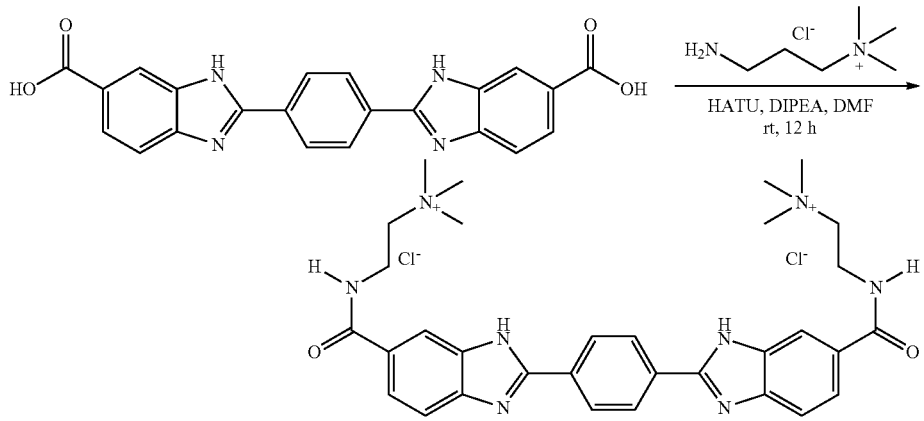

To a suspension of 2,2'-(1,4-phenylene)bis(1H-benzo[d]imidazole-6-carboxylic acid) (0.1 g, 0.20 mmol) in DMF (3 mL) at 0° C., was added HATU (0.24 g, 0.63 mmol), DIPEA (0.25 mL, 1.50 mmol) and the reaction mixture was stirred for 10 minutes. 3-amino-N,N,N-trimethylpropan-1-aminium chloride. (86 mg, 0.63 mmol) was added to the above mixture at 0° C. and the reaction mixture was allowed to warm to room temperature and stirred for 12 hours. The reaction mixture was poured into water and stirred for 15 minutesafter 2 hours the product precipitated. The product was collected by filtration under vacuum. The product was suspended in methanol (5.0 mL), sonicated for 5 min. filtered the under vacuum, washed with methanol (5.0 mL) and dried it to obtained 2,2'-((2,2'-(1,4-phenylene)bis(1H-benzo[d]imidazole-6,6'-carbonyl))bis(azanediyl))bis(N,N,N-trimethylethanaminium) chloride. 1H NMR (DMSO-d6, 400 MHz) δ: 8.86 (s, 2H), 8.41 (s, 4H), 8.19 (s, 2H), 7.83-7.72 (m, 4H), 3.73 (s, 4H), 3.54 (s, 4H), 3.17 (s, 18H), MS (ESI+APCl): m/z=284 [M/2].

Example 23

Synthesis of 2,2'-(1,4-phenylene)bis(N-(2-(dimethylamino)ethyl)-N-methyl-1H-benzo[d]imidazole-6-carboxamide)

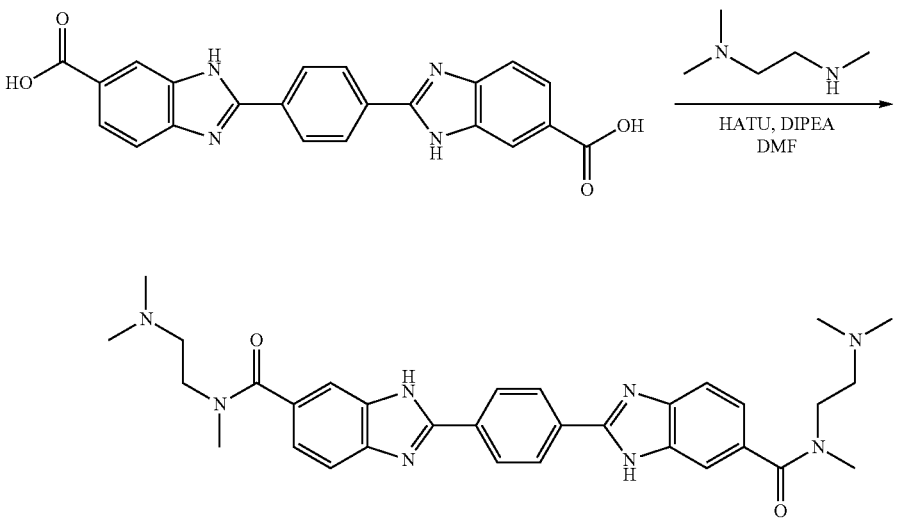

A solution of 2,2'-(1,4-phenylene)bis(1H-benzo[d]imidazole-6-carboxylic acid) (50 mg, 0.126 mmol) in DMF (3 ml) was treated with HATU (100 mg, 0.26 mmol) and DIPEA (130 μL, 0.75 mmol) in DMF (3 ml) for 5 min. N,N,N'-trimethylethylenediamine (28 mg, 0.27 mmol) was added and stirring continued overnight. The solvent was removed under vacuum and the residue washed with ether then purified using a C-18 column and a gradient of 0-100% MeOH in water containing 0.1% TFA. 1H NMR (CD3OD, 400 MHz) δ: 8.42 (s, 4H), 7.94 (br s, 2H), 7.84 (d, J=8.5 Hz, 2H), 7.62 (d, J=8.5 Hz, 2H), 4.02-3.91 (m, 4H), 3.52 (d, J=5.8 Hz, 4H), 3.15 (s, 6H), 3.06 (br s, 12H), MS (ESI): m/z=567 [M+H]+.

Example 24

Synthesis of 2,2'-(1,4-phenylene)bis(N-(2-(diethylamino)ethyl)-1H-benzo[d]imidazole]-6-carboxamide)

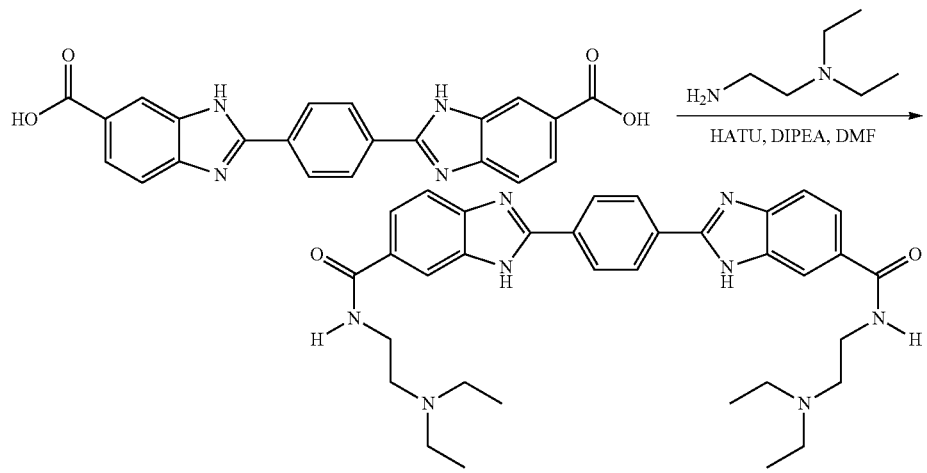

To a suspension of 2,2'-(1,4-phenylene)bis(1H-benzo[d]imidazole-6-carboxylic acid (0.15 g, 0.37 mmol) in DMF (15 mL) at 0° C., was added HATU (0.35 g, 0.94 mmol), DIPEA (0.50 mL, 3.00 mmol) and the reaction mixture was stirred for 15 minutes. N1,N1-diethylethane-1,2-diamine (0.10 g, 0.94 mmol) was added to the above mixture at 0° C. and the reaction mixture was allowed to warm to room temperature and stirred for 16 hours. The reaction mixture was concentrated under vacuum to obtain crude product as brown syrupy liquid. The crude product poured onto ice-cold water (50 mL), and stirred for 15 minutes, whereupon the product precipitated. The product was collected by filtration under vacuum, washed with methanol (20 mL) and dried it to obtain 2,2'-(1,4-phenylene)bis(N-(2-(diethylamino)ethyl)-1H-benzo[d]imidazole]-6-carboxamide.

1H NMR (CD3OD, 400 MHz) δ: 8.23 (s, 4H), 8.14 (brs, 2H), 7.76-7.74 (m, 2H), 7.62 (brs, 2H), 3.70 (t, J=6.0 Hz, 4H), 3.33-3.24 (m, 12H), 1.28 (t, J=7.2 Hz, 12H). MS (ESI+APCl): m/z=595 [M+H]+.

Example 25

Synthesis of 2,2'-(1,4-phenylene)bis(N-(2-(diisopropylamino)ethyl)-1H-benzo[d]imidazole]-6-carboxamide)(Compound 34)

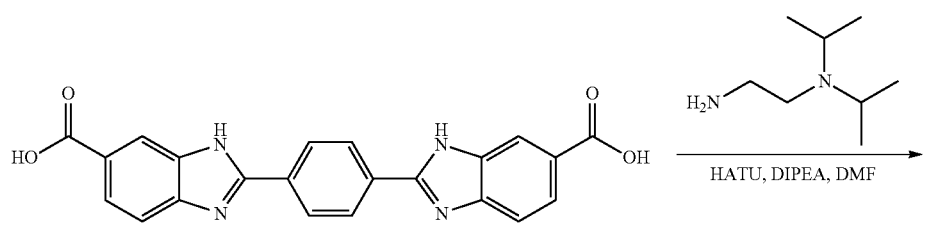

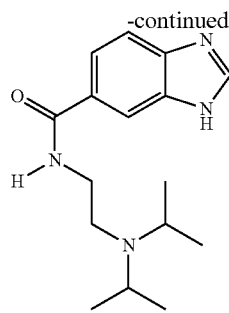
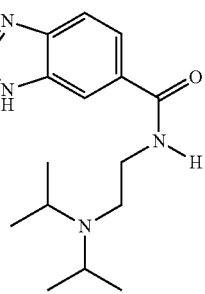

To a suspension of 2,2'-(1,4-phenylene)bis(1H-benzo[d]imidazole-6-carboxylic acid (0.15 g, 0.37 mmol) in DMF (15 mL) at 0° C., was added HATU (0.35 g, 0.94 mmol), DIPEA (0.5 mL, 3.00 mmol) and the reaction mixture was stirred for 15 minutes. N1,N1-diisopropylethane-1,2-diamine (0.13 g, 0.94 mmol) was added to the above mixture at 0° C. and the reaction mixture was allowed to warm to room temperature and stirred for 16 hours. The reaction mixture was concentrated under vacuum to obtain crude product as brown syrupy liquid. The crude product was poured onto ice-cold water (50 mL), and stirred for 15 minutes, whereupon the product precipitated. The product was collected by filtration under vacuum, washed with methanol (15 mL) and dried to obtain 2,2'-(1,4-phenylene) bis(N-(2-(diisopropylamino)ethyl)-1H-benzo[d]imidazole]-6-carboxamide.

1H NMR (CD3OD, 400 MHz) δ: 8.23 (s, 4H), 8.16-8.15 (m, 2H), 7.75-7.61 (m, 4H), 3.76 (t, J=6.0 Hz, 4H), 3.67 (t, J=6.0 Hz, 4H), 3.30 (brs, 4H), 1.34 (d, J=5.2 Hz, 24H). UPLC MS m/z=651 [M+H]+.

Example 26

Synthesis of N-(2-(dimethylamino)ethyl)-2-(4-(6-((3-(dimethylamino)propyl)carbamoyl)-1H-benzo[d]imidazol-2-yl)phenyl)-1H-benzo[d]imidazole-6-carboxamide (Compound 35)

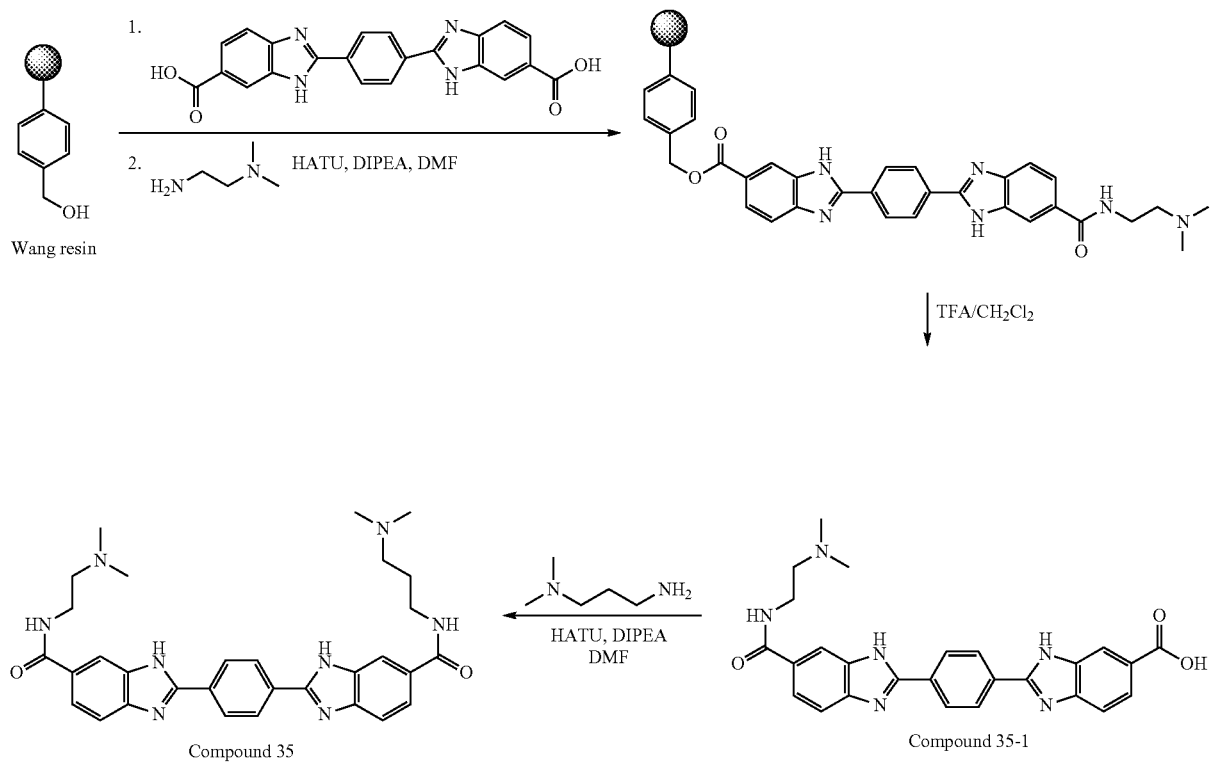

Wang resin (300 mg, 0.28 mmol) was swelled in DMF for 1 hour then treated with a solution of 2,2'-(1,4-phenylene)bis(1H-benzo[d]imidazole-6-carboxylic acid) (170 mg, 0.43 mmol) HATU (350 mg, 0.92 mmol) and DIPEA (3654, 2.0 mmol) that had been premixed for 5 min. The beads were mixed in the solution overnight then the solution removed and the beads washed with DMF (×5) and a solution of 2-(Dimethylamino)ethylamine (10% in DMF, 3 ml) added. The beads were mixed for 2 hours, the solution removed and the beads washed with DMF (×5). To the beads was added HATU (175 mg) and DIPEA (190 µL) and the beads mixed for 1 hour. The beads were washed with DMF (×5) and a solution of 2-(Dimethylamino)ethylamine (10% in DMF, 3 ml) added and the beads mixed in the solution for 4 hours. The beads were washed with DMF (×3), dichloromethane (×3) and then treated with 50% TFA/dichloromethane (3 ml) for 2 hours. The cleavage cocktail was transferred to a falcon tube and ether (8 ml) added. A precipitate was formed and on centrifugation, the resultant greenish pellet was washed with ether then dried to give 20 mg (0.043 mmol) of crude Compound 35-1 that was treated with HATU (18 mg, 0.047 mmol) and DIPEA (22 µL, 0.126 mmol) in DMF for 5 minutes before adding 3-(dimethylamino)-1-propylamine (5 mg, 0.049 mmol) and stirring overnight. The solvent was removed under vacuum and the crude product washed with ether and purified using a C-18 column and a gradient of 0-100% MeOH in water containing 0.1% TFA to afford Compound 35. 1H NMR (CD3OD, 400 MHz) δ: 8.39 (s, 4H), 8.29 (d, J=8.4 Hz, 2H), 7.99-7.93 (m, 2H), 7.81 (d, J=8.4 Hz, 2H), 3.83 (t, J=5.7 Hz, 2H), 3.55 (t, J=6.6 Hz, 2H), 3.44 (t, J=5.9 Hz, 2H), 3.24 (t, J=7.5 Hz, 2H), 3.20 (s, 6H), 2.94 (s, 6H), 2.12-2.05 (m, 2H), MS (ESI): m/z=553 [M+H]+.

Example 27

2,2'-(1,4-phenylene)bis(N-(3-(dimethylamino)propyl)-1H-benzo[d]imidazole-6-carboxamide)

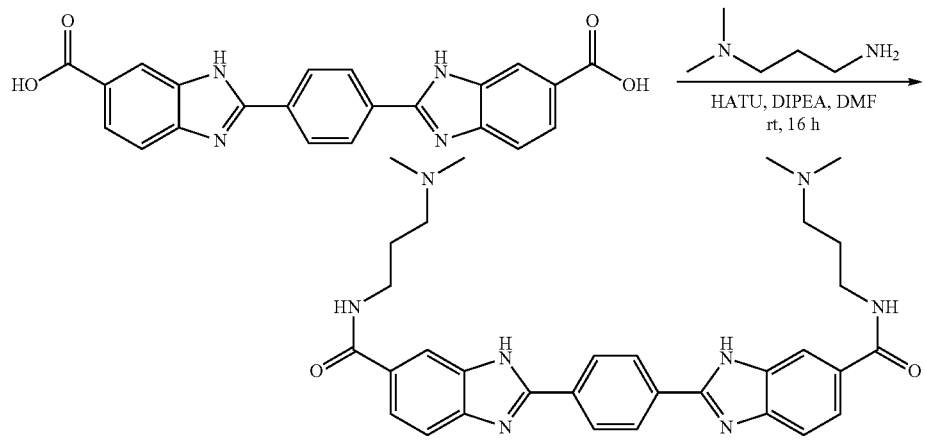

To a solution of 2,2'-(1,4-phenylene)bis(1H-benzo[d]imidazole-6-carboxylic acid) (0.50 g, 1.25 mmol) in DMF (20 mL) at 0° C., was added HATU (1.05 g, 2.76 mmol), DIPEA (1.30 mL, 7.53 mmol) and the reaction mixture was stirred for 10 minutes. N, N'-Dimethylpropane-1,3-diamine (0.28 g, 2.76 mmol) was added to the above mixture in one lot at 0° C. and the reaction mixture was allowed to warm to room temperature and stirred for 16 hours. The reaction mixture was poured onto ice, whereupon the product precipitated. The precipitated product was collected by filtration under vacuum, washed with methanol (10 mL), and dried to obtain the crude product. The product was purified by silica gel chromatography (1:1 methanol:aq. ammonium hydroxide). The fractions containing pure product were combined and concentrated under vacuum to obtain bis(2-(dimethylamino)ethyl) 2,2'-(1,4-phenylene)bis(N-(3-(dimethylamino)propyl)-1H-benzo[d]imidazole-6-carboxamide). 1H NMR (DMSO-d6, 400 MHz) δ: 13.2 (brs, 2H), 8.58-8.53 (d, J=19.6 Hz, 1H), 8.39 (s, 4H), 8.22 (s, 1H), 8.04 (m, 1H), 7.77-7.61 (m, 4H), 3.33-3.32 (m, 4H), 2.35-2.32 (m, 4H), 2.19 (s, 12H), 1.72-1.69 (m, 4H). MS (ESI+APCl): m/z=567 [M+H]+.

Example 28

Synthesis of N-(2-((2-aminoethyl)(methyl)amino)ethyl)-2-(4-(6-((2-(dimethylamino)ethyl)carbamoyl)-1H-benzo[d]imidazol-2-yl)phenyl)-1H-benzo[d]imidazole-6-carboxamide

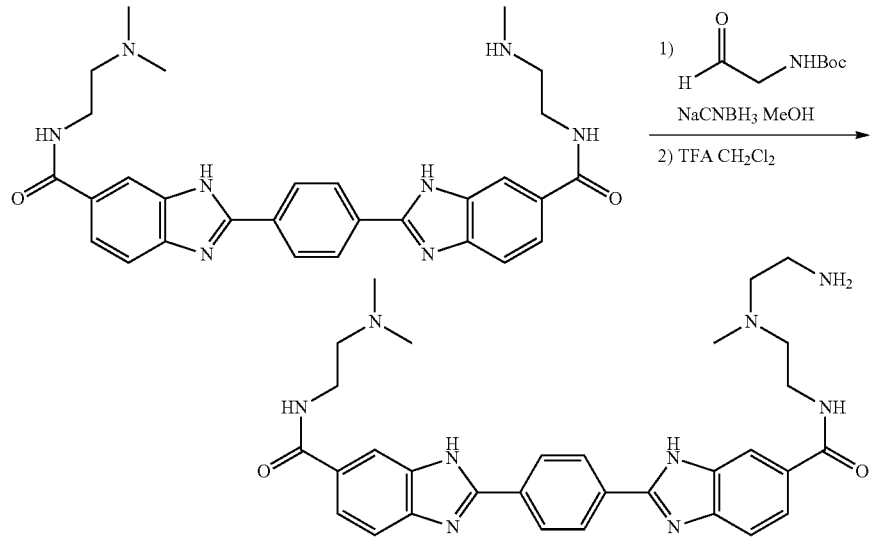

To a solution of N-(2-(dimethylamino)ethyl)-2-(4-(6-((2-(methylamino)ethyl)carbamoyl)-1H-benzo[d]imidazol-2-yl)phenyl)-1H-benzo[d]imidazole-6-carboxamide (63 mg, 0.12 mmol) in MeOH (2 ml) was added N-Boc-2-aminoacetaldehyde (25 mg, 0.157 mmol) and the mixture stirred for 1 hour before adding sodium cyanoborohydride (8.0 mg, 0.13 mmol) and stirring continued overnight. LCMS analysis showed in-complete reaction and more aldehyde (20 mg) and sodium cyanoborohydride (6 mg) were added and the mixture stirred for 8 hours. LCMS analysis still showed in-complete reaction and more aldehyde (10 mg) and sodium cyanoborohydride (5 mg) were added and stirring continued overnight. LCMS showed complete consumption of starting material hence the solvent was removed under vacuum. The crude material was purified using a C-18 column and a gradient of 0-100% MeOH in water containing 0.1% TFA. The clean fractions were combined, concentrated and dried to give 56 mg of crude product. The crude product was treated with a TFA cocktail (4 ml dichloromethane/2.0 ml TFA) for 2 hours, upon which the reaction contents were transferred to a falcon tube and ether (8 ml) added. A white precipitate was formed and after centrifugation the liquid phase was decanted and the white pellet washed with ether. The title compound was obtained after drying under vacuum. 1H NMR (CD3OD, 400 MHz) δ: 8.39 (s, 4H), 8.29 (br s, 2H), 7.96 (t, J=1.6 Hz, 1H), 7.94 (t, J=1.6 Hz, 1H), 7.80 (d, J=4.7 Hz, 1H), 7.78 (d, J=4.7 Hz, 1H), 3.86-3.81 (m, 4H), 3.65-3.56 (m, 2H), 3.51-3.39 (m, 6H), 3.20 (s, 9H), MS (ESI): m/z=568 [M+H]+.

Example 29

Synthesis of 2,2'-(1,4-phenylene)bis(N-(2-guanidinoethyl)-1H-benzo[d]imidazole-6-carboxamide (Compound 38)

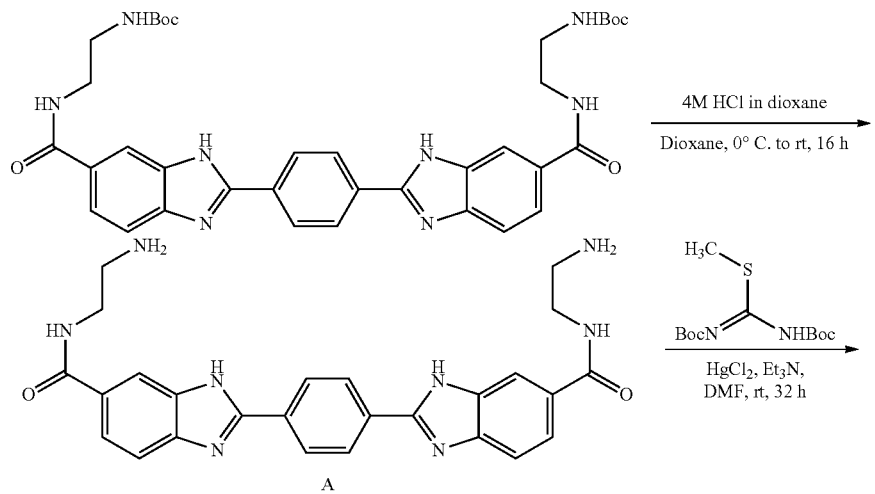

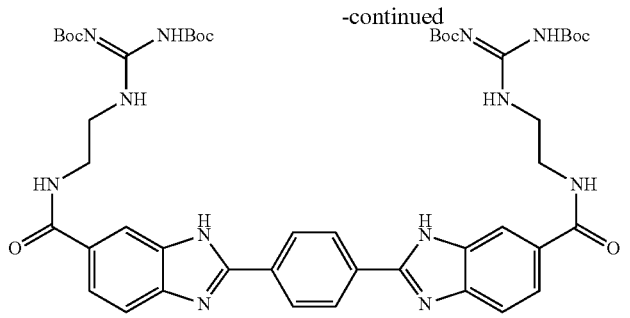

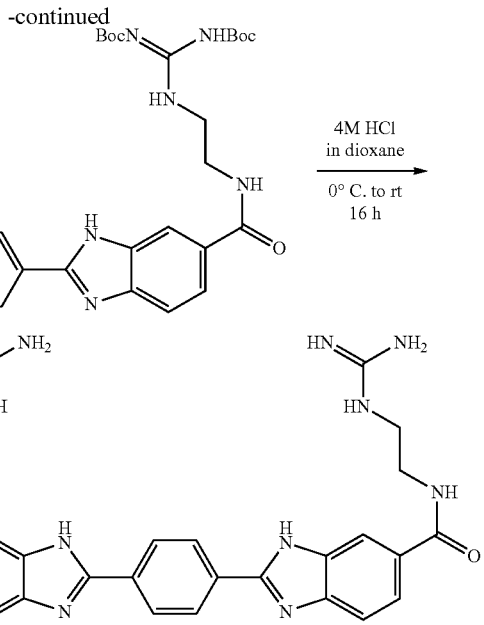

Step 1: Synthesis of 2,2'-(1,4-phenylene)bis(N-(2-aminoethyl)-1H-benzo[d]imidazole-6-carboxamide To a solution of di-tert-butyl(((2,2'-(1,4-phenylene)bis(1H-benzo[d]imidazole-6,6'-carbonyl))bis(azanediyl))bis(ethane-2,1-diyl))dicarbamate (170 mg, 0.24 mmol) in 1,4-dioxane (5.0 mL) at 0° C. was added 4M HCl in 1,4-dioxane (2.0 mL) and the reaction mixture was stirred at room temperature for 16 hours. The reaction mixture was concentrated under reduced pressure to obtain the crude product. The product was triturated with methanol (10 mL), filtered under vacuum, washed with methanol (5.00 mL), and dried to obtain 2,2'-(1,4-phenylene)bis(N-(2-aminoethyl)-1H-benzo[d]imidazole-6-carboxamide as hydrochloride salt.

1H NMR (DMSO-d6, 400 MHz) δ: 8.85 (brs, 2H), 8.51 (brs, 4H), 8.29 (s, 2H), 8.00 (brs, 6H), 7.92 (d, J=8.0 Hz, 2H), 7.77 (d, J=8.4 Hz, 2H), 3.58-3.56 (m, 4H), 3.04-3.03 (m, 4H). MS (ESI+APCl): m/z=481 [M+H]−.

Step 2: Synthesis of Intermediate B:

To a solution of 2,2'-(1,4-phenylene)bis(N-(2-aminoethyl)-1H-benzo[d]imidazole-6-carboxamide (70 mg, 0.14 mmol) in DMF (5.0 mL) and Et3N (0.12 mL, 0.87 mmol) was added 1,3-bis(tert-butoxycarbonyl)-2-methyl-2-thiopseudourea (126 mg, 0.43 mmol) followed with mercury (II) chloride (117 mg, 0.43 mmol), and the reaction mixture was stirred at room temperature for 32 hours. The reaction mixture was poured onto ice and the precipitated material was filtered under vacuum, washed with water (10.0 mL), and dried to obtain the crude product, which was purified by silica gel chromatography (1:4 methanol:dichloromethane).

The fractions containing pure product were combined and concentrated under vacuum to obtain intermediate B.

1H NMR (DMSO-d6, 400 MHz) δ: 13.27 (s, 2H), 11.52 (d, J=4.0 Hz, 2H), 8.62-8.48 (m, 4H), 8.38 (brs, 4H), 8.22 (brs, 1H), 8.05 (s, 1H), 7.79-7.72 (m, 3H), 7.59 (d, J=8.0 Hz, 1H), 3.54-3.46 (m, 8H), 1.47 (s, 18H), 1.41 (s, 18H). MS (ESI+APCl): m/z=967 [M+H]+.

Synthesis of 2,2'-(1,4-phenylene)bis(N-(2-guanidinoethyl)-1H-benzo[d]imidazole-6-carboxamide To a solution of intermediate B (20 mg, 0.02 mmol) in 1,4-dioxane (3.0 mL) at 0° C. was added 4M HCl in 1,4-dioxane (1.0 mL) and the reaction mixture was stirred at room temperature for 16 hours. The reaction mixture was concentrated under reduced pressure to obtain the crude product. The product was triturated with methanol (10.0 mL), filtered under vacuum, washed with methanol (5.00 mL), and dried to obtain 2,2'-(1,4-phenylene)bis(N-(2-guanidinoethyl)-1H-benzo[d]imidazole-6-carboxamide hydrochloride salt.

1H NMR (CD3OD, 400 MHz) δ: 8.37 (brs, 4H), 8.26 (d, J=0.8 Hz, 2H), 7.95 (dd, J=8.4, 1.6 Hz, 2H), 7.79 (d, J=8.4 Hz, 2H), 3.53 (t, J=6.0 Hz, 4H), 3.38 (t, J=6.0 Hz, 4H). MS (ESI+APCl): m/z=567 [M+H]+.

Example 30

Synthesis of (2S,2'S)-dimethyl 2,2'-((2,2'-(1,4-phenylene)bis(1H-benzo[d]imidazole-6,6'-carbonyl))bis(azanediyl))bis(5-guanidinopentanoate

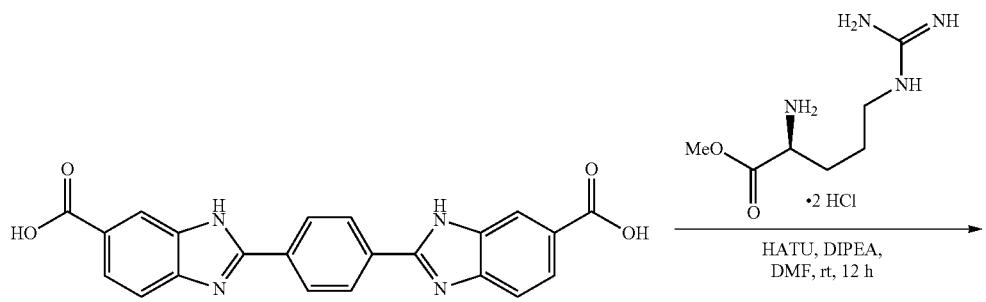

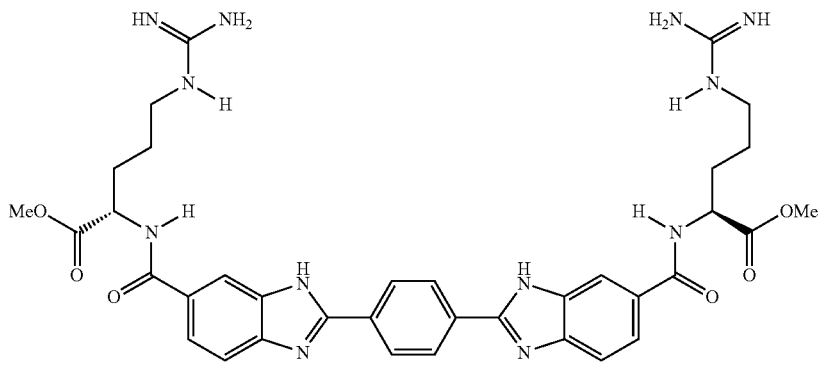

To a suspension of 2,2'-(1,4-phenylene)bis(1H-benzo[d]imidazole-6-carboxylic acid) (0.25 g, 0.62 mmol) in DMF (10 mL) at 0° C., was added HATU (0.60 g, 1.57 mmol), DIPEA (0.66 mL, 3.76 mmol) and the reaction mixture was stirred for 10 minutes. (S)-Methyl 2-amino-5-guanidinopentanoate dihydrochloride (0.36 g, 1.38 mmol) was added to the above mixture at 0° C. and the reaction mixture was allowed to warm to room temperature and stirred for 12 hours. The reaction mixture was concentrated under vacuum and the crude product was diluted with ice-cold water (10 mL), and stirred for 15 minutes, whereupon the product precipitated. The product was collected by filtration under vacuum. The product was purified by prep-HPLC (please refer to the prep-HPLC details) followed by purification using Sep-Pak cartridge to obtain (2S,2'S)-dimethyl 2,2'-((2,2'-(1,4-phenylene)bis(1H-benzo[d]imidazole-6,6'-carbonyl))bis(azanediyl))bis(5-guanidinopentanoate). 1H NMR (DMSO-d6, 400 MHz) δ: 8.59-8.57 (m, 2H), 8.34-8.31 (m, 4H), 8.12 (s, 2H), 7.59-7.58 (m, 2H), 7.50-7.48 (m, 2H), 4.50-4.48 (m, 2H), 3.66 (s, 6H), 3.16-3.15 (m, 4H), 1.86-1.82 (m, 4H), 1.65-1.58 (m, 4H). MS (ESI+APCl): m/z=739 [M+H]+.

Example 31

Synthesis of 2,2'-(1,4-phenylene)bis(N-(2-(pyrrolidin-1-yl)ethyl)-1H-benzo[d]imidazole-6-carboxamide)

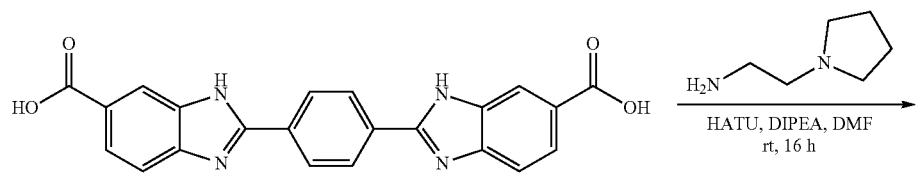

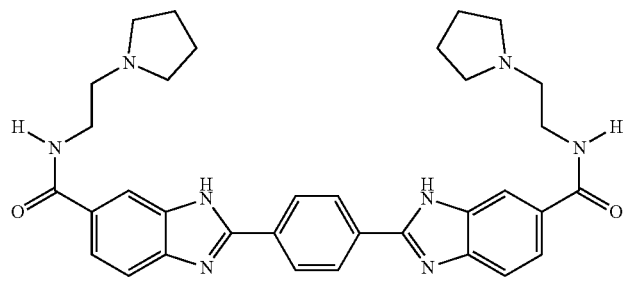

To a suspension of 2,2'-(1,4-phenylene)bis(1H-benzo[d]imidazole-6-carboxylic acid) (0.15 g, 0.37 mmol) in DMF (5.00 mL) at 0° C., was added HATU (0.42 g, 1.12 mmol), DIPEA (0.39 mL, 2.25 mmol) and the reaction mixture was stirred for 15 minutes. 2-(pyrrolidin-1-yl)ethanamine (0.10 g, 0.94 mmol) was added to the above mixture at 0° C. and the reaction mixture was allowed to warm to room temperature and stirred for 16 hours. The reaction mixture was concentrated under vacuum and the crude product was diluted with ice-cold water (10 mL), and stirred for 15 minutes, whereupon the product precipitated. The product was collected by filtration under vacuum, washed with methanol (10 mL), and dried under vacuum. The product was purified by silica gel chromatography [1:4 (10% ammonium hydroxide in methanol):dichloromethane]. The fractions containing the pure product were combined and concentrated under vacuum to obtain 2,2'-(1,4-phenylene)bis(N-(2-(pyrrolidin-1-yl)ethyl)-1H-benzo[d]imidazole-6-carboxamide. 1H NMR (DMSO-d6, 400 MHz) δ: 13.29 (brs, 2H), 8.53-8.48 (m, 2H), 8.42-8.38 (m, 4H), 8.23-8.05 (m, 2H), 7.78-7.62 (m, 4H), 3.45-3.34 (m, 4H), 2.62 (t, J=7.2 Hz, 4H), 2.59-2.51 (m, 8H), 1.74-1.70 (m, 8H). MS (ESI+APCl): m/z=591 [M+H]+.

Example 32

Synthesis of 2,2'-(1,4-phenylene)bis(N-(2-(piperidin-1-yl)ethyl)-1H-benzo[d]imidazole-6-carboxamide) (Compound 41)

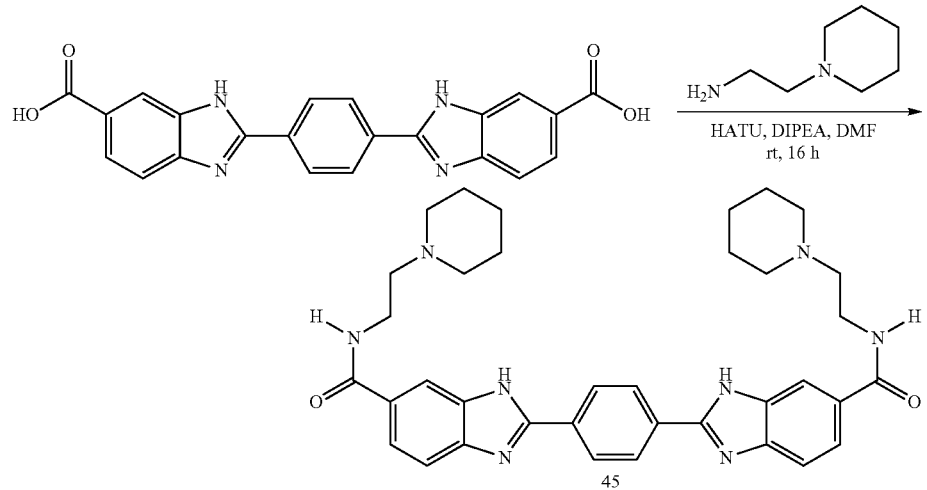

To a suspension of 2,2'-(1,4-phenylene)bis(1H-benzo[d]imidazole-6-carboxylic acid) (0.10 g, 0.25 mmol) in DMF (5.00 mL) at 0° C., was added HATU (0.21 g, 0.55 mmol), DIPEA (0.27 mL, 1.50 mmol) and the reaction mixture was stirred for 15 minutes. 2-(Piperidin-1-yl)ethanamine (70 mg, 0.55 mmol) was added to the above mixture at 0° C. and the reaction mixture was allowed to warm to room temperature and stirred for 16 hours. The reaction mixture was concentrated under vacuum and the crude product was diluted with ice-cold water (10 mL), and stirred for 15 minutes, whereupon the product precipitated. The product was collected by filtration under vacuum, washed with methanol (5 mL), and dried under vacuum. The product was purified by silica gel chromatography [1:4 (10% ammonium hydroxide in methanol):dichloromethane]. The fractions containing the pure product were combined and concentrated under vacuum to obtain 2,2'-(1,4-phenylene)bis(N-(2-(piperidin-1-yl)ethyl)-1H-benzo[d]imidazole-6-carboxamide). 1H NMR (DMSO-d6, 400 MHz) δ: 13.28 (brs, 2H), 8.50-8.39 (m, 6H), 8.22 (s, 1H), 8.04 (s, 1H), 7.77-7.61 (m, 4H), 3.45-3.38 (m, 4H), 2.47-2.36 (m, 12H), 1.55-1.44 (m, 8H), 1.42-1.32 (m, 4H), MS (ESI+APCl): m/z=619 [M+H]+.

Example 33

Synthesis of 2,2'-(1,4-phenylene)bis(N-(2-morpholinoethyl)-1H-benzo[d]imidazole-6-carboxamide)

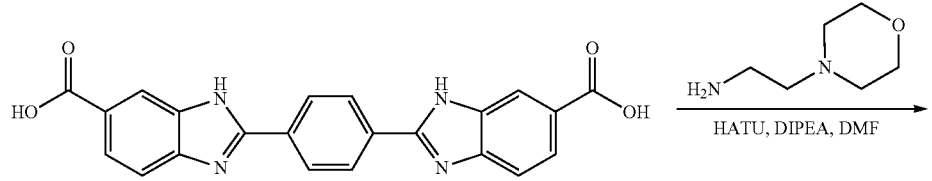

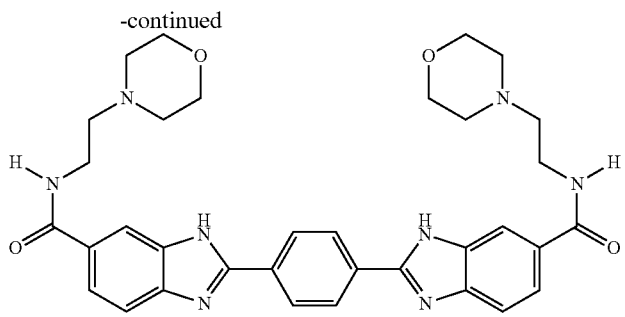

A solution of 2,2'-(1,4-phenylene)bis(1H-benzo[d]imidazole-6-carboxylic acid) (50 mg, 0.126 mmol) in DMF (3 ml) was treated with HATU (100 mg, 0.26 mmol) and DIPEA (130 μL, 0.75 mmol) for 5 minutes before adding 4-(2-Aminoethyl)-morpholine (36 mg, 0.28 mmol). After stirring overnight, the reaction formed a precipitate and the contents of the reaction were transferred to a falcon tube. Centrifugation gave a compound that was washed with water (×2) and then purified using a C-18 column and a gradient of 0-100% MeOH in water containing 0.1% TFA to afford 2,2'-(1,4-phenylene)bis(N-(2-morpholinoethyl)-1H-benzo[d]imidazole-6-carboxamide). 1H NMR (CD3OD, 400 MHz) δ: 8.39 (s, 4H), 8.3 (br s, 2H), 7.96 (dd, J=1.2, 8.6 Hz, 2H), 7.81 (d, J=8.6 Hz, 2H), 4.19-4.02 (m, 4H), 3.8 (t, J=5.7 Hz, 8H), 3.77-3.64 (m, 4H), 3.47 (t, J=5.7 Hz, 4H), 3.29-3.15 (m, 4H), MS (ESI): m/z=623 [M+H]+.

Example 34

Synthesis of 2-(4-(6-((2-(piperidin-1-yl)ethyl)carbamoyl)-1H-benzo[d]imidazol-2-yl)phenyl)-1H-benzo[d]imidazole-6-carboxylic Acid to warm to room temperature and stirred for 12 hours. The reaction mixture was poured in to water and stirred for 15 minutes, whereupon the product precipitated. The product was collected by filtration under vacuum, and washed with methanol (10 mL). The obtained compound was purified by prep on an HPLC X-Bridge C18@10 μm OBD (250×4.6 mm, 10 μm) column; mobile phase, A=0.1% TFA in water and B=CH3CN; Flow rate: 40 mL/min, Injection volume: 700 μL, Runtime: 15 minutes gradient: 95-70% A, 05-30% B (0.0-10 min); UV detection at 220 nm). Fractions containing only the pure product were combined for concentration to obtain 2-(4-(6-((2-(piperidin-1-yl)ethyl)carbamoyl)-1H-benzo[d]imidazol-2-yl)phenyl)-1H-benzo[d]imidazole-6-carboxylic acid.

1H NMR (CD3OD, 400 MHz)) δ: 8.31 (s, 1H), 8.28 (d, J=3.2 Hz, 4H), 8.19 (s, 1H), 8.04-8.02 (m, 1H), 7.86-7.83 (m, 1H), 7.71-7.69 (m, 2H), 3.74 (t, J=11.6 Hz, 2H), 3.65 (d, J=11.6 Hz, 2H), 3.30 (t, J=12.0 Hz, 2H), 2.97 (t, J=24.4 Hz, 2H), 1.92-1.89 (m, 2H), 1.75-1.66 (m, 3H), 1.52-1.43 (m, 1H). MS (ESI+APCl) m/z 509 [M+H]+.

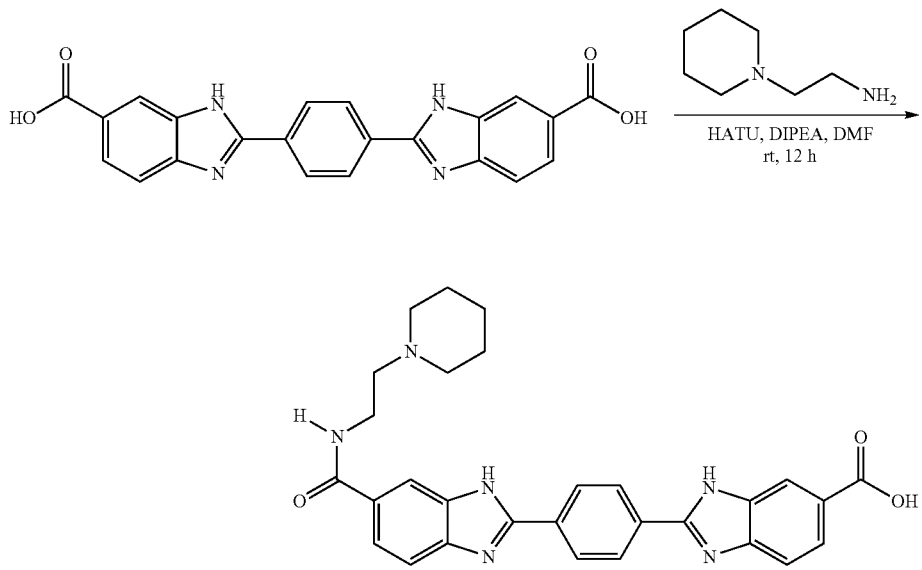

To a suspension of 2,2'-(1,4-phenylene)bis(1H-benzo[d]imidazole-6-carboxylic acid) (0.50 g, 1.25 mmol) in DMF (5 mL) at 0° C., was added HATU (0.57 g, 1.50 mmol), DIPEA (0.43 mL, 2.52 mmol) and 2-(piperidin-1-yl)ethanamine (0.13 g, 1.00 mmol), and the reaction mixture was allowed

Example 35

Synthesis of N-(2-(4-methylpiperazin-1-yl)-2-(piperidin-1-yl)ethyl)carbamoyl)-1H-benzo[d]imidazol-2-yl)phenyl)-1H-benzo[d]imidazole-6-carboxamide (azanediyl))bis(ethane-2,1-diyl))bis(piperazine-1-carboxylate)

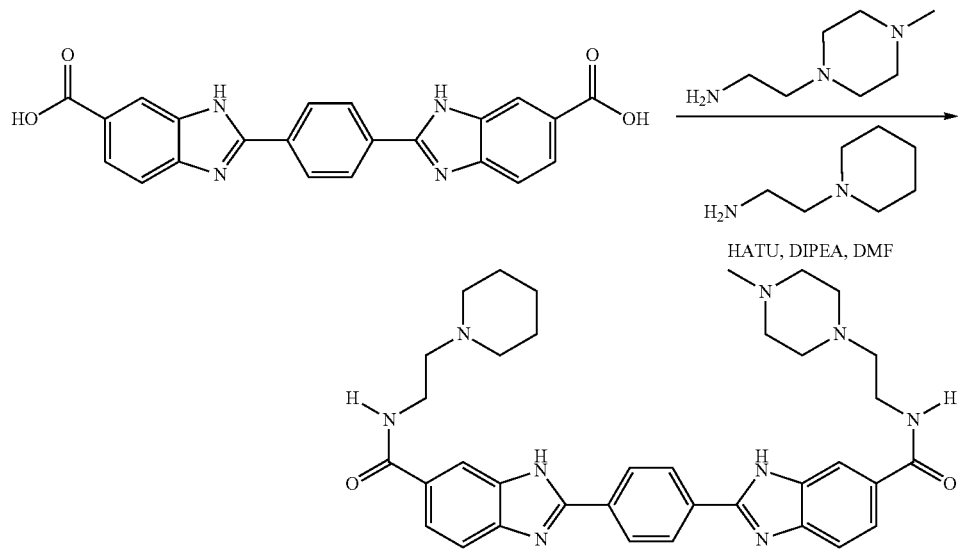

To a suspension of 2,2'-(1,4-phenylene)bis(1H-benzo[d]imidazole-6-carboxylic acid) (0.30 g, 0.75 mmol) in DMF (5.0 mL) at 0° C., was added HATU (0.63 g, 1.65 mmol), DIPEA (0.52 mL, 3.00 mmol), 2-(piperidin-1-yl)ethanamine (78 mg, 0.60 mmol) and 2-(4-methylpiperazin-1-yl)ethanamine (86 mg, 0.60 mmol), and the reaction mixture was allowed to warm to room temperature and stirred for 12 hours. The reaction mixture was concentrated under vacuum and the crude product was diluted with methanol (20 mL), and stirred for 15 minutes, whereupon the product precipitated. The product was collected by filtration under vacuum, washed with methanol (10 mL), and dried under vacuum. The obtained compound was purified by prep HPLC on a X-Bridge C18@10 μm OBD (250×4.6 mm, 10 μm) column; mobile phase, A=0.1% TFA in water and B=CH3CN; Flow rate: 40 mL/min, Injection volume: 800 μL, Runtime: 15 minutesgradient: 90-75% A, 10-25% B (0.0-10 min); UV detection at 220 nm). Fractions containing only the pure product were combined for concentration to obtain N-(2-(4-methylpiperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide.

1H NMR (CD3OD, 400 MHz) δ: 8.28 (s, 4H), 8.18-8.14 (m, 2H), 7.83-7.78 (m, 2H), 7.69-7.66 (m, 2H), 3.74 (t, J=12 Hz, 2H), 3.65 (d, J=12.8 Hz, 2H), 3.55 (t, J=12.4 Hz, 2H), 3.29 (t, J=12.4 Hz, 3H), 3.25 (s, 4H), 2.96-2.90 (m, 4H), 2.78 (s, 3H), 2.76-2.72 (m, 3H), 1.93-1.89 (m, 2H), 1.78-1.70 (m, 3H), 1.50-1.45 (m, 1H). MS (ESI+APCl): m/z 635 [M+2H]+.

Example 36

Synthesis of 2,2'-(1,4-phenylene)bis(N-(2-(4-methylpiperazin-1-yl)ethyl)-1H-benzo[d]imidazole-6-carboxamide) (Compound 45)

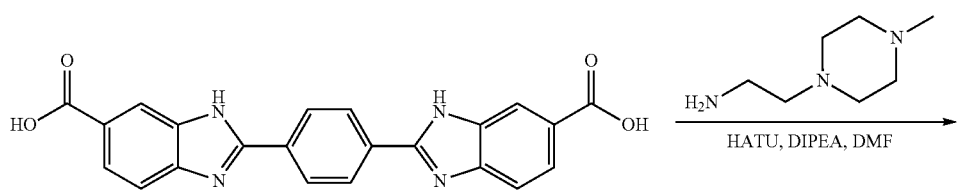

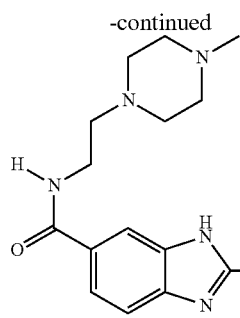
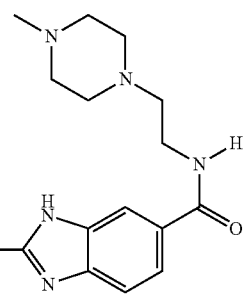

To a suspension of 2,2'-(1,4-phenylene)bis(1H-benzo[d]imidazole-6-carboxylic acid) (0.20 g, 0.50 mmol) in DMF (10.0 mL) at 0° C., was added HATU (0.47 g, 1.25 mmol), DIPEA (0.7 mL, 4.01 mmol) and the reaction mixture was stirred for 15 minutes. 2-(4-Methylpiperazin-1-yl)ethanamine (0.17 g, 1.25 mmol) was added to the above mixture at 0° C. and the reaction mixture was allowed to warm to room temperature and stirred for 16 hours. The reaction mixture was concentrated under vacuum and the crude product was diluted with methanol (20 mL), and stirred for 15 minutes, whereupon the product precipitated. The product was collected by filtration under vacuum, washed with methanol (10 mL), and dried under vacuum. The obtained compound was purified by prep HPLC on a X-Select C-18 (30×150 mm, 10 μm) column; mobile phase, A=0.1% TFA in water and B=CH3CN; Flow rate: 30 mL/min, Injection volume: 400 μL, Runtime: 20 minutes-gradient: 95-40% A, 05-60% B (0.0-15 min); UV detection at 220 nm). Fractions containing only the pure product were combined for concentration to obtain 2,2'-(1,4-phenylene)bis(N-(2-(4-methylpiperazin-1-yl)ethyl)-1H-benzo[d]imidazole-6-carboxamide).

1H NMR (CD3OD, 400 MHz) δ: 8.32 (s, 4H), 8.18 (s, 2H), 7.85 (dd, J=8.4, 1.2 Hz, 2H), 7.71 (d, J=8.8 Hz, 2H), 3.60 (t, J=6.4 Hz, 4H), 3.32 (brs, 8H), 3.08-3.03 (m, 8H), 2.92 (t, J=6.4 Hz, 4H), 2.81 (s, 6H). MS (ESI+APCl): m/z 649 [M+H]+.

Example 37

Synthesis of di-tert-butyl 4,4'-(((2,2'-(1,4-phenylene)bis(1H-benzo[d]imidazole-6,6'-carbonyl))bis(azanediyl))bis(ethane-2,1-diyl))bis(piperazine-1-carboxylate)

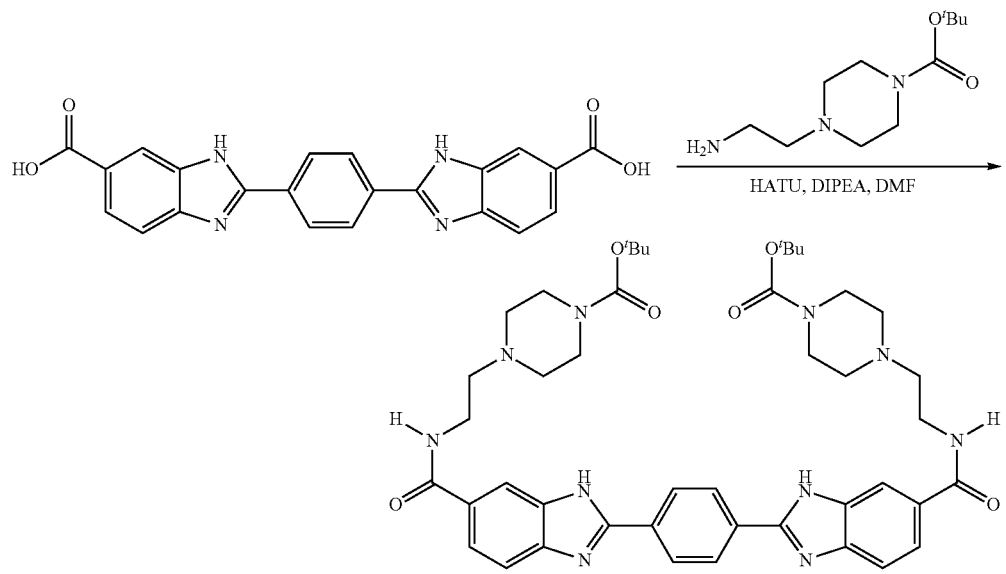

To a suspension of 2,2'-(1,4-phenylene)bis(1H-benzo[d]imidazole-6-carboxylic acid) (0.10 g, 0.25 mmol) in DMF (5.0 mL) at 0° C., was added HATU (0.28 g, 0.75 mmol), DIPEA (0.26 mL, 1.5 mmol) and the reaction mixture was stirred for 10 minutes. tert-Butyl 4-(2-aminoethyl)piperazine-1-carboxylate (0.144 g, 0.62 mmol) was added to the above mixture at 0° C. and the reaction mixture was allowed to warm to room temperature and stirred for 8 hours. The reaction mixture was concentrated under vacuum and the crude product was diluted with ice-cold water (10 mL), and stirred for 15 minutes, whereupon the product precipitated. The product was collected by filtration under vacuum, washed with water (20 mL), and dried under vacuum. The product was purified by silica gel chromatography [1:4 (10% ammonium hydroxide in methanol):dichloromethane]. The fractions containing the pure product were combined and concentrated under vacuum and triturated with hot EtOAc (10 mL) to obtain di-tert-butyl 4,4'-(((2,2'-(1,4-phenylene)

bis(1H-benzo[d]imidazole-6,6'-carbonyl))bis(azanediyl))bis(ethane-2,1-diyl))bis(piperazine-1-carboxylate). 1H NMR (CD3OD, 400 MHz) δ: 8.21-8.19 (m, 4H), 8.06 (s, 2H), 7.70-7.68 (m, 2H), 7.58 (d, J=8.4 Hz, 2H), 3.51 (t, J=6.4 Hz, 4H), 3.45-3.43 (m, 8H), 2.71 (t, J=6.0 Hz, 4H), 2.65-2.61 (m, 8H), 1.39 (s, 18H). UPLC MS: m/z=821 [M+H]+.

Example 38

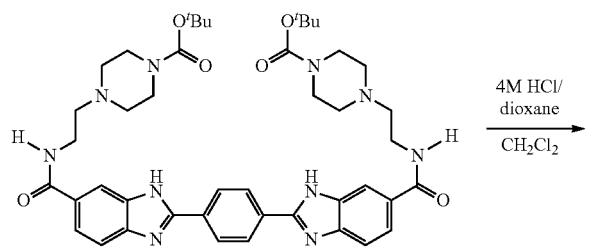

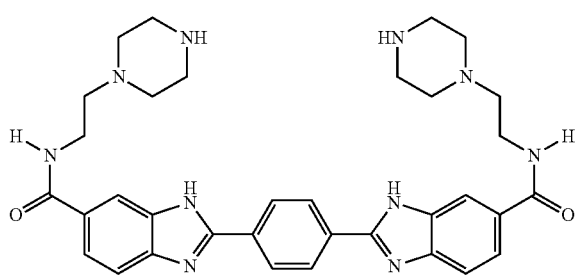

To a suspension of di-tert-butyl 4,4'-(((2,2'-(1,4-phenylene)bis(1H-benzo[d]imidazole-6,6'-carbonyl))bis(azanediyl))bis(ethane-2,1-diyl))bis(piperazine-1-carboxylate) (40 mg, 0.04 mmol) in dichloromethane (5.0 mL) at 0° C., was added HCl (4M in dioxane, 0.2 mL) and the reaction mixture was allowed to warm to room temperature and stirred for 4 hours. The reaction mixture was concentrated under vacuum and the crude product was triturated in 10% methanol in dichloromethane (20 mL), the product was collected by filtration under vacuum, washed with dichloromethane (10 mL), and dried under vacuum. The obtained compound was purified by Sep-Pak cartridge (Eluted with 20 mL of 10% aqueous ammonia in methanol) concentrated under vacuum to obtain 2,2'-(1,4-phenylene)bis(N-(2-(piperazin-1-yl)ethyl)-1H-benzo[d]imidazole-6-carboxamide).

1H NMR (CD3OD, 400 MHz) δ: 8.23 (s, 4H), 8.05 (s, 2H), 7.64-7.61 (m, 2H), 7.57-7.55 (m, 2H), 3.50 (t, J=6.8 Hz, 4H), 2.78 (t, J=4.8 Hz, 8H), 2.57-2.41 (m, 12H). MS (ESI+APCl): m/z 621 [M+H]+.

Example 39

Synthesis of 2,2'-(1,4-phenylene)bis(N-(3-(piperidin-1-yl)propyl)-1H-benzo[d]imidazole-6-carboxamide)

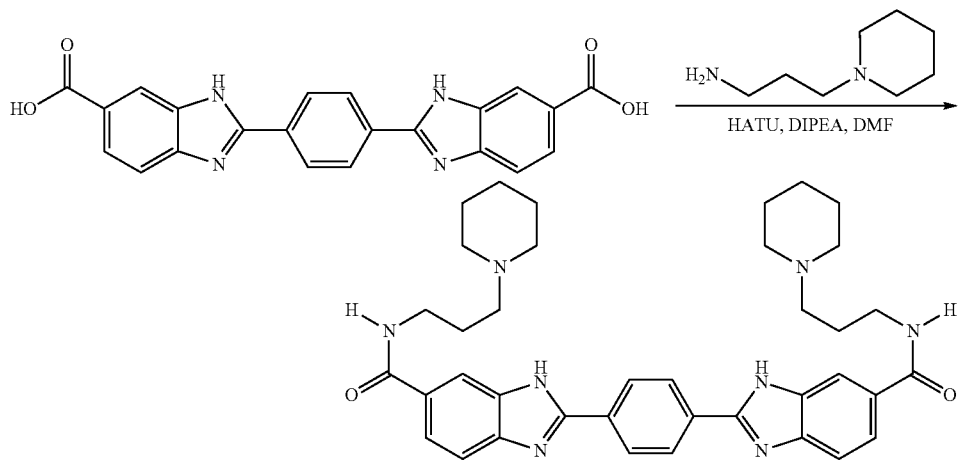

To a suspension of 2,2'-(1,4-phenylene)bis(1H-benzo[d]imidazole-6-carboxylic acid) (0.30 g, 0.75 mmol) in DMF (5 mL) at 0° C., was added HATU (0.72 g, 1.88 mmol), DIPEA (0.75 mL, 4.52 mmol) and the reaction mixture was stirred for 10 minutes. 3-(piperidin-1-yl)propan-1-amine (0.27 g, 1.88 mmol) was added to the above mixture at 0° C. and the reaction mixture was allowed to warm to room temperature and stirred for 12 hours. The reaction mixture was poured in to water and stirred for 15 minutes, whereupon the product precipitated. The product was collected by filtration under vacuum. The solid product was suspended in methanol (5.0 mL), sonicated for 5 minutes filtered under vacuum, washed with methanol (5.0 mL×2 times) and dry to obtain 2,2'-(1,4-phenylene)bis(N-(3-(piperidin-1-yl)propyl)-1H-benzo[d]imidazole-6-carboxamide).

1H NMR (DMSO-d6, 300 MHz)) δ: 13.19 (brs, 2H), 8.36 (s, 4H), 8.26 (s, 2H), 8.12 (s, 2H), 7.75 (d, J=6.0 Hz, 2H), 7.64 (d, J=9.0 Hz, 2H), 3.37-3.31 (m, 4H), 2.37 (t, J=9.6 Hz, 12H), 1.74 (t, J=13.8 Hz, 4H), 1.51-1.49 (m, 8H), 1.40-1.38 (m, 4H). MS (ESI+APFCl): m/z 647 [M+H]+.

Example 40

Synthesis of tert-butyl (2-(2-(4-(6-((2-(dimethyl-amino)ethyl)carbamoyl)-1H-benzo[d]imidazol-2-yl)phenyl)-1H-benzo[d]imidazole-6-carboxamido)ethyl)carbamate

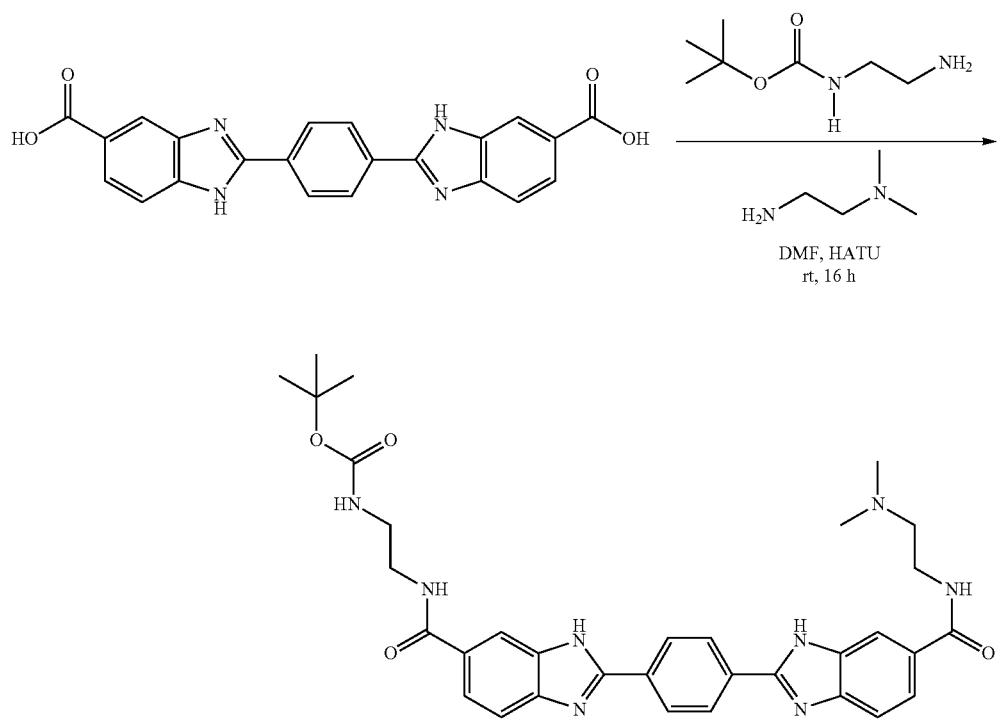

To a solution of 2-(4-(6-carboxyl-1H-benzo[d]imidazol-2-yl)phenyl)-1H-benzo[d]imidazole-5-carboxylic acid (500 mg, 1.25 mmol) in DMF (15 mL) at 0° C., was added HATU (710 mg, 1.88 mmol), DIPEA (1.38 mL, 7.53 mmol) and the reaction mixture was stirred for 10 minutes. tert-Butyl (2-aminoethyl) carbamate (200 mg, 1.25 mmol) and N1,N1-dimethylethane-1,2-diamine (110 mg, 1.25 mmol) was added to the above mixture at 0° C. and the reaction mixture was allowed to warm to room temperature and stirred for 16 hours. The reaction mixture was poured onto ice, whereupon the product precipitated. The compound was collected by filtration under vacuum, washed with water (10.0 mL), and dried to obtain the product. The product was purified by by prep-HPLC and the fractions containing only the pure product were combined and concentrated under vacuum and dried to obtain tert-butyl (2-(2-(4-(6-((2-(dimethylamino) ethyl)carbamoyl)-1H-benzo[d]imidazol-2-yl)phenyl)-1H-benzo[d]imidazole-6-carboxamido)ethyl)carbamate as formate salt.

1H NMR (DMSO-d6, 400 MHz) δ: 8.49-8.43 (m, 2H), 8.39 (brs, 4H), 8.24 (s, 2H), 8.15 (brs, 2H), 7.77 (d, J=8.4 Hz, 2H), 7.66 (d, J=8.4 Hz, 2H), 6.96 (t, J=5.6 Hz, 1H), 3.43-3.38 (m, 4H), 3.35-3.31 (m, 2H), 3.16-3.12 (m, 2H), 2.23 (s, 6H), 1.38 (s, 9H). MS (ESI+APCl): m/z=611 [M+H]+.

Example 41

Synthesis of di-tert-butyl(((2,2'-(1,4-phenylene)bis (1H-benzo[d]imidazole-6,6'-carbonyl))bis (azanediyl))bis(ethane-2,1-diyl))dicarbamate (Compound 50)

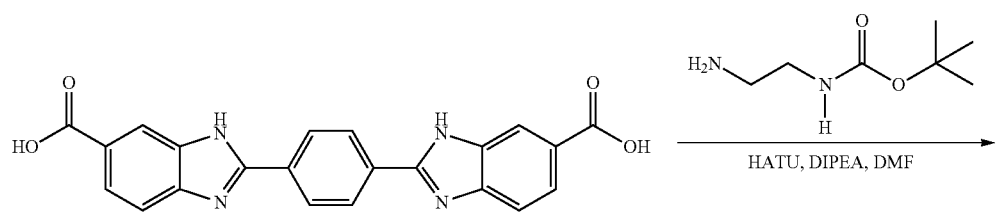

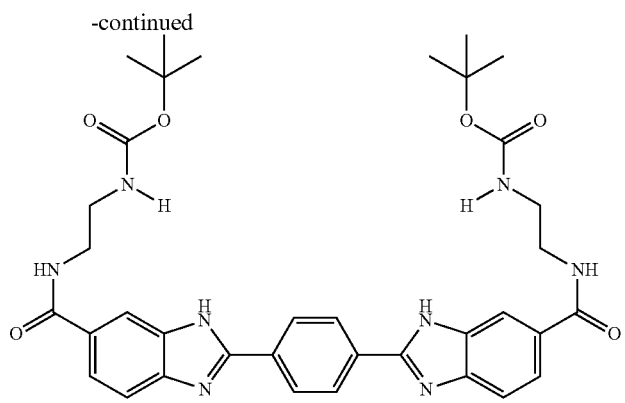

To a solution of 2,2'-(1,4-phenylene)bis(1H-benzo[d]imidazole-6-carboxylic acid) (0.3 g, 0.75 mmol) in DMF (15.0 mL) at 0° C., was added HATU (0.34 g, 0.90 mmol), DIPEA (0.41 mL, 2.25 mmol) and the reaction mixture was stirred for 10 minutes. tert-Butyl (2-aminoethyl) carbamate (0.16 g, 1.50 mmol) was added to the above mixture at 0° C. and the reaction mixture was allowed to warm to room temperature and stirred for 16 hours. The reaction mixture was poured in to ice and the precipitated compound was filtered under vacuum and dried to obtain the crude product. The product was washed with methanol, and dried under vacuum to obtain di-tert-butyl(((2,2'-(1,4-phenylene)bis(1H-benzo[d]imidazole-6,6'-carbonyl))bis(azanediyl))bis(ethane-2,1-diyl))dicarbamate. 1H NMR (DMSO-d6, 400 MHz) δ: 13.27 (s, 2H), 8.47 (brs, 2H), 8.39 (s, 4H), 8.23 (brs, 1H), 8.05 (brs, 1H), 7.76-7.61 (m, 4H), 6.95 (s, 2H), 3.32 (brs, 4H), 3.14 (brs, 4H), 1.38 (s, 18H). MS (ESI+APCI): m/z=683 [M+H]+.

Example 42

Synthesis of 2,2'-(1,4-phenylene)bis(N-(2-acetamidoethyl)-1H-benzo[d]imidazole-6-carboxamide)

A solution of 2,2'-(1,4-phenylene)bis(1H-benzo[d]imidazole-6-carboxylic acid) (Compound 11, 50 mg, 0.126 mmol) in DMF (3 ml) was treated with HATU (100 mg, 0.26 mmol) and DIPEA (130 μL, 0.75 mmol) for 5 minutes before adding N-acetylethylenediamine (28 mg, 0.27 mmol). After stirring overnight, the reaction formed a precipitate and the contents of the reaction were transferred to a falcon tube. Centrifugation gave a compound that was washed with water (×2) and then purified using a C-18 column and a gradient of 0-100% MeOH in water containing 0.1% TFA to afford 2,2'-(1,4-phenylene)bis(N-(2-acetamidoethyl)-1H-benzo[d]imidazole-6-carboxamide). 1H NMR (DMSO-d6, 400 MHz) δ: 8.62 (t, J=5.2, 10.7 Hz, 2H, —NH), 8.41 (s, 4H), 8.19 (br s, 2H), 8.04 (t, J=5.6, 11.2 Hz, 2H), 7.85 (dd, J=1.3, 8.5 Hz, 2H), 7.74 (d, J=8.5 Hz, 2H), 3.36 (q, J=5.8, 12 Hz, 4H), 3.25 (q, J=5.8, 12 Hz, 4H), 1.83 (s, 6H), MS (ESI): m/z=567 [M+H]+.

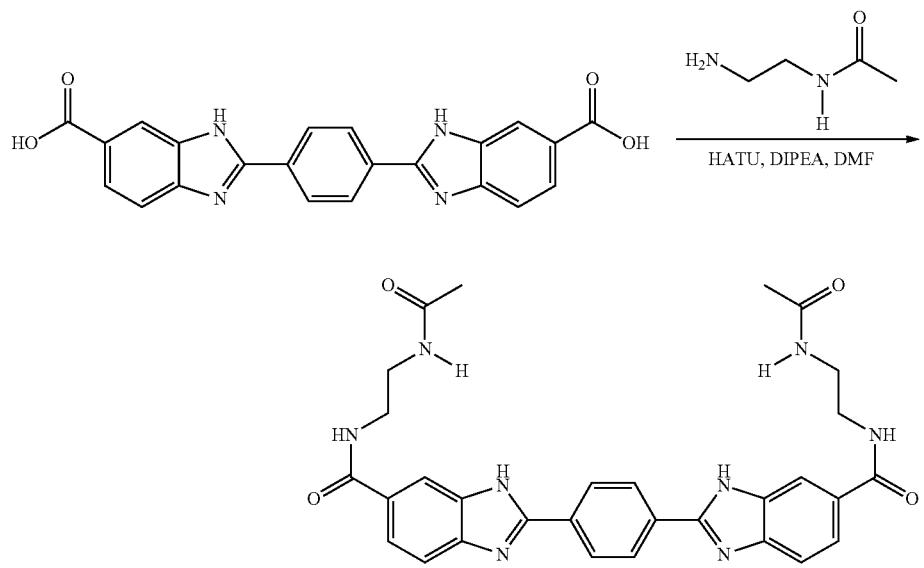

Example 43

Synthesis of 2,2'-(1,4-phenylene)bis(N-propyl-1H-benzo[d]imidazole-6-carboxamide)

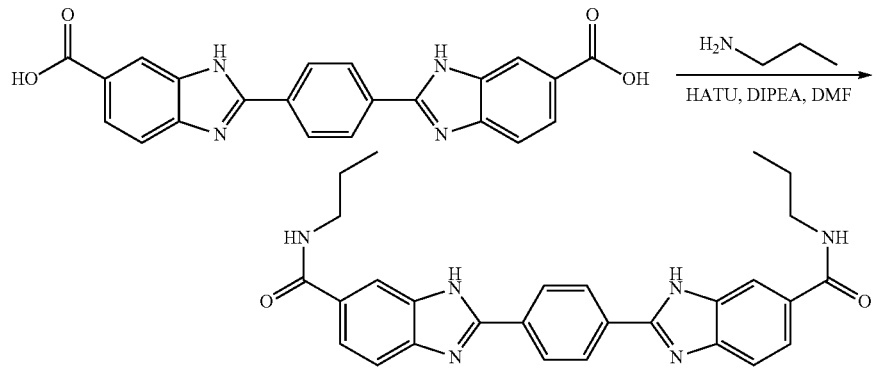

A solution of 2,2'-(1,4-phenylene)bis(1H-benzo[d]imidazole-6-carboxylic acid) (Compound 11, 50 mg, 0.126 mmol) in DMF (3 ml) was treated with HATU (100 mg, 0.26 mmol) and DIPEA (130 μL, 0.75 mmol) for 5 minutes before adding propylamine (16 mg, 0.27 mmol). After stirring overnight, the reaction formed a precipitate and the contents of the reaction were transferred to a falcon tube. Centrifugation gave a compound that was washed with water (×2) and then purified using a C-18 column and a gradient of 0-100% MeOH in water containing 0.1% TFA to afford 2,2'-(1,4-phenylene)bis(N-propyl-1H-benzo[d]imidazole-6-carboxamide). 1H NMR (CD3OD, 400 MHz) δ: 8.40 (s, 4H), 8.25 (br s, 2H), 7.95 (dd, J=1.6, 8.5 Hz, 2H), 7.82 (d, J=8.5 Hz, 2H), 3.40 (t, J=7.0 Hz, 4H), 1.69 (t, J=7.0 Hz, 6H), MS (ESI): m/z=481 [M+H]+.

Example 44

Synthesis of 2,2'-(1,4-phenylene)bis(N-(2-methoxyethyl)-1H-benzo[d]imidazole-6-carboxamide)

A solution of 2,2'-(1,4-phenylene)bis(1H-benzo[d]imidazole-6-carboxylic acid) (Compound 11, 50 mg, 0.126 mmol) in DMF (3 ml) was treated with HATU (100 mg, 0.26 mmol) and DIPEA (130 μL, 0.75 mmol) for 5 minutes before adding 2-Methoxy ethylamine (20 mg, 0.27 mmol). After stirring overnight, the solvent was removed under vacuum and to the crude material added water (5 ml). Centrifugation gave a pellet that was then purified using a C-18 column and a gradient of 0-100% MeOH in water containing 0.1% TFA to afford 2,2'-(1,4-phenylene)bis(N-(2-methoxyethyl)-1H-benzo[d]imidazole-6-carboxamide). 1H NMR (CD3OD, 400 MHz) δ: 8.43 (s, 4H), 8.29 (br s, 2H), 7.99 (dd, J=1.6, 8.6 Hz, 2H), 7.85 (dd, J=0.6, 8.6 Hz, 2H), 3.65 (s, 8H), 3.44 (s, 6H), MS (ESI): m/z=513 [M+H]+.

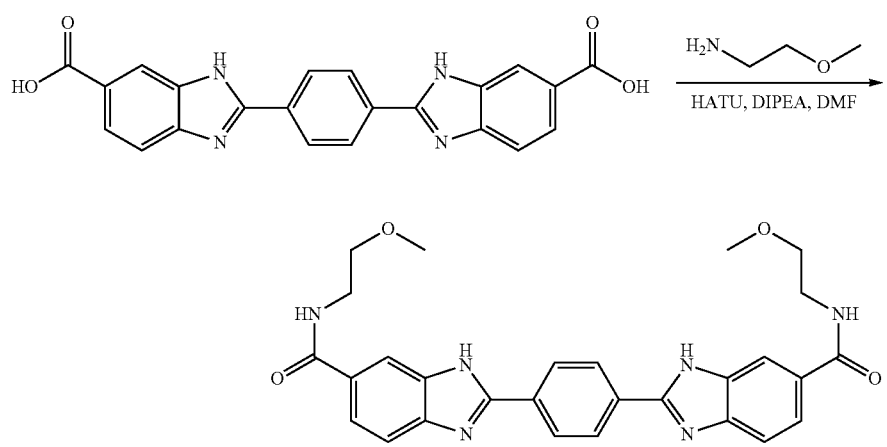

Example 45 bis(2-(dimethylamino)ethyl) 2,2'-(1,4-phenylene)bis(1H-benzo[d]imidazole-6-carboxylate)

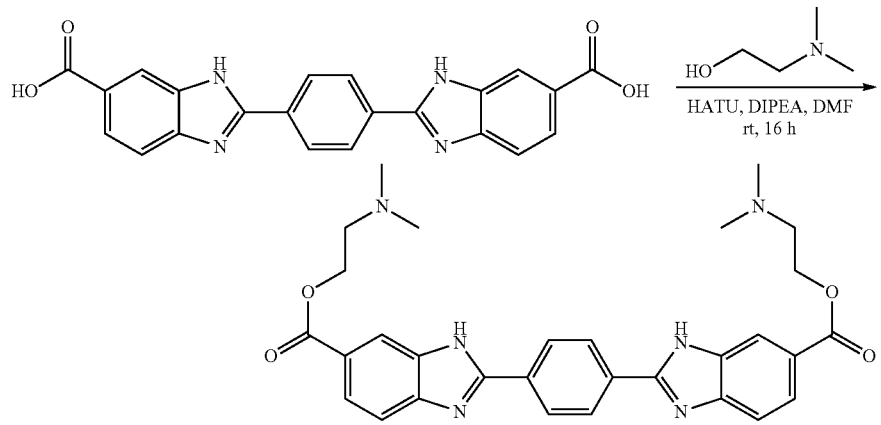

To a solution of 2-(dimethylamino)ethanol (74 mg, 0.82 mmol) in DMF (10 mL) at 0° C., was added HATU (0.35 g, 0.94 mmol), DIPEA (0.36 mL, 2.25 mmol) and the reaction mixture was stirred for 10 minutes. 2,2'-(1,4-phenylene)bis(1H-benzo[d]imidazole-6-carboxylic acid) (0.15 g, 0.37 mmol) was added to the above mixture in one lot at 0° C. and the reaction mixture was allowed to warm to room temperature and stirred for 16 hours. The reaction mixture was poured onto ice and the precipitated compound was filtered under vacuum and dried to obtain the crude product, which was purified by silica gel chromatography (1:4 methanol:dichloromethane). The fractions containing pure product were combined and concentrated under vacuum to obtain bis(2-(dimethylamino)ethyl) 2,2'-(1,4-phenylene)bis(1H-benzo[d]imidazole-6-carboxylate). 1H NMR (DMSO-d6, 400 MHz) δ: 13.5 (brs, 2H), 8.41-8.39 (m, 4H), 8.37 (s, 1H), 8.18 (s, 1H), 7.93-7.87 (m, 2H), 7.80 (d, J=8.4 Hz, 1H), 6.68 (d, J=8.0 Hz, 1H), 4.48-4.45 (m, 4H), 2.96-2.90 (m, 4H), 2.42 (s, 12H). MS (ESI+APCl): m/z=541 [M+H]+.

Example 46

Synthesis of 2,2'-((2,2'-(1,4-phenylene)bis(1H-benzo[d]imidazole-6,6'-carbonyl))bis(oxy))bis(N,N,N-trimethylethanaminium) chloride

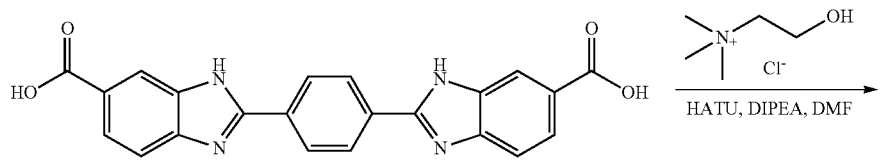

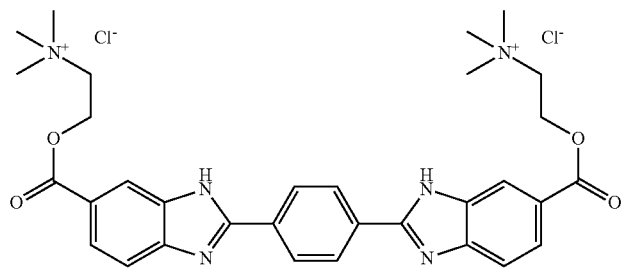

To a solution of 2,2'-(1,4-phenylene)bis(1H-benzo[d]imidazole-6-carboxylic acid) (0.50 g, 1.25 mmol) in DMF (10 mL) at 0° C., was added HATU (1.05 g, 2.76 mmol), DIPEA (1.80 mL, 10.30 mmol) and the reaction mixture was stirred for 10 minutes. 2-Hydroxy-N,N,N-trimethylethanaminium chloride (0.38 g, 2.76 mmol) was added to the above mixture in one lot at 0° C. and the reaction mixture was allowed to warm to room temperature and stirred for 8 hours. The reaction mixture was poured onto ice, whereupon the product precipitated. The precipitated product was collected by filtration under vacuum, washed with EtOH (10 mL), and dried to obtain the crude product. The crude product was refluxed in EtOH (20 mL) and collected by filtration under vacuum, dried to obtain 2,2'-((2,2'-(1,4-phenylene)bis(1H-benzo[d]imidazole-6,6'-carbonyl))bis(oxy))bis(N,N,N-trimethylethanaminium) chloride. 1H NMR (DMSO-d6, 400 MHz) δ: 13.71 (brs, 2H), 8.42 (s, 4H), 8.31 (s, 2H), 7.91 (d, J=7.6 Hz, 2H), 7.74 (d, J=7.6 Hz, 2H), 4.79-4.75 (m, 4H), 3.89-3.85 (m, 4H), 3.34 (s, 18H). UPLC MS m/z=570, 285 [M, M/2]+.

Example 47

Synthesis of bis(3-(dimethylamino)propyl) 2,2'-(1,4-phenylene)bis(1H-benzo[d]imidazole-6-carboxylate

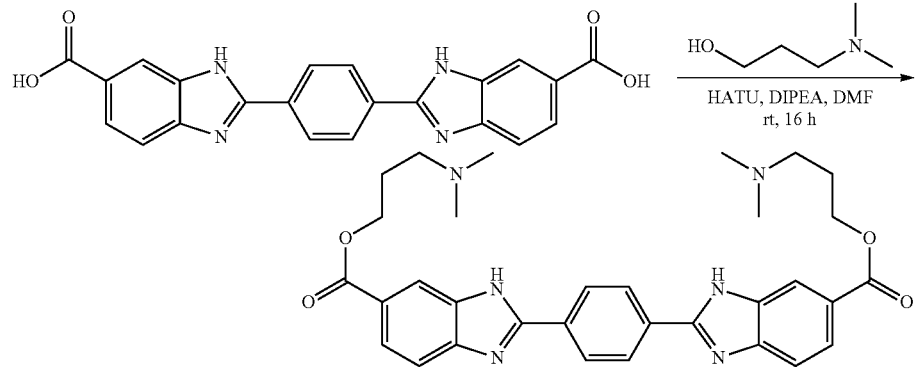

To a suspension of 2,2'-(1,4-phenylene)bis(1H-benzo[d]imidazole-6-carboxylic acid) (0.15 g, 0.37 mmol) in DMF (10 mL) at 0° C., was added HATU (0.35 g, 0.94 mmol), DIPEA (0.36 mL, 2.25 mmol) and the reaction mixture was stirred for 10 minutes. 3-(dimethylamino)propan-1-ol (85 mg, 0.82 mmol) was added to the above mixture at 0° C. and the reaction mixture was allowed to warm to room temperature and stirred for 16 hours. The reaction mixture was concentrated under vacuum and the crude product was diluted with ice-cold water (10 mL), and stirred for 15 minutes, whereupon the product precipitated. The product was collected by filtration under vacuum, washed with methanol (10 mL), and dried under vacuum. The product was purified by silica gel chromatography [1:4 (10% ammonium hydroxide in methanol):dichloromethane]. The fractions containing the pure product were combined and concentrated under vacuum and triturated with EtOH (10 mL) to obtain bis(3-(dimethylamino)propyl) 2,2'-(1,4-phenylene)bis(1H-benzo[d]imidazole-6-carboxylate. 1H NMR (DMSO-d6, 400 MHz) δ: 13.43 (brs, 2H), 8.44-8.40 (m, 4H), 8.30-8.24 (m, 2H), 7.88 (d, J=8.0 Hz, 2H), 7.79-7.72 (m, 2H), 4.33 (t, J=6.4 Hz, 4H), 2.39 (t, J=7.2 Hz, 4H), 2.17 (s, 12H), 1.89 (t, J=6.8 Hz, 4H), MS (ESI+APCl): m/z=569 [M+H]+.

Example 48

Synthesis of 2,2'-((2,2'-(1,4-phenylene)bis(1H-benzo[d]imidazole-6,2-diyl))bis(oxy))bis(N,N-dimethylethanamine)

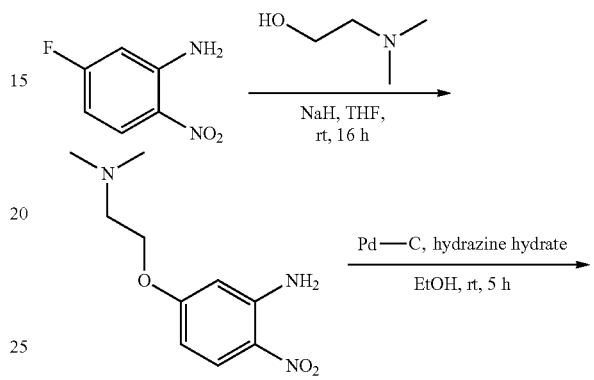

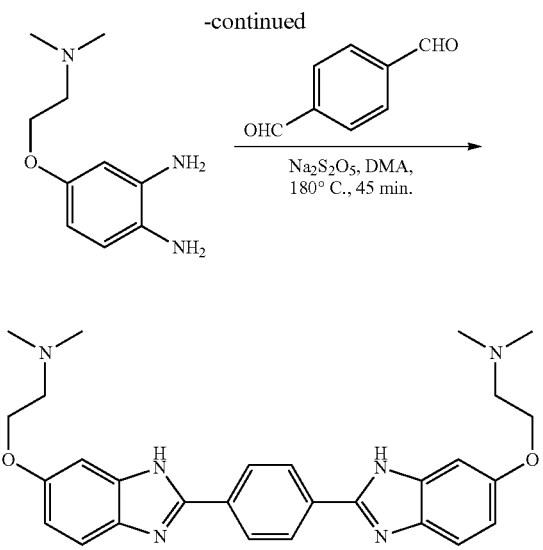

Step 1. Synthesis of 5-(2-(dimethylamino) ethoxy)-2-nitroaniline

A solution of 2-(dimethylamino) ethanol (0.85 g, 9.61 mmol) in THF (35.0 mL) was added to a suspension of NaH (0.63 g, 16.0 mmol) in THF (10.0 mL) at 0° C. under N2 atmosphere, and the mixture was stirred for 10 minutes. A solution of 5-fluoro-2-nitroaniline (1.00 g, 6.41 mmol) in THF (10.0 mL) was added to the above mixture and the reaction mixture was allowed to warm to room temperature and stirred for 16 hours. The reaction mixture was poured onto ice, where upon the product precipitated. The precipitated product was collected by filtration under vacuum, washed with water (20 mL), and dried to obtain the crude product. The product was purified by silica gel column chromatography using methanol:dichloromethane (1:9). Fractions containing the product were combined and concentrated under vacuum to obtain 5-(2-(dimethylamino) ethoxy)-2-nitroaniline.

1H NMR (DMSO-d6, 400 MHz) δ: 8.07 (d, J=9.6 Hz, 1H), 6.31 (dd, J=9.6, 2.4 Hz, 1H), 6.17-6.16 (m, 3H), 4.07 (t, J=5.6 Hz, 2H), 2.73 (t, J=5.6 Hz, 2H), 2.33 (s, 6H). MS (ESI+APCl) m/z 226 [M+H]+.

Step 2. Synthesis of 4-(2-(dimethylamino) ethoxy)benzene-1,2-diamine

To a solution of 5-(2-(dimethylamino) ethoxy)-2-nitroaniline (0.70 g, 3.11 mmol) in ethanol (35.0 mL), was added hydrazine monohydrate (1.40 mL), 10% Pd/C (0.35 g) and the reaction mixture was stirred at room temperature for 2 hours. The reaction mixture was filtered through a celite-pad, and the celite pad was washed with dichloromethane (20 mL), and concentrated under vacuum to obtain the crude product. The product was purified by silica gel column chromatography using methanol:dichloromethane (1:9). Fractions containing the product were combined and concentrated under vacuum to obtain 4-(2-(dimethylamino) ethoxy)benzene-1,2-diamine.

1H NMR (DMSO-d6, 400 MHz) δ: 6.39 (d, J=8.0 Hz, 1H), 6.15 (d, J=2.0 Hz, 1H), 5.98-5.95 (m, 1H), 4.47 (brs, 2H), 4.00 (brs, 2H), 3.82 (t, J=6.0 Hz, 2H), 2.52 (t, J=6.0 Hz, 2H), 2.18 (s, 6H). MS (ESI+APCl) m/z 196 [M+H]+.

Step 3. Synthesis of 2,2'-((2,2'-(1,4-phenylene)bis(1H-benzo[d]imidazole-6,2-diyl))bis(oxy))bis(N,N-dimethylethanamine)

In a microwave vial, a mixture of terephthalaldehyde (0.40 g, 2.05 mmol), 4-(2-(dimethylamino) ethoxy)benzene-1,2-diamine (0.13 g, 1.02 mmol) and sodium metabisulfite (0.38 g, 2.05 mmol) in DMA (5.0 mL) was heated at 180° C. for 45 min. The reaction mixture was cooled to room temperature and the contents were slowly poured into ice-cold water and stirred for 10 minutes, whereupon, a material precipitated. The material was collected by filtration under vacuum and washed with water (2×50 mL). The obtained material was purified by prep HPLC on a X-Select C-18 (30×150 mm, 10 μm) column; mobile phase, A=0.1% TFA in water and B=CH3CN; Flow rate: 30 mL/min, Injection volume: 400 μL, Runtime: 20 minutes, gradient: 95-40% A, 05-60% B (0.0-15 min); UV detection at 220 nm). Fractions containing only the pure product were combined for concentration to obtain 2,2'-((2,2'-(1,4-phenylene)bis(1H-benzo[d]imidazole-6,2-diyl))bis(oxy))bis(N,N-dimethylethanamine).

1H NMR (CD3OD, 400 MHz) δ: 8.10 (s, 4H), 7.43 (d, J=8.0 Hz, 2H), 7.04 (s, 2H), 6.89-6.86 (m, 2H), 4.07 (t, J=8.0 Hz, 4H), 2.72 (t, J=8.0 Hz, 4H), 2.28 (s, 12H). MS (ESI+APCl) m/z 485 [M+H]+.

Example 49

Synthesis of 3,3'-((2,2'-(1,4-phenylene)bis(1H-benzo[d]imidazole-6,2-diyl))bis(oxy))bis(N,N-dimethylpropan-1-amine)

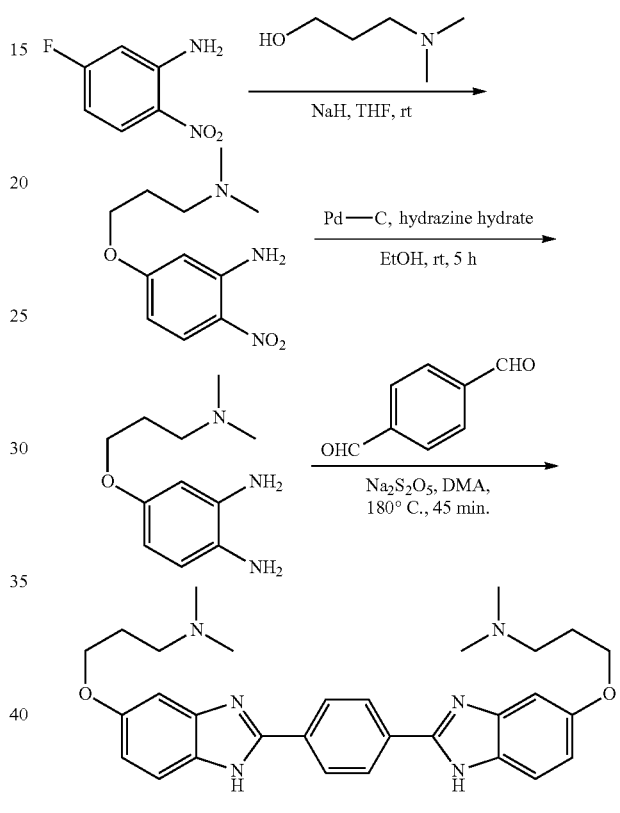

Step 1. Synthesis of 5-(3-(dimethylamino)propoxy)-2-nitroaniline

To a stirred solution of 3-(dimethylamino)propan-1-ol (0.99 g, 9.61 mmol) in dry THF (10.0 mL), at 0° C. under N2 atmosphere, was added NaH (60% suspension in oil, 769 mg, 19.2 mmol) portion wise over a period of 10 minutes. The reaction mixture was stirred for an additional 10 minutes and a solution of 5-fluoro-2-nitroaniline (1.00 g, 6.41 mmol) in THF (20.0 mL) was added in a dropwise manner over 15 minutes, maintaining the temperature at 0° C. After complete addition, the reaction mixture was warmed to 50° C. and stirred for 24 hours. The reaction mixture was cooled to room temperature and the contents were poured onto ice and extracted with EtOAc (2×50 mL). The combined organic extracts were washed with brine (30 mL), dried over anhydrous sodium sulfate, and concentrated under vacuum to obtain the crude product. The product was purified by silica gel column chromatography using methanol:dichloromethane (1:9). The fractions containing the product were combined and concentrated under vacuum to obtain 5-(3-(dimethylamino) propoxy)-2-nitroaniline.

1H NMR (400 MHz, CDCl3): 8.06 (d, J=9.6 Hz, 1H), 6.28 (dd, J=2.8 Hz, 9.6 Hz, 1H), 6.16 (d, J=2.4 Hz, 3H), 4.03 (t, J=6.4 Hz, 2H), 2.45 (t, J=7.2 Hz, 2H) 2.26 (brs, 6H), 1.96 (t, J=6.8 Hz, 2H).

Step 2. Synthesis of 4-(3-(dimethylamino)propoxy)benzene-1,2-diamine

To a solution of 5-(3-(dimethylamino)propoxy)-2-nitroaniline (0.57 g, 2.38 mmol) in EtOH (20.0 mL), hydrazine monohydrate (2.0 mL) and 10% Pd/C (50 mg) were added and the reaction mixture was stirred at room temperature for 5 hours. The reaction mixture was filtered through a celite pad, and the pad was washed with EtOH (50 mL). The combined filtrate was concentrated under reduced pressure to obtain 4-(3-(dimethylamino) propoxy)benzene-1,2-diamine.

1H NMR (400 MHz, CDCl3): 6.62 (d, J=8.4 Hz, 1H), 6.32 (d, J=2.4 Hz, 1H), 6.25 (dd, J=2.8 Hz, 8.4 Hz, 1H), 3.92 (t, J=6.4 Hz, 2H), 3.48 (brs, 2H), 2.75 (brs, 2H), 2.44 (t, J=7.6 Hz, 2H) 2.26 (brs, 6H), 1.96 (t, J=7.2 Hz, 2H).

Step 3. Synthesis of 3,3'-((2,2'-(1,4-phenylene)bis(1H-benzo[d]imidazole-6,2-diyl))bis(oxy))bis(N,N-dimethylpropan-1-amine)

In a microwave vial, a mixture of terephthalaldehyde (96 mg, 0.72 mmol), 4-(3-(dimethylamino)propoxy)benzene-1,2-diamine (0.30 g, 1.44 mmol) and sodium metabisulfite (0.27 g, 1.44 mmol) in DMA (5.0 mL) was heated at 180° C. for 45 min. The reaction mixture was cooled to room temperature and the contents were slowly poured into ice-cold water and stirred for 10 minutes, whereupon, a material precipitated. The material was collected by filtration under vacuum and washed with water (2×50 mL). The obtained material was purified by preparative HPLC on a Gemini 10 µm NX (250×4.6 mm, 10 µm) column; mobile phase, A=0.1% TFA in water and B=CH3CN; Flow rate: 30 mL/min, Injection volume: 700 µL, Runtime: 20 minutes, gradient: 45-95% A, 05-55% B (0.0-15 min); UV detection at 220 nm). The fractions containing only the pure product were combined for concentration to yield 3,3'-((2,2'-(1,4-phenylene)bis(1H-benzo[d]imidazole-6,2-diyl))bis(oxy))bis(N,N-dimethylpropan-1-amine).

1H NMR (400 MHz, CD3OD): 8.09 (s, 4H), 7.28 (d, J=8.4 Hz, 2H), 7.01 (s, 2H), 6.83 (dd, J=2.0 Hz, 8.8 Hz, 2H), 3.98 (t, J=6.0 Hz, 4H) 2.48 (t, J=8.0 Hz, 4H), 1.95 (brs, 12H), 1.95-1.88 (m, 4H). MS (ESI+APCl) m/z 513 [M+H]+.

Example 50

Synthesis of 2,2'-((2,2'-(1,4-phenylene)bis(1H-benzo[d]imidazole-6,2-diyl))bis(sulfanediyl))bis(N,N-dimethylethanamine)

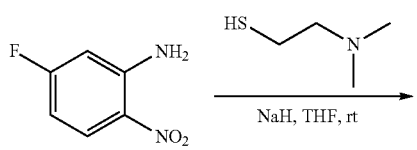

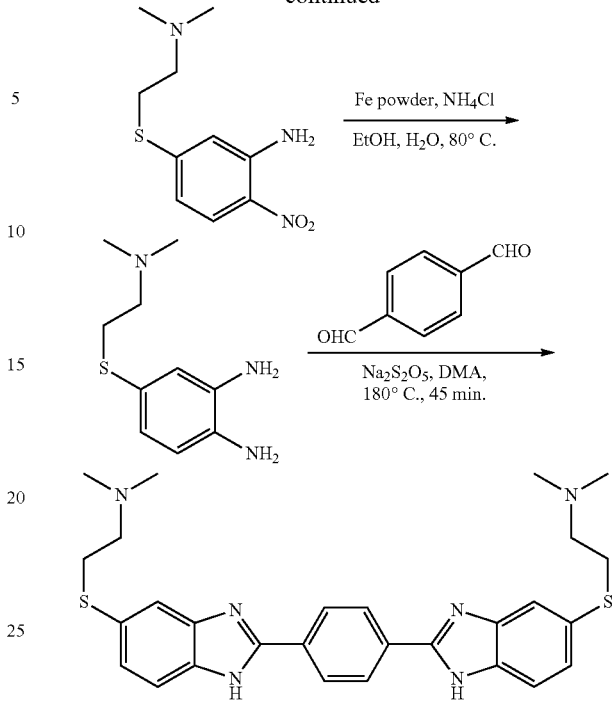

Synthesis of 5-(2-(dimethylamino)ethyl)thio)-2-nitroaniline

A solution of 2-(dimethylamino)ethane thiol (2.10 g, 15.38 mmol) in THF (35.0 mL) was added to a suspension of NaH (1.02 g, 25.64 mmol) in THF (10.0 mL) at 0° C. under N2 atmosphere, and the mixture was stirred for 10 minutes. A solution of 5-fluoro-2-nitroaniline (1.60 g, 10.25 mmol) in THF (10.0 mL) was added to the above mixture and the reaction mixture was allowed to warm to room temperature and stirred for 16 hours. The reaction mixture was poured onto ice and extracted with EtOAc (2×60 mL). The combined organic extracts were washed with brine (30 mL), dried over sodium sulfate and concentrated under vacuum to obtain the crude product. The product was purified by silica gel column chromatography using methanol:dichloromethane (1:9). The fractions containing the product were combined and concentrated under vacuum to obtain 5-(2-(dimethylamino)ethyl)thio)-2-nitroaniline.

1H NMR (DMSO-d6, 400 MHz) δ: 7.85 (d, J=9.2 Hz, 1H), 7.45 (s, 2H), 6.83 (d, J=2.0 Hz, 1H), 6.50 (dd, J=9.2, 2.0 Hz, 1H), 3.09 (t, J=6.8 Hz, 2H), 2.52 (t, J=7.2 Hz, 2H), 2.18 (s, 6H). MS (ESI+APCl) m/z 242 [M+H]+.

Synthesis of 4-((2-(dimethylamino)ethyl)thio)benzene-1,2-diamine

To a solution of 5-(2-(dimethylamino)ethyl)thio)-2-nitroaniline (1.50 g, 6.22 mmol) in mixture of ethanol (60.0 mL) and water (30.0 mL) was added Fe powder (1.70 g, 31.12 mmol), ammonium chloride (1.64 g, 31.12 mmol) and the reaction mixture was heated at 80° C. for 5 hours. The reaction mixture was cooled to room temperature and filtered through a celite-pad. The pad was washed with methanol (20 mL), and the filtrate was concentrated under vacuum to yield the crude product. The product was purified by silica gel column chromatography using methanol:dichloromethane (1:9). Fractions containing the product were combined and concentrated under vacuum to give 4-((2-(dimethylamino)ethyl)thio) benzene-1,2-diamine.

1H NMR (DMSO-d6, 400 MHz) δ: 6.59 (d, J=1.6 Hz, 1H), 6.47-6.42 (m, 2H), 4.56-4.54 (m, 4H), 2.77-2.74 (m, 2H), 2.38 (t, J=7.6 Hz, 2H), 2.13 (s, 6H). MS (ESI+APCl) m/z 212 [M+H]+.

Synthesis of 2,2'-((2,2'-(1,4-phenylene)bis(1H-benzo[d]imidazole-6,2-diyl))bis(sulfanediyl))bis(N,N-dimethylethanamine)

In a microwave vial, a mixture of terephthalaldehyde (95 mg, 0.71 mmol), 4-((2-(dimethylamino)ethyl)thio) benzene-1,2-diamine (300 mg, 1.42 mmol) and sodium metabisulfite (268 mg, 1.42 mmol) in DMA (5.0 mL) was heated at 180° C. for 45 min. The reaction mixture was cooled to room temperature and the contents were slowly poured into methanol (60 mL) and stirred for 10 minutes, whereupon a material precipitated. The material was filtered through a celite-pad, the pad was washed with methanol (2×20 mL), and the filtrate was concentrated under vacuum to yield the crude product. The obtained brown syrupy liquid was purified by prep HPLC on an Atlantis T-3 (30×150 mm, 10 μm) column; mobile phase, A=0.1% TFA in water and B=CH3CN; Flow rate: 30 mL/min, Injection volume: 200 μL, Runtime: 20 minutes, gradient: 90-40% A, 10-60% B (0.0-15 min); UV detection at 220 nm). Fractions containing only the pure product were combined for concentration to obtain 2,2'-((2,2'-(1,4-phenylene)bis(1H-benzo[d]imidazole-6,2-diyl))bis(sulfanediyl))bis(N,N-dimethylethanamine).

1H NMR (CD3OD, 400 MHz) δ: 8.18 (s, 4H), 7.61 (s, 2H), 7.47 (d, J=8.4 Hz, 2H), 7.19 (d, J=8.4 Hz, 2H), 2.94 (t, J=7.6 Hz, 4H), 2.49 (t, J=8.0 Hz, 4H), 2.15 (s, 12H). MS (ESI+APCl) m/z 517 [M+H]+.

Example 51

Synthesis of 3,3'-((2,2'-(1,4-phenylene)bis(1H-benzo[d]imidazole-6,2-diyl))bis(sulfanediyl))bis(N,N-dimethylpropan-1-amine) (Compound 60)

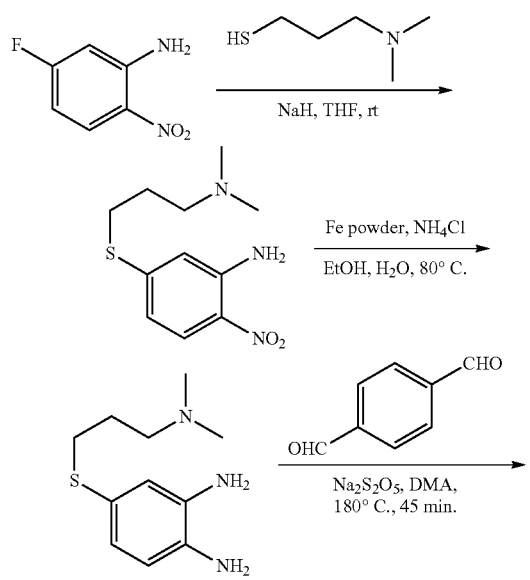

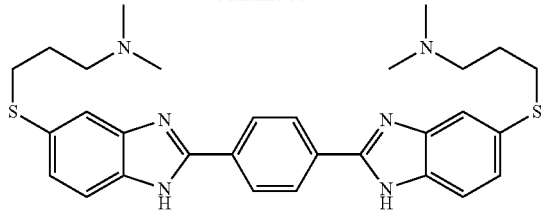

Synthesis of 5-((3-(dimethylamino)propyl)thio)-2-nitroaniline

A solution of 3-(dimethylamino)propane-1-thiol (1.71 g, 14.42 mmol) in THF (30.0 mL) was added to a suspension of NaH (0.96 g, 24.03 mmol) in THF (15.0 mL) at 0° C. under $N_2$ atmosphere, and the mixture was stirred for 10 minutes. A solution of 5-fluoro-2-nitroaniline (1.50 g, 9.61 mmol) in THF (15.0 mL) was added to the above mixture and the reaction mixture was allowed to warm to room temperature and stirred for 16 hours. The reaction mixture was poured onto ice and extracted with EtOAc (2×60 mL). The combined organic extracts were washed with brine (30 mL), dried over sodium sulfate and concentrated under vacuum to obtain the crude product. The product was purified by silica gel chromatography using methanol:dichloromethane (1:9). The fractions containing the product were combined and concentrated under vacuum to obtain 5-((3-(dimethylamino) propyl)thio)-2-nitroaniline.

1H NMR (CDCl3, 400 MHz) δ: 8.01 (d, J=8.8 Hz, 1H), 6.59 (d, J=2.0 Hz, 1H), 6.55 (dd, J=9.2, 2.0 Hz, 1H), 6.14 (s, 2H), 3.01 (t, J=7.2 Hz, 2H), 2.40 (t, J=6.8 Hz, 2H), 2.23 (s, 6H), 1.89-1.75 (m, 2H). MS (ESI+APCl) m/z 256 [M+H]+.

Synthesis of 4-((3-(dimethylamino)propyl)thio)benzene-1,2-diamine

To a solution of 5-((3-(dimethylamino) propyl)thio)-2-nitroaniline (1.70 g, 6.66 mmol) in mixture of ethanol (70.0 mL) and water (35.0 mL) was added Fe powder (1.83 g, 33.33 mmol), ammonium chloride (1.76 g, 33.33 mmol) and the reaction mixture was heated at 80° C. for 5 hours. The reaction mixture was cooled to room temperature and filtered through a celite-pad, the pad was washed with methanol (20 mL), and the filtrate was concentrated under vacuum to obtain the crude product. The product was purified by silica gel column chromatography using methanol:dichloromethane (1:9). Fractions containing the product were combined and concentrated under vacuum to obtain 4-((3-(dimethylamino) propyl)thio)benzene-1,2-diamine.

1H NMR (CD3OD, 400 MHz) δ: 6.75 (d, J=2.0 Hz, 1H), 6.62 (dd, J=8.0, 2.0 Hz, 1H), 6.55 (d, J=8.0 Hz, 1H), 3.12-3.08 (m, 2H), 2.73-2.69 (m, 8H), 1.85-1.77 (m, 2H). MS (ESI+APCl) m/z 226 [M+H]+.

Synthesis of 3,3'-((2,2'-(1,4-phenylene)bis(1H-benzo[d]imidazole-6,2-diyl))bis(sulfanediyl))bis(N,N-dimethylpropan-1-amine)

In a microwave vial, a mixture of terephthalaldehyde (148 mg, 1.11 mmol), 4-((3-(dimethylamino) propyl)thio)benzene-1,2-diamine (500 mg, 2.22 mmol) and sodium metabisulfite (557 mg, 2.22 mmol) in DMA (6.0 mL) was heated at 180° C. for 45 min. The reaction mixture was cooled to room temperature and the contents were slowly poured into methanol (60 mL) and stirred for 10 minutes, whereupon a material precipitated. The material was filtered through a celite-pad, the pad was washed with methanol (2×20 mL), and the filtrate concentrated under vacuum to obtain the crude product. The obtained brown syrupy liquid was purified by prep HPLC on a X-Bridge C-18 (30×150 mm, 10 μm) column; mobile phase, A=0.1% TFA in water and B=CH3CN; Flow rate: 40 mL/min, Injection volume: 350 μL, Runtime: 20 minutes, gradient: 90-70% A, 10-30% B (0.0-15 min); UV detection at 220 nm). Fractions containing only the pure product were combined for concentration to obtain 3,3'-((2,2'-(1,4-phenylene)bis(1H-benzo[d]imidazole-6,2-diyl))bis(sulfanediyl))bis(N,N-dimethylpropan-1-amine).

1H NMR (CD3OD, 400 MHz) δ: 8.15 (s, 4H), 7.58 (s, 2H), 7.49 (d, J=8.4 Hz, 2H), 7.25 (dd, J=8.4, 1.6 Hz, 2H), 2.89 (t, J=7.2 Hz, 4H), 2.37 (t, J=7.6 Hz, 4H), 2.11 (s, 12H), 1.75-1.67 (m, 4H). MS (ESI+APCl) m/z 545 [M+H]+.

Example 52

Synthesis of N1,N1'-((2,2'-(1,4-phenylene)bis(1H-benzo[d]imidazole-6,2-diyl))bis(methylene))bis(N2,N2'-dimethylethane-1,2-diamine) and N1-((2-(4-(6-((methoxy(methyl)amino)methyl)-1H-benzo[d]imidazol-2-yl)phenyl)-1H-benzo[d]imidazol-6-yl)methyl)-N2,N2'-dimethylethane-1,2-diamine Step 1. Synthesis of 2,2'-(1,4-phenylene)bis(N-methoxy-N-methyl-1H-benzo[d]imidazole-6-carboxamide)

To a solution of 2,2'-(1,4-phenylene)bis(1H-benzo[d]imidazole-6-carboxylic acid) (1.00 g, 2.51 mmol) in DMF (10 mL) at 0° C., was added HATU (2.10 g, 5.52 mmol), DIPEA (2.70 mL, 15.0 mmol) and the reaction mixture was stirred for 10 minutes. N,O-dimethylhydroxylamine hydrochloride (0.54 g, 5.52 mmol) was added to the above mixture in one lot at 0° C., the reaction mixture was allowed to warm to room temperature, and stirred for 16 hours. The reaction mixture was concentrated under vacuum and the crude product was diluted with ice-cold water (20 mL), and stirred for 15 minutes, whereupon the product precipitated. The product was collected by filtration under vacuum, washed with methanol (10 mL), and dried under vacuum to obtain 2,2'-(1,4-phenylene)bis(N-methoxy-N-methyl-1H-benzo[d]imidazole-6-carboxamide). 1H NMR (DMSO-d6, 400 MHz) δ: 8.39 (s, 4H), 7.92 (brs, 2H), 7.67 (brs, 2H), 7.53 (d, J=8 Hz, 2H), 3.58 (s, 6H), 3.31 (s, 6H), MS (ESI+APCl): m/z=485 [M+H]+.

Step 2. Synthesis of 2,2'-(1,4-phenylene)bis(1H-benzo[d]imidazole-6-carbaldehyde)

To a solution of 2,2'-(1,4-phenylene)bis(N-methoxy-N-methyl-1H-benzo[d]imidazole-6-carboxamide) (0.50 g, 1.03 mmol) in dry THF (30.0 mL) at −78° C., was added

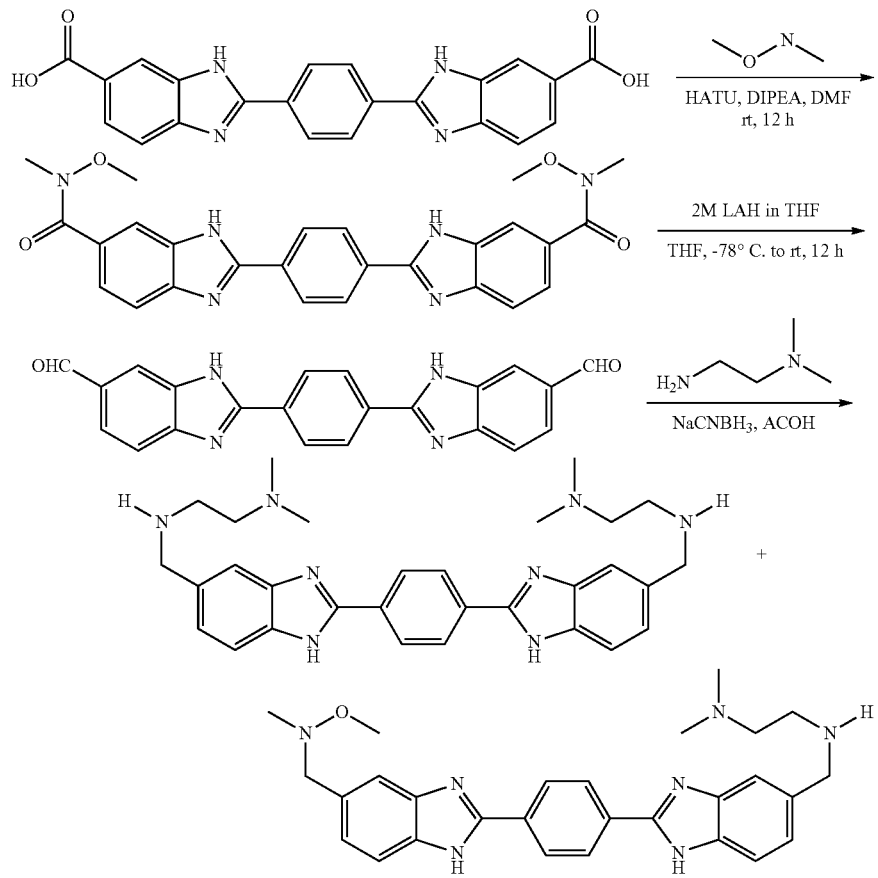

LAH (2.0 M in THF, 5.16 mL 10.3 mmol) dropwise and the reaction mixture was gradually warmed to room temperature and stirred for 16 hours. The reaction mixture was quenched by the dropwise addition of saturated aqueous sodium sulfate (5.0 mL) at −78° C., filtered through a celite pad, the pad washed with 10% methanol in dichloromethane (25 mL), and the filtrate was concentrated under vacuum and dried to obtain the crude compound (0.32 g). The analysis of the crude compound by MS analysis indicated formation of 4a (2-(4-(6-((methoxy(methyl)amino)methyl)-1H-benzo[d]imidazol-2-yl)phenyl)-1H-benzo[d]imidazole-6-carbaldehyde) as major product, MS (ESI+APCl): m/z=412 [M+H]+; and the desired compound 2,2'-(1,4-phenylene)bis(1H-benzo[d]imidazole-6-carbaldehyde) as minor product MS (ESI+APCl): m/z=367 [M+H]+; crude product was directly used in the next step without purification.

Step 3. Synthesis of N1,N1'-((2,2'-(1,4-phenylene)bis(1H-benzo[d]imidazole-6,2-diyl))bis(methylene))bis(N2,N2'-dimethylethane-1,2-diamine)

To a solution of crude compound 2,2'-(1,4-phenylene)bis(1H-benzo[d]imidazole-6-carbaldehyde) (0.32 g, 0.87 mmol) in methanol/dichloromethane (1:1, 10 mL) was added N1,N1'-dimethylethane-1,2-diamine (0.17 g, 1.92 mmol) and acetic acid (0.3 mL) and the reaction mixture stirred was stirred at room temperature for 12 hours. To this reaction mixture was added NaCNBH$_3$ (0.27 g, 4.37 mmol) at 0° C., and the mixture was stirred at room temperature for 6 hours. The reaction mixture was concentrated under vacuum and the crude product was diluted with ice-cold water (10 mL), and stirred for 15 minutes, whereupon the product precipitated. The product was collected by filtration under vacuum, washed with methanol (5.0 mL), and dried under vacuum to obtain crude product (0.21 g) which was purified by Prep HPLC on a Gemini@10 µm NX (250×4.6 mm, 10 µm) column; mobile phase, A=0.1% TFA in water and B=CH3CN; Flow rate: 30 mL/min, Injection volume: 700 µL, Runtime: 20 minutes, gradient: 10-80% A, 20-90% B (0.0-15 min); UV detection at 220 nm). Fractions containing the desired product were combined and concentrated to afford N1,N1'-((2,2'-(1,4-phenylene)bis(1H-benzo[d]imidazole-6,2-diyl))bis(methylene))bis(N2,N2'-dimethylethane-1,2-diamine): 1H NMR (400 MHz, DMSO-d6): 12.96 (s, 2H), 8.32 (s, 4H), 7.64-7.49 (m, 4H), 7.25-7.18 (m, 2H), 3.87 (s, 4H), 2.67-2.62 (m, 4H), 2.39-2.38 (m, 4H), 2.13 (s, 12H), MS (ESI): m/z=511 [M+H]+.

N1-((2-(4-(6-((methoxy(methyl)amino)methyl)-1H-benzo[d]imidazol-2-yl)phenyl)-1H-benzo[d]imidazol-6-yl)methyl)-N2,N2'-dimethylethane-1,2-diamine, a by-product resulting from over-reduction of the Weinreb amide intermediate, was also isolated:

1H NMR (400 MHz, DMSO-d6): 12.97 (s, 2H), 8.33 (s, 4H), 7.61-7.51 (m, 4H), 7.22 (s, 2H), 3.86 (s, 3H), 3.33 (s, 4H), 2.67-2.66 (m, 2H), 2.56 (s, 3H), 2.33-2.32 (m, 2H), 2.13 (s, 6H), MS (ESI): m/z=484 [M+H]+.

Example 53

Synthesis of N,N'-(2,2'-(1,4-phenylene)bis(1H-benzo[d]imidazole-6,2-diyl))bis(2-(dimethylamino)acetamide)

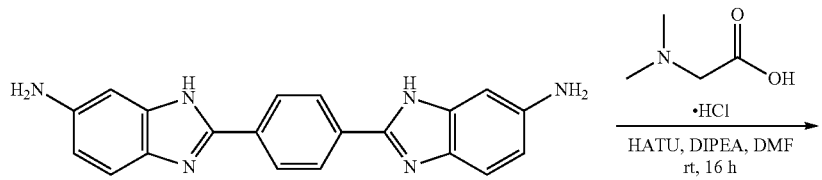

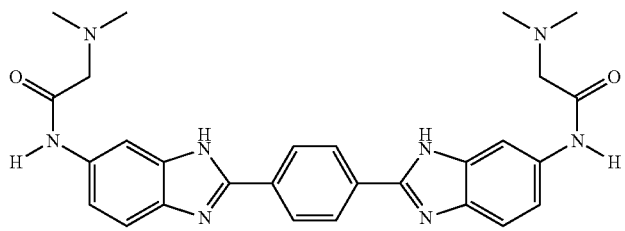

To a solution of 2-(dimethylamino)acetic acid hydrochloride (90 mg, 0.64 mmol) in DMF (5.0 mL) at 0° C., was added HATU (0.27 g, 0.73 mmol), DIPEA (0.31 mL, 1.75 mmol) and the reaction mixture was stirred for 10 minutes. 2,2'-(1,4-Phenylene)bis(1H-benzo[d]imidazol-6-amine) (0.1 g, 0.29 mmol) was added to the above mixture in one lot at 0° C. and the reaction mixture was allowed to warm to room temperature and stirred for 16 hours. The reaction mixture was poured onto ice and the precipitated material was filtered under vacuum and dried to obtain the crude product, which was purified by silica gel chromatography (1:4 methanol:dichloromethane). The fractions containing pure product were combined and concentrated under vacuum to obtain N,N'-(2,2'-(1,4-phenylene)bis(1H-benzo[d]imidazole-6,2-diyl))bis(2-(dimethylamino)acetamide).

1H NMR (DMSO-d6, 400 MHz) δ: 12.98 (brs, 1H), 12.93 (brs, 1H), 9.82 (brs, 1H), 9.72 (brs, 1H), 8.32-8.28 (m, 4H), 8.18-8.06 (m, 2H), 7.60-7.32 (m, 4H), 3.11 (s, 4H), 2.31 (s, 12H). MS (ESI+APCl): m/z=511 [M+H]+.

Example 54

Synthesis of 1,1'-(2,2'-(1,4-phenylene)bis(1H-benzo[d]imidazole-6,2-diyl))bis(3-(2-(dimethylamino)ethyl)urea)

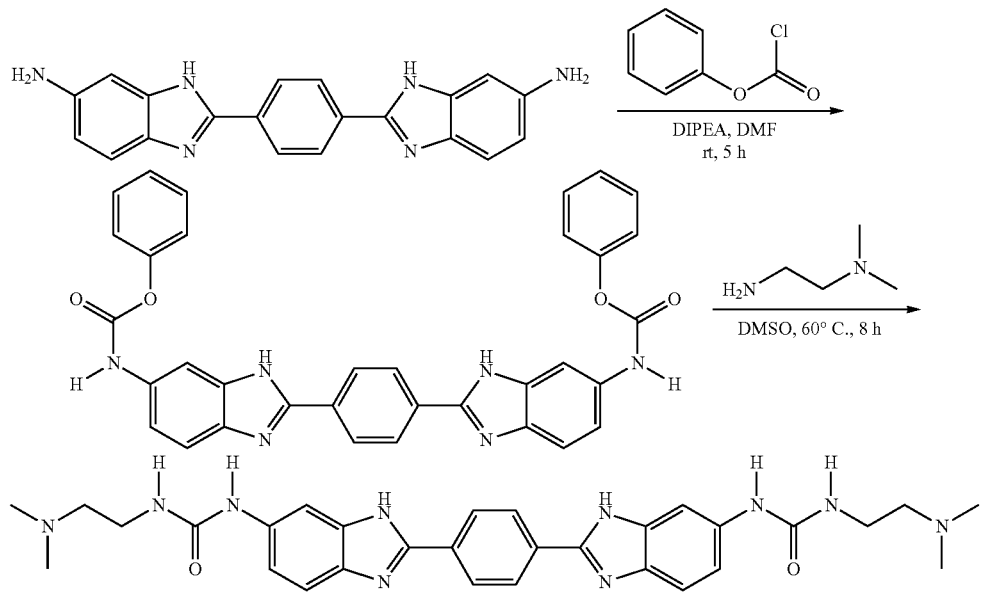

Step 1. Synthesis of diphenyl (2,2'-(1,4-phenylene)bis(1H-benzo[d]imidazole-6,2-diyl))dicarbamate To a solution of 2,2'-(1,4-phenylene)bis(1H-benzo[d]imidazol-6-amine) (200 mg, 0.58 mmol) in DMF (10 mL) at 0° C., was added DIPEA (0.28 mL, 1.76 mmol) and the reaction mixture was stirred for 10 minutes. Phenyl chloroformate (0.23 mL, 1.46 mmol) was added slowly to the above mixture at 0° C. and the reaction mixture was allowed to warm to room temperature and stirred for 5 hours. The reaction mixture was poured onto ice and the precipitated material was filtered under vacuum and dried to obtain the crude product. The crude product was triturated with EtOAc (20 mL), filtered under vacuum, washed with EtOAc (10 mL), and dried to obtain diphenyl (2,2'-(1,4-phenylene)bis(1H-benzo[d]imidazole-6,2-diyl))dicarbamate. MS (ESI): m/z=581 [M+H]+.

Step 2. Synthesis of 1,1'-(2,2'-(1,4-phenylene)bis(1H-benzo[d]imidazole-6,2-diyl))bis(3-(2-(dimethylamino)ethyl)urea To a solution of diphenyl (2,2'-(1,4-phenylene)bis(1H-benzo[d]imidazole-6,2-diyl))dicarbamate (150 mg, 0.25 mmol) in DMSO (5.0 mL) was added N,N'-dimethylethane-1,2-diamine (0.10 mL, 0.64 mmol) and the reaction mixture was stirred at 60° C. for 8 hours. The reaction mixture was poured onto ice and the precipitated material was filtered under vacuum, washed with water (2×10 mL), and dried to obtain the crude product, which was purified by silica gel chromatography [1:4 (10% ammonium hydroxide in methanol):dichloromethane]. The fractions containing the product were combined and concentrated under vacuum to yield the product. The obtained product was triturated with methanol (10 mL), filtered under vacuum, washed with methanol (5 mL), and dried under vacuum to yield 1,1'-(2,2'-(1,4-phenylene)bis(1H-benzo[d]imidazole-6,2-diyl))bis(3-(2-(dimethylamino)ethyl)urea. 1H NMR (DMSO-d6, 400 MHz) δ: 12.82-12.74 (m, 2H), 8.74-8.60 (m, 2H), 8.36-8.24 (m, 4H), 7.95-7.80 (m, 2H), 7.52-7.39 (m, 2H), 7.18-6.92 (m, 2H), 6.08-6.02 (m, 2H), 3.22-3.18 (m, 4H), 2.35 (t, J=6.0 Hz, 4H), 2.19 (s, 12H). MS (ESI): m/z=569 [M+H]+.

Example 55

Synthesis of N,N'-(2,2'-(1,4-phenylene)bis(1H-benzo[d]imidazole-6,2-diyl))bis(3-guanidinopropanamide)

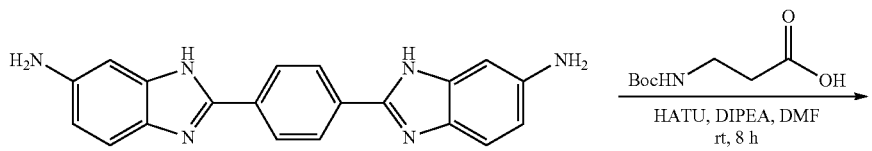

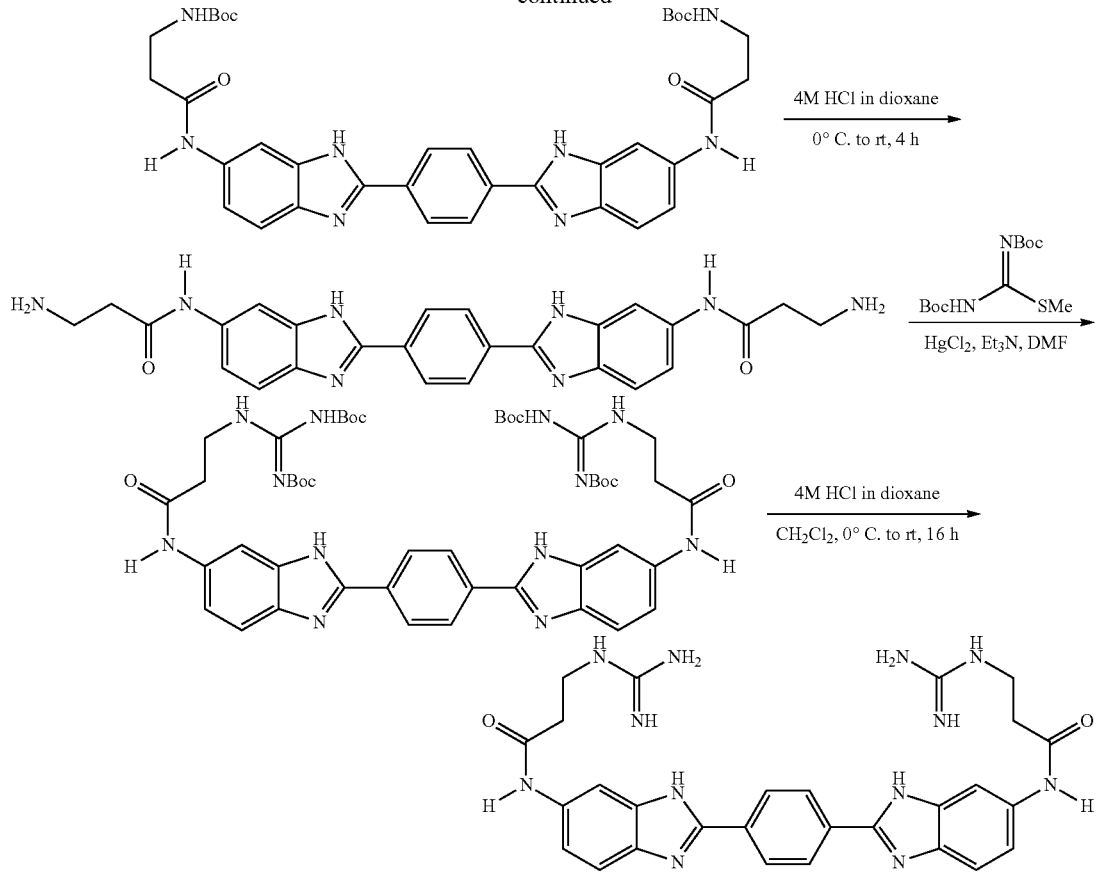

Step 1. Synthesis of di-tert-butyl (((2,2'-(1,4-phenylene)bis(1H-benzo[d]imidazole-6,2-diyl))bis(azanediyl))bis(3-oxopropane-3,1-diyl))dicarbamate To a suspension of 2,2'-(1,4-phenylene)bis(1H-benzo[d]imidazol-6-amine) (0.10 g, 0.29 mmol) in DMF (5.00 mL) at 0° C., was added HATU (0.24 g, 0.64 mmol), DIPEA (0.30 mL, 1.76 mmol) and the reaction mixture was stirred for 10 minutes. 3-((tert-butoxycarbonyl)amino)propanoic acid (0.12 g, 0.64 mmol) was added to the above mixture at 0° C. and the reaction mixture was allowed to warm to room temperature and stirred for 8 hours. The reaction mixture was poured into water and stirred for 15 minutes, whereupon the product precipitated. The product was collected by filtration under vacuum. The product was triturated with hot methanol (15 mL), and the product was filtered when hot under vacuum, washed with methanol (5.0 mL) and dried to obtain di-tert-butyl (((2,2'-(1,4-phenylene)bis(1H-benzo[d]imidazole-6,2-diyl))bis(azanediyl))bis(3-oxopropane-3,1-diyl))dicarbamate.

1H NMR (DMSO-d6, 400 MHz) δ: 13.09 (brs, 2H), 10.01 (s, 2H), 8.29 (s, 4H), 8.13 (s, 2H), 7.56 (d, J=8.0 Hz, 2H), 7.31-7.29 (m, 2H), 3.27-3.22 (m, 8H), 1.39 (s, 18H). MS (ESI+APCl): m/z=683 [M+H]+.

Step 2. Synthesis of N,N'-(2,2'-(1,4-phenylene)bis(1H-benzo[d]imidazole-6,2-diyl))bis(3-aminopropanamide)

To a solution of di-tert-butyl (((2,2'-(1,4-phenylene)bis(1H-benzo[d]imidazole-6,2-diyl))bis(azanediyl))bis(3-oxopropane-3,1-diyl))dicarbamate (0.12 g, 0.175 mmol) in dichloromethane (5.0 mL) at 0° C., was added 4M HCl in 1,4-dioxane (0.5 mL) and the reaction mixture was stirred at room temperature for 4 hours. The reaction mixture was concentrated under reduced pressure to obtain the crude product. The product was triturated with 1:9 methanol, dichloromethane (10 mL) and filtered under vacuum, washed with dichloromethane (5.00 mL), and dried to obtain N,N'-(2,2'-(1,4-phenylene)bis(1H-benzo[d]imidazole-6,2-diyl))bis(3-aminopropanamide) hydrochloride salt.

MS (ESI+APCl): m/z=483 [M+H]+.

Step 3. Synthesis of 2,2'-(1,4-phenylene)bis(N-(2-aminoethyl)-1H-benzo[d]imidazole-6-carboxamide)

To a solution of N,N'-(2,2'-(1,4-phenylene)bis(1H-benzo[d]imidazole-6,2-diyl))bis(3-aminopropanamide) hydrochloride salt (78 mg, 0.161 mmol) in DMF (10 mL) and Et3N (0.13 mL, 0.97 mmol) was added 1,3-bis(tert-butoxycarbonyl)-2-methyl-2-thiopseudourea (0.117 g, 0.40 mmol) followed with mercury (II) chloride (92 mg, 0.33 mmol), and the reaction mixture was stirred at room temperature for 8 hours. The reaction mixture was poured onto ice and the precipitated material was filtered under vacuum, washed with water (10.0 mL), and dried to obtain the crude product, which was purified by silica gel chromatography (1:4 methanol:dichloromethane). The fractions containing pure product were combined and concentrated under vacuum to afford the title compound.

1H NMR (DMSO-d6, 400 MHz) δ: 12.96-12.90 (m, 2H), 11.50 (s, 2H), 10.10-10.01 (m, 2H), 8.62-8.15 (m, 6H), 7.60-7.46 (m, 2H), 7.40-7.20 (m, 2H), 3.63-3.61 (m, 4H), 2.67-2.64 (m, 4H), 1.47-1.40 (m, 36H). MS (ESI+APCl): m/z=968 [M+2H]+.

Synthesis of N,N'-(2,2'-(1,4-phenylene)bis(1H-benzo[d]imidazole-6,2-diyl))bis(3-guanidinopropanamide)

To a solution of 2,2'-(1,4-phenylene)bis(N-(2-aminoethyl)-1H-benzo[d]imidazole-6-carboxamide) (75 mg, 0.07 mmol) in dichloromethane (5.0 mL) at 0° C., was added 4M HCl in 1,4-dioxane (0.5 mL) and the reaction mixture was stirred at room temperature for 4 hours. The reaction mixture was concentrated under reduced pressure to yield the crude product. The product was triturated with 1:9 methanol: dichloromethane (10 mL) and concentrated under vacuum to obtain the crude product. The product was purified by prep HPLC on an X-Bridge C-18 (30×150 mm, 10 µm) column; mobile phase, A=0.1% TFA in water and B=CH₃CN; Flow rate: 40 mL/min, Injection volume: 1000 µL, Runtime: 15 minutes, gradient: 90-70% A, 10-30% B (0.0-15 min); UV detection at 220 nm. Fractions containing only the pure product were combined for concentration to obtain N,N'-(2,2'-(1,4-phenylene)bis(1H-benzo[d]imidazole-6,2-diyl))bis(3-guanidinopropanamide) TFA salt.

1H NMR (CD3OD, 400 MHz) δ: 8.31 (d, J=1.6 Hz, 2H), 8.24 (s, 4H), 7.65-7.63 (m, 2H), 7.42 (dd, J=8.8, 1.6 Hz, 2H), 3.49 (t, J=6.0 Hz, 4H), 2.68 (t, J=6.0 Hz, 4H). MS (ESI+APCl): m/z=567 [M+H]+.

Example 56

Synthesis of 1N,N'-(2,2'-(1,4-phenylene)bis(1H-benzo[d]imidazole-6,2-diyl))bis(2,2-dimethylhydrazinecarboxamide) (Compound 66)

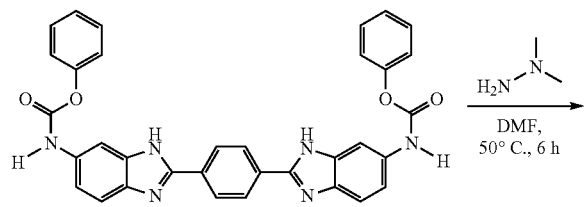

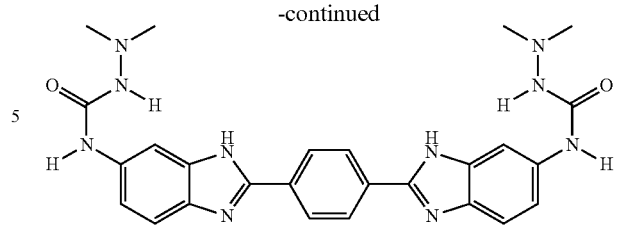

Step 1. Synthesis of 1N,N'-(2,2'-(1,4-phenylene)bis(1H-benzo[d]imidazole-6,2-diyl))bis(2,2-dimethylhydrazinecarboxamide)

To a solution of diphenyl (2,2'-(1,4-phenylene)bis(1H-benzo[d]imidazole-6,2-diyl))dicarbamate (0.10 g, 0.17 mmol) in DMF (5.0 mL) was added 1,1-dimethylhydrazine (0.02 mL, 0.34 mmol) and the reaction mixture was stirred at 50° C. for 6 hours. The reaction mixture was poured onto ice and the precipitated material was filtered under vacuum, washed with water (2×10 mL), and dried to obtain the crude product, which was purified by silica gel chromatography [1:4 (10% ammonium hydroxide in methanol):dichloromethane]. The fractions containing the product were combined and concentrated under vacuum to obtain 80 mg of the product which was still impure, which was re-purified by mass triggered HPLC purification first on a Gemini@10 µm NX (150×30 mm, 10 µm) column; mobile phase, A=0.1% TFA in water and B=CH₃CN; Flowrate: 30 mL/min, Injection volume: 6004, Runtime: 20 minutes, Detection: 220 nm then a second time on a Gemini@10 µm NX (150×30 mm, 10 µm) column; mobile phase, A=10 mM ammonium bicarbonate in water and B=CH₃CN; Flowrate: 30 mL/min, Injection volume: 3004, Runtime: 20 minutes, Detection: 220 nm to obtain N,N'-(2,2'-(1,4-phenylene)bis(1H-benzo[d]imidazole-6,2-diyl))bis(2,2-dimethylhydrazinecarboxamide). 1H NMR (DMSO-d6, 400 MHz) δ: 12.84-12.78 (m, 2H), 8.68-8.58 (m, 2H), 8.30-8.25 (m, 4H), 8.05-7.93 (m, 2H), 7.52-7.24 (m, 6H), 2.53 (s, 12H). UPLC MS: m/z=513 [M+H]+.

Example 57

Synthesis of 2,2'-(1,4-phenylene)bis(N',N'-dimethyl-1H-benzo[d]imidazole-6-carbohydrazide)

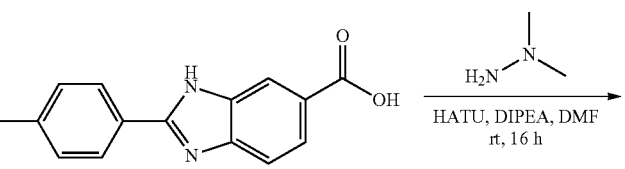

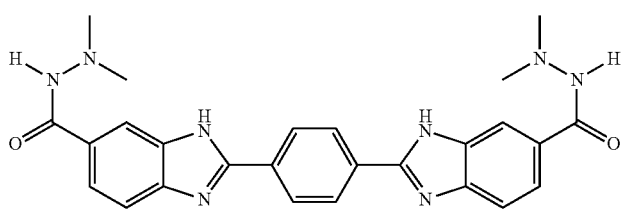

To a suspension of 2,2'-(1,4-phenylene)bis(1H-benzo[d]imidazole-6-carboxylic acid) (0.10 g, 0.25 mmol) in DMF (5.00 mL) at 0° C., was added HATU (0.21 g, 0.55 mmol), DIPEA (0.27 mL, 1.50 mmol) and the reaction mixture was stirred for 15 minutes. N,N'-dimethylhydrazine (30 mg, 0.55 mmol) was added to the above mixture at 0° C. and the reaction mixture was allowed to warm to room temperature and stirred for 16 hours. The reaction mixture was concentrated under vacuum and the crude product was diluted with ice-cold water (10 mL), and stirred for 15 minutes, whereupon the product precipitated. The product was collected by filtration under vacuum, washed with methanol (5.0 mL), and dried under vacuum. The product was purified by silica gel chromatography [1:4 (10% ammonium hydroxide in methanol):dichloromethane]. The fractions containing the pure product were combined and concentrated under vacuum to obtain 2,2'-(1,4-phenylene)bis(N',N'-dimethyl-1H-benzo[d]imidazole-6-carbohydrazide). 1H NMR (DMSO-d6, 400 MHz) δ: 13.28 (brs, 2H), 9.48 (s, 2H), 8.39 (s, 4H), 8.08 (s, 2H), 7.70-7.66 (d, 4H), 2.64 (s, 12H), MS (ESI+APCl): m/z=483 [M+H]+.

Example 58

Synthesis of 2,2'-(1,4-phenylene)bis(N-(2-(dimethylamino)ethyl)-N-methyl-1H-benzo[d]imidazole-6-carboxamide)

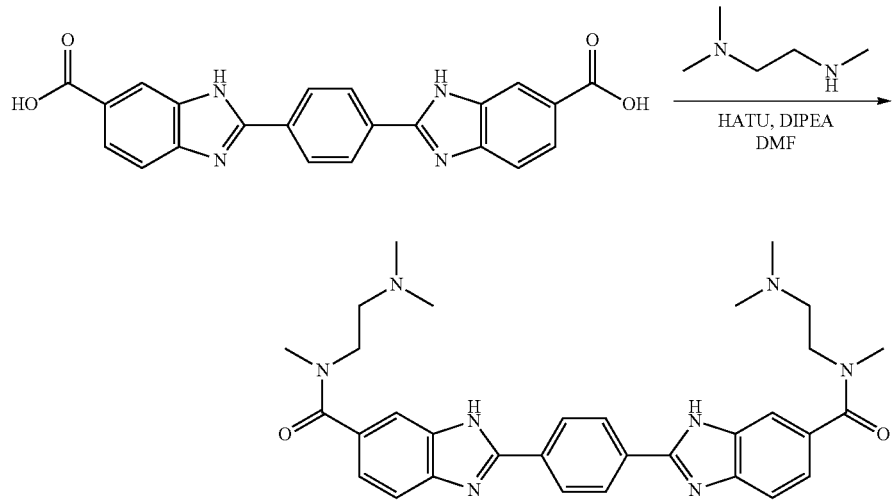

A solution of 2,2'-(1,4-phenylene)bis(1H-benzo[d]imidazole-6-carboxylic acid) (50 mg, 0.126 mmol) in DMF (3 ml) was treated with HATU (100 mg, 0.26 mmol) and DIPEA (130 μL, 0.75 mmol) in DMF (3 ml) for 5 min. N,N,N'-trimethylethylenediamine (28 mg, 0.27 mmol) was added and stirring continued overnight. The solvent was removed under vacuum and the residue washed with ether then purified on a a C-18 column and a gradient of 0-100% MeOH in water containing 0.1% TFA. 1H NMR (CD3OD, 400 MHz) δ: 8.42 (s, 4H), 7.94 (br s, 2H), 7.84 (d, J=8.5 Hz, 2H), 7.62 (d, J=8.5 Hz, 2H), 4.02-3.91 (m, 4H), 3.52 (d, J=5.8 Hz, 4H), 3.15 (s, 6H), 3.06 (br s, 12H), MS (ESI): m/z=567 [M+H]+.

Example 59

Synthesis of 2,2'-(1,4-phenylene)bis(1H-benzo[d]imidazole-6-carboxamide)

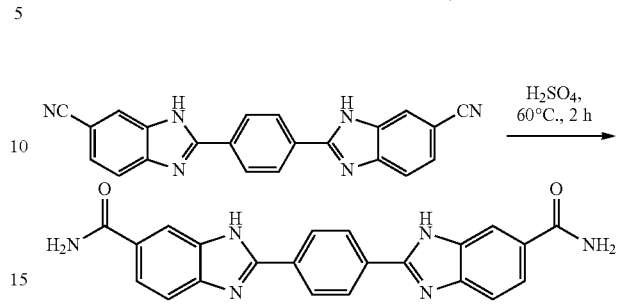

A mixture of 2,2'-(1,4-phenylene) bis(1H-benzo[d]imidazole-6-carbonitrile) (0.20 g, 0.55 mmol) and conc. $H_2SO_4$ (3.00 mL) was stirred at 60° C. for 2 hours. The reaction mixture was poured into ice and neutralized with aqueous saturated potassium carbonate solution, whereupon the product precipitated. The precipitated product was collected by filtration under vacuum and dried. The crude product was triturated with hot methanol, filtered under vacuum, washed with MTBE (25.0 mL) and dried to obtain 2,2'-(1,4-phenylene)bis(1H-benzo[d]imidazole-6-carboxamide). 1H NMR (DMSO-d6, 400 MHz): 13.27 (d, J=10 Hz, 2H), 8.39 (brs, 4H), 8.28 (s, 1H), 8.09 (s, 1H), 8.03 (d, J=19.2 Hz, 2H), 7.84 (d, J=9.2 Hz, 1H), 7.79 (d, J=8.4 Hz, 1H), 7.71 (d, J=8.4 Hz, 1H), 7.59 (d, J=8.4 Hz, 1H), 7.31 (d, J=17.2 Hz, 2H). MS (ESI+APCl) m/z 397 [M+H]+.

Example 60

Synthesis of 2,2'-(1,4-phenylene)bis(N-hydroxy-1H-benzo[d]imidazole-6-carboximidamide)

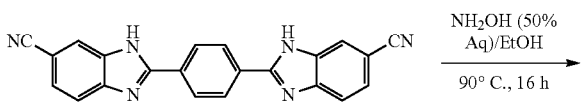

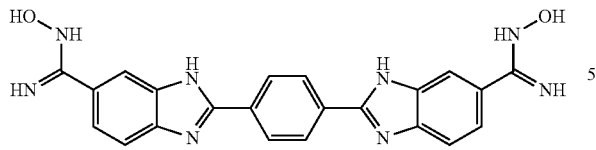

To a suspension of 2,2'-(1,4-phenylene)bis(1H-benzo[d]imidazole-6-carbonitrile) (0.15 g, 0.42 mmol) in ethanol (5.0 mL) was added hydroxylamine (50% in water, 0.33 mL, 5.0 mmol) in a sealed tube and stirred at 90° C. for 16 hours. The reaction mixture was cooled to room temperature and the product was collected by filtration under vacuum, washed with methanol (5 mL), and dried under vacuum. The product was triturated with hot methanol (10 mL) and dried under vacuum to obtain 2,2'-(1,4-phenylene)bis(N-hydroxy-1H-benzo[d]imidazole-6-carboximidamide). 1H NMR (DMSO-d6, 400 MHz) δ: 13.22 (brs, 2H), 9.65 (brs, 2H), 8.36 (brs, 4H), 8.01 (s, 1H), 7.83 (s, 1H), 7.62-7.60 (m, 4H), 5.98 (brs, 3H), MS (ESI+APCl): m/z=427 [M+H]+.

Example 61

Synthesis of 2,2'-(1,4-phenylene)bis(1H-benzo[d]imidazole-6-carboximidamide) acetate

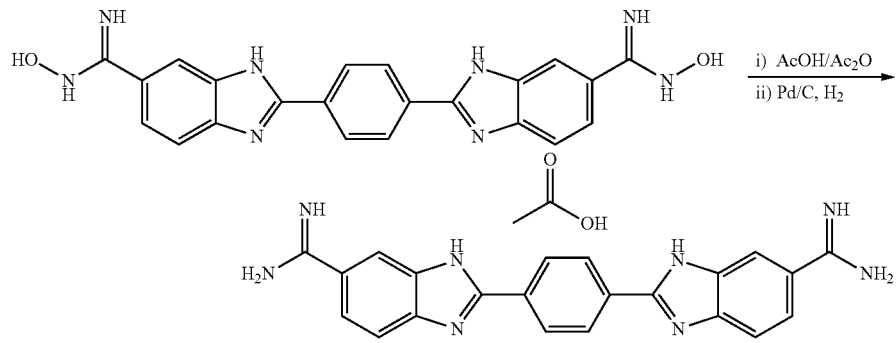

To a suspension of 2,2'-(1,4-phenylene)bis(N-hydroxy-1H-benzo[d]imidazole-6-carboximidamide) (50 mg, 0.12 mmol) in glacial acetic acid (2.00 mL) was slowly added acetic anhydride (0.1 mL) and stirred at room temperature for 16 hours. 10% Pd/C (10 mg) was added in one lot and the reaction mixture was hydrogenated (~1 atmospheric pressure; balloon pressure) at room temperature for 6 hours. The reaction mixture was filtered through a celite bed and washed with methanol (10.0 mL). The filtrate was concentrated under vacuum and the residue was triturated with methanol (10.0 mL), filtered under vacuum, washed with methanol (5.00 mL) and dried to obtain 2,2'-(1,4-phenylene)bis(1H-benzo[d]imidazole-6-carboximidamide) acetate. 1H NMR (DMSO-d6, 400 MHz) δ: 11.7-10.0 (m, 2H), 8.39 (brs, 4H), 8.12 (s, 2H), 7.74-7.72 (m, 2H), 7.65-7.58 (m, 2H), 1.77 (s, 6H), MS (ESI+APCl): m/z=395 [M+H]+.

Example 62

Synthesis of methyl 4-((2-((2-(2-(4-(6-((2-(dimethylamino)ethyl)carbamoyl)-1H-benzo[d]imidazol-2-yl)phenyl)-1H-benzo[d]imidazole-6-carboxamido)ethyl)(methyl)amino)ethyl)amino)-4-oxobutanoate

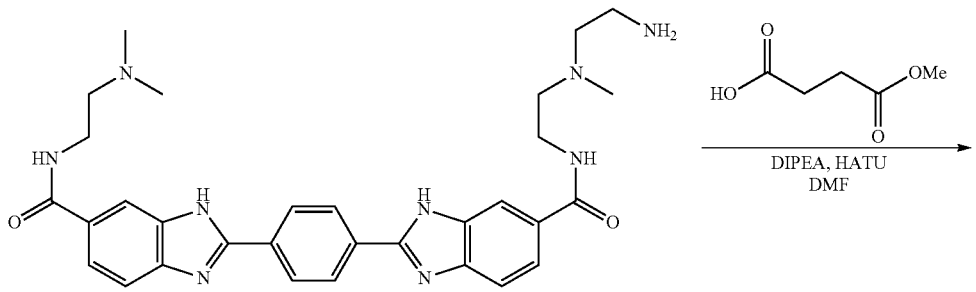

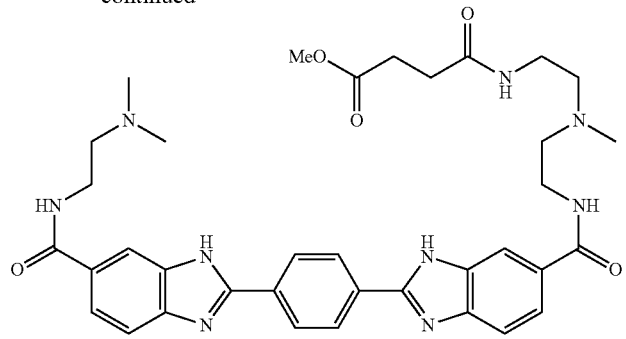

HATU (13 mg, 0.034 mmol), DIPEA (40 μL, 0.23 mmol) and mono-Methyl succinate (5.0 mg, 0.038 mmol) were mixed in DMF (500 μL) for 5 minutes before adding 3-(dimethylamino)-N-(2-(4-(6-(3-(hex-5-yn-1-yl(methyl)amino)propanamido)-1H-benzo[d]imidazol-2-yl)phenyl)-1H-benzo[d]imidazol-6-yl)propenamide (18 mg, 0.032 mmol) and stirring for 4 hours. The solvent was removed under vacuum and the resultant crude material washed with ether then purified using a C-18 column and a gradient of 0-100% MeOH in water containing 0.1% TFA. 1H NMR (CD3OD, 400 MHz) δ: 8.42 (s, 4H), 8.32 (br s, 2H), 7.99 (d, J=8.6 Hz, 2H), 7.83 (d, J=8.5 Hz, 2H), 3.83 (t, J=5.8 Hz, 4H), 3.70-3.57 (m, 4H), 3.56 (s, 3H), 3.44 (t, J=5.9 Hz, 4H), 3.10 (s, 3H), 3.02 (s, 6H), 2.51-2.41 (m, 4H), MS (ESI): m/z=682 [M+H]+.

Example 63

Synthesis of N-[2-(dimethylamino)ethyl]-2-[4-(6-[N-{2-[(hex-5-yn-1-yl)(methyl)amino]ethyl}carbamoyl]-1H-benzo[d]imidazol-2-yl)phenyl]-1H-benzimidazole-6-carboxamide To a solution of N-(2-(dimethylamino)ethyl)-2-(4-(6-((2-(methylamino)ethyl)carbamoyl)-1H-benzo[d]imidazol-2-yl)phenyl)-1H-benzo[d]imidazole-6-carboxamide (30 mg, 0.057 mmol) in MeOH (1 ml) was added 5-hexynal (8 mg, 0.083 mmol) and sodium cyanoborohydride (6 mg, 0.09 mmol) and the mixture stirred overnight. The solvent was removed under vacuum and the crude product purified using a C-18 column and gradient of 0-100% MeOH in water containing 0.1% TFA to afford the title compound. 1H NMR (CD3OD, 400 MHz) δ: 8.40 (s, 4H), 8.30 (br s, 2H), 7.98-7.93 (m, 2H), 7.80 (d, J=8.6 Hz, 2H), 3.87-3.78 (m, 2H), 3.58-3.35 (m, 6H), 3.04-2.98 (m, 9H), 2.33 (m, 3H), 1.97-1.87 (m, 2H), 1.69-1.58 (m, 2H), MS (ESI): m/z=605 [M+H]+.

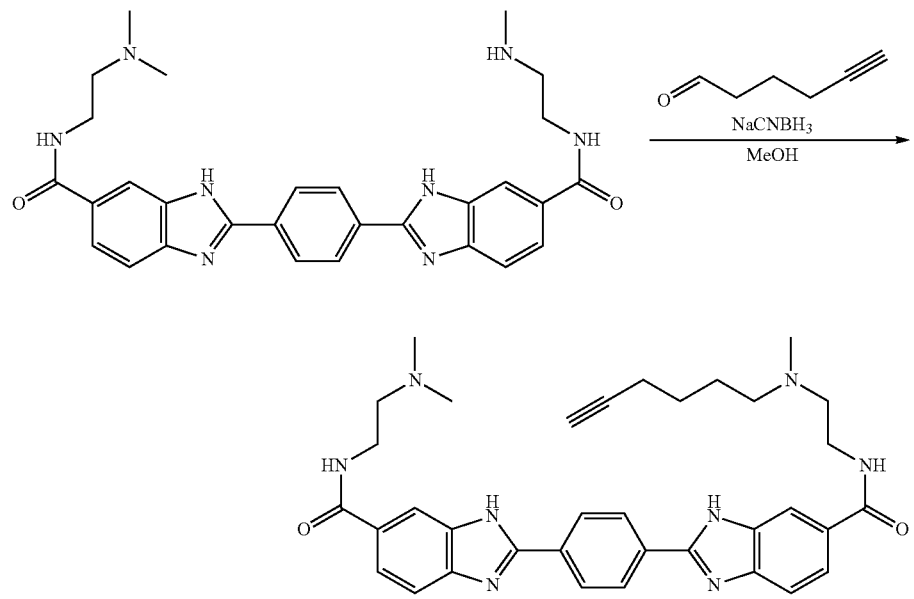

Example 64

Synthesis of N-(2-((4-(1-(3-aminopropyl)-1H-1,2,3-triazol-4-yl)butyl)(methyl)amino)ethyl)-2-(4-(6-((2-(dimethylamino)ethyl)carbamoyl)-1H-benzo[d]imidazol-2-yl)phenyl)-1H-benzo[d]imidazole-6-carboxamide

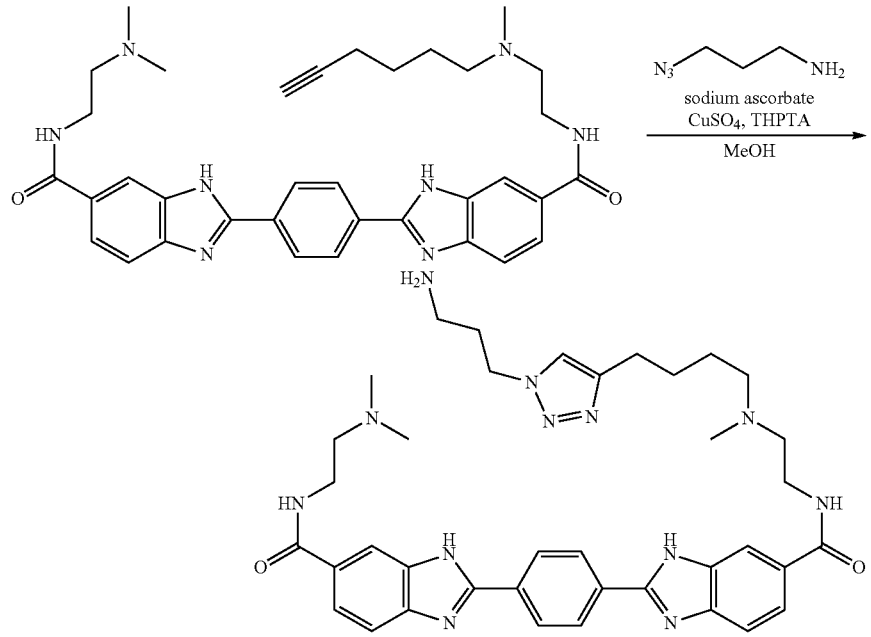

To a solution of N-[2-(dimethylamino)ethyl]-2-[4-(6-[N-{2-[(hex-5-yn-1-yl)(methyl)amino]ethyl}carbamoyl]-1H-benzo[d]imidazol-2-yl)phenyl]-1H-benzimidazole-6-carboxamide (80 mg, 0.13 mmol) in MeOH (1 ml) was added 3-azidopropylamine (20 mg, 0.2 mmol), and 35μL each of the solutions of 0.1 M copper sulfate, 0.1 M THPTA and 0.1 M sodium ascorbate. The reaction was stirred for 1 hour upon which a blue color was observed. A solution of the sodium ascorbate (20 μL) was added and the mixture stirred for another 4 hours. The solvent was removed under vacuum and the crude material purified using a C-18 column and a gradient of 0-100% MeOH in water containing 0.1% TFA to afford the title compound. 1H NMR (CD3OD, 400 MHz) δ: 8.40 (s, 4H), 8.32-8.28 (m, 2H), 7.98-7.92 (m, 2H), 7.83-7.78 (m, 3H), 4.50 (t, J=6.8 Hz, 2H), 3.86-3.80 (m, 4H), 3.57-3.36 (m, 6H), 3.02 (s, 6H), 3.0 (s, 3H), 2.99-2.94 (m, 2H), 2.79 (t, J=7.4 Hz, 2H), 2.29-2.19 (m, 2H), 1.91-1.73 (m, 4H), MS (ESI): m/z=705 [M+H]+.

Example 65

Synthesis of 2-(4-(6-amino-1H-benzo[d]imidazol-2-yl)phenyl)-N-(4,4',5,5'-tetrahydro-1H-[1,2'-biimidazol]-2-yl)-1H-benzo[d]imidazol-6-amine (Compound 75)

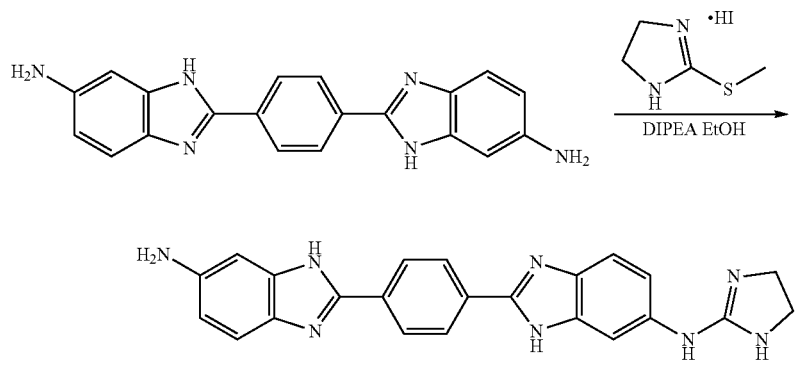

Compound 24

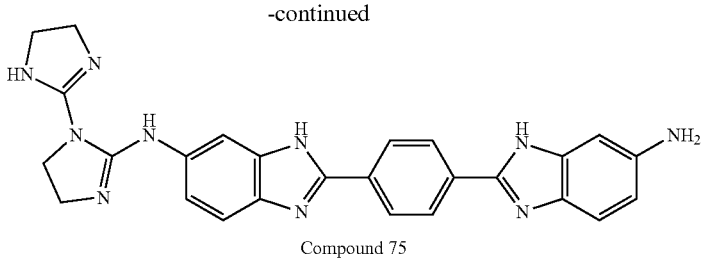

Compound 75

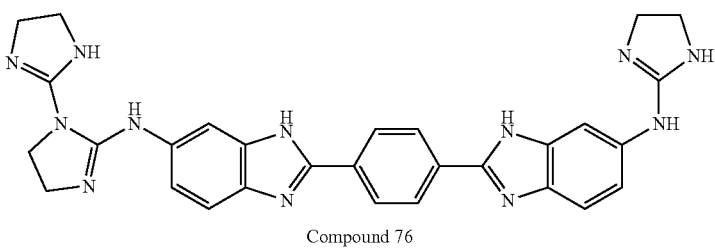

Compound 76

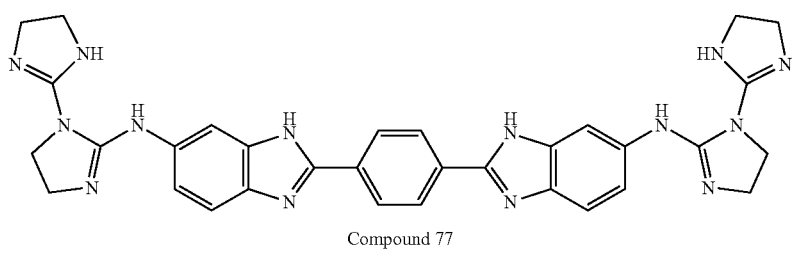

Compound 77

To a suspension of 2,2'-(1,4-phenylene)bis(1H-benzo[d]imidazol-6-amine) (100 mg, 0.29 mmol) in EtOH (3 ml) was added 2-Methylthio-2-imidazoline hydriodide (170 mg, 0.7 mmol) and DIPEA (300 μL, 1.7 mmol) and the mixture heated at 80° C. overnight. LCMS analysis showed the formation of multiple products. The solvent was removed under vacuum and the crude material purified using a C-18 column and a gradient of 0-100% MeOH in water containing 0.1% TFA. The fractions with the desired products were concentrated and further purification done by reverse phase HPLC using a gradient of 0-60% MeOH in water containing 0.1% TFA over 60 minutes to give multiple compounds Compound 24; 1H NMR (CD3OD, 400 MHz) δ: 8.42-8.35 (m, 4H), 7.84 (dd, J=0.5, 4.3 Hz, 1H), 7.77-7.71 (m, 2H), 7.49 (d, J=1.6 Hz, 1H), 7.41 (dd, J=2.0, 8.7 Hz, 1H), 7.27 (dd, J=2.0, 8.7 Hz, 1H), 3.82 (s, 4H), MS (ESI): m/z=409 [M+H]+. Compound 75; 1H NMR (CD3OD, 400 MHz) δ: 8.45-8.33 (m, 4H), 7.76 (d, J=8.6 Hz, 1H), 7.74 (d, J=8.6 Hz, 1H), 7.51 (d, J=1.8 Hz, 1H), 7.40 (d, J=1.8 Hz, 1H), 7.30-7.24 (m, 2H), 4.08-4.02 (m, 2H), 3.90 (s, 4H), 3.69-3.62 (m, 2H), MS (ESI): m/z=477 [M+H]+. Compound 76; 1H NMR (CD3OD, 400 MHz) δ: 8.44 (d, J=8.8 Hz, 2H), 8.34 (d, J=8.8 Hz, 2H), 7.79-7.75 (m, 2H), 7.66-7.64 (m, 1H), 7.40-7.38 (m, 1H), 7.31 (dd, J=2.0, 8.6 Hz, 1H), 7.27 (dd, J=2.0, 8.6 Hz, 1H), 4.08-4.02 (m, 2H), 3.90 (s, 4H), 3.80 (s, 4H), 3.68-3.62 (m, 2H), MS (ESI): m/z=545. Compound 77; 1H NMR (CD3OD, 400 MHz) δ: 8.40 (s, 4H), 7.75 (d, J=8.6 Hz, 2H), 7.37 (d, J=1.5 Hz, 2H), 7.23 (dd, J=1.9, 8.6 Hz, 2H), 4.08-4.0 (m, 4H), 3.90 (s, 8H), 3.69-3.60 (m, 4H), MS (ESI): m/z=613 [M+H]+.

Example 66

Synthesis of 2,2'-(2-bromo-1,4-phenylene)bis(N-(2-(dimethylamino)ethyl)-1H-benzo[d]imidazole-6-carboxamide)

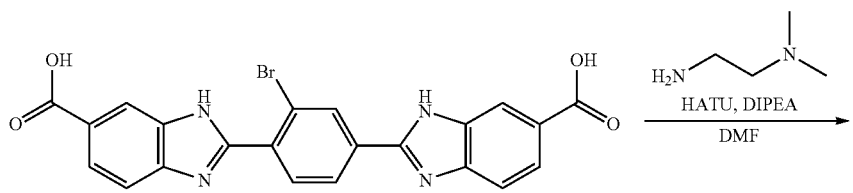

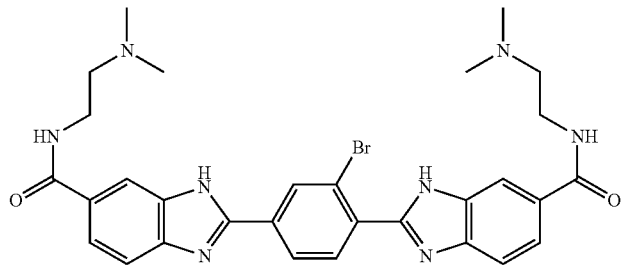

2,2'-(2-bromo-1,4-phenylene)bis(1H-benzo[d]imidazole-6-carboxylic acid) (200 mg, 0.42 mmol), HATU (340 mg, 0.89 mmol) and DIPEA (440 μL, 2.52 mmol) were mixed in DMF (6 ml) for 5 minutes before adding 2-(Dimethylamino)-ethylamine (100 μL, 0.92 mmol) and stirring overnight. The solvent was removed under vacuum and the residue washed with ether. The product was then purified using a C18-column and a gradient of 0-100% MeOH in water containing 0.1% TFA. 1H NMR (CD3OD, 400 MHz) δ: 8.65 (d, J=1.7 Hz, 1H), 8.34-8.27 (m, 3H), 8.02 (d, J=8.1 Hz, 1H), 7.97 (dd, J=1.6, 8.6 Hz, 1H), 7.92 (dd, J=1.6, 8.5 Hz, 1H), 7.8 (d, J=8.6 Hz, 1H), 7.77 (d, J=8.5 Hz, 1H), 3.85 (m, 4H), 3.46-3.40 (m, 4H), 3.0 (s, 12H), MS (ESI): m/z=617 [M+H]+.

Example 67

Synthesis of 4,4'-bis(6-nitro-1H-benzo[d]imidazol-2-yl)-1,1'-biphenyl

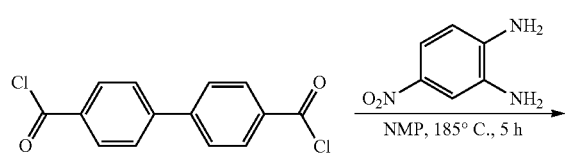

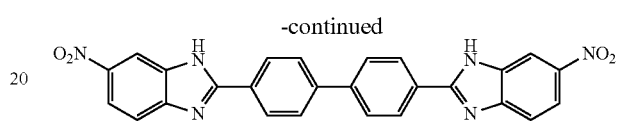

To a solution of [1,1'-biphenyl]-4,4'-dicarbonyl dichloride (0.25 g, 0.89 mmol) in anhydrous NMP (5.0 mL), under N2 atmosphere, was added 4-nitro-1,2-phenylene diamine (0.28 g, 1.80 mmol) at room temperature, 12 hours, and the reaction mixture was heated at 185° C. for 5 hours. The reaction mixture was cooled to 60° C., and the contents were slowly poured into ice-cold water and stirred for 10 minutes, whereupon, a material precipitated. The material was collected by filtration under vacuum and washed with water (2×50 mL). The obtained material was suspended in ethanol and the mixture was refluxed for 15 min. The material was filtered while the contents were still hot under vacuum, washed with ethanol (25 mL), and dried under vacuum to obtain 4,4'-bis(6-nitro-1H-benzo[d]imidazol-2-yl)-1,1'-biphenyl. 1H NMR (DMSO-d6, 400 MHz) δ: 8.49 (d, J=2.4 Hz, 2H), 8.36 (d, J=8.8 Hz, 4H), 8.15 (dd, J=8.8 Hz, 2.4 Hz, 2H), 8.06 (d, J=8.85 Hz, 4H), 7.80 (d, J=9.2 Hz, 2H). MS (ESI): m/z=475 [M−H]+.

Example 68

2,2'-([1,1'-biphenyl]-4,4'-diyl)bis(1H-benzo[d]imidazol-6-amine)

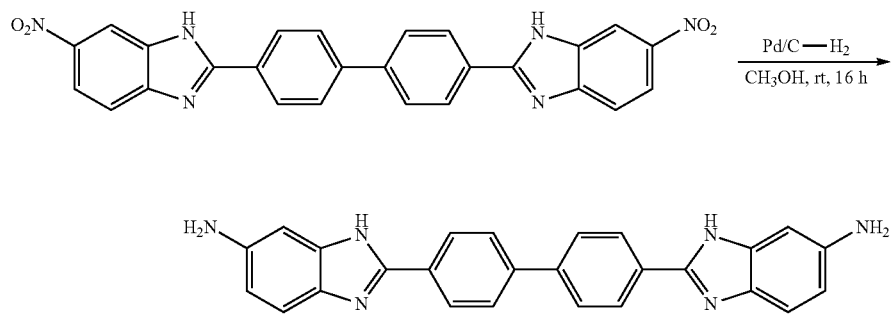

A mixture of 4,4'-bis(6-nitro-1H-benzo[d]imidazol-2-yl)-1,1'-biphenyl (200 mg, 0.42 mmol), 10% Pd/C (20 mg), in methanol (20.0 mL), was hydrogenated, using a H2 balloon, at room temperature for 16 hours. The reaction mixture was filtered through celite, washed with methanol (2×35 mL) and concentrated under reduced pressure. The product was purified by silica gel column chromatography to obtain 2,2'-([1,1'-biphenyl]-4,4'-diyl)bis(1H-benzo[d]imidazol-6-amine). 1H NMR (DMSO-d6, 400 MHz) δ: 12.32 (s, 1H), 8.17 (d, J=8.4 Hz, 4H), 7.92 (d, J=8.4 Hz, 4H), 7.30 (d, J=7.6 Hz, 2H), 6.69 (s, 2H), 6.55 (d, J=8.4 Hz, 2H), 4.98 (s, 4H), MS (ESI): m/z=417 [M+H]+.

Example 69

Synthesis of 1,1'-([5,5'-bibenzo[d]oxazole]-2,2'-diylbis(4,1-phenylene))diguanidine Step 1. Synthesis of Boc-protected intermediate:

Triethyl amine (0.26 mL, 1.87 mmol) was added to a solution of 2,2'-([1,1'-biphenyl]-4,4'-diyl)bis(1H-benzo[d]imidazol-6-amine) (0.13 g, 0.31 mmol) in DMF (5.0 mL) and then added 1,3-bis(tert-butoxycarbonyl)-2-methyl-2-thiopseudourea (0.22 g, 0.78 mmol), mercury (II) chloride (0.17 g, 0.62 mmol) at 0° C. The reaction mixture was stirred at room temperature for 16 hours, and was poured onto ice, whereupon the product precipitated. The precipitated product was collected by filtration under vacuum and dried to obtain the crude product. The product was purified by column chromatography using neutral alumina in methanol:dichloromethane (1:9). The fractions containing the product were combined and concentrated under vacuum to obtain the intermediate. 1H NMR (DMSO-d6, 400 MHz) δ: 13.06 (d, J=7.6 Hz, 2H), 11.51 (d, J=18 Hz, 2H), 10.10 (d, J=30 Hz, 2H), 8.29 (t, J=8.4 Hz, 4H), 8.01 (t, J=18.4 Hz, 6H), 7.63 (d, J=8.4 Hz, 1H), 7.51 (d, J=8.4 Hz, 1H), 7.23 (d, J=8.4 Hz, 1H), 7.14 (d, J=8.4 Hz, 1H), 1.53 (s, 18H), 1.42 (d, J=8.0 Hz, 18H).

Step 2. Synthesis of 1,1'-(2,2'-([1,1'-biphenyl]-4,4'-diyl)bis(1H-benzo[d]imidazole-6,2-diyl))diguanidine HCl (4.0 M in dioxane, 5.0 mL) was added to a solution of compound A (80 mg, 0.08 mmol) in dichloromethane (5.0 mL) at 0° C. and the reaction mixture was stirred at room temperature for 16 hours. The obtained compound was purified by prep-HPLC to give 1,1'-(2,2'-([1,1'-biphenyl]-4,4'-diyl)bis(1H-benzo[d]imidazole-6,2-diyl))diguanidine as TFA salt. 1H NMR (CD3OD, 400 MHz) δ: 8.19 (d, J=8.4 Hz, 4H), 7.97 (d, J=8.4 Hz, 4H), 7.74 (s, 1H), 7.71 (d, J=0.4 Hz, 1H), 7.50 (d, J=1.6 Hz, 2H), 7.28 (dd, J=2.0, J=8.4, Hz, 2H); MS (ESI): m/z=499 [M–H]–.

Example 70

Synthesis of 1,4-bis(1-methyl-1H-benzo[d]imidazol-2-yl)benzene

N-1-methylbenzene-1,2-diamine (0.25 g, 2.04 mmol) was dissolved in anhydrous NMP (5.0 mL) and terephthaloyl chloride (0.20 g, 1.02 mmol) was added. The reaction was placed under argon and the reaction was stirred at room temperature for 12 hours, then it was heated to 185° C. for 5 hours. Reaction progress was monitored by TLC and after the completion of SM, the reaction was cooled to 60° C. and poured into ice cold water and stirred for 10 min. The resulting material was filtered and washed with water (50 mL). Then the resulting material was purified by silica-gel column chromatography (5% methanol in dichloromethane) to obtain of 1,4-bis(1-methyl-1H-benzo[d]imidazol-2-yl)benzene. 1H NMR (400 MHz, DMSO-d6): 8.18 (s, 4H), 7.84 (dd, J=7.6 Hz, 10 Hz, 4H), 7.52-7.43 (m, 4H), 4.04 (s, 6H), MS (ESI): m/z=339 [M−H]−.

Example 71

Synthesis of 2,2'-(1,4-phenylene)bis(1-methyl-1H-benzo[d]imidazol-5-amine) (Compound 83), 2-[4-(6-amino-1-methyl-1H-benzimidazol-2-yl)phenyl]-1-methyl-1H-benzimidazol-5-amine (Compound 84), and 2,2'-(1,4-phenylene)bis(1-methyl-1H-benzimidazol-6-amine) (Compound 85)

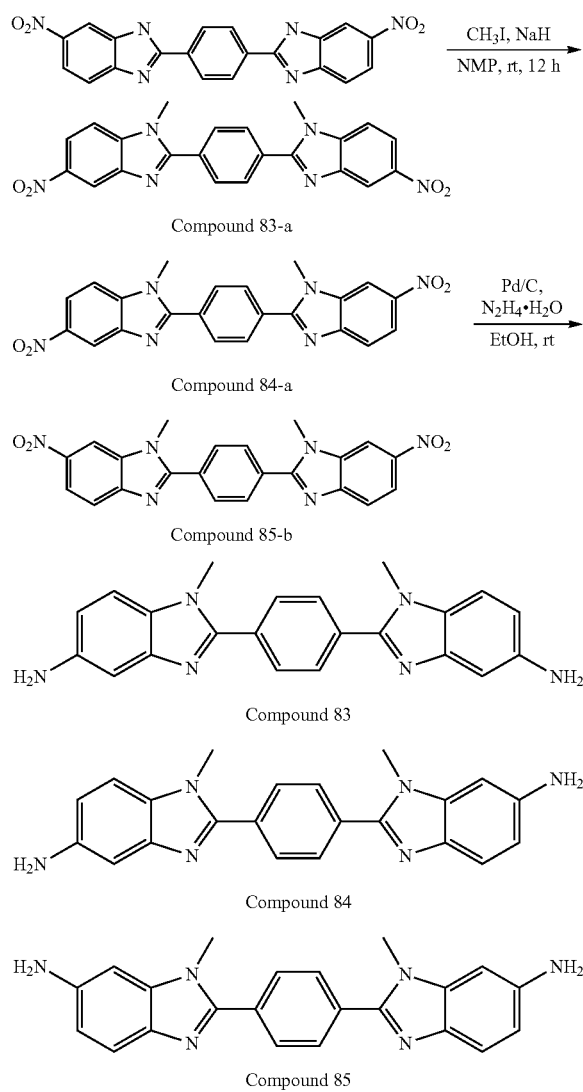

Compound 83-a

Compound 84-a

Compound 85-b

Compound 83

Compound 84

Compound 85

Step 1. Synthesis of 2,2'-(1,4-phenylene)bis(1-methyl-5-nitro-1H-benzimidazole) (Compound 83-a), 1-methyl-2-[4-(1-methyl-6-nitro-1H-benzimidazol-2-yl)phenyl]-5-nitro-1H-benzimidazole (Compound 84-a) and 2,2'-(1,4-phenylene)bis(1-methyl-6-nitro-1H-benzimidazole) (Compound 85-a)

To a solution of 1,4-bis(6-nitro-1H-benzo[d]imidazol-2-yl)benzene (2.00 g, 5.0 mmol) in anhydrous NMP (20 mL), at 0° C. was added NaH (60% dispersion in oil, 0.50 g, 12.5 mmol) in a portion wise manner over 10 min. Methyl iodide (2.01 g, d=2.28 g/mmol, 0.88 mL, 15.0 mmol) was added dropwise over a period of 5 minutes and the reaction mixture was allowed to stir at room temperature for 16 hours. The reaction mixture was slowly poured into ice-cold water (20 mL) and the precipitated material was collected by filtration under vacuum and dried. The crude product was crystallized from hot ethanol, filtered and dried under vacuum to give intermediates A', B', and C'. 1H NMR (400 MHz, DMSO-d6): 8.75 (d, J=2.0 Hz, 1H), 8.63 (d, J=2.0 Hz, 1H), 8.27 (dd, J=8.8 Hz, 2.0 Hz, 1H), 8.28-8.14 (m, 5H), 7.93 (d, J=8.4 Hz, 2H), 4.11 (s, 3H), 4.06 (s, 3H). MS (ESI): m/z=429 [M+H]+.

Step 2. Synthesis of 2,2'-(1,4-phenylene)bis(1-methyl-1H-benzo[d]imidazol-5-amine) (Compound 83), 2-[4-(6-amino-1-methyl-1H-benzimidazol-2-yl)phenyl]-1-methyl-1H-benzimidazol-5-amine (Compound 84), and 2,2'-(1,4-phenylene)bis(1-methyl-1H-benzimidazol-6-amine) (Compound 85)

To a solution of the product mixture of Step 1 (0.50 g, 1.168 mmol) in EtOH (20 mL) under argon atmosphere, was added hydrazine monohydrate (80% aqueous solution, 1.0 mL), 10% Pd/C (50 mg) at room temperature and the reaction mixture was stirred for 16 hours. The reaction mixture was filtered through a pad of celite under vacuum and the pad was washed with methanol:dichloromethane (1:9; 30 mL). The filtrate was concentrated under vacuum to obtain the product as a mixture of three isomers. The isomers were separated by silica-gel chromatography [7% CMA (chloroform:methanol:dichloromethane, 8.0:1.8:0.2) in dichloromethane; isocratic elution] to afford the title compounds:

Compound 83: 1H NMR (400 MHz, DMSO-d6): 7.98 (s, 4H), 7.31 (s, 1H), 7.29 (s, 1H), 6.83 (d, J=1.6 Hz, 2H), 6.68 (d, J=2 Hz, 1H), 6.66 (d, J=2 Hz, 1H), 4.86 (brs, 4H), 3.86 (s, 6H). MS (ESI): m/z=369 [M+H]+.

Compound 84: 1H NMR (400 MHz, DMSO-d6): 7.96 (s, 4H), 7.37 (d, J=8.8 Hz, 1H), 7.29 (d, J=8.8 Hz, 1H), 6.83 (d, J=2 Hz, 1H), 6.69-6.60 (m, 3H), 4.99 (s, 4H), 3.86 (s, 3H), 3.80 (s, 3H). MS (ESI): m/z=369 [M+H]+.

Compound 85: 1H NMR (400 MHz, DMSO-d6): 7.94 (s, 4H), 7.36 (d, J=8.4 Hz, 2H), 6.63-6.59 (m, 4H), 5.11 (brs, 4H), 3.80 (s, 6H). MS (ESI): m/z=369 [M+H]+.

Example 72

Synthesis of 1,1'-(2,2'-(1,4-phenylene)bis(1-methyl-1H-benzo[d]imidazole-5,2-diyl))diguandidine

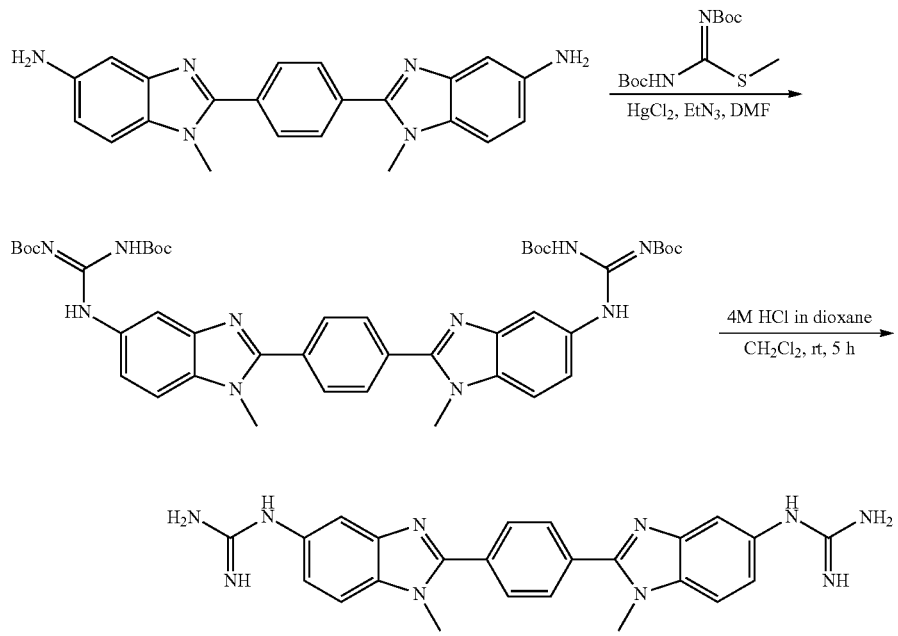

Step 1. Synthesis of Boc-Protected Intermediate

To a solution of 2,2'-(1,4-phenylene)bis(1-methyl-1H-benzo[d]imidazol-5-amine) (50 mg, 0.135 mmol) in DMF (5.0 mL) and Et3N (1.1 mL) and added 1,3-bis(tert-butoxycarbonyl)-2-methyl-2-thiopseudourea (98.5 mg, 0.339 mmol) followed with mercury (II) chloride (73.6 mg, 0.271 mmol), and the reaction mixture was stirred at room temperature for 24 hours. The reaction mixture was concentrated under vacuum to obtain the crude product. The product was triturated with 10% methanol in dichloromethane (25 mL), filtered under vacuum and dried to give the intermediate. 1H NMR (DMSO-d6, 400 MHz) δ: 11.52 (s, 2H), 10.10 (brs, 2H), 8.08 (brs, 6H), 7.64 (d, J=8.4 Hz, 2H), 7.32 (d, J=8 Hz, 2H), 3.98 (s, 6H), 1.54 (s, 18H), 1.41 (s, 18H). MS (ESI+APCl): m/z=853 [M+H]+.

Step 2. Synthesis of 1,1'-(2,2'-(1,4-phenylene)bis(1-methyl-1H-benzo[d]imidazole-5,2-diyl))diguanidine To a solution of the product of Step 1 (30 mg, 0.035 mmol) in dichloromethane (5.0 mL) at 0° C. was added 4M HCl in 1,4-dioxane (2.0 mL) and the reaction mixture was stirred at room temperature for 5 hours. The reaction mixture was concentrated under reduced pressure to obtain the crude product. The product was diluted with pentane (10 mL), and stirred at room temperature for 5 min. The product was collected by filtration under vacuum, washed with pentane (10 mL), and dried to obtain 1,1'-(2,2'-(1,4-phenylene)bis (1-methyl-1H-benzo[d]imidazole-5,2-diyl)). 1H NMR (CD3OD, 400 MHz) δ: 8.12 (brs, 4H), 7.83 (d, J=8.8 Hz, 2H), 7.68 (s, 2H), 7.39 (d, J=8.8 Hz, 2H), 4.04 (s, 6H), MS (ESI+APCl): m/z=453 [M+H]+.

Example 73

Synthesis of 2-[4-(6-guanidino-1-methyl-1H-benzimidazol-2-yl)phenyl]-1-methyl-1H-5-guanidino-benzimidazole

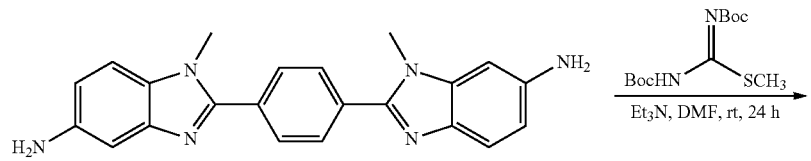

-continued

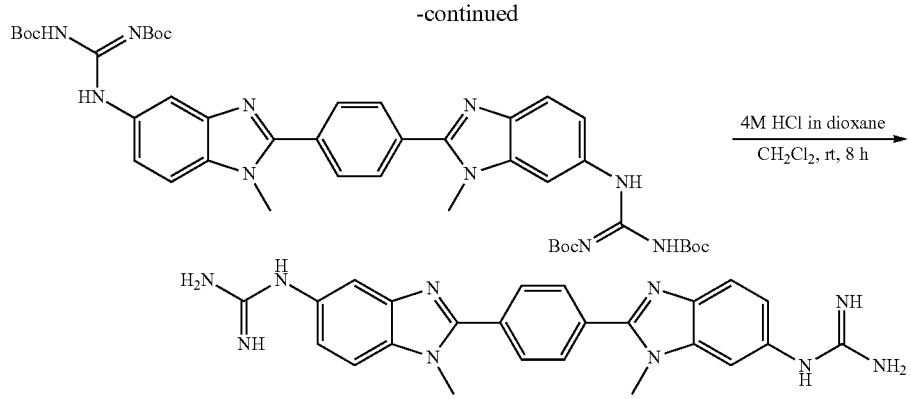

Step 1. Synthesis of Boc-Protected Intermediate

To a solution of 2-(4-(6-amino-1-methyl-1H-benzo[d]imidazol-2-yl)phenyl)-1-methyl-1H-benzo[d]imidazol-5-amine (50 mg, 0.135 mmol) in DMF (5.0 mL) and Et3N (1.1 mL) and added 1,3-bis(tert-butoxycarbonyl)-2-methyl-2-thiopseudourea (98.5 mg, 0.339 mmol) followed with mercury (II) chloride (73.6 mg, 0.271 mmol), and the reaction mixture was stirred at room temperature for 24 hours. The reaction mixture was poured upon ice, whereupon the product precipitated. The crude product was purified by column chromatography (20% EtOAc in hexane), the desired fractions were concentrated under reduced pressure to give the intermediate.

1H NMR (DMSO-d6, 400 MHz) δ: 11.53 (d, J=4.4 Hz, 2H), 10.16 (s, 1H), 10.10 (s, 1H), 8.08 (brs, 5H), 7.87 (s, 1H), 7.69 (d, J=2.2 Hz, 1H), 7.64 (d, J=8.8 Hz, 1H), 7.43 (d, J=8.8 Hz, 1H), 7.32 (d, J=8.4 Hz, 1H), 3.97 (s, 3H), 3.94 (s, 3H), 1.54 (s, 18H), 1.41 (s, 18H). MS (ESI+APCl): m/z=853 [M+H]+.

Step 2. Synthesis of 2-[4-(6-guanidino-1-methyl-1H-benzimidazol-2-yl)phenyl]-1-methyl-1H-5-guanidino-benzimidazole To a solution of the product of Step 1 (50 mg, 0.058 mmol) in dichloromethane (5.0 mL) at 0° C. was added 4M HCl in 1,4-dioxane (1.0 mL) and the reaction mixture was stirred at room temperature for 8 hours. The reaction mixture was concentrated under reduced pressure, washed with pentane and dried to obtain the title compound.

1H NMR (DMSO-d6, 400 MHz) δ: 10.16 (s, 1H), 10.04 (s, 1H), 8.20 (brs, 4H), 7.91 (d, J=8.8 Hz, 1H), 7.85 (d, J=8.8 Hz, 1H), 7.78 (s, 1H), 7.69 (d, J=1.6 Hz, 1H), 7.53-7.48 (m, 8H), 7.34 (d, J=2 Hz, 1H), 7.24 (d, J=8 Hz, 1H), 4.06 (s, 3H), 4.05 (s, 3H). MS (ESI+APCl): m/z=453 [M+H]+.

Example 74

Synthesis of 1,1'-(2,2'-(1,4-phenylene)bis(1-methyl-1H-benzo[d]imidazole-6,2-diyl))diguanidine

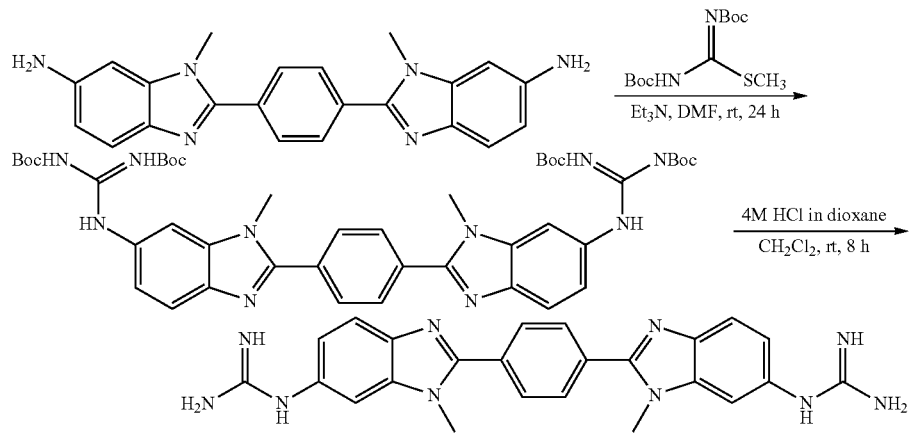

Step 1. Synthesis of Boc-Protected Intermediate

To a solution of 2,2'-(1,4-phenylene)bis(1-methyl-1H-benzo[d]imidazol-6-amine) (50 mg, 0.135 mmol) in DMF (5.0 mL) and Et3N (1.1 mL) and added 1,3-bis(tert-butoxycarbonyl)-2-methyl-2-thiopseudourea (98.5 mg, 0.339 mmol) followed with mercury (II) chloride (73.6 mg, 0.271 mmol), and the reaction mixture was stirred at room temperature for 24 hours. The reaction mixture was poured onto ice, whereupon the product precipitated. The precipitated material was triturated with 2:8 methanol:dichloromethane (30 mL), filtered under vacuum and dried to give the intermediate. 1H NMR (DMSO-d6, 400 MHz) δ: 11.53 (s, 2H), 10.16 (s, 2H), 8.08 (brs, 6H), 7.88 (s, 2H), 7.69 (d, J=8.4 Hz, 2H), 3.94 (s, 6H), 1.54 (s, 18H), 1.43 (s, 18H). MS (ESI+APCl): m/z=853 [M+H]+.

Step 2. Synthesis of 1,1'-(2,2'-(1,4-phenylene)bis(1-methyl-1H-benzo[d]imidazole-6,2-diyl))diguanidine To a solution of the product of Step 1 (30 mg, 0.035 mmol) in dichloromethane (5.0 mL) at 0° C. was added 4M HCl in 1,4-dioxane (2.0 mL) and the reaction mixture was stirred at room temperature for 5 hours. The reaction mixture was concentrated under reduced pressure to obtain the crude product. The product was triturated with pentane (10 mL), filtered under vacuum, washed with pentane (10 mL), and dried to obtain 1,1'-(2,2'-(1,4-phenylene)bis(1-methyl-1H-benzo[d]imidazole-6,2-diyl))diguanidine. 1H NMR (DMSO-d6, 400 MHz) δ: 9.83 (s, 2H), 8.17 (brs, 4H), 7.84 (d, J=8.8 Hz, 2H), 7.75 (s, 2H), 7.38 (brs, 7H), 7.25 (d, J=8.4 Hz, 2H), 4.03 (s, 6H). MS (ESI+APCl): m/z=453 [M+H]+.

Example 75

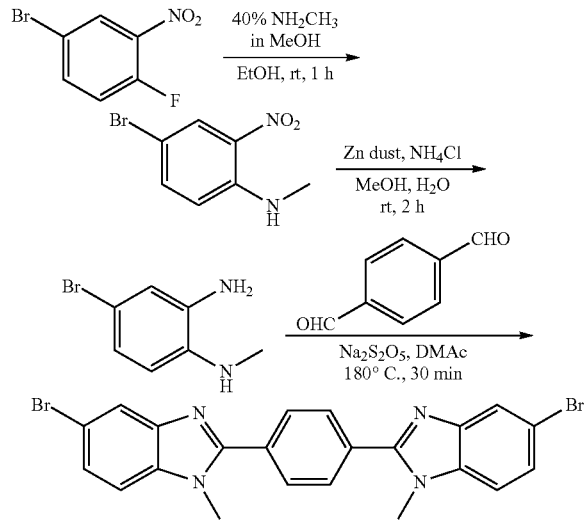

Step 1. Synthesis of 4-bromo-N-methyl-2-nitroaniline

To a solution of 4-bromo-1-fluoro-2-nitrobenzene (0.50 g, 2.28 mmol), in EtOH (10 mL), 40% methylamine in methanol (1.0 mL) was added and stirred at room temperature for 1 hour. The precipitated material was filtered and washed with hexanes and dried to obtain 4-bromo-N-methyl-2-nitroaniline. 1H NMR (400 MHz, DMSO-d6) δ: 8.24 (brs, 1H), 8.15 (d, J=2.4 Hz, 1H), 7.67 (dd, J=2.4 Hz and 9.2 Hz, 1H), 6.98 (d, J=9.2 Hz, 1H), 2.94 (d, J=4.8 Hz, 3H).

Step 2. Synthesis of 4-bromo-N1-methylbenzene-1,2-diamine

To a solution of 4-bromo-N-methyl-2-nitroaniline (0.30 g, 1.29 mmol), in methanol:water (2:1, 15 mL), zinc dust (0.84 g, 12.9), was added followed by portion wise addition of ammonium chloride (0.68 g, 12.98 mmol) over a period of 15 minutes. After complete addition, the reaction mixture was stirred at room temperature for 2 h. The reaction mixture was filtered on celite pad, washed with EtOAc (100 mL). The organic layer was washed with saturated aqueous sodium bicarbonate solution (50 mL), water (50 mL), brine (50 mL), dried over anhydrous sodium sulfate and concentrated under vacuum to obtain 4-bromo-N1-methylbenzene-1,2-diamine. 1H NMR (400 MHz, DMSO-d6) δ: 6.65 (d, J=2 Hz, 1H), 6.60 (dd, J=2.4 Hz and 8.4 Hz, 1H), 6.26 (d, J=8.4 Hz, 1H), 4.76-4.71 (m, 3H), 2.67 (d, J=4.4 Hz, 3H).

Step 3. Synthesis of 1,4-bis(5-bromo-1-methyl-1H-benzo[d]imidazol-2-yl)benzene (Compound 89)

In a microwave vial, a mixture of 4-bromo-N1-methylbenzene-1,2-diamine (0.15 g, 0.74 mmol), terephthalaldehyde (0.13 g, 0.37 mmol) and sodium metabisulfite (0.19 g, 0.895 mmol) in anhydrous N,N-dimethylacetamide (5.0 mL) was heated at 180° C. for 30 min. The reaction mixture was cooled to room temperature and slowly poured into ice cold water (30 mL). The precipitated product was collected by filtration under vacuum to obtain the crude product. The product was recrystallized from hot ethanol, filtered under vacuum and dried to obtain 1,4-bis(5-bromo-1-methyl-1H-benzo[d]imidazol-2-yl)benzene. 1H NMR (400 MHz, DMSO-d6) δ: 8.08 (s, 4H), 7.93 (d, J=1.6 Hz, 2H), 7.69 (s, 1H), 7.67 (s, 1H), 7.58 (d, J=2 Hz, 1H), 7.46 (d, J=2 Hz, 1H), 3.97 (s, 6H); MS (ESI+APCl): m/z=497 [M+H]+.

Example 76

Synthesis of 1,4-Bis(6-bromo-1-methyl-1H-benzo[d]imidazol-2-yl)benzene

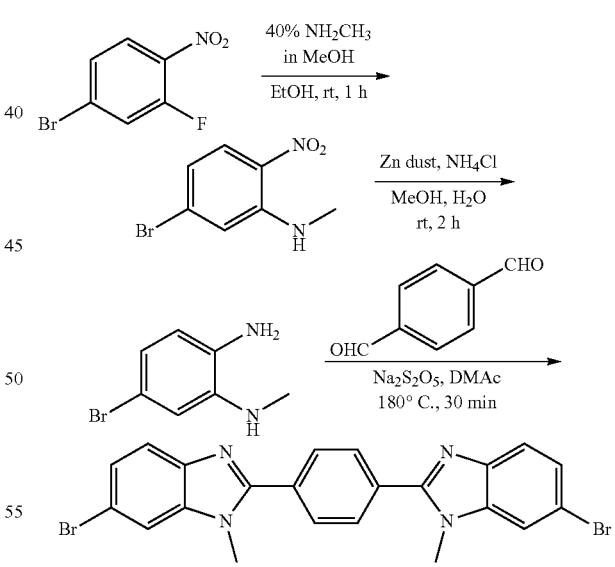

Synthesis of 5-bromo-N-methyl-2-nitroaniline

To a solution of 4-bromo-2-fluoro-1-nitrobenzene (0.50 g, 2.28 mmol), in EtOH (10 mL), methylamine (40% wt/v in methanol, 1.0 mL) was added and stirred at room temperature for 1 hour. The precipitated material was filtered under vacuum, washed with hexanes and dried to obtain 5-bromo-N-methyl-2-nitroaniline. 1H NMR (400 MHz, DMSO-d6)

δ: 8.24 (brs, 1H), 7.98 (d, J=8.8 Hz, 1H), 7.16 (d, J=2 Hz 1H), 6.82 (dd, J=2 Hz and 9.2 Hz, 1H), 2.94 (d, J=4.8 Hz, 3H).

Synthesis of 5-bromo-N1-methylbenzene-1,2-diamine

To a solution of 5-bromo-N-methyl-2-nitroaniline (0.40 g, 1.73 mmol) in a mixture of methanol:water (2:1, 15.0 mL), zinc dust (1.12 g, 17.3 mmol) was added followed by portion wise addition of ammonium chloride (0.91 g, 17.3 mmol) over a period of 15 minutes. After complete addition, the reaction mixture was stirred at room temperature for 2 hours. The reaction mixture was filtered on celite pad and washed with EtOAc (100 mL). The organic layer was washed with saturated aqueous sodium bicarbonate solution (50 mL), water (50 mL), brine (50 mL), dried over anhydrous sodium sulfate and concentrated under vacuum to obtain 5-bromo-N1-methylbenzene-1,2-diamine. 1H NMR (400 MHz, DMSO-d6) δ: 6.51 (dd, J=2.4 Hz and 8 Hz, 1H), 6.44 (d, J=8.4 Hz, 1H), 6.39 (d, J=2 Hz, 1H), 4.88 (d, J=5.2 Hz, 1H), 4.60 (s, 2H), 2.68 (d, J=4.8 Hz, 3H).

Synthesis of 1,4-bis(6-bromo-1-methyl-1H-benzo[d]imidazol-2-yl)benzene (Compound 90)

In a microwave vial, a mixture of 5-bromo-N1-methylbenzene-1,2-diamine (0.20 g, 0.99 mmol), terephthalaldehyde (66 mg, 0.49 mmol) and sodium metabisulfite (0.22 g, 1.19 mmol) in anhydrous N,N'-dimethylacetamide (5.00 mL) was heated at 180° C. for 30 min. The reaction mixture was cooled to room temperature and slowly poured into ice cold water (30 mL). The precipitated product was collected by filtration under vacuum to obtain the crude product. The product was recrystallized from hot methanol, filtered under vacuum and dried to obtain 1,4-bis(6-bromo-1-methyl-1H-benzo[d]imidazol-2-yl)benzene. 1H NMR (400 MHz, DMSO-d6) δ: 8.08 (s, 4H), 7.98 (s, 2H), 7.68 (d, J=8.4 Hz, 2H), 7.41 (d, J=8.4 Hz, 2H), 3.96 (s, 6H); MS (ESI+APCl): m/z=497 [M+H]+.

Examples 77-78 Intentionally Skipped

Example 79

Synthesis of 2,2'-bis(4-nitrophenyl)-1H,1'H-5,5'-bibenzo[d]imidazole

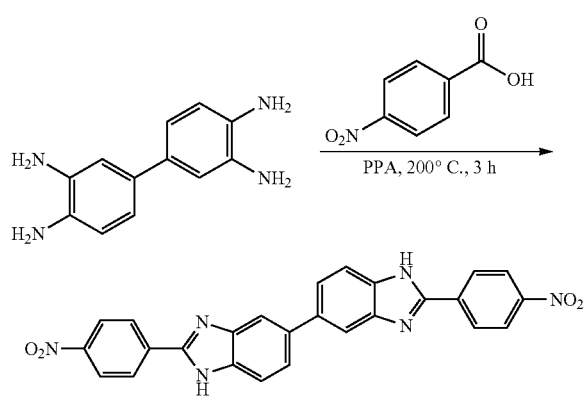

A mixture of [1,1'-biphenyl]-3,3',4,4'-tetraamine (0.1 g, 0.467 mmol), 4-nitrobenzoic acid (0.15 g, 0.934 mmol) and PPA (5.0 mL) were stirred at 200° C. for 90 min. The reaction mixture was poured into crushed ice, whereupon the product precipitated. The product was collected by filtration under vacuum, washed with aqueous potassium carbonate solution (10 mL), water (10 mL) and dried under vacuum. The crude product was triturated with a mixture of methanol:dichloromethane (1:4, 20 mL), filtered, washed with dichloromethane (30 mL), and dried under vacuum to obtain 2,2'-bis(4-nitrophenyl)-1H,1'H-5,5'-bibenzo[d]imidazole. 1H NMR (400 MHz, DMSO-d6): δ 13.45 (s, 2H), 8.45 (dd, J=8.4 Hz, 17.6 Hz, 8H), 8.04 (s, 1H), 7.83 (d, J=19.2 Hz, 2H), 7.65 (brs, 3H); MS (ESI+APCl) m/z 477 [M+H].

Example 80

Synthesis of 4,4'-(1H,1'H-[5,5'-bibenzo[d]imidazole]-2,2'-diyl)dianiline (Compound 95)

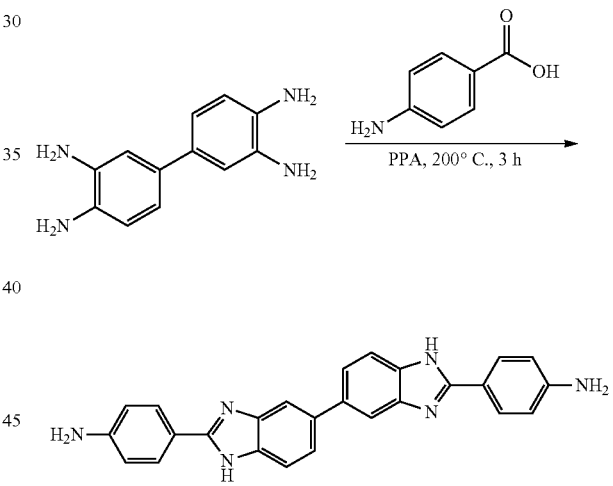

A mixture of [1,1'-biphenyl]-3,3',4,4'-tetraamine (400 mg, 1.86 mmol), 4-aminobenzoic acid (512 mg, 3.73 mmol), and PPA (20 mL) was stirred at 200° C. for 3 hours. The reaction mixture was poured into crushed ice, whereupon the product precipitated. The product was collected by filtration under vacuum, washed with aqueous potassium carbonate solution (25 mL), water (25 mL) and dried under vacuum. The crude product was triturated with a mixture of methanol:dichloromethane (1:4, 50 mL), filtered, washed with dichloromethane (30 mL), and dried under vacuum to obtain 4,4'-(1H, 1'H-[5,5'-bibenzo[d]imidazole]-2,2'-diyl)dianiline. 1H NMR (400 MHz, CD3OD): δ 7.76-7.74 (m, 4H), 7.67 (s, 2H), 7.50 (d, J=8.4 Hz, 2H), 7.43 (d, J=1.6 Hz, 1H), 7.41 (d, J=1.6 Hz, 1H), 6.69-6.72 (m, 4H); MS (ESI+APCl) m/z 417 [M+H].

Example 81

Synthesis of 1,1'-(1H,1'H-[5,5'-bibenzo[d]imidazole]-2,2'-diylbis(4,1-phenylene))-diguanidine

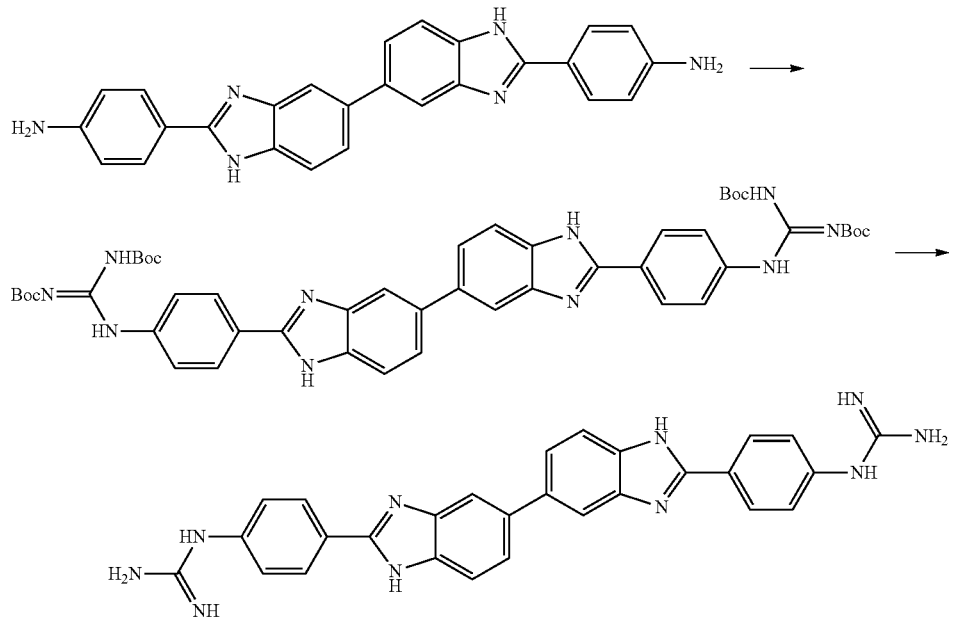

Step 1. Synthesis of Boc-Protected Intermediate

Triethyl amine (0.20 mL) was added to a solution of 4,4'-(1H,1'H-[5,5'-bibenzo[d]imidazole]-2,2'-diyl)dianiline (100 mg, 0.240 mmol) in DMF (10.0 mL) and then added 1,3-bis(tert-butoxycarbonyl)-2-methyl-2-thiopseudourea (0.17 g, 0.60 mmol), mercury (II) chloride (0.13 g, 0.48 mmol) at 0° C. The reaction mixture was stirred at room temperature for 24 hours. The reaction mixture was poured onto ice and the product was collected by filtration under vacuum and dried. The product was washed with a mixture of methanol:dichloromethane (1:9, 50 mL) and the filtrate was concentrated under vacuum. The product obtained was purified by neutral alumina chromatography (100% EtOAc as eluent). Fractions containing the product were combined and concentrated under vacuum to give the intermediate. 1H NMR (400 MHz, DMSO-d6): δ 11.3 (s, 2H), 10.1 (s, 2H), 8.17 (d, J=8.4 Hz, 4H), 7.94 (s, H), 7.78-7.72 (m, 6H), 7.63-7.54 (m, 3H), 1.53 (s, 18H), 1.43 (s, 18H), MS (ESI+APCl) m/z 901 [M+H].

Step 2. Synthesis of 1,1'-(1H,1'H-[5,5'-bibenzo[d]imidazole]-2,2'-diylbis(4,1-phenylene))diguanidine 4M HCl in dioxane (2.00 mL) was added to a solution of the product of Step 1 (0.05 g, 0.05 mmol) in dichloromethane (5.00 mL) at 0° C. The reaction mixture was stirred at room temperature for 8 hours. The obtained material was filtered under vacuum, washed with dichloromethane (10 mL) and dried to obtain 1,1'-(1H,1'H-[5,5'-bibenzo[d]imidazole]-2,2'-diylbis(4,1-phenylene))diguanidine. 1H NMR (400 MHz, CD3OD): δ 8.17 (d, J=8.8 Hz, 4H), 8.09 (s, 2H), 7.94-7.88 (m, 4H), 7.57 (d, J=8.8 Hz, 4H), MS (ESI+APCl) m/z 501 [M+H].

Example 82

Synthesis of 1,1'-(1H,1'H-[5,5'-bibenzo[d]imidazole]-2,2'-diylbis(4,1-phenylene))diurea

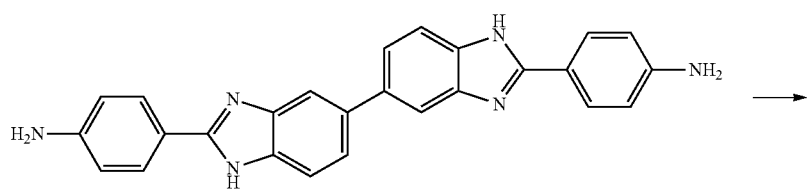

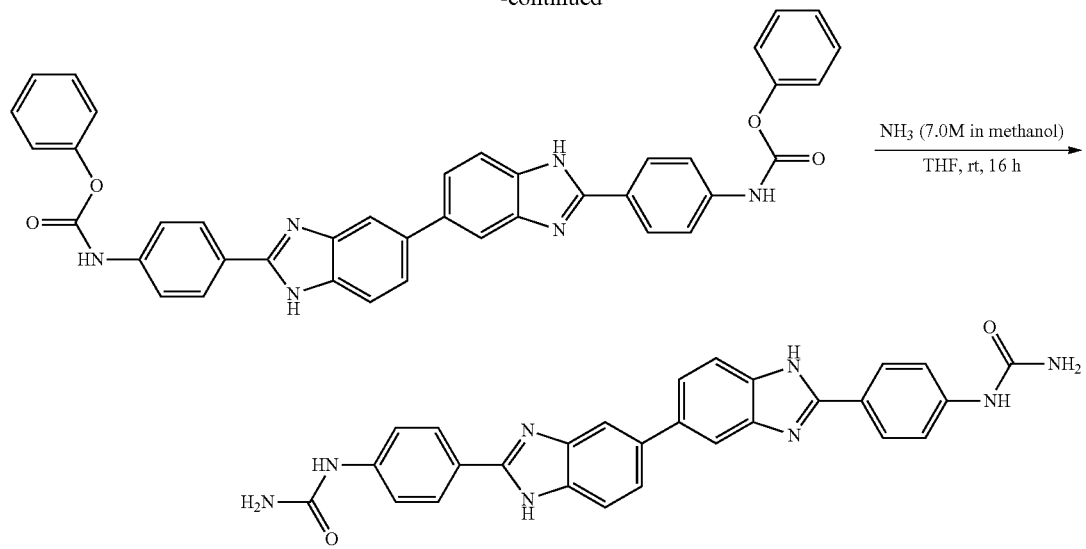

Step 1. Synthesis of diphenyl (1H,1'H-[5,5'-bibenzo[d]imidazole]-2,2'-diylbis(4,1-phenylene))dicarbamate To a solution of 4-4'-[1H,1'H-[5,5'-bibenzo[d]imidazole]-2,2'-diyl)dianiline (0.20 g, 0.48 mmol) in DMF (15.0 mL) at 0° C., was added DIPEA (0.26 mL, 1.44 mmol) and the reaction mixture was stirred for 10 minutes. Phenyl chloroformate (0.18 mL, 1.44 mmol) was added slowly to the above mixture at 0° C. over a period of 5 minutes. After complete addition, the reaction mixture was warmed to room temperature and stirred for 5 hours. The reaction mixture was poured onto ice and the precipitated material was filtered under vacuum and dried to obtain the crude product. The crude product was triturated with methanol (10 mL), filtered under vacuum, washed with methanol (10 mL), and dried to obtain diphenyl (1H,1'H-[5,5'-bibenzo[d]imidazole]-2,2'-diylbis(4,1-phenylene))dicarbamate. MS (ESI): m/z=656 [M+H]+. The crude product was used directly in the next step.

Synthesis of 1,1'-(1H,1'H-[5,5'-bibenzo[d]imidazole]-2,2'-diylbis(4,1phenylene))diurea To a solution of diphenyl (1H,1'H-[5,5'-bibenzo[d]imidazole]-2,2'-diylbis(4,1-phenylene))dicarbamate (0.22 g, 0.33 mmol) in THF (15.0 mL) at 0° C. was added NH3 (7.0 M in methanol, 5.0 mL) and the reaction mixture was stirred at room temperature for 16 hours. The reaction mixture was concentrated under vacuum to obtain the crude product. The product was triturated with methanol (10 mL), filtered under vacuum, washed with methanol (10 mL), and dried to obtain 1,1'-(1H,1'H-[5,5'-bibenzo[d]imidazole]-2,2'-diylbis(4,1-phenylene))diurea. 1H NMR (DMSO-d6, 400 MHz) δ: 12.76 (brs, 2H), 8.81 (s, 2H), 8.06 (d, J=8.4 Hz, 4H), 7.88 (bs, 1H), 7.70 (bs, 2H), 7.59-7.51 (m, 7H), 5.99 (s, 4H). MS (ESI): m/z=503 [M+H]+.

Example 83

Synthesis of 2,2'-(1,4-phenylene)bis(N-hydroxy-1H-benzo[d]imidazole-6-carboximidamide)

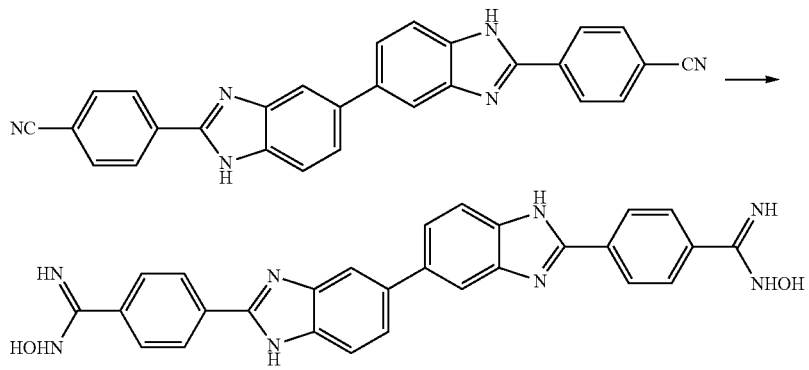

To a suspension of 4,4'-(1H,1'H-[5,5'-bibenzo[d]imidazole]-2,2'-diyl)dibenzonitrile (0.20 g, 0.45 mmol) in ethanol (10 mL), THF (4.0 mL) was added hydroxylamine (50% in water, 1.0 mL) in a sealed tube and stirred at 90° C. for 16 hours. The reaction mixture was cooled to room temperature and the product was collected by filtration under vacuum, washed with methanol (5 mL), and dried under vacuum. The product was triturated with hot methanol (10 mL) and dried under vacuum to obtain 4,4'-(1H,1'H-[5,5'-bibenzo[d]imidazole]-2,2'-diyl)bis(N-hydroxybenzimidamide). 1H NMR (DMSO-d6, 400 MHz) δ: 13.20 (brs, 2H), 10.18 (brs, 2H), 8.27 (d, J=8.0 Hz, 4H), 7.90-7.88 (m, 6H), 7.73 (d, J=8.0 Hz, 2H), 7.62 (d, J=8.4 Hz, 2H), 6.98 (brs, 3H), MS (ESI+APCl): m/z=503 [M+H]+.

Example 84

Synthesis of 4,4'-(1H,1'H-[5,5'-bibenzo[d]imidazole]-2,2'-diyl)dibenzimidamide acetate To a suspension of 4,4'-(1H,1'H-[5,5'-bibenzo[d]imidazole]-2,2'-diyl)bis(N-hydroxybenzimidamide) (0.30 g, 0.59 mmol) in glacial acetic acid (20.0 mL) was slowly added acetic anhydride (1.00 mL) and stirred at room temperature for 16 hours. 10% Pd/C (10 mg) was added in one lot and the reaction mixture was hydrogenated (~1 atmospheric pressure; balloon pressure) at room temperature for 6 hours. The reaction mixture was filtered through a celite bed and washed with methanol (10.0 mL). The filtrate was concentrated under vacuum and the residue was triturated with methanol (15.0 mL), filtered under vacuum, washed with methanol (5.00 mL) and dried to obtain 4,4'-(1H,1'H-[5,5'-bibenzo[d]imidazole]-2,2'-diyl)dibenzimidamide acetate. 1H NMR (DMSO-d6, 400 MHz) δ: 10.4-9.54 (brs, 2H), 8.41 (d, J=8.4 Hz, 4H), 8.00 (d, J=8.8 Hz, 4H), 7.92 (s, 2H), 7.76-7.74 (m, 2H), 7.65-7.62 (m, 2H). MS (ESI+APCl): m/z=471 [M+H]+.

Example 85

Synthesis of 4,4'-(1H,1'H-[5,5'-bibenzo[d]imidazole]-2,2'-diyl)dibenzonitrile

In a microwave vial, a mixture of [1,1'-biphenyl]-3,3',4,4'-tetraamine (100 mg, 0.46 mmol), 4-cyano benzaldehyde (122 mg, 0.932 mmol) and sodium metabisulfite (177 mg, 0.932 mmol) in anhydrous DMA (5 mL) was heated at 170° C. for 45 min. The reaction mixture was cooled to room temperature and slowly poured into ice cold water (100 mL). The precipitated product was collected by filtration under vacuum and the crude product was recrystallized from hot EtOH to obtain 4,4'-(1H,1'H-[5,5'-bibenzo[d]imidazole]-2,2'-diyl)dibenzonitrile. 1H NMR (400 MHz, DMSO-d6) δ: 8.38 (d, J=8.4 Hz, 4H), 8.06 (d, J=8.4 Hz, 4H), 7.93 (s, 2H), 7.76 (d, J=8.4 Hz, 2H), 7.65 (d, J=8.0 Hz, 2H); MS (ESI+APCl) m/z 435.1 [M−H]−;

Example 86

Synthesis of 4,4'-(1H,1'H-[5,5'-bibenzo[d]imidazole]-2,2'-diyl) dibenzamide

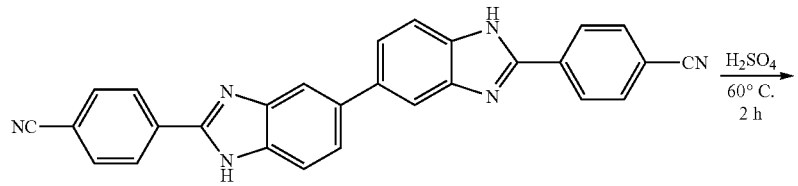

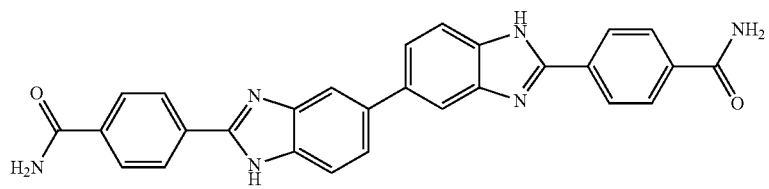

To a solution of 4,4'-(1H,1'H-[5,5'-bibenzo[d]imidazole]-2,2'-diyl) dibenzonitrile (100 mg, 0.22 mmol) in conc. $H_2SO_4$ (3.0 mL) was stirred at 60° C. for 2 hours. The reaction mixture was poured onto ice and neutralized with aqueous saturated potassium carbonate solution and the product was collected by filtration under vacuum and dried. The crude product was crystallized in methanol to obtain 4,4'-(1H,1'H-[5,5'-bibenzo[d]imidazole]-2,2'-diyl) dibenzamide. 1H NMR (DMSO-d6, 400 MHz) δ: 13.11 (brs, 2H), 8.28 (d, J=8.4 Hz, 4H), 8.10 (s, 2H), 8.06 (d, J=8.4 Hz, 4H), 7.89 (s, 2H), 7.72 (d, J=7.2 Hz, 2H), 7.60 (d, J=8.4 Hz, 2H), 7.49 (s, 2H). MS (ESI+APCl) m/z 471 [M−H]−.

Example 87

Synthesis of 4,4'-(1H,1'H-[5,5'-bibenzo[d]imidazole]-2,2'-diyl)dibenzoic acid

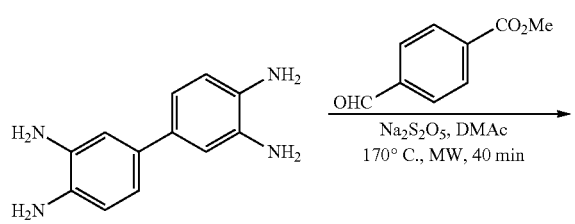

In a microwave vial, a mixture of [1,1'-biphenyl]-3,3',4,4'-tetraamine (500 mg, 2.33 mmol), methyl 4-formylbenzoate 2a (842 mg, 5.13 mmol) and sodium metabisulfite (1.33 g, 1.40 mmol) in anhydrous DMAc (10 mL) was heated at 180° C. for 40 min. The reaction mixture was cooled to room temperature and slowly poured into ice cold water (100 mL). The precipitated product was collected by filtration under vacuum. The crude product was recrystallized from hot methanol (30 mL) and dried to obtain dimethyl 4,4'-(1H,1'H-[5,5'-bibenzo[d]imidazole]-2,2'-diyl)dibenzoate. 1H NMR (400 MHz, DMSO-d6) δ: 13.22 (brs, 2H), 8.36 (d, J=8.4 Hz, 4H), 8.15 (d, J=8.4 Hz, 4H), 8.01 (s, 2H), 7.80-7.59 (m, 4H), 3.91 (s, 6H), MS (ESI+APCl): m/z=503 [M+H]+, 501 [M−H]+.

Example 88

Synthesis of 4,4'-(1H,1'H-[5,5'-bibenzo[d]imidazole]-2,2'-diyl)dibenzoic Acid (Method 1)

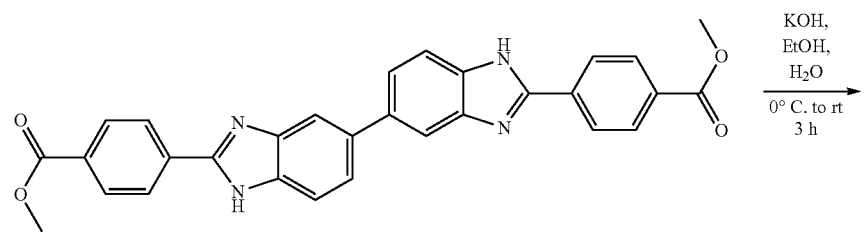

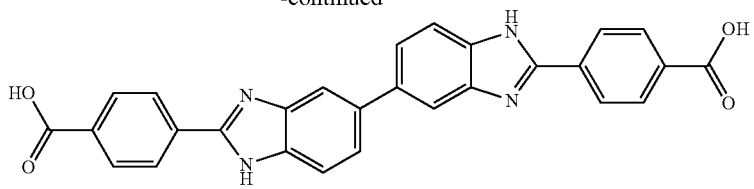

A solution of KOH (1.00 g, 17.92 mmol) in water (20 mL) was added to dimethyl 4,4'-(1H,1'H-[5,5'-bibenzo[d]imidazole]-2,2'-diyl)dibenzoate (1.80 g, 3.58 mmol) in EtOH (20 mL) slowly at 0° C. and stirred at room temperature for 5 hours. The reaction mixture was poured into crushed ice, acidified with aqueous 2 N HCl solution to pH ~2, and the resulting precipitate was collected by filtration, washed with water (20 mL) and dried under vacuum. The crude product was recrystallized from hot methanol (40 mL) and dried to obtain 4-(cyanomethyl)benzoic acid. 1H NMR (400 MHz, DMSO-d6): δ 8.44 (d, J=8.4 Hz, 4H), 8.17 (d, J=8.4 Hz, 4H), 7.99 (s, 2H), 7.85 (d, J=8.8 Hz, 2H), 7.77 (d, J=8.4 Hz, 2H). MS (ESI+APCl): m/z=475 [M+H]+, 473 [M−H]+.

Example 89

Synthesis of 4,4'-(1H,1'H-[5,5'-bibenzo[d]imidazole]-2,2'-diyl)dibenzoic Acid (Method 2)

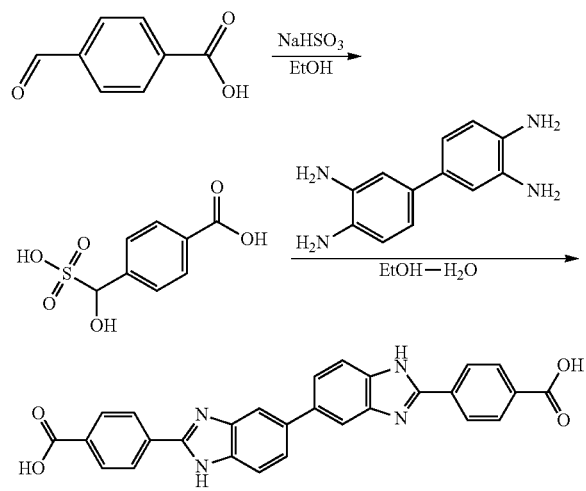

A suspension of 4-carboxybenzaldehyde (1.0 g, 6.67 mmol) in EtOH (30 ml) was cooled to 0° C. and a solution of sodium bisulfite (700.0 mg, 6.73 mmol) in water (10 ml) added dropwise. The cold-bath was removed and the mixture stirred for 1 hour. To the solution was added 3,3'-diaminobenzidine tetrahydrochloride (1.15 g, 3.2 mmol) and water (20 ml) and the mixture heated at reflux for 3 hours. After cooling, the mixture was filtered and the residue washed with water (×3) and methanol (×2). The product was dried under vacuum. 1H NMR (DMSO-d6, 400 MHz) δ: 8.37 (d, J=8.2 Hz, 4H), 8.17 (d, J=8.2 Hz, 4H), 7.98 (s, 2H), 7.82 (d, J=8.4 Hz, 2H), 7.74 (d, J=8.2 Hz, 2H), MS (ESI): m/z=475 [M+H]+.

Example 90

Synthesis of 2,2'-bis(4-bromophenyl)-1H,1'H-5,5'-bibenzo[d]imidazole

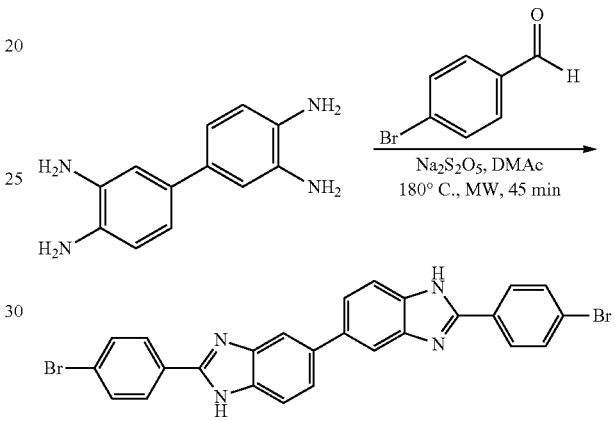

In a microwave vial, a mixture of [1,1'-biphenyl]-3,3',4,4'-tetraamine (200 mg, 0.934 mmol), 4-bromobenzaldehyde (345 mg, 1.869 mmol) and sodium metabisulfite (355 mg, 1.869 mmol) in anhydrous DMA (5 mL) was heated at 180° C. for 45 min. The reaction mixture was cooled to room temperature and slowly poured into ice cold water (100 mL). The precipitated product was collected by filtration under vacuum and the crude product was washed with methanol to obtain 2,2'-bis(4-bromophenyl)-1H,1'H-5,5'-bibenzo[d]imidazole. 1H NMR (400 MHz, DMSO-d6) δ: 13.13 (bs, 2H), 8.15 (d, J=8.4 Hz, 4H), 7.86 (s, 2H), 7.79 (d, J=8.4 Hz, 4H), 7.70 (d, J=8.0 Hz, 2H), 7.59 (d, J=8.0 Hz, 2H); MS (ESI+APCl): m/z=545 [M+H]+.

Example 91

Synthesis of 4,4'-(1H,1'H-[5,5'-bibenzo[d]imidazole]-2,2'-diyl)diphenol

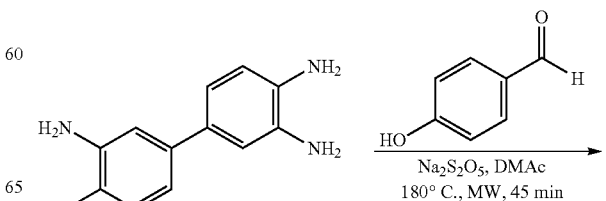

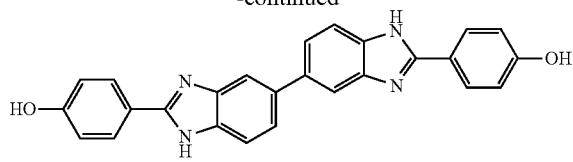

In a microwave vial, a mixture of [1,1'-biphenyl]-3,3',4,4'-tetraamine (0.10 g, 0.50 mmol), 4-hydroxybenzaldehyde (0.12 g, 1.0 mmol) and sodium metabisulfite (0.20 g, 1.10 mmol) in anhydrous N,N-dimethylacetamide (3.0 mL) was heated at 180° C. for 45 min. The reaction mixture was cooled to room temperature and slowly poured into ice cold water (30 mL). The precipitated product was collected by filtration under vacuum and dried to obtain 0.20 g of crude compound, out of which 0.10 g was purified by neutral alumina chromatography (2:8; methanol:dichloromethane). The fractions containing the product were combined and concentrated under vacuum and dried to obtain 4,4'-(1H,1'H-[5,5'-bibenzo[d]imidazole]-2,2'-diyl)diphenol. 1H NMR (400 MHz, DMSO-d6) δ: 12.72 (brs, 2H), 9.96 (s, 2H), 8.03 (d, J=8.4 Hz, 4H), 7.77 (s, 2H), 7.61 (d, J=8.0 Hz, 2H), 7.50 (dd, J=8.0 Hz and 1.6 Hz, 2H), 6.93 (d, J=8.8 Hz, 4H); MS (ESI+APCl): m/z=419 [M+H]+.

Example 92

Synthesis of 2,2'-bis(4-methoxyphenyl)-1H,1'H-5,5'-bibenzo[d]imidazole

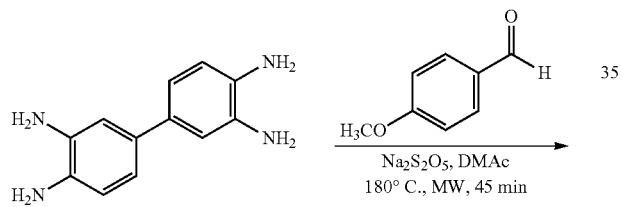

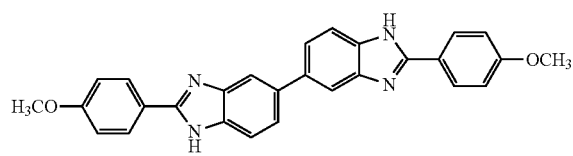

In a microwave vial, a mixture of [1,1'-biphenyl]-3,3',4,4'-tetraamine (0.10 g, 0.50 mmol), 4-methoxybenzaldehyde (0.13 g, 1.0 mmol) and sodium metabisulfite (0.20 g, 1.10 mmol) in anhydrous N,N-dimethylacetamide (3.0 mL) was heated at 180° C. for 45 min. The reaction mixture was cooled to room temperature and slowly poured into ice cold water (30 mL). The precipitated product was collected by filtration under vacuum and dried to obtain 0.2 g of the crude compound, out of which 0.11 g was purified by neutral alumina chromatography (1:9 methanol:dichloromethane). The fractions containing the product were combined and concentrated under vacuum to obtain 2,2'-bis(4-methoxyphenyl)-1H,1'H-5,5'-bibenzo[d]imidazole. 1H NMR (400 MHz, DMSO-d6) δ: 12.81 (brs, 2H), 8.15 (d, J=8.8 Hz, 4H), 7.90-7.51 (m, 6H), 7.13 (d, J=8.8 Hz, 4H), 3.86 (s, 6H); MS (ESI+APCl): m/z=447 [M+H]+.

Example 93

Synthesis of (2,2'-bis(4-(1H-imidazol-1-yl)phenyl)-1H,3'H-5,5'-bibenzo[d]imidazole)

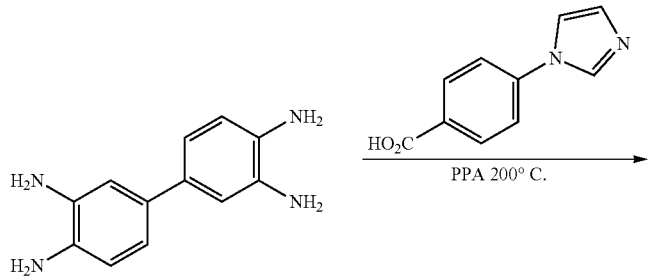

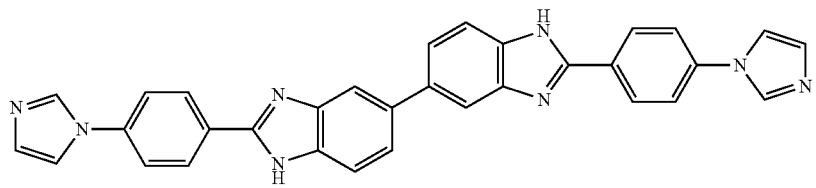

4-(1H-Imidazole-1-yl)benzoic acid (250 mg, 1.3 mmol) and polyphosphoric acid (10 mL) were heated to 200° C. and [1,1'-biphenyl]-3,3',4,4'-tetramine (241 mg, 1.19 mmol) was added. The reaction stirred at 200° C. overnight. The reaction mixture was cooled to −100° C. and poured into water. The resulting material was filtered and washed with water followed by methanol. Then the material was washed with saturated sodium bicarbonate and filtered again. The material was washed with water and methanol and then dried to afford the title compound. 1H NMR (DMSO-d6): δ 13.09 (s, 2H), 8.43 (s, 2H), 8.35 (d, 2H, J=9), 7.90 (m, 8H), 7.91 (d, 2H, J=9), 7.75 (dd, 2H, J=1.4, 8), 7.18 (s, 2H) ppm. (C32H23N8) calculated mass 519.2046 (M+H+); mass found 519.2058 (M+H+).

Example 94

Synthesis of 4,4'-(1H,1'H-[5,5'-bibenzo[d]imidazole]-2,2'-diyl)bis(N-(2-(dimethylamino)ethyl)benzamide)

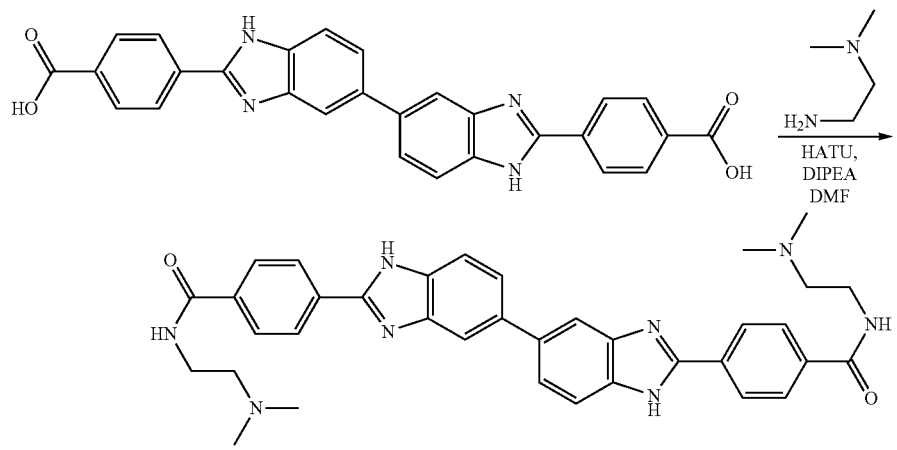

4,4'-(1H,1'H-[5,5'-bibenzo[d]imidazole]-2,2'-diyl)dibenzoic acid (100 mg, 0.21 mmol), HATU (176 mg, 0.46 mmol) and DIPEA (220 μL, 1.26 mmol) were mixed in DMF for 5 minutes before adding 2-(Dimethylamino)-ethylamine (50 uL, 0.46 mmol) and stirring overnight. The solvent was removed under vacuum, the residue washed with ether and the crude product purified using a C-18 column and a gradient of 0-100% MeOH in water containing 0.1% TFA. 1H NMR (CD3OD, 400 MHz) δ: 8.28 (d, J=8.7 Hz, 4H), 8.17 (d, J=8.7 Hz, 4H), 8.06 (m, 2H), 7.90 (m, 4H), 3.83 (t, J=5.7 Hz, 4H), 3.43 (t, J=5.7 Hz, 4H), 3.20 (s, 12H), MS (ESI): m/z=615 [M+H]+.

Example 95

Synthesis of 4-(2'-(4-cyanophenyl)-1H,1'H-[5,5'-bibenzo[d]imidazol]-2-yl)-N-(2-(dimethylamino)ethyl)benzamide

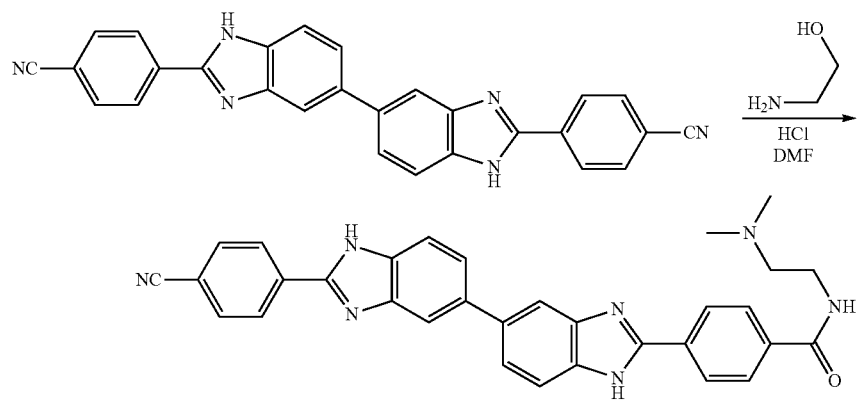

A mixture of 4,4'-(1H,1'H-[5,5'-bibenzo[d]imidazole]-2,2'-diyl)dibenzonitrile (65 mg), ethanolamine (200 μL), HCl (4N in dioxane, 80 μL) and DMF (2 ml) was heated at 160° C. in a sealed tube overnight and DMF removed under vacuum. The crude material was washed with ether then purified using a C-18 column and a gradient of 0-100% MeOH in water containing 0.1% TFA to afford the title compound. 4,4'-(1H,1'H-[5,5'-bibenzo[d]imidazole]-2,2'-diyl)bis(N-(2-(dimethylamino)ethyl)benzamide) was also obtained as a by-product. 1H NMR (CD3OD, 400 MHz) δ: 8.32-8.24 (m, 4H), 8.18 (d, J=8.0 Hz, 2H), 8.08-8.97 (m, 4H), 7.90 (br s, 2H), 7.84 (d, J=6.4 Hz, 2H), MS (ESI): m/z=526 [M+H]+.

Example 96

Synthesis of N-(2-(dimethylamino)ethyl)-4-(2'-(4-((2-(methylamino)ethyl)carbamoyl)phenyl)-1H,1'H-[5,5'-bibenzo[d]imidazol]-2-yl)benzamide (Compound 110) and 4,4'-(1H,1'H-[5,5'-bibenzo[d]imidazole]-2,2'-diyl)bis(N-(2-(methylamino)ethyl)benzamide) (Compound 111)

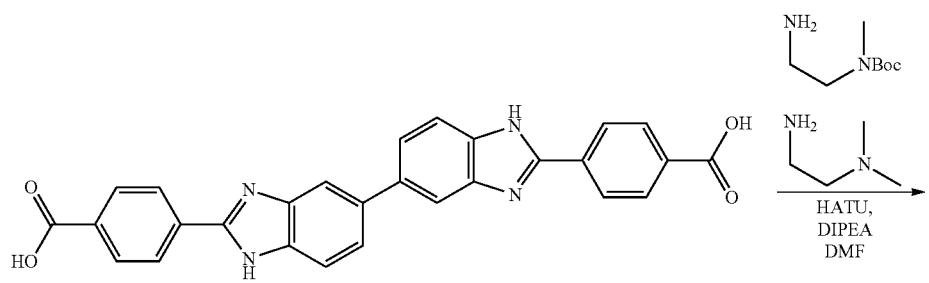

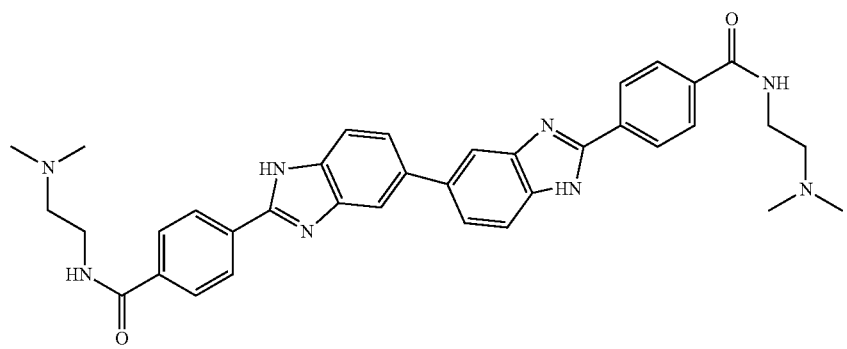

Compound 108

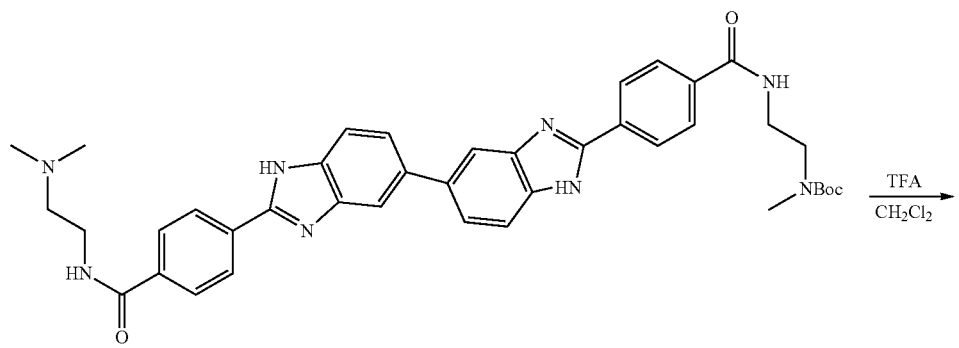

Compound 110-a

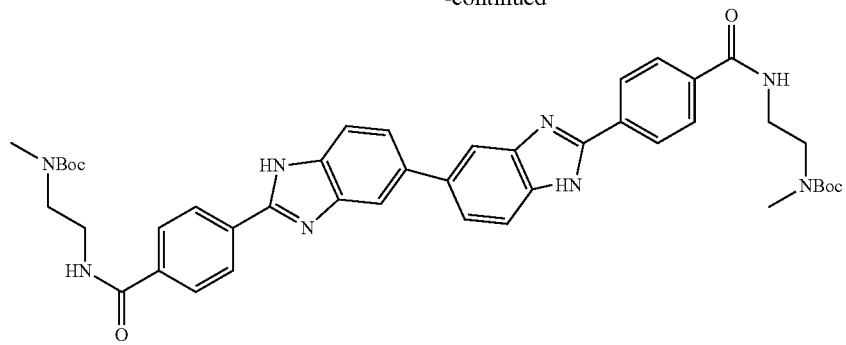

Compound 111-a

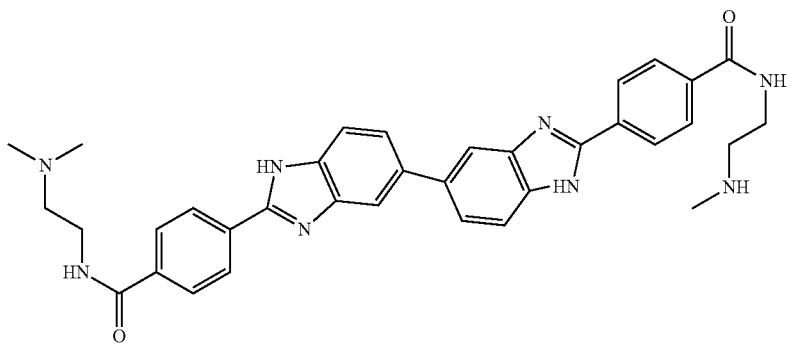

Compound 110

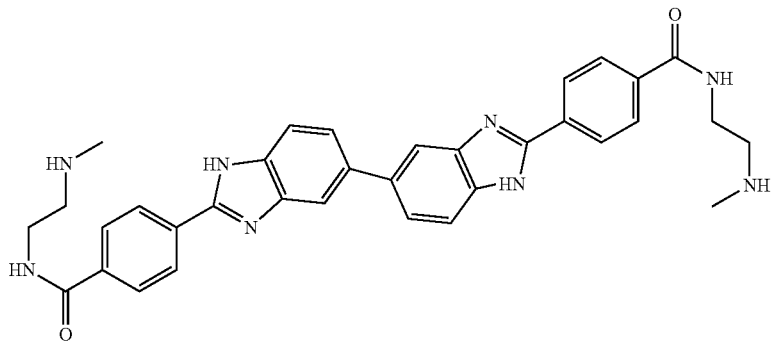

Compound 111

To a solution of 4,4'-(1H,1'H-[5,5'-bibenzo[d]imidazole]-2,2'-diyl)dibenzoic acid (400 mg, 0.84 mmol) in DMF (12 ml) was added HATU (700 mg, 1.84 mmol) and DIPEA (900 uL, 5.17 mmol) and the mixture stirred for 5 min. To the reaction mixture was added Boc-N-methylethelenediamine (146 mg, 0.84 mmol) and 2-(Dimethylamino)ethylamine (74 mg, 0.84 mmol) and the mixture stirred at room temperature overnight. The solvent was removed under vacuum and the residue washed with ether to remove trace amount of solvent. The crude material was purified using a C-18 column and a gradient of 0-100% MeOH in water containing 0.1% TFA to afford Compound 108, Boc-protected Compound 110 and Boc-protected Compound 111. Concentration of fractions containing the Boc-protected compounds led to partial cleavage of the Boc-group. Consequently, the Boc-group was cleaved using 30% TFA to afford Compound 110 and Compound 111. Compound 110; 1H NMR (DMSO-d6, 400 MHz) δ: 9.49 (br s, 1H, —NH), 8.90-8.84 (m, 2H, —NH), 8.51 (br s, 2H, —NH), 8.35 (d, J=7.5 Hz, 4H), 8.10 (d, J=7.5 Hz, 4H), 7.97 (br s, 2H), 7.80 (d, J=8.4 Hz, 2H), 7.71 (d, J=8.4 Hz, 2H), 3.67-3.63 (m, 2H), 3.62-3.55 (m, 2H), 3.33-3.29 (m, 2H), 3.17-3.12 (m, 2H), 2.88 (d, J=4.7 Hz, 6H), 2.64 (t, J=5.3 Hz, 3H), MS (ESI): m/z=601 [M+H]+. Compound 111; 1H NMR (DMSO-d6, 400 MHz) δ: 8.84 (t, J=5.6 Hz, 2H, —NH), 8.49 (br s, 4H), 8.34 (d, J=8.4 Hz, 4H), 8.09 (d, J=8.5 Hz, 4H), 7.96 (br s, 2H), 7.70 (dd, J=1.4, 8.5 Hz, 2H), 3.62-3.58 (m, 4H), 3.16-3.09 (m, 4H), 2.64 (t, J=5.3 Hz, 6H), MS (ESI): m/z=587 [M+H]+

Example 97

Synthesis of 4,4'-(1H,1'H-[5,5'-bibenzo[d]imidazole]-2,2'-diyl)bis(N-(2-(diethylamino)ethyl)benzamide)

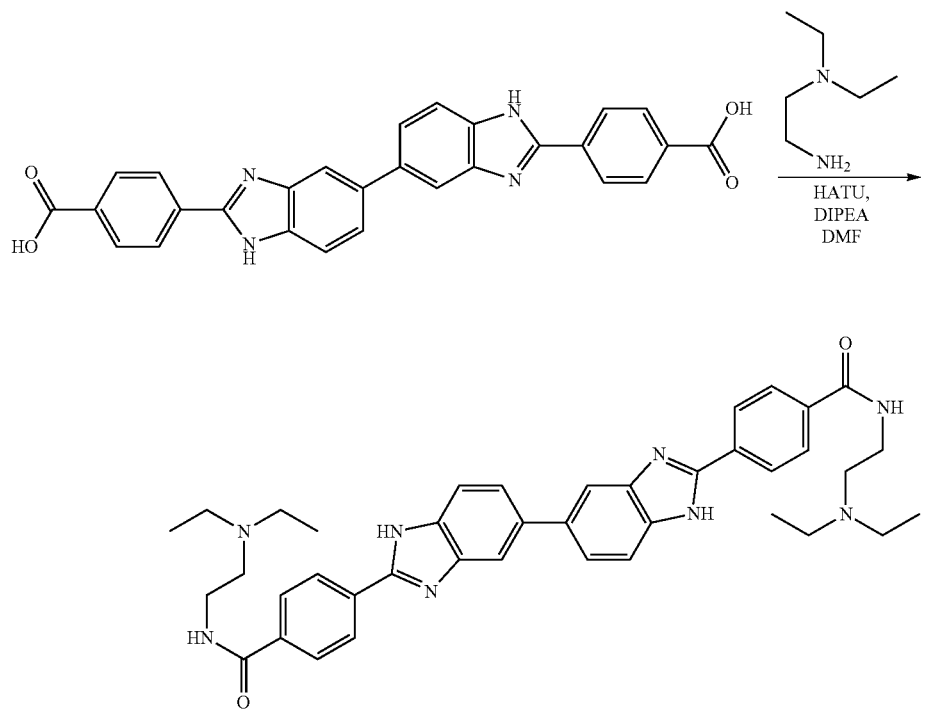

To a solution of 4,4'-(1H,1'H-[5,5'-bibenzo[d]imidazole]-2,2'-diyl)dibenzoic acid (0.20 g, 0.42 mmol) in DMF (5.0 mL) at 0° C., was added HATU (0.35 g, 0.92 mmol), DIPEA (0.44 mL, 2.52 mmol) and the reaction mixture was stirred for 10 minutes. N1,N1-Diethylethane-1,2-diamine (0.11 g, 0.92 mmol) was added to the above mixture in one lot at 0° C. and the reaction mixture was allowed to warm to room temperature and stirred for 8 hours. The reaction mixture was poured onto ice, whereupon the product precipitated. The precipitated product was collected by filtration under vacuum, washed with methanol (15 mL), and dried to obtain the crude product. The crude product was refluxed in methanol (20 mL) and collected by filtration under vacuum, washed with methanol (10 mL) and dried to obtain 4,4'-(1H,1'H-[5,5'-bibenzo[d]imidazole]-2,2'-diyl)bis(N-(2-(diethylamino)ethyl)benzamide). 1H NMR (CD3OD 400 MHz) δ: 8.16 (d, J=8.4 Hz, 4H), 7.97 (d, J=8.4 Hz, 4H), 7.82 (s, 2H), 7.66 (d, J=8.4 Hz, 2H), 7.58 (dd, J=8.4 Hz, 1.2 Hz, 2H), 3.69 (t, J=6.4 Hz, 4H), 3.31-3.29 (m, 4H), 3.26-3.23 (m, 8H), 1.27 (t, J=7.2 Hz, 12H). UPLC MS m/z=671 [M+H]+.

Example 98

Synthesis of 4,4'-(1H,1'H-[5,5'-bibenzo[d]imidazole]-2,2'-diyl)bis(N-(2-(disopropylamino)ethyl)benzamide)

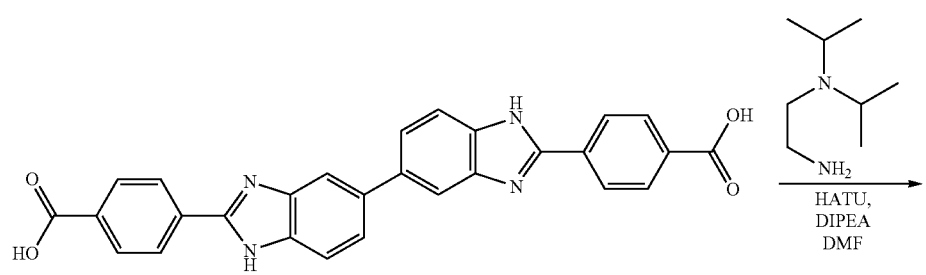

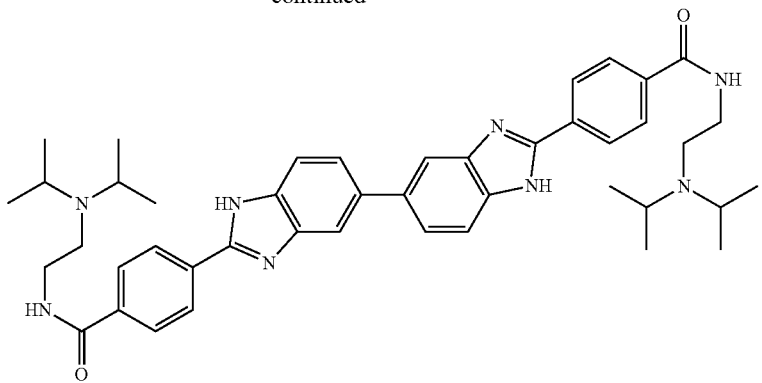

To a suspension of 4,4'-(1H,1'H-[5,5'-bibenzo[d]imidazole]-2,2'-diyl)dibenzoic acid (0.15 g, 0.31 mmol) in DMF (5.0 mL) at 0° C., was added HATU (0.26 g, 0.69 mmol) and DIPEA (0.32 mL, 1.89 mmol), and the reaction mixture was stirred for 15 minutes. N,N-Diisopropylethane-1,2-diamine (0.13 g, 0.94 mmol) was added to the above mixture at 0° C. and the reaction mixture was allowed to warm to room temperature and stirred for 8 h. The reaction mixture was concentrated under vacuum to obtain the crude product as a brown syrupy liquid. The crude product was poured into ice-cold water (40 mL), and stirred for 10 minutes, whereupon the product precipitated. The product was collected by filtration under vacuum, washed with methanol (20 mL), and then purified by preparative HPLC. Fractions containing only the pure product were combined for concentration to yield 4,4'-(1H,1'H-[5,5'-bibenzo[d]imidazole]-2,2'-diyl)bis (N-(2-(diisopropylamino)ethyl)benzamide) TFA salt (40 mg, 17%). 1H NMR (CD3OD, 400 MHz) δ: 8.19 (d, J=8.4 Hz, 4H), 8.06 (d, J=8.0 Hz, 4H), 7.95 (s, 2H), 7.79 (s, 4H), 3.79-3.72 (m, 4H), 3.68 (t, J=6.8 Hz, 4H), 3.31 (t, J=6.4 Hz, 4H), 1.34 (t, J=6.4 Hz, 24H). MS (ESI+APCl): m/z=728 [M+H]+.

Example 99

Synthesis of N-(2-(dimethylamino)ethyl)-4-(2'-(4-((2-(hex-5-yn-1-yl(methyl)amino)ethyl)carbamoyl) phenyl)-1H,1'H-[5,5'-bibenzo[d]imidazol]-2-yl)benzamide

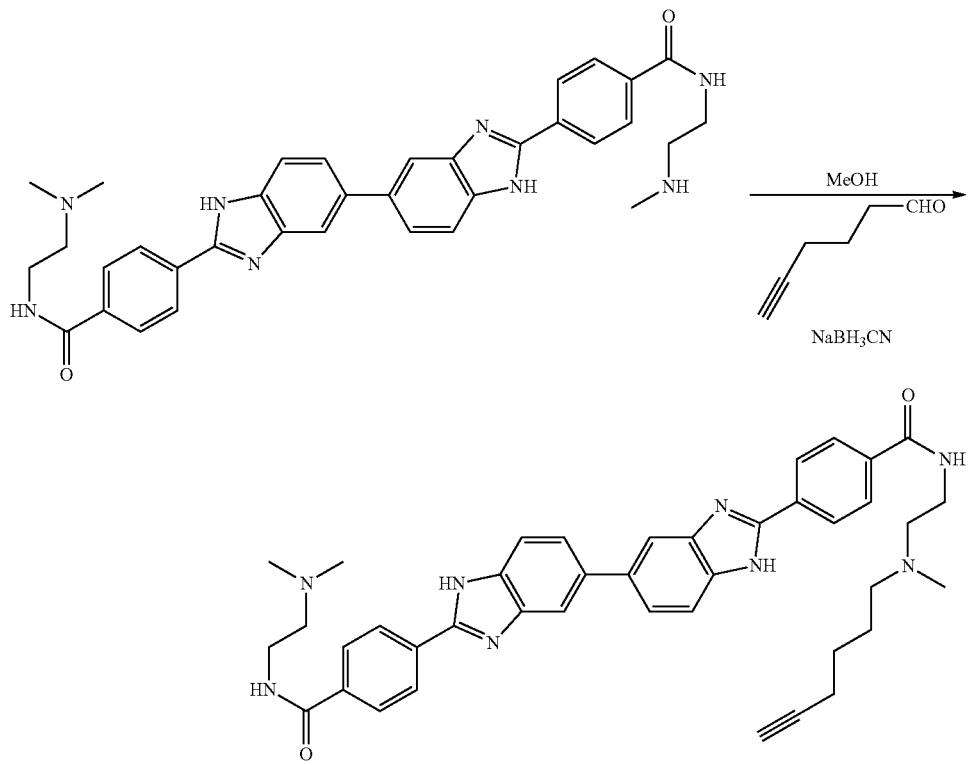

To a solution of N-(2-(Dimethylamino)ethyl)-4-(2'-(4-((2-(methylamino)ethyl) carbamoyl)phenyl)-1H,1'H-[5,5'-bibenzo[d]imidazol]-2-yl)benzamide (160 mg, 0.27 mmol) in MeOH (3 ml) was added 5-hyxanal (30 mg, 0.31 mmol) and sodium cyanoborohydride (20 mg, 0.31 mmol) and the mixture stirred at room temperature overnight. The solvent was removed under vacuum and the crude material purified using a C-18 column and a gradient of 0-100% MeOH in water containing 0.1% TFA. 1H NMR (CD3OD, 400 MHz) δ: 8.28 (d, J=8.4 Hz, 4H), 8.16 (d, J=8.4 Hz, 4H), 8.04 (s, 2H), 7.88-7.85 (m, 4H), 3.82 (t, J=5.8 Hz, 4H), 3.43 (t, J=5.8 Hz, 4H), 3.20 (s, 6H), 3.01 (s, 3H), 2.34-2.23 (m, 4H), 2.20 (t, J=2.6 Hz, 1H), 1.97-1.86 (m, 2H), 1.68-1.60 (m, 2H), MS (ESI): m/z=681 [M+H]+.

Example 100

Synthesis of 4,4'-(1H,1'H-[5,5'-bibenzo[d]imidazole]-2,2'-diyl)bis(N-(2-(pyrrolidin-1-yl)ethyl)benzamide)

To a suspension of 4,4'-(1H,1'H-[5,5'-bibenzo[d]imidazole]-2,2'-diyl)dibenzoic acid (0.20 g, 0.42 mmol) in DMF (20 mL) at 0° C., was added HATU (0.48 g, 1.26 mmol), DIPEA (0.4 mL, 2.53 mmol) and the reaction mixture was stirred for 15 minutes. 2-(pyrrolidin-1-yl)ethanamine (0.10 g, 0.92 mmol) was added to the above mixture at 0° C. and the reaction mixture was allowed to warm to room temperature and stirred for 16 hours. The reaction mixture was poured onto ice-cold water (50 mL), and stirred for 15 minutes, whereupon the product precipitated. The product was collected by filtration under vacuum. The crude product was purified by silica gel chromatography [1:4 (10% ammonium hydroxide in methanol):dichloromethane]. The fractions containing the pure product were combined and concentrated under vacuum to obtain 4,4'-(1H,1'H-[5,5'-bibenzo[d]imidazole]-2,2'-diyl)bis(N-(2-(pyrrolidin-1-yl)ethyl)benzamide). 1H NMR (CD3OD, 400 MHz) δ: 8.11 (dd, J=2 Hz, 6.8 Hz, 4H), 7.93 (dd, J=3.2 Hz, 6.8 Hz, 4H), 7.79 (brs, 2H), 7.63 (d, J=8.0 Hz, 2H), 7.55 (dd, J=1.6 Hz, 8.4 Hz, 2H), 3.50 (t, J=6.8 Hz, 4H), 2.68 (t, J=6.8 Hz, 4H), 2.58 (brs, 8H), 1.77-1.74 (m, 8H). MS (ESI+APCl): m/z=667 [M+H]+.

Example 101

Synthesis of 4,4'-(1H,1'H-[5,5'-bibenzo[d]imidazole]-2,2'-diyl)bis(N-(2-(piperidin-1-yl)ethyl)benzamide)

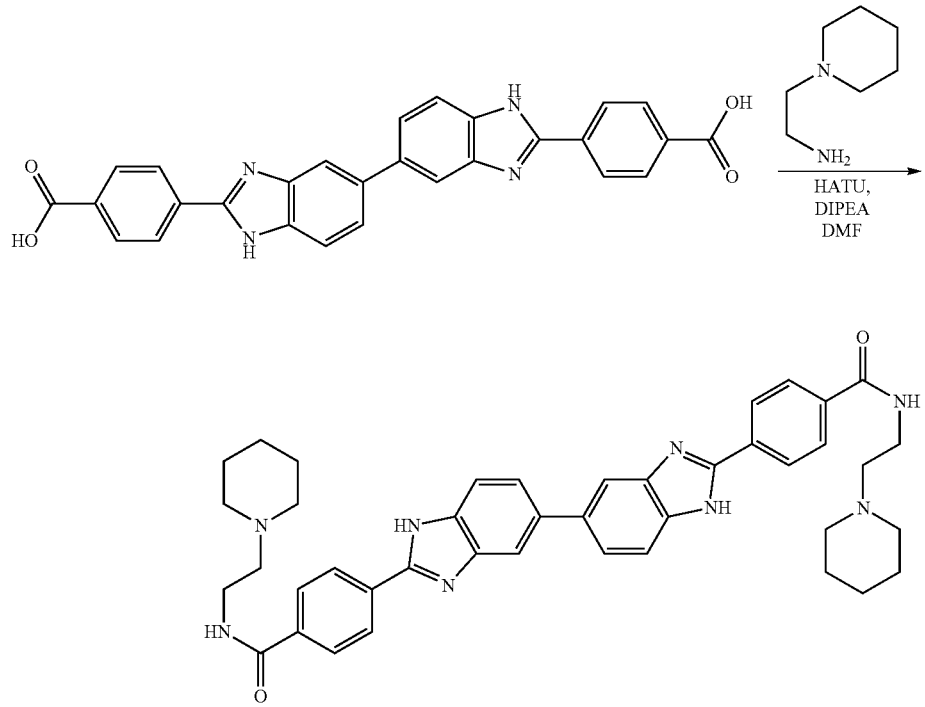

To a solution of 4,4'-(1H,1'H-[5,5'-bibenzo[d]imidazole]-2,2'-diyl)dibenzoic acid (0.10 g, 0.21 mmol) in DMF (5.0 mL) at 0° C., was added HATU (0.17 g, 0.46 mmol), DIPEA (0.30 mL, 1.68 mmol) and the reaction mixture was stirred for 10 minutes. 2-(piperidin-1-yl)ethanamine (60 mg, 0.46 mmol) was added to the above mixture in one lot at 0° C. and the reaction mixture was allowed to warm to room temperature and stirred for 8 hours. The reaction mixture was poured onto ice, whereupon the product precipitated. The precipitated product was collected by filtration under vacuum, washed with methanol (10 mL), and dried to obtain the crude product. The crude product was refluxed in methanol (20 mL) and collected by filtration under vacuum when hot, washed with methanol (10 mL) and dried to obtain 4,4'-(1H,1'H-[5,5'-bibenzo[d]imidazole]-2,2'-diyl)bis(N-(2-(piperidin-1-yl)ethyl)benzamide). 1H NMR (CD3OD 400 MHz) δ: 8.14 (d, J=8.4 Hz, 4H), 8.03 (d, J=8.4 Hz, 4H), 7.91 (s, 2H), 7.77 (s, 4H), 3.71 (t, J=6.0 Hz, 4H), 3.63-3.60 (m, 4H), 3.27 (t, J=6.0 Hz, 4H), 2.91 (t, J=1.2 Hz, 4H), 1.93-1.67 (m, 10H), 1.46-1.43 (m, 2H). UPLC MS m/z=695 [M+H]+.

Example 102

Synthesis of 4,4'-(1H,1'H-[5,5'-bibenzo[d]imidazole]-2,2'-diyl)bis(N-(2-(4-methylpiperazin-1-yl)ethyl)benzamide)

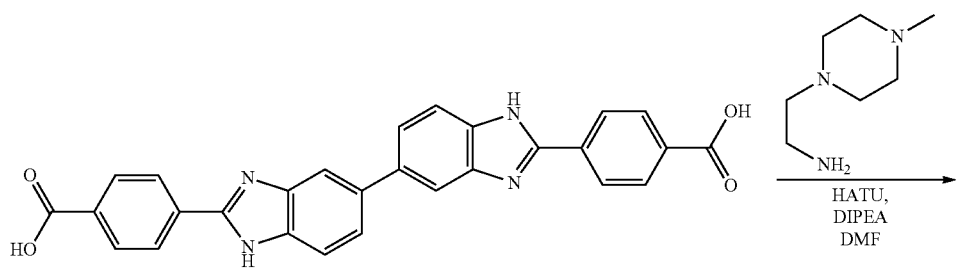

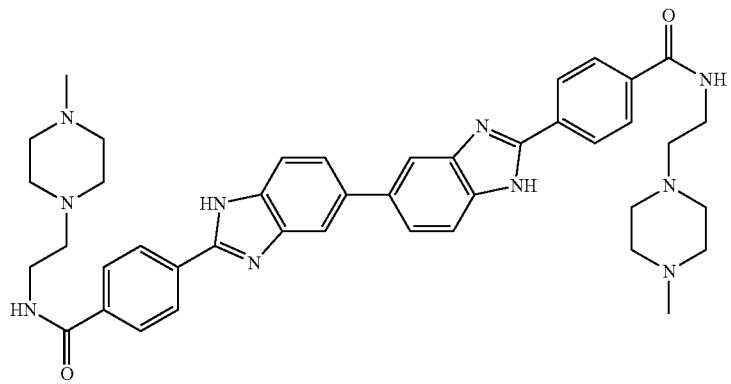

To a solution of 4,4'-(1H,1'H-[5,5'-bibenzo[d]imidazole]-2,2'-diyl)dibenzoic acid (100 mg, 0.2 mmol) in DMF (3 ml) was added HATU (170 mg, 0.45 mmol) and DIPEA (180 µL, 1.0 mmol). The mixture was stirred for 5 minutes before adding 2-(4-methyl-piperazin-1-yl) ethylamine (63 mg, 0.44 mmol) and stirring overnight. The solvent was removed under vacuum and the residue washed with ether to remove trace amounts of solvent. The crude material was purified using a C-18 column and a gradient of 0-100% MeOH in water containing 0.1% TFA. 1H NMR (CD3OD, 400 MHz) δ: 8.28 (d, J=8.6 Hz, 4H), 8.16 (d, J=8.6 Hz, 4H), 8.11 (m, 2H), 7.97-7.93 (m, 4H), 3.68 (t, J=6.2 Hz, 4H), 3.46-3.35 (br s, 8H), 3.27-3.02 (m, 8H), 2.97 (t, J=6.2 Hz, 4H), 2.91 (s, 6H), MS (MALDI): m/z=725 [M+H]+.

Examples 103-104 Intentionally Skipped

Example 105

Synthesis of 3,3'-(1H,1'H-[5,5'-bisbenzo[d]imidazole]-2,2'-diyl)dibenzonitrile

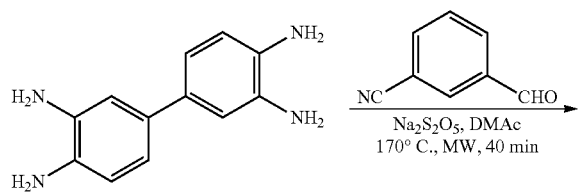

In a microwave vial, a mixture of [1,1'-biphenyl]-3,3',4,4'-tetraamine (0.10 g, 0.46 mmol), 3-cyanobenzaldehyde (0.135 g, 1.027 mmol) and sodium metabisulfite (0.195 g, 1.027 mmol) in anhydrous DMAc (5.0 mL) was heated at 170° C. for 40 min. The reaction mixture was cooled to room temperature and slowly poured into ice cold water (100 mL). The precipitated product was collected by filtration under vacuum and the crude product was recrystallized from hot ethanol and dried to obtain 3,3'-(1H,1'H-[5,5'-bibenzo[d]imidazole]-2,2'-diyl)dibenzonitrile. 1H NMR (400 MHz, DMSO-d6) δ: 13.15 (brs, 2H), 8.60 (s, 2H), 8.53 (d, J=8.0 Hz, 2H), 7.98 (d, J=7.6 Hz, 2H), 7.91 (bs, 2H), 7.81 (t, J=7.6 Hz, 2H); 7.74 (d, J=8.4 Hz, 2H), 7.62 (dd, J=1.2 Hz, 8.4 Hz, 2H). MS (ESI+APCl): m/z=437 [M+H]+.

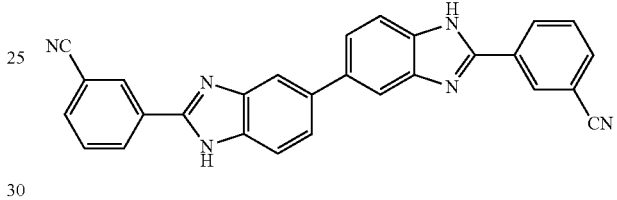

Example 106

Synthesis of 1,1'-dimethyl-2,2'-bis(4-aminophenyl)-1H,1'H-5,5'-bibenzimidazole (Compound 122) and 1,3'-dimethyl-2,2'-bis(4-aminophenyl)-1H,3'H-5,5'-bibenzimidazole (Compound 121)

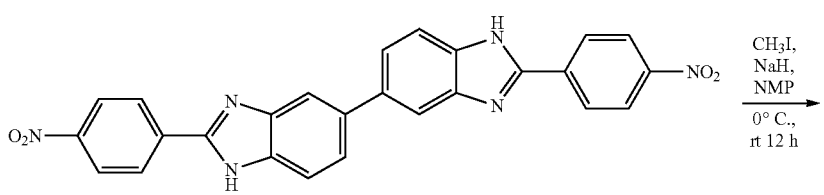

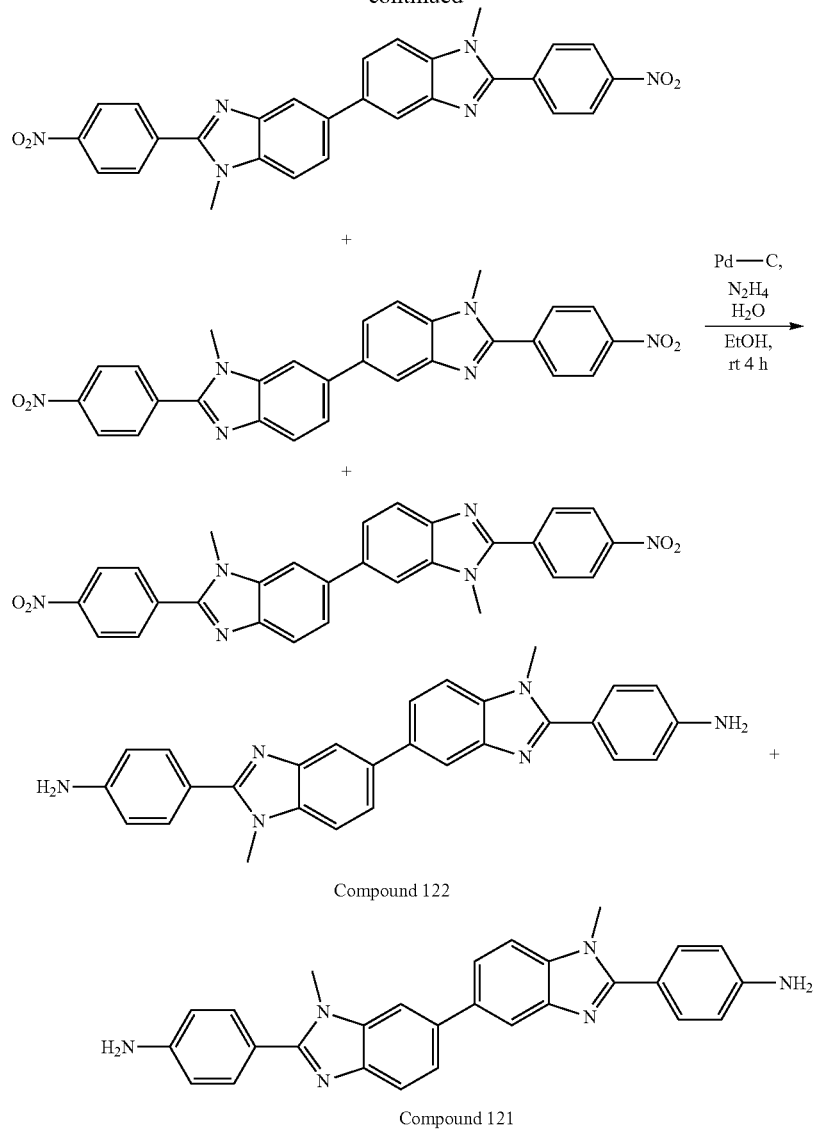

Compound 122

Compound 121

Step 1. Synthesis of Intermediate Nitro Compounds (Mixture of Three Regioisomers)

To a solution of 2,2'-bis(4-nitrophenyl)-1H,1'H-5,5'-bibenzo[d]imidazole (0.5 g, 1.05 mmol) in anhydrous NMP (10 mL), at 0° C. was added NaH (60% dispersion in oil, 0.12 g, 3.15 mmol) in a portion wise manner after 10 minutes methyl iodide (0.29 g, 2.10 mmol) was added dropwise over 5 min. After complete addition, the reaction mixture was warmed to room temperature and stirred for 12 hours. The reaction mixture was slowly poured into ice-cold water (50 mL) and the precipitated material was collected by filtration under vacuum and dried. The crude product was crystallized from hot ethanol, filtered and dried under vacuum to obtain an inseparable mixture of the three dinitro isomers. 1H NMR (400 MHz, DMSO-d6): 8.42 (d, J=8.0 Hz, 4H), 8.22 (d, J=8.0 Hz, 4H), 8.13 (d, J=16.8 Hz, 1H), 8.07 (d, J=4.0 Hz, 1H), 7.85-7.70 (m, 4H) 4.06 (d, J=4.4 Hz, 3H), 4.00 (s, 3H), MS (ESI): m/z=505 [M+H]+.

Step 2. Synthesis of 1,1'-dimethyl-2,2'-bis(4-aminophenyl)-1H,1'H-5,5'-bibenzimidazole (Compound 122) and 1,3'-dimethyl-2,2'-bis(4-aminophenyl)-1H, 3'H-5,5'-bibenzimidazole (Compound 121)

To a solution of the product of Step 1 (0.50 g, 0.99 mmol) in EtOH (50 mL) under argon atmosphere, was added hydrazine monohydrate (80% aqueous solution, 3.0 mL), 10% Pd/C (100 mg) at room temperature and the reaction mixture was stirred for 12 hours. The reaction mixture was filtered through a pad of elite under vacuum and the pad was washed with methanol:dichloromethane (1:9; 100 mL). The filtrate was concentrated under vacuum to obtain the product as a mixture of three isomers. The mixture was purified by silica-gel chromatography [5% MeOH in dichloromethane; isocratic elution] to afford the two title compounds (third isomer not isolated). Compound 122-1: 1H NMR (400 MHz, DMSO-d6): 7.90 (s, 2H), 7.66-7.57 (m, 8H), 6.71 (d, J=8.4 Hz, 4H), 5.62 (s, 4H), 3.93 (s, 6H), MS (ESI): m/z=445 [M+H]+. Compound 121: 1H NMR (400 MHz, DMSO-d6): 7.95 (s, 1H), 7.86 (s, 1H), 7.65-7.54 (m, 8H), 6.71 (dd, J=1.2 Hz, 8.4 Hz, 4H), 5.62 (d, J=3.2 Hz, 4H), 3.92 (s, 3H). MS (ESI): m/z=445 [M+H]+.

Example 108

Synthesis of 2,2'-(1H,1'H-[5,5'-bibenzo[d]imidazole]-2,2'-diylbis(4,1-phenylene))diacetamide (Compound 124)

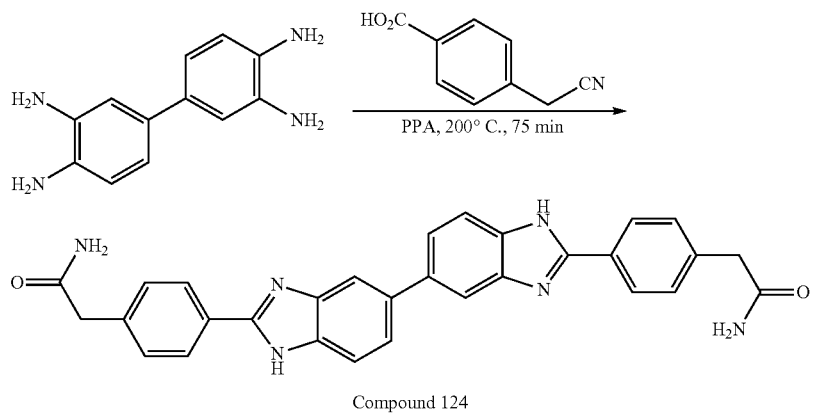

Compound 124

A mixture of [1,1'-biphenyl]-3,3',4,4'-tetraamine (0.1 g, 0.46 mmol), 4-(cyanomethyl)benzoic acid (0.15 g, 0.98 mmol), and PPA (5.0 mL) was stirred at 200° C. for 75 min. The reaction mixture was poured into crushed ice, whereupon the product precipitated. The product was collected by filtration under vacuum, washed with aqueous K2CO3 solution (50 mL), water (25 mL) and dried under vacuum. The crude product was triturated with hot ethanol and dried under vacuum to obtain 2,2'-(1H,1'H-[5,5'-bibenzo[d]imidazole]-2,2'-diylbis(4,1-phenylene))diacetamide. 1H NMR (400 MHz, DMSO-d6): δ 12.95 (brs, 2H), 8.14 (d, J=8.0 Hz, 4H), 7.94-7.72 (m, 4H), 7.57-7.55 (m, 4H), 7.45 (d, J=8.4 Hz, 4H), 6.96 (s, 2H), 3.47 (s, 4H). MS (ESI+APCl) m/z 501 [M+H]+.

Example 109

Synthesis of tert-butyl 4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazine-1-carboxylate

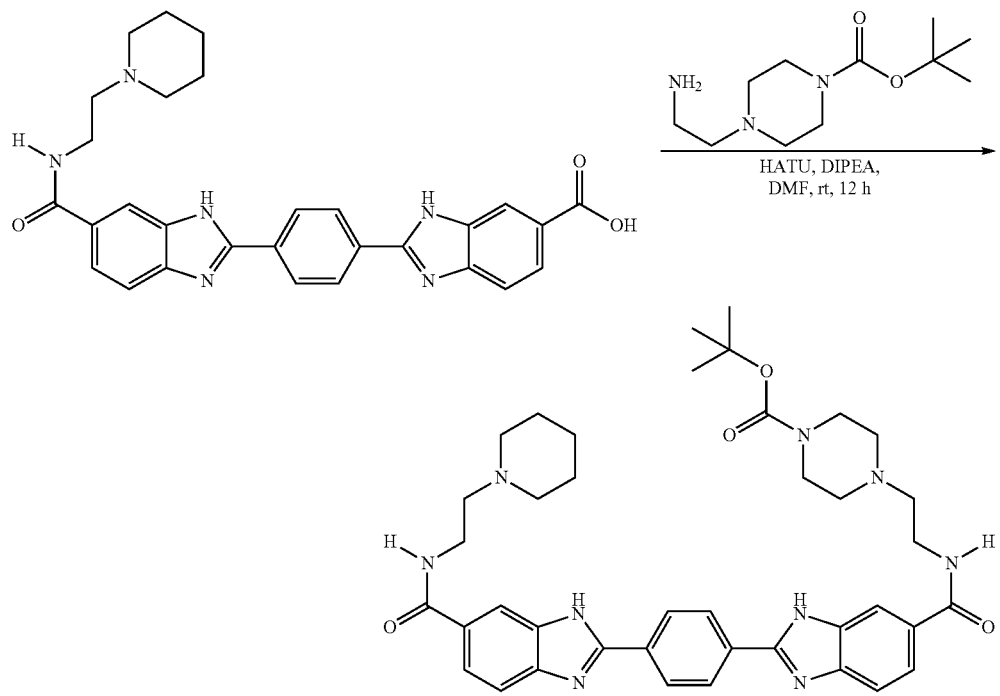

To a suspension of 2-(4-(6-((2-(piperidin-1-yl)ethyl)carbamoyl)-1H-benzo[d]imidazol-2-yl)phenyl)-1H-benzo[d]imidazole-6-carboxylic acid (0.20 g, 0.39 mmol; crude) in DMF (5 mL) at 0° C., was added HATU (0.18 g, 0.47 mmol), DIPEA (0.13 mL, 0.78 mmol) and tert-butyl 4-(2-aminoethyl)piperazine-1-carboxylate (71 mg, 0.31 mmol) to the above mixture at 0° C. and the reaction mixture was allowed to warm to room temperature and stirred for 12 h. The reaction mixture was poured in to water and stirred for 15 mins, whereupon the product precipitated. The product was purified by prep HPLC on an X-bridge C18@10 μm (30×150 mm, 10 μm) column; mobile phase, A=0.1% TFA in H2O and B=CH3CN; Flow rate: 40 mL/min, Injection volume: 400 μL, Runtime: 20 min, gradient: 90-65% A, 10-35% B (0.0-15 min); (UV detection at 220 nm). Fractions containing only the pure product were combined and concentrated under reduced pressure to obtain tert-butyl 4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazine-1-carboxylate.

Example 110

Synthesis of N-(2-(piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (Compound 126)

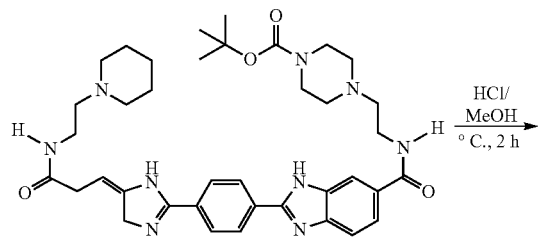

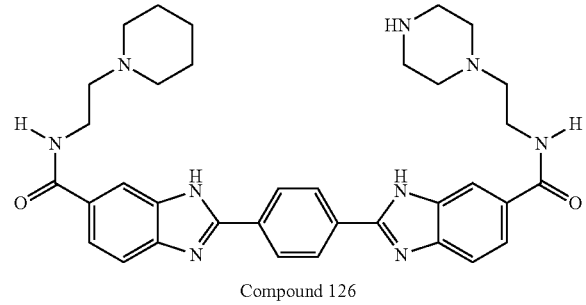

Compound 126

To a suspension of tert-butyl 4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazine-1-carboxylate (35 mg, 0.05 mmol) in MeOH (1.0 mL) at 0° C., was added HCl (3.0 M in MeOH, 1.0 mL), and the reaction mixture was stirred for 2 h. The reaction mixture was concentrated under vacuum to obtain the N-(2-(piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide hydrochloride. 1H NMR (MeOD, 400 MHz) δ: 8.41 (s, 4H), 8.39 (d, J=16.4 Hz, 2H), 8.10-8.04 (m, 2H), 7.86 (d, J=8.8 Hz, 2H), 3.82 (t, J=10.8 Hz, 2H), 3.77 (t, J=12.0 Hz, 2H), 3.65-3.60 (m, 8H), 3.46 (brs, 2H), 3.32 (t, J=12.0 Hz, 2H), 3.26 (brs, 2H), 2.97 (t, J=24 Hz, 2H), 1.92-1.88 (m, 2H), 1.79-1.71 (m, 3H), 1.52-1.44 (m, 1H). MS (ESI+APCl) m/z 620.1 [M+H]+.

Example 111

Synthesis of 2,2'-bis(4-(pyrrolidin-1-ylmethyl)phenyl)-1H,1'H-5,5'-bibenzo[d]imidazole (Compound 127)

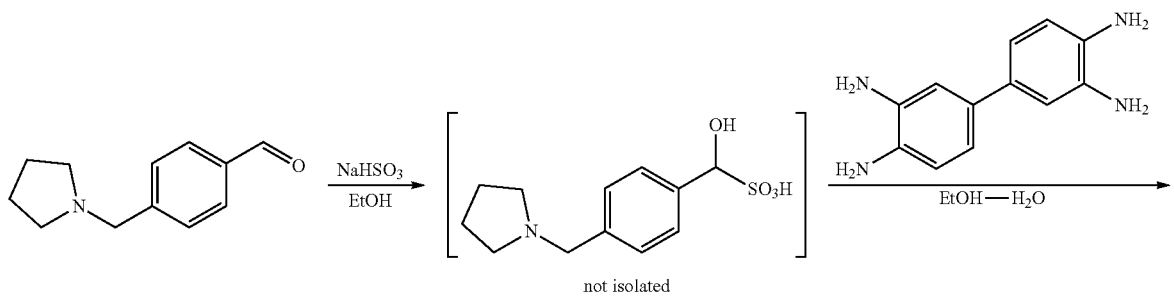

not isolated

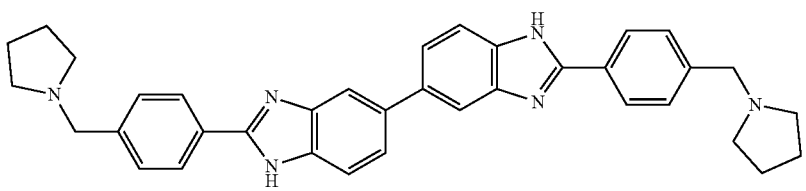

A solution of 4-(pyrrolidin-1-ylmethyl)benzaldehyde (105 mg, 0.56 mmol) in EtOH was cooled to 0° C. and a solution of sodium bisulfite (60 mg, 0.58 mmol) in water (1.5 ml) added dropwise. The cold-bath was removed and the mixture stirred for 1 h before adding 3,3'-diaminobenzidine tetrahydrochloride (100 mg, 0.28 mmol) and water (1.5 ml) followed by heating at reflux for 3 h. After cooling, the mixture was filtered and the yellow powder washed with water then dried over vacuum to give 55 mg of the title compound. 1H NMR (DMSO, 400 MHz) δ: 13.1 (br s, 2H), 8.30 (d, 4H), 7.96 (br s, 2H), 7.80 (br s, 2H), 7.72 (d, 4H), 7.68 (br s, 2H), 4.42 (s, 4H), 3.25 (br s, 8H), 2.0 (br s, 8H)

Example 112

Synthesis of Glycine-Based Dimers (Compounds 128-132)

To a solution of N-(2-(dimethylamino)ethyl)-4-(2'-(4-((2-(hex-5-yn-1-yl(methyl)amino)ethyl)carbamoyl)phenyl)-1H,1'H-[5,5'-bibenzo[d]imidazol]-2-yl)benzamide (E-1148, 5 mg, 0.00735 mmol) in anhydrous DMF (700 ul) was added Cu(I) catalyst (4 mg, 0.0067 mmol; prepared as described by Ozcubukcu et al Org. Lett., 2009, 11, 4680-4683), peptoid linker (0.5 equiv.; see Preparation 10) and DIPEA (30 ul, 0.172 mmol). The mixture was sonicated to dissolve all the catalyst and form a homogeneous solution then heated in a microwave at 110° C. for 2 h. The solvent was removed in-vacuo and the crude material purified by reverse phase HPLC using a gradient of 0-100% MeOH in water containing 0.1% TFA. Purity was determined using analytical HPLC and mass measured using MALDI. MS (MALDI, [M+H]+); Compound 128=1857, Compound 129=1956, Compound 130=2055, Compound 131=2154 and Compound 132=2253.

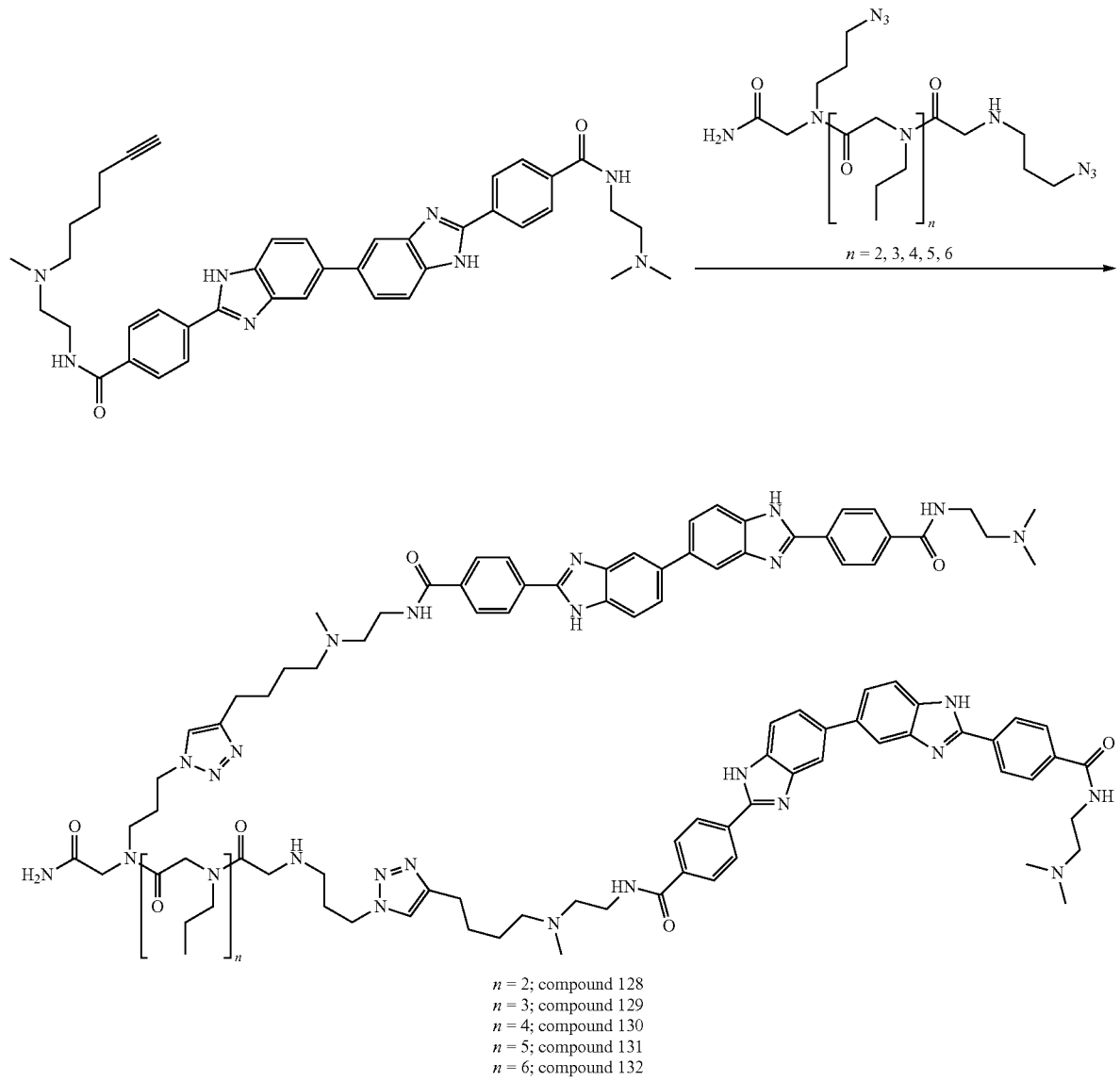

n = 2; compound 128
n = 3; compound 129
n = 4; compound 130
n = 5; compound 131
n = 6; compound 132

Example 113

Synthesis of Alanine-Based Dimers (Compounds 133-136)

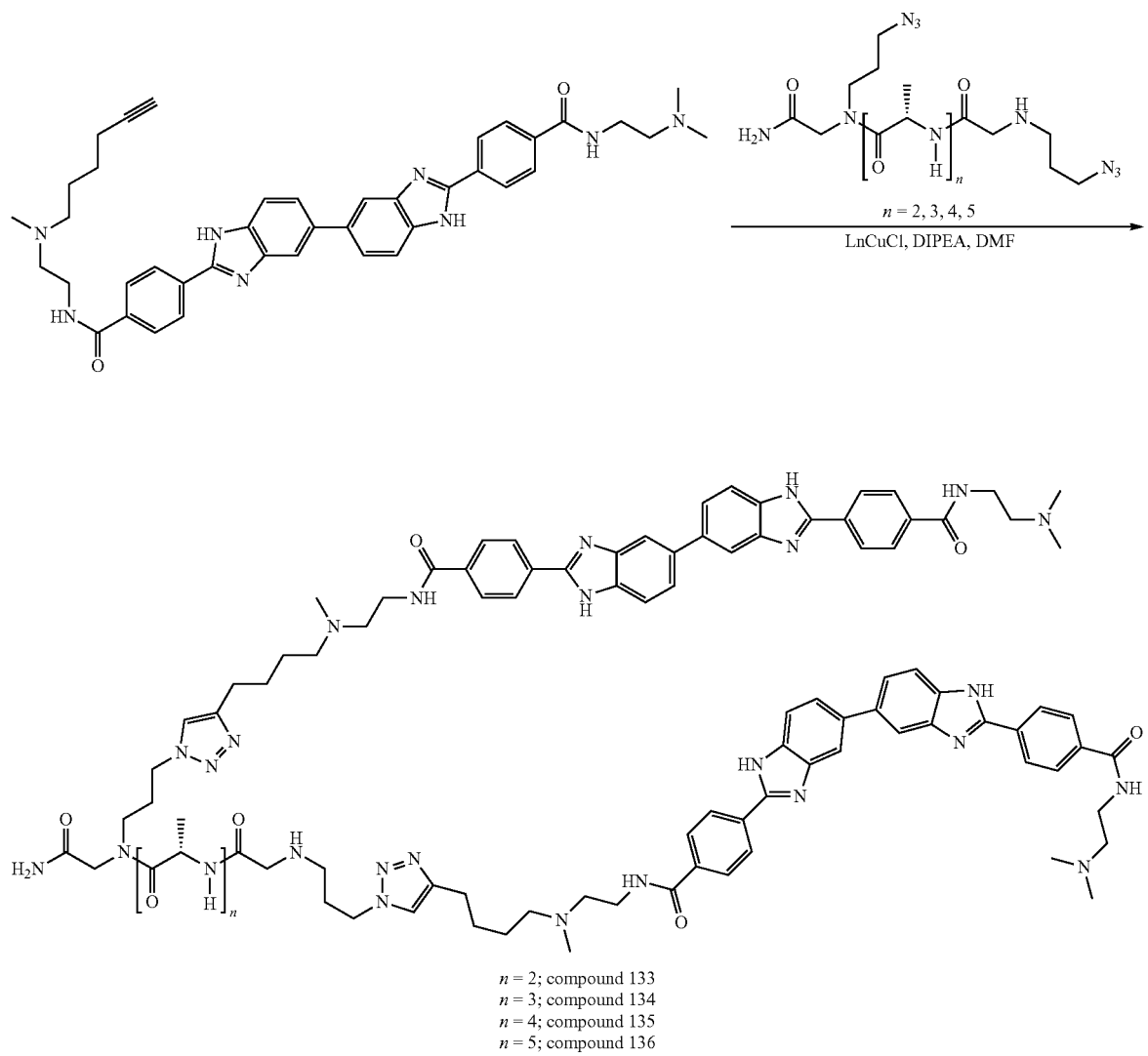

n = 2; compound 133
n = 3; compound 134
n = 4; compound 135
n = 5; compound 136

To a solution of N-(2-(dimethylamino)ethyl)-4-(2'-(4-((2-(hex-5-yn-1-yl(methyl)amino)ethyl)carbamoyl)phenyl)-1H,1'H-[5,5'-bibenzo[d]imidazol]-2-yl)benzamide (compound 114, 5 mg, 0.00735 mmol) in anhydrous DMF (700 ul) was added Cu(I) catalyst 1 (4 mg, 0.0067 mmol; prepared as described by Ozcubukcu et al Org. Lett., 2009, 11, 4680-4683), the peptide linker (0.5 equiv.; see Preparation 9) and DIPEA (30 ul, 0.172 mmol). The mixture was sonicated to dissolve all the catalyst and form a homogeneous solution then heated in a microwave at 110° C. for 2 h. The solvent was removed in-vacuo and the crude material purified by reverse phase HPLC using a gradient of 0-100% MeOH in water containing 0.1% TFA. Purity was determined using analytical HPLC and mass measured using MALDI. MS (MALDI, [M+H]+); Compound 133=1800, Compound 134=1871, Compound 135=1942, Compound 136=2013.

Example 114

Synthesis of N-(2-(2-((1-((6S,9S,12S,15S)-4-(2-amino-2-oxoethyl)-22-(4-((2-(2-(4-(2'-(4-((2-(dimethylamino)ethyl)carbamoyl)phenyl)-3H,3'H-[5,5'-bibenzo[d]imidazol]-2-yl)-N-methylbenzamido)ethoxy)ethoxy)methyl)-1H-1,2,3-triazol-1-yl)-6,7,9,10,12,13,15,16-octamethyl-5,8,11,14,17-pentaoxo-4,7,10,13,16,19-hexaazadocosyl)-1H-1,2,3-triazol-4-yl)methoxy)ethoxy)ethyl)-4-(2'-(4-((2-(dimethylamino)ethyl)carbamoyl)phenyl)-3H,3'H-[5,5'-bibenzo[d]imidazol]-2-yl)-N-methylbenzamide (Compound 430)

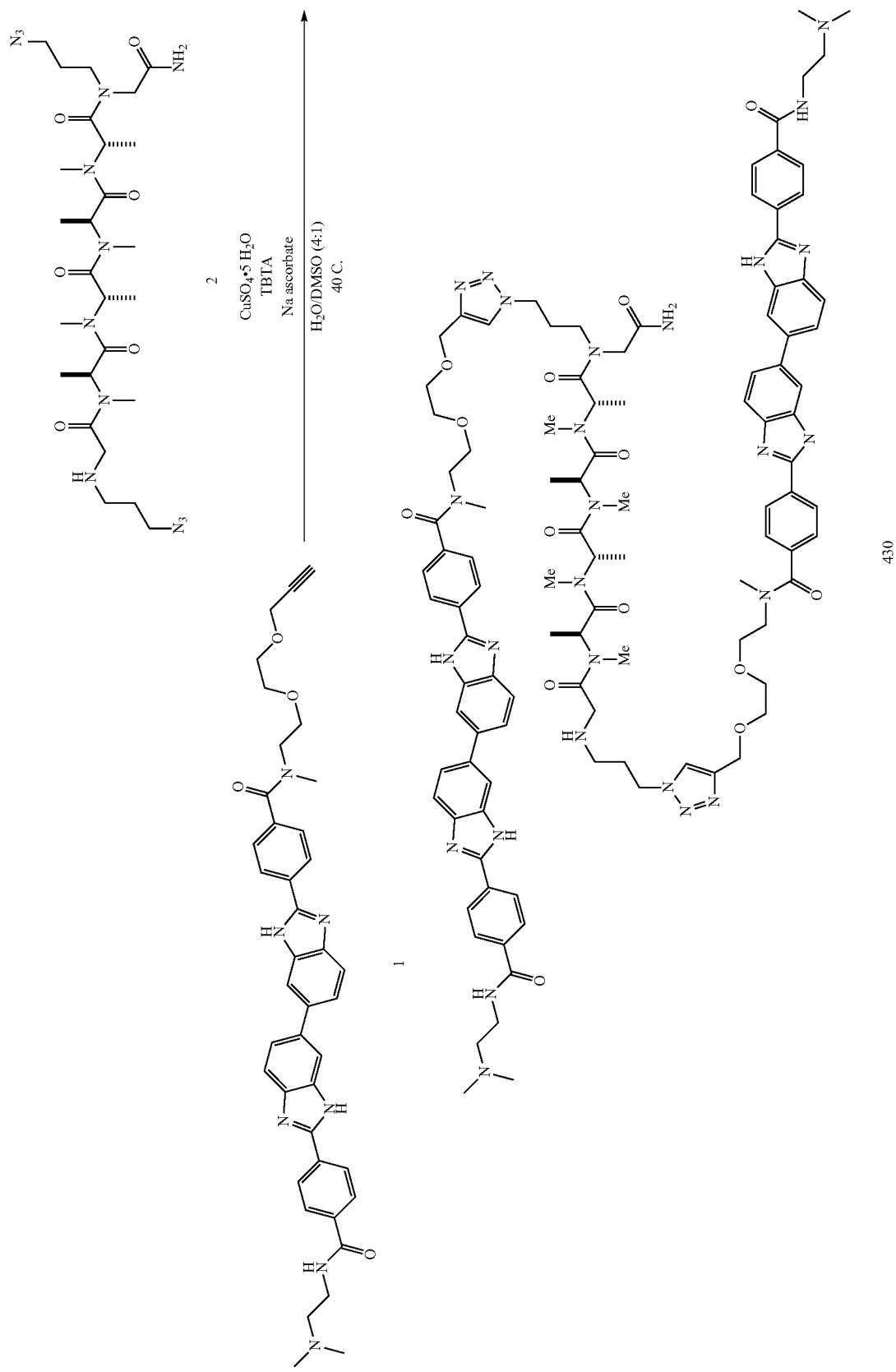

To a stirred solution of 4-(2'-(4-((2-(dimethylamino)ethyl) carbamoyl)phenyl)-3H,3'H-[5,5'-bibenzo[d]imidazol]-2-yl)-N-methyl-N-(2-(2-(prop-2-yn-1-yloxy)ethoxy)ethyl) benzamide 1 (120 uL, 0.1 M in DMSO) was added (S)-N-(2-amino-2-oxoethyl)-2-((2S,5S,8S)-15-azido-N,2,3,5,6,8,9-heptamethyl-4,7,10-trioxo-3,6,9,12-tetraazapentadecanamido)-N-(3-azidopropyl)propanamide 2 (60 uL, 0.1 M in DMSO). Tris[(1-benzyl-1H-1,2,3-triazol-4-yl)methyl]amine (TBTA) (60 uL, 6×10$^{-6}$ mol in DMSO) was added with sodium ascorbate solution (2.4×10$^{-5}$ mol in 760 uL water). Copper sulfate pentahydrate (1.2×10$^{-6}$ mol in

Example 115

Synthesis of (S)—N-(2-amino-2-oxoethyl)-N-(3-(4-((2-(2-(4-(2'-(4-((2-(dimethylamino)ethyl)carbamoyl)phenyl)-3H,3'H-[5,5'-bibenzo[d]imidazol]-2-yl)-N-methylbenzamido)ethoxy)ethoxy)methyl)-1H-1,2,3-triazol-1-yl)propyl)-1-((3-(4-((2-(2-(4-(2'-(4-((2-(dimethylamino)ethyl)carbamoyl)phenyl)-3H,3'H-[5,5'-bibenzo[d]imidazol]-2-yl)-N-methylbenzamido) ethoxy)ethoxy)methyl)-1H-1,2,3-triazol-1-yl)propyl) glycyl-L-prolyl-L-prolyl-L-prolyl)pyrrolidine-2-carboxamide (Compound 432)

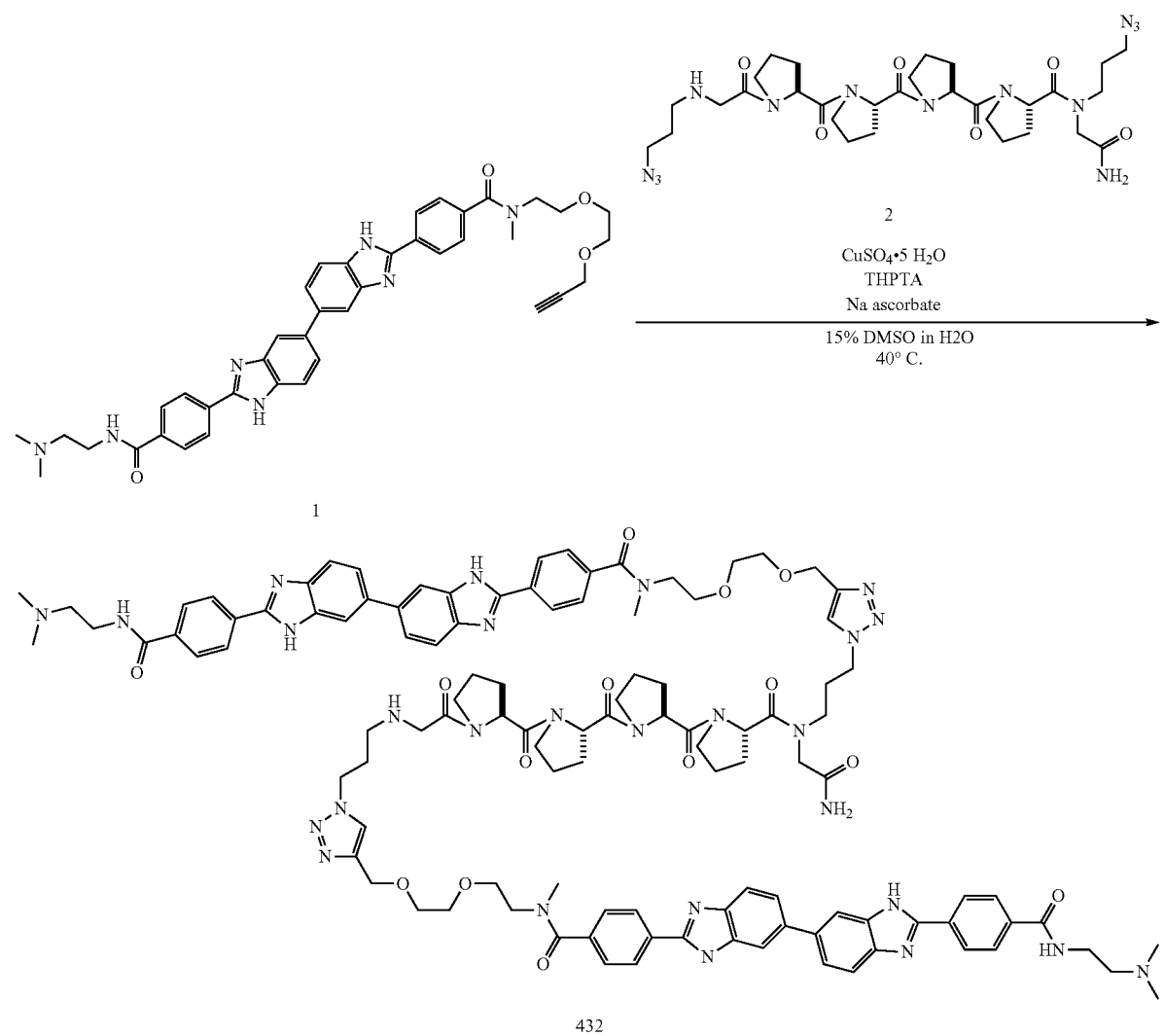

200 uL water) was added and the reaction heated to 40° C. for 24 hours. Crude analysis by LCMS showed high conversion to product. Water (3 mL) was added, the reaction mixture was filtered, and the product purified via preparatory reverse-phase HPLC. Concentration of the fractions containing product afforded title compound 430. LCMS: m/z=669.4 [(M+3H$^+$)/3] MALDI: m/z=2005.1653 [M$^+$]

Compound 431 was prepared in the same manner as compound 430. LCMS: m/z=728.1 [(M+3H$^+$)/3] MALDI: m/z=2181.1702 [M$^+$]

To a stirred solution of 4-(2'-(4-((2-(dimethylamino)ethyl) carbamoyl)phenyl)-1H,1'H-[5,5'-bibenzo[d]imidazol]-2-yl)-N-methyl-N-(2-(2-(prop-2-yn-1-yloxy)ethoxy)ethyl) benzamide 1 (120 uL, 0.1 M in DMSO) was added (S)-N-(2-amino-2-oxoethyl)-N-(3-azidopropyl)-1-((3-azidopropyl)glycyl-L-prolyl-L-prolyl-L-prolyl)pyrrolidine-2-carboxamide 2 (60 uL, 0.1 M in DMSO). Tris(3-hydroxypropyltriazolylmethyl)amine (THPTA) (32.0 mg) and copper sulfate pentahydrate (3.6 mg) were dissolved in water (6.12 mL) and sodium ascorbate (57 mg) added. This mixture was stirred for 3 minutes and then an aliquot (1.02 mL, $2.4E^{-6}$ mol copper sulfate, $1.2E^{-5}$ mol THPTA, $4.80E^{-5}$ mol sodium ascorbate) of it was added to the mixture of alkyne and bis-azide. The reaction mixture was stirred and heated to 40° C. for 24 hours. Crude analysis by LCMS showed high conversion to product. Water (3 mL) added, filtered, and purified via preparatory reverse-phase HPLC. Concentration of the fractions containing product afforded title compound 432. LCMS: m/z=685.4 [(M+3H$^+$)/3] MALDI: m/z=2053.3464 [M$^+$]

Compounds 433, 437, and 438 were prepared in the same manner as compound 432.

Compound 433: LCMS: m/z=744.1 [(M+3H$^+$)/3] MALDI: m/z=2229.3584 [M$^+$]

Compound 437: LCMS: m/z=620.6 [(M+3H$^+$)/3] MALDI: m/z=1859.0642 [M$^+$]

Compound 438: LCMS: m/z=679.4 [(M+3H$^+$)/3] MALDI: m/z=2035.1136 [M$^+$]

Example 116

Synthesis of (S)-N-(2-amino-2-oxoethyl)-N-(3-(4-((4-(2'-(4-((2-(dimethylamino)ethyl)carbamoyl)phenyl)-3H,3'H-[5,5'-bibenzo[d]imidazol]-2-yl)benzamido)methyl)-1H-1,2,3-triazol-1-yl)propyl)-1-((3-(4-((4-(2'-(4-((2-(dimethylamino)ethyl)carbamoyl)phenyl)-3H,3'H-[5,5'-bibenzo[d]imidazol]-2-yl)benzamido)methyl)-1H-1,2,3-triazol-1-yl)propyl)glycyl-L-prolyl-L-prolyl-L-prolyl)pyrrolidine-2-carboxamide (Compound 434)

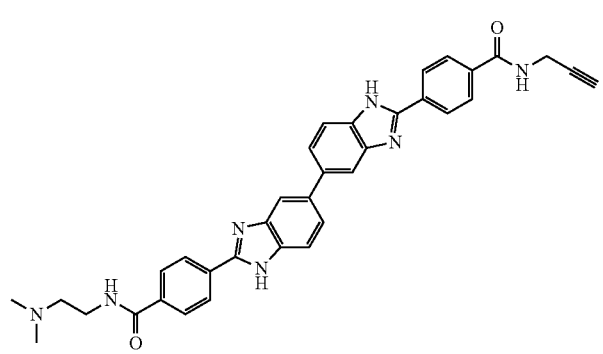

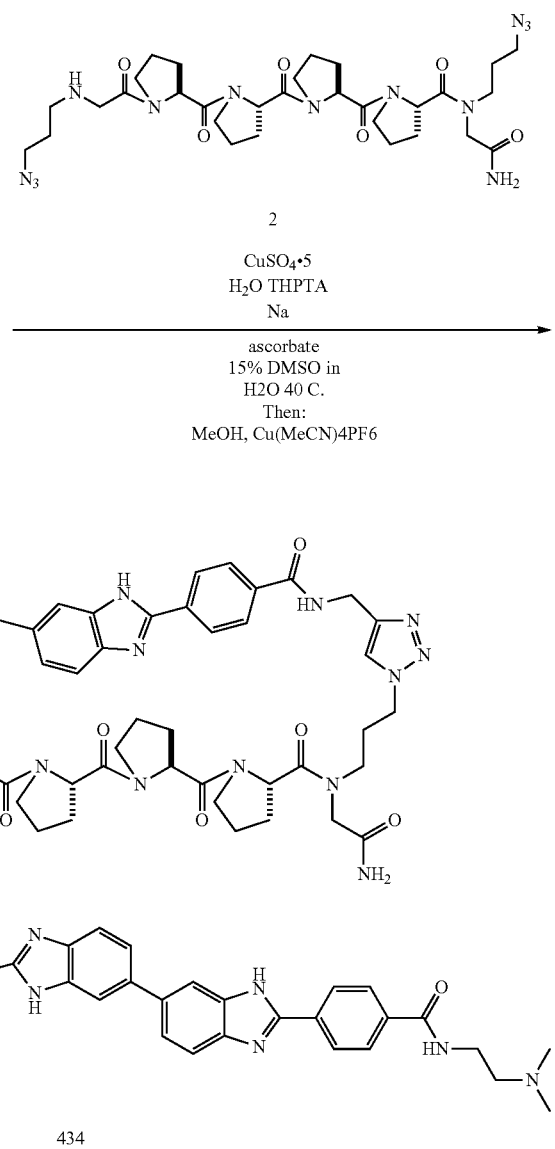

To a stirred solution of N-(2-(dimethylamino)ethyl)-4-(2'-(4-(prop-2-yn-1-ylcarbamoyl)phenyl)-1H,1'H-[5,5'-bibenzo[d]imidazol]-2-yl)benzamide 1 (120 uL, 0.1 M in DMSO) was added (S)-N-(2-amino-2-oxoethyl)-N-(3-azidopropyl)-1-((3-azidopropyl)glycyl-L-prolyl-L-prolyl-L-prolyl)pyrrolidine-2-carboxamide 2 (60 uL, 0.1 M in DMSO). Tris(3-hydroxypropyltriazolylmethyl)amine (THPTA) (32.0 mg)

and copper sulfate pentahydrate (3.6 mg) were dissolved in water (6.12 mL) and sodium ascorbate (57 mg) added. This mixture was stirred for 3 minutes and then an aliquot (1.02 mL, $2.4E^{-6}$ mol copper sulfate, $1.2E^{-5}$ mol THPTA, $4.80E^{-5}$ mol sodium ascorbate) of it was added to the mixture of alkyne and bis-azide. The reaction mixture was stirred and heated to 40° C. for 24 hours. Crude analysis by LCMS showed zero conversion to product. The reaction was observed to have gelled overnight and MeOH was added to decrease viscosity. Additionally, $Cu(MeCN)_4PF_6$ (5 mg, $1.34E^{-5}$ mol) was added and the reaction kept at 40° C. for another 24 hour period. Crude LCMS showed some conversion to product. Water (3 mL) added, filtered, and purified via preparatory reverse-phase HPLC. Concentration of the fractions containing product afforded title compound 434. LCMS: m/z=617.4 [(M+3H$^+$)/3] MALDI: m/z=1849.1777 [M$^+$]

Compounds 435 and 436 were prepared in the same manner as compound 434.

Compound 435: LCMS: m/z=636.0 [(M+3H$^+$)/3] MALDI: m/z=1905.0106 [M$^+$]

Compound 436: MALDI: m/z=1973.0516 [M$^+$]

Example 117

Synthesis of N-((7R,10R,13R,16R)-5-(2-amino-2-oxoethyl)-1-(4-(2'-(4-((2-(dimethylamino)ethyl)carbamoyl)phenyl)-1H,1'H-[5,5'-bibenzo[d]imidazol]-2-yl)phenyl)-7,10,13,16-tetramethyl-1,6,9,12,15,18-hexaoxo-2,5,8,11,14,17-hexaazanonadecan-19-yl)-N-(2-aminoethyl)-4-(2'-(4-((2-(dimethylamino)ethyl)carbamoyl)phenyl)-1H,1'H-[5,5'-bibenzo[d]imidazol]-2-yl)benzamide (Compound 443 or Compound 444), 4-(2'-(4-(((7R,10R,13R,16R)-5-(2-amino-2-oxoethyl)-1-(4-(2'-(4-((2-(dimethylamino)ethyl)carbamoyl)phenyl)-1H,1'H-[5,5'-bibenzo[d]imidazol]-2-yl)phenyl)-7,10,13,16-tetramethyl-1,6,9,12,15,18-hexaoxo-2,5,8,11,14,17,20-heptaazadocosan-22-yl)carbamoyl)phenyl)-1H,1'H-[5,5'-bibenzo[d]imidazol]-2-yl)-N-(2-(dimethylamino)ethyl)benzamide (Compound 443 or Compound 444)

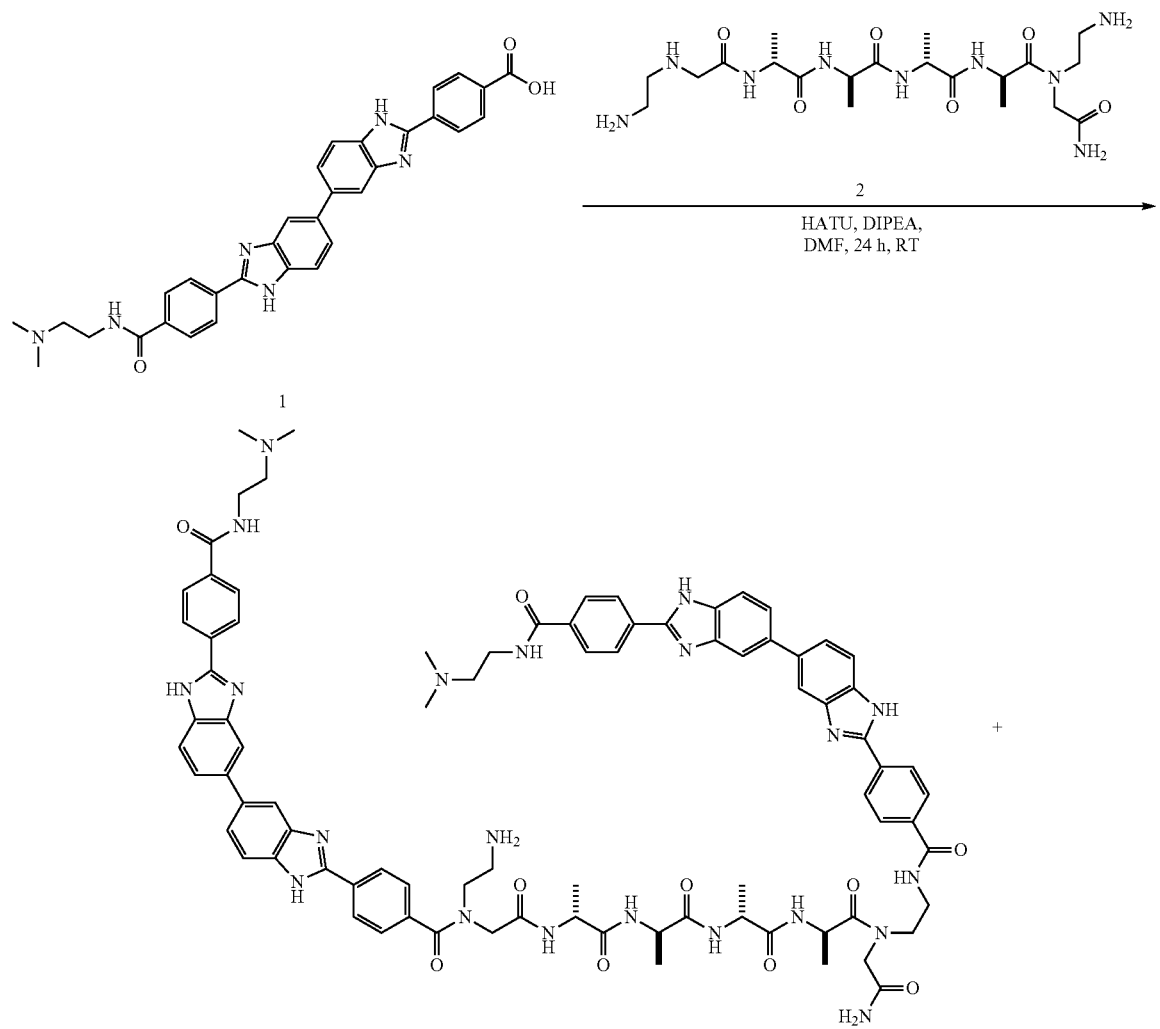

-continued

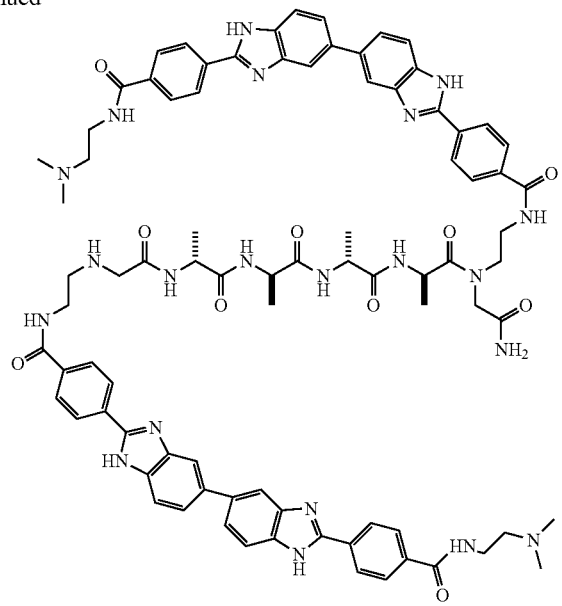

443 or 444

To a stirred solution of 4-(2'-(4-((2-(dimethylamino)ethyl)carbamoyl)phenyl)-1H,1'H-[5,5'-bibenzo[d]imidazol]-2-yl)benzoic acid 1 (12 mg, $2.20E^{-5}$ mol, 2.2 equiv.) in DMF (100 uL) was added 1-[Bis(dimethylamino)methylene]-1H-1,2,3-triazolo[4,5-b]pyridinium 3-oxid hexafluorophosphate (HATU) (9 mg, $2.20E^{-5}$ mol, 2.2 equiv.) and N,N-Diisopropylethylamine (DIPEA) (18 uL, $1.00E^{-4}$ mol, 10 equiv.). After this mixture was stirred at RT for 5 minutes, a solution of (R)-2-((2R,5R,8R)-14-amino-2,5,8-trimethyl-4,7,10-trioxo-3,6,9,12-tetraazatetradecanamido)-N-(2-amino-2-oxoethyl)-N-(2-aminoethyl)propanamide 2 (100 uL, 0.1 M in DMF) was added and the reaction allowed to stir at RT for 24 hours. Crude LCMS showed the formation of all three products. Water (3 mL) was added, the reaction filtered, and purified via preparatory reverse-phase HPLC. Concentration of the fractions containing product afforded title compounds 443 (first eluting dimer on HPLC), 444 (second eluting dimer on HPLC)

443: MALDI: m/z=1554.7848 [M⁺]
444: MALDI: m/z=1554.8333 [M⁺]

Compounds 447, 448, 405, and 206 were prepared in the same manner as compounds 443 and 444.

Compound 447 (first eluting dimer on HPLC): MALDI: m/z=1528.6985 [M⁺]

Compound 448 (second eluting dimer on HPLC): MALDI: m/z=1528.6613 [M⁺]

Compound 405 MS (ESI+APCI) m/z 718 [(M+2H)/2]⁺.

Compound 206: MS (ESI+APCI) m/z=705 [M+H]⁺.

Example 118

Synthesis of (S)—N-(2-amino-2-oxoethyl)-N-(3-(4-((4-(2'-(4-((2-(dimethylamino)ethyl)carbamoyl)phenyl)-3H,3'H-[5,5'-bibenzo[d]imidazol]-2-yl)benzamido)methyl)-1H-1,2,3-triazol-1-yl)propyl)-1-((3-(4-((4-(2'-(4-((2-(dimethylamino)ethyl)carbamoyl)phenyl)-3H,3'H-[5,5'-bibenzo[d]imidazol]-2-yl)benzamido)methyl)-1H-1,2,3-triazol-1-yl)propyl)glycyl-L-prolyl)pyrrolidine-2-carboxamide (Compound 445)

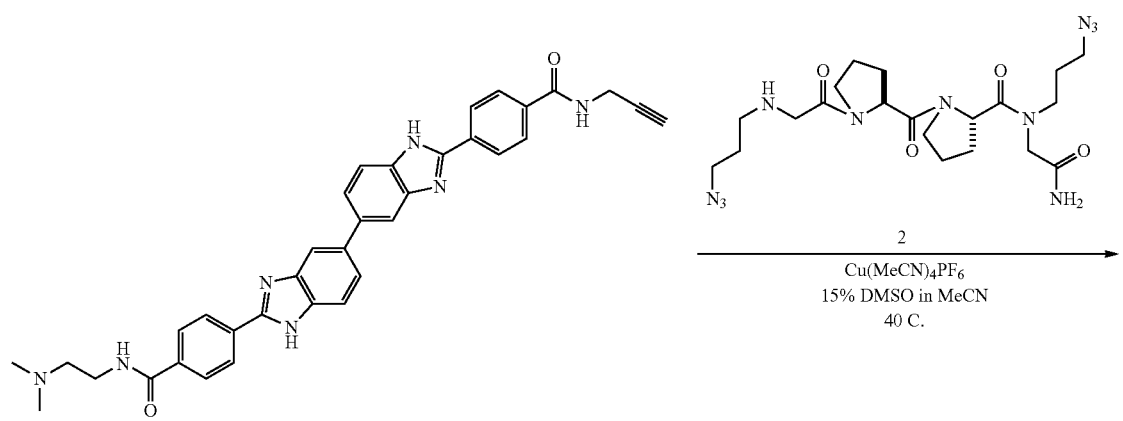

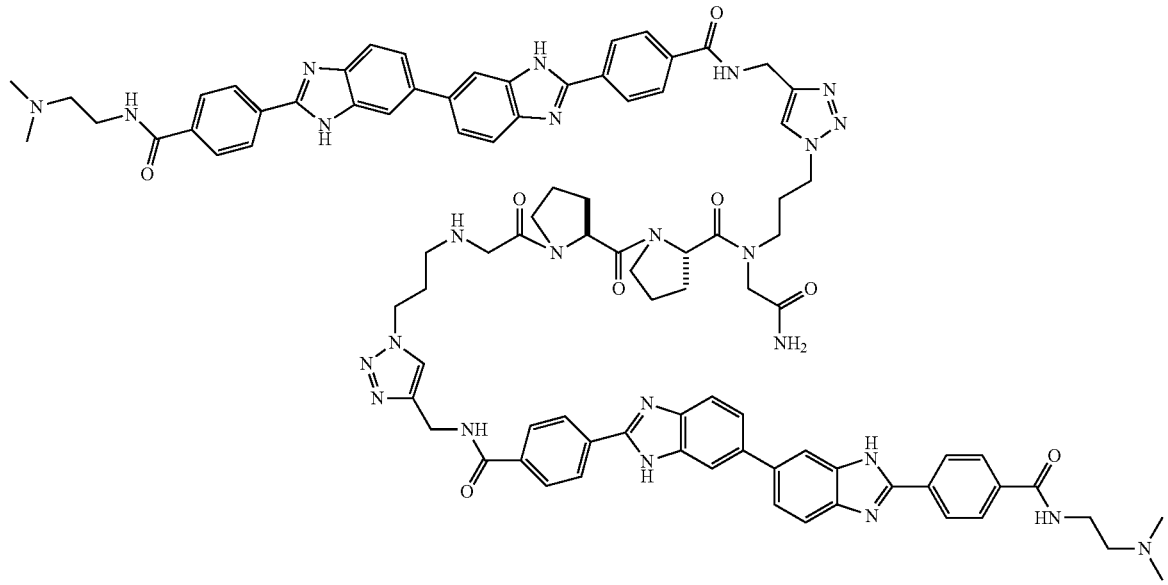

445

To a stirred solution of N-(2-(dimethylamino)ethyl)-4-(2'-(4-(prop-2-yn-1-ylcarbamoyl)phenyl)-1H,1'H-[5,5'-bibenzo[d]imidazol]-2-yl)benzamide 1 (120 uL, 0.1 M in DMSO) was added (S)-N-(2-amino-2-oxoethyl)-N-(3-azidopropyl)-1-((3-azidopropyl)glycyl-L-prolyl)pyrrolidine-2-carboxamide 2 (60 uL, 0.1 M in DMSO). Tetrakis(acetonitrile)copper (I) hexafluorophosphate (1.0 mg) in MeCN (1.02 mL) added. This mixture was stirred for 24 hours and LCMS analysis indicated no product formation. More tetrakis(acetonitrile)copper(I) hexafluorophosphate (1.0 mg) and TBTA (3.0 mg) added and stirred for 16 hours. No product by LCMS. More tetrakis(acetonitrile)copper(I) hexafluorophosphate (1.0 mg) in MeOH (100 uL) and stirred for 16 hours. Small amount of product observed by LCMS. Water (2 mL) added, filtered, and purified via preparatory reverse-phase HPLC multiple times. Concentration of the fractions containing product afforded title compound 445. MALDI: m/z=1654.7852 [M⁺]

Compound 446 was prepared in the same manner as compound 445.

Compound 446: MALDI: m/z=1778.7858 [M⁺]

Example 119

Synthesis of N-(2-(4-(2-azidoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (Compound 172)

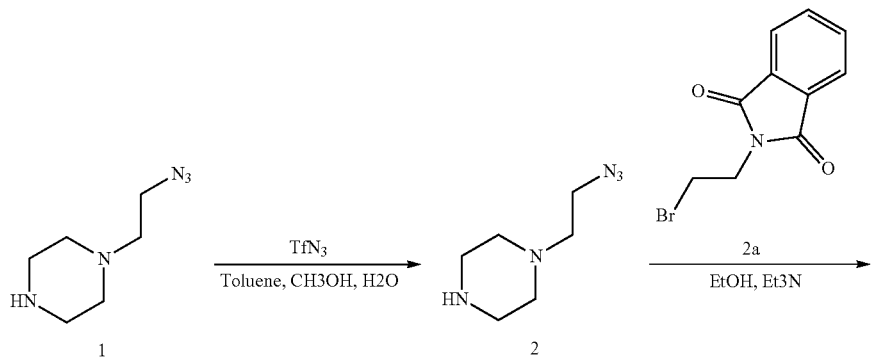

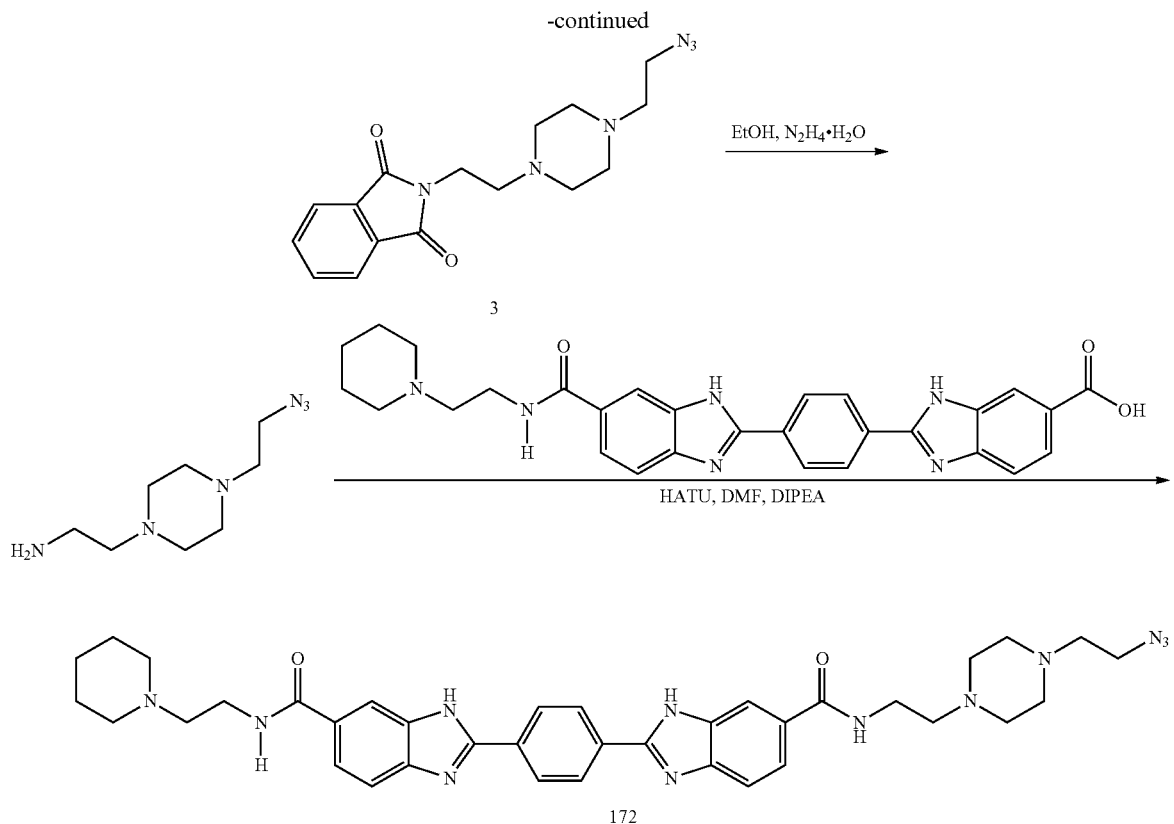

Synthesis of 1-(2-azidoethyl) piperazine

In situ Preparation of TfN$_3$: To a solution of trifluromethanesulfonic anhydride (2.00 g, 7.0 mmol) in water (10 mL) and toluene (10 mL) was added sodium azide (2.30 g, 35.0 mmol) and the reaction mixture was stirred at r.t for 2 h. A solution of 2-(piperazin-1-yl)ethan-1-amine (0.92 g, 7.00 mmol) in methanol (10.0 mL) was added to the above mixture (TfN$_3$ prepared in situ) at 0° C. and the reaction mixture was allowed to warm to r.t and stirred for 12 h. The reaction mixture was poured in to water (100 mL) and extracted with EtOAc (2×100 mL). The combined organic extracts were washed with brine (50 mL), dried over anhydrous Na$_2$SO$_4$ and concentrated under vacuum to obtain 1-(2-azidoethyl)piperazine (0.80 g, crude). The crude product was used directly in the next step.

Synthesis of 2-(2-(4-(2-azidoethyl)piperazin-1-yl)ethyl)isoindoline-1,3-dione: To a solution of 1-(2-azidoethyl)piperazine (800 mg, 5.00 mmol) in EtOH (15.0 mL), was added 2-(2-bromoethyl)isoindoline-1,3-dione (1.50 g, 6.20 mmol) followed with triethylamine (1.33 mL, 10.3 mmol) and the reaction mixture was refluxed for 12 h. The reaction mixture was cooled to r.t and concentrated EtOH under vacuum. Diluted the residue with water (50 mL) and extracted with EtOAc (2×50 mL). The combined EtOAc extract were washed with brine (50 mL), dried over anhydrous Na2SO4, filtered and concentrated under vacuum to obtain 2-(2-(4-(2-azidoethyl)piperazin-1-yl)ethyl)isoindoline-1,3-dione (1.2 g, crude). The crude product was directly used in the next step.

Synthesis of 2-(4-(2-azidoethyl)piperazin-1-yl)ethan-1-amine

To a solution of 2-(2-(4-(2-azidoethyl)piperazin-1-yl)ethyl)isoindoline-1,3-dione (1.20 g, 3.60 mmol) in EtOH (20.0 mL), was added hydrazine hydrate (80% in water, 1.00 mL) and the reaction mixture was refluxed for 1 h. The reaction mixture was cooled to r.t and EtOH was concentrated under vacuum. The residue was diluted with EtOAc (50.0 mL) and the mixture was stirred at r.t for 1 h. The solids were filtered under vacuum, washed with EtOAc (30 mL), and the filtrate was concentrated under vacuum to obtain 2-(4-(2-azidoethyl)piperazin-1-yl)ethan-1-amine.

Synthesis of N-(2-(4-(2-azidoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide: To a solution of 2-(4-(6-((2-(piperidin-1-yl)ethyl)carbamoyl)-1H-benzo[d]imidazol-2-yl)phenyl)-1H-benzo[d]imidazole-6-carboxylic acid (150 mg, 0.29 mmol) in DMF (3.00 mL) at 0° C., was added HATU (167 mg, 0.44 mmol), DIPEA (0.10 mL, 0.58 mmol) and the reaction mixture was stirred at r.t for 5 minutes. 2-(4-(2-azidoethyl)piperazin-1-yl)ethan-1-amine (116 mg, 0.58 mmol) was added to the above mixture at 0° C. and the reaction mixture was stirred at r.t for 12 h. The reaction mixture was concentrated under vacuum to obtain the crude product and the product was purified by C18 chromatography (CH$_3$CN:H$_2$O; 4:1). The fractions containing the product were combined for concentration. The isolated product still contained impurities. The product was re-purified by prep-HPLC. Fractions containing only the pure product were combined for concentration to obtain the title compound. MS (ESI+ APCl): m/z=689 [M+H]$^+$.

Example 120

Synthesis of 2,2'-(2-nitro-1,4-phenylene)bis(N-(2-(piperidin-1-yl)ethyl)-1H-benzo[d]imidazole-6-carboxamide) (Compound 173)

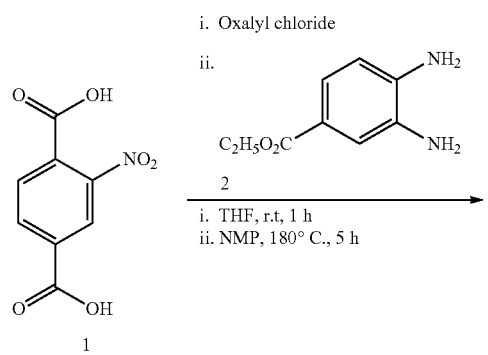

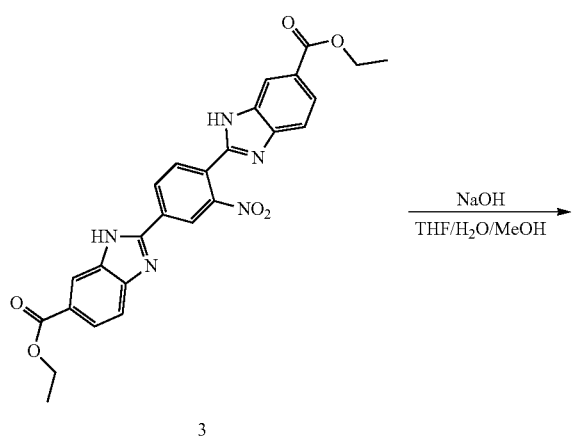

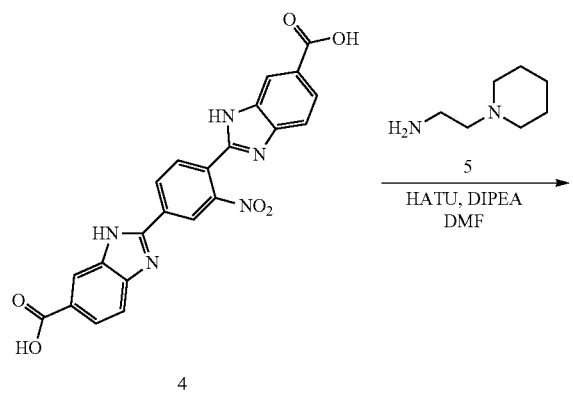

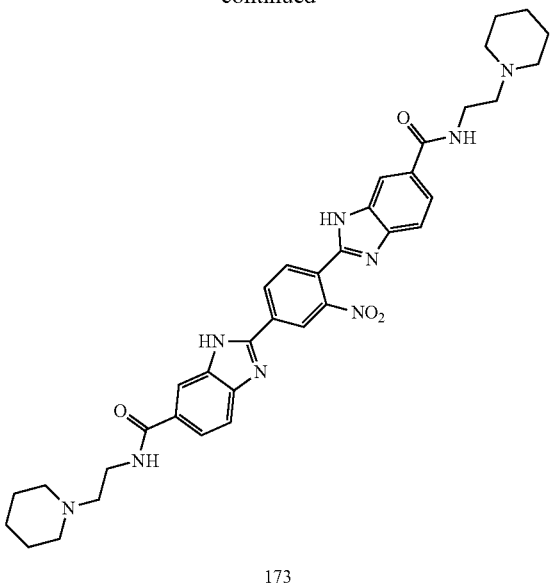

173

Synthesis of diethyl 2,2'-(2-nitro-1,4-phenylene)bis(1H-benzo[d]imidazole-6-carboxylate): To a solution of 2-nitroterephthalic acid (0.40 g, 1.89 mmol) in THF (10.0 mL) at 0° C. was added oxalylchloride (0.48 mL, 5.68 mmol), DMF (catalytic) and the reaction mixture stirred at r.t for 1 h. The reaction mixture was concentrated under reduced pressure to obtain the crude product (380 mg). A solution of ethyl 3,4-diaminobenzoate (0.55 g, 3.06 mmol) in NMP (10 mL) was added to the above crude product at 0° C. and the reaction mixture was stirred at r.t for 16 h, and heated to 180° C. for 5 h. The reaction mixture was cooled to r.t and the contents were poured onto ice, whereupon the product precipitated. The product was filtered under vacuum, washed with water (10.0 mL), and dried to obtain the crude product. The product was purified by silica gel chromatography (1:4 CH$_3$OH:CH$_2$Cl$_2$). The fractions containing only the pure product were combined for concentration to obtain diethyl 2,2'-(2-nitro-1,4-phenylene)bis(1H-benzo[d]imidazole-6-carboxylate).

Synthesis of 2,2'-(2-nitro-1,4-phenylene)bis(1H-benzo[d]imidazole-6-carboxylic acid): To a solution of diethyl 2,2'-(2-nitro-1,4-phenylene)bis(1H-benzo[d]imidazole-6-carboxylate) (0.30 g, 0.60 mmol) in a mixture of CH$_3$OH (6.0 mL), THF (6.0 mL) and H$_2$O (7.0 mL) at 0° C., was added NaOH (72 mg, 1.80 mmol) and the reaction mixture was stirred at r.t for 16 h. The reaction mixture was acidified with 2N aqueous HCl (10.0 mL) and the precipitated solids were filtered under vacuum, washed with H$_2$O (8.0 mL) and dried to obtain 2,2'-(2-nitro-1,4-phenylene)bis(1H-benzo[d]imidazole-6-carboxylic acid)

Synthesis of 2,2'-(2-nitro-1,4-phenylene)bis(N-(2-(piperidin-1-yl)ethyl)-1H-benzo[d]imidazole-6-carboxamide): To a suspension of 2,2'-(2-nitro-1,4-phenylene)bis(1H-benzo[d]imidazole-6-carboxylic acid) (190 mg, 0.42 mmol) in DMF (10.0 mL) at 0° C., was added HATU (406 mg, 1.07 mmol), DIPEA (0.47 mL, 2.56 mmol) and 2-(piperdin-1-yl)ethan-1-amine (137 mg, 1.07 mmol) and the reaction mixture was stirred at r.t for 16 h. The reaction mixture was poured in to water and stirred for 15 mins, whereupon the product precipitated. The product was collected by filtration under vacuum, washed with water (10 mL) and dried. The product was purified by prep-HPLC. Fractions containing only the pure product were combined for concentration to afford the title compound MS (ESI+APCl): m/z=664 [M+H]$^+$.
Compound 174 was prepared in the same manner as compound 173. Compound 174: MS (ESI+APCl): m/z=637 [M+H]$^+$.
Example 121
Synthesis of 2,2'-(1,4-phenylene)bis(N-(2-(methyl ((2S,3R,4R,5R)-2,3,4,5,6-pentahydroxyhexyl) amino)ethyl)-1H-benzo[d]imidazole-6-carboxamide) (175)
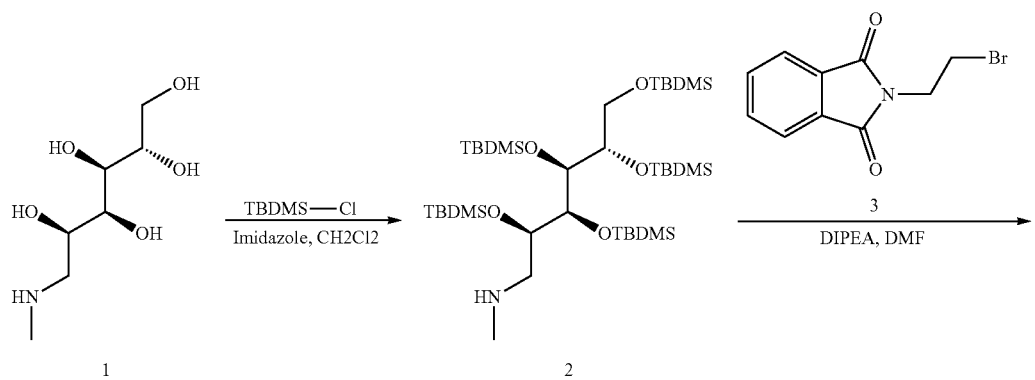
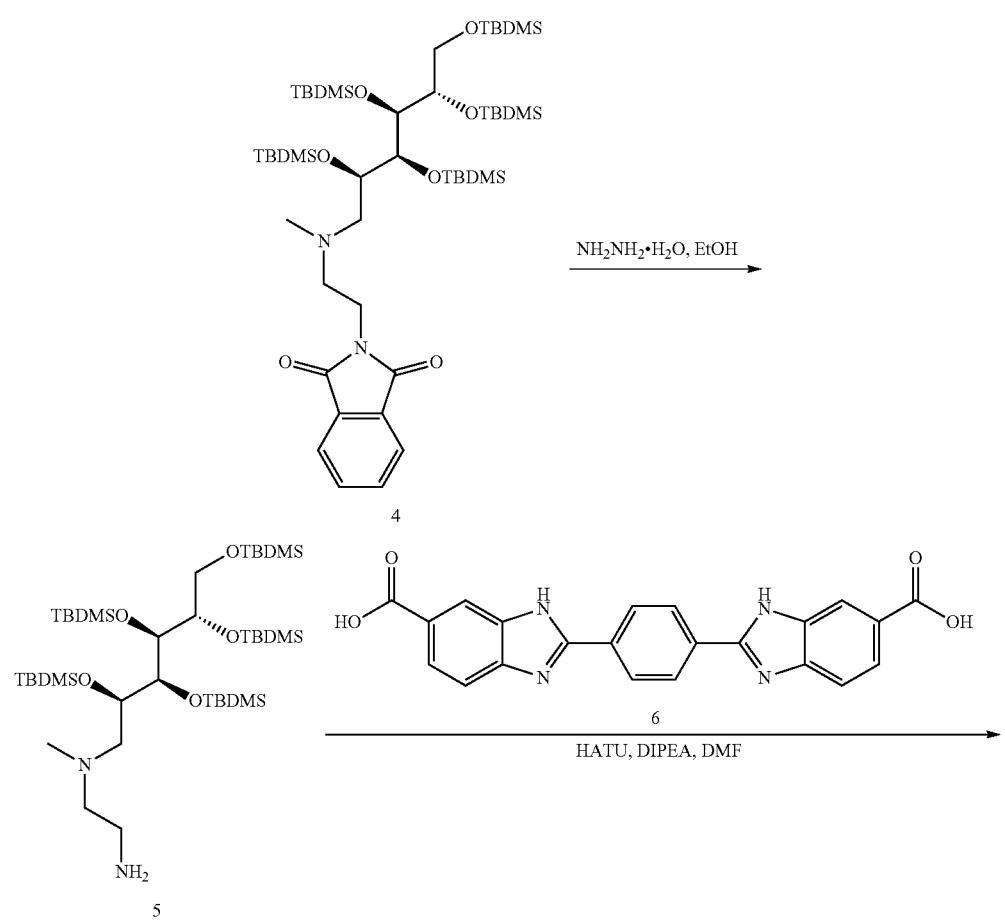

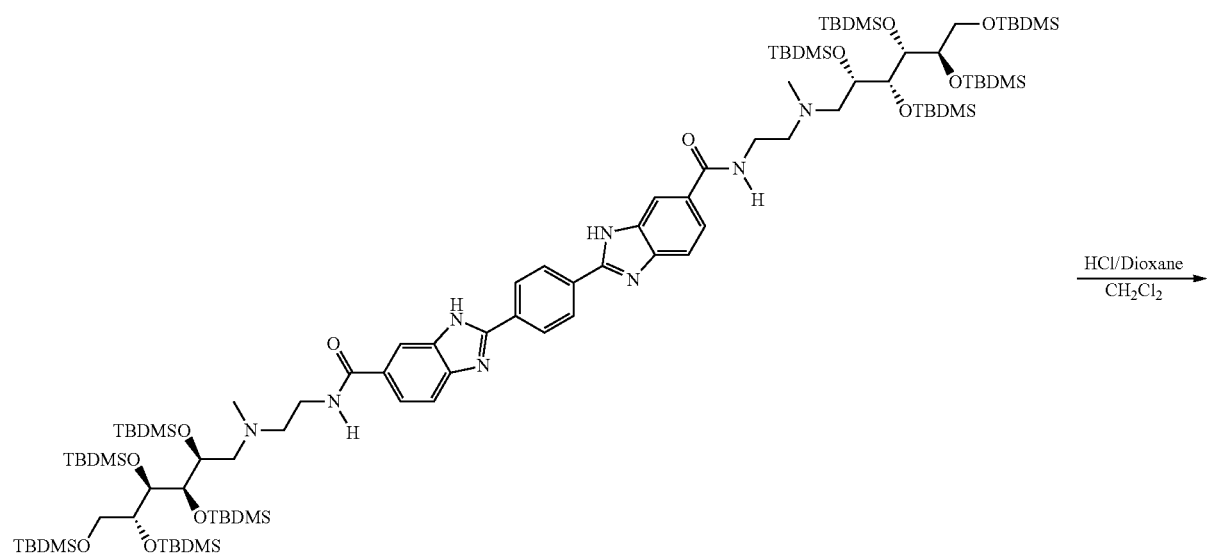
7
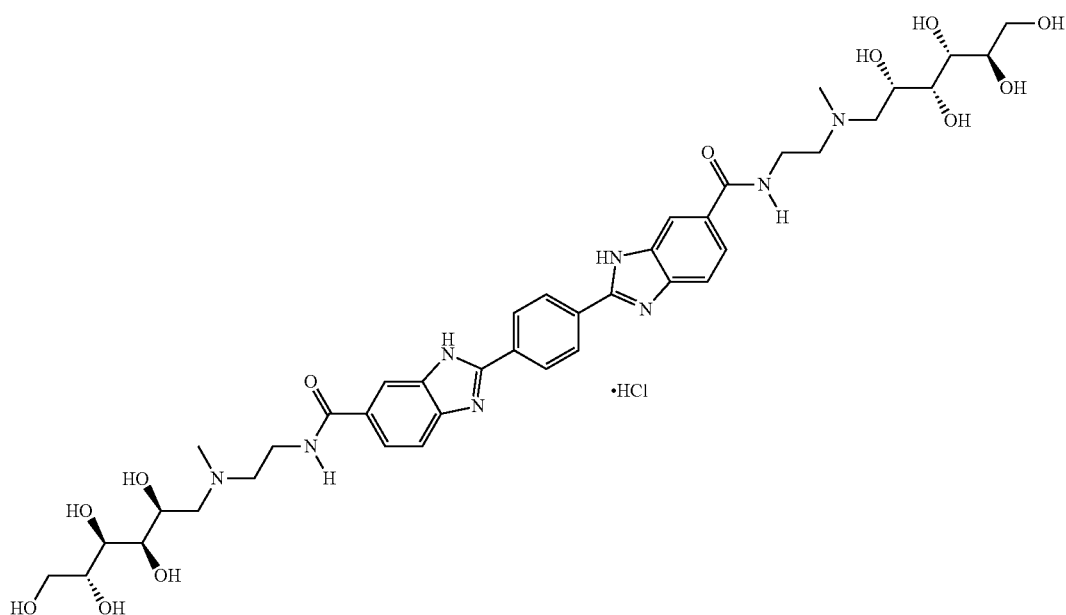
175

Synthesis of (2R,3S,4S,5S)-2,3,4,5,6-pentakis((tert-butyldimethylsilyl)oxy)-N-methylhexan-1-amine: To a stirred solution of (2S,3S,4S,5R)-6-(methylamino)hexane-1,2,3,4,5-pentaol (2.00 g, 10.25 mmol) in CH$_2$Cl$_2$ (50.0 mL), at 0° C. under N$_2$ atmosphere, was added imidazole (6.98 g, 102.5 mmol), followed with TBDMS-Cl (15.45 g, 102.5 mmol) and the reaction mixture was stirred at r.t for 24 h. The reaction mixture was diluted with CH$_2$Cl$_2$ (150 mL), washed with water (100 mL), brine (50 mL), dried over anhydrous Na$_2$SO$_4$, and concentrated under vacuum. The crude product was purified by silica gel chromatography, (EtOAc:Hexane, 1:9) to obtain (2R,3S,4S,5S)-2,3,4,5,6-pentakis((tert-butyldimethylsilyl)oxy)-N-methylhexan-1-amine Synthesis of 2-(2-(methyl((2R,3S,4S,5S)-2,3,4,5,6-pentakis((tert-butyldimethylsilyl)oxy)hexyl)amino)ethyl)isoindoline-1,3-dione: To a solution of (2R,3S,4S,5S)-2,3,4,5,6-pentakis((tert-butyldimethylsilyl)oxy)-N-methylhexan-1-amine (4.30 g, 5.61 mmol) in DMF (45.00 mL) was added 2-(2-bromoethyl)isoindoline-1,3-dione (2.85 g, 11.2 mmol), followed with DIPEA (2.58 mL, 14.0 mmol) and the reaction mixture was stirred at 90° C. for 8 h. The reaction mixture was cooled to r.t, and diluted with ice-cold water (50 mL) and extracted with EtOAc (2×100 mL). The combined organic extracts were washed with brine (50 mL), dried over anhydrous Na$_2$SO$_4$, and concentrated under vacuum the crude product. The product was purified by silica gel chromatography (MeOH:CH$_2$Cl$_2$, 1:9) to obtain 2-(2-(methyl((2R,3S,4S,5S)-2,3,4,5,6-pentakis((tert-butyldimethylsilyl)oxy)hexyl)amino)ethyl) isoindoline-1,3-dione Synthesis of N1-methyl-N1-((2R,3S,4S,5S)-2,3,4,5,6-pentakis((tert-butyldimethylsilyl)oxy)hexyl)ethane-1,2-diamine: To a solution of 2-(2-(methyl((2R,3S,4S,5S)-2,3,4,5,6-pentakis((tert-butyldimethylsilyl)oxy)hexyl)amino)ethyl)isoindoline-1,3-dione (2.80 g, crude) in EtOH (25.0 mL) was added N$_2$H$_4$.H$_2$O (0.50 mL) and the reaction mixture was stirred at 90° C. for 1 h. The reaction mixture was cooled to r.t, whereupon solids precipitated. The solids were filtered under vacuum and washed with EtOH (10 mL). The filtrate was concentrated under vacuum to obtain N1-methyl-N1-((2R,3S,4S,5S)-2,3,4,5,6-pentakis((tert-butyldimethylsilyl)oxy)hexyl)ethane-1,2-diamine Synthesis of Intermediate-7: To a suspension of 2,2'-(1,4-phenylene)bis(1H-benzo[d]imidazole-6-carboxylic acid) (0.39 g, 0.98 mmol) in DMF (10.0 mL) at 0° C., was added HATU (0.83 g, 2.17 mmol) followed with DIPEA (1.46 mL, 7.91 mmol) and the reaction mixture was stirred at r.t for 10 minutes. N1-methyl-N1-((2R,3S,4S,5S)-2,3,4,5,6-pentakis((tert-butyldimethylsilyl)oxy)hexyl)ethane-1,2-diamine (1.60 g, 1.98 mmol) was added to the above mixture at 0° C., and the reaction mixture was allowed to warm to r.t and stirred for 12 h. The reaction mixture was concentrated under vacuum and the product was diluted with ice-cold water (40 mL), and stirred for 15 mins, whereupon the product precipitated. The product was collected by filtration under vacuum, washed with CH$_3$OH (10 mL), and dried under vacuum to obtain intermediate-7 (2.10 g, crude) as a brown solid. The crude product was directly used in the next reaction.

Synthesis of 2,2'-(1,4-phenylene)bis(N-(2-(methyl((2S,3R,4R,5R)-2,3,4,5,6-pentahydroxyhexyl)amino)ethyl)-1H-benzo[d]imidazole-6-carboxamide): To a suspension of intermediate-7 (1.00 g crude, 0.57 mmol) in CH$_2$Cl$_2$ (20 mL) at 0° C., was added HCl (4M in dioxane, 2.20 mL, 8.56 mmol). The reaction mixture was stirred at r.t for 14 h, and concentrated under reduced pressure to obtain the product. The product was triturated with MeOH (10 mL), filtered and dried to obtain the title compound. MS (ESI+APCl): m/z=839 [M+H]$^+$.

Example 122

Synthesis of 2,2'-(2-amino-1,4-phenylene)bis(N-(2-(piperidin-1-yl)ethyl)-1H-benzo[d]imidazole-6-carboxamide) (Compound 176)

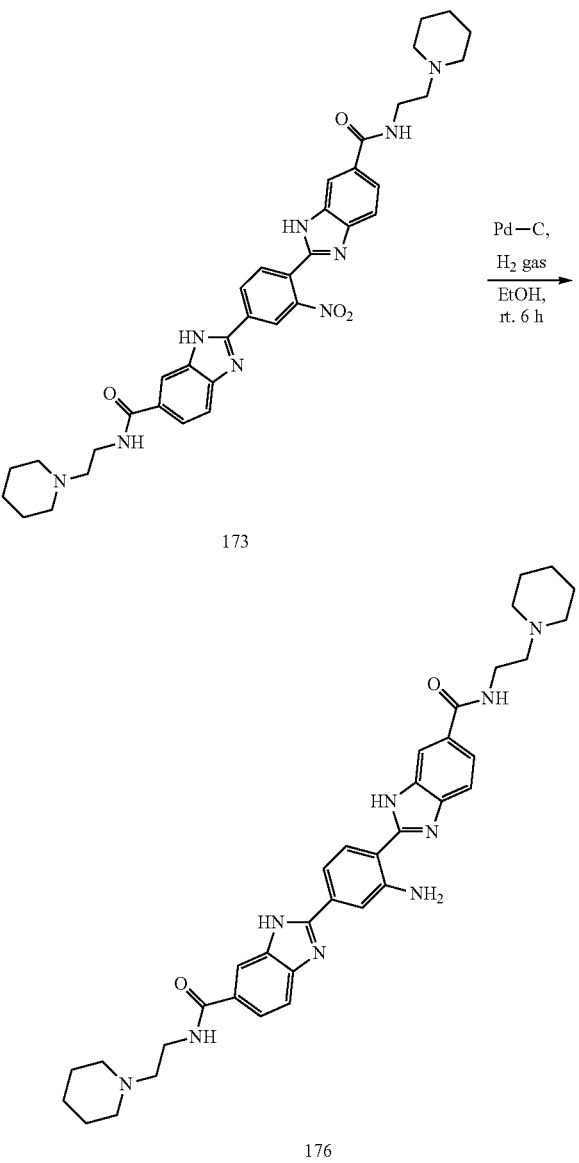

To a solution of 2,2'-(2-nitro-1,4-phenylene)bis(N-(2-(piperidin-1-yl)ethyl)-1H-benzo[d]imidazole-6-carboxamide) (147 mg, 0.22 mmol) in EtOH (20.0 mL) under N$_2$ atmosphere at r.t, was added 10% Pd/C (80 mg) and the reaction mixture was hydrogenated under balloon pressure (~1 atms) for 6 h. The reaction mixture was filtered through a pad of celite under vacuum and the pad was washed with EtOH (10 mL). The filtrate was concentrated under vacuum to obtain the crude product. The product was purified by prep-HPLC. Fractions containing only the pure product were combined for concentration to obtain the title compound. MS (ESI+APCl): m/z=634 [M+H]$^+$.

Example 123

Synthesis of tert-butyl (2-oxo-2-((2-oxo-2-(((1-(2-(4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazin-1-yl)ethyl)-1H-1,2,3-triazol-4-yl)methyl)amino)ethyl)amino)ethyl)carbamate) (Compound 177)

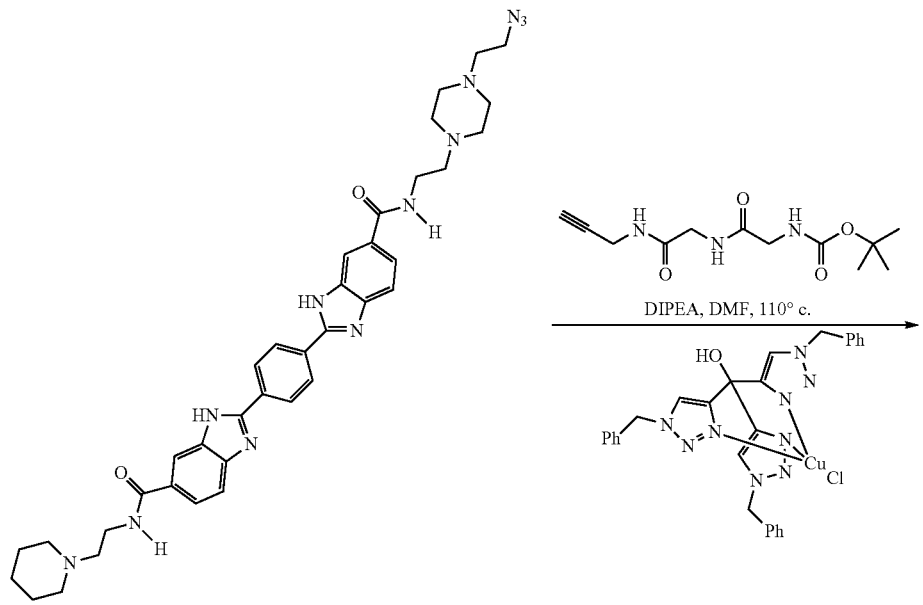

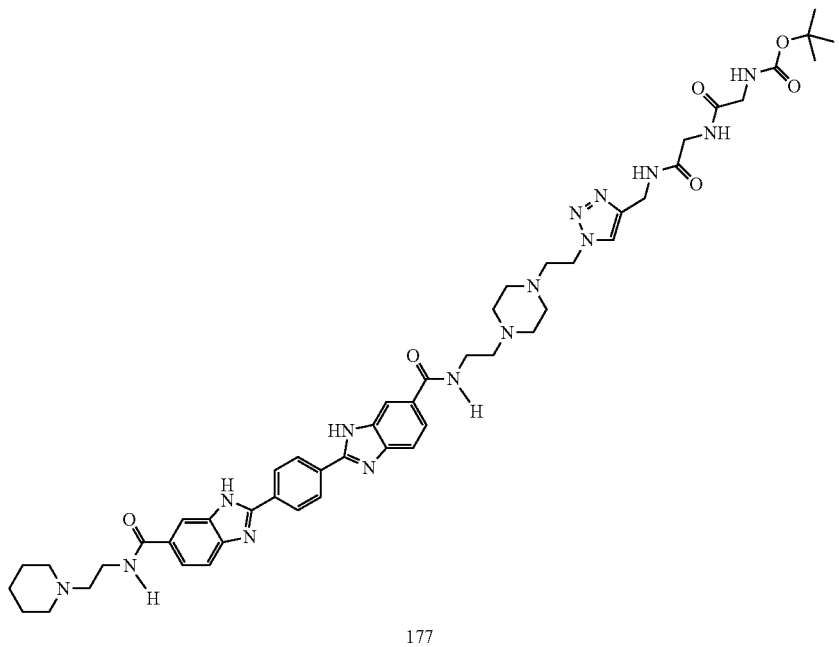

To a solution of N-(2-(4-(2-azidoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (40 mg, 0.058 mmol) in anhydrous DMF (10.0 mL) was added Cu(I) catalyst (31 mg, 0.052 mmol); [The copper (I) catalyst used was made using procedure reported by Ozcubukcu et al Org. Lett., 2009, 11, 4680-4683], tert-butyl (2-oxo-2-((2-oxo-2-(prop-2-yn-1-ylamino)ethyl)amino)ethyl)carbamate (16 mg, 0.058 mmol) followed with DIPEA (0.28 mL, 1.624 mmol), and the mixture was heated in microwave reactor at 110° C. for 2 h. The solvent was removed under reduced pressure and the crude product was purified by prep-HPLC. The fractions containing only the pure product were combined for concentration to obtain the title compound. MS (ESI+APCl) m/z 958 [M+H]⁺.

Example 124

Synthesis of N-(2-(4-(2-(4-((2-(2-aminoacetamido)acetamido)methyl)-1H-1,2,3-triazol-1-yl)ethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (Compound 178)

To a solution of tert-butyl (2-oxo-2-((2-oxo-2-(((1-(2-(4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazin-1-yl)ethyl)-1H-1,2,3-triazol-4-yl)methyl)amino)ethyl)amino)ethyl)carbamate (35 mg, 0.036 mmol) in anhydrous DCM (3.0 mL) was added trifluroacetic acid (0.03 mL, 0.36 mmol) at 0° C. and the reaction mixture was stirred at r.t for 3 h. The solvent was removed under reduced pressure and the crude product was purified by prep-HPLC. The fractions containing only the pure product were combined for concentration to give the title compound. MS (ESI+APCl) m/z 858 [M+H]⁺.

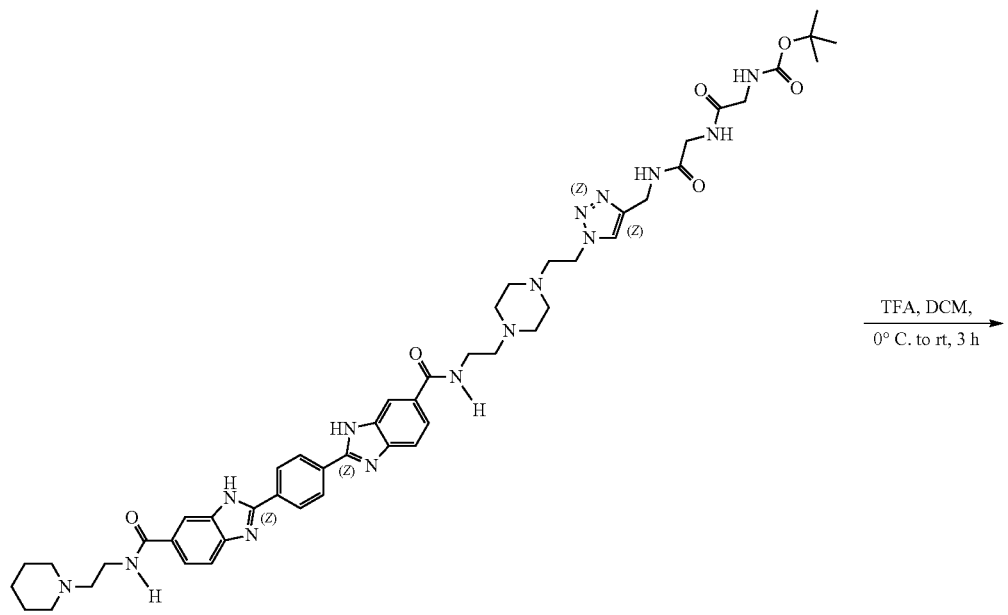

177

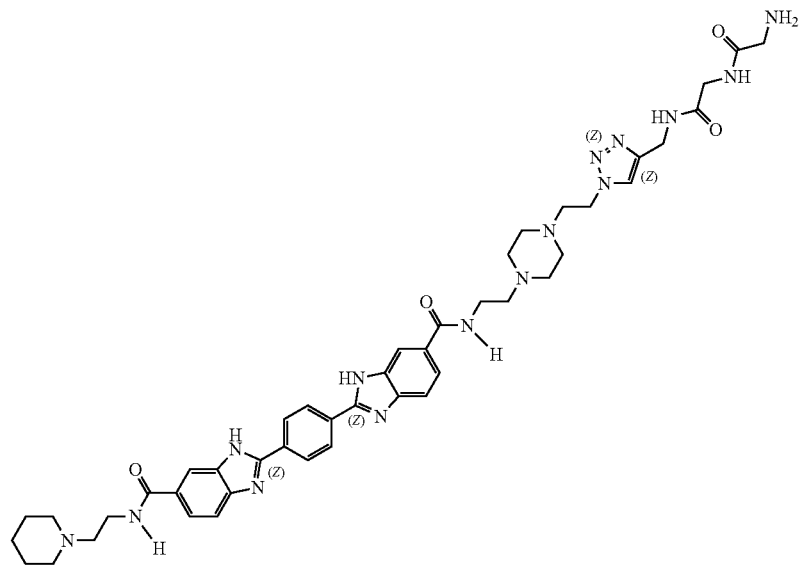

178

Example 125
Synthesis of 2,2'-((((1,4-phenylenebis(1H-benzo[d]imidazole-2,6-diyl))bis(oxy))bis(ethane-2,1-diyl))bis(oxy))bis(N,N-dimethylethan-1-amine) (Compound 179)
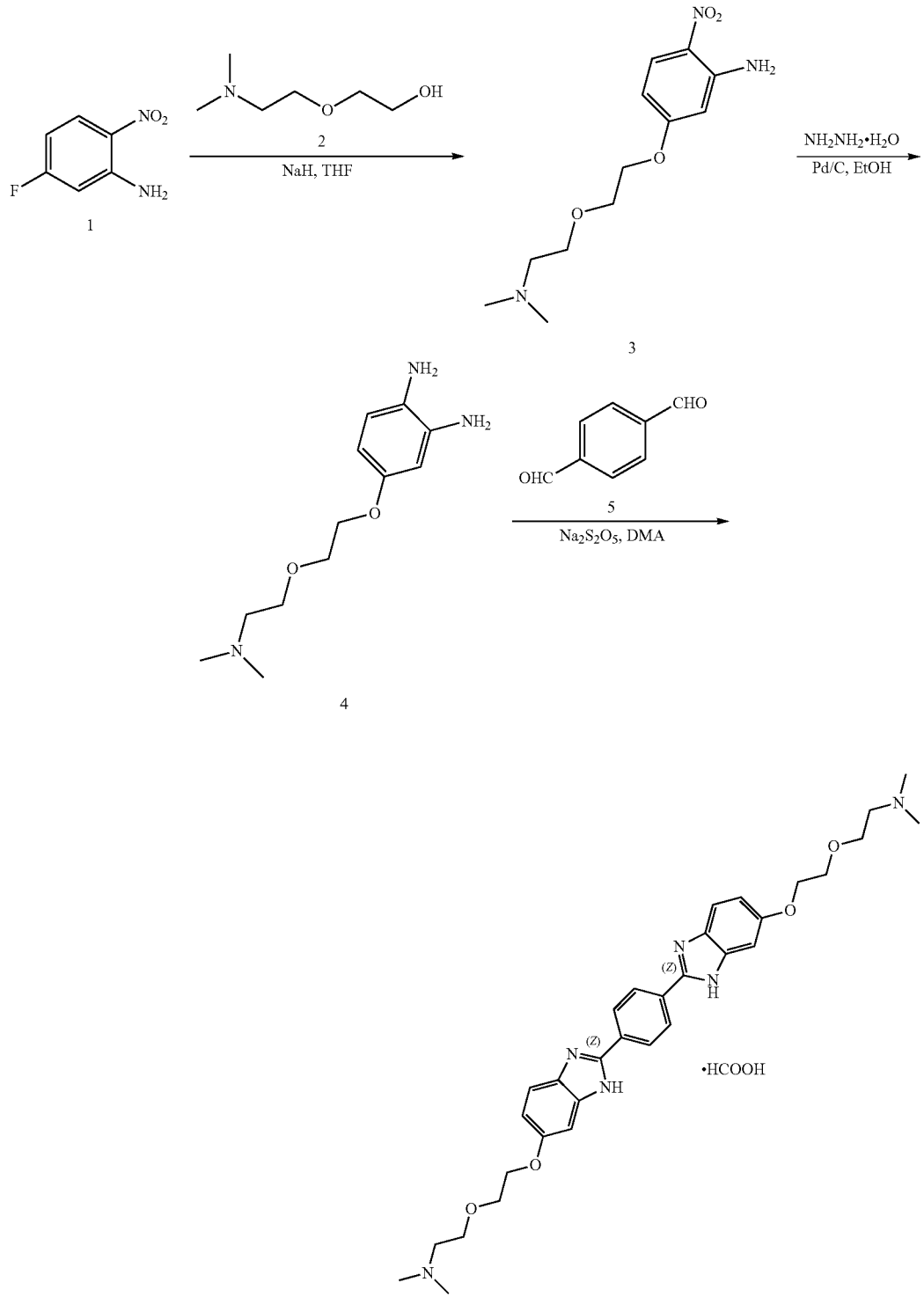

Synthesis of 5-(2-(2-(dimethylamino)ethoxy)ethoxy)-2-nitroaniline: To a stirred solution of 2-(2-(dimethylamino)ethoxy)ethan-1-ol (1.02 g, 7.69 mmol) in dry THF (10.0 mL), at 0° C. under N₂ atmosphere, was added NaH (60% suspension in oil, 0.64 g, 16.02 mmol) portion wise over a period of 10 minutes. The reaction mixture was stirred for an additional 10 minutes and a solution of 5-fluoro-2-nitroaniline (1.00 g, 6.41 mmol) in THF (10.0 mL) was added in a drop wise manner over 15 minutes, maintaining the temperature at 0° C. After complete addition, the reaction mixture was warmed to 60° C. and stirred for 14 h. The reaction mixture was cooled to r.t and the contents were poured onto ice and extracted with EtOAc (2×50 mL). The combined organic extracts were washed with brine (30 mL), dried over anhydrous Na₂SO₄, and concentrated under vacuum to obtain the crude product. The product was purified by silica gel chromatography using CH₃OH:CH₂Cl₂ (1:9). The fractions containing the product were combined and concentrated under vacuum to obtain 5-(2-(2-(dimethylamino)ethoxy)ethoxy)-2-nitroaniline Synthesis of 4-(2-(2-(dimethylamino)ethoxy)ethoxy)benzene-1,2-diamine: To a solution of 5-(2-(2-(dimethylamino)ethoxy)ethoxy)-2-nitroaniline (1.00 g, 3.72 mmol) in EtOH (20.0 mL), hydrazine monohydrate (1.50 mL) and 10% Pd/C (0.25 g) were added and the reaction mixture was stirred at r.t for 5 h. The reaction mixture was filtered through a celite pad, and the pad was washed with EtOH (50 mL). The combined filtrate was concentrated under reduced pressure to obtain 4-(2-(2-(dimethylamino)ethoxy)ethoxy)benzene-1,2-diamine. The crude product was used directly in the next step.

Synthesis of 2,2'-(((((1,4-phenylenebis(1H-benzo[d]imidazole-2,6-diyl))bis(oxy))bis(ethane-2,1-diyl))bis(oxy))bis(N,N-dimethylethan-1-amine): In a microwave vial, a mixture of terephthalaldehyde (0.16 g, 1.15 mmol), 4-(2-(2-(dimethylamino)ethoxy)ethoxy)benzene-1,2-diamine (0.55 g, 2.30 mmol) and Na₂S₂O₅ (0.52 g, 2.76 mmol) in DMA (5.0 mL) was heated at 170° C. for 40 min. The reaction mixture was cooled to r.t and the contents were slowly poured into ice-cold water and stirred for 10 min, whereupon, a dark yellow solid precipitated. The yellow solid was collected by filtration under vacuum and washed with water (2×50 mL) and dried to obtain the crude product. The product was purified by prep HPLC. Fractions containing only the pure product were combined for concentration to obtain the title compound. MS (ESI+APCl) m/z 573 [M+H]⁺.

Compounds 180, 181, 182, 184, 186, 187, 188, 191, 192, 193, 195, 207, and 210 were prepared in the same manner as compound 179.

Compound 180: MS (ESI+APCl) m/z 569 [M+H]⁺.
Compound 181: MS (ESI): m/z=509 [M+H]⁺.
Compound 182: MS (ESI): m/z=426 [M+H]⁺.
Compound 184: MS (ESI) m/z 599 [M+H]⁺.
Compound 186: MS (ESI): m/z=569 [M+H]⁺.
Compound 187: MS (ESI+APCl) m/z 569 [M+H]⁺.
Compound 188: MS (ESI+APCl) m/z 456 [M+H]⁺.
Compound 191: MS (ESI): m/z=565 [M+H]⁺.
Compound 192: MS (ESI) m/z=569 [M+H]⁺.
Compound 193: MS (ESI): m/z=456 [M+H]⁺.
Compound 195: MS (ESI): m/z=454 [M+H]⁺.
Compound 207: MS (ESI): m/z=633 [M+H]⁺.
Compound 210: MS (ESI): m/z=605 [M+H]⁺.

Example 126

Synthesis of 3,3'-((1H,1'H-[5,5'-bibenzo[d]imidazole]-2,2'-diylbis(2,6-di-tert-butyl-4,1-phenylene))bis(oxy))bis(N,N-dimethylpropan-1-amine) (Compound 375) and 2,6-di-tert-butyl-4-(2'-(3,5-di-tert-butyl-4-(3-(dimethylamino)propoxy)phenyl)-1H,1'H-[5,5'-bibenzo[d]imidazol]-2-yl)phenol (Compound 372)

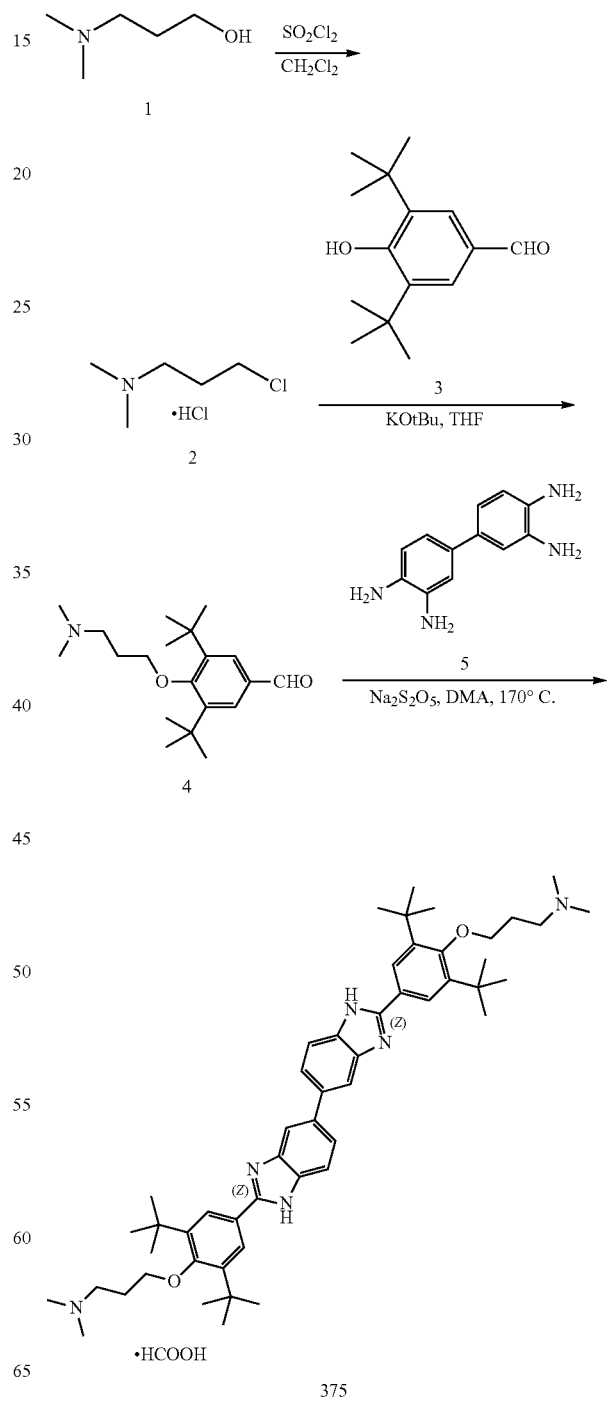

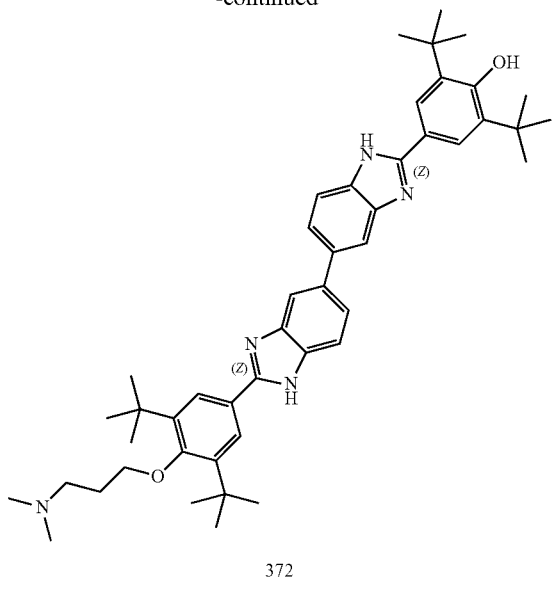

372

Synthesis of 3-chloro-N,N-dimethylpropan-1-amine hydrochloride: To a solution of 3-(dimethylamino)propan-1-ol (5.00 g, 48.5 mmol) in CH$_2$Cl$_2$ (15.0 mL) was added thionyl chloride (20.0 mL) at 0° C. and the reaction mixture was stirred at 60° C. for 2 h. The reaction mixture was cooled to r.t. and concentrated under vacuum to obtain 3-chloro-N,N-dimethylpropan-1-amine hydrochloride.

Synthesis of 3,5-di-tert-butyl-4-(3-(dimethylamino)propoxy)benzaldehyde: To a solution of 3,5-di-tert-butyl-4-hydroxybenzaldehyde (2.00 g, 8.54 mmol) in THF (15.0 mL) was added 3-chloro-N,N-dimethylpropan-1-amine hydrochloride (1.61 g, 10.25 mmol) followed with KO$^t$Bu (2.87 g, 25.6 mmol) and the reaction mixture was stirred at 65° C. for 30 h. The reaction mixture was cooled to r.t. and the contents were poured onto water and extracted with (1:9, CH$_3$OH:CH$_2$Cl$_2$) (2×100 mL). The combined organic extracts were washed with brine (100 mL), dried over anhydrous Na$_2$SO$_4$, filtered and concentrated under vacuum to obtain the crude product. The product was purified by silica gel column chromatography (1:9, CH$_3$OH:CH$_2$Cl$_2$). The fractions containing the product were combined and concentrated under vacuum to obtain 3,5-di-tert-butyl-4-(3-(dimethylamino)propoxy)benzaldehyde.

Synthesis of 3,3'-((1H,1'H-[5,5'-bibenzo[d]imidazole]-2,2'-diylbis(2,6-di-tert-butyl-4,1-phenylene))bis(oxy))bis(N,N-dimethylpropan-1-amine) and 2,6-di-tert-butyl-4-(2'-(3,5-di-tert-butyl-4-(3-(dimethylamino)propoxy)phenyl)-1H,1'H-[5,5'-bibenzo[d]imidazol]-2-yl)phenol: In a microwave vial, a mixture of 3,5-di-tert-butyl-4-(3-(dimethylamino)propoxy)benzaldehyde (0.48 g, 1.51 mmol), [1,1'-biphenyl]-3,3',4,4'-tetraamine (0.16 g, 0.75 mmol) and Na$_2$S$_2$O$_5$ (0.34 g, 1.81 mmol) in DMA (6.0 mL) was heated at 170° C. for 40 min. The reaction mixture was cooled to r.t and the contents were slowly poured into water (60 mL) and stirred for 10 min, whereupon, a solid precipitated. The solid was filtered and washed with water (20 mL) and dried to obtain the crude product. The product was purified by prep HPLC. Fractions containing only the pure product were combined for concentration to obtain 3,3'-((1H,1'H-[5,5'-bibenzo[d]imidazole]-2,2'-diylbis(2,6-di-tert-butyl-4,1-phenylene))bis(oxy))bis(N,N-dimethylpropan-1-amine) (15 mg, 1.3%) as an off white solid and 2,6-di-tert-butyl-4-(2'-(3,5-di-tert-butyl-4-(3-(dimethylamino)propoxy)phenyl)-1H,1'H-[5,5'-bibenzo[d]imidazol]-2-yl)phenol.

Compound 375: MS (ESI+APCl): m/z 813 [M+H]$^+$.
Compound 372: MS (ESI+APCl): m/z 728 [M+H]$^+$.

Example 127

Synthesis of 1,4-bis(6-((1,2,2,6,6-pentamethylpiperidin-4-yl)oxy)-1H-benzo[d]imidazol-2-yl)benzene (Compound 183)

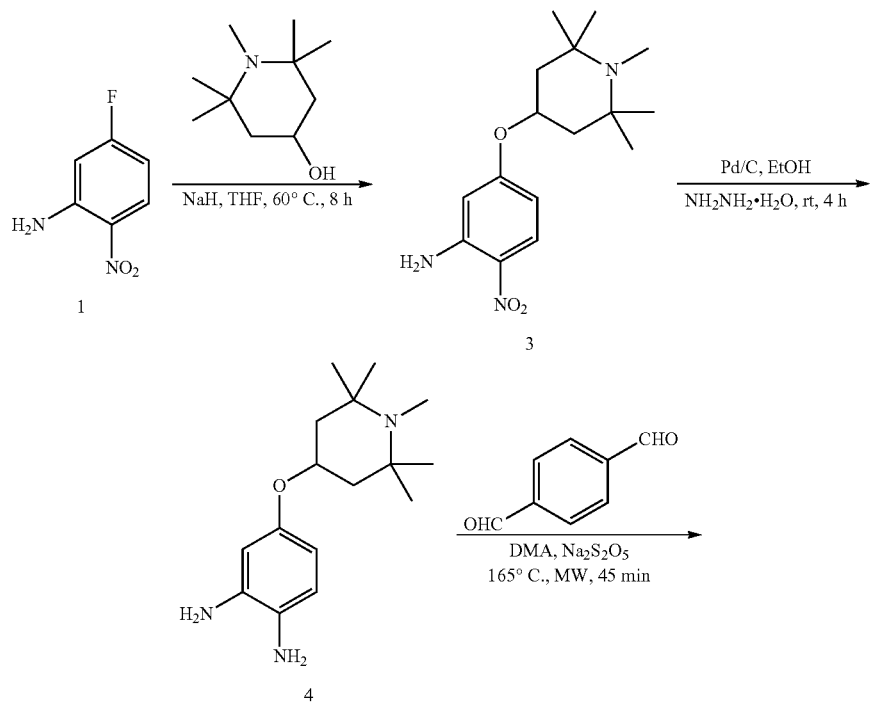

-continued

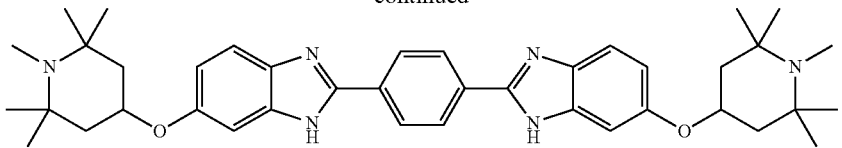

183

Synthesis of 2-nitro-5-((1,2,2,6,6-pentamethylpiperidin-4-yl)oxy)aniline: To a stirred solution of 1,2,2,6,6-pentamethylpiperidin-4-ol (3.29 g, 19.2 mmol) in dry THF (20.0 mL) at 0° C. under $N_2$ atmosphere, was added sodium hydride (1.22 g, 51.2 mmol) portion wise over a period of 10 minutes. The reaction mixture was stirred for an additional 10 minutes and a solution of 5-fluoro-2-nitroaniline (2.00 g, 12.8 mmol) in THF (20.0 mL) was added in a drop wise manner over 15 minutes, maintaining the temperature at 0° C. After complete addition, the reaction mixture was warmed to 60° C. and stirred for 8 h. The reaction mixture was cooled to r.t and the contents were poured onto ice and extracted with EtOAc (2×50 mL). The combined organic extracts were washed with brine solution (30 mL), dried over anhydrous $Na_2SO_4$, and concentrated under vacuum to obtain the crude product. The product was purified by silica gel column chromatography using $CH_3OH:CH_2Cl_2$ (2:8). The fractions containing the product were combined and concentrated under vacuum to obtain 2-nitro-5-((1,2,2,6,6-pentamethylpiperidin-4-yl)oxy)aniline.

Synthesis of 4-((1,2,2,6,6-pentamethylpiperidin-4-yl)oxy)benzene-1,2-diamine: To a solution of 2-nitro-5-((1,2,2,6,6-pentamethylpiperidin-4-yl)oxy)aniline (1.90 g, 6.18 mmol) in EtOH (15.0 mL), hydrazine mono hydrate (4.0 mL) and palladium on carbon (0.50 g) were added and the reaction mixture was stirred at r.t for 4 h. The reaction mixture was filtered through a celite pad, and the pad was washed with EtOH (50 mL). The combined filtrate was concentrated under reduced pressure to obtain 4-((1,2,2,6,6-pentamethylpiperidin-4-yl)oxy)benzene-1,2-diamine. The crude product was used directly in the next step.

Synthesis of 1,4-bis(6-((1,2,2,6,6-pentamethylpiperidin-4-yl)oxy)-1H-benzo[d]imidazol-2-yl)benzene: In a microwave vial, a mixture of 4-((1,2,2,6,6-pentamethylpiperidin-4-yl)oxy)benzene-1,2-diamine (0.50 g, 1.80 mmol), terephthalaldehyde (0.12 g, 0.90 mmol) and $Na_2S_2O_5$ (0.41 g, 2.16 mmol) in DMA (5.0 mL) was heated at 165° C. for 45 min. The reaction mixture was cooled to r.t and the contents were slowly poured into ice-cold water and stirred for 10 min, whereupon, a dark yellow solid precipitated. The yellow solid was collected by filtration under vacuum and washed with water (2×50 mL), and dried under vacuum. The obtained solid was purified by mass triggered HPLC (please refer to the HPLC conditions). Fractions containing only the pure product were combined for concentration to obtain the title compound. MS (ESI): m/z=649 [M+H]$^+$.

Example 128

Synthesis of N-(2-(4-(2-aminoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (Compound 185)

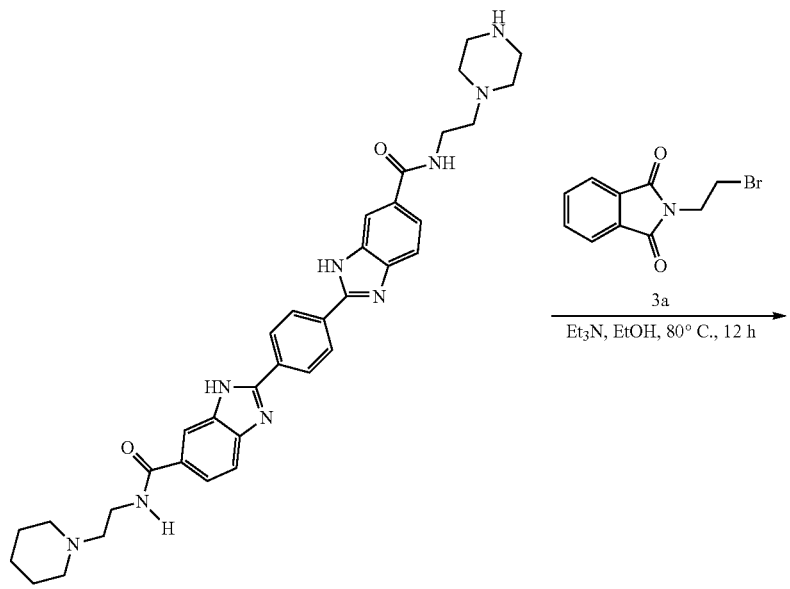

E-1089

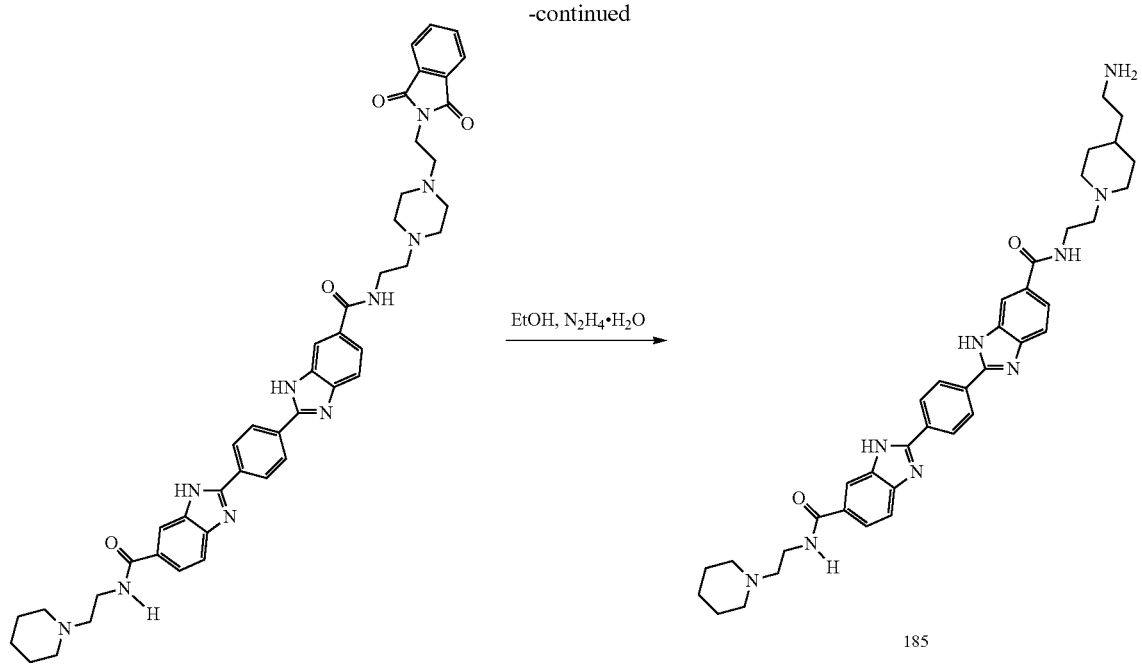

Synthesis of N-(2-(4-(2-(1,3-dioxoisoindolin-2-yl)ethyl) piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide: To a solution of N-(2-(piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (180 mg, 0.29 mmol) in EtOH (5.0 mL), was added 2-(2-bromoethyl)isoindoline-1,3-dione (110 mg, 0.43 mmol) followed with triethylamine (0.08 mL, 0.58 mmol) and the reaction mixture was refluxed for 12 h. The reaction mixture was cooled to r.t and concentrated EtOH under vacuum. The residue was diluted with acetonitrile (5 mL) and the mixture was stirred at r.t for 10 min. The solids were filtered under vacuum, washed with acetonitrile (3.0 mL) dried under vacuum to obtain N-(2-(4-(2-(1,3-dioxoisoindolin-2-yl)ethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide. The crude product was directly used in the next step.

Synthesis of N-(2-(4-(2-aminoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide: To a solution of N-(2-(4-(2-(1,3-dioxoisoindolin-2-yl)ethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (140 mg, 0.17 mmol) in EtOH (2.0 mL), was added hydrazine hydrate (80% in water, 0.50 mL) and the reaction mixture was refluxed for 1 h. The reaction mixture was cooled to r.t and EtOH was concentrated under vacuum. The product was purified by prep HPLC. Fractions containing only the pure product were combined for concentration to obtain the title compound. MS (ESI+APCl): m/z=663 [M+H]$^+$.

Example 129

1,4-Bis(6-methoxy-1H-benzo[d]imidazol-2-yl)benzene (Compound 189)

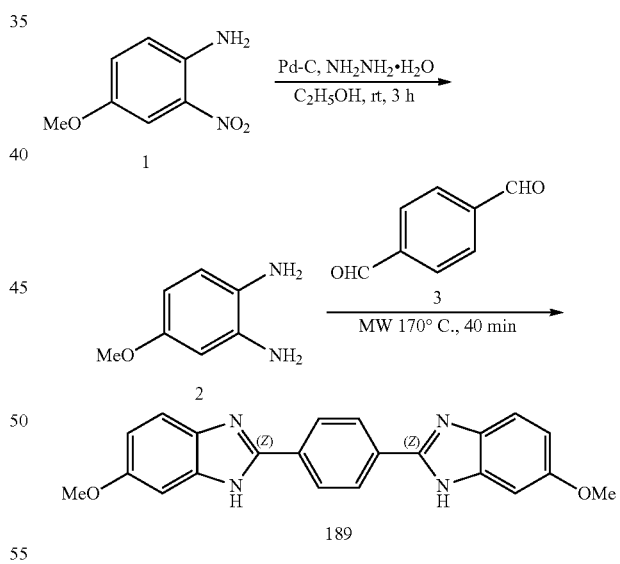

Synthesis of 4-methoxybenzene-1,2-diamine: To a solution of 4-methoxy-2-nitroaniline (1.0 g, 5.952 mmol) in EtOH (10.0 mL) at 0° C., was added N$_2$H$_4$.H$_2$O (5.0 mL) followed with 10% Pd—C (200 mg), and the reaction mixture was stirred at room temperature for 3 h. The reaction mixture was filtered through a celite-pad, and the pad was washed with EtOH (15 mL). The filtrate was concentrated under vacuum to obtain 4-methoxybenzene-1,2-diamine.

Synthesis of 1,4-bis(6-methoxy-1H-benzo[d]imidazol-2-yl)benzene: In a microwave vial, a mixture of 4-methoxy-benzene-1,2-diamine (0.8 g, 5.79 mmol), terephthalaldehyde (0.39 g, 2.89 mmol) and Na$_2$S$_2$O$_5$ (1.10 g, 5.79 mmol) in DMA (5.0 mL) was heated at 170° C. for 40 min. The reaction mixture was cooled to r.t and the contents were slowly poured into water (50 mL) and stirred for 10 min, whereupon, a solid precipitated. The solid was filtered and washed with water (20 mL) and dried to obtain the crude product. The product was purified by silica gel chromatography using CH$_3$OH:CH$_2$Cl$_2$ (1:9), followed by Sep-pak cartridge [CH$_3$OH (5% NH$_3$):CH$_2$Cl$_2$, 1:4]. purification. Fractions containing only the pure product were combined for concentration to afford the title compound. MS (ESI+APCl): m/z=371 [M+H]$^+$.

Compound 249 was prepared in the same manner as compound 189. MS (ESI): m/z=428 [M+H]$^+$.

Example 130

1,4-bis(6-methoxy-1H-benzo[d]imidazol-2-yl)benzene (Compound 190)

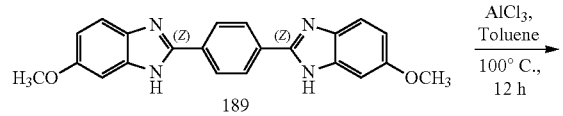

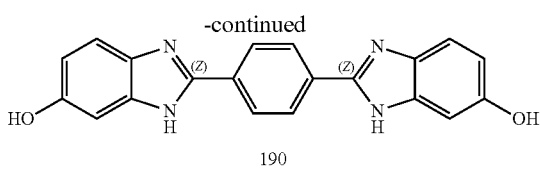

Synthesis of 2,2'-(1,4-phenylene)bis(1H-benzo[d]imidazol-6-ol): To a solution of 1,4-bis(6-methoxy-1H-benzo[d]imidazol-2-yl)benzene (250 mg, 0.67 mmol) in toluene (7.0 mL) at r.t, was added AlCl$_3$ (534 mg, 4.02 mmol) and heated to 100° C. for 12 h. The reaction mixture was cooled to r.t and the contents were slowly poured into water (50 mL) and stirred for 10 min, whereupon, a solid precipitated. The solid was filtered and washed with water (20 mL) and dried to obtain the crude product. The product was purified by prep HPLC. Fractions containing only the pure product were combined for concentration to afford the title compound. MS (ESI+APCl): m/z=343 [M+H]$^+$.

Example 131

Synthesis of 4,4'-((1,4-phenylenebis(1H-benzo[d]imidazole-2,6-diyl))bis(oxy))bis(N,N-dimethylbutan-1-amine) (Compound 197) and 2-(4-(6-(4-(dimethylamino)butoxy)-1H-benzo[d]imidazol-2-yl)phenyl)-1H-benzo[d]imidazol-6-ol (Compound 200)

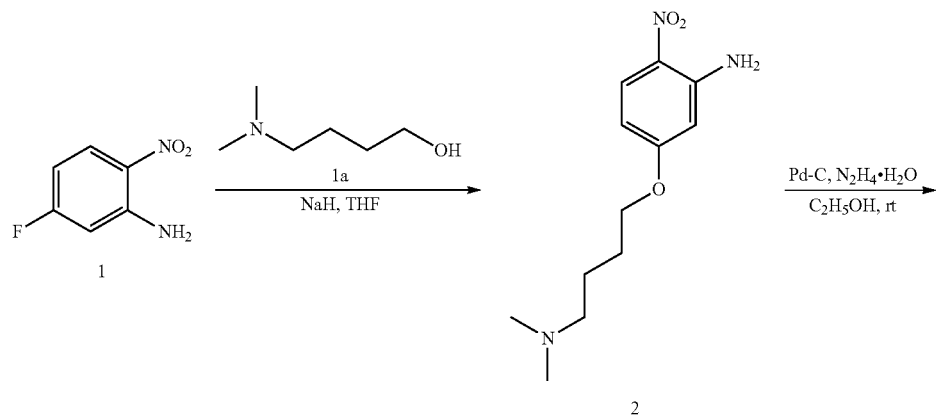

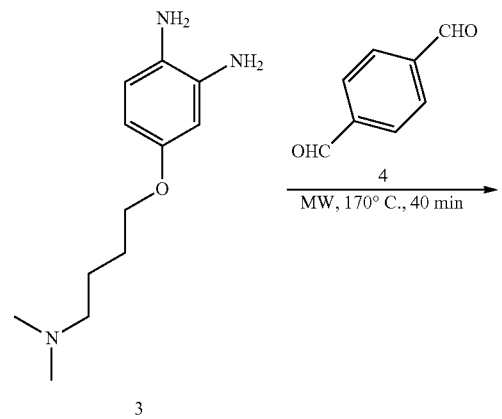

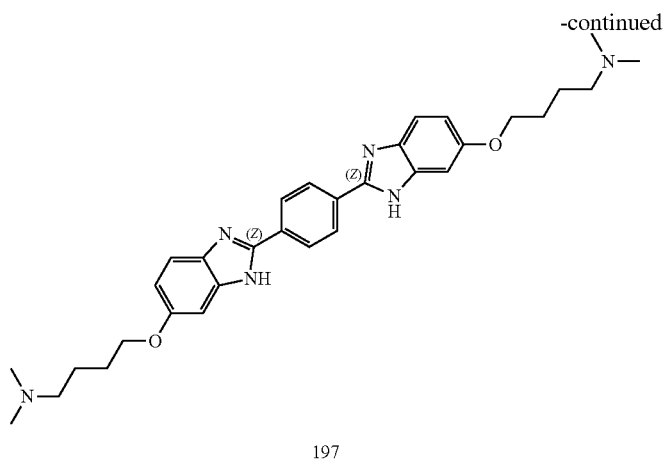

Synthesis of 5-(4-(dimethylamino)butoxy)-2-nitroaniline: To a stirred solution of 4-(dimethylamino)butan-1-ol (1.80 g, 15.4 mmol) in dry THF (50.0 mL), at 0° C. under $N_2$ atmosphere, was added NaH (60% suspension in oil, 1.50 g, 38.5 mmol) portion wise over a period of 10 minutes. The reaction mixture was stirred for an additional 10 minutes and a solution of 5-fluoro-2-nitroaniline (2.00 g, 12.81 mmol) in THF (10.0 mL) was added in a drop wise manner over 15 minutes, maintaining the temperature at 0° C. After complete addition, the reaction mixture was stirred at 70° C. for 12 h. The reaction mixture was cooled to r.t and the contents were poured onto ice and extracted with EtOAc (3×100 mL). The combined organic extracts were washed with brine (100 mL), dried over anhydrous $Na_2SO_4$, and concentrated under vacuum to obtain the crude product. The product was purified by silica gel chromatography using $CH_3OH:CH_2Cl_2$ (1:9). The fractions containing the product were combined and concentrated under vacuum to obtain 5-(4-(dimethylamino)butoxy)-2-nitroaniline.

Synthesis of 4-(4-(dimethylamino)butoxy)benzene-1,2-diamine: To a solution of 5-(4-(dimethylamino)butoxy)-2-nitroaniline (1.20 g, 4.74 mmol) in EtOH (30.0 mL), hydrazine monohydrate (5.0 mL) and 10% Pd/C (0.80 g) were added and the reaction mixture was stirred at r.t for 4 h. The reaction mixture was filtered through a celite pad, and the pad was washed with EtOH (2×50 mL). The combined filtrate was concentrated under reduced pressure to obtain 4-(4-(dimethylamino)butoxy)benzene-1,2-diamine Synthesis of 4,4'-((1,4-phenylenebis(1H-benzo[d]imidazole-2,6-diyl))bis(oxy))bis(N,N-dimethylbutan-1-amine) (197) and 2-(4-(6-(4-(dimethylamino)butoxy)-1H-benzo[d]imidazol-2-yl)phenyl)-1H-benzo[d]imidazol-6-ol (200): In a microwave vial, a mixture of 4-(4-(dimethylamino)butoxy)benzene-1,2-diamine (0.90 g, crude), and $Na_2S_2O_5$ (0.76 g, 4.03 mmol) in DMA (7.0 mL) was heated at 170° C. for 40 min. The reaction mixture was cooled to r.t and the contents were slowly poured into ice-cold water and stirred for 10 min, whereupon a solid precipitated. The solid was collected by filtration under vacuum and washed with water (20 mL) and dried to obtain the crude product. The product was purified and separated by prep HPLC. Fractions containing only the pure product were combined for concentration to obtain 4,4' the title compounds. (197): MS (ESI): m/z=541 [M+H]$^+$. (200): MS (ESI): m/z=442 [M+H]$^+$.

Compounds 203 and 204 were prepared in the same manner as compound 197. Compound 203: MS (ESI): m/z=537 [M+H]$^+$. Compound 204: MS (ESI+APCI): m/z=440 [M+H]$^+$.

Example 132

Synthesis of 1,4-bis(6-((1-methylpiperidin-4-yl)methoxy)-1H-benzo[d]imidazol-2-yl)benzene (Compound 198) and 2-(4-(6-((1-methylpiperidin-4-yl)methoxy)-1H-benzo[d]imidazol-2-yl)phenyl)-1H-benzo[d]imidazol-6-ol (Compound 194)

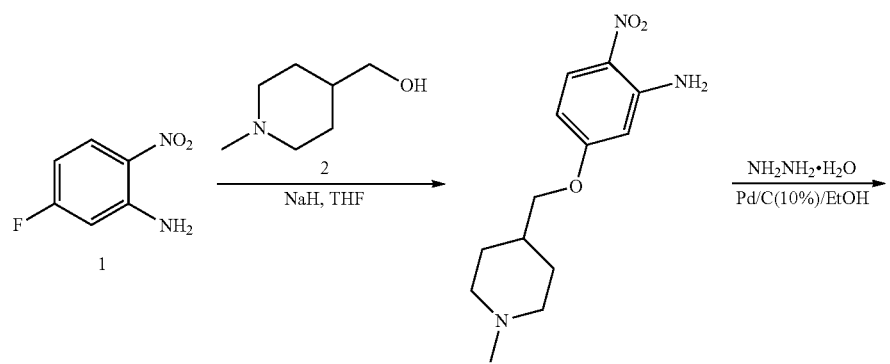

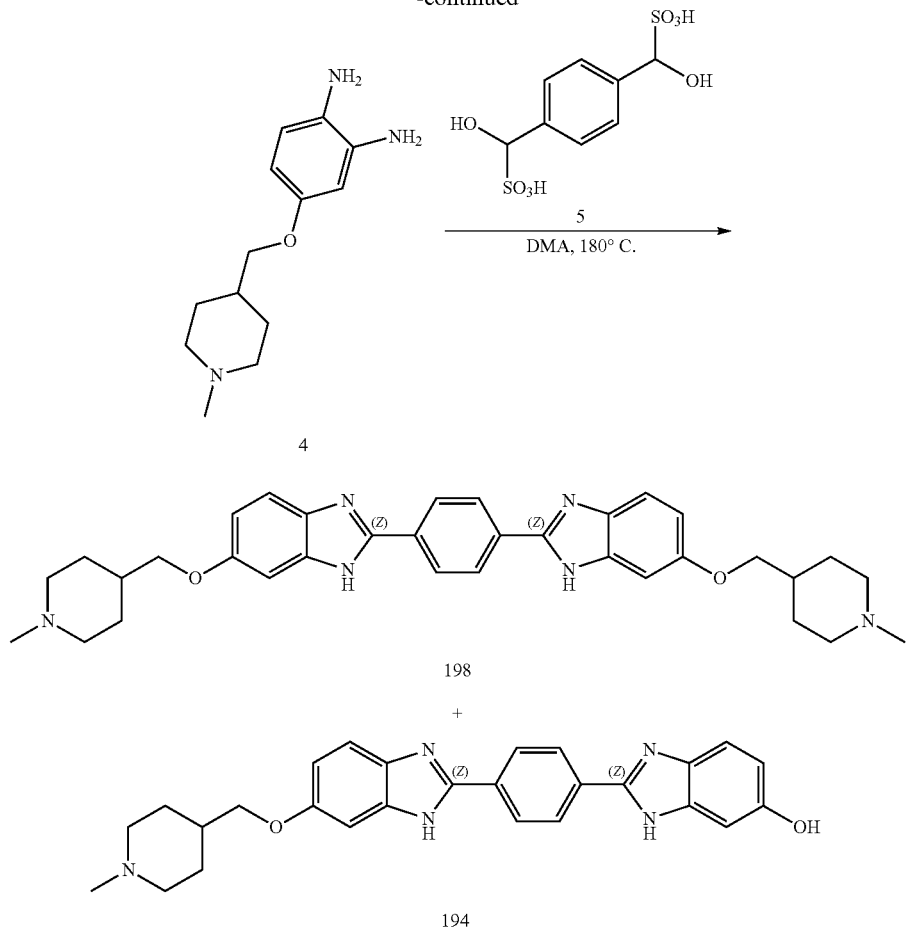

Synthesis of 5-((1-methylpiperidin-4-yl)methoxy)-2-nitroaniline: To a stirred solution of (1-methylpiperidin-4-yl)methanol (5.17 g, 40.0 mmol) in dry THF (20.0 mL), at 0° C. under $N_2$ atmosphere, was added NaH (60% suspension in oil, 2.56 g, 64.1 mmol) portion wise over a period of 10 minutes. The reaction mixture was stirred for an additional 10 minutes and a solution of 5-fluoro-2-nitroaniline (2.50 g, 16.0 mmol) in THF (10.0 mL) was added in a drop wise manner over 15 minutes, maintaining the temperature at 0° C. After complete addition, the reaction mixture was stirred at 60° C. for 16 h. The contents were poured onto ice and extracted with EtOAc (2×100 mL). The combined organic extracts were washed with brine (100 mL), dried over anhydrous $Na_2SO_4$, filtered and concentrated under vacuum to obtain the crude product. The product was purified by silica gel chromatography using $CH_3OH:CH_2Cl_2$ (1:9). The fractions containing the product were combined and concentrated under vacuum to obtain 5-((1-methylpiperidin-4-yl)methoxy)-2-

Synthesis of 4-((1-methylpiperidin-4-yl)methoxy)benzene-1,2-diamine: To a solution of 5-((1-methylpiperidin-4-yl)methoxy)-2-nitroaniline (1.30 g, 4.90 mmol) in EtOH (20.0 mL), hydrazine monohydrate (1.20 mL) and 10% Pd/C (0.25 g) were added and the reaction mixture was stirred at r.t for 5 h. The reaction mixture was filtered through a celite pad, and the pad was washed with EtOH (80 mL). The combined filtrate was concentrated under reduced pressure to obtain 4-((1-methylpiperidin-4-yl)methoxy)benzene-1,2-diamine. The crude product was directly used in the next step.

Synthesis of 1,4-bis(6-((1-methylpiperidin-4-yl)methoxy)-1H-benzo[d]imidazol-2-yl)benzene (198) and 2-(4-(6-((1-methylpiperidin-4-yl)methoxy)-1H-benzo[d]imidazol-2-yl)phenyl)-1H-benzo[d]imidazol-6-ol (194): To a suspension of 4-((1-methylpiperidin-4-yl)methoxy)benzene-1,2-diamine (0.75 g, 3.19 mmol) in DMA (10.0 mL) was added 1,4-phenylenebis(hydroxymethanesulfonic acid) (0.475 g, 1.59 mmol) and the reaction mixture was stirred at 180° C. for 4 h. The reaction mixture was cooled to r.t and poured onto ice, whereupon a solid precipitated. The precipitated solids were filtered under vacuum, washed with water (20.0 mL), and dried to obtain the crude product. The crude product was purified and separated by prep-HPLC. Fractions containing only the pure product were combined for concentration to obtain the title compounds. Compound 198: MS (ESI): m/z=565 [M+H]$^+$. Compound 194: MS (ESI): m/z=454 [M+H]$^+$.

Compounds 196, 199, 208, 209, 211, 212, 214, and 219 were prepared in the same manner as compound 198. Compound 196: MS (ESI): m/z=440 [M+H]$^+$. Compound 199: MS (ESI): m/z=537 [M+H]$^+$. Compound 208: MS (ESI) m/z=537 [M+H]$^+$. Compound 211: MS (ESI): m/z=599 [M+H]$^+$. Compound 209: MS (ESI): m/z=470 [M+H]$^+$. Compound 212: MS (ESI): m/z=597 [M+H]$^+$. Compound 214: MS (ESI) m/z=593 [M+H]$^+$. Compound 219: MS (ESI): m/z=593 [M+H]$^+$.

Example 133

Synthesis of 3,3'-((2,2'-(1,4-phenylene)bis(1H-benzo[d]imidazole-6,2-diyl))bis(oxy))bis(N,N-dimethylpropan-1-amine) (Compound 201)

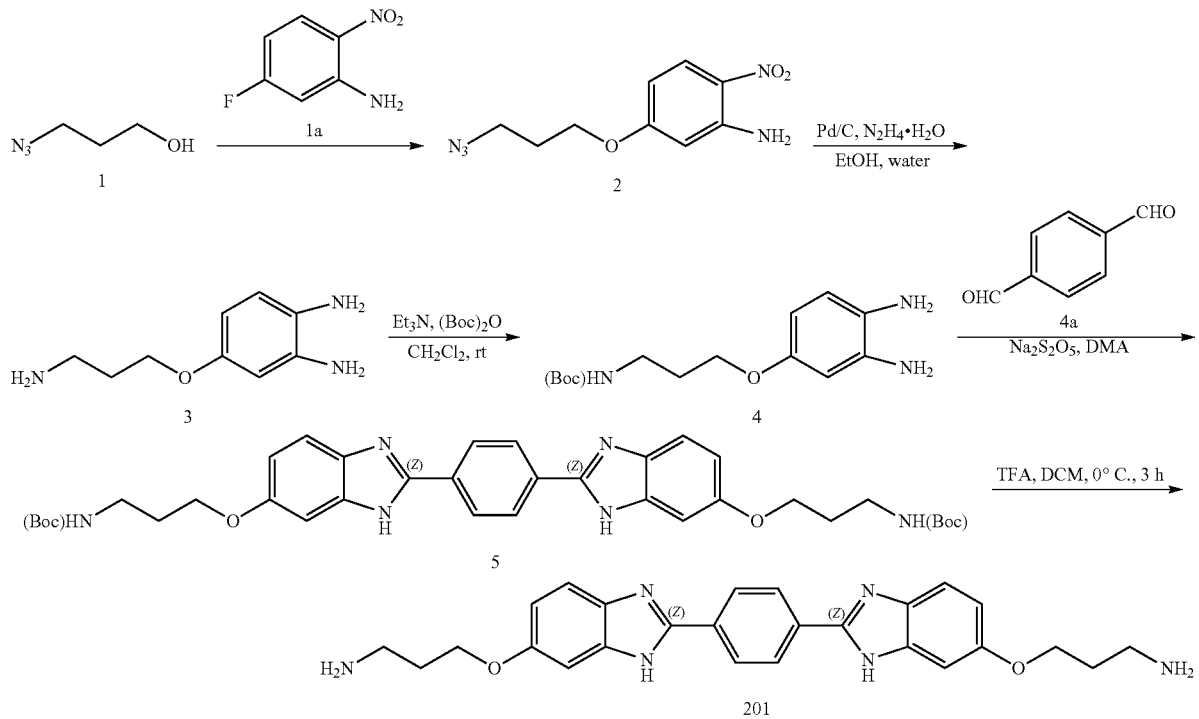

Synthesis of 5-(3-(dimethylamino)propoxy)-2-nitroaniline: To a stirred solution of 3-azidopropan-1-ol (2.00 g, 19.8 mmol) in dry THF (10.0 mL), at 0° C. under $N_2$ atmosphere, was added NaH (60% suspension in oil, 1.18 g, 49.5 mmol) portion wise over a period of 5 minutes. The reaction mixture was stirred for an additional 10 minutes and a solution of 5-fluoro-2-nitroaniline (3.08 g, 19.8 mmol) in THF (20.0 mL) was added in a drop wise manner over 10 minutes, maintaining the temperature at 0° C. After complete addition, the reaction mixture was warmed to 60° C. and stirred for 12 h. The reaction mixture was cooled to r.t and the contents were poured onto ice and extracted with EtOAc (2×100 mL). The combined organic extracts were washed with brine (60 mL), dried over anhydrous $Na_2SO_4$, and concentrated under vacuum to obtain the crude product. The product was purified by silica gel column chromatography using EtOAc:Hexane (1:1). The fractions containing the product were combined and concentrated under vacuum to obtain 5-(3-azidopropoxy)-2-nitroaniline. MS (ESI) m/z=238 [M+H]⁺.

Synthesis of 4-(3-(dimethylamino)propoxy)benzene-1,2-diamine: To a solution of 5-(3-azidopropoxy)-2-nitroaniline (1.00 g, 2.38 mmol) in EtOH (20.0 mL), was added hydrazine monohydrate (4.0 mL) and 20% Pd/C (200 mg) and the reaction mixture was stirred at r.t for 5 h. The reaction mixture was filtered through a celite pad, and the pad was washed with EtOH (50 mL). The combined filtrate was concentrated under reduced pressure to obtain 4-(3-aminopropoxy)benzene-1,2-diamine The crude product was directly used in the next step.

Synthesis of tert-butyl (3-(3,4-diaminophenoxy)propyl)carbamate: To a solution of 4-(3-aminopropoxy)benzene-1,2-diamine (0.70 g, 3.86 mmol) in DCM (20 mL) was added triethylamine (0.95 mL, 7.70 mmol) and Boc anhydride (1.00 g, 4.66 mmol), and the reaction mixture was stirred at r.t for 12 h. The contents were poured into water and extracted with EtOAc (2×100 mL). The combined organic extracts were washed with brine (60 mL), dried over anhydrous $Na_2SO_4$, and concentrated under vacuum to obtain tert-butyl (3-(3,4-diaminophenoxy)propyl)carbamate. The product was used directly in the next step without purification.

Synthesis of di-tert-butyl (((1,4-phenylenebis(1H-benzo[d]imidazole-2,6-diyl))bis(oxy))bis(propane-3,1-diyl))dicarbamate: In a microwave vial, a mixture of tert-butyl (3-(3,4-diaminophenoxy)propyl)carbamate (0.50 g, 2.14 mmol), terephthalaldehyde (142 mg, 1.06 mmol), and $Na_2S_2O_5$ (0.27 g, 2.14 mmol) in DMA (5.0 mL) was heated at 180° C. for 45 min. The reaction mixture was cooled to r.t and the contents were slowly poured into ice-cold water and stirred for 10 min, whereupon, a dark yellow solid precipitated. The yellow solid was collected by filtration under vacuum and washed with water (2×50 mL) to obtained di-tert-butyl (((1,4-phenylenebis(1H-benzo[d]imidazole-2,6-diyl))bis(oxy))bis(propane-3,1-diyl))dicarbamate. The crude compound was directly used in next step.

Synthesis of 3,3'-((1,4-phenylenebis(1H-benzo[d]imidazole-2,6-diyl))bis(oxy))bis(propan-1-amine): To a suspension di-tert-butyl (((1,4-phenylenebis(1H-benzo[d]imidazole-2,6-diyl))bis(oxy))bis(propane-3,1-diyl))dicarbamate (0.18 g, 0.27 mmol) in DCM (5.0 mL) at 0° C., was added TFA (0.30 mL, 2.71 mmol), and the reaction mixture was stirred at r.t. for 2 h. The reaction mixture was concentrated under vacuum to obtain the crude product. The product was purified by prep HPLC. The fractions containing only the pure product were combined for concentration to obtain the title compound. MS (ESI) m/z=457 [M+H]⁺.

Example 134

Synthesis of 3,3'-(2,2'-(1,4-phenylene)bis(1H-benzo[d]imidazole-6,6'-sulfonyl))bis(N,N-dimethylpropan-1-amine) (Compound 202)

was diluted with water (8 mL) and extracted with EtOAc (2×100 mL). The combined organic extracts were dried over anhydrous Na₂SO₄ and concentrated under reduced pressure. The product was purified by silica gel chromatography using CH₃OH:CH₂Cl₂ (1:9). The fractions containing the product were combined for concentration to obtain 5-((3-(dimethylamino)propyl)sulfonyl)-2-nitroaniline.

Synthesis of 4-((3-(dimethylamino)propyl)sulfonyl)benzene-1,2-diamine: To a solution of 5-((3-(dimethylamino)

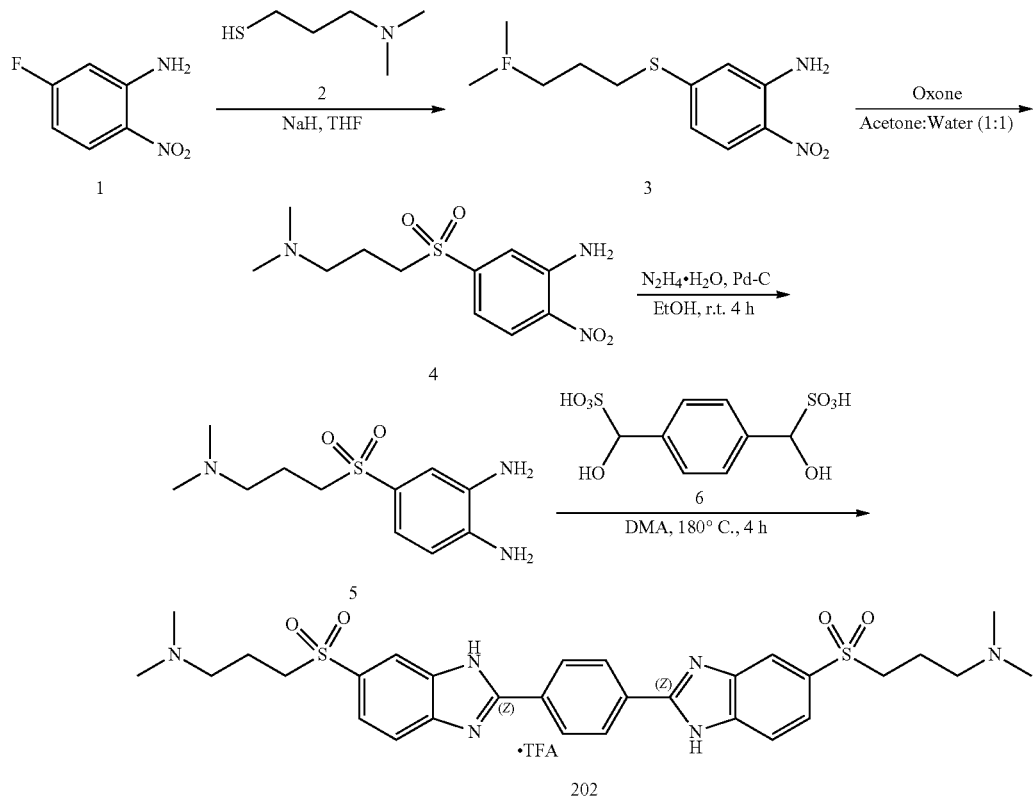

Synthesis of 5-((3-(dimethylamino)propyl)thio)-2-nitroaniline: To a stirred solution of 3-(dimethylamino)propane-1-thiol (2.31 g, 19.22 mmol) in dry THF (25 mL), at 0° C. under N₂ atmosphere, was added NaH (60% suspension in oil, 1.51 g, 38.4 mmol) portion wise over a period of 10 minutes. The reaction mixture was stirred for an additional 10 minutes and a solution of 5-fluoro-2-nitroaniline (3.00 g, 19.2 mmol) in THF (10.0 mL) was added in a drop wise manner over 5 minutes, maintaining the temperature at 0° C. After complete addition, the reaction mixture was heated at 70° C. for 16 h. The contents were poured onto ice and extracted with EtOAc (2×100 mL). The combined organic extracts were washed with brine solution (50 mL), dried over anhydrous Na₂SO₄ and concentrated under vacuum to obtain the crude product. The product was purified by silica gel column chromatography using CH₃OH:CH₂Cl₂ (1:9). The fractions containing the product were combined and concentrated under vacuum to obtain 5-((3-(dimethylamino)propyl)thio)-2-nitroaniline.

Synthesis of 5-((3-(dimethylamino)propyl)sulfonyl)-2-nitroaniline: To a solution of 5-((3-(dimethylamino)propyl)thio)-2-nitroaniline (700 mg, 2.74 mmol) in acetone (8 mL) and water (8 mL) was added oxone (6.75 g, 10.9 mmol) at r.t. and the mixture was stirred 16 h. The reaction mixture propyl)sulfonyl)-2-nitroaniline (685 mg, 2.384 mmol) in EtOH (25.0 mL) was added hydrazine monohydrate (6.00 mL) and 20% Pd/C (254 mg, 2.384 mmol), and the reaction mixture was stirred at r.t. for 4 h. The reaction mixture was filtered through a celite pad, and the pad was washed with EtOH (2×50 mL). The combined filtrate were concentrated under vacuum to obtain 4-((3-(dimethylamino)propyl)sulfonyl)benzene-1,2-diamine. The crude product was directly used in the next step.

Synthesis of 3,3'-(2,2'-(1,4-phenylene)bis(1H-benzo[d]imidazole-6,6'-sulfonyl))bis(N,N-dimethylpropan-1-amine) (202): To a suspension of 4-((3-(dimethylamino)propyl)sulfonyl)benzene-1,2-diamine (90 mg, 0.35 mmol) in DMA (5.0 mL), was added 1,4-phenylenebis(hydroxymethanesulfonic acid) (52 mg, 0.17 mmol) and the reaction mixture was stirred at 180° C. for 5 h. The reaction mixture was cooled to r.t. and poured onto ice, whereupon, the product precipitated. The precipitated product was filtered under vacuum, washed with water (20.0 mL), and dried to obtain the crude product. The crude product was purified by prep-HPLC. Fractions containing only the pure product were combined for concentration to obtain the title compound. MS (ESI): m/z=609 [M+H]⁺.

Example 135
Synthesis of 3-((2-(4-(6-(3-aminopropoxy)-1H-benzo[d]imidazol-2-yl)phenyl)-1H-benzo[d]imidazol-6-yl)oxy)-N,N-dimethylpropan-1-amine3 (Compound 205)
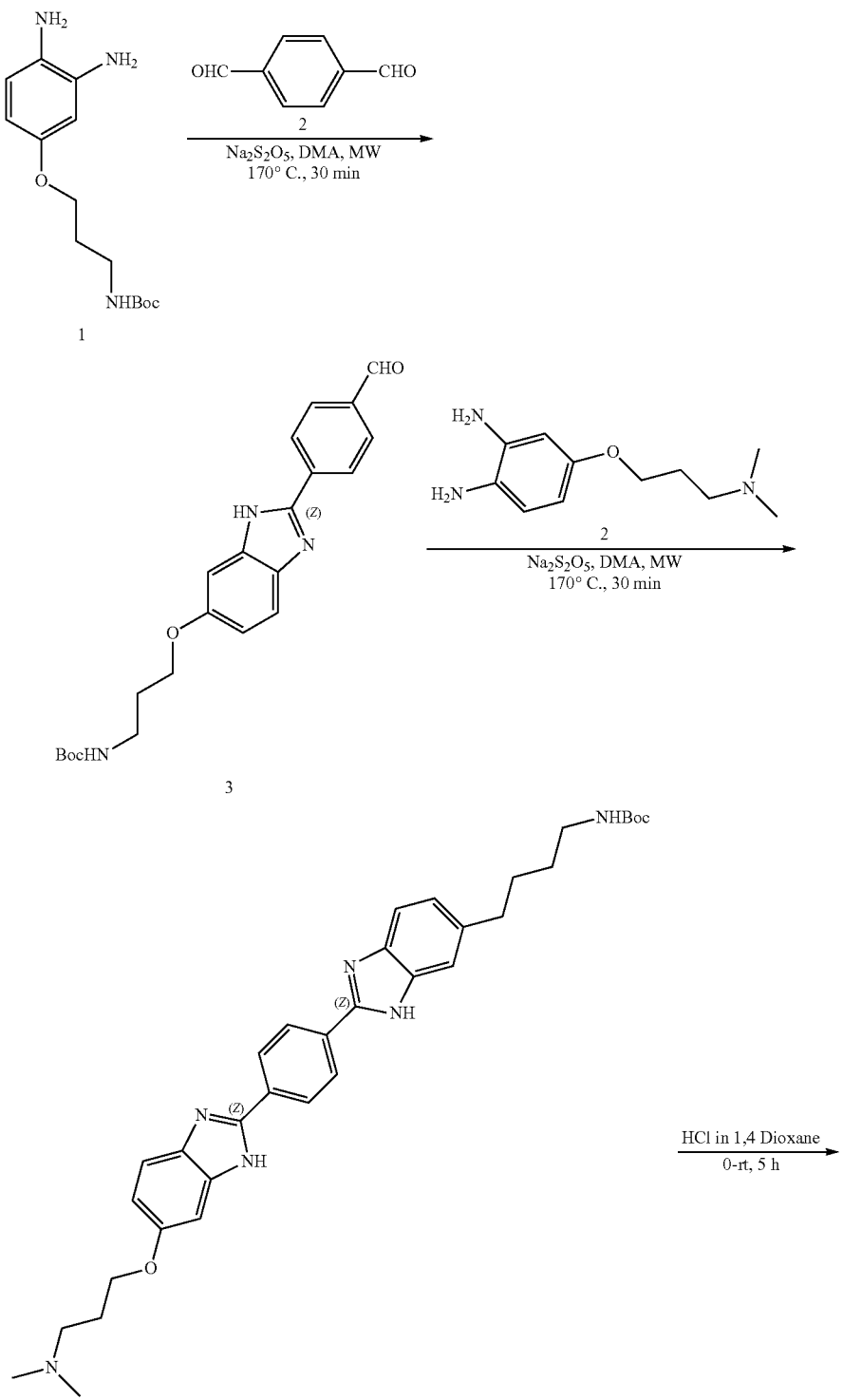

-continued

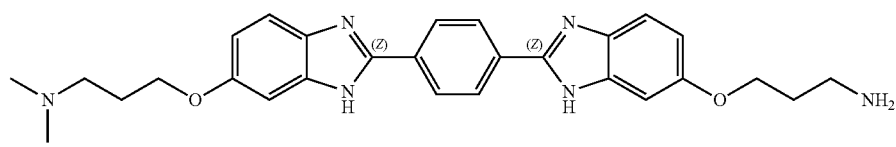

205

Synthesis of tert-butyl (3-((2-(4-formylphenyl)-1H-benzo[d]imidazol-6-yl)oxy)propyl)carbamate: To a solution of tert-butyl (3-(3,4-diaminophenoxy)propyl) carbamate (0.20 g, 0.711 mmol) in DMA (7.0 ml) was added sodium metabisulfite (0.23 g, 0.85 mmol) and the mixture was heated at 170° C. for 40 min. The reaction mixture was poured onto ice-cold water, whereupon the product precipitated. The product was filtered under reduced pressure, washed with water (30 mL) and dried to obtain (3-((2-(4-formylphenyl)-1H-benzo[d]imidazol-6-yl)oxy)propyl)carbamate. The crude product was directly used in the next step without purification.

Synthesis of tert-butyl (3-((2-(4-(6-(3-(dimethylamino)propoxy)-1H-benzo[d]imidazol-2-yl)phenyl)-1H-benzo[d]imidazol-6-yl)oxy)propyl)carbamate: To a solution of tert-butyl (3-((2-(4-formylphenyl)-1H-benzo[d]imidazol-6-yl)oxy)propyl)carbamate (0.25 g, 0.62 mmol) in and sodium metabisulfite (0.14 g, 0.76 mmol) in DMA (8.0 mL) was heated at 170° C. for 40 min. The reaction mixture was poured on to ice-cold water, whereupon the product precipitated. The product was filtered under reduced pressure, washed with water (20 mL) and dried to obtain tert-butyl (3-((2-(4-(6-(3-(dimethylamino)propoxy)-1H-benzo[d]imidazol-2-yl)phenyl)-1H-benzo[d]imidazol-6-yl)oxy)propyl)carbamate. The crude product was directly used in the next step without purification.

Synthesis of 3-((2-(4-(6-(3-aminopropoxy)-1H-benzo[d]imidazol-2-yl)phenyl)-1H-benzo[d]imidazol-6-yl)oxy)-N,N-dimethylpropan-1-amine (205): HCl (4.0 M in dioxane, 3.0 mL) was added to tert-butyl (3-((2-(4-(6-(3-(dimethylamino)propoxy)-1H-benzo[d]imidazol-2-yl)phenyl)-1H-benzo[d]imidazol-6-yl)oxy)propyl)carbamate (100 mg, 0.17 mmol) at 0° C. and the mixture was stirred at r.t, for 5 h. The reaction mixture was concentrated under reduced pressure and co-distilled with 1,4 dioxane (2×5 mL) to obtain the product. The product was triturated with MTBE (2×5 mL), filtered under vacuum and washed with MTBE (10 mL) to obtain the crude product. The crude product was purified by mass triggered prep-HPLC. The fractions containing the pure product were combined and concentrated under vacuum to obtain the title compound. MS (ESI+APCl): m/z=485 [M+H]⁺.

Example 136

Synthesis of N,N'-(((((carbonylbis(azanediyl))bis(ethane-2,1-diyl))bis(piperazine-4,1-diyl))bis(ethane-2,1-diyl))bis(2-(4-(6-((2-(piperidin-1-yl)ethyl)carbamoyl)-1H-benzo[d]imidazol-2-yl)phenyl)-1H-benzo[d]imidazole-6-carboxamide) (Compound 406)

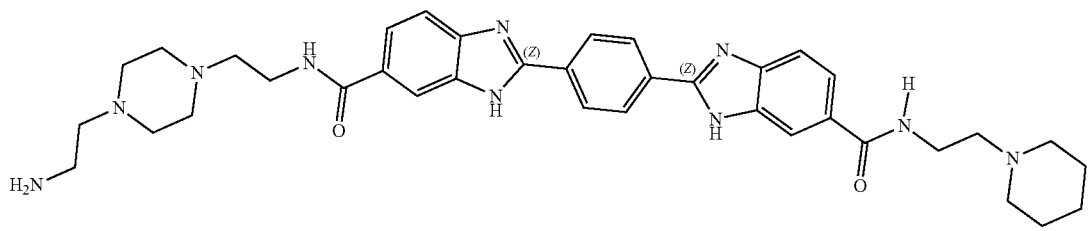

185

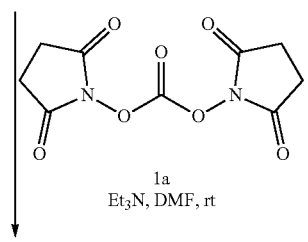

1a
Et₃N, DMF, rt

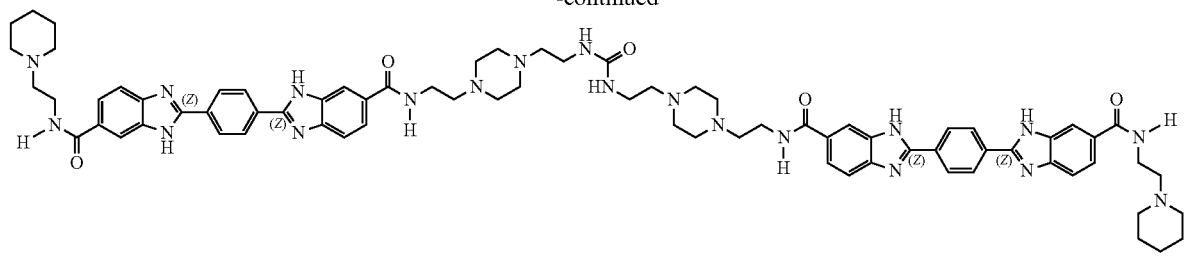

406

Synthesis of N,N'-(((((carbonylbis(azanediyl))bis(ethane-2,1-diyl))bis(piperazine-4,1-diyl))bis(ethane-2,1-diyl))bis (2-(4-(6-((2-(piperidin-1-yl)ethyl)carbamoyl)-1H-benzo[d]imidazol-2-yl)phenyl)-1H-benzo[d]imidazole-6-carboxamide): To a solution of N-(2-(4-(2-aminoethyl)piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide (51.8 mg, 0.08 mmol) in a mixture of CH$_3$CN:DMF (1 mL: 0.5 mL) was added bis(2,5-dioxopyrrolidin-1-yl) carbonate (10 mg, 0.04 mmol) and the mixture was stirred at r.t for 12 h. The reaction mixture was purified by C18 column chromatography using water: CH$_3$CN (1:1). The fractions containing the product were combined for concentration to obtain the product, which was found to be impure. The product was re-purified by prep HPLC. The fractions containing only the pure product were combined for concentration to obtain the title compound. MS (ESI+APCl) m/z 677 [(M+2H)/2]$^+$.

Example 137

Synthesis of 1,1'-(((((1,4-phenylenebis(1H-benzo[d]imidazole-2,6-diyl))bis(oxy))bis(methylene))bis(3,1-phenylene))bis(N,N-dimethylmethanamine) (Compound 213)

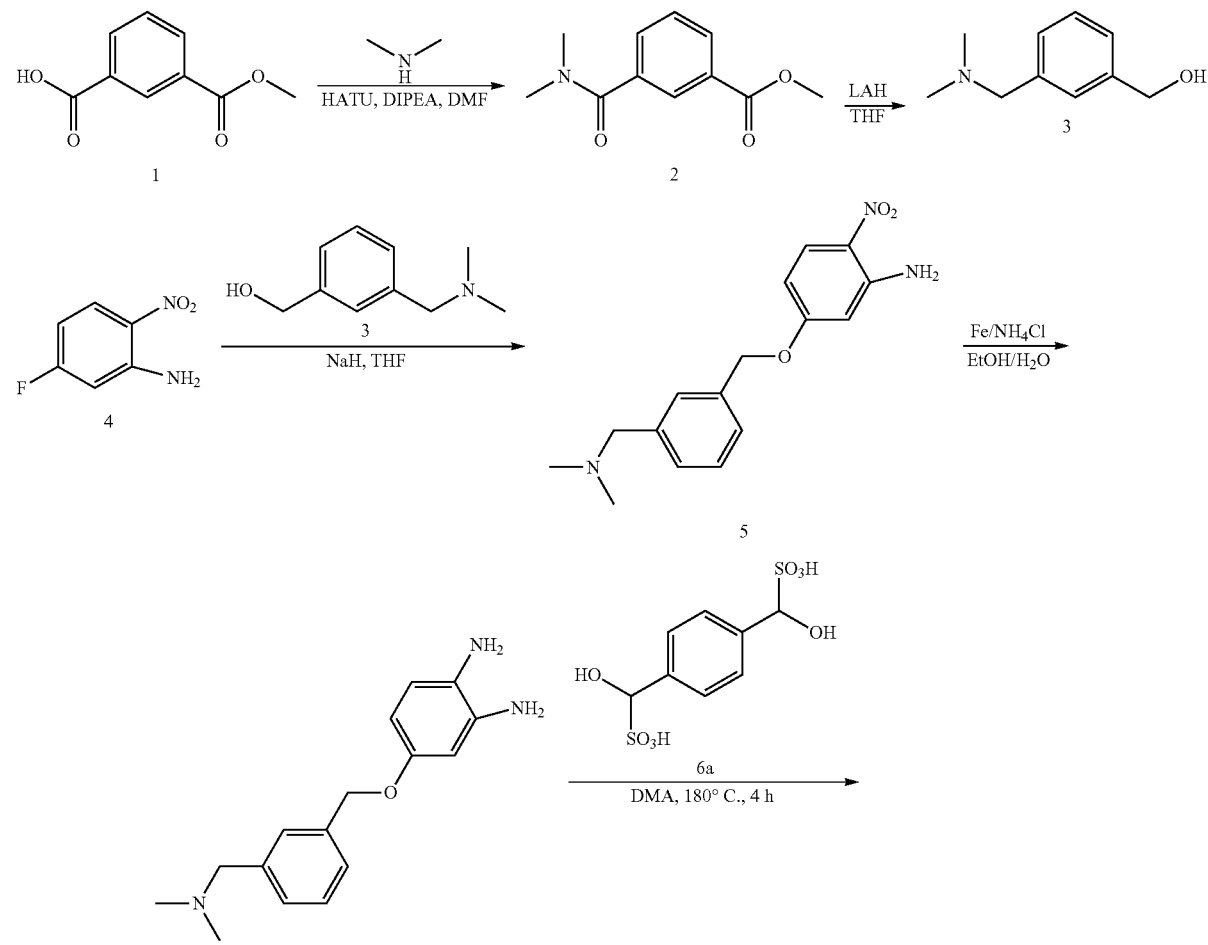

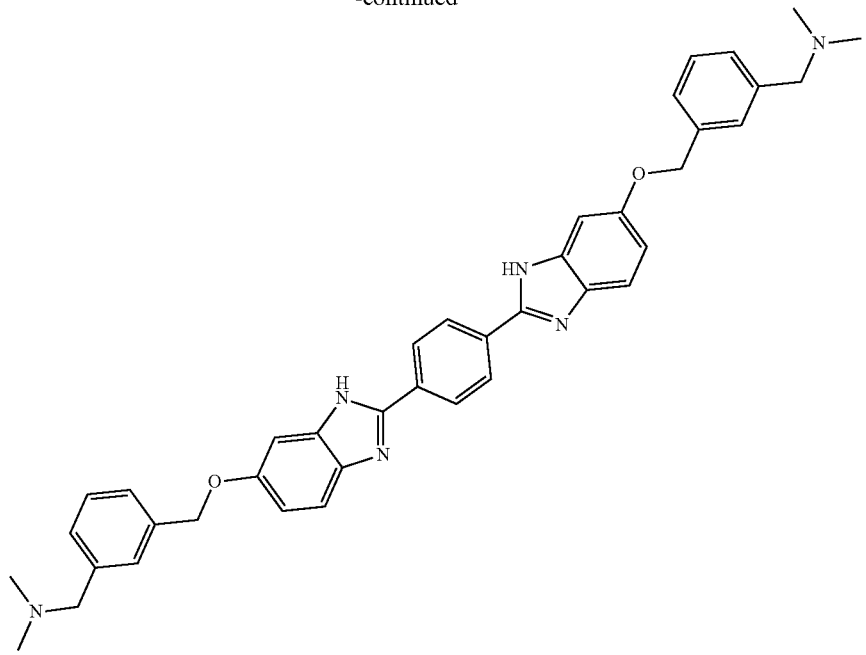

213

Synthesis of methyl 3-(dimethylcarbamoyl)benzoate: To a solution of 3-(methoxycarbonyl)benzoic acid (5.00 g, 27.8 mmol) in DMF (60.0 mL) at 0° C., was added HATU (15.8 g, 41.6 mmol), DIPEA (12.1 mL, 69.4 mmol) and the reaction mixture was stirred for 10 minutes. Dimethylamine (2.0 M in THF) (16.6 mL, 33.3 mmol) was added to the above mixture at 0° C. and the reaction mixture was stirred at r.t for 16 h. The contents were poured onto ice and extracted with EtOAc (2×100 mL). The combined organic extracts were washed with brine (100 mL), dried over anhydrous $Na_2SO_4$, filtered and concentrated under vacuum to obtain the crude product. The product was purified by silica gel chromatography (1:9 $CH_3OH:CH_2Cl_2$) to obtain methyl 3-(dimethylcarbamoyl)benzoate.

Synthesis of (3-((dimethylamino)methyl)phenyl)methanol: To a solution of methyl 3-(dimethylcarbamoyl)benzoate (4.00 g, 19.3 mmol) in THF (60.0 mL) at 0° C. was added a solution of LAH (2.0 M in THF) (57.9 mL, 116 mmol) drop wise slowly over a period of 30 mins. After complete addition, the reaction mixture was gradually warmed to r.t and stirred for 14 h. The reaction mixture was quenched with saturated aqueous solution of $Na_2SO_4$ at 0° C. and stirred for 15 min, whereupon solids precipitated. The precipitated solids were filtered through celite bed and the bed was washed with EtOAc (100 mL) and concentrated under vacuum to obtain the product (3-((dimethylamino)methyl)phenyl)methanol. The crude product was directly used for the next step.

Synthesis of 5-((3-((dimethylamino)methyl)benzyl)oxy)-2-nitroaniline: To a stirred solution of (3-((dimethylamino)methyl)phenyl)methanol (1.59 g, 9.61 mmol) in dry THF (15.0 mL), at 0° C. under $N_2$ atmosphere, was added NaH (60% suspension in oil, 0.77 g, 19.2 mmol) portion wise over a period of 10 minutes. The reaction mixture was stirred for an additional 10 minutes and a solution of 5-fluoro-2-nitroaniline (1.00 g, 6.41 mmol) in THF (10.0 mL) was added in a drop wise manner over 15 minutes, maintaining the temperature at 0° C. After complete addition, the reaction mixture was stirred at r.t for 12 h. The contents were poured onto ice and extracted with EtOAc (2×100 mL). The combined organic extracts were washed with brine (100 mL), dried over anhydrous $Na_2SO_4$, filtered and concentrated under vacuum to obtain the crude product. The product was purified by silica gel column chromatography using $CH_3OH:CH_2Cl_2$ (1:9). The fractions containing the product were combined and concentrated under vacuum to obtain 5-((dimethylamino)methyl)benzyl)oxy)-2-nitroaniline.

Synthesis of 4-((3-((dimethylamino)methyl)benzyl)oxy)benzene-1,2-diamine: To a solution of 5-((3-((dimethylamino)methyl)benzyl)oxy)-2-nitroaniline (0.35 g, 1.16 mmol) in EtOH (12.0 mL) was added Fe powder (0.22 g, 5.81 mmol) followed with a solution of $NH_4Cl$ (0.31 g, 5.81 mmol) in $H_2O$ (3.00 mL) and reaction mixture stirred at 60° C. for 2 h. The reaction mixture was filtered through celite pad and the pad was washed with EtOH (30.0 mL). The combined filtrate was concentrated under vacuum to obtain a residue. The residue was diluted with a mixture of MeOH:$CH_2Cl_2$ (1:9, 100 mL), washed with $H_2O$ (50 mL), brine solution (50 mL), dried over anhydrous $Na_2SO_4$, and concentrated under vacuum to obtain 4-((3-((dimethylamino)methyl)benzyl)oxy)benzene-1,2-diamine. The crude product was directly used in the next step.

Synthesis of 1,1'-(((((1,4-phenylenebis(1H-benzo[d]imidazole-2,6-diyl))bis(oxy))bis(methylene))bis(3,1-phenylene))bis(N,N-dimethylmethanamine): To a suspension of 4-((3-((dimethylamino)methyl)benzyl)oxy)benzene-1,2-diamine (0.21 g, 0.79 mmol) in DMA (5.0 mL) was added 1,4-phenylenebis(hydroxymethanesulfonic acid) (0.19 g, 0.39 mmol) and the reaction mixture was stirred for 4 h at 180° C. The reaction mixture was cooled to r.t and poured onto ice, whereupon the solids precipitated. The precipitated solids were filtered under vacuum, washed with water (20.0 mL), and dried to obtain the crude product. The product was purified by prep-HPLC. Fractions containing only the pure product were combined for concentration to give the title compound. MS (ESI+APCl) m/z=637 [M+H]+.

Compound 217 was prepared in the same manner as compound 213. MS (ESI+APCl) m/z=637 [M+H]+.

Example 138

Synthesis of 3,3'-((2,2'-(1,4-phenylene)bis(1H-benzo[d]imidazole-7,2-diyl))bis(oxy))bis(N,N-dimethylpropan-1-amine) (Compound 215) and 2-(4-(7-(3-(dimethylamino)propoxy)-1H-benzo[d]imidazol-2-yl)phenyl)-1H-benzo[d]imidazol-7-ol (Compound 216)

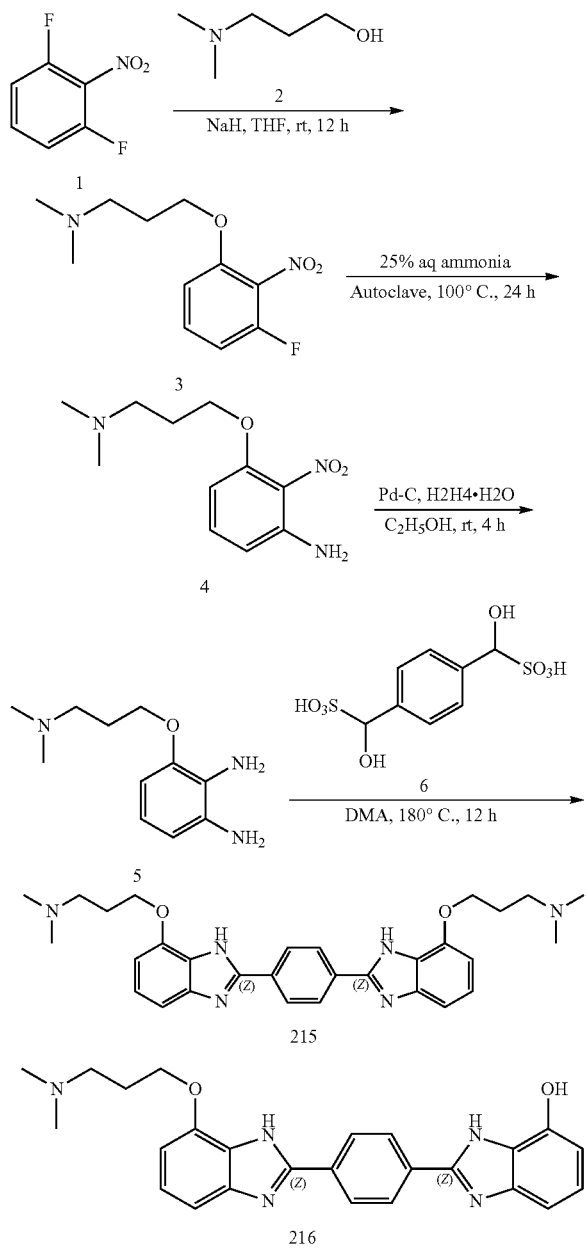

Synthesis of 3-(3-fluoro-2-nitrophenoxy)-N,N-dimethylpropan-1-amine: To a stirred solution of 3-(dimethylamino)propan-1-ol (3.24 g, 31.4 mmol) in dry THF (10 ml), at 0° C. under $N_2$ atmosphere, was added sodium hydride (60% suspension in oil, 2.51 g, 62.9 mmol) portion wise over a period of 10 minutes. The reaction mixture was stirred for an additional 10 minutes and a solution of 1,3-difluoro-2-nitrobenzene (5.00 g, 31.4 mmol) in THF (10.0 mL) was added in a drop wise manner over 15 minutes, maintaining the temperature at 0° C. After complete addition, the reaction mixture was warmed to 60° C. and stirred for 14 h. The reaction mixture was cooled to r.t and the contents were poured onto ice and extracted with $CH_3OH:CH_2Cl_2$ (1:9). The combined organic extracts were washed with brine (50 mL), dried over anhydrous $Na_2SO_4$ and concentrated under vacuum to obtain the crude product. The product was purified by silica gel column chromatography using $CH_3OH:CH_2Cl_2$ (1:9). The fractions containing the product were combined and concentrated under vacuum to obtain 3-(3-fluoro-2-nitrophenoxy)-N,N-dimethylpropan-1-amine.

Synthesis of 3-(3-(dimethylamino)propoxy)-2-nitroaniline: In an auto clave 25% aq. ammonia (20.0 mL, 231 mmol) was added to 3-(3-fluoro-2-nitrophenoxy)-N,N-dimethylpropan-1-amine (2.00 g, 8.26 mmol) and the reaction mixture was stirred at 100° C. for 24 h. The reaction mixture was cooled to r.t, and the mixture was concentrated under reduce pressure to obtain the crude compound. The product was purified by silica gel chromatography using $CH_3OH:CH_2Cl_2$ (1.5:8.5). The fractions containing the product were combined and concentrated under vacuum to obtain 3-(3-(dimethylamino)propoxy)-2-nitroaniline.

Synthesis of 3-(3-(dimethylamino)propoxy)benzene-1,2-diamine): To a solution of 3-(3-(dimethylamino)propoxy)-2-nitroaniline (1.80 g, 7.52 mmol) in EtOH (20 mL), was added hydrazine monohydrate (0.2 mL) followed with 10% Pd/C (200 mg), and the reaction mixture was stirred at r.t for 5 h. The reaction mixture was filtered through a celite pad, and the pad was washed with EtOH (50 mL). The combined filtrate was concentrated under reduced pressure to obtain 3-(3-(dimethylamino)propoxy)benzene-1,2-diamine. The crude product was used directly in the next step.

Synthesis of 3,3'-((2,2'-(1,4-phenylene)bis(1H-benzo[d]imidazole-7,2-diyl))bis(oxy))bis(N,N-dimethylpropan-1-amine) (E-215) and 2-(4-(7-(3-(dimethylamino)propoxy)-1H-benzo[d]imidazol-2-yl)phenyl)-1H-benzo[d]imidazol-7-ol (E-216): To the solution of 3-(3-(dimethylamino)propoxy)benzene-1,2-diamine (800 mg, 3.82 mmol) in N,N-dimethylacetamide (10 mL) was added 1,4-phenylenebis (hydroxy methanesulfonic acid) (570 mg, 1.91 mmol) and the mixture was heated at 180° C. for 24 h. The reaction mixture was cooled to r.t and the contents were slowly poured into ice-cold water and stirred for 10 min, whereupon, a dark yellow solid precipitated. The yellow solid was collected by filtration under vacuum, washed with water (2×50 mL), and dried to obtain the crude product. The product was purified and separated by prep HPLC. Fractions containing only the pure product were combined for concentration to give the title compounds. Compound 215: MS (ESI+APCl): m/z=513 [M+H]+. Compound 216: MS (ESI+APCl): m/z=428 [M+H]+.

Example 139
Synthesis of 1,1'-((1r,1'r,4r,4'r)-(((1,4-phenylenebis(1H-benzo[d]imidazole-2,6-diyl))bis(oxy))bis(methylene))bis(cyclohexane-4,1-diyl))bis(N,N-dimethylmethanamine) (Compound 218)
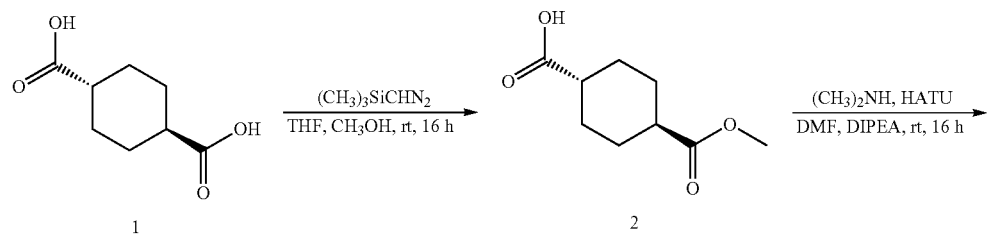
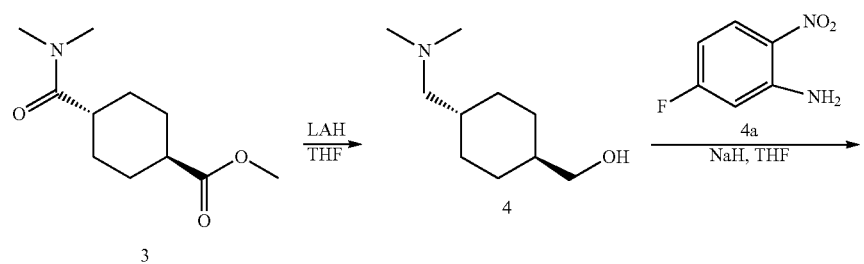
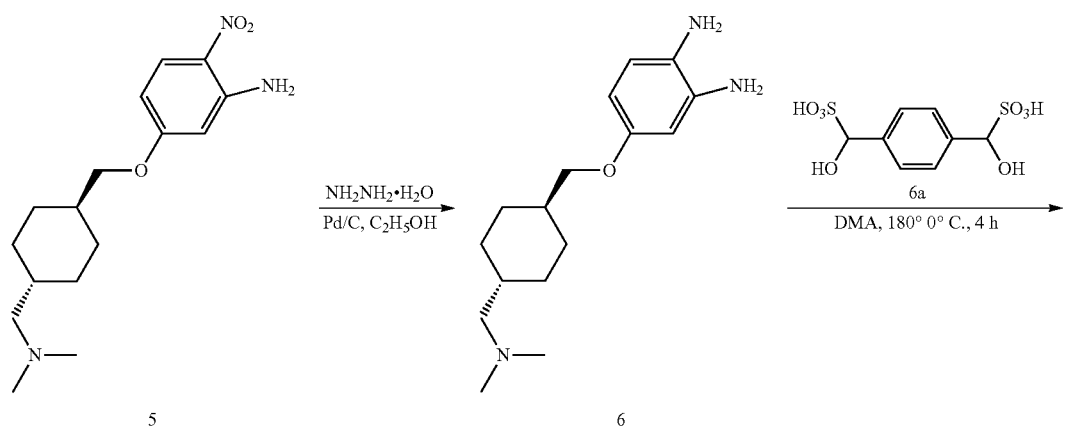

-continued

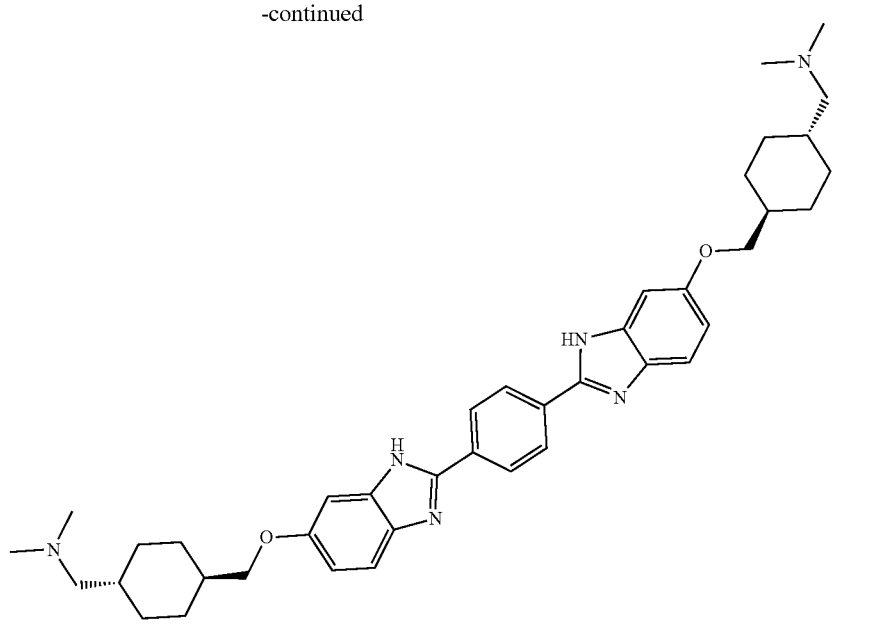

218

Synthesis of (1r,4r)-4-(methoxycarbonyl)cyclohexane-1-carboxylic acid: Trimethylsilyldiazomethane (2.0 M hexanes, 2.9 mL) was added to a solution of (1r,4r)-cyclohexane-1,4-dicarboxylic acid (1.0 g, 5.81 mmol) in 4:1 THF/MeOH (60 mL), and the mixture was stirred at r.t for 16 h. The reaction mixture was concentrated under vacuum, whereupon a solid was obtained. The solid was diluted with a mixture of 1:1 EtOAc/hexanes (50 mL), and the mixture was stirred at r.t for 15 mins. The mixture was filtered through a celite pad, under vacuum, and the pad was washed with 1:1 EtOAc/hexanes (2×25 mL). The combined filtrates were concentrated under vacuum to obtain the crude product. The crude product was purified by silica-gel column chromatography using 1:2 EtOAc/hexanes containing 0.1 percent AcOH, as an eluent. The fractions containing the product were combined for concentration to obtain (1r,4r)-4-(methoxycarbonyl)cyclohexane-1-carboxylic acid Synthesis of methyl (1r,4r)-4-(dimethylcarbamoyl)cyclohexane-1-carboxylate: To a solution of (1r,4r)-4-(methoxycarbonyl)cyclohexane-1-carboxylic acid (2.60 g, 13.9 mmol) in DMF (25.0 mL) at 0° C., was added HATU (7.96 g, 20.9 mmol) followed with DIPEA (7.51 mL, 41.9 mmol) and the reaction mixture was stirred for 10 minutes. Dimethylamine (2.0 M in THF, 10.4 mL, 20.9 mmol) was added to the above mixture at 0° C. and the reaction mixture was stirred at r.t for 16 h. The contents were poured onto ice cold water, and extracted with EtOAc (2×100 mL). The combined organic extracts were washed with brine (100 mL), dried over anhydrous $Na_2SO_4$, filtered and concentrated under vacuum to obtain methyl (1r,4r)-4-(dimethylcarbamoyl)cyclohexane-1-carboxylate. The crude product was directly used in the next step.

Synthesis of ((1r,4r)-4-((dimethylamino)methyl)cyclohexyl)methanol: To a solution of methyl (1r, 4r)-4-(dimethylcarbamoyl)cyclohexane-1-carboxylate (1.50 g, 7.03 mmol) in THF (30.0 mL), under $N_2$ atmosphere at 0° C., was added a solution of $LiAlH_4$ (2.0 M in THF, 21.1 mL, 42.2 mmol) drop wise over a period of 30 mins. After complete addition, the reaction mixture was gradually warmed to r.t and stirred for additional 14 h. The reaction mixture was quenched with saturated aqueous solution of $Na_2SO_4$ at 0° C. and stirred for 15 min, whereupon solids precipitated. The precipitated solids were filtered through celite pad and the pad was washed with EtOAc (100 mL). The filtrate was concentrated under vacuum to obtain ((1r, 4r)-4-((dimethylamino)methyl)cyclohexyl)methanol. The crude product was directly used in the next step.

Synthesis of 5-(((1r,4r)-4-((dimethylamino)methyl)cyclohexyl)methoxy)-2-nitroaniline: To a stirred solution of ((1r, 4r)-4-((dimethylamino)methyl)cyclohexyl)methanol (2.19 g, 12.8 mmol) in dry THF (20.0 mL), under $N_2$ atmosphere at 0° C., was added NaH (60% suspension in oil, 0.77 g, 19.2 mmol) portion wise over a period of 10 minutes. The reaction mixture was stirred for an additional 10 minutes and a solution of 5-fluoro-2-nitroaniline (1.00 g, 6.41 mmol) in THF (10.0 mL) was added in a drop wise manner over 15 minutes, maintaining the temperature at 0° C. After complete addition, the reaction mixture was stirred at 60° C. for 12 h. The contents were poured onto ice and extracted with EtOAc (2×100 mL). The combined organic extracts were washed with brine (100 mL), dried over anhydrous $Na_2SO_4$, filtered and concentrated under vacuum to obtain the crude product. The product was purified by silica gel column chromatography using $CH_3OH:CH_2Cl_2$ (1:9). The fractions containing the product were combined and concentrated under vacuum to obtain 5-(((1r,4r)-4-((dimethylamino)methyl)cyclohexyl)methoxy)-2-nitroaniline.

Synthesis of 4-(((1r,4r)-4-((dimethylamino)methyl)cyclohexyl)methoxy)benzene-1,2-diamine: To a solution of 5-(((1r,4r)-4-((dimethylamino)methyl)cyclohexyl)methoxy)-2-nitroaniline (85 mg, 0.277 mmol) in EtOH (5.0 mL) was added hydrazine hydrate (0.2 mL) followed with Pd/C (20 mg) and the reaction mixture was stirred at r.t for 4 h. The reaction mixture was filtered through a celite pad, and the pad was washed with EtOH (2×10 mL). The combined filtrate were concentrated under vacuum to obtain 4-(((1r,4r)-4-((dimethylamino)methyl)cyclohexyl)methoxy)benzene-1,2-diamine. The crude product was directly used in the next step.

Synthesis of 1,1'-(((1r,1'r,4r,4'r)-(((1,4-phenylenebis(1H-benzo[d]imidazole-2,6-diyl))bis(oxy))bis(methylene))bis(cyclohexane-4,1-diyl))bis(N,N-dimethylmethanamine) (Compound 218): To a suspension of 4-(((1r,4r)-4-((dimethylamino)methyl)cyclohexyl) methoxy)benzene-1,2-diamine (65 mg, 0.23 mmol) in DMA (2.50 mL) was added 1,4-phenylenebis(hydroxymethanesulfonic acid) (35 mg, 0.12 mmol) and the reaction mixture was stirred at 180° C. for 4 h. The reaction mixture was cooled to r.t and poured onto ice, whereupon the solids precipitated. The precipitated solids were filtered under vacuum, washed with water (5.0 mL), and dried to obtain the crude product. The product was purified by prep-HPLC. Fractions containing only the pure product were combined for concentration to obtain the title compound. MS (ESI+APCI) m/z=649 [M+H]$^+$.

Example 140

Synthesis of 4,4'-(2,2'-(1,4-phenylene)bis(1H-benzo[d]imidazole-6,2-diyl))bis(N,N-dimethylbutan-1-amine) (Compound 220)

h. The reaction mixture was cooled to r.t and the contents were filtered through a celite pad and the pad was washed with EtOAc (2×30 mL). The combined filtrate was concentrated under vacuum to obtain the crude product. The product was purified by silica gel chromatography using EtOAc:Hexanes (3:7). The fractions containing the product were combined and concentrated under vacuum to obtain 4-(4-amino-3-nitrophenyl) but-3-yn-1-ol.

Synthesis of 4-(4-amino-3-nitrophenyl)but-3-yn-1-yl methanesulfonate: To a stirred solution of 4-(4-amino-3-nitrophenyl) but-3-yn-1-ol (1.00 g, 4.56 mmol) in CH$_2$Cl$_2$ (30.0 mL), at 0° C. under N$_2$ atmosphere, was added trimethylamine (2.80 mL, 19.4 mmol) followed with mesylchloride (0.50 mL, 6.84 mmoldropwise over a period of 5 min. After complete addition, the reaction mixture was stirred at r.t for 2 h. The reaction mixture poured onto ice and extracted with EtOAc (2×50 mL). The combined organic extracts were washed with brine (50 mL), dried over anhydrous Na$_2$SO$_4$ and concentrated under vacuum to obtain 4-(4-amino-3-nitrophenyl) but-3-yn-1-yl methane sulfonate. The crude product was directly used in the next step.

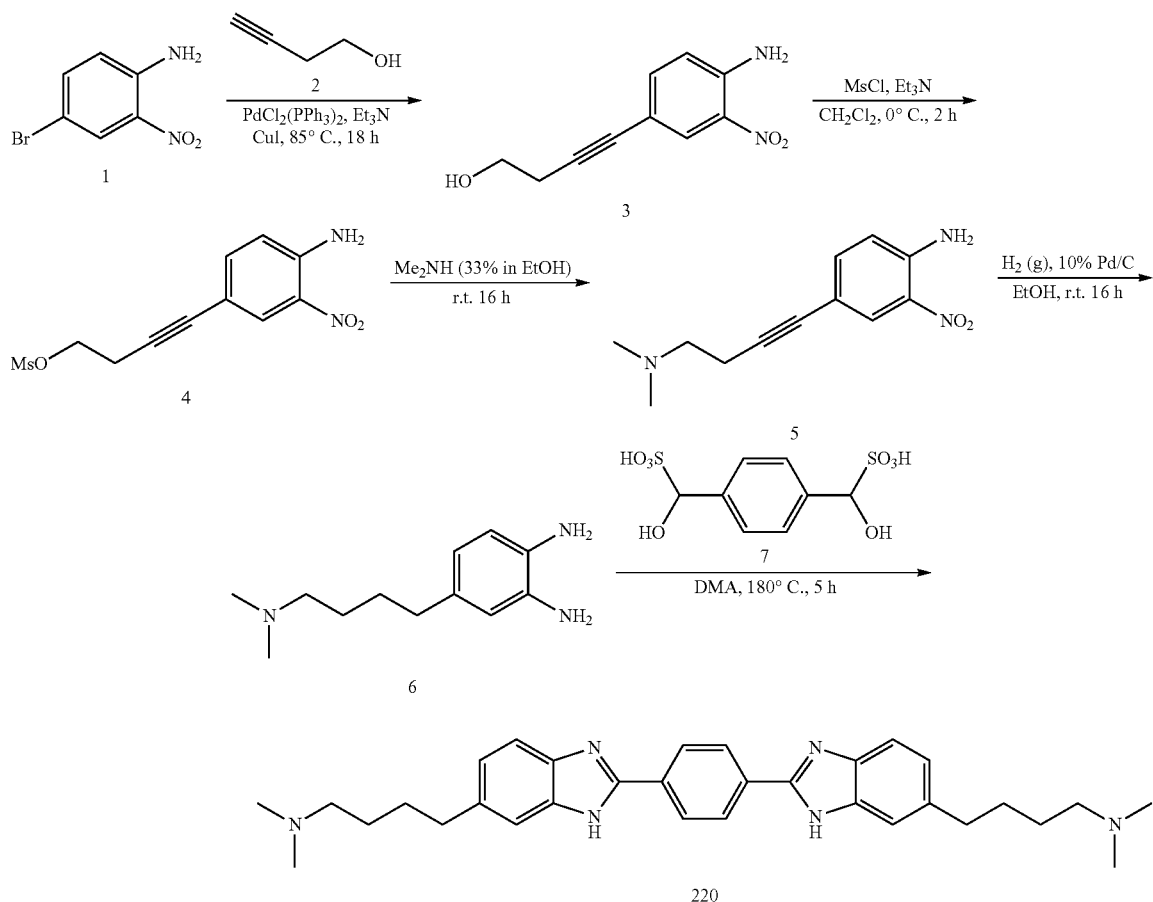

Synthesis of 4-(4-amino-3-nitrophenyl)but-3-yn-1-ol: A stirred solution of 4-bromo-2-nitroaniline (5.00 g, 23.0 mmol), but-3-yn-1-ol (2.40 g, 34.6 mmol), copper(I) iodide (878.2 mg, 4.6 mmol) in trimethylamine (30.0 mL), was degassed using N$_2$(g) for 5 min, and bis(triphenylphosphine) palladium(II) chloride (809 mg, 1.52 mmol) was added in one lot, and the reaction mixture was heated at 75° C. for 8

Synthesis of 4-(4-(dimethylamino)but-1-yn-1-yl)-2-nitroaniline: To 4-(4-amino-3-nitrophenyl) but-3-yn-1-yl methane sulfonate (1.30 g, 4.57 mmol), placed in a sealed tube, was added Me$_2$NH (33% in EtOH, 25.0 mL, 5.36 mmol). The tube was sealed and the mixture was stirred at r.t for 16 h. The reaction mixture was concentrated under vacuum to obtain the crude product. The product was purified by silica gel chromatography using MeOH:CH$_2$Cl$_2$ (2:8). The fractions containing the product were combined and concentrated under vacuum to obtain 4-(4-(dimethylamino) but-1-yn-1-yl)-2-nitroaniline Synthesis of 4-(4-(dimethylamino)butyl)benzene-1,2-diamine: To a solution of 4-(4-(dimethylamino)but-1-yn-1-yl)-2-nitroaniline (600 mg, 2.57 mmol) in EtOH (25 mL), at r.t under N$_2$ atmosphere, was added 10% Pd/C (80 mg) the reaction mixture was hydrogenated at r.t for 4 h. The reaction mixture was filtered through a celite pad, and the pad was washed with EtOH (2×50 mL). The combined filtrate were concentrated under vacuum to obtain 4-(4-(dimethylamino)butyl)benzene-1,2-diamine. The crude product was used directly in the next step.

Synthesis of 4,4'-(2,2'-(1,4-phenylene)bis(1H-benzo[d]imidazole-6,2-diyl))bis(N,N-dimethylbutan-1-amine) (220): To a stirred suspension of 4-(4-(dimethylamino)butyl) benzene-1,2-diamine (200 mg, 0.96 mmol) in DMA (15.0 mL), at r.t under N$_2$ atmosphere, was added 1,4-phenylenebis (hydroxymethanesulfonic acid) (144 mg, 0.48 mmol) and the reaction mixture was heated at 180° C. for 5 h. The reaction mixture was cooled to r.t and the contents were poured onto ice, whereupon the product precipitated. The precipitated solids were filtered under vacuum, washed with water (20.0 mL), and dried to obtain the crude product. The crude product was purified by prep-HPLC. Fractions containing only the pure product were combined for concentration to obtain the title compound. MS (ESI): m/z=509 [M+H]$^+$.

Example 141

Synthesis of 2,2'-(1,1'-(2,2'-(1,4-phenylene)bis(1H-benzo[d]imidazole-6,2-diyl))bis(1H-1,2,3-triazole-4,1-diyl))bis(N,N-dimethylethanamine (Compound 221)

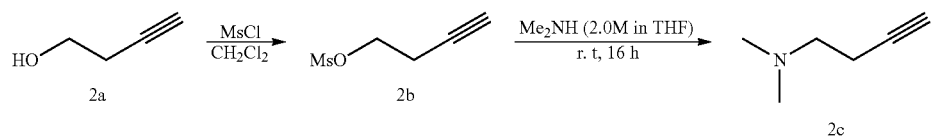

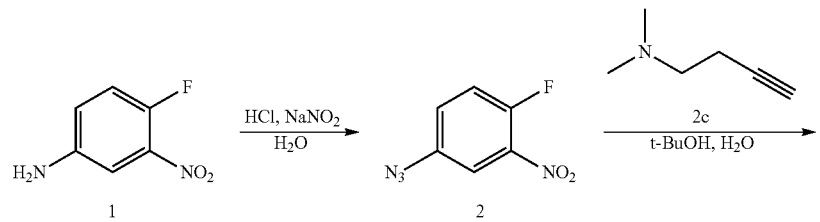

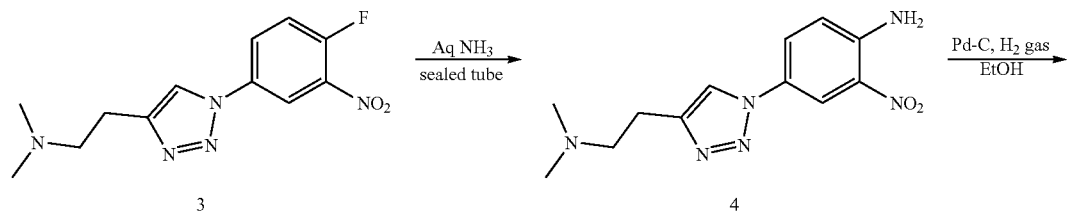

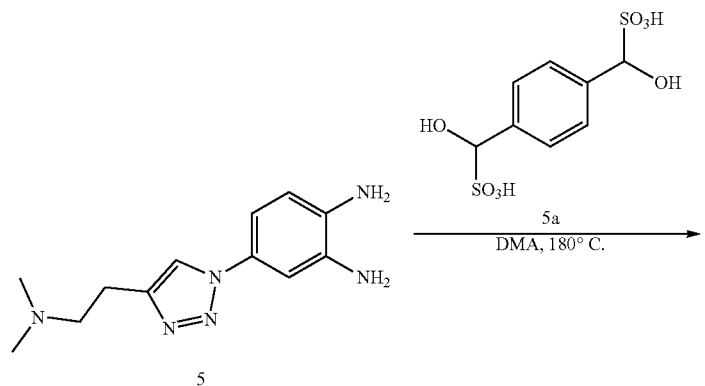

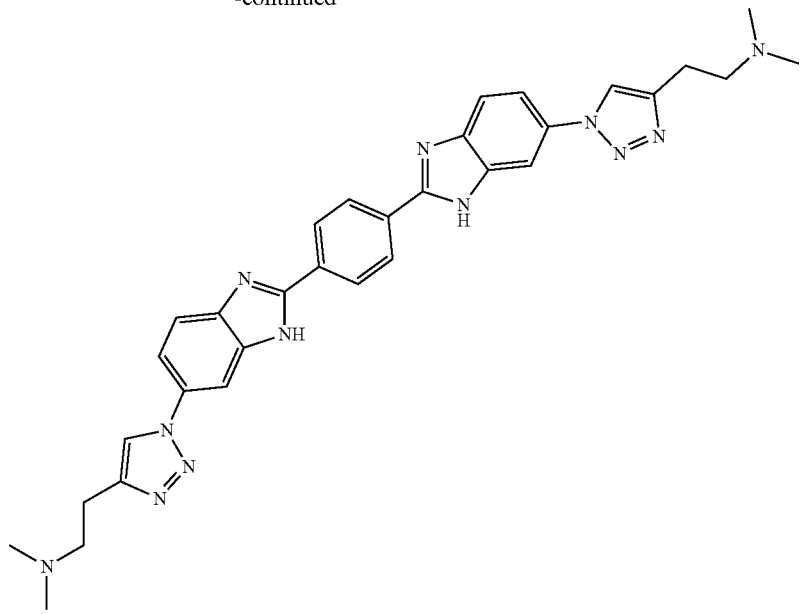

221

Synthesis of but-3-yn-1-yl methane sulfonate: To a stirred solution of but-3-yn-1-ol (10.0 g, 143 mmol) in CH$_2$Cl$_2$ (150 mL), at 0° C. under N2 atmosphere, was added triethylamine (19.9 mL, 143 mmol) followed with methane sulfonyl chloride (11.1 mL, 143 mmol) in a drop wise manner over 10 minutes, and the reaction mixture was stirred at r.t for 2 h. The reaction mixture were poured on to water and extracted with CH$_2$Cl$_2$ (2×50 mL). The combined organic extracts were washed with brine (50 mL), dried over anhydrous Na$_2$SO$_4$, filtered and concentrated under vacuum to obtain but-3-yn-1-yl methane sulfonate. The crude product was directly used in the next step.

Synthesis of N,N-dimethylbut-3-yn-1-amine: To but-3-yn-1-yl methane sulfonate (8.00 g, 54.0 mmol), placed in a sealed tube, was added Me$_2$NH (2.0 M in THF, 160 mL) at 0° C., and the reaction mixture was stirred at r.t for 16 h. The reaction mixture was directly distilled using a short path condenser, to collect N,N-dimethylbut-3-yn-1-amine (70 mL) as a molar solution in THF. Note: the boiling point of the product is 86° C. at 1 atmosphere pressure.

Synthesis of 4-azido-1-fluoro-2-nitrobenzene: To a stirred solution of 4-fluoro-3-nitroaniline (3.00 g, 19.2 mmol) in 6 N HCl (70.0 mL) at 0° C. was added a solution of sodium nitrite (1.32 g, 19.2 mmol) in H$_2$O (10.0 mL), and the reaction mixture at the same temperature for 10 min. A solution of sodium azide (1.87 g, 28.8 mmol) in H$_2$O (10.0 mL) was added in a drop wise manner to the above mixture over 15 minutes, maintaining the temperature at 0° C. After complete addition, the reaction mixture was stirred at 0° C. for 4 h, whereupon a yellow solid precipitated. The yellow solid was filtered under vacuum, washed with water (2×50 mL), and dried to obtain 4-azido-1-fluoro-2-nitrobenzene.

Synthesis of 2-(1-(4-fluoro-3-nitrophenyl)-1H-1,2,3-triazol-4-yl)-N,N-dimethylethanamine: To a stirred solution of 4-azido-1-fluoro-2-nitrobenzene (2.00 g, 10.9 mmol) in a mixture of tert-BuOH (50.0 mL) and H$_2$O (50.0 mL) was added copper(II) sulfate pentahydrate (0.55 g, 2.19 mmol) followed with L-ascorbic acid sodium salt (39.6 mg, 2.19 mmol), and the mixture was stirred at r.t for 16 h. The contents were poured onto water (100 mL) and extracted with EtOAc (3×50 mL). The combined organic extracts were washed with brine (50 mL), dried over anhydrous Na$_2$SO$_4$, filtered and concentrated under vacuum to obtain the crude product. The product was purified by silica gel column chromatography using CH$_3$OH:CH$_2$Cl$_2$ (1:9). The fractions containing the product were combined and concentrated under vacuum to obtain 2-(1-(4-fluoro-3-nitrophenyl)-1H-1,2,3-triazol-4-yl)-N,N-dimethylethanamine.

Synthesis of 4-(4-(2-(dimethylamino)ethyl)-1H-1,2,3-triazol-1-yl)-2-nitroaniline: In a sealed tube a solution of 2-(1-(4-fluoro-3-nitrophenyl)-1H-1,2,3-triazol-4-yl)-N,N-dimethylethanamine (1.80 g, 6.45 mmol) in aq. NH$_3$ (50.0 mL) was heated at 70° C. for 16 h. The reaction mixture was cooled to r.t, whereupon a brown solid precipitated. The brown solid was filtered under vacuum, washed with water (2×50 mL), and dried to obtain the crude product. The product was triturated with EtOAc (50 mL), filtered the product under vacuum, washed with EtOAc (20 mL), and dried to obtain 4-(4-(2-(dimethylamino)ethyl)-1H-1,2,3-triazol-1-yl)-2-nitroaniline.

Synthesis of 4-(4-(2-(dimethylamino)ethyl)-1H-1,2,3-triazol-1-yl)benzene-1,2-diamine: To a solution of 4-(4-(2-(dimethylamino)ethyl)-1H-1,2,3-triazol-1-yl)-2-nitroaniline (400 mg, 1.45 mmol) in EtOH (20.0 mL) under N$_2$ atmosphere, was added 10% Pd—C (231 mg) and the reaction mixture was hydrogenated (balloon pressure~1 atms) at r.t for 3 h. The reaction mixture was filtered through a celite pad, and the pad was washed with EtOH (20 mL). The combined filtrate was concentrated under reduced pressure to obtain 4-(4-(2-(dimethylamino)ethyl)-1H-1,2,3-triazol-1-yl)benzene-1,2-diamine. The crude product was directly used in the next step.

Synthesis of 2,2'-(1,1'-(2,2'-(1,4-phenylene)bis(1H-benzo[d]imidazole-6,2-diyl))bis(1H-1,2,3-triazole-4,1-diyl))bis(N,N-dimethylethanamine) (221): To a stirred solution of 1,4-phenylenebis(hydroxymethanesulfonic acid) (303 mg, 1.01 mmol) in DMA (15.0 mL) was added 4-(4-(2-(dimethylamino)ethyl)-1H-1,2,3-triazol-1-yl)benzene-1,2-diamine (500 mg, 2.03 mmol) and the reaction mixture was heated at 180° C. for 4 h. The reaction mixture was cooled to 60° C. and concentrated under vacuum to obtain the crude product. The product was purified by mass triggered Prep-HPLC. The fractions containing only the pure product were combined and concentrated under vacuum to obtain the title compound. MS (ESI): m/z=587 [M+H]$^+$.

Example 142

Synthesis of 3-((2-(4-(5-(3-(dimethylamino) propoxy)-1H-benzo[d]imidazol-2-yl)phenyl)-1H-benzo[d]imidazol-5-yl)oxy)propan-1-ol (Compound 222)

was added palladium on carbon (0.50 g, 4.71 mmol) followed with hydrazine monohydrate (1.48 mL, 47.1 mmol), and the reaction mixture was hydrogenated at r.t for 14 h. The reaction mixture was filtered through a celite pad, and the pad was washed with EtOH (2×50 mL). The combined filtrates were concentrated under reduced pressure to obtain 3-(3,4-diaminophenoxy)propan-1-ol.

Synthesis of 4-(5-(3-hydroxypropoxy)-1H-benzo[d]imidazol-2-yl)benzaldehyde: In a microwave vial, a mixture of 3-(3,4-diaminophenoxy)propan-1-ol (0.70 g, 3.84 mmol), terephthalaldehyde (0.77 g, 5.76 mmol) and sodium metabisulfate (0.73 g, 3.84 mmol) in DMA (10 mL) was heated at 180° C. for 40 min. The reaction mixture was cooled to r.t and the contents were slowly poured into water (50 mL) and stirred for 10 min, whereupon, a brown solid precipi-

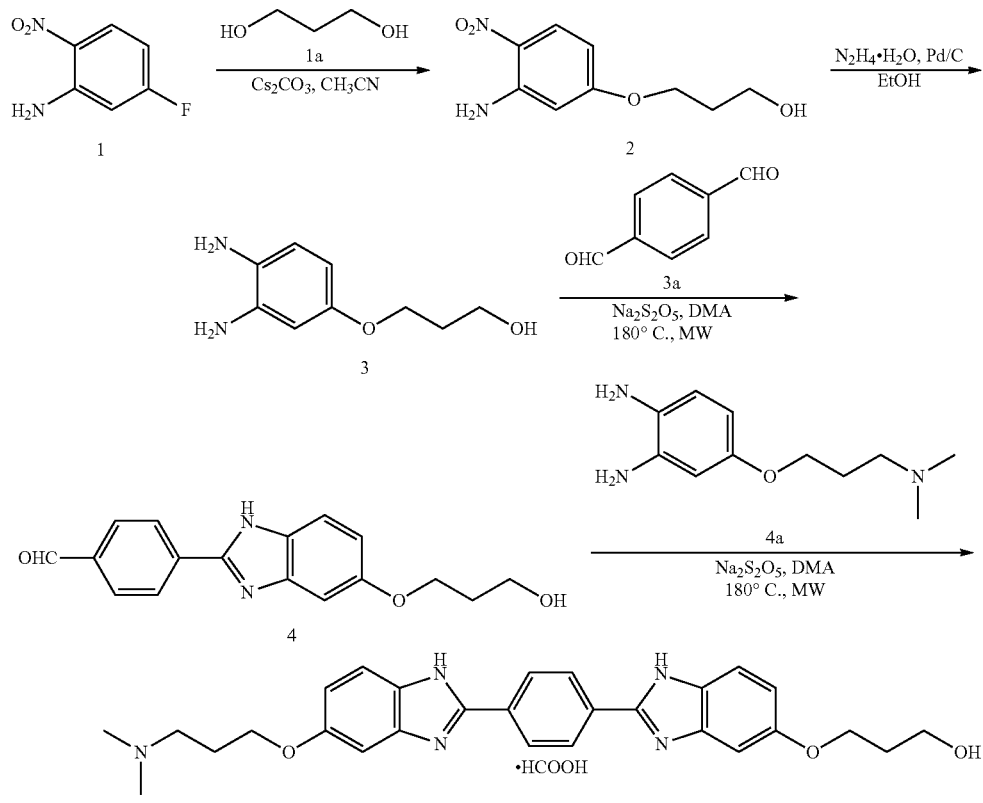

Synthesis of 3-(3-amino-4-nitrophenoxy)propan-1-ol: To a stirred solution of propane-1,3-diol (0.97 g, 12.8 mmol) in acetonitrile (20 mL), under N$_2$ atmosphere, was added Cs$_2$CO$_3$ (3.13 g, 9.61 mmol) followed with 5-fluoro-2-nitroaniline (1.00 g, 6.41 mmol) and the reaction mixture was heated at 60° C. for 15 h. The reaction mixture was cooled to r.t, diluted with water (50 mL) and stirred for 15 min, whereupon, the product precipitated as a yellow solid. The product was collected by filtration under vacuum and washed with water (2×50 mL), and dried under vacuum. The obtained solid was purified by silica gel chromatography using (4:1) (DCM:MeOH). The fractions containing the product were combined and concentrated under vacuum to obtain 3-(3-amino-4-nitrophenoxy) propan-1-ol.

Synthesis of 3-(3,4-diaminophenoxy)propan-1-ol: To a stirred solution of 3-(3-amino-4-nitrophenoxy)propan-1-ol (1.00 g, 4.71 mmol) in EtOH (25 ml), under N$_2$ atmosphere, tated. The brown solid was filtered under vacuum and washed with water (2×50 mL), and dried to obtain the crude product. The product was purified by silica gel chromatography using DCM:MeOH (4:1). The fractions containing the product were combined for concentration to obtain 4-(5-(3-hydroxypropoxy)-1H-benzo[d]imidazol-2-yl)benzaldehyde Synthesis of 3-((2-(4-(5-(3-(dimethylamino)propoxy)-1H-benzo[d]imidazol-2-yl)phenyl)-1H-benzo[d]imidazol-5-yl)oxy)propan-1-ol:

In a microwave vial, a mixture of 4-(5-(3-hydroxypropoxy)-1H-benzo[d]imidazol-2-yl)benzaldehyde (100 mg, 0.34 mmol), 4-(3-(dimethylamino)propoxy)benzene-1,2-diamine (70.6 mg, 0.34 mmol) and sodium metabisulfate (64.2 mg, 0.34 mmol) in DMA (1.50 mL) was heated at 180° C. for 40 min. The reaction mixture was cooled to r.t and the contents were concentrated under vacuum to obtain the crude residue. The residue was diluted with water (10 mL)

and stirred for 10 min, whereupon, a brown solid precipitated. The brown solid was filtered under vacuum, washed with water (2×5.0 mL) and dried to obtain the crude product. The product was purified by mass triggered HPLC. The fractions containing only the pure product were combined for concentration to obtain the title compound. MS (ESI): m/z=486 [M+H]⁺.

Compound 224 was prepared in the same manner as compound 222. MS (ESI): m/z=500 [M+H]⁺.

Example 143

Synthesis of 3,3'-((1,4-phenylenebis(1H-benzo[d]imidazole-2,5-diyl))bis(oxy))bis(propan-1-ol) (Compound 223)

vacuum, washed with water (2×50 mL), and dried to obtain the crude product. The product was purified by silica gel chromatography using CH$_2$Cl$_2$:MeOH (4:1). The fractions containing the compound-2 were combined for concentration to obtain 4-(5-(3-hydroxypropoxy)-1H-benzo[d]imidazol-2-yl)benzaldehyde (580 mg, 51% yield) as a yellow solid. The fractions containing 223 was concentrated and was found to be impure. The impure product was re-purified by mass triggered HPLC. The fractions containing only the pure product were combined for concentration to obtain the title compound. MS (ESI): m/z=459 [M+H]⁺.

Compounds 225 and 246 were prepared in the same manner as compound 223. Compound 225: MS (ESI):

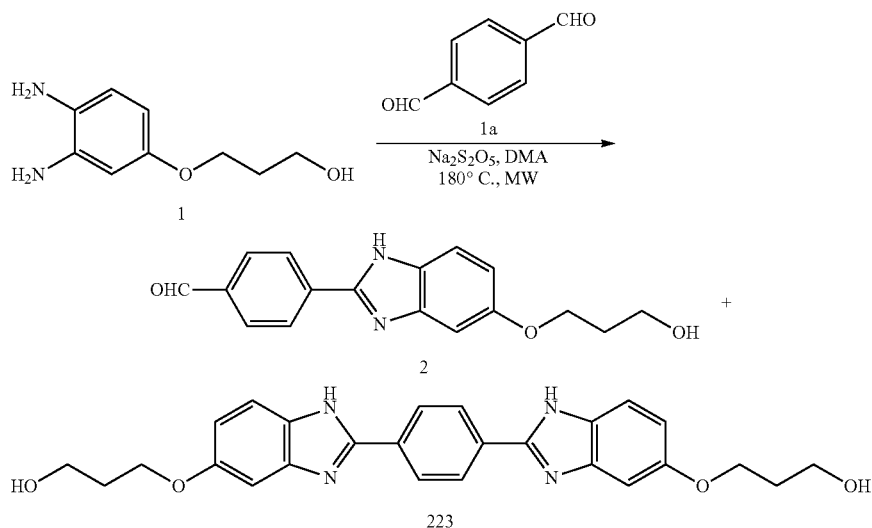

Synthesis of 3,3'-((1,4-phenylenebis(1H-benzo[d]imidazole-2,5-diyl))bis(oxy))bis(propan-1-ol): In a microwave vial, a mixture of 3-(3,4-diaminophenoxy)propan-1-ol (0.70 g, 3.84 mmol), terephthalaldehyde (0.77 g, 5.76 mmol) and sodium metabisulfate (0.73 g, 3.84 mmol) in DMA (10.0 mL) was heated at 180° C. for 40 min. The reaction mixture was cooled to r. t and the contents were slowly poured into water (50 mL) and stirred for 10 min, whereupon, a brown solid precipitated. The brown solid was filtered under m/z=487 [M+H]⁺. Compound 246: MS (ESI+APCl): m/z=412 [M+H]⁺.

Example 144

Synthesis of 4,4'-((2,2'-(1,4-phenylene)bis(1H-benzo[d]imidazole-6,2-diyl))bis(oxy))bis(N,N-dimethylbut-2-yn-1-amine) (Compound 226)

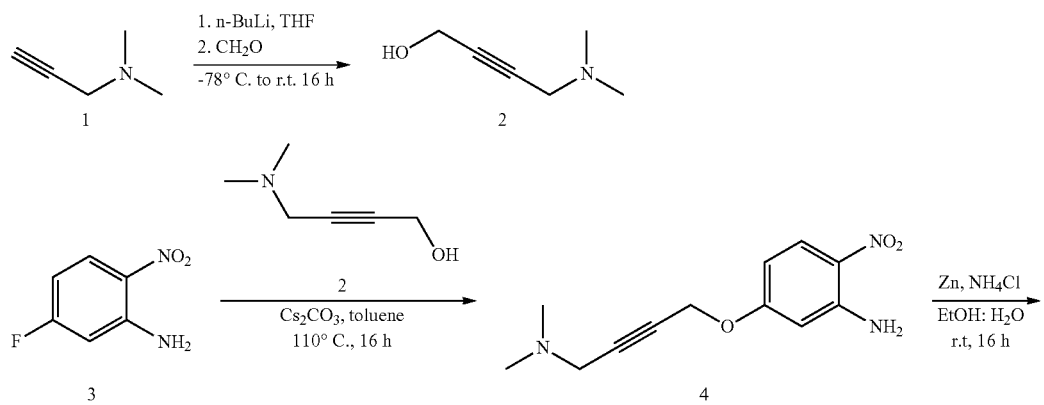

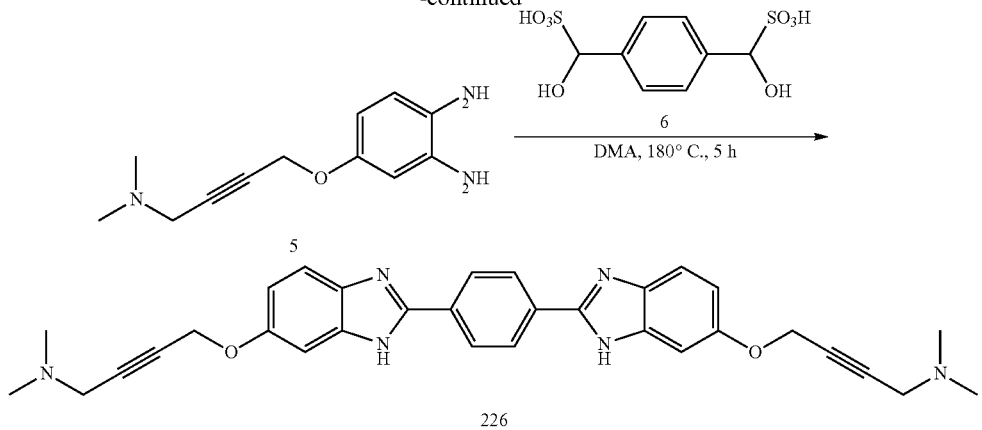

226

Synthesis of 4-(dimethylamino) but-2-yn-1-ol: To a solution of N,N-dimethylprop-2-yn-1-amine (5.00 g, 60.1 mmol) in THF (300 mL), at −78° C. under argon atmosphere, was added n-BuLi (2.5 M in hexane, 28.8 mL, 72.5 mmol) in a drop wise manner over 10 minutes, and the reaction mixture was stirred for 1 h. Paraformaldehyde (0.72 g, 24.1 mmol) was added and the reaction mixture was stirred at r.t for 16 h. The reaction mixture was quenched with aq. saturated $NH_4Cl$ solution and extracted with EtOAc (2×100 mL). The combined organic extracts were dried over anhydrous $Na_2SO_4$ and concentrated to obtain 4-(dimethylamino) but-2-yn-1-ol.

Synthesis of 5-((4-(dimethylamino)but-2-yn-1-yl)oxy)-2-nitroaniline: In a sealed tube, a solution of 4-(dimethylamino)but-2-yn-1-ol (4.35 g, 38.4 mmol) in dry toluene (45.0 mL), was added $Cs_2CO_3$ (10.8 g, 33.3 mmol) followed with 4-fluorobenzaldehyde (4.00 g, 25.6 mmol)), and the reaction mixture was heated at 110° C. for 16 h. The reaction mixture was cooled to r.t and the contents were poured on to ice cold water, and the aqueous phase was extracted with EtOAc (2×100 mL). The combined EtOAc extracts were washed with brine (50 mL), dried over anhydrous $Na_2SO_4$, filtered and concentrated under vacuum to obtain the crude product. The product was purified by silica gel column chromatography using $CH_3OH:CH_2Cl_2$ (1:9). The fractions containing the product were combined and concentrated under vacuum to obtain 5-((4-(dimethylamino) but-2-yn-1-yl)oxy)-2-nitroaniline.

Synthesis of 4-((4-(dimethylamino)but-2-yn-1-yl)oxy) benzene-1,2-diamine: To a solution of 5-((3-((dimethylamino)methyl)benzyl)oxy)-2-nitroaniline (0.30 g, 1.24 mmol) in EtOH (25.0 mL) was added zinc powder (0.78 g, 12.0 mmol) followed with a solution of $NH_4Cl$ (0.64 g, 12.0 mmol) in $H_2O$ (5.00 mL) and the reaction mixture was stirred at r.t for 16 h. The reaction mixture was filtered through a celite pad and the pad was washed with EtOH (30 mL), and the filtrate was concentrated under vacuum to obtain the product. The product was diluted with a mixture of $MeOH:CH_2Cl_2$ (1:9, 50 mL), and washed with water (30 mL), brine (30 mL), dried over anhydrous $Na_2SO_4$ and concentrated under vacuum to obtain 4-((4-(dimethylamino) but-2-yn-1-yl)oxy)benzene-1,2-diamine. The crude product was directly used for the next step.

Synthesis of 4,4'-((2,2'-(1,4-phenylene)bis(1H-benzo[d] imidazole-6,2-diyl))bis(oxy))bis(N,N-dimethylbut-2-yn-1-amine)(226): To a suspension of 4-(4-(dimethylamino) butyl) benzene-1,2-diamine (0.20 g, 0.91 mmol) in DMA (15.0 mL), at r.t under $N_2$ atmosphere, was added 1,4-phenylenebis(hydroxymethanesulfonic acid) (0.14 g, 0.46 mmol), and the reaction mixture was stirred for at 180° C. for 5 h. The reaction mixture was cooled to r.t and poured onto ice, whereupon the product precipitated. The precipitated solids were filtered under vacuum, washed with water (20.0 mL), and dried to obtain the crude product. The crude product was purified by prep-HPLC. Fractions containing only the pure product were combined for concentration to obtain MS (ESI) m/z=533 [M+H]⁺.

Example 145

Synthesis of 1,1'-(1,1'-((2,2'-(1,4-phenylene)bis(1H-benzo[d]imidazole-6,2-diyl))bis(oxy))bis(ethane-2,1-diyl))bis(1H-1,2,3-triazole-1,4-diyl))bis(N,N-dimethylmethanamine) (Compound 227)

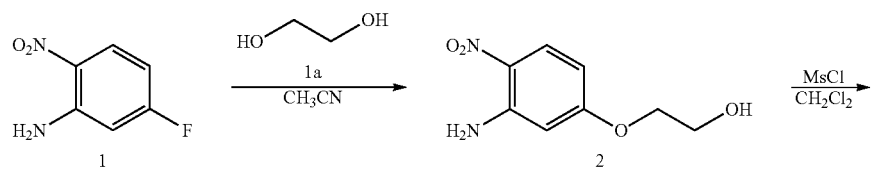

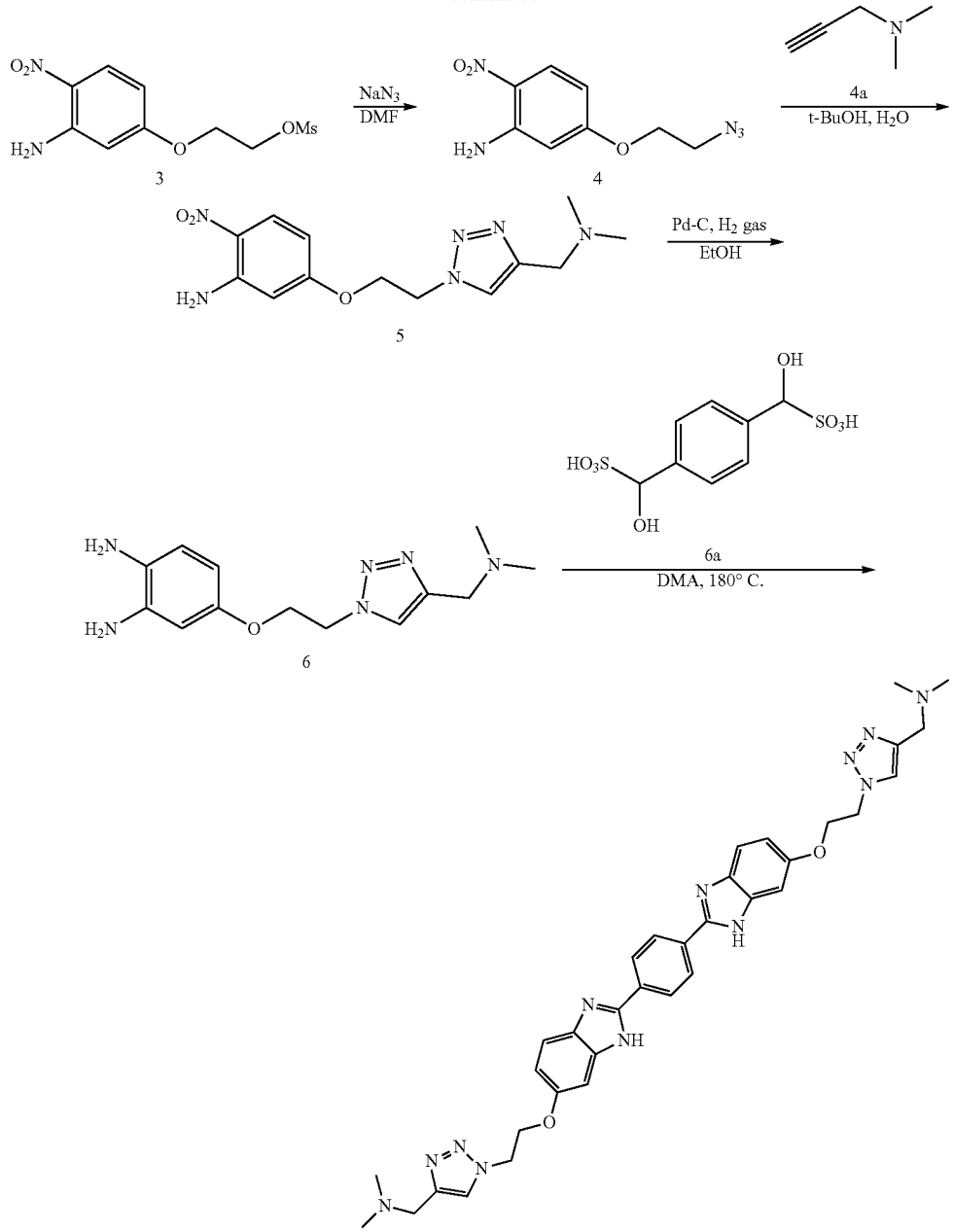

Synthesis of 2-(3-amino-4-nitrophenoxy)ethanol: To a stirred solution of ethane-1,2-diol (7.95 g, 128 mmol) in acetonitrile (100 mL), at r.t under $N_2$ atmosphere, was added $Cs_2CO_3$ (13.6 g, 41.6 mmol) followed with 5-fluoro-2-nitroaniline (5.00 g, 32.0 mmol), and the reaction mixture was heated at 60° C. for 16 h. The reaction mixture was cooled to r.t and contents were poured onto ice cold water and the aqueous phase was extracted with EtOAc (3×50 mL). The combined EtOAc extracts were washed with brine (50 mL), dried over anhydrous $Na_2SO_4$, filtered and concentrated under vacuum to obtain 2-(3-amino-4-nitrophenoxy)ethanol.

Synthesis of 2-(3-amino-4-nitrophenoxy)ethylmethanesulfonate: To a stirred solution of 2-(3-amino-4-nitrophenoxy)ethanol (2.50 g, 12.6 mmol) in $CH_2Cl_2$ (50.0 mL), at 0° C. under $N_2$ atmosphere, was added triethylamine (7.03 mL, 50.5 mmol) followed with methane sulfonyl chloride (1.96 mL, 25.2 mmol) in a drop wise manner over 10 minutes, and the reaction mixture was stirred at r.t for 3 h. The reaction mixture was poured on to water and extracted with $CH_2Cl_2$ (2×50 mL). The combined organic extracts were washed with brine (50 mL), dried over anhydrous $Na_2SO_4$, filtered and concentrated under vacuum to obtain 2-(3-amino-4-nitrophenoxy)ethylmethanesulfonate. The crude product was directly used in the next step.

Synthesis of 5-(2-azidoethoxy)-2-nitroaniline: To a stirred solution of 2-(3-amino-4-nitrophenoxy)ethyl methane sulfonate (2.50 g, 9.05 mmol) in DMF (50.0 mL), at r.t under N₂ atmosphere, was added sodium azide (1.76 g, 27.1 mmol), and the reaction mixture was heated at 60° C. for 16 h. The reaction mixture was cooled to r.t and the contents were slowly poured onto water (50 mL) and stirred for 10 min, whereupon, a yellow solid precipitated. The yellow solid was filtered under vacuum, washed with water (2×50 mL), and dried to obtain 5-(2-azidoethoxy)-2-nitroaniline.

Synthesis of 5-(2-(4((dimethylamino)methyl)-1H-1,2,3-triazol-1-yl)ethoxy)-2-nitroaniline: To a stirred solution of 5-(2-azidoethoxy)-2-nitroaniline (2.00 g, 9.41 mmol) and N,N-dimethylprop-2-yn-1-amine (2.34 g, 28.2 mmol) in a mixture of tert-BuOH (50.0 mL) and H₂O (50.0 mL), at r.t, was added copper(II) sulfate pentahydrate (0.35 g, 1.41 mmol) followed with L-ascorbic acid sodium salt (0.27 g, 1.41 mmol), and the mixture was stirred at r.t for 16 h. The contents were poured onto water (100 mL) and extracted with EtOAc (3×50 mL). The combined organic extracts were washed with brine (50 mL), dried over anhydrous Na₂SO₄, filtered and concentrated under vacuum to obtain the crude product. The product was purified by silica gel column chromatography using CH₃OH:CH₂Cl₂ (1:9). The fractions containing the product were combined and concentrated under vacuum to obtain 5-(2-(4-((dimethylamino)methyl)-1H-1,2,3-triazol-1-yl)ethoxy)-2-nitroaniline.

methyl)-1H-1,2,3-triazol-1-yl)ethoxy)benzene-1,2-diamine. The crude product was directly used in the next step.

Synthesis of 1,1'-(1,1'-(((2,2'-(1,4-phenylene)bis(1H-benzo[d]imidazole-6,2-diyl))bis(oxy))bis(ethane-2,1-diyl)) bis(1H-1,2,3-triazole-4,1-diyl))bis(N,N-dimethylmethanamine) (227): To a stirred solution of 4-(2-(4-((dimethylamino)methyl)-1H-1,2,3-triazol-1-yl)ethoxy) benzene-1,2-diamine (500 mg, 1.80 mmol) in DMA (25.0 mL), at r.t under N2 atmosphere, was added 1,4-phenylenebis(hydroxymethanesulfonic acid) (270 mg, 0.90 mmol) and the reaction mixture was heated at 180° C. for 3 h. The reaction mixture was cooled to 60° C. and concentrated under vacuum to obtain crude product. The product was purified by mass triggered Prep-HPLC. The fractions containing only the pure product were combined and concentrated under vacuum to obtain the title compound. MS (ESI): m/z=647 [M+H]⁺.

Example 146

Synthesis of 3-((2-(4-(6-(3-(dimethylamino) propoxy)-1H-benzo[d]imidazol-2-yl)phenyl)-1H-benzo[d]imidazol-6-yl)thio)-N,N-dimethylpropan-1-amine (Compound 228)

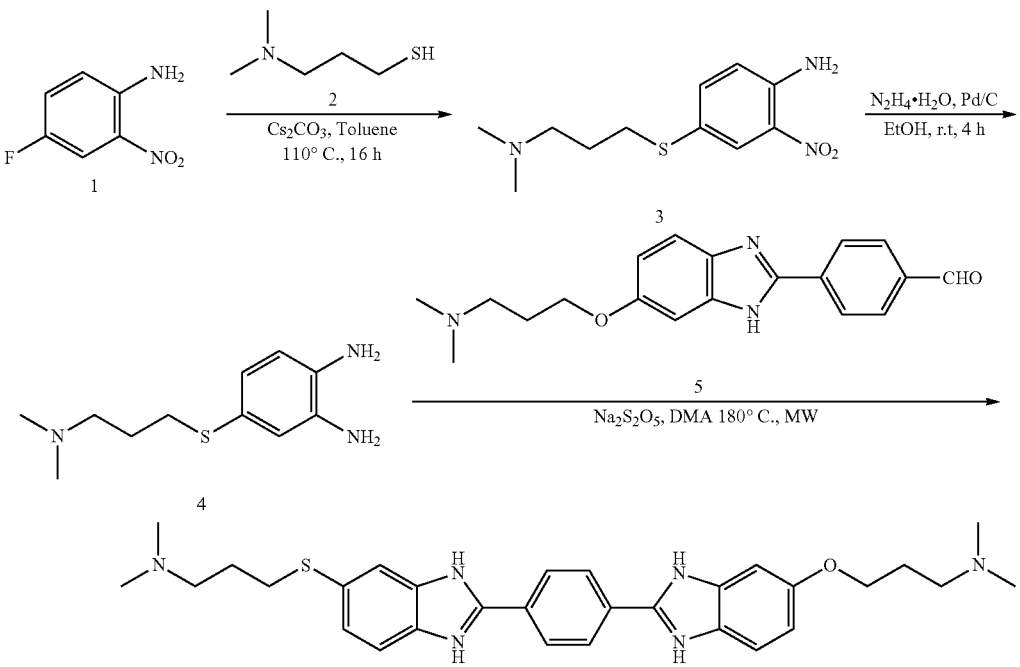

Synthesis of 4-(2-(4-((dimethylamino)methyl)-1H-1,2,3-triazol-1-yl)ethoxy)benzene-1,2-diamine: To a solution of 5-(2-(4-((dimethylamino)methyl)-1H-1,2,3-triazol-1-yl) ethoxy)-2-nitroaniline (1.75 g, 5.71 mmol) in EtOH (40.0 mL), at r.t under N₂ atmosphere, was added 10% Pd—C (608 mg) and reaction mixture was hydrogenated (balloon pressure~1 atms) at r.t for 3 h. The reaction mixture was filtered through a celite pad, and the pad was washed with EtOH (20 mL), the combined filtrate was concentrated under reduced pressure to obtain 4-(2-(4-((dimethylamino)

Synthesis of 4-((3-(dimethylamino)propyl)thio)-2-nitroaniline: To a solution of 3-(dimethylamino)propane-1-thiol (1.14 g, 9.61 mmol) in dry toluene (45.0 mL), placed in a sealed tube, was added Cs₂CO₃ (9.39 g, 28.8 mmol) followed with 4-fluorobenzaldehyde (1.50 g, 9.61 mmol). The tube was sealed and the reaction mixture was heated at 110° C. for 16 h. The reaction mixture was cooled to r.t and the contents were poured on to ice cold water, and the aqueous phase was extracted with EtOAc (2×100 mL). The combined EtOAc extracts were washed with brine (50 mL), dried over anhydrous Na₂SO₄, filtered and concentrated under vacuum to obtain the crude product. The product was purified by silica gel column chromatography using $CH_3OH:CH_2Cl_2$ (1:9). The fractions containing the product were combined and concentrated under vacuum to obtain 4-((3-(dimethylamino) propyl)thio)-2-nitroaniline.

Synthesis of 4-((3-(dimethylamino)propyl)thio)benzene-1,2-diamine: To a solution of 4-((3-(dimethylamino)propyl)thio)-2-nitroaniline (0.30 g, 1.17 mmol) in EtOH (15.0 mL), at r.t under $N_2$ atmosphere, was added hydrazine monohydrate (5.00 mL) followed with 10% Pd/C (80 mg) the reaction mixture was stirred at r.t for 4 h. The reaction mixture was filtered through a celite pad, and the pad was washed with EtOH (2×25 mL). The combined filtrate were concentrated under vacuum to obtain 4-((3-(dimethylamino)propyl)thio)benzene-1,2-diamine. The crude product was directly used in the next step without purification.

Synthesis of 3-((2-(4-(6-(3-(dimethylamino)propoxy)-1H-benzo[d]imidazol-2-yl)phenyl)-1H-benzo[d]imidazol-6-yl)thio)-N,N-dimethylpropan-1-amine (228): In a microwave vial, a mixture of 4-((3-(dimethylamino)propyl)thio)benzene-1,2-diamine (0.20 g, 0.88 mmol), 4-(6-(3-(dimethylamino)propoxy)-1H-benzo[d]imidazol-2-yl)benzaldehyde (0.23 g, 0.71 mmol) and sodium metabisulfate (0.16 g, 0.88 mmol) in DMA (10.0 mL) was heated at 180° C. for 40 min. The reaction mixture was cooled to r. t and the contents were slowly poured into water (50 mL) and stirred for 10 min, whereupon, a brown solid precipitated. The brown solid was filtered under vacuum and washed with water (2×50 mL), and dried to obtain the crude product. The product was purified by mass triggered HPLC. The fractions containing only the pure product were combined for concentration to obtain the title compound. MS (ESI): m/z=529 [M+H]$^+$.

Example 147

Synthesis of 4,4'-((2,2'-(1,4-phenylene)bis(1H-benzo[d]imidazole-6,2-diyl))bis(oxy))dibenzonitrile (Compound 229)

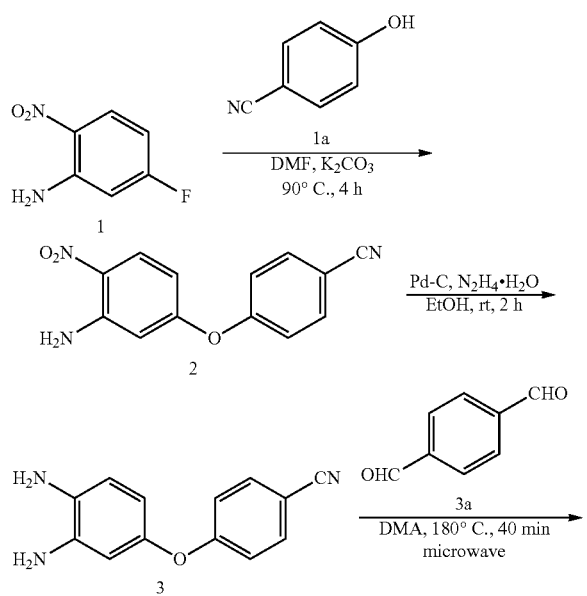

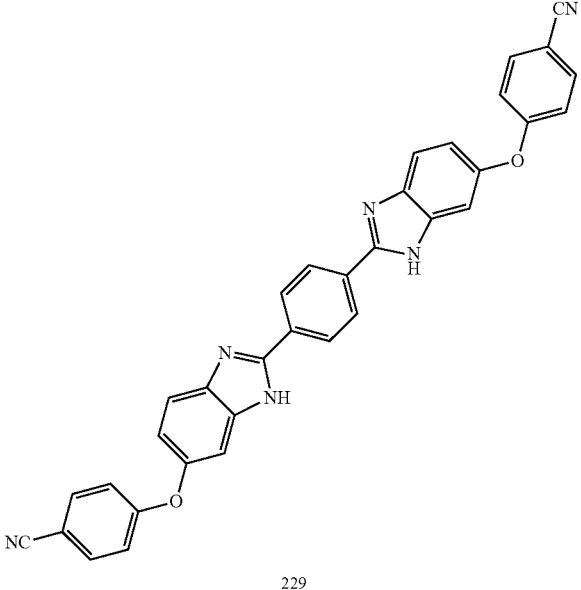

229

Synthesis of 4-(3-amino-4-nitrophenoxy)benzonitrile: To a stirred solution of 4-hydroxybenzonitrile (1.67 g, 14.1 mmol) in DMF (40.0 mL), at r.t under $N_2$ atmosphere, was added $K_2OC_3$ (4.43 g, 32.0 mmol) followed with 5-fluoro-2-nitroaniline (2.00 g, 12.8 mmol), and the reaction mixture was heated at 90° C. for 4 h. The reaction mixture was cooled to r.t and contents were poured onto ice cold water and the aqueous phase was extracted with EtOAc (3×50 mL). The combined EtOAc extracts were washed with brine (50 mL), dried over anhydrous $Na_2SO_4$, filtered and concentrated under vacuum to obtain 4-(3-amino-4-nitrophenoxy).

Synthesis of 4-(3,4-diaminophenoxy)benzonitrile: To a solution of 4-(3-amino-4-nitrophenoxy)benzonitrile (1.70 g, 6.66 mmol) in EtOH (80.0 mL), at r.t under $N_2$ atmosphere, was added 10% Pd—C (850 mg) followed with hydrazine monohydrate (1.00 mL, 6.66 mmol) and the reaction mixture was stirred at r.t for 2 h. The reaction mixture was filtered through a celite pad, and the pad was washed with EtOH (20 mL), the combined filtrate was concentrated under reduced pressure to obtain 4-(3,4-diaminophenoxy)benzonitrile. The crude product was directly used in the next step.

Synthesis of 4,4'-((2,2'-(1,4-phenylene)bis(1H-benzo[d]imidazole-6,2-diyl))bis(oxy))dibenzonitrile: In a microwave vial, a mixture of 4-(3,4-diaminophenoxy)benzonitrile (400 mg, 1.77 mmol), terephthalaldehyde (119 mg, 0.88 mmol) and sodium metabisulfate (338 mg, 1.77 mmol) in DMA (10.0 mL) was heated at 180° C. for 40 min. The reaction mixture was cooled to r. t and the contents were slowly poured into water (50 mL) and stirred for 10 min, whereupon, a brown solid precipitated. The brown solid was filtered under vacuum, washed with water (2×5.0 mL) and dried to obtain the crude product. The product was purified by mass triggered HPLC. The fractions containing only the pure product were combined for concentration to obtain the title compound. MS (ESI): m/z=545 [M+H]$^+$.

Example 148

Synthesis of 3,3'-((2,2'-(1,4-phenylene)bis(1H-benzo[d]imidazole-6,2-diyl))bis(oxy))dibenzonitrile) (Compound 230)

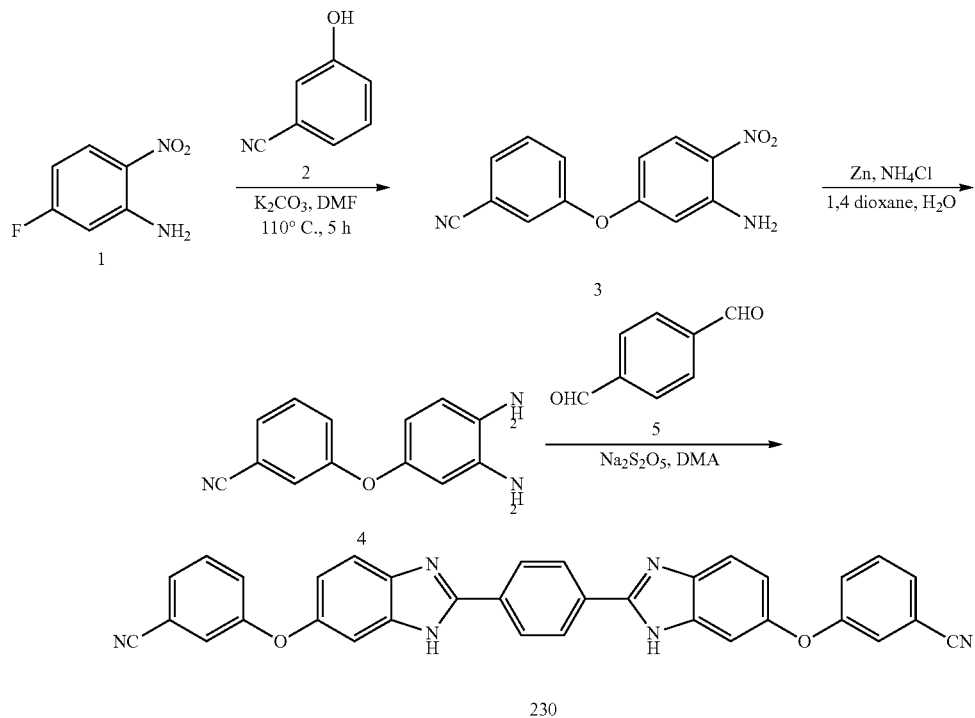

Synthesis of 3-(3-amino-4-nitrophenoxy)benzonitrile: To a solution of 5-fluoro-2-nitroaniline (2.00 g, 12.8 mmol) in DMF (20.0 mL), at r.t under argon atmosphere, was added $K_2OC_3$ (3.54 g, 25.6 mmol) followed with 3-hydroxybenzonitrile (1.83 g, 15.3 mmol) and the reaction mixture was stirred at 100° C. for 5 h. The reaction mixture was cooled to r.t and poured onto ice, whereupon the product precipitated. The precipitated solids were filtered under vacuum, washed with water (20.0 mL), and dried to obtain 3-(3-amino-4-nitrophenoxy)benzonitrile.

Synthesis of 3-(3,4-diaminophenoxy)benzonitrile: To a solution of 3-(3-amino-4-nitrophenoxy)benzonitrile (0.80 g, 3.13 mmol) in 1,4 dioxane (20.0 mL) was added zinc powder (1.63 g, 25.1 mmol) followed with a solution of $NH_4Cl$ (1.34 g, 12.0 mmol) in $H_2O$ (5.00 mL), and the reaction mixture was stirred at r.t for 3 h. The reaction mixture was filtered through a celite pad and the pad was washed with EtOAc (30 mL). The filtrate was washed with water (20.0 mL) and concentrated under vacuum to obtain 3-(3,4-diaminophenoxy)benzonitrile. The crude product was directly used in the next step.

Synthesis of 3,3'-((2,2'-(1,4-phenylene)bis(1H-benzo[d]imidazole-6,2-diyl))bis(oxy))dibenzonitrile: In a microwave vial, a mixture of 3-(3,4-diaminophenoxy)benzonitrile (0.60 g, 2.66 mmol), terephthalaldehyde (0.18 g, 1.33 mmol) and sodium metabisulfate (0.50 g, 2.66 mmol) in DMA (7.00 mL) was heated at 180° C. for 40 min. The reaction mixture was cooled to r.t and the contents were poured onto ice water (50.0 mL), whereupon the product precipitated. The precipitated solids were filtered under vacuum, washed with water (20.0 mL), and dried to obtain the crude product. The crude product was purified by prep-HPLC. Fractions containing only the pure product were combined for concentration to obtain the title compound. MS (ESI) m/z=545 [M+H]$^+$.

Example 149

Synthesis of 2,2'-(4,4'-(((2,2'-(1,4-phenylene)bis(1H-benzo[d]imidazole-6,2-diyl))bis(oxy))bis(methylene))bis(1H-1,2,3-triazole-4,1-diyl))bis(N,N-dimethylethanamine) (Compound 231)

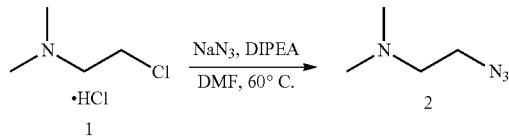

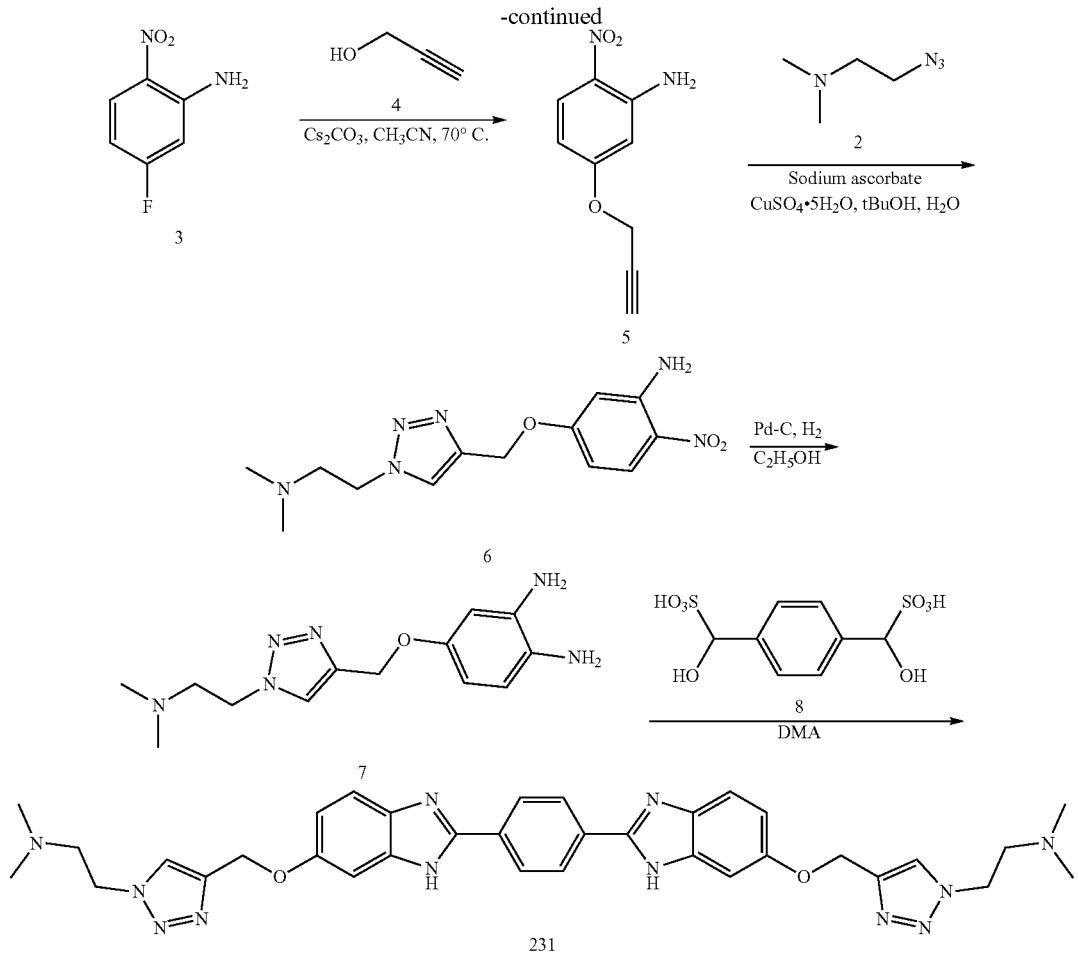

Synthesis of 2-azido-N,N-dimethylethanamine: To a stirred solution of 2-chloro-N,N-dimethylethan-1-amine hydrochloride (2.00 g, 13.8 mmol) in DMF (20.0 mL), at r.t under N₂ atmosphere, was added sodium azide (2.71 g, 41.7 mmol) portion wise over a period of 5 min. After complete addition the reaction mixture was heated at 60° C. for 6 h. The reaction mixture was cooled to r. t and the contents were slowly poured onto water (50 mL) and extracted with MTBE (2×100 mL). The combined organic extracts were washed with brine (100 mL), dried over anhydrous Na₂SO₄, filtered and concentrated under vacuum to obtain 2-azido-N,N-dimethylethan-1-amine.

Synthesis of 2-nitro-5-(prop-2-yn-1-yloxy)aniline: To a stirred solution of prop-2-yn-1-ol (5.39 g, 96.0 mmol) in acetonitrile (50 mL), at r.t under N₂ atmosphere, was added cesium carbonate (15.6 g, 48.0 mmol) followed with 5-fluoro-2-nitroaniline (5.00 g, 32.0 mmol), and the reaction mixture was heated at 60° C. for 16 h. The reaction mixture was cooled to r.t and contents were poured onto ice cold water and the aqueous phase was extracted with EtOAc (3×100 mL). The combined EtOAc extracts were washed with brine (50 mL), dried over anhydrous Na₂SO₄, filtered and concentrated under vacuum. The product was purified by silica gel column chromatography using CH₃OH:CH₂Cl₂ (1:9). The fractions containing the pure product were combined and concentrated under vacuum to obtain 2-nitro-5-(prop-2-yn-1-yloxy)aniline Synthesis of 5-((1-(2-(dimethylamino)ethyl)-1H-1,2,3-triazol-4-yl)methoxy)-2-nitroaniline: To a stirred solution of 2-nitro-5-(prop-2-yn-1-yloxy)aniline (1.00 g, 5.20 mmol) and 2-azido-N,N-dimethylethan-1-amine (1.78 g, 15.6 mmol) in a mixture of tert-BuOH (5.00 mL) and H₂O (5.00 mL), at r.t under N₂ atmosphere, was added copper(II) sulfate pentahydrate (0.19 g, 0.78 mmol) followed with L-ascorbic acid sodium salt (0.15 g, 0.78 mmol), and the mixture was stirred at r.t for 16 h. The contents were poured onto water (50.0 mL), whereupon the product precipitated. The precipitated product was filtered under vacuum, washed with water (30.0 mL), and dried to obtain 5-((1-(2-(dimethylamino)ethyl)-1H-1,2,3-triazol-4-yl)methoxy)-2-nitroaniline.

Synthesis of 4-((1-(2-(dimethylamino)ethyl)-1H-1,2,3-triazol-4-yl)methoxy)benzene-1,2-diamine: To a solution of 5-((1-(2-(dimethylamino)ethyl)-1H-1,2,3-triazol-4-yl)methoxy)-2-nitroaniline (1.10 g, 3.59 mmol) in EtOH (20.0 mL), at r.t under N₂ atmosphere, was added 10% Pd—C (500 mg) and the reaction mixture was hydrogenated (balloon pressure~1 atms) at r.t for 5 h. The reaction mixture was filtered through a celite pad, and the pad was washed with EtOH (2×50 mL). The combined filtrates were concentrated under reduced pressure to obtain 4-((1-(2-(dimethylamino)ethyl)-1H-1,2,3-triazol-4-yl)methoxy)benzene-1,2-diamine. The crude product was directly used in the next step.

Synthesis of 2,2'-(4,4'-(((2,2'-(1,4-phenylene)bis(1H-benzo[d]imidazole-6,2-diyl))bis(oxy))bis(methylene))bis (1H-1,2,3-triazole-4,1-diyl))bis(N,N-dimethylethanamine) (231): To a stirred solution of 4-((1-(2-(dimethylamino)

ethyl)-1H-1,2,3-triazol-4-yl)methoxy)benzene-1,2-diamine (0.80 g, 2.89 mmol) in DMA (25.0 mL), at r.t under $N_2$ atmosphere, was added 1,4-phenylenebis(hydroxymethanesulfonic acid (0.42 g, 1.44 mmol) and the reaction mixture was heated at 180° C. for 5 h. The reaction mixture was cooled to 60° C. and concentrated under vacuum to obtain crude product. The product was purified by mass triggered Prep-HPLC. The fractions containing only the pure product were combined and concentrated under vacuum to obtain the title compound. MS (ESI): m/z=647 [M+H]$^+$.

Example 150

Synthesis of 2-(4-(6-(3-(dimethylamino)propoxy)-1H-benzo[d]imidazol-2-yl)phenyl)-N-(2-(pyrrolidin-1-yl)ethyl)-1H-benzo[d]imidazole-6-carboxamide (Compound 232)

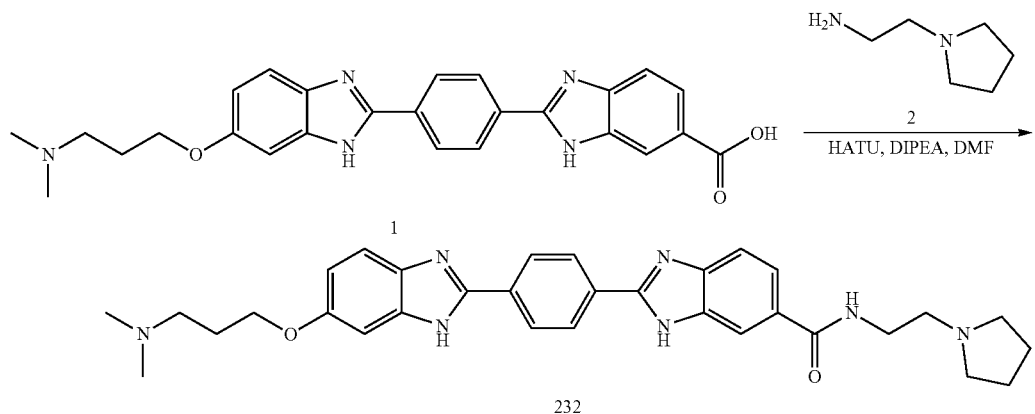

Synthesis of 2-(4-(6-(3-(dimethylamino)propoxy)-1H-benzo[d]imidazol-2-yl)phenyl)-N-(2-(pyrrolidin-1-yl)ethyl)-1H-benzo[d]imidazole-6-carboxamide (232): To a stirred solution of 2-(4-(6-(3-(dimethylamino)propoxy)-1H-benzo[d]imidazol-2-yl)phenyl)-1H-benzo[d]imidazole-6-carboxylic acid (0.20 g, 0.43 mmol) in DMF (5.00 mL), at 0° C. under $N_2$ atmosphere, was added 2-(pyrrolidin-1-yl)ethanamine (0.07 g, 0.65 mmol), DIPEA (0.11 g, 0.87 mmol) followed with HATU (0.20 g, 0.52 mmol) and the reaction mixture was stirred at r.t for 16 h. The reaction mixture was poured on to ice cooled water (25.0 mL), whereupon the product precipitated. The product was filtered under vacuum, washed with $H_2O$ (10 mL), and dried to obtain the crude product. The product was purified by prep-HPLC. Fractions containing only the pure product were combined for concentration to obtain the title compound. MS (ESI): m/z=552 [M+H]$^+$.

Compounds 238, 239, and 266 were prepared in the same manner as compound 232. Compound 238: MS (ESI) m/z 526 [M+H]$^+$. Compound 239: MS (ESI): m/z=540 [M+H]$^+$. Compound 266: MS (ESI): m/z=527 [M+H]$^+$.

Example 151

Synthesis of (2E,2'E)-4,4'-((2,2'-(1,4-phenylene)bis(1H-benzo[d]imidazole-6,2-diyl))bis(oxy))bis(N,N-dimethylbut-2-en-1-amine) (Compound 233)

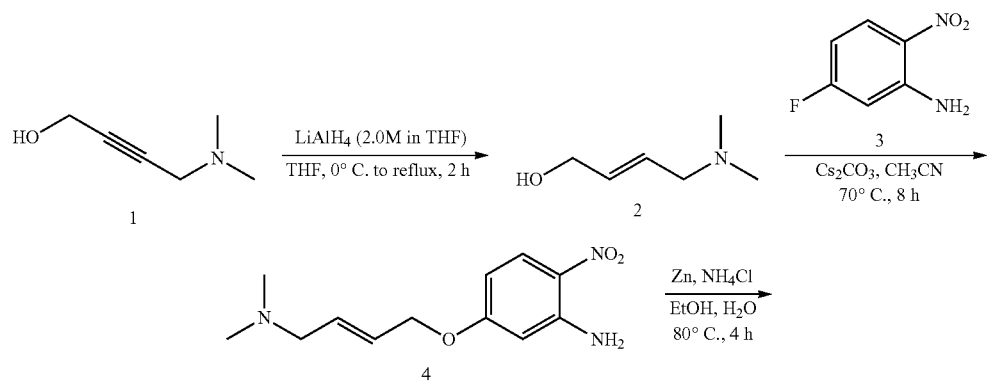

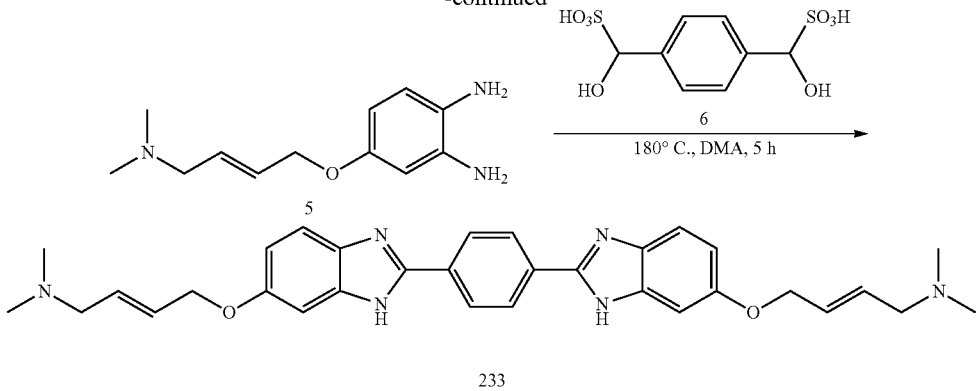

Synthesis of (E)-4-(dimethylamino)but-2-en-1-ol: To a stirred solution of 4-(dimethylamino)but-2-yn-1-ol (2.00 g, 17.7 mmol) in dry THF (20.0 mL), at 0° C. under $N_2$ atmosphere, was added $LiAlH_4$ (2 M in THF, 13.1 mL, 26.1 mmol) in a dropwise manner over 15 min. After complete addition, the reaction mixture was stirred at 70° C. for 2 h. The reaction mixture was cooled to 0° C. and quenched with 20% aq. NaOH (20 mL), poured onto ice-cold water and extracted with EtOAc (2×100 mL). The combined organic extracts were washed with brine (50 mL), dried over anhydrous $Na_2SO_4$ and concentrated under vacuum to obtain the crude product. The crude product was purified by fractional distillation, and the desired product was collected at 65° C. to obtain (E)-4-(dimethylamino)but-2-en-1-ol.

Synthesis of (E)-5-((4-(dimethylamino)but-2-en-1-yl)oxy)-2-nitroaniline: To a stirred solution of (E)-4-(dimethylamino)but-2-en-1-ol (885 mg, 7.69 mmol) in $CH_3CN$ (10.0 mL), at r.t under $N_2$ atmosphere, was added $Cs_2CO_3$ (1.87 g, 5.76 mmol) followed with 5-fluoro-2-nitroaniline (600 mg, 3.84 mmol), and the reaction mixture was heated at 70° C. for 8 h. The reaction mixture was cooled to r.t and contents were poured onto ice cold water and the aqueous phase was extracted with EtOAc (3×50 mL). The combined EtOAc extracts were washed with brine (50 mL), dried over anhydrous $Na_2SO_4$, filtered and concentrated under vacuum to obtain the crude product. The product was purified by silica gel chromatography using EtOAc:Hexanes (1:1). The fractions containing the product were combined and concentrated under vacuum to obtain (E)-5-((4-(dimethylamino)but-2-en-1-yl)oxy)-2-nitroaniline.

Synthesis of (E)-4-((4-(dimethylamino)but-2-en-1-yl)oxy)benzene-1,2-diamine: To a solution of (E)-5-((4-(dimethylamino)but-2-en-1-yl)oxy)-2-nitroaniline (450 mg, 1.79 mmol) in EtOH (10.0 mL) was added zinc powder (585 mg, 8.95 mmol) followed with an aqueous solution of $NH_4Cl$ (479 mg, 8.95 mmol) in $H_2O$ (3.00 mL), and the reaction mixture was stirred at 80° C. for 4 h. The reaction mixture was filtered through a celite pad and the pad was washed with EtOAc (30 mL). The filtrate was washed with water (20.0 mL) and concentrated under vacuum to obtain (E)-4-((4-(dimethylamino)but-2-en-1-yl)oxy)benzene-1,2-diamine The crude product was directly used in the next step.

Synthesis of (2E,2′E)-4,4′-((2,2′-(1,4-phenylene)bis(1H-benzo[d]imidazole-6,2-diyl))bis(oxy))bis(N,N-dimethylbut-2-en-1-amine) (233): To a suspension of (E)-4-((4-(dimethylamino)but-2-en-1-yl)oxy)benzene-1,2-diamine (250 mg, 1.13 mmol) in DMA (10.0 mL) was added 1,4-phenylenebis(hydroxy methanesulfonic acid) (168 mg, 0.56 mmol) and the reaction mixture was stirred at 180° C. for 5 h. The reaction mixture was cooled to r.t and poured onto ice, whereupon the solids precipitated. The precipitated solids were filtered under vacuum, washed with water (20.0 mL), and dried to obtain the crude product. The product was purified by prep-HPLC. Fractions containing only the pure product were combined for concentration to obtain the title compound. MS (ESI+APCI): m/z=537 $[M+H]^+$.

Example 152

Synthesis of (((2,2′-(1,4-phenylene)bis(1H-benzo[d]imidazole-6,2-diyl))bis(oxy))bis(3,1-phenylene))dimethanamine) (Compound 234)

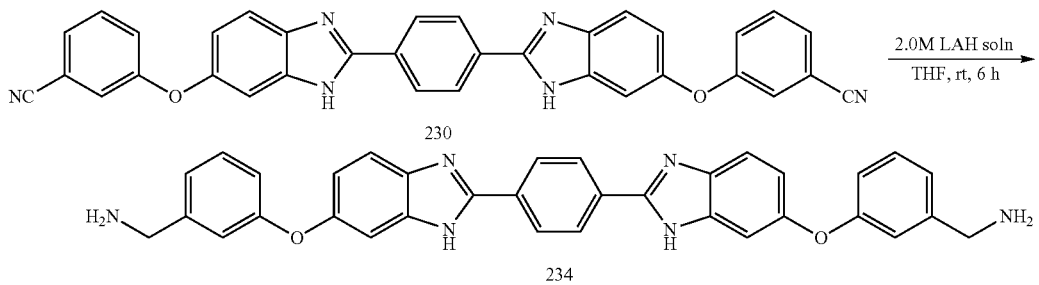

Synthesis of (((2,2′-(1,4-phenylene)bis(1H-benzo[d]imidazole-6,2-diyl))bis(oxy))bis(3,1-phenylene))dimethanamine: To a stirred solution of compound 230 (3,3′-((2,2′-(1,4-phenylene)bis(1H-benzo[d]imidazole-6,2-diyl))bis (oxy))dibenzonitrile) (0.60 g, 1.12 mmol) in THF (60.0 mL), at 0° C. under Ar atmosphere, was added LiAlH₄ (2.0 M in THF, 0.42 g, 11.0 mmol) in a dropwise manner over a period of 10 min. After complete addition, the reaction mixture was gradually allowed to reach r.t and continued stirring for 6 h. The reaction mixture was cooled to 0° C. and quenched the excess LiAlH₄ with aqueous saturated Na₂SO₄ solution, whereupon solids precipitated. The precipitated solids were filtered under vacuum, washed with 10% MeOH in DCM (100 mL). The filtrate was washed with brine (20 mL) and concentrated under vacuum to obtain the crude product. The crude product was purified by prep-HPLC. Fractions containing only the pure product were combined for concentration to obtain the title compound. MS (ESI) m/z=553 [M+H]⁺.

Example 153

Synthesis of 3-((2-(4-(6-(3-azidopropoxy)-1H-benzo[d]imidazol-2-yl)phenyl)-1H-benzo[d]imidazol-6-yl)oxy)-N,N-dimethylpropan-1-amine (Compound 235)

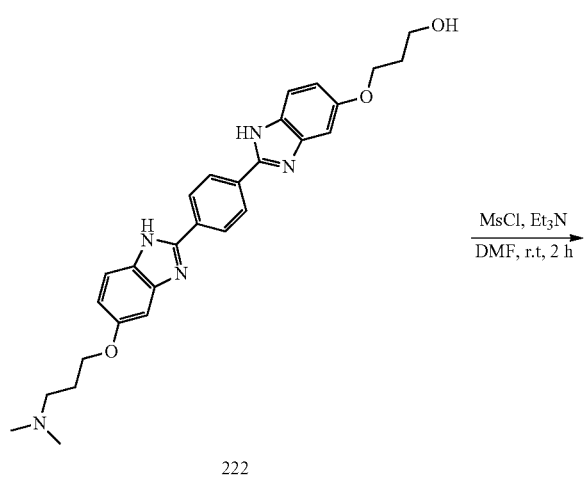

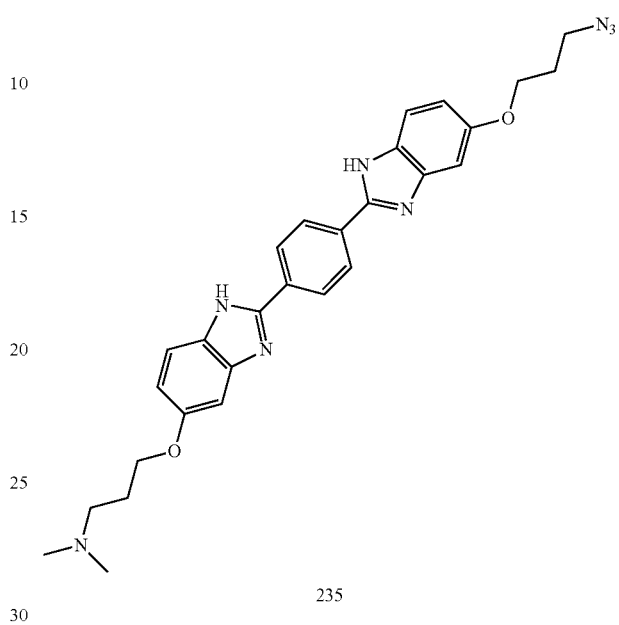

Synthesis of 3-((2-(4-(5-(3-(dimethylamino)propoxy)-1H-benzo[d]imidazol-2-yl)phenyl)-1H-benzo[d]imidazol-5-yl)oxy)propyl methane sulfonate: To a stirred solution of compound 222 (3-((2-(4-(5-(3-(dimethylamino)propoxy)-1H-benzo[d]imidazol-2-yl)phenyl)-1H-benzo[d]imidazol-5-yl)oxy)propan-1-ol) (500 mg, 1.03 mmol) in DMF (15.0 mL), at 0° C. under N₂ atmosphere, was added Et₃N (0.28 mL, 2.05 mmol) followed with methane sulfonyl chloride (0.09 mL, 1.23 mmol) in a dropwise manner. After complete addition, the reaction mixture was stirred at r.t for 2 h. The reaction mixture was concentrated under vacuum to obtain 3-((2-(4-(5-(3-(dimethylamino) propoxy)-1H-benzo[d]imidazol-2-yl)phenyl)-1H-benzo[d]imidazol-5-yl)oxy)propyl methane sulfonate. The crude product was used directly in the next step.

Synthesis of 3-((2-(4-(5-(3-azidopropoxy)-1H-benzo[d]imidazol-2-yl)phenyl)-1H-benzo[d]imidazol-5-yl)oxy)-N,N-dimethylpropan-1-amine: To a stirred solution of 3-((2-(4-(5-(3-(dimethylamino)propoxy)-1H-benzo[d]imidazol-2-yl)phenyl)-1H-benzo[d]imidazol-5-yl)oxy)propyl methane sulfonate (500 mg, 0.88 mmol) in DMF (15.0 mL) was added sodium azide (115 mg, 1.77 mmol), and the reaction mixture was stirred at 60° C. for 12 h. The reaction mixture was cooled to r.t and the contents were slowly poured into ice-cold water and stirred for 10 min, whereupon a solid precipitated. The solid was collected by filtration under vacuum, washed with water (20 mL) and dried to obtain the crude product. The product was purified by MS-triggered prep HPLC. Fractions containing only the pure product were combined for concentration to the title compound. MS (ESI): m/z=511 [M+H]$^+$.

Example 154

Synthesis of (((2,2'-(1,4-phenylene)bis(1H-benzo[d]imidazole-6,2-diyl))bis(oxy))bis(4,1-phenylene))dimethanamine (Compound 236)

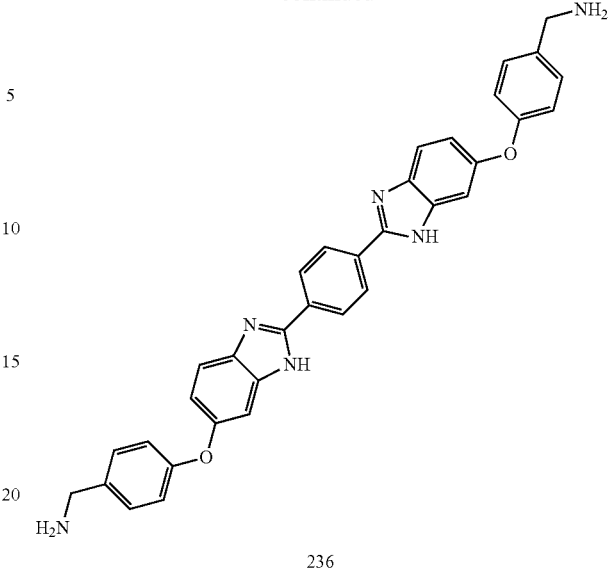

236

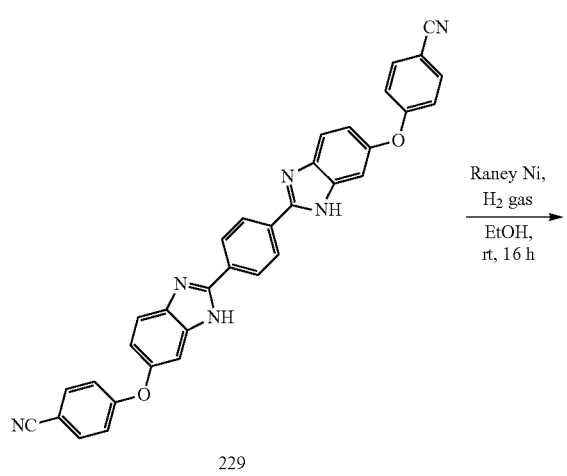

229

Synthesis of (((2,2'-(1,4-phenylene)bis(1H-benzo[d]imidazole-6,2-diyl))bis(oxy))bis(4,1-phenylene))dimethanamine: To a stirred solution of compound 229 (4,4'-((2,2'-(1,4-phenylene)bis(1H-benzo[d]imidazole-6,2-diyl))bis(oxy))dibenzonitrile) (450 mg, 0.82 mmol) in EtOH (20.0 mL), at r.t under N$_2$ atmosphere, was added Raney Ni (100 mg) and the reaction mixture was hydrogenated (balloon pressure~1 atms) at r.t for 16 h. The reaction mixture was filtered through a celite pad, and the pad was washed with EtOH (2×20 mL). The combined filtrates were concentrated under reduced pressure to obtain the crude product. The product was purified by mass triggered HPLC. The fractions containing only the pure product were combined for concentration to obtain the title compound. MS (ESI): m/z=553 [M+H]$^+$.

Example 155

Synthesis of 2-(4-(6-(3-(dimethylamino)propoxy)-1H-benzo[d]imidazol-2-yl)phenyl)-N-(2-(piperidin-1-yl)ethyl)-1H-benzo[d]imidazole-6-carboxamide (Compound 237)

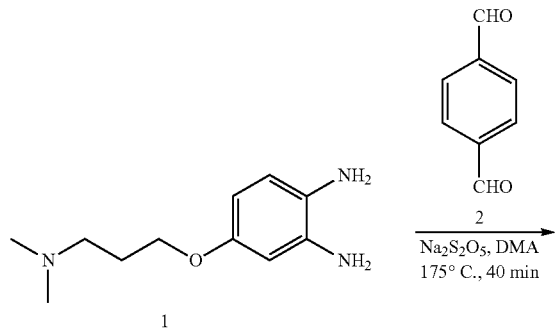

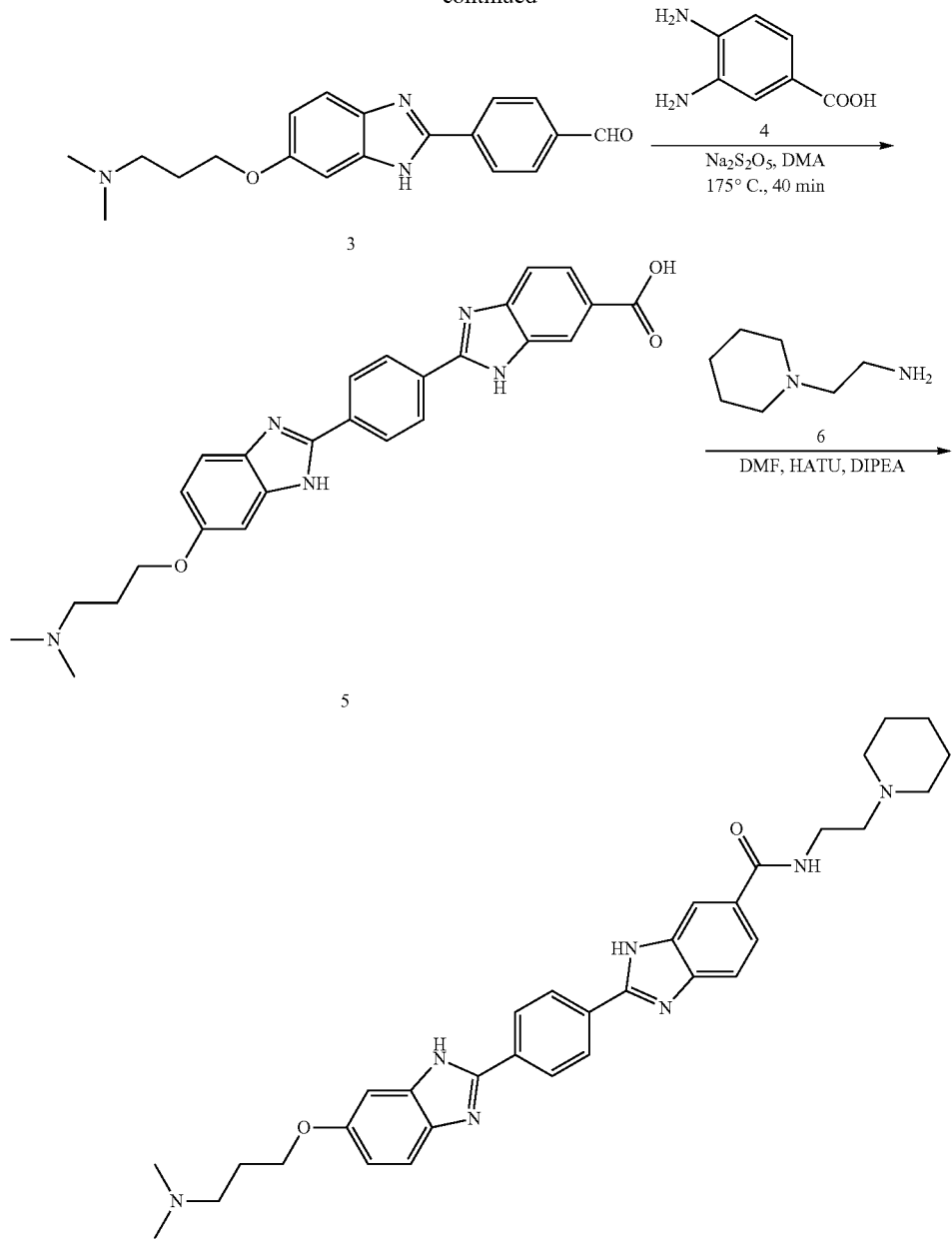

Synthesis of 4-(6-(3-(dimethylamino)propoxy)-1H-benzo[d]imidazol-2-yl)benzaldehyde: In a microwave vial, 4-(3-(dimethylamino)propoxy)benzene-1,2-diamine (100 mg, 0.47 mmol), terephthalaldehyde (77 mg, 0.57 mmol) and sodium metabisulfite (91 mg, 0.47 mmol) in DMA (5.00 mL) was heated at 175° C. for 40 min. The reaction mixture was cooled to r.t and poured onto ice cold water, where upon the product precipitated. The solid was filtered under vacuum and washed with water (2×50 mL) and dried under vacuum to obtain the crude product. The product was purified by silica gel column chromatography using CH₃OH:CH₂Cl₂ (1:4). The fractions containing the product were combined and concentrated under vacuum to obtain 4-(6-(3-(dimethylamino)propoxy)-1H-benzo[d]imidazol-2-yl)benzaldehyde.

Synthesis of 2-(4-(6-(3-(dimethylamino)propoxy)-1H-benzo[d]imidazol-2-yl)phenyl)-1H-benzo[d]imidazole-6-carboxylic acid: In a microwave vial, a mixture of 4-(3-(dimethylamino) propoxy)benzene-1,2-diamine (2.00 g, 9.56 mmol), 4-(3-(dimethylamino)propoxy)benzene-1,2-diamine (2.00 g, 9.56 mmol) and sodium metabisulfite (1.82 g, 9.56 mmol) in DMA (24.0 mL) was heated at 180° C. for 40 min. The reaction mixture was cooled to r.t, and the solvent was co-distilled with toluene (10 mL) under reduced pressure and dried to obtain the crude product. The crude product was purified by trituration with CMA (MeOH:CH₂Cl₂: NH₄OH) (3×50 mL), filtered under vacuum, washed with CMA and dried to obtain 2-(4-(6-(3-(dimethylamino) propoxy)-1H-benzo[d]imidazol-2-yl)phenyl)-1H-benzo[d] imidazole-6-carboxylic acid. The crude product was directly used in the next step.

Synthesis of 2-(4-(6-(3-(dimethylamino)propoxy)-1H-benzo[d]imidazol-2-yl)phenyl)-N-(2-(piperidin-1-yl)ethyl)-1H-benzo[d]imidazole-6-carboxamide (237): To a stirred solution 2-(4-(6-(3-(dimethylamino)propoxy)-1H-benzo[d]imidazol-2-yl)phenyl)-1H-benzo[d]imidazole-6-carboxylic acid (0.20 g, 0.43 mmol) in DMF (12.0 mL) at 0° C. under $N_2$ atmosphere, was added 2-(piperidin-1-yl)ethanamine (67 mg, 0.52 mmol), DIPEA (0.17 g, 1.38 mmol) followed with HATU (0.25 g, 0.65 mmol), and the reaction mixture was stirred at r.t for 16 h. The solvent was concentrated under reduced pressure and dried to obtain the crude product. The crude product was purified by prep-HPLC. The fractions containing only pure product were combined for concentration to obtain the title compound. MS (ESI+APCl): m/z=566 [M+H]$^+$.

Example 156

Synthesis of N,N-dimethyl-3-((2-(4-(6-(4,4,4-trifluorobutoxy)-1H-benzo[d]imidazol-2-yl)phenyl)-1H-benzo[d]imidazol-6-yl)oxy)propan-1-amine (Compound 240)

extracts were washed with brine (50 mL), dried over anhydrous $Na_2SO_4$, filtered and concentrated under vacuum to obtain the crude product. The product was purified by silica gel chromatography using $CH_3OH:CH_2Cl_2$ (1:9). The fractions containing the product were combined and concentrated under vacuum to obtain 2-nitro-5-(4,4,4-trifluorobutoxy)aniline Synthesis of 4-(4,4,4-trifluorobutoxy)benzene-1,2-diamine: To a stirred solution of 2-nitro-5-(4,4,4-trifluorobutoxy)aniline (600 mg, 2.27 mmol) in EtOH (10.0 mL) and was added Fe powder (761 mg, 13.6 mmol), followed with a solution of $NH_4Cl$ (729 mg, 13.63 mmol) in $H_2O$ (5.00 mL), and the reaction mixture was heated at 90° C. for 2 h. The reaction mixture was cooled to r.t and filtered through a celite pad, and the pad was washed with EtOH (20 mL). The combined filtrate was concentrated and crude was poured on to water and extracted with EtOAc (2×50 mL). The combined organic extracts were washed with brine (50 mL), dried over anhydrous $Na_2SO_4$, filtered and concentrated under vacuum to obtain the 4-(4,4,4-trifluorobutoxy)benzene-1,2-diamine The crude product was directly used in the next step.

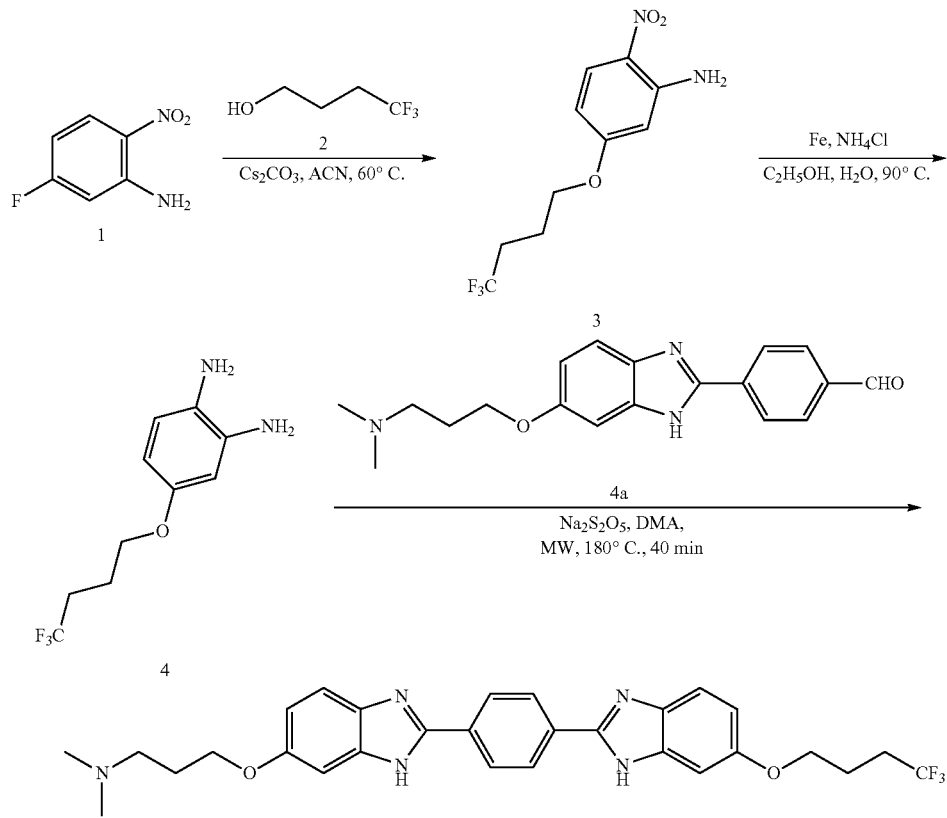

Synthesis of 2-nitro-5-(4,4,4-trifluorobutoxy)aniline: To a stirred solution of 4,4,4-trifluorobutan-1-ol (2.46 g, 19.2 mmol) in $CH_3CN$ (30.0 mL) was added $Cs_2CO_3$ (8.35 g, 25.6 mmol) followed with 5-fluoro-2-nitroaniline (2.00 g, 12.8 mmol) and the reaction mixture was stirred at 60° C. 16 h. The reaction mixture was cooled to r.t and the contents were poured on to ice cold water, and the aqueous phase was extracted with EtOAc (2×100 mL). The combined EtOAc Synthesis of N,N-dimethyl-3-((2-(4-(6-(4,4,4-trifluorobutoxy)-1H-benzo[d]imidazol-2-yl)phenyl)-1H-benzo[d]imidazol-6-yl)oxy)propan-1-amine (240): In a microwave vial, a mixture of 4-(4,4,4-trifluorobutoxy)benzene-1,2-diamine (0.21 g, 0.92 mmol), 4-(6-(3-(dimethylamino)propoxy)-1H-benzo[d]imidazol-2-yl)benzaldehyde (0.20 g, 0.62 mmol) and sodium metabisulfate (0.13 g, 0.68 mmol) in DMA (6.00 mL) was heated at 180° C. for 40 min. The reaction mixture was cooled to r. t and the contents were slowly poured into water (50 mL) and stirred for 10 min, whereupon, a brown solid precipitated. The brown solid was filtered under vacuum and washed with water (2×50 mL), and dried to obtain the crude product. The product was purified by mass triggered HPLC. The fractions containing only the pure product were combined for concentration to obtain the title compound. MS (ESI): m/z=538 [M+H]$^+$.

Example 157

4-((2-(4-(6-(3-(dimethylamino)propoxy)-1H-benzo[d]imidazol-2-yl)phenyl)-1H-benzo[d]imidazol-6-yl)oxy)butanenitrile (Compound 241)

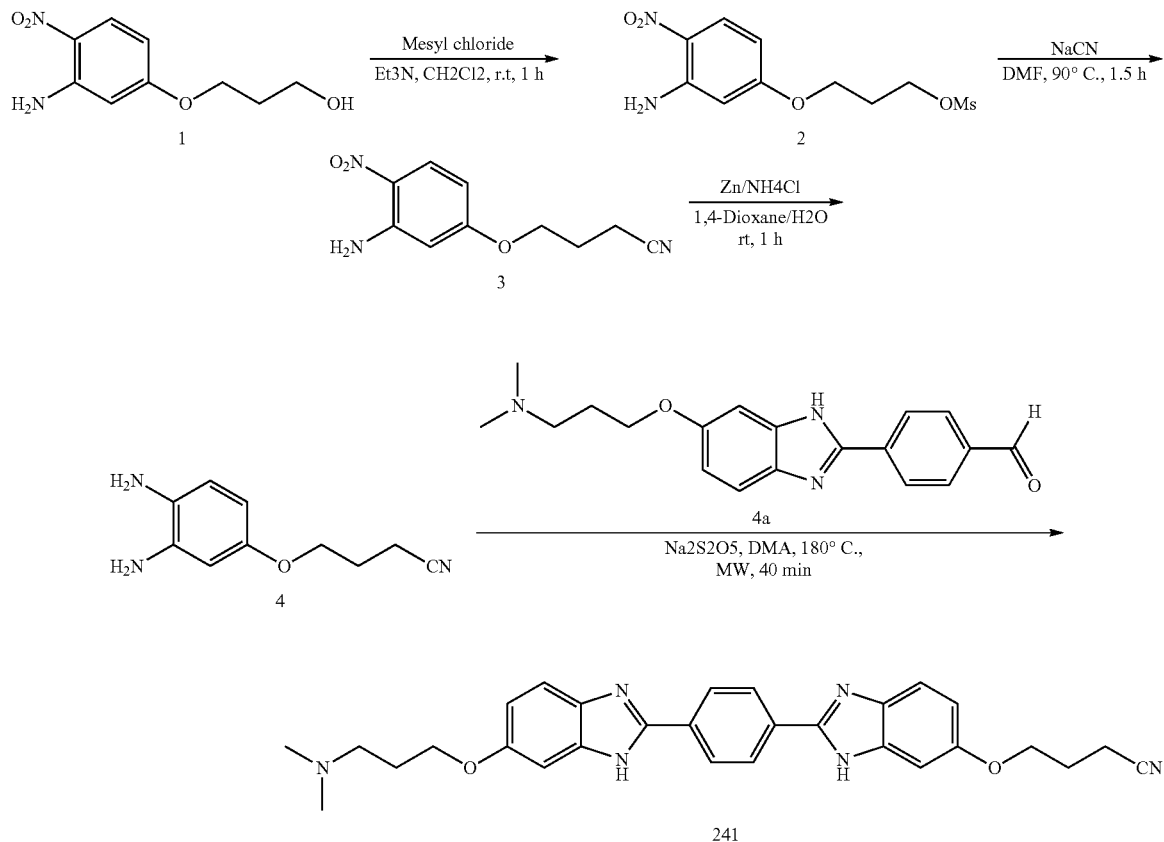

Synthesis of 3-(3-amino-4-nitrophenoxy)propyl methanesulfonate: To a stirred solution of 3-(3-amino-4-nitrophenoxy)propan-1-ol (2.00 g, 9.42 mmol) in CH$_2$Cl$_2$ (20.0 mL), at 0° C. under N$_2$ atmosphere, was added Et$_3$N (3.94 mL, 28.3 mmol) followed with methane sulfonyl chloride (1.10 mL, 14.1 mmol) in a drop wise manner over 10 minutes, and the reaction mixture was stirred at r.t for 2 h. The reaction mixture were poured on to water and extracted with CH$_2$Cl$_2$ (2×20 mL). The combined organic extracts were washed with brine (50 mL), dried over anhydrous Na$_2$SO$_4$, filtered and concentrated under vacuum to obtain 3-(3-amino-4-nitrophenoxy)propyl methanesulfonate. The crude product was directly used for the next step.

Synthesis of 4-(3-amino-4-nitrophenoxy)butanenitrile: To a stirred solution of 3-(3-amino-4-nitrophenoxy)propyl methanesulfonate (2.40 g, 8.21 mmol) in DMF (20.0 mL), at r.t under N$_2$ atmosphere, was added NaCN (0.81 g, 16.5 mmol) and the reaction mixture was heated at 90° C. for 1.5 h. The reaction mixture was cooled to r.t and the contents were poured onto ice cold water, and the aqueous phase was extracted with EtOAc (3×50 mL). The combined EtOAc extracts were washed with brine (50 mL), dried over anhydrous Na$_2$SO$_4$, filtered and concentrated under vacuum to obtain the crude product. The product was purified by silica gel column chromatography using CH$_3$OH:CH$_2$Cl$_2$ (1:9). The fractions containing the product were combined and concentrated under vacuum to obtain 4-(3-amino-4-nitrophenoxy)butanenitrile. MS (ESI): m/z=222 [M+H]$^+$.

Synthesis of 4-(3,4-diaminophenoxy)butanenitrile: To a solution of 4-(3-amino-4-nitrophenoxy)butanenitrile (1.20 g, 5.42 mmol) in EtOH (20.0 mL) was added zinc powder (2.84 g, 43.4 mmol) followed with a solution of NH$_4$Cl (2.32 g, 43.4 mmol) in H$_2$O (5.00 mL), and the reaction mixture was stirred at r.t for 2 h. The reaction mixture was filtered through a celite pad and the pad was washed with EtOH (30 mL), and the filtrate was concentrated under vacuum to obtain 4-(3,4-diaminophenoxy)butanenitrile. The crude product was directly used for the next step.

Synthesis of 4-((2-(4-(6-(3-(dimethylamino)propoxy)-1H-benzo[d]imidazol-2-yl)phenyl)-1H-benzo[d]imidazol-6-yl)oxy)butanenitrile (241): In a microwave vial, a mixture of 4-(3,4-diaminophenoxy)butanenitrile (355 mg, 1.85 mmol), 4-(6-(3-(dimethylamino)propoxy)-1H-benzo[d]imidazol-2-yl)benzaldehyde (400 mg, 1.23 mmol) and Na$_2$S$_2$O$_5$ (282 mg, 1.48 mmol) in DMA (10.0 mL) was heated at 180° C. for 40 min. The reaction mixture was cooled to r.t and the contents were slowly poured into water (50 mL) and stirred for 10 min, whereupon, a brown solid precipitated. The brown solid was filtered under vacuum, washed with water (2×5.0 mL), and dried to obtain the crude product. The product was purified by mass triggered HPLC. The fractions containing only the pure product were combined for concentration to obtain the title compound. MS (ESI): m/z=495 [M+H]$^+$.

Example 158

Synthesis of 1,1'-(((2,2'-(1,4-phenylene)bis(1H-benzo[d]imidazole-6,2-diyl))bis(oxy))bis(4,1-phenylene))bis(N,N-dimethylmethanamine (Compound 242)

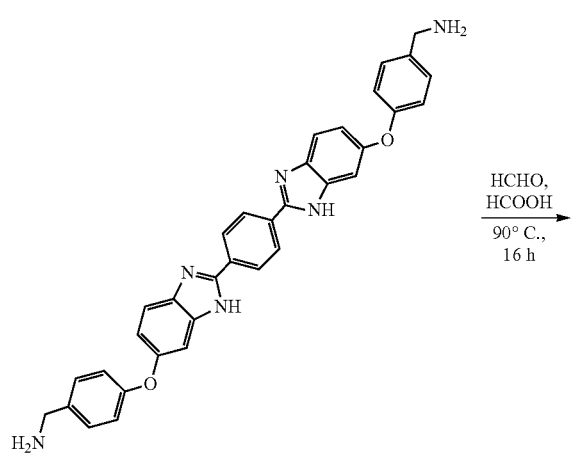

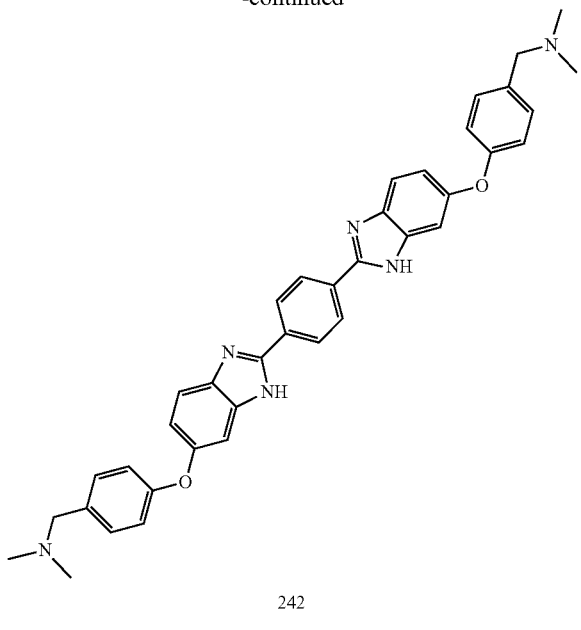

Synthesis of 1,1'-(((2,2'-(1,4-phenylene)bis(1H-benzo[d]imidazole-6,2-diyl))bis(oxy))bis(4,1-phenylene))bis(N,N-dimethylmethanamine: To a stirred solution of (((2,2'-(1,4-phenylene)bis(1H-benzo[d]imidazole-6,2-diyl))bis(oxy))bis(4,1-phenylene))dimethanamine (200 mg, 0.36 mmol) in formic acid (2.00 mL), at r.t was added formaldehyde (37% wt/v in H$_2$O, 0.50 mL, 18.1 mmol) and the reaction mixture was heated at 90° C. for 16 h. The reaction mixture was cooled to r.t and the contents were poured onto ice cold water, and the aqueous phase was basified with 6N NaOH (3.0 mL), whereupon a brown solid precipitated. The brown solid was filtered under vacuum, washed with water (2×10.0 mL) and dried to obtain the crude product. The product was purified by mass triggered HPLC. The fractions containing only the pure product were combined for concentration to obtain the title compound. MS (ESI): m/z=609 [M+H]$^+$.

Compound 243 was prepared in the same manner as compound 242. MS (ESI) m/z=609 [M+H]$^+$.

Example 159

Synthesis of (2Z,2'Z)-4,4'-((2,2'-(1,4-phenylene)bis(1H-benzo[d]imidazole-6,2-diyl))bis(oxy))bis(N,N-dimethylbut-2-en-1-amine) (Compound 244)

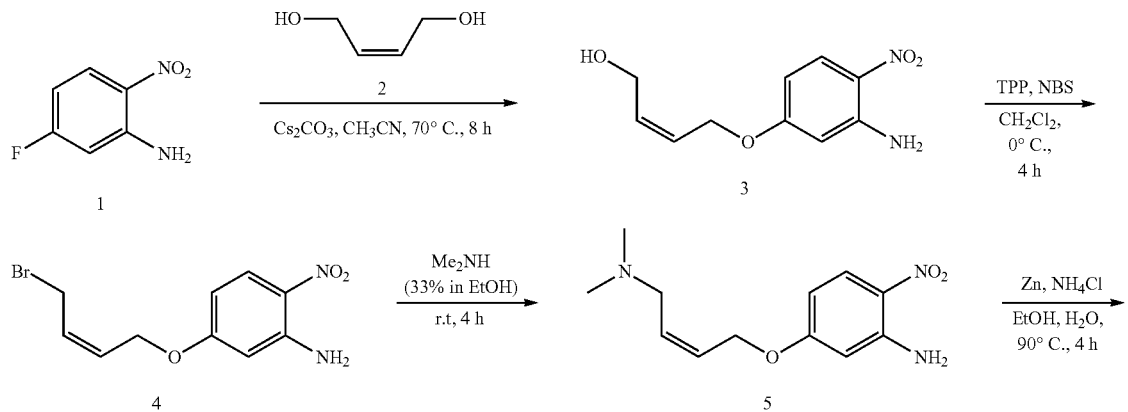

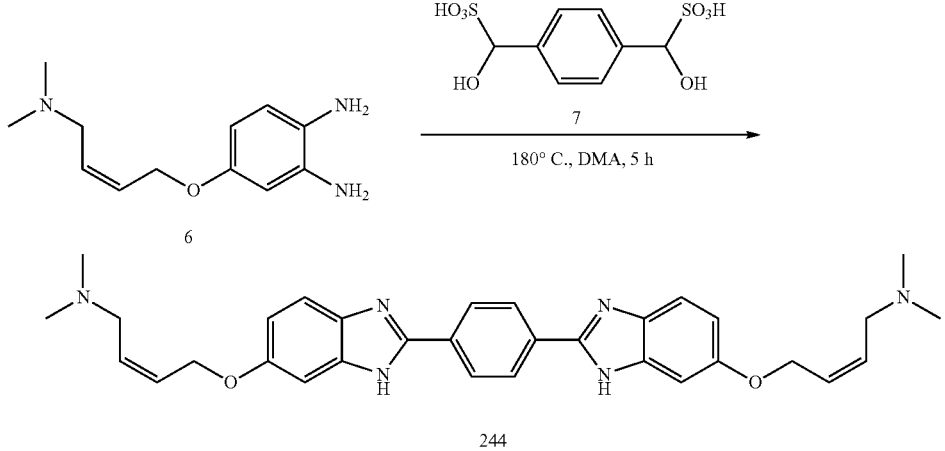

Synthesis of (Z)-4-(3-amino-4-nitrophenoxy)but-2-en-1-ol: To a solution of (Z)-but-2-ene-1,4-diol (2.25 g, 25.6 mmol) in $CH_3CN$ (20.0 mL), at r.t under Ar (g) atmosphere, was added $Cs_2CO_3$ (6.26 g, 19.2 mmol) followed with 5-fluoro-2-nitroaniline (2.00 g, 12.8 mmol) and the reaction mixture was stirred at 70° C. for 8 h. The reaction mixture was filtered through a celite-pad, and the pad was washed with EtOAc (50 mL). The filtrate was concentrated under vacuum to obtain the crude product. The product was purified by silicagel chromatography. Fractions containing only the pure product were combined for concentration to obtain (Z)-4-(3-amino-4-nitrophenoxy)but-2-en-1-ol.

Synthesis of (Z)-5-((4-bromobut-2-en-1-yl)oxy)-2-nitroaniline: To a stirred solution of (Z)-4-(3-amino-4-nitrophenoxy)but-2-en-1-ol (1.40 g, 6.24 mmol) in $CH_2Cl_2$ (20.0 mL), at r.t under $N_2$ atmosphere, was added $Ph_3P$ (2.45 g, 9.37 mmol) in a single lot. The mixture was cooled to 0° C., and added NBS (1.66 g, 9.37 mmol) in a portion wise manner over a period of 5 min. After complete addition, the reaction mixture was stirred at r.t for 4 h. The reaction mixture was slowly poured onto water (20 mL) and extracted with EtOAc (2×100 mL). The combined organic extracts were washed with brine (50 mL), dried over anhydrous $Na_2SO_4$, filtered and concentrated under vacuum to obtain the crude compound. The product was purified by silica gel column chromatography using EtOAc:Hexane (3:7). The fractions containing the pure product were combined and concentrated under vacuum to obtain (Z)-5-((4-bromobut-2-en-1-yl)oxy)-2-nitroaniline.

Synthesis of (Z)-5-((4-(dimethylamino)but-2-en-1-yl)oxy)-2-nitroaniline: In a sealed tube, $Me_2NH$ (33% in EtOH, 10.0 mL) was added to (Z)-5-((4-bromobut-2-en-1-yl)oxy)-2-nitroaniline (896 mg, 3.12 mmol), and the reaction mixture was stirred for at r.t for 4 h. The reaction mixture was concentrated under vacuum to obtain the crude product. The crude product was triturated in hot methanol to obtain (Z)-5-((4-(dimethylamino)but-2-en-1-yl)oxy)-2-nitroaniline.

Synthesis of (Z)-4-((4-(dimethylamino)but-2-en-1-yl)oxy)benzene-1,2-diamine: To a solution of (Z)-5-((4-(dimethylamino)but-2-en-1-yl)oxy)-2-nitroaniline (535 mg, 2.12 mmol) in EtOH (10.0 mL) was added zinc powder (696 mg, 10.65 mmol) followed with a solution of $NH_4Cl$ (569 mg, 10.65 mmol) in water (5.00 ml), and the reaction mixture was stirred at 90° C. for 4 h. The reaction mixture was filtered through a celite pad and the pad was washed with EtOAc (40 mL). The filtrate was washed with water (25.0 mL), dried over anhydrous $Na_2SO_4$, and concentrated under vacuum to obtain (Z)-4-((4-(dimethylamino)but-2-en-1-yl)oxy)benzene-1,2-diamine. The crude product was directly used in the next step.

Synthesis of (2Z,2'Z)-4,4'-((2,2'-(1,4-phenylene)bis(1H-benzo[d]imidazole-6,2-diyl))bis(oxy))bis(N,N-dimethylbut-2-en-1-amine) (244): To a stirred solution of (Z)-4-((4-(dimethylamino)but-2-en-1-yl)oxy)benzene-1,2-diamine (270 mg, 1.22 mmol) in anhydrous DMA (5.00 mL), at r.t under $N_2$ atmosphere, was added 1,4-phenylenebis(hydroxymethanesulfonic acid) (364 mg, 1.22 mmol) and the reaction mixture was heated at 180° C. for 5 h. The reaction mixture was cooled to r.t and concentrated under vacuum to obtain crude product. The product was purified by mass triggered Prep-HPLC. The fractions containing only the pure product were combined and concentrated under vacuum to obtain the title compound. MS (ESI+APCl): m/Z=537 $[M+H]^+$.

Example 160

Synthesis of 3-((2-(4-(6-methoxy-1H-benzo[d]imidazol-2-yl)phenyl)-1H-benzo[d]imidazol-6-yl)oxy)-N,N-dimethylpropan-1-amine (Compound 245)

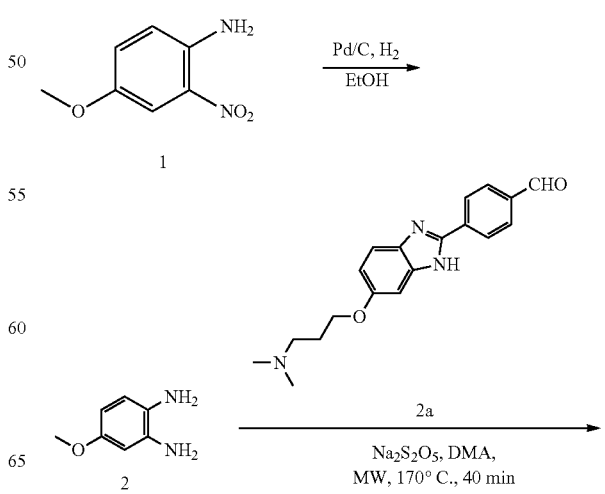

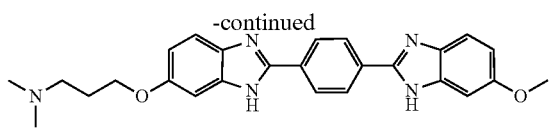

245

Synthesis of 4-methoxybenzene-1,2-diamine: To a solution of 4-methoxy-2-nitroaniline (0.50 g, 2.97 mmol) in EtOH (15.0 mL), under $N_2$ atmosphere, was added 10% Pd—C (150 mg) and the reaction mixture was hydrogenated (balloon pressure~1 atms) at r.t for 14 h. The reaction mixture was filtered through a celite pad, and the pad was washed with EtOH (50 mL). The combined filtrate was concentrated under reduced pressure to obtain 4-methoxybenzene-1,2-diamine. The crude product was directly used in the next step.

Synthesis of 3-((2-(4-(6-methoxy-1H-benzo[d]imidazol-2-yl)phenyl)-1H-benzo[d]imidazol-6-yl)oxy)-N,N-dimethylpropan-1-amine (245): In a microwave vial, a mixture of 4-methoxybenzene-1,2-diamine (0.16 g, 1.16 mmol), 4-(6-(3-(dimethylamino)propoxy)-1H-benzo[d]imidazol-2-yl)benzaldehyde (0.25 g, 0.77 mmol) and $Na_2S_2O_5$ (0.15 g, 0.77 mmol) in DMA (6.00 mL) was heated at 170° C. for 40 min. The reaction mixture was cooled to r. t and the contents were slowly poured into water (50 mL) and stirred for 10 min, whereupon, a brown solid precipitated. The brown solid was filtered under vacuum, washed with water (2×50 mL), and dried to obtain the crude product. The product was purified by mass triggered HPLC. The fractions containing only the pure product were combined for concentration to obtain the title compound. MS (ESI): m/z=442 $[M+H]^+$.

Example 161

Synthesis of 1,1'-(1,1'-(2,2'-(1,4-phenylene)bis(1H-benzo[d]imidazole-6,2-diyl))bis(1H-1,2,3-triazole-4,1-diyl))bis(N,N-dimethylmethanamine (Compound 247)

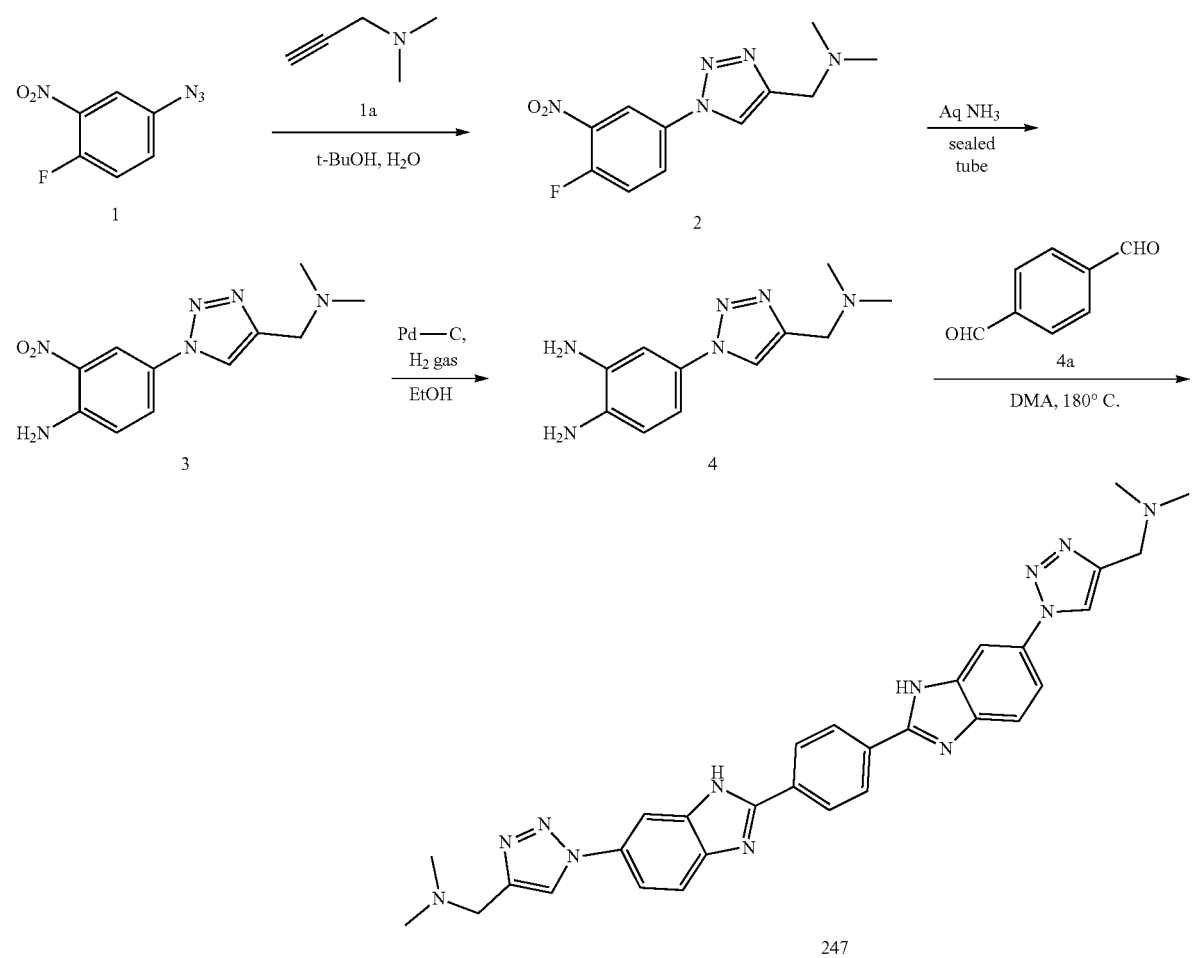

247

Synthesis of 1-(1-(4-fluoro-3-nitrophenyl)-1H-1,2,3-triazol-4-yl)-N,N-dimethylmethanamine: To a stirred solution of 4-azido-1-fluoro-2-nitrobenzene (1.50 g, 8.24 mmol) in a mixture of tert-BuOH (50.0 mL) and $H_2O$ (50.0 mL) was added N,N-dimethylprop-2-yn-1-amine (1.36 g, 16.5 mmol), copper(II) sulfate pentahydrate (0.41 g, 1.64 mmol) followed with L-ascorbic acid sodium salt (0.32 g, 1.64 mmol), and the mixture was stirred at r.t for 5 h. The contents were poured onto water (100 mL) and extracted with EtOAc (3×50 mL). The combined organic extracts were washed with brine (50 mL), dried over anhydrous $Na_2SO_4$, filtered and concentrated under vacuum to obtain 1-(1-(4-fluoro-3-nitrophenyl)-1H-1,2,3-triazol-4-yl)-N,N-dimethylmethanamine. The crude product was directly used in the next step.

Synthesis of 4-(4-((dimethylamino)methyl)-1H-1,2,3-triazol-1-yl)-2-nitroaniline: In a sealed tube a solution of 1-(1-(4-fluoro-3-nitrophenyl)-1H-1,2,3-triazol-4-yl)-N,N-dimethylmethanamine (1.40 g, 5.28 mmol) in aq. $NH_3$ (50.0 mL) was heated at 80° C. for 16 h. The reaction mixture was cooled to r.t, whereupon a brown solid precipitated. The brown solid was filtered under vacuum, washed with water (2×20 mL), and dried to obtain 4-(4-((dimethylamino)methyl)-1H-1,2,3-triazol-1-yl)-2-nitroaniline.

Synthesis of 4-(4-((dimethylamino)methyl)-1H-1,2,3-triazol-1-yl)benzene-1,2-diamine: To a solution of 4-(4-((dimethylamino)methyl)-1H-1,2,3-triazol-1-yl)-2-nitroaniline (1.00 g, 3.81 mmol) in EtOH (50.0 mL), at r.t under $N_2$ atmosphere, was added 10% Pd—C (406 mg) and the reaction mixture was hydrogenated (balloon pressure~1 atms) at r.t for 6 h. The reaction mixture was filtered through a celite pad, and the pad was washed with EtOH (40 mL). The combined filtrate was concentrated under reduced pressure to obtain 4-(4-((dimethylamino)methyl)-1H-1,2,3-triazol-1-yl)benzene-1,2-diamine. The crude product was directly used in the next step.

Synthesis of 1,1'-(1,1'-(2,2'-(1,4-phenylene)bis(1H-benzo[d]imidazole-6,2-diyl))bis(1H-1,2,3-triazole-4,1-diyl))bis(N,N-dimethylmethanamine: In a microwave vial, a mixture of 4-(4-((dimethylamino)methyl)-1H-1,2,3-triazol-1-yl)benzene-1,2-diamine (400 mg, 1.72 mmol), terephthalaldehyde (115 mg, 0.86 mmol) and $Na_2S_2O_5$ (327 mg, 1.72 mmol) in DMA (6.0 mL) was heated at 180° C. for 40 min. The reaction mixture was cooled to r. t and the contents were slowly poured into water (50 mL) and stirred for 10 min, whereupon, a brown solid precipitated. The brown solid was filtered under vacuum and washed with water (2×50 mL), and dried to obtain the crude product. The product was purified by mass triggered HPLC. The fractions containing only the pure product were combined for concentration to obtain the title compound. MS (ESI): m/z=559 $[M+H]^+$.

Example 162

Synthesis of 4-((2-(4-(5-(3-(dimethylamino)propoxy)-1H-benzo[d]imidazol-2-yl)phenyl)-1H-benzo[d]imidazol-5-yl)oxy)butanoic acid (Compound 248)

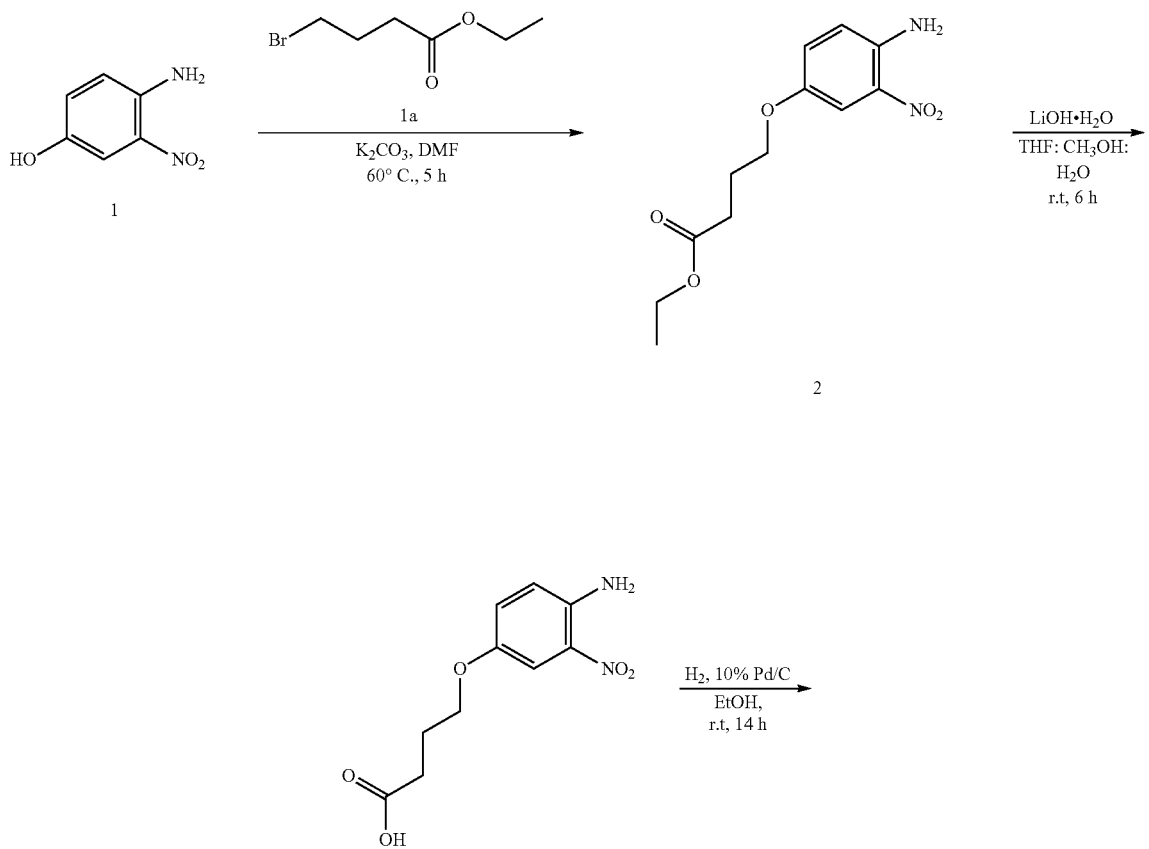

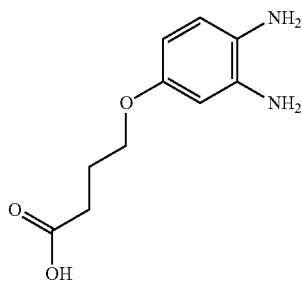

4

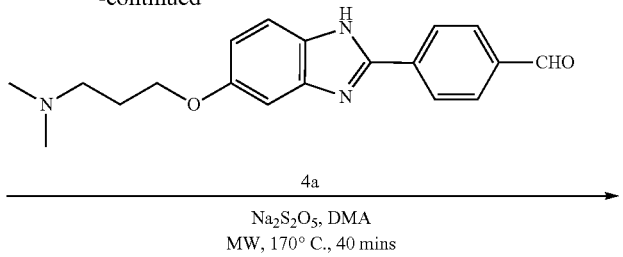

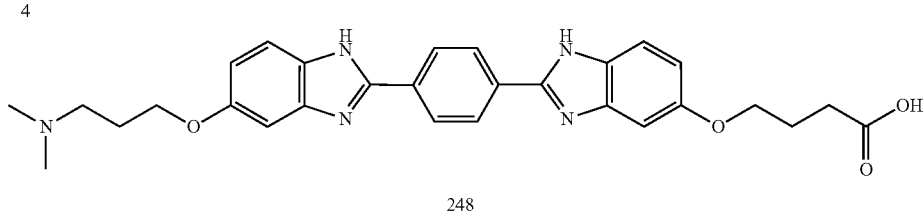

248

Synthesis of ethyl 4-(4-amino-3-nitrophenoxy)butanoate: To a stirred solution of 4-amino-3-nitrophenol (5.00 g, 32.4 mmol) in DMF (75.0 mL) was added $K_2OC_3$ (8.97 g, 64.9 mmol) followed with ethyl 4-bromobutanoate (8.23 g, 42.2 mmol) and the reaction mixture was stirred at 60° C. 16 h. The reaction mixture was cooled to r.t and the contents were poured on to ice cold water, and the aqueous phase was extracted with EtOAc (2×200 mL). The combined EtOAc extracts were washed with brine (150 mL), dried over anhydrous $Na_2SO_4$, filtered and concentrated under vacuum to obtain the crude product. The product was purified by silica gel chromatography using $CH_3OH:CH_2Cl_2$ (1:9). The fractions containing the product were combined and concentrated under vacuum to obtain ethyl 4-(4-amino-3-nitrophenoxy)butanoate.

Synthesis of 4-(4-amino-3-nitrophenoxy)butanoic acid: To a solution of ethyl 4-(4-amino-3-nitrophenoxy)butanoate (5.00 g, 18.6 mmol) in mixture of $CH_3OH$ (20.0 mL), THF (30.0 mL), and $H_2O$ (15.0 mL) at 0° C., was added LiOH (1.34 g, 56.0 mmol) and the reaction mixture was stirred at r.t for 6 h. The reaction mixture was acidified with 2N aqueous HCl (15.0 mL) and the contents were poured onto water and extracted with EtOAc (2×150 mL). The combined organic extracts were washed with brine (100 mL), dried over anhydrous $Na_2SO_4$, filtered and concentrated under vacuum to obtain 4-(4-amino-3-nitrophenoxy)butanoic acid. The crude product was used directly in the next step.

Synthesis of 4-(3,4-diaminophenoxy)butanoic acid: To a solution of 4-(4-amino-3-nitrophenoxy)butanoic acid (4.10 g, 17.0 mmol) in EtOH (60.0 mL) under $N_2$ atmosphere, was added 10% Pd—C (800 mg) and the reaction mixture was hydrogenated (balloon pressure ~1 atms) at r.t for 14 h. The reaction mixture was filtered through a celite pad, and the pad was washed with EtOH (100 mL). The combined filtrate was concentrated under reduced pressure to obtain 4-(3,4-diaminophenoxy)butanoic acid. The crude product was directly used in the next step.

Synthesis of 4-((2-(4-(5-(3-(dimethylamino)propoxy)-1H-benzo[d]imidazol-2-yl)phenyl)-1H-benzo[d]imidazol-5-yl)oxy)butanoic acid (248): In a microwave vial, a mixture of 4-(3,4-diaminophenoxy)butanoic acid (1.95 g, 9.28 mmol), 4-(5-(3-(dimethylamino)propoxy)-1H-benzo[d]imidazol-2-yl)benzaldehyde (2.00 g, 6.18 mmol) and $Na_2S_2O_5$ (1.29 g, 6.80 mmol) in DMA (20.0 mL) was heated at 170° C. for 40 min. The reaction mixture was cooled to r.t and the contents were slowly poured into water (50 mL) and stirred for 10 min, whereupon, a brown solid precipitated. The brown solid was filtered under vacuum and washed with water (2×50 mL), and dried to obtain the crude product. The product was purified by mass triggered HPLC. The fractions containing only the pure product were combined for concentration to obtain the title compound. MS (ESI): m/z=514 $[M+H]^+$.

Example 163

Synthesis of 2-(4-(6-(3-(dimethylamino)propoxy)-1H-benzo[d]imidazol-2-yl)phenyl)-1H-benzo[d]imidazole-6-carboxylic acid (Compound 250)

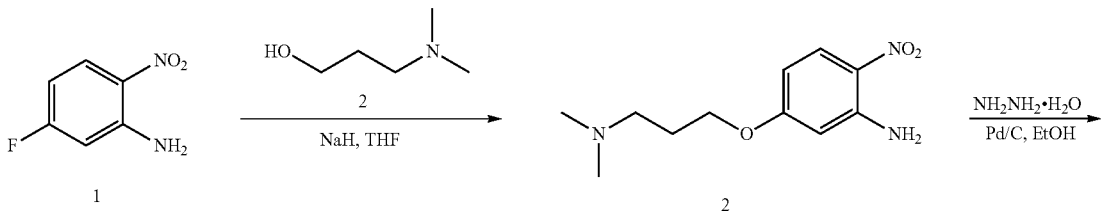

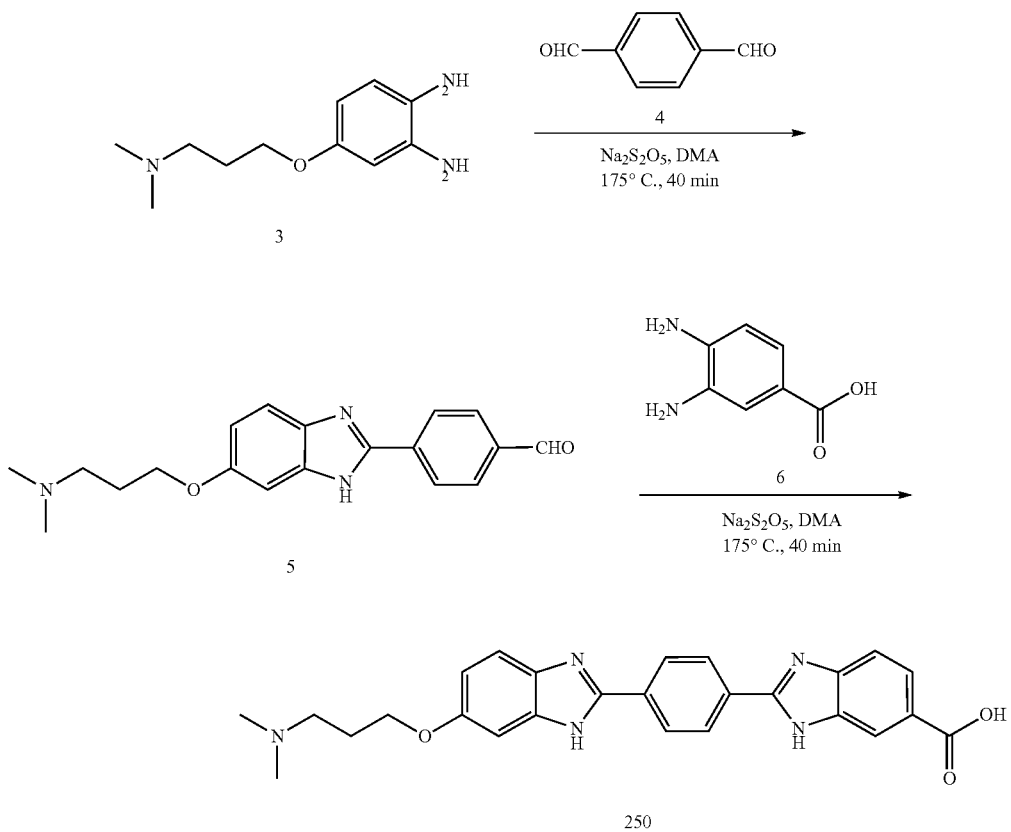

Synthesis of 5-(3-(dimethylamino)propoxy)-2-nitroaniline: To a stirred solution of 3-(dimethylamino)propan-1-ol (4.90 g, 48.0 mmol) in dry THF (100 mL), at 0° C. under $N_2$ atmosphere, was added NaH (60% suspension in oil, 3.80 g, 96.2 mmol) portion wise over a period of 10 minutes. The reaction mixture was stirred for an additional 10 minutes and a solution of 5-fluoro-2-nitroaniline (5.00 g, 32.0 mmol) in THF (30.0 mL) was added in a drop wise manner over 15 minutes, maintaining the temperature at 0° C. After complete addition, the reaction mixture was stirred at r.t for 12 h. The contents were poured onto ice and extracted with EtOAc (2×100 mL). The combined organic extracts were washed with brine (100 mL), dried over anhydrous $Na_2SO_4$, filtered and concentrated under vacuum to obtain the crude product. The product was purified by silica gel column chromatography using $CH_3OH:CH_2Cl_2$ (1:9). The fractions containing the product were combined and concentrated under vacuum to obtain 5-(3-(dimethylamino) propoxy)-2-nitroaniline.

Synthesis of 4-(3-(dimethylamino)propoxy)benzene-1,2-diamine: To a solution of 5-(3-(dimethylamino)propoxy)-2-nitroaniline (2.50 g, 10.4 mmol) in EtOH (100 mL), hydrazine monohydrate (5.00 mL) and 10% Pd/C (500 mg) were added and the reaction mixture was stirred at r.t for 5 h. The reaction mixture was filtered through a celite pad, and the pad was washed with EtOH (2×50 mL). The combined filtrate were concentrated under vacuum to obtain 4-(3-(dimethylamino) propoxy)benzene-1,2-diamine.

Synthesis of 4-(6-(3-(dimethylamino)propoxy)-1H-benzo[d]imidazol-2-yl)benzaldehyde: In a microwave vial, 4-(3-(dimethylamino)propoxy)benzene-1,2-diamine (2.00 g, 9.56 mmol), terephthalaldehyde (1.93 g, 14.3 mmol) and $Na_2S_2O_5$ (1.81 g, 9.56 mmol) in DMA (24.0 mL) was heated at 175° C. for 40 min. The reaction mixture was cooled to r.t and poured onto ice cold water, where upon the product precipitated. The solid was filtered under vacuum and washed with water (2×50 mL), and dried to obtain the crude product. The product was purified by silica gel column chromatography using $CH_3OH:CH_2Cl_2$ (1:4). The fractions containing the product were combined and concentrated under vacuum to obtain 4-(6-(3-(dimethylamino)propoxy)-1H-benzo[d]imidazol-2-yl)benzaldehyde.

Synthesis of 2-(4-(6-(3-(dimethylamino)propoxy)-1H-benzo[d]imidazol-2-yl)phenyl)-1H-benzo[d]imidazole-6-carboxylic acid (250): In a microwave vial, a mixture of 4-(3-(dimethylamino) propoxy)benzene-1,2-diamine (0.75 g, 2.32 mmol), 4-(3-(dimethylamino)propoxy)benzene-1,2-diamine (0.42 g, 2.78 mmol) and $Na_2S_2O_5$ (0.44 g, 2.32 mmol) in DMA (10.0 mL) was heated at 180° C. for 40 min. The reaction mixture was cooled to r.t, and the solvent was co-distilled with toluene (10.0 mL) under reduced pressure and dried to obtain the crude product. The crude product was purified by trituration with CMA ($MeOH:CH_2Cl_2:NH_4OH$, 3×50 mL), filtered under vacuum, washed with CMA (10 mL), and dried to obtain an impure product. The product was purified by prep-HPLC. Fractions containing only the pure product were combined for concentration to obtain the title compound. MS (ESI+APCl): m/z=456 $[M+H]^+$.

Example 164

Synthesis of 1,1'-(1,1'-(2,2'-(1,4-phenylene)bis(1H-benzo[d]imidazole-6,2-diyl))bis(1H-1,2,3-triazole-4,1-diyl))bis(N,N-dimethylmethanamine (Compound 251)

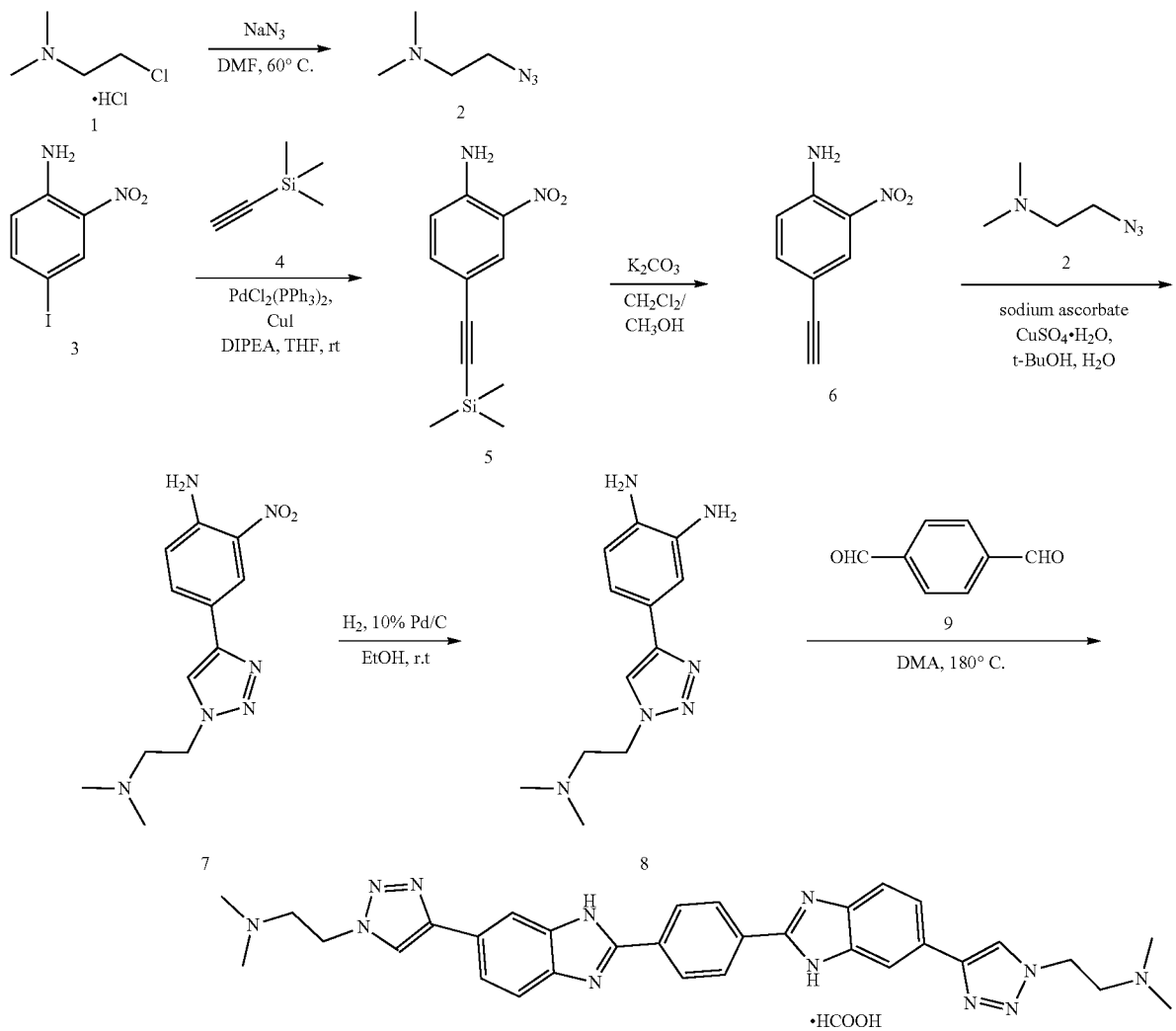

Synthesis of 2-azido-N,N-dimethylethanamine: To a stirred solution of 2-chloro-N,N-dimethylethan-1-amine hydrochloride (5.00 g, 34.7 mmol) in DMF (30.0 mL), at r.t under $N_2$ atmosphere, was added sodium azide (6.77 g, 104 mmol) portion wise over a period of 10 min. After complete addition the reaction mixture was heated at 60° C. for 6 h. The reaction mixture was cooled to r. t and the contents were slowly poured onto water (100 mL) and extracted with MTBE (2×250 mL). The combined organic extracts were washed with brine (100 mL), dried over anhydrous $Na_2SO_4$, filtered and concentrated under vacuum to obtain 2-azido-N,N-dimethylethanamine.

Synthesis of 2-nitro-4-((trimethylsilyl)ethynyl)aniline: To a stirred solution of 4-iodo-2-nitroaniline (2.50 g, 9.47 mmol) in THF (25.0 mL), copper (I) iodide (0.36 g, 1.89 mmol) and DIPEA (10.0 mL, 56.8 mmol), de-gassed with argon gas for 5 min, was added ethynyltrimethylsilane (1.02 g, 10.4 mmol) drop wise over a period of 5 min. After complete addition, the reaction mixture was stirred at r.t for 3 h. The reaction mixture was diluted with water (50 mL) and extracted with EtOAc (3×75 mL). The combined EtOAc extracts were washed with brine (50 mL), dried over anhydrous $Na_2SO_4$, filtered and concentrated under vacuum. The product was purified by silica gel column chromatography using EtOAc:Hexanes (1:9). The fractions containing the product were combined and concentrated under vacuum to obtain 2-nitro-4-((trimethylsilyl)ethynyl)aniline.

Synthesis of 4-ethynyl-2-nitroaniline: To a stirred solution of 2-nitro-4-((trimethylsilyl)ethynyl)aniline (2.20 g, 9.39 mmol) in $CH_2Cl_2:CH_3OH$ (50.0 mL), at r.t under $N_2$ atmosphere, was added potassium carbonate (1.94 g, 14.0 mmol), and the mixture was stirred at r.t for 16 h. The reaction mixture was diluted with water (50 mL) and extracted with CH$_2$Cl$_2$ (3×100 mL). The combined CH$_2$Cl$_2$ extracts were washed with brine (50 mL), dried over anhydrous Na$_2$SO$_4$, filtered and concentrated under vacuum. The product was purified by silica gel column chromatography using CH$_3$OH:CH$_2$Cl$_2$ (0.5:9.5). The fractions containing the product were combined and concentrated under vacuum to obtain 4-ethynyl-2-nitroaniline.

Synthesis of 4-(1-(2-(dimethylamino)ethyl)-1H-1,2,3-triazol-4-yl)-2-nitroaniline: To a stirred solution of 4-ethynyl-2-nitroaniline (1.10 g, 6.78 mmol) and 2-azido-N,N-dimethylethanamine (2.32 g, 20.3 mmol) in a mixture of tert-BuOH (25.0 mL) and H$_2$O (25.0 mL), at r.t under N$_2$ atmosphere, was added copper(II) sulfate pentahydrate (0.10 g, 0.67 mmol) followed with L-ascorbic acid sodium salt (0.13 g, 0.67 mmol), and the mixture was stirred at r.t for 16 h. The contents were poured onto water (50.0 mL) and extracted with EtOAc (2×100 mL). The combined EtOAc extracts were washed with brine (50 mL), dried over anhydrous Na$_2$SO$_4$, filtered and concentrated under vacuum. The product was purified by silica gel column chromatography using CH$_3$OH:CH$_2$Cl$_2$ (0.5:9.5). The fractions containing the product were combined and concentrated under vacuum to obtain 4-(1-(2-(dimethylamino)ethyl)-1H-1,2,3-triazol-4-yl)-2-nitroaniline.

Synthesis of 4-(1-(2-(dimethylamino)ethyl)-1H-1,2,3-triazol-4-Abenzene-1,2-diamine: To a solution of 4-(1-(2-(dimethylamino)ethyl)-1H-1,2,3-triazol-4-yl)-2-nitroaniline (0.70 g, 2.53 mmol) in EtOH (25.0 mL), at r.t under N$_2$ atmosphere, was added 10% Pd—C (300 mg) and the reaction mixture was hydrogenated (balloon pressure~1 atms) at r.t for 5 h. The reaction mixture was filtered through a celite pad, and the pad was washed with EtOH (40 mL). The combined filtrate was concentrated under reduced pressure to obtain 4-(1-(2-(dimethylamino)ethyl)-1H-1,2,3-triazol-4-Abenzene-1,2-diamine The crude product was directly used in the next step.

Synthesis of 2,2'-(4,4'-(2,2'-(1,4-phenylene)bis(1H-benzo[d]imidazole-6,2-diyl))bis(1H-1,2,3-triazole-4,1-diyl))bis(N,N-dimethylethanamine): In a microwave vial, a mixture of 4-(1-(2-(dimethylamino)ethyl)-1H-1,2,3-triazol-4-yl)benzene-1,2-diamine (600 mg, 2.43 mmol), terephthalaldehyde (163 mg, 1.21 mmol) and Na$_2$S$_2$O$_5$ (463 mg, 2.43 mmol) in DMA (10.0 mL) was heated at 180° C. for 40 min. The reaction mixture was concentrated under vacuum to obtain the crude product. The product was purified by mass triggered HPLC. The fractions containing only the pure product were combined for concentration to obtain the title compound. MS (ESI): m/z=587 [M+H]$^+$.

Example 165

Synthesis of tert-butyl 4-((2-(4-(5-(3-(dimethylamino)propoxy)-1H-benzo[d]imidazol-2-yl)phenyl)-1H-benzo[d]imidazol-5-yl)oxy)butanoate (Compound 252)

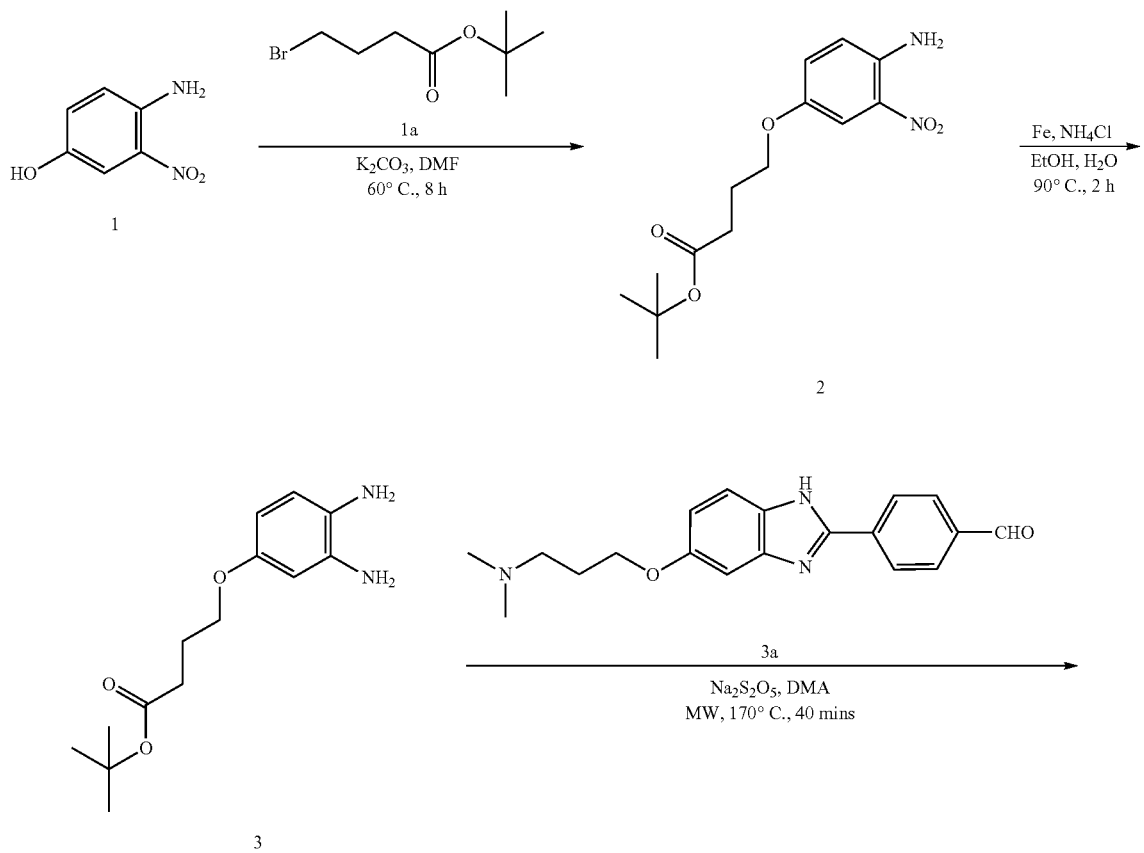

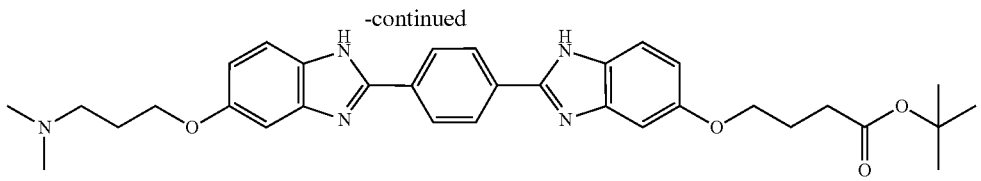

252

Synthesis of tert-butyl 4-(4-amino-3-nitrophenoxy)butanoate: To a stirred solution of 4-amino-3-nitrophenol (5.00 g, 32.4 mmol) in anhydrous DMF (75.0 mL) was added $K_2OC_3$ (8.97 g, 64.9 mmol) followed with tert-butyl 4-bromobutanoate (8.69 g, 38.9 mmol) and the reaction mixture was stirred at 60° C. 16 h. The reaction mixture was cooled to r.t and the contents were poured on to ice cold water, and the aqueous phase was extracted with EtOAc (2×200 mL). The combined EtOAc extracts were washed with brine (150 mL), dried over anhydrous $Na_2SO_4$, filtered and concentrated under vacuum to obtain the crude product. The product was purified by silica gel chromatography using $CH_3OH:CH_2Cl_2$ (1:9). The fractions containing the product were combined and concentrated under vacuum to obtain tert-butyl 4-(4-amino-3-nitrophenoxy)butanoate.

Synthesis of tert-butyl 4-(3,4-diaminophenoxy)butanoate: To a stirred solution of tert-butyl 4-(4-amino-3-nitrophenoxy)butanoate (1.00 g, 3.35 mmol) in EtOH (15.0 mL) and was added Fe powder (0.94 g, 16.87 mmol), followed with a solution of $NH_4Cl$ (0.90 g, 16.87 mmol) in $H_2O$ (5.00 mL), and the reaction mixture was heated at 90° C. for 2 h. The reaction mixture was cooled to r.t and filtered through a celite pad, and the pad was washed with EtOH (20 mL). The combined filtrate was concentrated and crude was poured on to water and extracted with EtOAc (2×50 mL). The combined organic extracts were washed with brine (50 mL), dried over anhydrous $Na_2SO_4$, filtered and concentrated under vacuum to obtain tert-butyl 4-(3,4-diaminophenoxy)butanoate. The crude product was directly used in the next step.

Synthesis of tert-butyl 4-((2-(4-(5-(3-(dimethylamino)propoxy)-1H-benzo[d]imidazol-2-yl)phenyl)-1H-benzo[d]imidazol-5-yl)oxy)butanoate (252): In a microwave vial, a mixture of tert-butyl 4-(3,4-diaminophenoxy)butanoate (0.67 g, 2.51 mmol), 4-(5-(3-(dimethylamino)propoxy)-1H-benzo[d]imidazol-2-yl)benzaldehyde (0.54 g, 1.67 mmol) and $Na_2S_2O_5$ (0.35 g, 1.84 mmol) in DMA (7.50 mL) was heated at 170° C. for 40 min. The reaction mixture was cooled to r.t and the contents were slowly poured into water (50 mL) and stirred for 10 min, whereupon, a brown solid precipitated. The brown solid was filtered under vacuum and washed with water (2×50 mL), and dried to obtain the crude product. The product was purified by silica gel chromatography using $CH_3OH:CH_2Cl_2$ (2:8). The fractions containing only the pure product were combined for concentration to obtain Compound 252. MS (ESI): m/z=570 [M+H]$^+$.

Example 166

Synthesis of 3,3'-((1,3-phenylenebis(1H-benzo[d]imidazole-2,6-diyl))bis(oxy))bis(N,N-dimethylpropan-1-amine) (Compound 253)

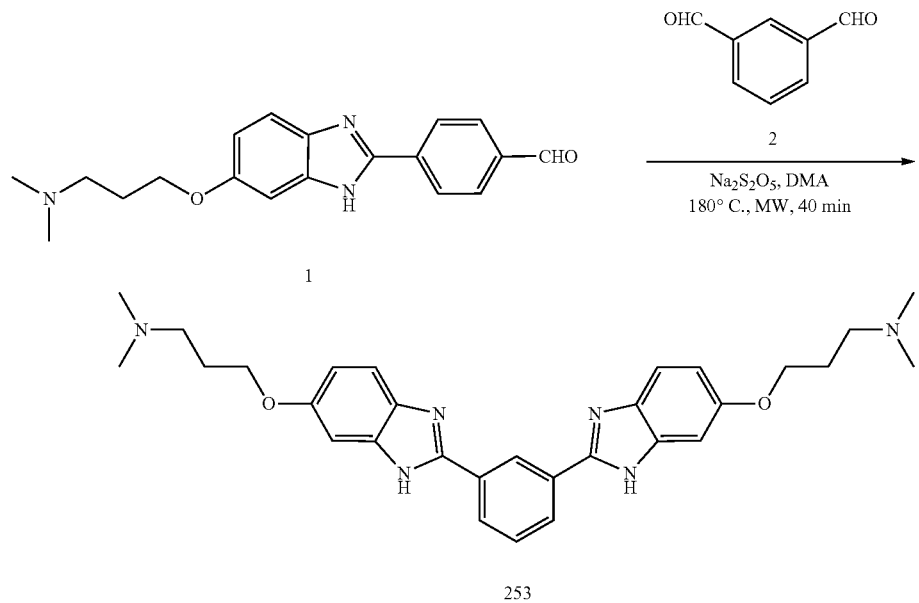

Synthesis of 3,3'-((1,3-phenylenebis(1H-benzo[d]imidazole-2,6-diyl))bis(oxy))bis(N,N-dimethylpropan-1-amine): In a microwave vial, a mixture of isophthalaldehyde (64.1 mg, 0.47 mmol), 4-(6-(3-(dimethylamino)propoxy)-1H- benzo[d]imidazol-2-yl)benzaldehyde (200 mg, 0.95 mmol) and $Na_2S_2O_5$ (182 mg, 0.95 mmol) in DMA (6.00 mL) was heated at 180° C. for 40 min. The reaction mixture was cooled to r. t and the contents were slowly poured into water (20 mL) and stirred for 10 min, whereupon, a brown solid precipitated. The brown solid was filtered under vacuum, washed with water (2×5.0 mL) and dried to obtain the crude product. The product was purified by mass triggered HPLC. The fractions containing only the pure product were combined for concentration to obtain the title compound. MS (ESI): m/z=513 $[M+H]^+$.

Example 167

Synthesis of tert-butyl 2-(4-(6-(3-(dimethylamino) propoxy)-1H-benzo[d]imidazol-2-yl)phenyl)-1H-benzo[d]imidazole-6-carboxylate (Compound 254)

Synthesis of tert-butyl 3,4-diaminobenzoate: To a stirred solution of tert-butyl 3,4-dinitrobenzoate (3.00 g, 11.1 mmol) in EtOH (60.0 mL) and was added Fe powder (6.25 g, 112 mmol), followed with a solution of $NH_4Cl$ (5.98 g, 112 mmol) in $H_2O$ (12.0 mL), and the reaction mixture was heated at 90° C. for 2 h. The reaction mixture was cooled to r.t and filtered through a celite pad, and the pad was washed with EtOH (40 mL). The combined filtrate was concentrated under vacuum and the residue was poured on to water (30 mL) and extracted with EtOAc (2×50 mL). The combined organic extracts were washed with brine (50 mL), dried over anhydrous $Na_2SO_4$, filtered and concentrated under vacuum to obtain the crude product. The product was purified by flash chromatography to obtain tert-butyl 3,4-diaminobenzoate.

Synthesis of tert-butyl 2-(4-(6-(3-(dimethylamino) propoxy)-1H-benzo[d]imidazol-2-yl)phenyl)-1H-benzo[d]imidazole-6-carboxylate (Compound 254): In a microwave

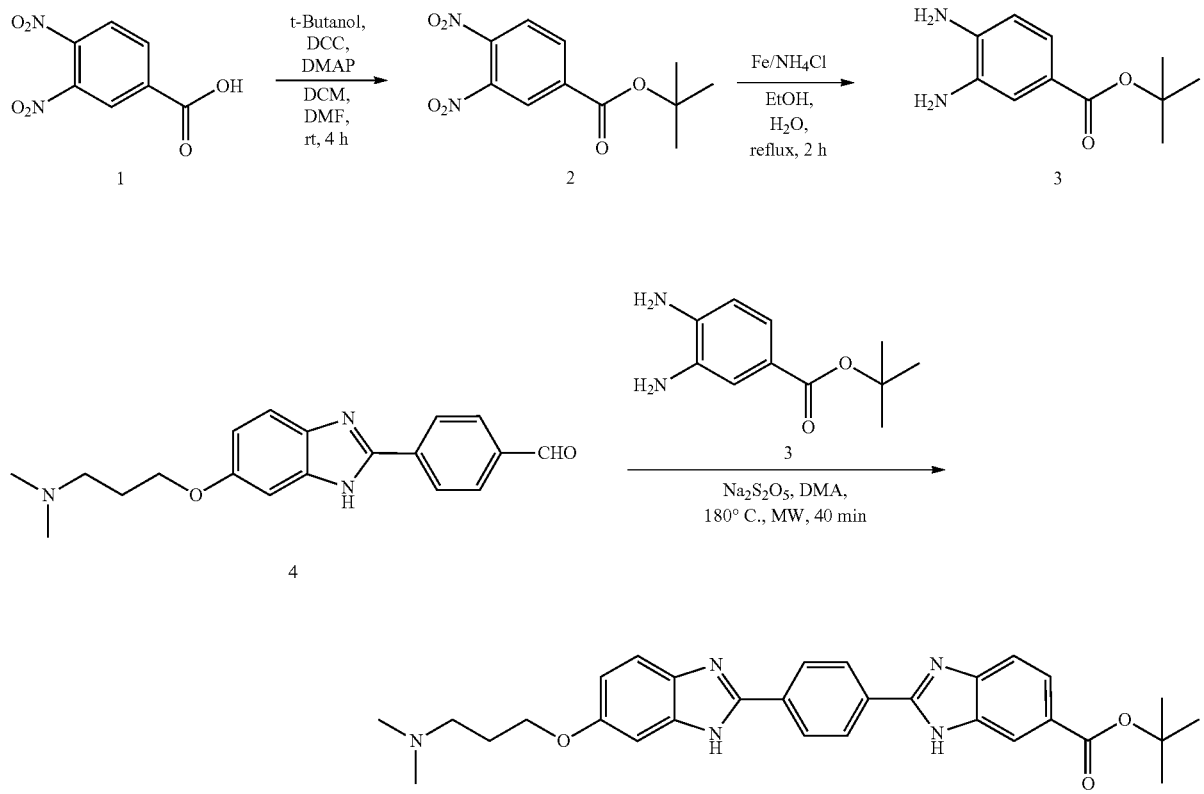

Synthesis of tert-butyl 3,4-dinitrobenzoate: To a stirred solution 3,4-dinitrobenzoic acid (3.00 g, 14.1 mmol) in $CH_2Cl_2$ (30.0 mL) and DMF (1.00 mL) at 0° C. under $N_2$ atmosphere, was added t-BuOH (2.03 mL, 21.2 mmol), DMAP (0.17 g, 1.41 mmol) followed with DCC (3.21 g, 15.5 mmol), and the reaction mixture was stirred at r.t for 16 h. The precipitate was filtered and washed with $CH_2Cl_2$ (20.0 mL). The filtrate was concentrated under vacuum and purified by silica-gel chromatography to obtain tert-butyl 3,4-dinitrobenzoate.

vial, a mixture of tert-butyl 3,4-diaminobenzoate (1.15 g, 5.57 mmol), 4-(6-(3-(dimethylamino)propoxy)-1H-benzo [d]imidazol-2-yl)benzaldehyde (1.20 g, 3.71 mmol) and sodium metabisulfate (846 mg, 4.45 mmol) in DMA (12.0 mL) was heated at 180° C. for 40 min. The reaction mixture was cooled to r. t and the contents were slowly poured into water (50 mL) and stirred for 10 min, whereupon, a brown solid precipitated. The brown solid was filtered under vacuum, washed with water (2×5.0 mL) and dried to obtain the crude product. The product was purified by silica gel chromatography to obtain the title compound. MS (ESI): m/z=512 $[M+H]^+$.

Example 168

Synthesis of 3,3'-((2,2'-(2-(prop-2-yn-1-yloxy)-1,4-phenylene)bis(1H-benzo[d]imidazole-6,2-diyl))bis(oxy))bis(N,N-dimethylpropan-1-amine)) (Compound 255) and 2,5-bis(6-(3-(dimethylamino)propoxy)-1H-benzo[d]imidazol-2-yl)phenol (256)

Synthesis of dimethyl 2-(prop-2-yn-1-yloxy)terephthalate: To a stirred solution of dimethyl 2-hydroxyterephthalate (0.75 g, 3.57 mmol) in DMF (8.00 mL) was added $K_2CO_3$ (0.98 g, 7.14 mmol) followed with 3-bromoprop-1-yn (8.69 g, 5.35 mmol) and the reaction mixture was stirred at r.t for 16 h. The reaction mixture was cooled to r.t and the contents were poured on to ice cold water (30 mL), and extracted with EtOAc (2×50 mL). The combined EtOAc

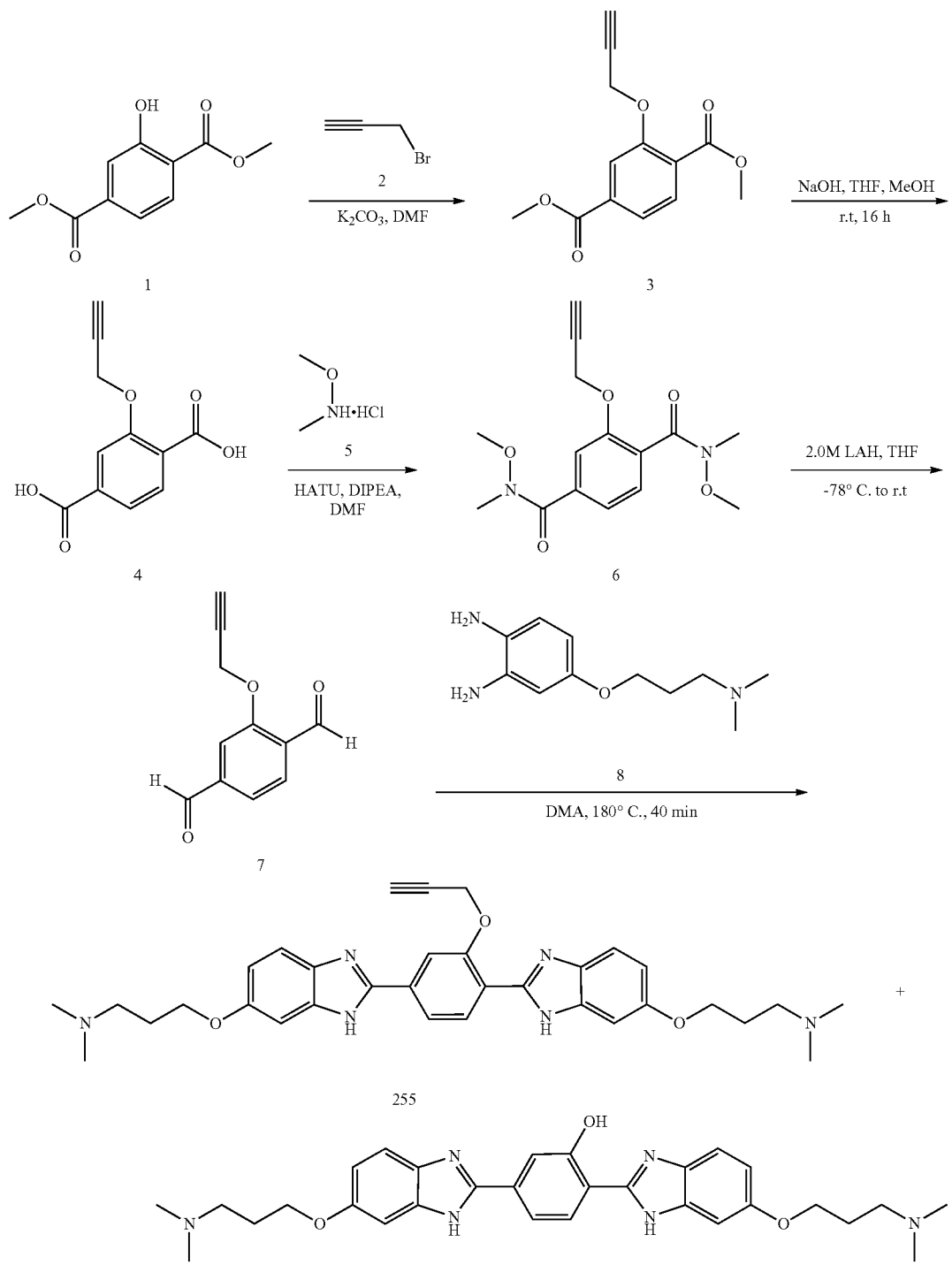

extracts were washed with brine (50 mL), dried over anhydrous $Na_2SO_4$, filtered and concentrated under vacuum to obtain the crude product. The product was purified by silica gel chromatography using $CH_3OH:CH_2Cl_2$ (1:9). The fractions containing the product were combined and concentrated under vacuum to obtain dimethyl 2-(prop-2-yn-1-yloxy)terephthalate Synthesis of 2-(prop-2-yn-1-yloxy)terephthalic acid: To a stirred solution of dimethyl 2-(prop-2-yn-1-yloxy)terephthalate (0.70 g, 2.82 mmol) in THF (10.0 mL), $H_2O$ (6.00 mL), and MeOH (3.00 mL), was added NaOH (0.56 g, 14.10 mmol), at r.t and the reaction mixture was heated at 90° C. for 2 h. The reaction mixture was concentrated under reduced pressure to remove THF, and the remaining contents were acidified to pH 2 using 2N aqueous HCl, whereupon a brown solid precipitated. The solid was filtered under vacuum, washed with water (10 mL), and dried under vacuum to obtain 2-(prop-2-yn-1-yloxy)terephthalic acid. The crude product was directly used in the next step.

Synthesis of N1,N4-dimethoxy-N1,N4-dimethyl-2-(prop-2-yn-1-yloxy)terephthalamide: To a suspension of 2-(prop-2-yn-1-yloxy)terephthalic acid (0.50 g, 2.27 mmol, crude) in DMF (10.0 mL), at 0° C. under $N_2$ atmosphere, was added HATU (2.16 g, 5.68 mmol), DIPEA (1.47 g, 11.3 mmol) and N,O-dimethylhydroxylamine hydrochloride (0.35 g, 5.68 mmol), and the reaction mixture was stirred at r.t for 2 h. The reaction mixture was poured on to ice cold water, and the aqueous phase was extracted with EtOAc (2×50 mL). The combined EtOAc extracts were washed with brine (50 mL), dried over anhydrous $Na_2SO_4$, filtered and concentrated under vacuum to obtain the crude product. The product was purified by silica gel chromatography using EtOAC:hexanes (3:7). The fractions containing the product were combined and concentrated under vacuum to obtain N1,N4-dimethoxy-N1,N4-dimethyl-2-(prop-2-yn-1-yloxy)terephthalamide Synthesis of 2-(prop-2-yn-1-yloxy)terephthalaldehyde: To a solution of N1,N4-dimethoxy-N1,N4-dimethyl-2-(prop-2-yn-1-yloxy)terephthalamide (0.35 g, 1.14 mmol) in THF (40.0 mL), under argon atmosphere at −78° C., was added $LiAlH_4$ (2.0 M in THF, 0.26 g, 6.86 mmol) in a dropwise manner over a period of 10 min. The reaction mixture was allowed to stir at r.t for 2 h. The reaction mixture was cooled to 0° C. and quenched with satd. aqueous $Na_2SO_4$ solution, whereupon white solids precipitated. The precipitated solids were filtered under vacuum and washed with 10% MeOH in DCM (2×50 mL). The organic layer was washed with brine (20 mL), dried over anhydrous $Na_2SO_4$, filtered and concentrated under reduced pressure to obtain the crude product. The product was purified by silica gel chromatography using EtOAC:hexanes (2:8). The fractions containing the product were combined and concentrated under vacuum to obtain 2-(prop-2-yn-1-yloxy)terephthalaldehyde Synthesis of 3,3'-((2,2'-(2-(prop-2-yn-1-yloxy)-1,4-phenylene)bis(1H-benzo[d]imidazole-6,2-diyl))bis(oxy))bis(N,N-dimethylpropan-1-amine) (255) and 2,5-bis(6-(3-(dimethylamino)propoxy)-1H-benzo[d]imidazol-2-yl)phenol (256): In a microwave vial, a mixture of 2-(prop-2-yn-1-yloxy)terephthalaldehyde (0.13 g, 0.69 mmol), 4-(3-(dimethylamino)propoxy)benzene-1,2-diamine (0.29 g, 1.38 mmol) and $Na_2S_2O_5$ (0.13 g, 0.69 mmol) in DMA (3.00 mL) was heated at 170° C. for 40 min. The reaction mixture was cooled to r.t and the contents were slowly poured into water (50 mL) and stirred for 10 min, whereupon, a brown solid precipitated. The brown solid was filtered under vacuum and washed with water (2×50 mL), and dried to obtain the crude product. The product was purified and separated by mass triggered HPLC. The fractions containing only the pure product were combined for concentration to obtain the title compounds. 255:

MS (ESI): m/z=567 $[M+H]^+$. 256: MS (ESI): m/z=529 $[M+H]^+$.

Compound 260 was prepared in the same manner as compound 255. MS (ESI): m/z=631 $[M+H]^+$.

Example 169

Synthesis of 3,3'-((2,2'-(2-chloro-1,4-phenylene)bis(1H-benzo[d]imidazole-6,2-diyl))bis(oxy))bis(N,N-dimethylpropan-1-amine) (Compound 257)

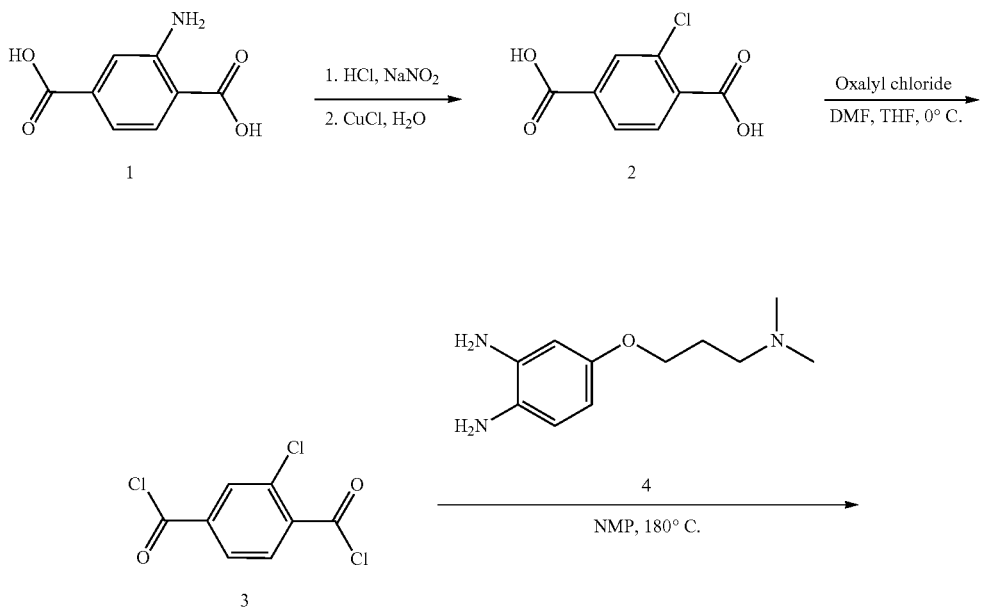

-continued

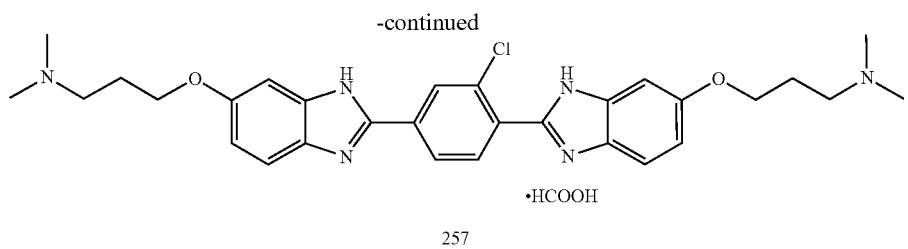

257

Synthesis of 2-chloroterephthalic acid: To a stirred solution of 2-aminoterephthalic acid (0.50 g, 2.76 mmol) in H$_2$O (5.00 mL) and Conc. HCl (1.50 mL) at 0° C., was added a solution of sodium nitrite (0.38 g, 5.52 mmol) in water (3.0 mL) in a drop wise manner over 10 min. After complete addition, the reaction mixture was stirred for 1 h. In another RB flask, Cu(I)Cl (1.21 g, 12.1 mmol) in Conc. HCl (8.00 mL) was cooled to 0° C. and set for slow stirring. The above solution of diazonium chloride was added portion wise over a period of 10 min. After complete addition, the reaction mixture was stirred at r.t for 3 h. The reaction mixture was poured on to cold water (50.0 mL), whereupon a pale yellow solid precipitated. The solid was filtered under vacuum, washed with water (20.0 mL), dried to obtain 2-chloroterephthalic acid Synthesis of 2-chloroterephthaloyl dichloride: To a solution of 2-chloroterephthalic acid (0.20 g, 0.97 mmol) in dry THF (5.00 ml), at 0° C., was added oxalyl chloride (1.00 mL) followed with a catalytic amount of DMF (0.01 mL) and the reaction mixture was stirred for 1 h. The reaction mixture was concentrated under reduced pressure at −35° C., and dried under vacuum to obtain 2-chloroterephthaloyl dichloride. The crude product was directly used in the next step.

Synthesis of 3,3'-((2,2'-(2-chloro-1,4-phenylene)bis(1H-benzo[d]imidazole-6,2-diyl))bis(oxy))bis(N,N-dimethyl-propan-1-amine): A mixture of 2-chloroterephthaloyl dichloride (0.23 g, 0.96 mmol) and 4-(3-(dimethylamino)propoxy)benzene-1,2-diamine (0.40 g, 1.93 mmol) in NMP (5.00 mL), was stirred at r.t for 16 h, and stirred for an additional 3 h at 180° C. The reaction mixture was cooled to r.t, and poured on to ice cold water (25.0 mL), whereupon the product precipitated. The obtained solid was filtered under vacuum, and washed with water (10.0 mL), and dried under vacuum to obtain the crude product. The crude was purified by prep-HPLC. The fractions contain only pure product was concentrated under reduced pressure to obtain the title compound. MS (ESI) m/z 547 [M+H]$^+$.

Example 170

Synthesis of 3,3'-((2,2'-(2-(2-methoxyethoxy)-1,4-phenylene)bis(1H-benzo[d]imidazole-6,2-diyl))bis(oxy))bis(N,N-dimethylpropan-1-amine)(Compound 258)

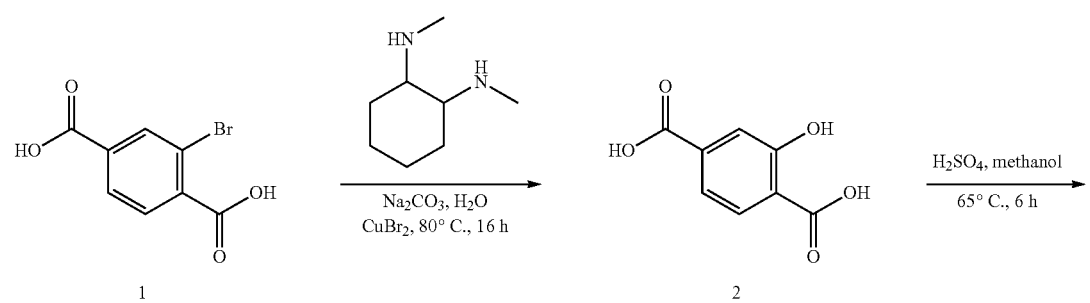

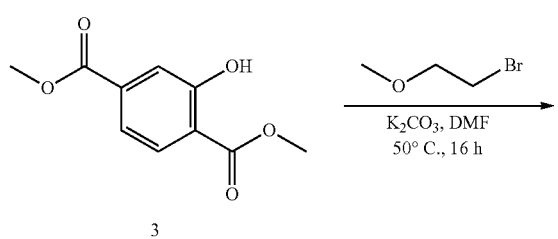

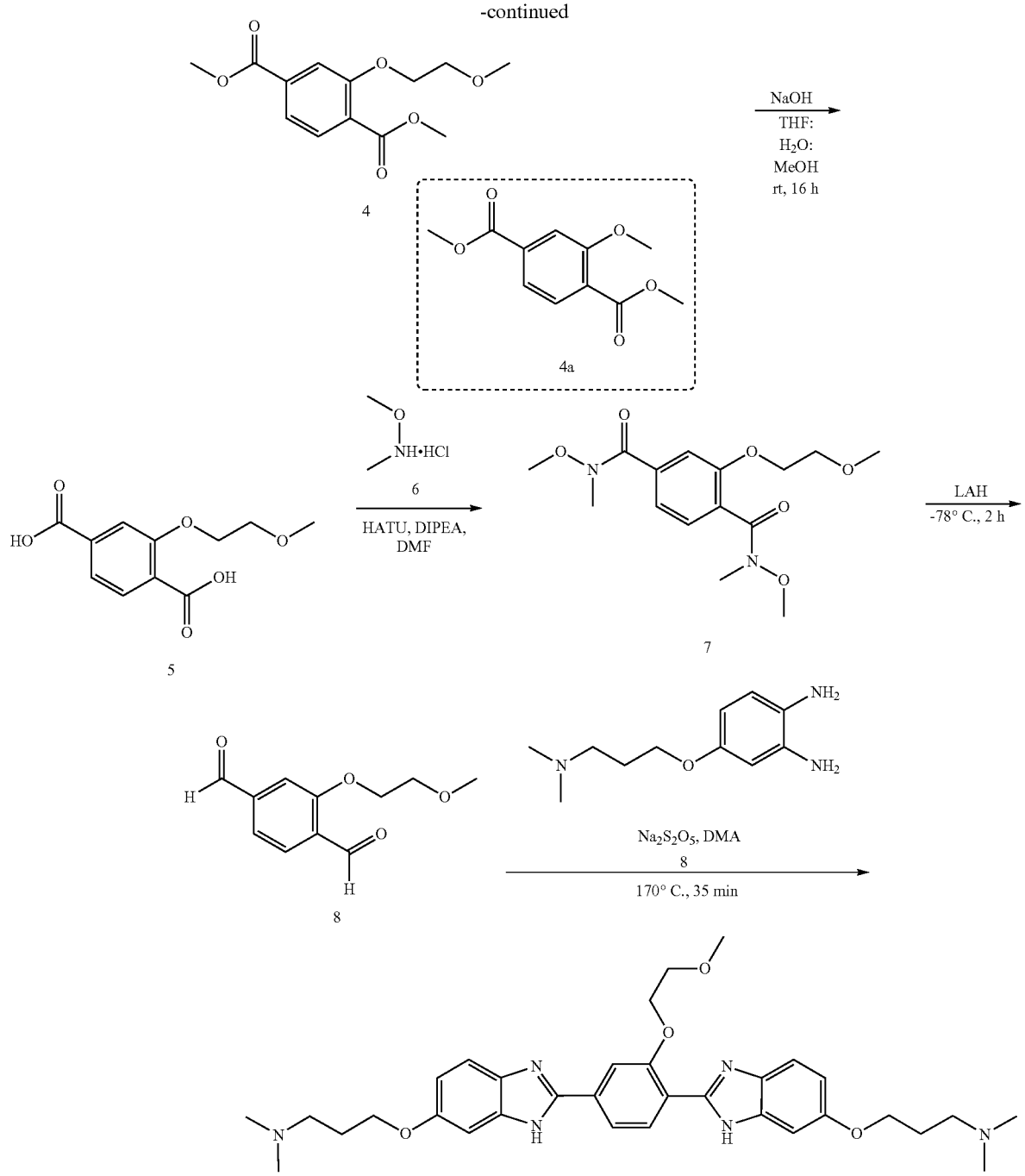

258

Synthesis of 2-hydroxyterephthalic acid: To a suspension of 2-bromoterephthalic acid (25.0 g, 102 mmol) in water (120 mL) at r.t under $N_2$ atmosphere, was added $Na_2CO_3$ (21.6 g, 204 mmol) and the reaction mixture was heated at 80° C. for 1 h. After 1 h, a solution of N1,N2-dimethylcyclohexane-1,2-diamine (0.29 g, 2.04 mmol) and copper(II) bromide (0.22 g, 1.02 mmol) in water (10.0 mL) was added to the above reaction mixture, and the mixture was heated at 80° C. for 16 h. The reaction mixture was cooled to r.t. and poured onto 2N aqueous HCl (20.0 mL) and stirred for 15 min, whereupon an off-white solid precipitated. The off white solid was collected by filtration under vacuum and washed with water (2×100 mL) to get 2-hydroxyterephthalic acid.

Synthesis of dimethyl 2-hydroxyterephthalate: To a solution of 2-hydroxyterephthalic acid (14.0 g, 77.0 mmol) in MeOH (100 mL) at 0° C., was added conc.$H_2SO_4$ (15.0 mL) and the reaction mixture was heated to reflux for 5 h. The reaction mixture was cooled to r.t and neutralized with satd. aqueous $NaHCO_3$ (50.0 mL) and extracted with EtOAc (3×100 mL). The combined organic extracts were washed with brine (100 mL), dried (Na$_2$SO$_4$), filtered and concentrated under vacuum to obtain dimethyl 2-hydroxyterephthalate.

Synthesis of dimethyl 2-(2-methoxyethoxy)terephthalate: To a stirred solution of dimethyl 2-hydroxyterephthalate (1.30 g, 3.57 mmol) in DMF (8.00 mL) was added K$_2$OC$_3$ (0.98 g, 7.14 mmol) followed with 1-bromo-2-methoxyethane (8.69 g, 5.35 mmol) and the reaction mixture was heated at 40° C. for 16 h. The reaction mixture was cooled to r.t and the contents were poured on to ice cold water, and the aqueous phase was extracted with EtOAc (2×100 mL). The combined EtOAc extracts were washed with brine (50 mL), dried over anhydrous Na$_2$SO$_4$, filtered and concentrated under vacuum to obtain the crude product. The product was purified by silica gel chromatography using EtOAC:hexane (3:7). The fractions containing the product were combined and concentrated under vacuum to obtain dimethyl 2-(2-methoxyethoxy)terephthalate.

Synthesis 2-(2-methoxyethoxy)terephthalic acid: To a stirred solution of dimethyl 2-(2-methoxyethoxy)terephthalate (0.40 g, 1.49 mmol) in THF (8.00 mL), H$_2$O (5.00 mL), and MeOH (3.00 mL), was added NaOH (0.29 g, 7.46 mmol), at r.t and the reaction mixture was stirred at r.t for 12 h. The reaction mixture was concentrated under reduced pressure to obtain a residue. The residue was diluted with H$_2$O (10.0 mL) and acidified to pH~2, using 2N aq.HCl, whereupon a brown solid precipitated. The precipitate was filtered under vacuum and washed with water (10 mL), and dried under vacuum to obtain 2-(2-methoxyethoxy)terephthalic acid. The crude product was directly used in the next step.

Synthesis of N1,N4-dimethoxy-2-(2-methoxyethoxy)-N1,N4-dimethylterephthalamide: To a suspension of 2-(2-methoxyethoxy)terephthalic acid (0.33 g, 1.34 mmol) in DMF (10.0 mL) at 0° C. under N$_2$ atmosphere, was added HATU (2.06 g, 5.52 mmol), DIPEA (1.07 g, 8.24 mmol) and N,O-dimethylhydroxylamine hydrochloride (0.40 g, 5.52 mmol), and the reaction mixture was stirred at r.t for 2 h. The reaction mixture was poured on to ice cold water, and the aqueous phase was extracted with EtOAc (2×100 mL). The combined EtOAc extracts were washed with brine (50 mL), dried over anhydrous Na$_2$SO$_4$, filtered and concentrated under vacuum to obtain the crude product. The product was purified by silica gel chromatography using EtOAC:hexane (3:7). The fractions containing the product were combined and concentrated under vacuum to obtain N1,N4-dimethoxy-2-(2-methoxyethoxy)-N1,N4-dimethylterephthalamide.

Synthesis of 2-(2-methoxyethoxy)terephthalaldehyde: To a solution of N1,N4-dimethoxy-2-(2-methoxyethoxy)-N1,N4-dimethylterephthalamide (0.40 g, 1.26 mmol) in THF (20.0 mL) under argon atmosphere, was added LiAlH$_4$ (2.0 M in THF, 1.80 mL, 3.68 mmol) at −78° C. in a dropwise manner over a period of 10 min. The reaction mixture was allowed to gradually reach r. t and stirred for 1 h. The reaction mixture was cooled to 0° C. and quenched with saturated aqueous Na$_2$SO$_4$ solution. The precipitated solids were filtered under vacuum, washed with 10% MeOH in CH$_2$Cl$_2$ (100 mL). The organic layer was washed with brine (20 mL) and concentrated under reduced pressure to obtain the crude product. The product was purified by silica gel chromatography using EtOAC:hexane (2:8). The fractions containing the product were combined and concentrated under vacuum to obtain 2-(2-methoxyethoxy)terephthalaldehyde.

Synthesis of 3,3'-((2,2'-(2-(2-methoxyethoxy)-1,4-phenylene)bis(1H-benzo[d]imidazole-6,2-diyl))bis(oxy))bis(N,N-dimethylpropan-1-amine)(258): In a microwave vial, a mixture of 2-(2-methoxyethoxy)terephthalaldehyde (0.10 g, 0.48 mmol), 4-(3-(dimethylamino)propoxy)benzene-1,2-diamine (0.20 g, 0.96 mmol) and Na$_2$S$_2$O$_5$ (0.83 g, 0.96 mmol) in DMA (3.00 mL) was heated at 170° C. for 40 min. The reaction mixture was cooled to r.t and the contents were slowly poured into water (50 mL) and stirred for 10 min, whereupon, a brown solid precipitated. The brown solid was filtered under vacuum and washed with water (2×50 mL), and dried to obtain the crude product. The product was purified by mass triggered HPLC. The fractions containing only the pure product were combined for concentration to the title compound. MS (ESI): m/z=587 [M+H]$^+$.

Example 171

Synthesis of 2-(2,5-bis(6-(3-(dimethylamino)propoxy)-1H-benzo[d]imidazol-2-yl)phenoxy)ethanol (Compound 259, 261 and 466

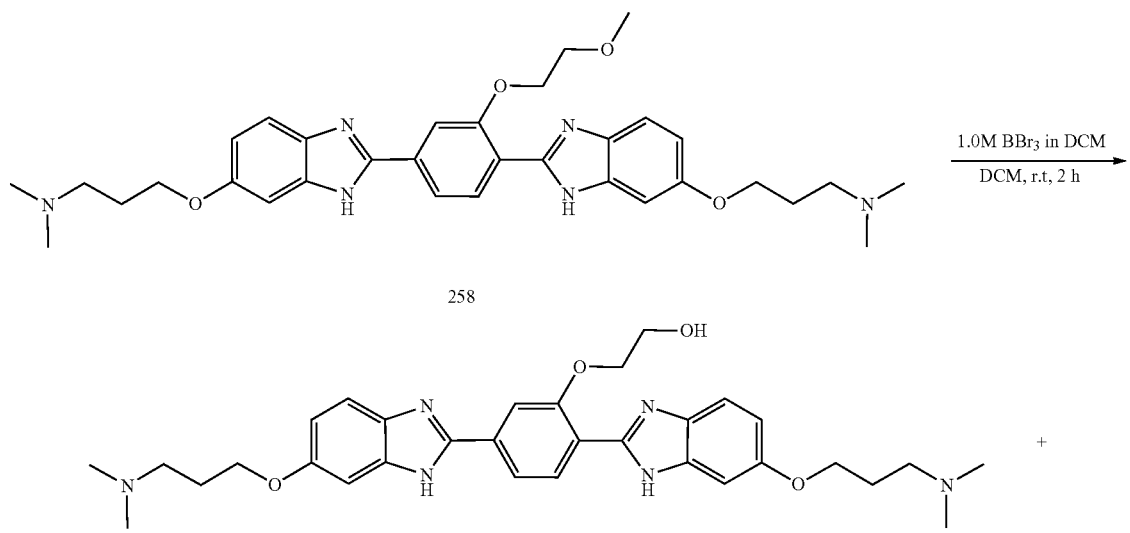

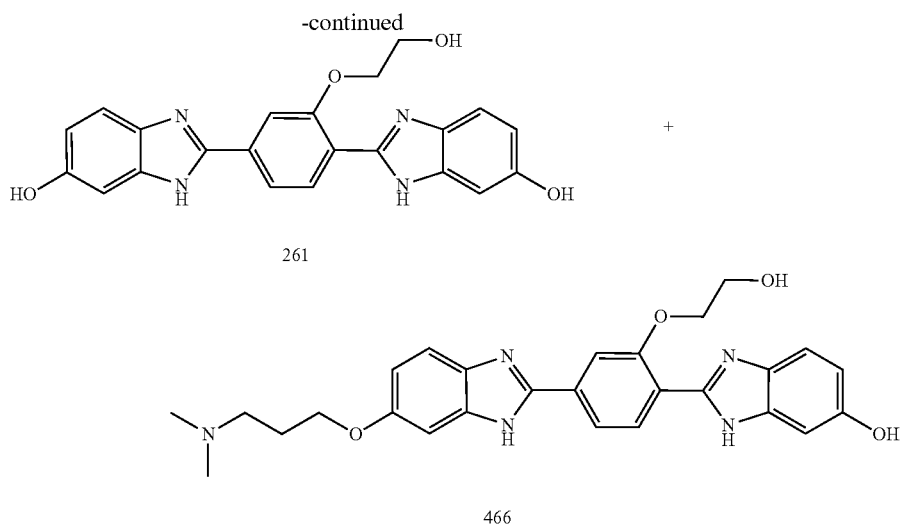

261

466

To a solution of 3,3'-((2,2'-(2-(2-methoxyethoxy)-1,4-phenylene)bis(1H-benzo[d]imidazole-6,2-diyl))bis(oxy))bis(N,N-dimethylpropan-1-amine (200 mg, 0.34 mmol) in CH$_2$Cl$_2$ (15.0 mL) at 0° C. under argon atmosphere, was added BBr$_3$ (2.0 M in CH$_2$Cl$_2$, 1.20 mL, 1.02 mmol) in a dropwise manner over a period of 10 min. After complete addition, the mixture was stirred at r.t for 1 h, neutralized with methanol (5.0 mL), and concentrated under reduced pressure to obtain the crude product. The product was purified by mass triggered HPLC. Fractions containing only the pure product were combined for concentration to obtain the title compounds. 259: MS (ESI): m/z=573 [M+H]$^+$. 261: MS (ESI): m/z=403 [M+H]$^+$. Compound 466: MS (ESI): m/z=488 [M+H]$^+$.

Example 172

Synthesis of 3-((2-(4-(6-(3-(dimethylamino)propoxy)-1H-benzo[d]imidazol-2-yl)-2-methoxy-5-(2-methoxyethoxy)phenyl)-1H-benzo[d]imidazol-5-yl)oxy)-N,N-dimethylpropan-1-amine (Compound 262)

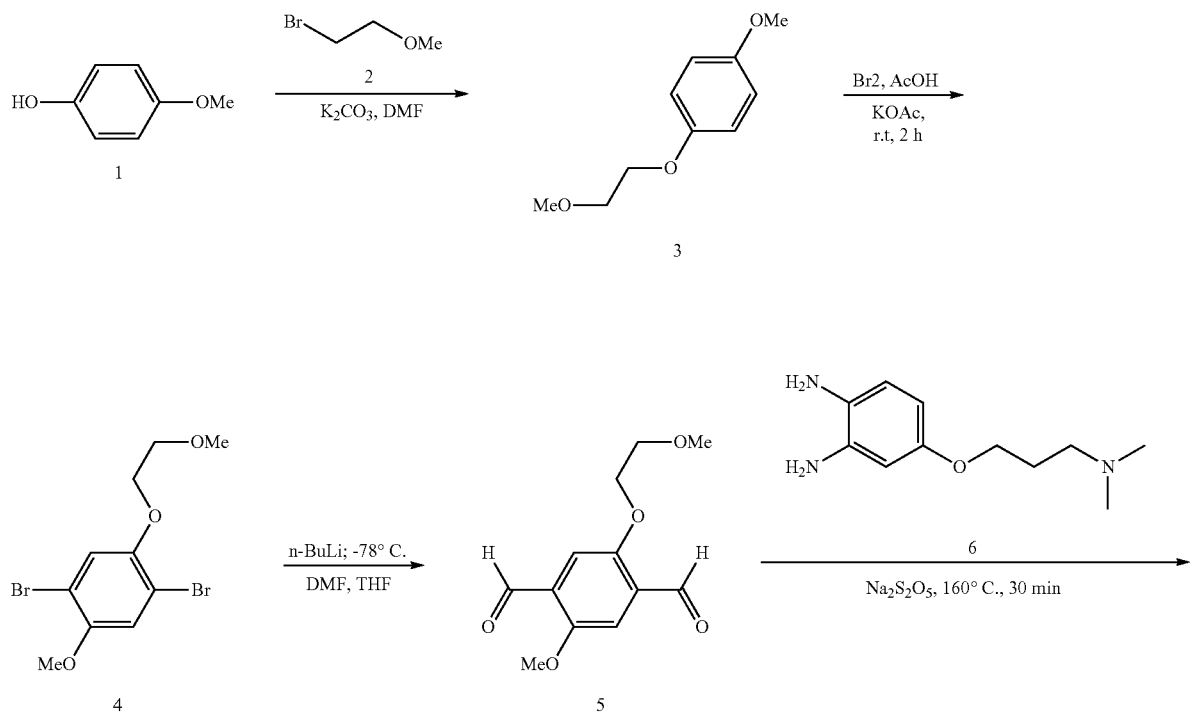

-continued

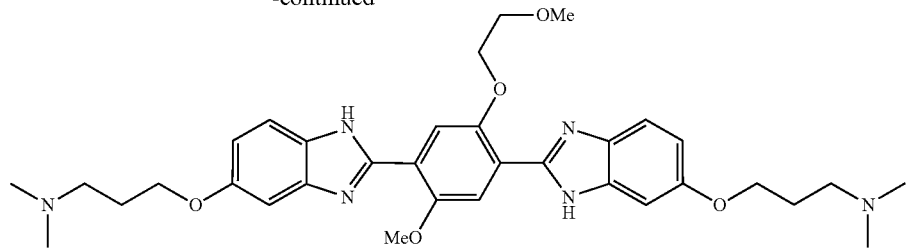

262

Synthesis of 1-methoxy-4-(2-methoxyethoxy)benzene: To a stirred solution of 4-methoxyphenol (1.50 g, 12.1 mmol) in anhydrous DMF (15.0 mL) at r.t under $N_2$ atmosphere, was added $K_2OC_3$ (3.34 g, 24.2 mmol) followed with 1-bromo-2-methoxyethane (2.01 g, 14.5 mmol) and the reaction mixture was stirred at 80° C. for 12 h. The reaction mixture was cooled to r.t and the contents were poured on to ice cold water (50 mL), and extracted with EtOAc (2×50 mL). The combined EtOAc extracts were washed with brine (50 mL), dried over anhydrous $Na_2SO_4$, filtered and concentrated under vacuum to obtain the crude product. The product was purified by silica gel chromatography using EtOAc:hexane (3:7). The fractions containing the product were combined and concentrated under vacuum to obtain 1-methoxy-4-(2-methoxyethoxy)benzene.

Synthesis of 1,4-dibromo-2-methoxy-5-(2-methoxyethoxy)benzene: To a stirred solution of 1-methoxy-4-(2-methoxyethoxy)benzene (1.20 g, 6.59 mmol) in AcOH (10.0 mL), was added a solution of bromine (2.10 g, 13.2 mmol) in AcOH (2.00 mL), at 10° C. and the reaction mixture stirred at the same temperature for 2 h. The reaction mixture was poured onto ice, whereupon, the product precipitated. The precipitated product was filtered under vacuum, washed with water (20.0 mL), and dried to obtain the crude product. The crude product was purified by silica gel chromatography using EtOAc:hexane (2:8). Fractions containing only the pure product were combined for concentration to obtain 1,4-dibromo-2-methoxy-5-(2-methoxyethoxy)benzene.

Synthesis of 2-methoxy-5-(2-methoxyethoxy)terephthalaldehyde: To a suspension of 1,4-dibromo-2-methoxy-5-(2-methoxyethoxy)benzene (0.50 g, 1.47 mmol) in THF (20.0 mL), at −78° C. under $N_2$ atmosphere, was added n-BuLi (2.0 M in Hexanes, 3.67 mL, 7.35 mmol), in a drop wise manner over a period of 10 min, and the reaction mixture was stirred at −78° C. for 2 h. Anhydrous DMF (0.55 mL, 7.35 mmol) was added to the above mixture at −78° C. and the mixture was gradually allowed to reach r.t and stirred for an additional 1 h. The reaction mixture was quenched with saturated aqueous $NH_4Cl$ solution, and the aqueous phase was extracted with EtOAc (2×50 mL). The combined EtOAc extracts were washed with brine (30 mL), dried over anhydrous $Na_2SO_4$, filtered and concentrated under vacuum to obtain the crude product. The product was purified by silica gel chromatography using EtOAC:hexanes (6:4). The fractions containing the product were combined and concentrated under vacuum to obtain 2-methoxy-5-(2-methoxyethoxy)terephthalaldehyde.

Synthesis of 3-((2-(4-(6-(3-(dimethylamino)propoxy)-1H-benzo[d]imidazol-2-yl)-2-methoxy-5-(2-methoxyethoxy)phenyl)-1H-benzo[d]imidazol-5-yl)oxy)-N,N-dimethylpropan-1-amine (262): In a microwave vial, a mixture of 2-methoxy-5-(2-methoxyethoxy)terephthalaldehyde (0.15 g, 0.63 mmol), 4-(3-(dimethylamino)propoxy)benzene-1,2-diamine (0.26 g, 1.26 mmol) and $Na_2S_2O_5$ (0.24 g, 1.26 mmol) in anhydrous DMA (5.00 mL) was heated at 170° C. for 40 min. The reaction mixture was cooled to r.t and the contents were slowly poured into water (50 mL) and stirred for 10 min, whereupon, a brown solid precipitated. The brown solid was filtered under vacuum and washed with water (2×20 mL), and dried to obtain the crude product. The product was purified by mass triggered HPLC. The fractions containing only the pure product were combined for concentration to obtain the title compound. MS (ESI): m/z=617 $[M+H]^+$.

Example 173

Synthesis of 3,3'-((2,2'-(2-(2-(dimethylamino)ethoxy)-1,4-phenylene)bis(1H-benzo[d]imidazole-6,2-diyl))bis(oxy))bis(N,N-dimethylpropan-1-amine) (Compound 263)

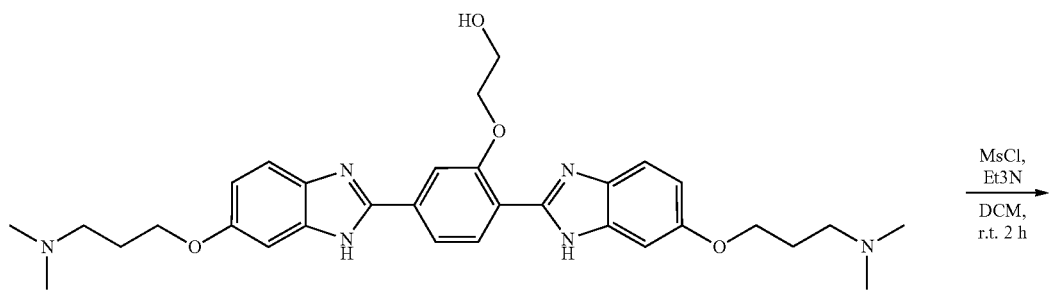

259

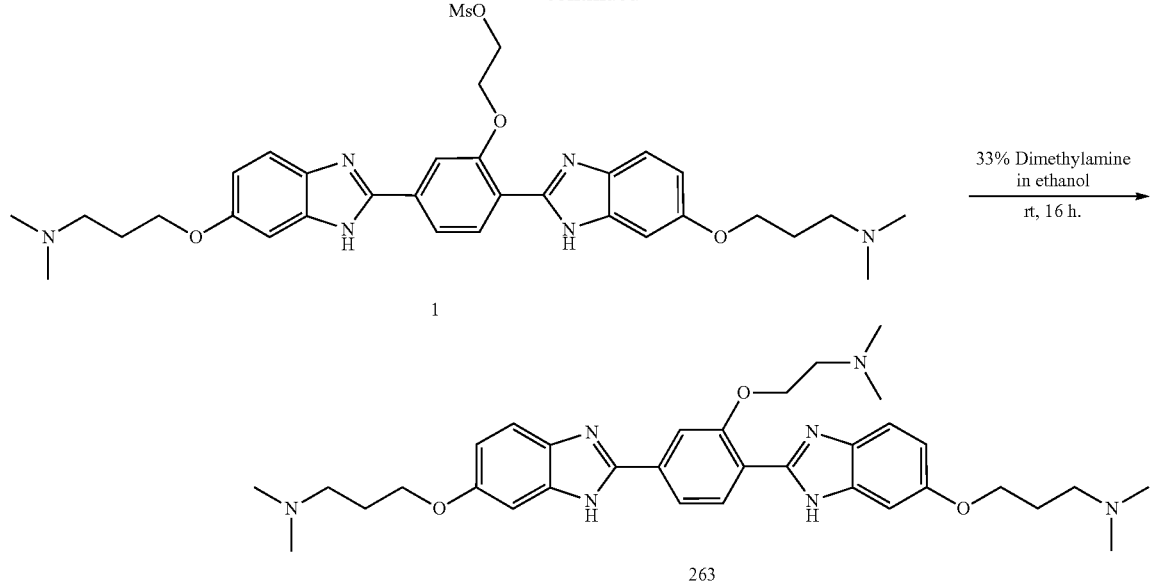

Synthesis of 2-(2,5-bis(6-(3-(dimethylamino)propoxy)-1H-benzo[d]imidazol-2-yl)phenoxy)ethyl methanesulfonate: To a stirred solution of Compound 259 (2-(2,5-bis(6-(3-(dimethylamino)propoxy)-1H-benzo[d]imidazol-2-yl)phenoxy)ethanol) (100 mg, 0.17 mmol) in anhydrous $CH_2Cl_2$ (10.0 mL), at 0° C. under $N_2$ atmosphere, was added $Et_3N$ (0.13 mL, 0.87 mmol) followed with methane sulfonyl chloride (30.0 mg, 0.26 mmol) in a dropwise manner. After complete addition, the reaction mixture was stirred at r.t for 2 h. The reaction mixture was concentrated under vacuum to obtain 2-(2,5-bis(6-(3-(dimethylamino)propoxy)-1H-benzo[d]imidazol-2-yl)phenoxy)ethyl methanesulfonate. The crude product was used directly in the next step.

Synthesis of 3,3'-((2,2'-(2-(2-(dimethylamino)ethoxy)-1,4-phenylene)bis(1H-benzo[d]imidazole-6,2-diyl))bis(oxy))bis(N,N-dimethylpropan-1-amine) (263): In a sealed tube, $Me_2NH$ (33% in EtOH, 10.0 mL) was added to 2-(2,5-bis(6-(3-(dimethylamino)propoxy)-1H-benzo[d]imidazol-2-yl)phenoxy)ethyl methanesulfonate (110 mg, 0.12 mmol), and the reaction mixture was stirred for at r.t for 16 h. The reaction mixture was concentrated under vacuum to obtain the crude product. The product was purified by mass triggered HPLC. The fractions containing only the pure product were combined for concentration to obtain the title compound. MS (ESI): m/z=600 $[M+H]^+$.

Example 174

Synthesis of 2-(4-(6-(3-(dimethylamino)propoxy)-1H-benzo[d]imidazol-2-yl)phenyl)-N-(2-guanidinoethyl)-1H-benzo[d]imidazole-6-carboxamide (Compound 264)

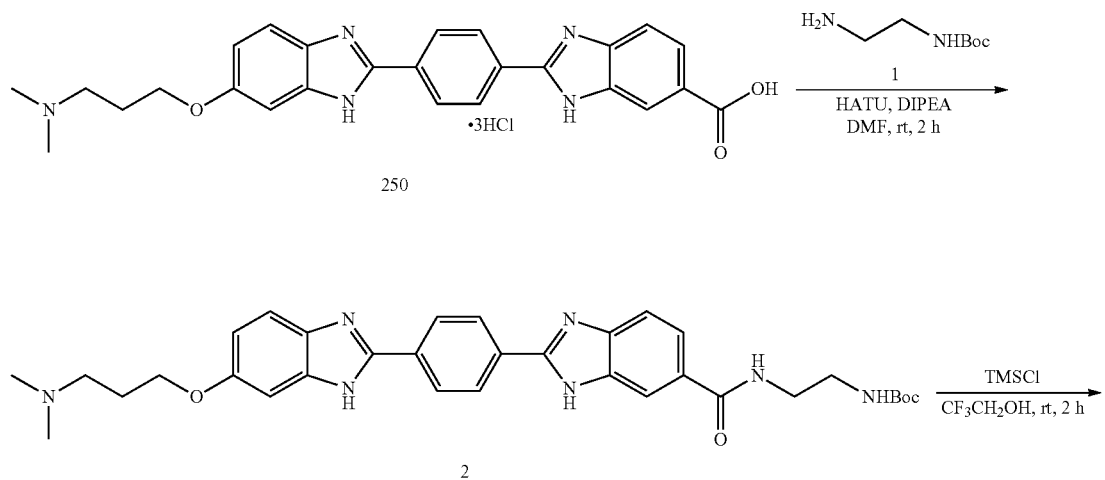

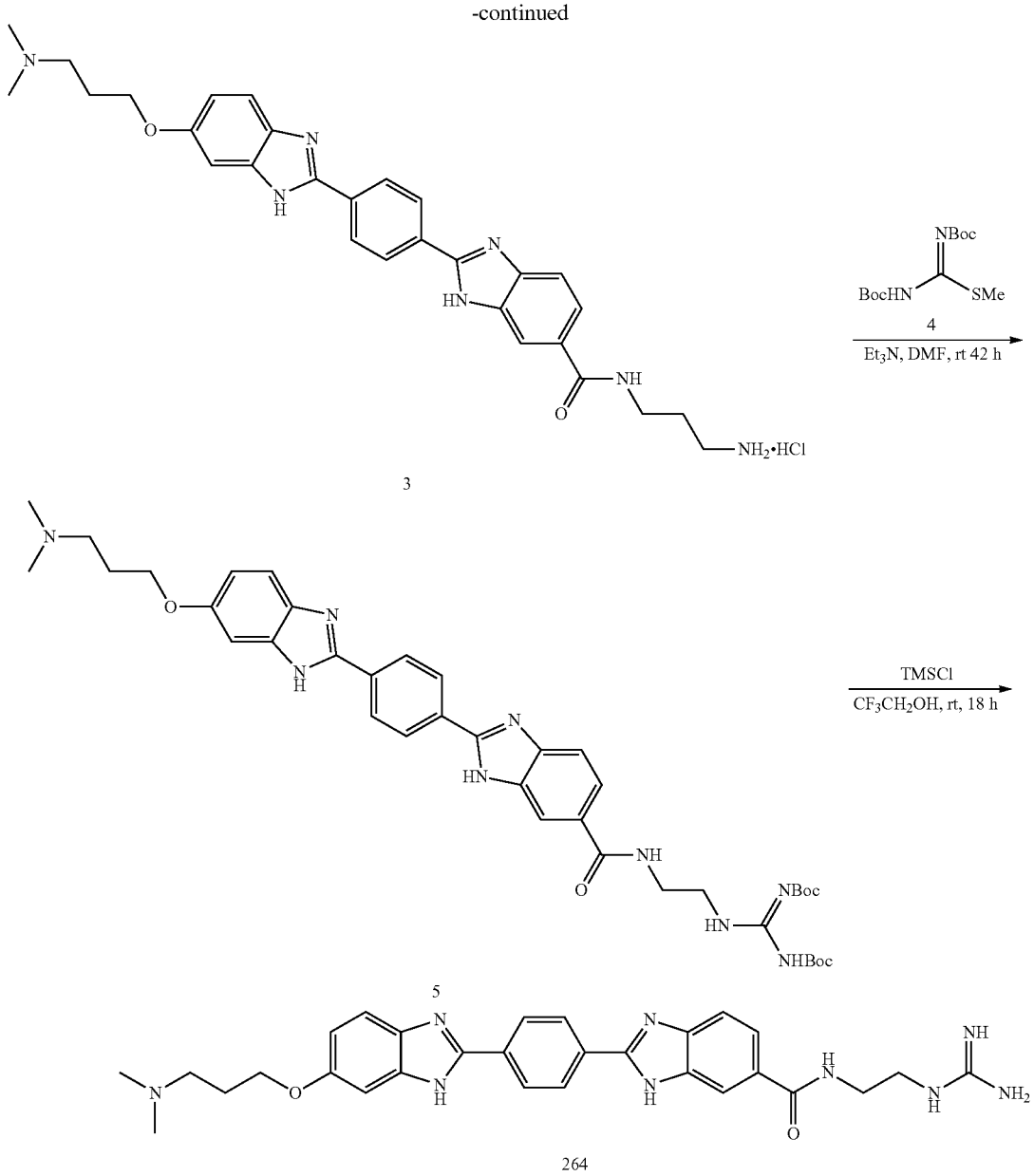

Synthesis of tert-butyl (2-(2-(4-(6-(3-(dimethylamino)propoxy)-1H-benzo[d]imidazol-2-yl)phenyl)-1H-benzo[d]imidazole-6-carboxamido)ethyl)carbamate: To a stirred solution of 2-(4-(6-(3-(dimethylamino)propoxy)-1H-benzo[d]imidazol-2-yl)phenyl)-1H-benzo[d]imidazole-6-carboxylic acid.3HCl (1.00 g, 1.78 mmol) in anhydrous DMF (20.0 mL), at 0° C. under N₂ atmosphere, was added HATU (0.81 g, 2.13 mmol), DIPEA (1.55 mL, 8.88 mmol) and tert-butyl (2-aminoethyl)carbamate (0.34 g, 2.13 mmol), and the reaction mixture was stirred at r.t for 2 h. The reaction mixture was concentrated under reduced pressure to remove DMF, and water (100 mL) was added to the residue, whereupon, a light yellow solid precipitated. The solids were filtered under vacuum, washed with EtOAc (100 mL), and dried to obtain tert-butyl (2-(2-(4-(6-(3-(dimethylamino)propoxy)-1H-benzo[d]imidazol-2-yl)phenyl)-1H-benzo[d]imidazole-6-carboxamido)ethyl)carbamate.

Synthesis of N-(2-aminoethyl)-2-(4-(6-(3-(dimethylamino)propoxy)-1H-benzo[d]imidazol-2-yl)phenyl)-1H-benzo[d]imidazole-6-carboxamide hydrochloride: To a stirred solution of tert-butyl (2-(2-(4-(6-(3-(dimethylamino)propoxy)-1H-benzo[d]imidazol-2-yl)phenyl)-1H-benzo[d]imidazole-6-carboxamido)ethyl)carbamate (800 mg, 1.34 mmol) in trifluoroethanol (16.0 mL) was added TMS-Cl (1.60 mL, 12.5 mmol), at rt and the mixture was stirred for 2 h. The reaction mixture was concentrated under reduced pressure to obtain crude product. The product was purified by trituration with EtOAc (50 mL), filtered under vacuum, washed with EtOAc (15 mL) and dried to obtain N-(2-aminoethyl)-2-(4-(6-(3-(dimethylamino)propoxy)-1H-benzo[d]imidazol-2-yl)phenyl)-1H-benzo[d]imidazole-6-carboxamide hydrochloride.4HCl.

Synthesis of compound 5: To a stirred solution of N-(2-aminoethyl)-2-(4-(6-(3-(dimethylamino)propoxy)-1H- benzo[d]imidazol-2-yl)phenyl)-1H-benzo[d]imidazole-6-carboxamide hydrochloride (750 mg, 1.17 mmol) in anhydrous DMF (20.0 mL), at 0° C. under $N_2$ atmosphere, was added compound 4 (408 mg, 1.40 mmol), DIPEA (0.81 mL, 5.85 mmol), and the reaction mixture was stirred at r.t for 42 h. The reaction mixture was concentrated under reduced pressure to obtain the crude product. The product was purified by silica gel chromatography using $CH_3OH$:$CH_2Cl_2$ (2.5:7.5). The fractions containing the product were combined for concentration to obtain compound 5.

Synthesis of 2-(4-(6-(3-(dimethylamino)propoxy)-1H-benzo[d]imidazol-2-yl)phenyl)-N-(2-guanidinoethyl)-1H-benzo[d]imidazole-6-carboxamide dihydrochloride (264): To a stirred solution of compound 5 (340 mg, 0.46 mmol) in trifluoroethanol (30.0 mL) was added TMS-Cl (1.00 mL, 7.82 mmol), at rt and the mixture was stirred for 18 h. The reaction mixture was concentrated under reduced pressure to obtain crude product. The product was purified by mass triggered HPLC. The fractions containing only the pure product were combined for concentration to obtain the title compound. MS (ESI): m/z=540 [M+H]$^+$.

Example 175

Synthesis of 3,3'-((2,2'-(2-(2-azidoethoxy)-1,4-phenylene)bis(1H-benzo[d]imidazole-6,2-diyl))bis(oxy))bis(N,N-dimethylpropan-1-amine) (Compound 265) and 3,3'-(((2-(2-chloroethoxy)-1,4-phenylene)bis(1H-benzo[d]imidazole-2,6-diyl))bis(oxy))bis(N,N-dimethylpropan-1-amine) (Compound 267)

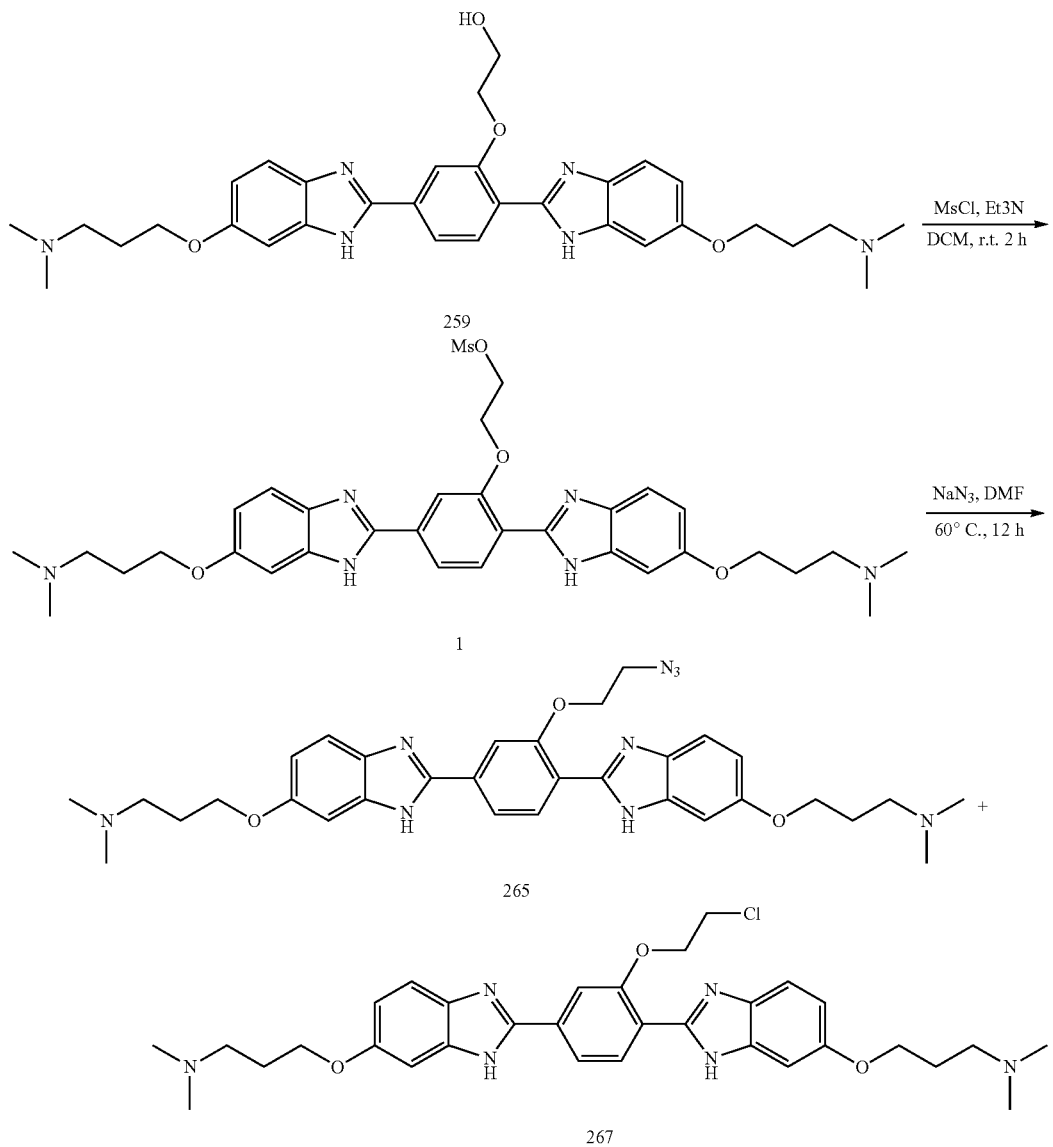

Synthesis of 2-(2,5-bis(6-(3-(dimethylamino)propoxy)-1H-benzo[d]imidazol-2-yl)phenoxy)ethyl methanesulfonate: To a stirred solution of Compound 259 (2-(2,5-bis(6-(3-(dimethylamino)propoxy)-1H-benzo[d]imidazol-2-yl)phenoxy)ethanol) (100 mg, 0.17 mmol) in anhydrous DCM (10.0 mL), at 0° C. under $N_2$ atmosphere, was added $Et_3N$ (0.13 mL, 0.87 mmol) followed with methane sulfonyl chloride (30.0 mg, 0.26 mmol) in a dropwise manner. After complete addition, the reaction mixture was stirred at r.t for 2 h. The reaction mixture was concentrated under vacuum to obtain 2-(2,5-bis(6-(3-(dimethylamino)propoxy)-1H-benzo[d]imidazol-2-yl)phenoxy)ethyl methanesulfonate. The crude product was used directly in the next step.

Synthesis of 3,3'-((2,2'-(2-(2-azidoethoxy)-1,4-phenylene)bis(1H-benzo[d]imidazole-6,2-diyl))bis(oxy))bis(N,N-dimethylpropan-1-amine) (265) and 3,3'-(((2-(2-chloroethoxy)-1,4-phenylene)bis(1H-benzo[d]imidazole-2,6-diyl))bis(oxy))bis(N,N-dimethylpropan-1-amine) (267): To a stirred solution of 3-((2-(4-(5-(3-(dimethylamino)propoxy)-1H-benzo[d]imidazol-2-yl)phenyl)-1H-benzo[d]imidazol-5-yl)oxy)propyl methane sulfonate (110 mg, 0.16 mmol) in anhydrous DMF (6 mL), at r.t under $N_2$ atmosphere, was added sodium azide (55 mg, 0.84 mmol), and the reaction mixture was stirred at 60° C. for 12 h. The reaction mixture was cooled to r.t and the contents were slowly poured into ice-cold water and stirred for 10 min, whereupon a solid precipitated. The solid was collected by filtration under vacuum, washed with water (10 mL) and dried to obtain the crude product. The product was purified and separated by mass triggered HPLC. The fractions containing only the pure product were combined for concentration to obtain the title compound. 265: MS (ESI): m/z=598 [M+H]$^+$. 267: MS (ESI): m/z=591 [M+H]$^+$.

Example 176

Synthesis of 2,5-bis(6-(3-(dimethylamino)propoxy)-1H-benzo[d]imidazol-2-yl)benzonitrile (Compound 268)

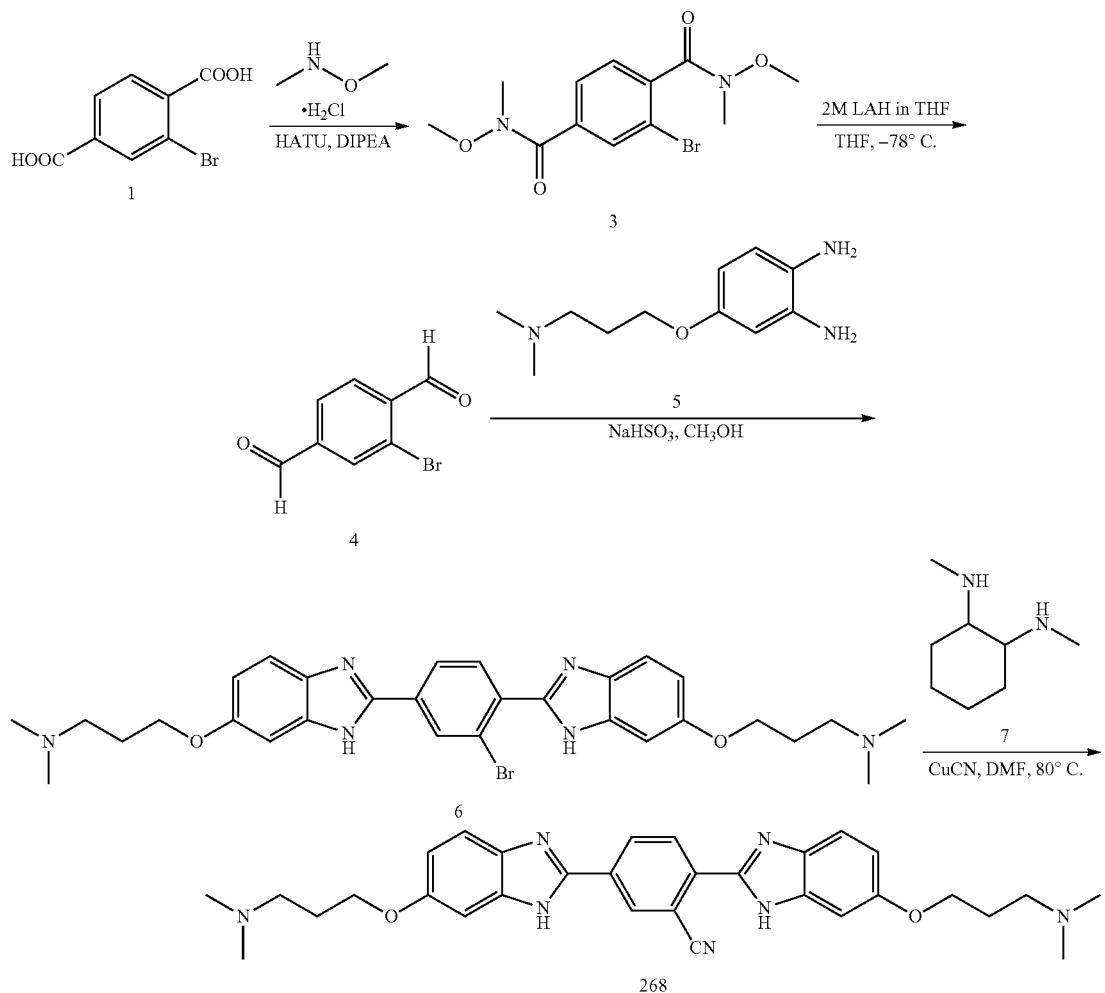

Synthesis of 2-bromo-N1,N4-dimethoxy-N1,N4-dimethylterephthalamide: To a stirred solution of 2-bromoterephthalic acid (3.00 g, 12.2 mmol) in DMF (50.0 mL), at 0° C. under $N_2$ atmosphere, was added HATU (13.9 g, 36.7 mmol), DIPEA (12.8 mL, 73.5 mmol) followed with N,O-dimethylhydroxylamine hydrochloride (2.99 g, 30.6 mmol), and the reaction mixture was stirred at r.t for 1 h. The reaction mixture was poured on to cold water (100 mL) and extracted with EtOAc (3×100 mL). The combined the organic extracts were washed with brine (100 mL), dried over anhydrous $Na_2SO_4$, filtered and concentrated under vacuum to obtain the crude product. The product was purified by silica gel chromatography using MeOH:$CH_2Cl_2$ (1:9). The fractions containing the product were combined and concentrated under vacuum to obtain 2-bromo-N1,N4-dimethoxy-N1,N4-dimethylterephthalamide Synthesis of 2-bromoterephthalaldehyde: To a solution of 2-bromo-N1,N4-dimethoxy-N1,N4-dimethylterephthalamide (2.50 g, 7.57 mmol) in dry THF (150 mL), at −78° C. under argon atmosphere, was added LiAlH$_4$ (2.0 M in THF, 11.3 mL, 22.7 mmol) in a dropwise manner over a period of 15 min. After complete addition, the reaction mixture was stirred at −78° C. for 1 h. The reaction mixture was quenched with saturated aqueous Na$_2$SO$_4$ solution (30.0 mL) and diluted with EtOAc (50 mL), and the mixture was gradually allowed to reach r.t and stirred for 20 min, whereupon a free flowing white solid precipitated. The mixture was filtered through a celite pad, and the pad was washed with EtOAc (2×50 mL). The combined filtrate was washed with brine (50 mL), dried over anhydrous Na$_2$SO$_4$, filtered and concentrated under vacuum to obtain the crude product. The product was purified by silica gel chromatography using EtOAc:Hexanes (4:6). The fractions containing the product were combined and concentrated under vacuum to obtain 2-bromoterephthalaldehyde.

Synthesis of 3,3'-((2,2'-(2-bromo-1,4-phenylene)bis(1H-benzo[d]imidazole-6,2-diyl))bis(oxy))bis(N,N-dimethylpropan-1-amine): To a stirred solution of 4-(3-(dimethylamino)propoxy)benzene-1,2-diamine (432 mg, 2.06 mmol) in MeOH (10 mL), at r.t under N$_2$ atmosphere, was added NaHSO$_3$ (293 mg, 2.82 mmol) followed with 2-bromoterephthalaldehyde (200 mg, 0.93 mmol), and the reaction mixture was stirred at 80° C. for 16 h. The reaction mixture was cooled to r.t and the contents were filtered through a celite pad under vacuum, and the pad was washed with MeOH (2×25 mL). The combined filtrate was concentrated under reduced pressure to obtain the crude product. The product was purified by silica gel chromatography using 5% NH$_4$OH in MeOH:CH$_2$Cl$_2$ (2:8). The fractions containing the product were combined and concentrated under vacuum to obtain 3,3'-((2,2'-(2-bromo-1,4-phenylene)bis(1H-benzo[d]imidazole-6,2-diyl))bis(oxy))bis(N,N-dimethylpropan-1-amine).

Synthesis of 2,5-bis(6-(3-(dimethylamino)propoxy)-1H-benzo[d]imidazol-2-yl)benzonitrile (268): To a stirred solution of 3,3'-((2,2'-(2-bromo-1,4-phenylene)bis(1H-benzo[d]imidazole-6,2-diyl))bis(oxy))bis(N,N-dimethylpropan-1-amine) (150 mg, 0.25 mmol), in DMF (10.0 mL), at r.t under N$_2$ atmosphere, were added Na$_2$CO$_3$ (53.8 mg, 0.50 mmol), CuCN (33.5 mg, 0.37 mmol) followed with N1,N2-dimethylcyclohexane-1,2-diamine (72.0 mg, 0.005) and the reaction mixture was stirred at 80° C. for 16 h. The reaction mixture was cooled to r.t and the contents were filtered through a celite bed under vacuum and the bed was washed with DMF (10 mL). The filtrate was concentrated under reduced pressure to get crude product. The product was purified by mass triggered prep-HPLC. The fractions containing only the pure product was concentrated under reduced pressure to obtain the title compound. MS (ESI): m/z=538 [M+H]$^+$.

Example 177

Synthesis of bis(2-(dimethylamino)ethyl) 2,2'-(2,5-dimethoxy-1,4-phenylene)bis(1H-benzo[d]imidazole-6-carboxylate) (Compound 269)

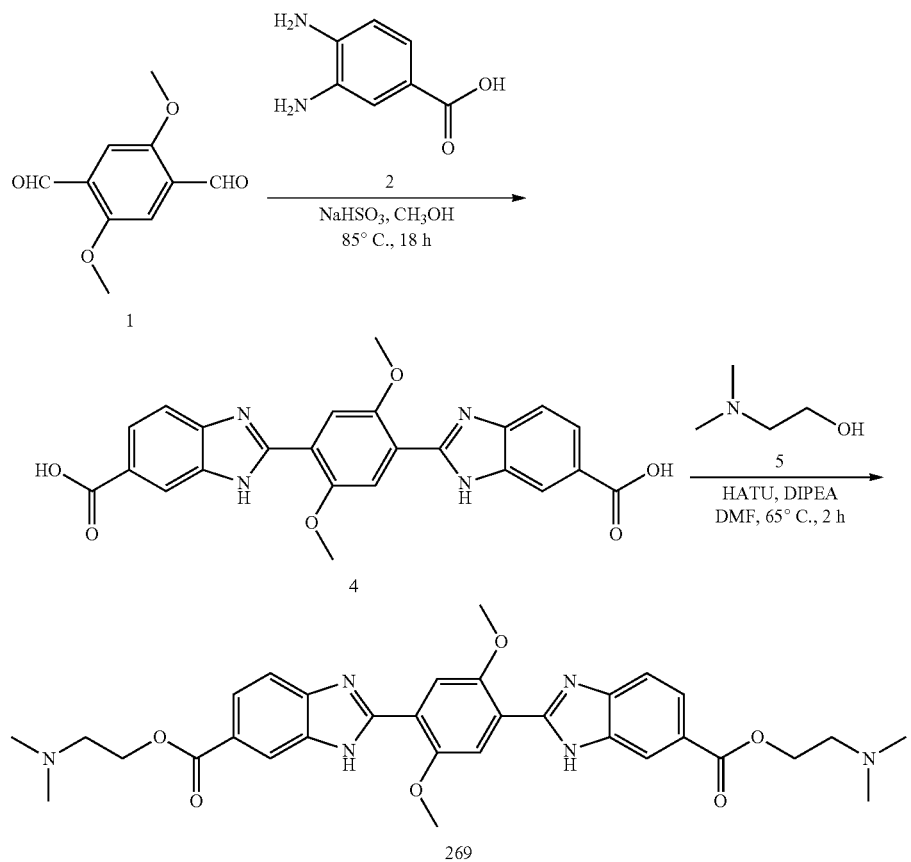

Synthesis of 2,2'-(2,5-dimethoxy-1,4-phenylene)bis(1H-benzo[d]imidazole-6-carboxylic acid): To a stirred solution of 2,5-dimethoxyterephthalaldehyde (200 mg, 1.03 mmol) in anhydrous CH$_3$OH (20.0 mL), at r.t under N$_2$ atmosphere, was added NaHSO$_3$ (322 mg, 3.09 mmol) followed with 3,4-diaminobenzoic acid (392 mg, 3.09 mmol) and the reaction mixture was stirred at 80° C. for 16 h. The reaction mixture was concentrated under reduced pressure to obtain the crude product. The product was purified by triturating with water (50 mL). The solids were filtered under vacuum, washed with EtOAc (50 mL) and dried to obtain 2,2'-(2,5-dimethoxy-1,4-phenylene)bis(1H-benzo[d]imidazole-6-carboxylic acid).

Synthesis of bis(2-(dimethylamino)ethyl) 2,2'-(2,5-dimethoxy-1,4-phenylene)bis(1H-benzo[d]imidazole-6-carboxylate) (269): To a stirred solution of 2,2'-(2,5-dimethoxy-1,4-phenylene)bis(1H-benzo[d]imidazole-6-carboxylic acid) (100 mg, 0.22 mmol) in anhydrous DMF (10.0 mL), at r.t under N$_2$ atmosphere, was added DIPEA (0.15 mL, 0.87 mmol), HATU (182 mg, 0.48 mmol) followed with 2-(dimethylamino)ethan-1-ol (78.0 mg, 0.87 mmol) and the reaction mixture was stirred at r.t for 30 mins. After 30 min, added additional amount of 2-(dimethylamino)ethan-1-ol (78 mg, 0.87 mmol) and the reaction mixture was stirred at 65° C. for additional 2 h. The reaction mixture was concentrated under reduced pressure to obtain the crude product. The product was purified by mass triggered HPLC. The fractions containing only the pure product were combined for concentration to obtain the title compound. MS (ESI): m/z=601 [M+H]$^+$.

Example 178

Synthesis of bis(2-(dimethylamino)ethyl) 2,2'-(2-fluoro-1,4-phenylene)bis(1H-benzo[d]imidazole-6-carboxylate) (Compound 270)

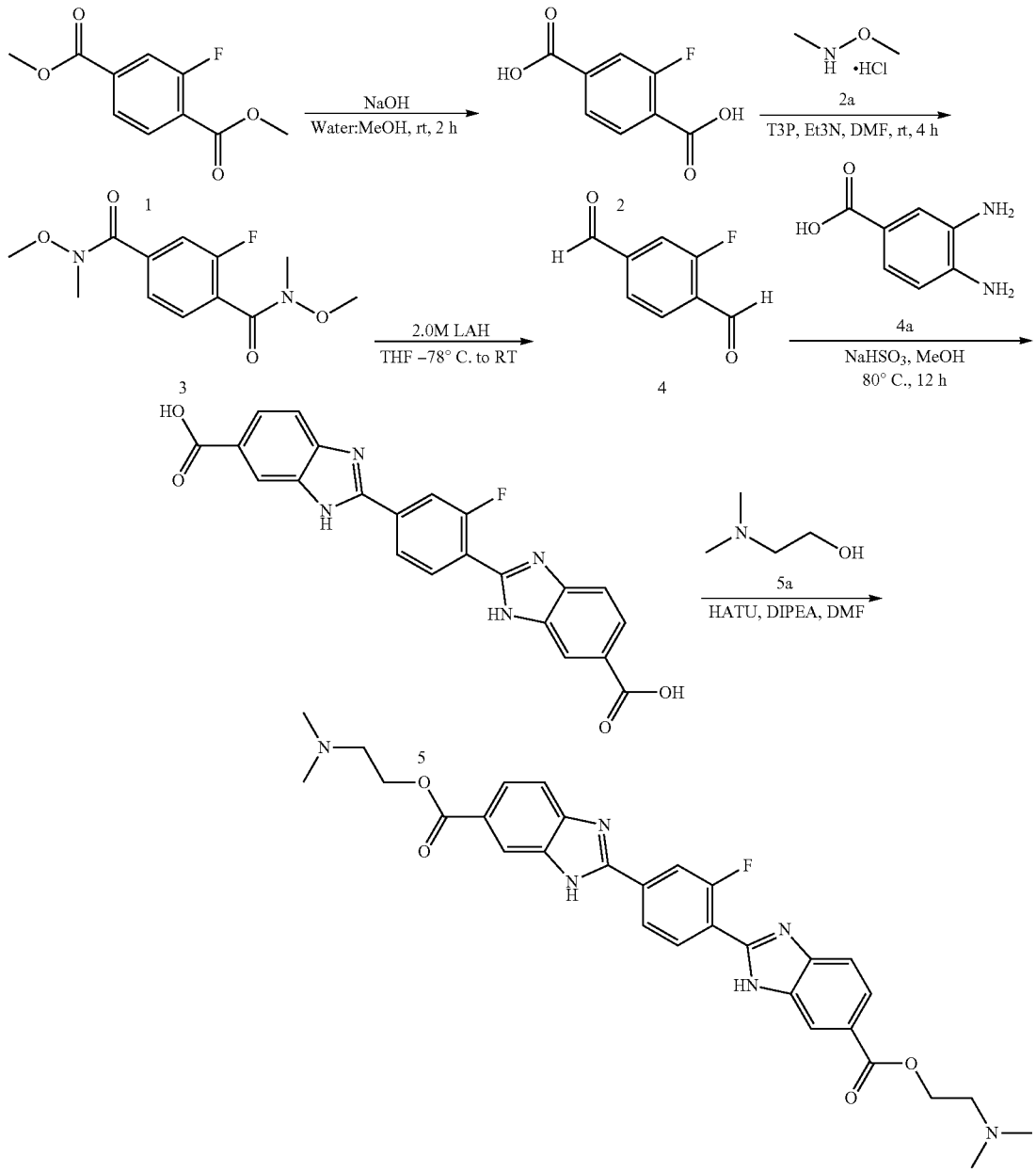

Synthesis of 2-fluoroterephthalic acid: To a stirred solution of dimethyl 2-fluoroterephthalate (1.00 g, 4.71 mmol) in a mixture of $CH_3OH$ (10.0 mL) and $H_2O$ (5.00 mL) at r.t, was added NaOH (0.94 g, 23.5 mmol) and the reaction mixture was stirred for 3 h. The reaction mixture was concentrated under reduced pressure to remove the volatile solvents, and the aqueous phase was acidified to pH 2 using 2N aqueous HCl, whereupon, a white solid precipitated. The solid was filtered under vacuum, washed with water (10 mL), and dried to obtain 2-fluoroterephthalic acid.

Synthesis of 2-fluoro-N1,N4-dimethoxy-N1,N4-dimethylterephthalamide: To a stirred solution of 2-fluoroterephthalic acid (0.80 g, 4.34 mmol) in anhydrous DMF (10.0 mL), at 0° C. under $N_2$ atmosphere, was added $Et_3N$ (1.21 mL, 8.69 mmol), T3P (50% solution in EtOAc, 6.92 mL, 10.86 mmol) followed with N, O-dimethylhydroxylamine hydrochloride (0.84 g, 8.69 mmol), and the reaction mixture was stirred at r.t for 4 h. The product was purified by silica gel chromatography using EtOAc:Hexanes (1:1). The fractions containing the product were combined for concentration to obtain 2-fluoro-N1,N4-dimethoxy-N1,N4-dimethylterephthalamide.

Synthesis of 2-fluoroterephthalaldehyde: To a stirred solution of 2-fluoro-N1,N4-dimethoxy-N1,N4-dimethylterephthalamide (0.70 g, 2.59 mmol) in anhydrous THF (10.0 mL), at −78° C. under argon atmosphere, was added $LiAlH_4$ (2.0 M in THF, 6.40 mL, 12.9 mmol) in a dropwise manner over a period of 10 min. The reaction mixture was gradually allowed to reach 0° C., and stirred for 1 h. The reaction mixture was cooled to −78° C. and quenched with saturated aqeuous $Na_2SO_4$ solution, diluted with water (50 mL), and the aqueous phase was extracted with EtOAc (2×50 mL). The combined EtOAc extracts were washed with water (50 mL), dried over anhydrous $Na_2SO_4$, filtered and concentrated under vacuum to obtain the crude product. The product was purified by silica gel chromatography using EtOAc:Hexanes (1:2). The fractions containing the product were combined and concentrated under vacuum to obtain 2-fluoroterephthalaldehyde.

Synthesis of 2,2'-(2-fluoro-1,4-phenylene)bis(1H-benzo[d]imidazole-6-carboxylic acid): To a stirred solution of 2-fluoroterephthalaldehyde (200 mg, 1.31 mmol) in anhydrous $CH_3OH$ (10.0 mL) at r.t under $N_2$ atmosphere, was added $NaHSO_3$ (274 mg, 2.63 mmol) followed with 3,4-diaminobenzoic acid (400 mg, 2.63 mmol) and the reaction mixture was stirred at 80° C. for 16 h. The reaction mixture was concentrated under reduced pressure to obtain the crude product. The product was purified by triturating with water (10 mL), to obtain free flowing solids. The solids were filtered under vacuum, washed with water (10 mL) and dried to obtain 2-(4-(6-carboxy-1H-benzo[d]imidazol-2-yl)-3-fluorophenyl)-1H-benzo[d]imidazole-5-carboxylic acid Synthesis of bis(2-(dimethylamino)ethyl) 2,2'-(2-fluoro-1,4-phenylene)bis(1H-benzo[d]imidazole-6-carboxylate): To a stirred solution of 2,2'-(2-fluoro-1,4-phenylene)bis(1H-benzo[d]imidazole-6-carboxylic acid) (150 mg, 0.36 mmol) in anhydrous DMF (2 mL) at r.t under $N_2$ atmosphere, was added DIPEA (0.15 mL, 1.00 mmol), HATU (274 mg, 0.72 mmol) followed with 2-(dimethylamino)ethan-1-ol (80 mg, 0.90 mmol) and the reaction mixture was stirred at 50° C. for 4 h. The reaction mixture was cooled to r.t and concentrated under reduced pressure to obtain the crude product. The product was purified by mass triggered HPLC. The fractions containing only the pure product were combined for concentration to the title compound. MS (ESI): m/z=559 $[M+H]^+$.

Example 179

Synthesis of Compound 271

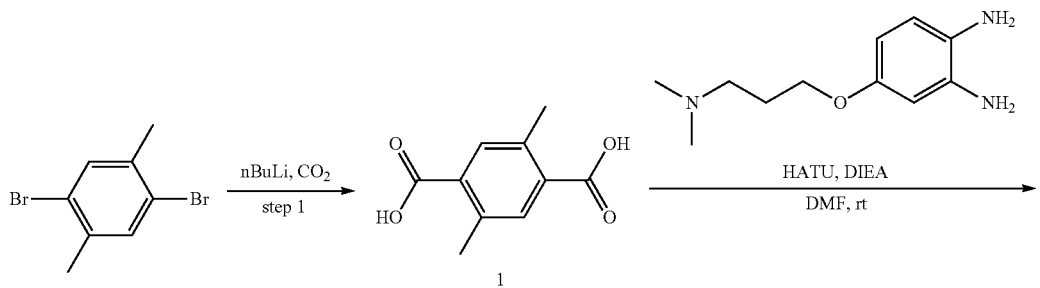

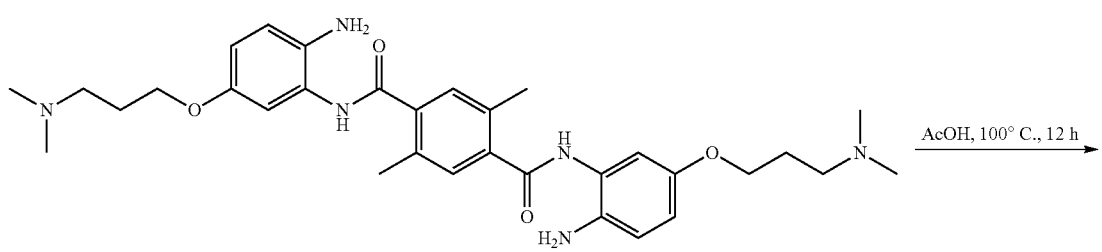

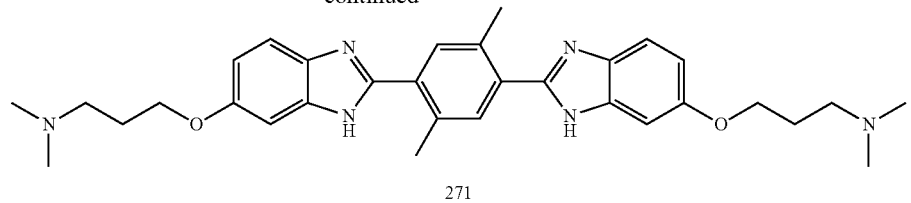

271

Synthesis of Compound 1: A stirred solution of 1,4-dibromo-2,5-dimethylbenzene (2.0 g, 7.58 mmol) in anhydrous tetrahydrofuran (60.0 mL) was cooled to −70° C. (dry ice/acetone bath) under a nitrogen atmosphere. Then n-Butyllithium (24.25 mL, 60.62 mmol, 2.5 M solution in pentane) was added dropwise, the reaction mixture was stirred for 2.5 h at −70° C. The yellow reaction solution was transferred via a cannula to a 1000 mL round-bottom flask containing excess dry ice under nitrogen atmosphere. After the $CO_2$ sublimated, the reaction was quenched with 5% $NH_4Cl$ (50 mL) and acidified with 1 M HCl to pH=3. The resulting solid was collected by filtration and dried in an oven to obtain 2,5-dimethylbenzene-1,4-dicarboxylic acid as a white solid.

Synthesis of Compound 2: Into a 100 ml round-bottom flask was added a solution of 2,5-dimethylbenzene-1,4-dicarboxylic acid (200 mg, 1.03 mmol, 1 eq) in N,N-Dimethylformamide (20 mL). To the solution was added 4-[3-(dimethylamino)propoxy]benzene-1,2-diamine (646.7 mg, 3.09 mmol, 3 eq), HATU (1174.8 mg, 3.09 mmol, 3 eq) and DIEA (665.6 mg, 5.15 mmol, 5 eq) separately. The reaction was stirring for 2 h at room temperature. Then the reaction mixture was diluted with 100 mL of brine, the resulting mixture was extracted with DCM 50 mL×3. The combined solution was washed with saturated 50 mL×3 NaHCO3 and 50 mL×3 brine, concentrated under reduced pressure and the residue was purified by silica gel column chromatography (50:1 to 10:1 DCM/MeOH) to afford N1,N4-bis([2-amino-5-[3-(dimethylamino)propoxy]phenyl])-2,5-dimethylbenzene-1,4-dicarboxamide MS (ESI): m/z=577 $[M+H]^+$.

Synthesis of 271: Into a 25-mL round-bottom flask purged and maintained at a nitrogen atmosphere, was placed a solution of N1,N4-bis([2-amino-5-[3-(dimethylamino)propoxy]phenyl])-2,5-dimethylbenzene-1,4-dicarboxamide (90 mg) in AcOH (5 mL), the reaction mixture was heated at 100° C. for 12 h. The reaction mixture was then concentrated and purified by preparative HPLC(Column: Xselect CSH OBD Column 30*150 mm 5 um n; Mobile Phase A: Water (0.05% TFA), Mobile Phase B: ACN; Flow rate: 60 mL/min; Gradient: 8% B to 18% B in 7 min; 254; 220 nm; Rt: 6.77 min). This afford (3-[[2-(4-[6-[3-(dimethylamino)propoxy]-1H-1,3-benzodiazol-2-yl]-2,5-dimethylphenyl)-1H-1,3-benzodiazol-6-yl]oxy]propyl)dimethylamine. MS (ESI): m/z=541 $[M+H]^+$.

Compound 272 was prepared in the same manner as compound 271. MS (ESI): m/z=527 $[M+H]^+$ Example 180

Synthesis of Compound 465

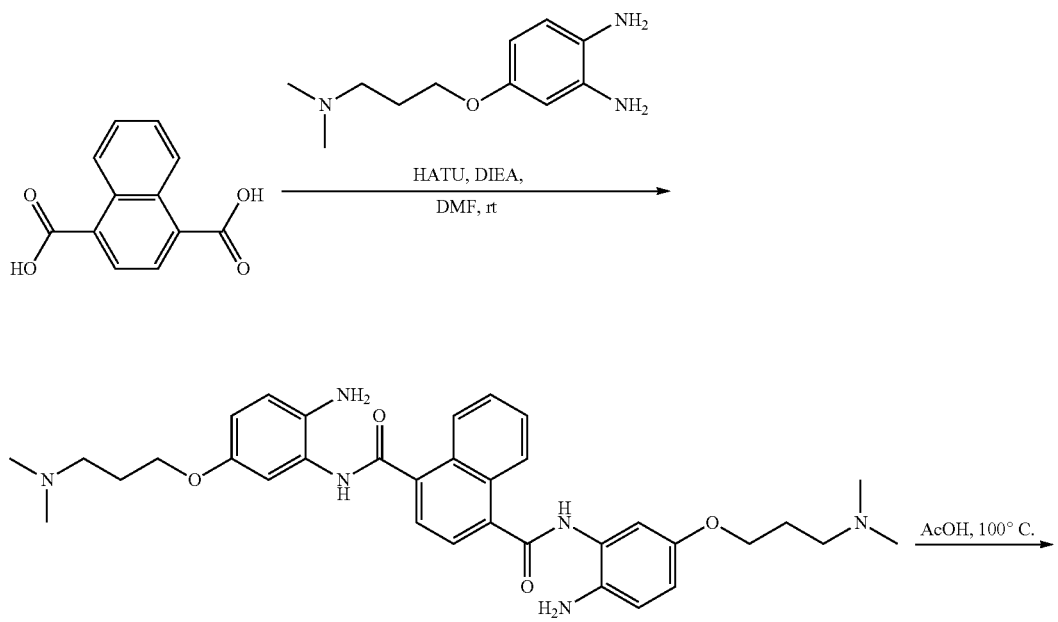

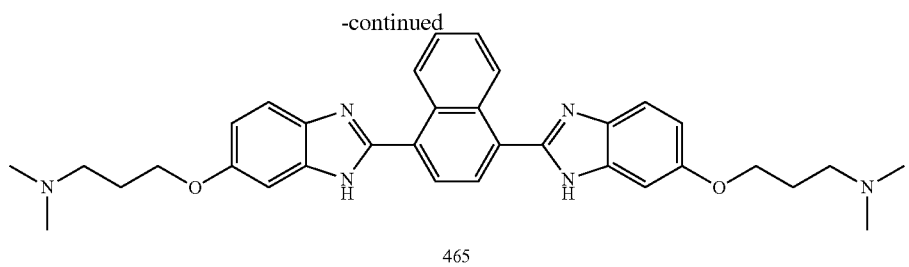

465

Synthesis of Compound 1:

Into a 100 mL of round-bottom flask, was added a solution of naphthalene-1,4-dicarboxylic acid (300 mg, 1.39 mmol, 1 eq) in N,N-Dimethylformamide (20 mL), then 4-[3-(dimethylamino)propoxy]benzene-1,2-diamine (871.3 mg, 4.16 mmol, 3 eq), HATU (1582.9 mg, 4.16 mmol, 3 eq) and DIEA (896.7 mg, 6.94 mmol, 5 eq) were added. The reaction mixture was stirring for 2 h at room temperature. Then the reaction mixture was diluted with 100 mL of brine, the resulting mixture was extracted with DCM 50 mL×3. The combined solution was washed with saturated 50 mL×3 NaHCO3 and 50 mL×3 brine, concentrated under reduced pressure and the residue was purified by silica gel column chromatography (50:1 to 5:1 DCM/MeOH) to afford N1,N4-bis([2-amino-5-[3-(dimethylamino)propoxy]phenyl])naphthalene-1,4-dicarboxmidea Synthesis of 465:

Into a 25-mL round-bottom flask purged and maintained at a nitrogen atmosphere, was placed a solution of N1,N4-bis([2-amino-5-[3-(dimethylamino)propoxy]phenyl])naphthalene-1,4-dicarboxamide (140 mg) in AcOH (5 mL), the reaction was heated at 100° C. for 12 h. The reaction mixture was then concentrated and purified by preparative HPLC This afforded the title compound. MS (ESI) m/z=563 [M+H]⁺.

Compounds 276 and 274 were prepared in the same manner as compound 465. Compound 276: MS (ESI) m/z=514 [M+H]+Compound 274: MS (ESI) m/z=515 [M+H]⁺.

Example 181

Synthesis of Compound 464

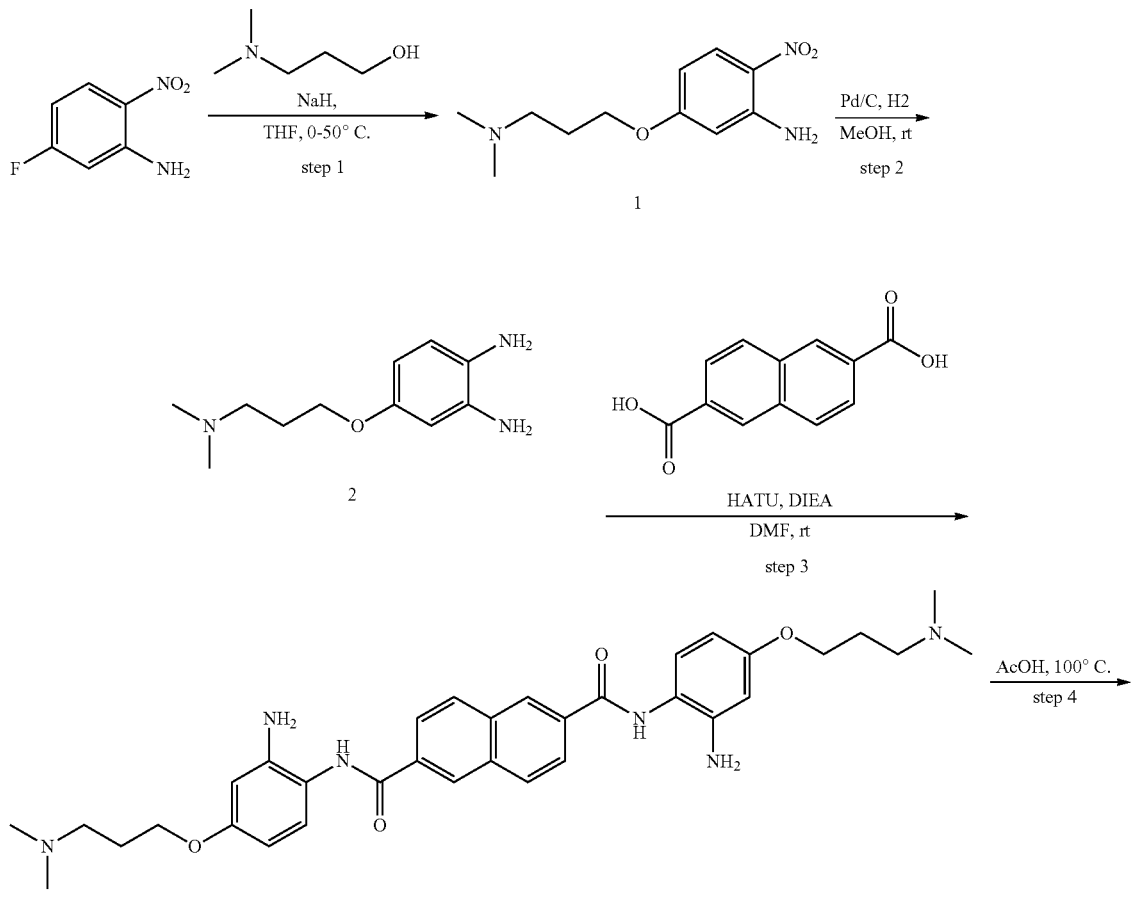

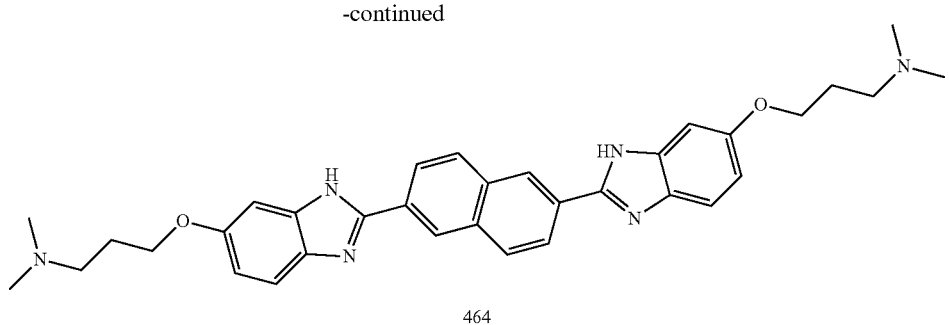

464

Synthesis of 5-(3-(dimethylamino)propoxy)-2-nitrobenzenamine Into a 50-mL 3-necked round-bottom flask purged and maintained with a nitrogen atmosphere, was placed a solution of 3-(dimethylamino)propan-1-ol (991.2 mg, 9.61 mmol, 1.50 equiv) in THF (10 mL). Then NaH (461.2 mg, 19.22 mmol, 3.00 equiv) was added in portion at 0° C. during a period of 10 minutes. Then a solution of 5-fluoro-2-nitroaniline (1 g, 6.41 mmol, 1 equiv) in anhydrous THF (20 mL) was added dropwise at 0° C. The resulting solution was stirred at 50° C. for 16 hours. The reaction was cooled to room temperature and quenched with ice-water (50 ml) carefully. The mixture was extracted with 3×10 ml ethyl acetate, the organic solution combined was washed with saturated NaCl solution 50 mL×3, dried over with anhydrous sodium sulfate and concentrated under vacuum. The residue was applied onto a silica gel column eluting with dichloromethane/methanol (10:1). This resulted in 5-[3-(dimethylamino)propoxy]-2-nitroaniline.

Synthesis of 4-[3-(dimethylamino)propoxy]benzene-1,2-diamine Into a 50-mL round-bottom flask purged and maintained in a nitrogen atmosphere, was placed a solution of 5-[3-(dimethylamino)propoxy]-2-nitroaniline (1 g, 4.18 mmol, 1 equiv) in methanol (20 mL). Then Pd/C (0.8 g, 7.52 mmol) was added in one portion. The reaction system was backfilled with hydrogen 3 times and the resulting solution was stirred for 16 hours at room temperature. The catalyst was filtered out and the solution was concentrated under vacuum. This resulted in 4-[3-(dimethylamino)propoxy]benzene-1,2-diamine which was used in the next step directly without further purification.

Synthesis of N2,N6-bis([2-amino-4-[3-(dimethylamino)propoxy]phenyl])naphthalene-2,6-dicarboxamide Into a 20-mL round-bottom flask purged and maintained in a nitrogen atmosphere, was placed a solution of naphthalene-2,6-dicarboxylic acid (300 mg, 1.39 mmol, 1 equiv) in DMF (5 ml). Then 4-[3-(dimethylamino)propoxy]benzene-1,2-diamine (871.3 mg, 4.16 mmol, 3.00 equiv), HATU (1582.9 mg, 4.16 mmol, 3.00 equiv) and DIEA (896.7 mg, 6.94 mmol, 5.00 equiv) were added separately. The resulting solution was stirred overnight at room temperature. The reaction mixture was diluted with 25 mL of water and the solid was collected by filtration, washed with MeOH and dried under vacuum at 50° C. This resulted in N2,N6-bis([2-amino-4-[3-(dimethylamino)propoxy]phenyl])naphthalene-2,6-dicarboxamide.

Synthesis of (3-[[2-(6-[5-[3-(dimethylamino)propoxy]-1H-1,3-benzodiazol-2-yl]naphthalen-2-yl)-1H-1,3-benzodiazol-5-yl]oxy]propyl)dimethylamine Into a 20-mL round-bottom flask purged and maintained with an inert atmosphere of nitrogen, was placed N2,N6-bis([2-amino-4-[3-(dimethylamino)propoxy]phenyl])naphthalene-2,6-dicarboxamide (600 mg, 1.00 mmol, 1 equiv) in acetic acid (6 mL). The resulting solution was stirred for overnight at 100° C. The solvent was concentrated under vacuum. The residue was dissolved in of MeOH. The crude product was purified by Prep-HPLC This resulted in the title compound. MS (ESI): m/z=563 [M+H]$^+$ Example 182

Synthesis of Compound 273

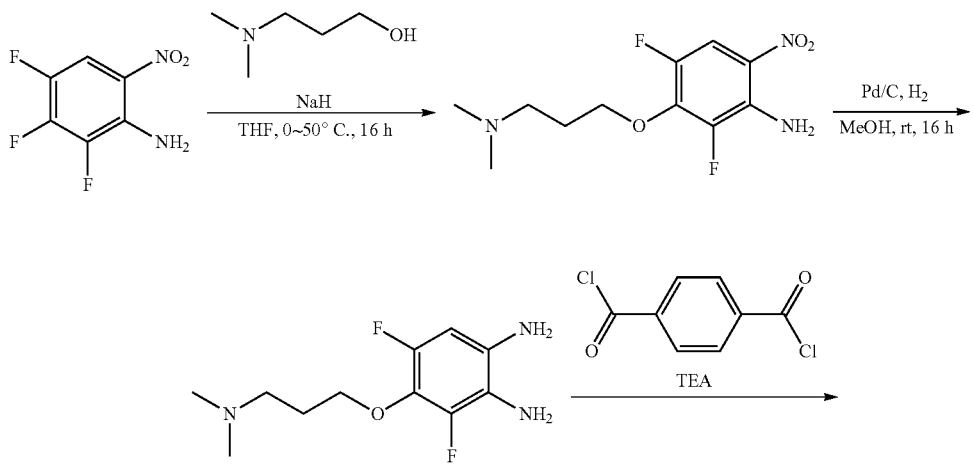

-continued

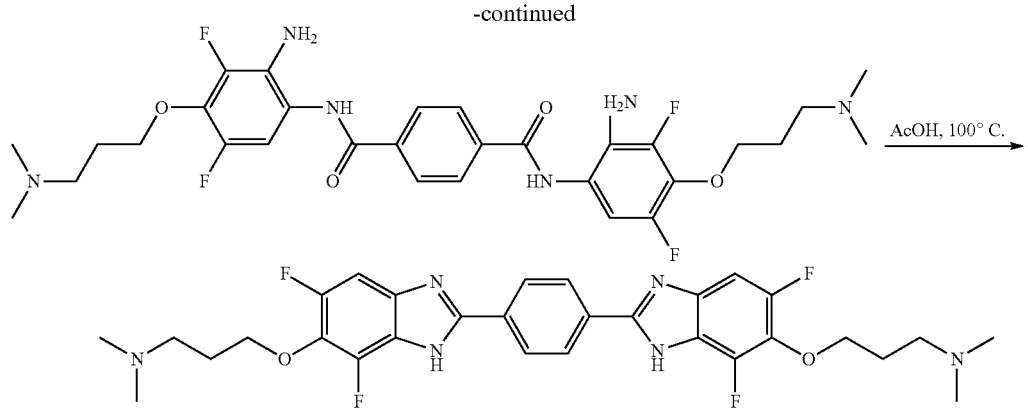

Synthesis of [3-(dimethylamino)propoxy]-2,4-difluoro-6-nitroaniline Into a 50-mL 3-necked round-bottom flask purged and maintained with an inert atmosphere of nitrogen, was placed a solution of 2,3,4-trifluoro-6-nitroaniline (1 g, 5.21 mmol, 1 equiv) in THF (10 mL). Then NaH (374.8 mg, 15.62 mmol, 3 equiv) was added portionwise at 0° C. The reaction mixture was stirred at 0° C. for 30 minutes. Then a solution of 3-(dimethylamino) propan-1-ol (805.6 mg, 7.81 mmol, 1.50 equiv) in anhydrous THF (10 mL) was added dropwise at 0° C. The resulting solution was stirred at 50° C. for 16 hours in an oil bath. After reaction completed, the reaction mixture was quenched with ice-water and extracted with DCM (5*10 ml), the organic layers were washed with saturated NaCl solution, dried over Na₂SO₄ and concentrated in vacuo. The residue was applied onto a silica gel column eluting with dichloromethane/methanol (10:1) to afford 3-[3-(dimethylamino)propoxy]-2,4-difluoro-6-nitroaniline.

Synthesis of 4-[3-(dimethylamino)propoxy]-3,5-difluorobenzene-1,2-diamine Into a 50-mL round-bottom flask purged and maintained in a nitrogen atmosphere, was placed a solution of 3-[3-(dimethylamino)propoxy]-2,4-difluoro-6-nitroaniline (1 g, 3.63 mmol, 1 equiv) in MeOH (20 mL). Then anhydrous Pd/C (0.8 g) was added carefully. The system was backfilled with hydrogen for several times and the resulting solution was stirred at room temperature for 16 hours. The catalyst was filtered out and the solvent was removed under reduced pressure to result in 4-[3-(dimethylamino)propoxy]-3,5-difluorobenzene-1,2-diamine Synthesis of N1,N4-bis([2-amino-4-[3-(dimethylamino)propoxy]-3,5-difluorophenyl])benzene-1,4-dicarboxamide Into a 50-mL of round-bottom flask under a nitrogen atmosphere, was placed a solution of 4-[3-(dimethylamino)propoxy]-3,5-difluorobenzene-1,2-diamine (750 mg, 3.06 mmol, 2 equiv) and TEA (930 mg, 18.35 mmol, 6 equiv) in anhydrous DCM (10 mL). Then a solution of benzene-1,4-dicarbonyl dichloride (310 mg, 3.06 mmol, 1 equiv) in anhydrous THF (5 mL) was added dropwise at 0° C. The resulting solution was stirred at rt for 16 hours. The reaction was quenched with water and the organic layer was washed with sat. brine (20 mL×3). The organic layer was concentrated in vacuo and the residue was purified by Prep-TLC (5:1 MeOH/DCM) to afford N1,N4-bis([2-amino-4-[3-(dimethylamino)propoxy]-3,5-difluorophenyl])benzene-1,4-dicarboxamide.

Synthesis of (3-[[2-(4-[6-[3-(dimethylamino)propoxy]-5,7-difluoro-1H-1,3-benzodiazol-2-yl]phenyl)-5,7-difluoro-1H-1,3-benzodiazol-6-yl]oxy]propyl)dimethylamine Into a 50-mL round-bottom flask purged and maintained with an inert atmosphere of nitrogen, was placed a solution of N1,N4-bis([2-amino-4-[3-(dimethylamino)propoxy]-3,5-difluorophenyl])benzene-1,4-dicarboxamide (500 mg, 0.81 mmol, 1 equiv) in AcOH (10 ml). The resulting solution was stirred at 100° C. for 5 hours. The resulting mixture was concentrated under vacuum. The crude product was purified by Prep-HPLC. This resulted in the title compound. MS (ESI): m/z=585 [M+H]⁺

Example 183

Synthesis of Compound 275

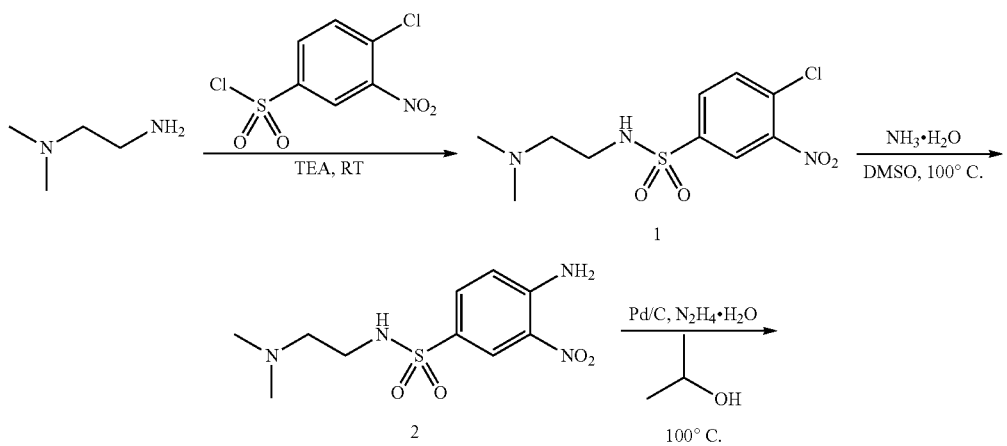

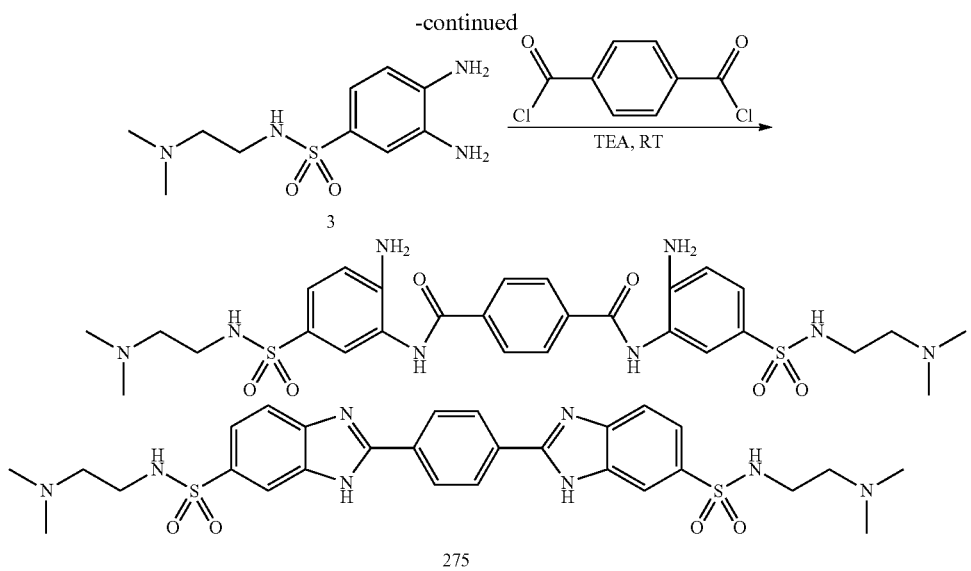

275

Synthesis of 4-chloro-N-(2-(dimethylamino)ethyl)-3-nitrobenzenesulfonamide Into a 250-mL round-bottom flask under a nitrogen atmosphere, was placed a solution of (2-aminoethyl)dimethylamine (2 g, 22.69 mmol, 1 equiv) and triethylamine (4.6 g, 45.38 mmol, 2.00 equiv) in anhydrous DCM (100 mL). Then 4-chloro-3-nitrobenzene-1-sulfonyl chloride (6.4 g, 24.96 mmol, 1.10 equiv) was added at 0°. The resulting solution was stirred for 3 hours at 25°. The reaction was then quenched by the addition of 50 mL of water/ice. The resulting solution was extracted with DCM (3×50 mL), dried over $Na_2SO_4$, filtered and concentrated in vacuo. The residue was purified by a silica gel column eluting with dichloromethane/methanol (10:1). This resulted in 4-chloro-N-[2-(dimethylamino)ethyl]-3-nitrobenzene-1-sulfonamide.

Synthesis of 4-amino-N-(2-(dimethylamino)ethyl)-3-nitrobenzenesulfonamide Into a 250-mL 3-necked round-bottom flask, was placed a solution of 4-chloro-N-[2-(dimethylamino)ethyl]-3-nitrobenzene-1-sulfonamide (6.2 g, 20.15 mmol, 1 equiv) in DMSO (50 mL). Then $NH_3 \cdot H_2O$ (10 mL, 30%) was added. The resulting solution was stirred for 12 hours at 100° C. in an oil bath. The reaction was quenched by water (100 mL). The resulting solution was extracted with ethyl acetate (100 mL×3) and the organic layers combined was dried over $Na_2SO_4$, filtered and concentrated in vacuo. This resulted in 4-amino-N-[2-(dimethylamino)ethyl]-3-nitrobenzene-1-sulfonamide.

Synthesis of 3,4-diamino-N-(2-(dimethylamino)ethyl)benzenesulfonamide Into a 500 mL of round-bottomed flask purged and maintained in a nitrogen atmosphere, was placed a solution of 4-amino-N-[2-(dimethylamino)ethyl]-3-nitrobenzene-1-sulfonamide (5 g, 17.34 mmol, 1 equiv) in methanol (100 mL). Then 0.2 g of anhydrous Pd/C (10%) was added. The system was backfilled with hydrogen several times and the reaction mixture was stirred for 6 hours at 25°. The catalyst was filtered out and the solution was concentrated in vacuo. This resulted in 3,4-diamino-N-[2-(dimethylamino)ethyl]benzene-1-sulfonamide which was used in the next step directly without further purification.

Synthesis of 2,2'-(1,4-phenylene)bis(N-(2-(dimethylamino)ethyl)-1H-benzo[d]imidazole-6-sulfonamide) Into a 50 mL of round-bottomed flask under a nitrogen atmosphere, was placed a solution of benzene-1,4-dicarbaldehyde (200 mg, 1.49 mmol, 1 equiv), 3,4-diamino-N-[2-(dimethylamino)ethyl]benzene-1-sulfonamide (1155.6 mg, 4.47 mmol, 3.00 equiv) and sulfonylideneoxidane sodium hydride (465.4 mg, 4.47 mmol, 3 equiv) in methanol (20 ml). The reaction mixture was refluxed for 8 hours. The reaction mixture was cooled to room temperature and concentrated in vacuo. The residue was purified by pre-HPLC. This resulted in the title compound. MS (ESI): m/z=611 [M+H]$^+$.

Example 184

Synthesis of Compound 276

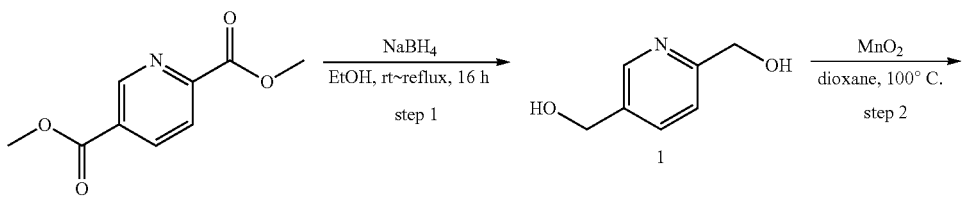

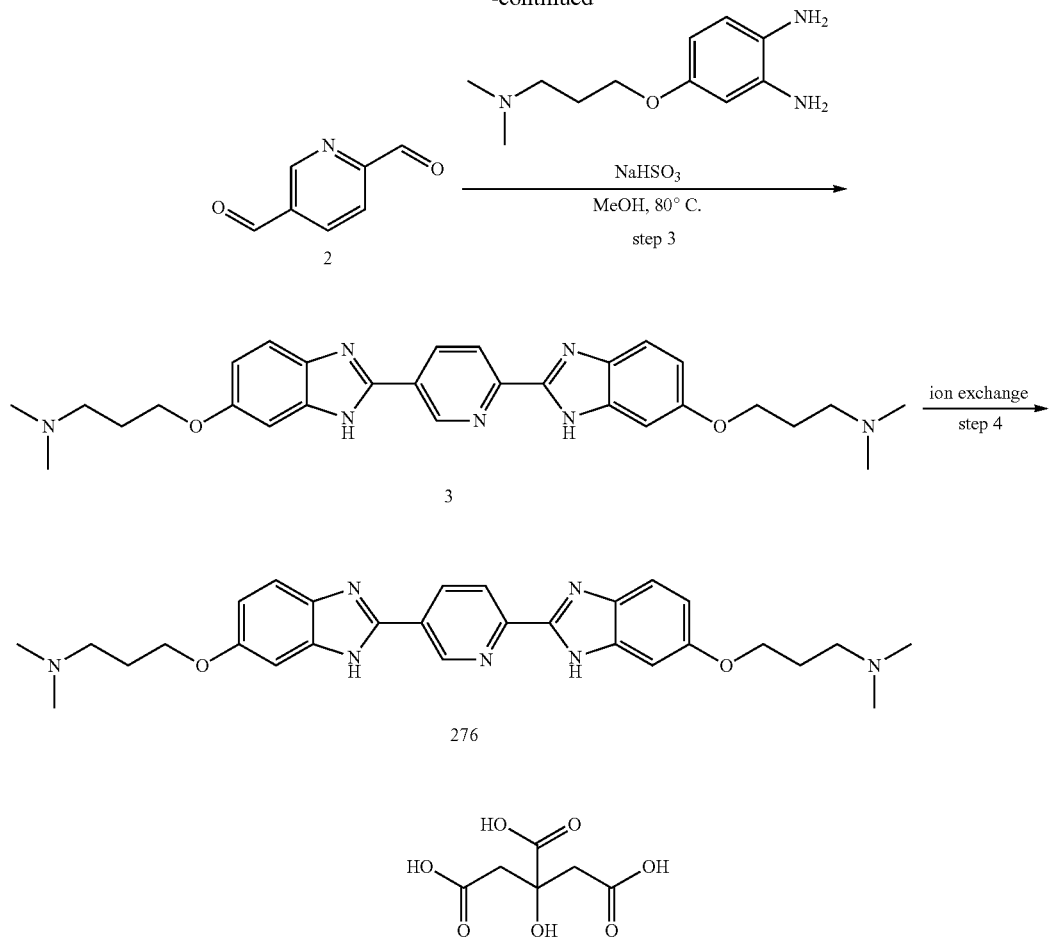

Synthesis of Compound 1: Into a 50 mL of round-bottom flask under a nitrogen atmosphere, was placed a stirred solution of dimethyl pyridine-2,5-dicarboxylate (3 g, 15.4 mmol, 1 equiv) in dry EtOH (20 mL), then NaBH$_4$ (2.9 g, 5 equiv) was added portionwised over a period of 10 minutes at 25° C. The reaction mixture was stirred at reflux for 16 hours. Then, the reaction mixture was cooled to room temperature and the contents were poured onto ice and extracted with DCM (10×20 ml). The combined organic layer were washed with brine (60 mL), dried over anhydrous Na$_2$SO$_4$, and concentrated under vacuum to obtain the crude product. The product was purified by silica gel column chromatography using DCM/MeOH (0% to 20%) to obtain pyridine-2,5-diyldimethanol Synthesis of Compound 2: Into a 100-mL round-bottom flask purged and maintained at a nitrogen atmosphere, was placed a solution of pyridine-2,5-diyldimethanol (1.4 g, 10 mmol, 1 equiv) in dioxane (10 mL). Then MnO$_2$ (8.8 g, 100 mmol, 10 equiv) was added carefully. The reaction was stirred at 100° C. for 3 hours. After the reaction completed, the catalyst was filtered off. The filtrate was concentrated under vacuum. This crude product was purified by prep-TLC (EA:PE=1:1) obtain pyridine-2,5-dicarbaldehyde Synthesis of Compound 3: Into a 50 mL of round-bottomed flask under a nitrogen atmosphere, was placed a solution of pyridine-2,5-dicarbaldehyde (400 mg, 2.96 mmol, 1 equiv), 4-(3-(dimethylamino)propoxy)benzene-1,2-diamine (1.86 g, 8.88 mmol, 3 equiv) and NaHSO3 (1.54 g, 14.8 mmol, 5 equiv) in methanol (50 mL). The reaction mixture was refluxed for 8 h. The reaction mixture was cooled to room temperature and the precipitate was collected by filtration, the crude product was purified by preparative HPLC. This afford 3,3'-(2,2'-(pyridine-2,5-diyl)bis(3H-benzo[d]imidazole-5,2-diyl))bis(oxy)bis(N,N-dimethylpropan-1-amine).

Synthesis of Compound 276: 3,3'-(2,2'-(pyridine-2,5-diyl)bis(3H-benzo[d]imidazole-5,2-diyl))bis(oxy)bis(N,N-dimethylpropan-1-amine) (220 mg, 0.43 mmol, 1 equiv) was dissolved in 10 mL (as less as possible) of a mixed solvent of MeOH/H2O (1/10: v/v). The solution was applied on an ion-exchange column and eluting with a mixed solvent of MeOH/H$_2$O (1/10: v/v). This resulted in the title compound. MS (ESI): m/z=514 [M+H]$^+$.

Treatment of the resin: 15-20 g of commercial available (Beijing Innochem Science & Technology Co. Ltd) anion-exchange resin (Dowex 1×8 (a), 100-200 mesh) was washed with 100 mL×3 of a mixed solvent of methanol and de-ionized water (1/10 v/v) in a 250-mL beaker and then treated as follows:

The suspension of resin in water was packed in a column (30 mm×400 mm, resin height: ~25 cm) and eluted with 1-2 volume of the column of de-ionized water, then eluted with 2 N NaOH for 2-3 volume of the column. After eluting with de-ionized water to neutral, the resin was eluted with 2-3 volume of the column of 2 N citric acid solution in de-ionized water. Then the column was eluted with mixed solvent of methanol and de-ionized water (1/10 v/v) until the eluent was near neutral.

Example 185

Synthesis of Compound 277

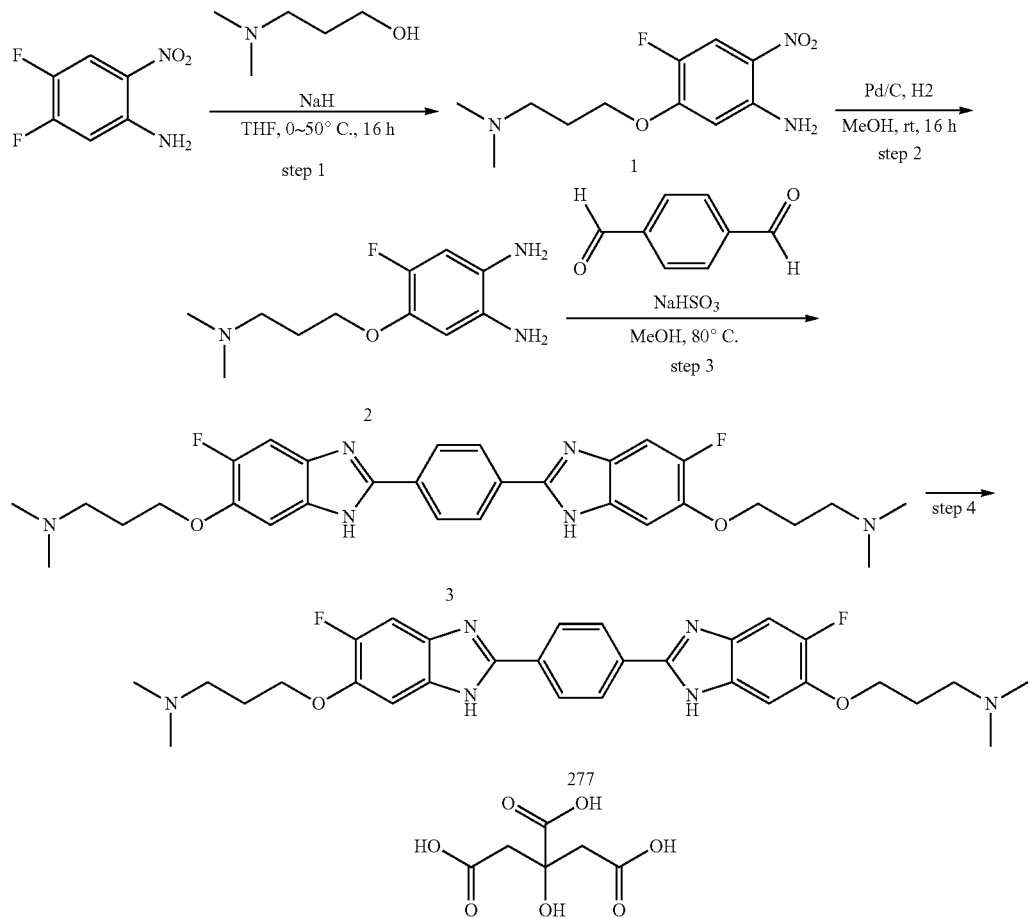

Synthesis of 5-(3-(dimethylamino)propoxy)-4-fluoro-2-nitrobenzenamine Into a 250-mL 3-necked round-bottom flask purged and maintained with an inert atmosphere of nitrogen, was placed a solution of 3-(dimethylamino)propan-1-ol (888.81 mg, 8.615 mmol, 1.5 equiv) in THF (50 mL). NaH (689.17 mg, 28.718 mmol, 3 equiv) was added portionwise at 0° C. The reaction mixture was stirred at 0° C. for 30 minutes. Then a solution of 4,5-difluoro-2-nitrobenzenamine (1 g, 5.744 mmol, 1.0 equiv) in anhydrous THF (50 mL) was added dropwise at 0° C. The resulting solution was stirred at 50° C. for 16 hours in an oil bath. After reaction completed, the reaction mixture was quenched with ice-water and extracted with DCM (5*10 ml), the organic layer was washed with saturated NaCl solution, dried over $Na_2SO_4$ and concentrated in vacuo. The residue was applied onto a silica gel column eluting with dichloromethane/methanol (10:1) to afford 5-(3-(dimethylamino)propoxy)-4-fluoro-2-nitrobenzenamine Synthesis of 4-(3-(dimethylamino)propoxy)-5-fluorobenzene-1,2-diamine Into a 50-mL round-bottom flask purged and maintained in a nitrogen atmosphere, was placed a solution of 5-(3-(dimethylamino)propoxy)-4-fluoro-2-nitrobenzenamine (1.3 g, 5.053 mmol, 1 equiv) in MeOH (20 mL). Then anhydrous Pd/C (0.8 g) was added carefully. The system was backfilled with hydrogen for several times and the resulting solution was stirred at room temperature for 16 hours. The catalyst was filtered out and the solvent was removed under reduced pressure to result in 4-(3-(dimethylamino)propoxy)-5-fluorobenzene-1,2-diamine.

Synthesis of 3,3'-(2,2'-(1,4-phenylene)bis(6-fluoro-3H-benzo[d]imidazole-5,2-diyl))bis(oxy)bis(N,N-dimethylpropan-1-amine) Into a 50-mL of round-bottom flask under a nitrogen atmosphere, was placed a solution of 4-(3-(dimethylamino)propoxy)-5-fluorobenzene-1,2-diamine (1.0 g, 4.4 mmol, 3 equiv), $NaHSO_3$ (776.1 mg, 7.46 mmol, 5 equiv) and terephthalaldehyde (200 mg, 1.49 mmol, 1 equiv) in anhydrous MeOH (10 mL). The resulting solution was stirred at 80° C. for 16 hours. The resulting mixture was concentrated under vacuum. The crude product was purified by Prep-HPLC. This resulted in 3,3'-(2,2'-(1,4-phenylene) bis(6-fluoro-3H-benzo[d]imidazole-5,2-diyl))bis(oxy)bis (N,N-dimethylpropan-1-amine).

Synthesis of (3-[[2-(4-[6-[3-(dimethylamino)propoxy]-5-fluoro-1H-1,3-benzodiazol-2-yl]phenyl)-5-fluoro-1H-1,3-benzodiazol-6-yl]oxy]propyl)dimethylamine; 2-hydroxypropane-1,2,3-tricarboxylic acid 330 mg of 3,3'-(2,2'-(1,4-phenylene)bis(6-fluoro-3H-benzo[d]imidazole-5,2-diyl))bis (oxy)bis(N,N-dimethylpropan-1-amine) was dissolved in 5 mL (as less as possible) of $MeOH/H_2O$ (1/10=v/v). The solution was applied on an ion-exchange column and eluting with a mixed solvent of MeOH/H2O (1/10: v/v). This afforded the title compound. MS (ESI): m/z=549 [M+H]+

Compounds 280, 281, 287, 289, and 295 were prepared in the same manner as compound 277. Compound 280: MS (ESI): m/z=549 [M+H]+Compound 281: MS (ESI): m/z=563 [M+H]$^+$ Compound 287: MS (ESI): m/z=549 [M+H]$^+$. Compound 289: MS (ESI) m/z=477 [M+H]$^+$. Compound 295: MS (ESI): m/z=565 [M+H]$^+$.

Treatment of the resin: 15-20 g of commercial available (Beijing Innochem Science & Technology Co. Ltd) anion-exchange resin (Dowex 1×8 (a), 100-200 mesh) was washed with 100 mL×3 of a mixed solvent of methanol and de-ionized water (1/10 v/v) in a 250-mL beaker and then treated as follows:

The suspension of resin in water was packed in a column (30 mm×400 mm, resin height: ~25 cm) and eluted with 1-2 volume of the column of de-ionized water, then eluted with 2 N NaOH for 2-3 volume of the column. After eluting with de-ionized water to neutral, the resin was eluted with 2-3 volume of the column of 2 N citric acid solution in de-ionized water. Then the column was eluted with mixed solvent of methanol and de-ionized water (1/10 v/v) until the eluent was near neutral.

Example 186

Synthesis of Compound 278

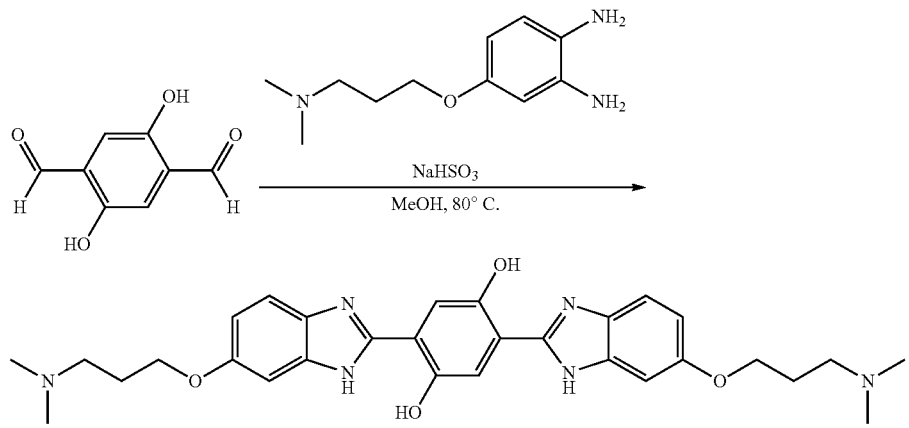

In a 40 ml of sealed tube was placed a solution of 2,5-dihydroxyterephthalaldehyde (200 mg, 1.0 mmol, 1 equiv), 4-(3-(dimethylamino)propoxy)benzene-1,2-diamine (756 mg, 3.6 mmol, 3 equiv) and NaHSO$_3$ (626 mg, 6.0 mmol, 5 equiv) in dry MeOH (15 mL). The resulting solution was stirred for 16 hours at 80° C. After reaction completed, the reaction mixture was concentrated under vacuum and the residue was purified by HPLC. This afforded the title compound. MS (ESI): m/z=545 [M+H]$^+$.

Compounds 290, 306, 312, and 316 were prepared in the same manner as compound 278. Compound 290: MS (ESI): m/z=573 [M+H]$^+$ Compound 306: MS (ESI) m/z=589 [M+H]$^+$. Compound 312: MS (ESI) m/z=527 [M+H]$^+$. Compound 316: MS (ESI): m/z=571 [M+H]$^+$ Example 187

Synthesis of Compound 279

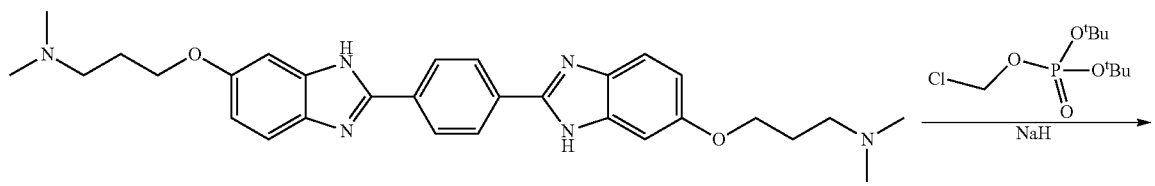

-continued

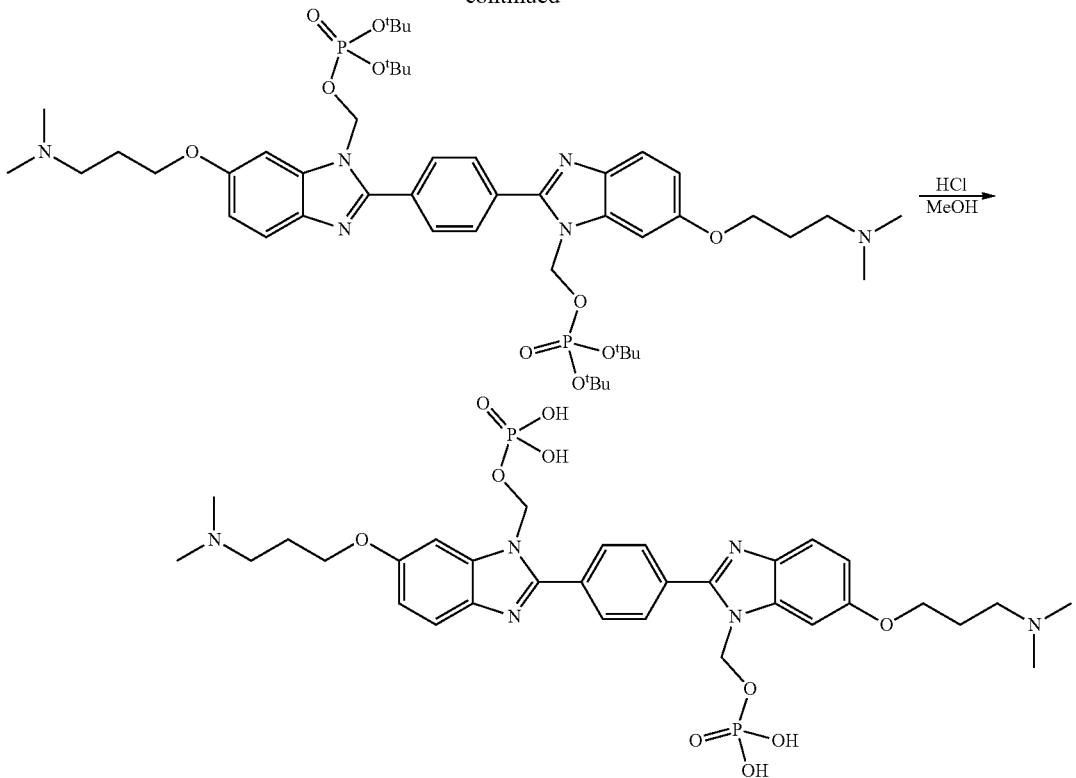

Synthesis of (1,4-phenylenebis(6-(3-(dimethylamino)propoxy)-1H-benzo[d]imidazole-2,1-diyl))bis(methylene) tetra-tert-butyl bis(phosphate) Into a 50-mL round-bottom flask, (3-[[2-(4-[6-[3-(dimethylamino)propoxy]-1H-1,3-benzodiazol-2-yl]phenyl)-1H-1,3-benzodiazol-6-yl]oxy]propyl)dimethylamine (1.1 g, 2.15 mmol, 1 equiv) was dissolved in dimethylformamide (20 mL), and a sodium hydride 60% suspension in mineral oil (515 mg, 12.9 mmol, 6 equiv) was added at 0° C. The resulting solution was stirred for 45 min at 25° C., then, the solution of phosphoric acid di-tert-butyl ester chloromethyl ester (2.22 g, 8.58 mmol, 4 equiv) in dimethylformamide (100 mL) was slowly added at 25° C. The reaction was stirred at 50° C. for 16 hours. The mixture was then diluted with dichloromethane (60 mL). The organic phase was then sequentially washed with water (30 mL), and brine (30 mL), dried over Na$_2$SO$_4$, filtered and concentrated. The crude product was purified by Prep-HPLC. product was obtained. This resulted in (2-[4-[1-([[bis(tert-butoxy)phosphoryl]oxy]methyl)-6-[3-(dimethylamino)propoxy]-1H-1,3-benzodiazol-2-yl]phenyl]-6-[3-(dimethylamino)propoxy]-1H-1,3-benzodiazol-1-yl)methyl di-tert-butyl phosphate Synthesis of (1,4-phenylenebis(6-(3-(dimethylamino)propoxy)-1H-benzo[d]imidazole-2,1-diyl))bis(methylene) bis(dihydrogenphosphate) Into a 50-mL round-bottom flask, was placed (2-[4-[1-[[bis(tert-butoxy)phosphoryl]oxy]methyl)-6-[3-(dimethylamino)propoxy]-1H-1,3-benzodiazol-2-yl]phenyl]-6-[3-(dimethylamino)propoxy]-1H-1,3-benzodiazol-1-yl)methyl di-tert-butyl phosphate (340 mg, 0.355 mmol, 1 equiv), hydrogen chloride in MeOH (4 mol/L, 20 mL). The resulting solution was stirred for 6 hr at 25° C. The resulting mixture was concentrated. The crude product was purified by Prep-HPLC with the following conditions (Column: XBridge Shield RP18 OBD Column 19*250 mm, 10 um; Mobile Phase A: Water (0.1% FA), Mobile Phase B: ACN; Flow rate: 25 mL/min; Gradient: 5% B to 10% B in 10 min; 254/220 nm; Rt: 8.5 min). product was obtained. This resulted in the title compound.

MS (ESI): m/z=733 [M+H]$^+$

Example 188

Synthesis of Compound 282

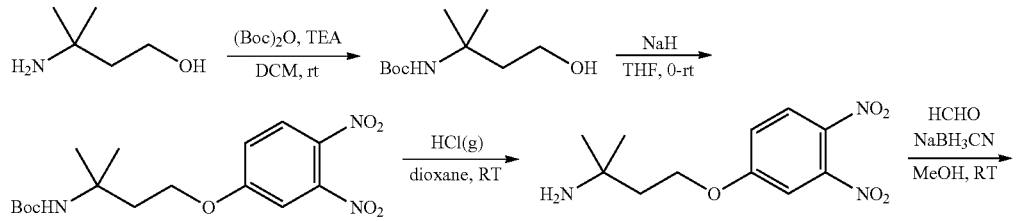

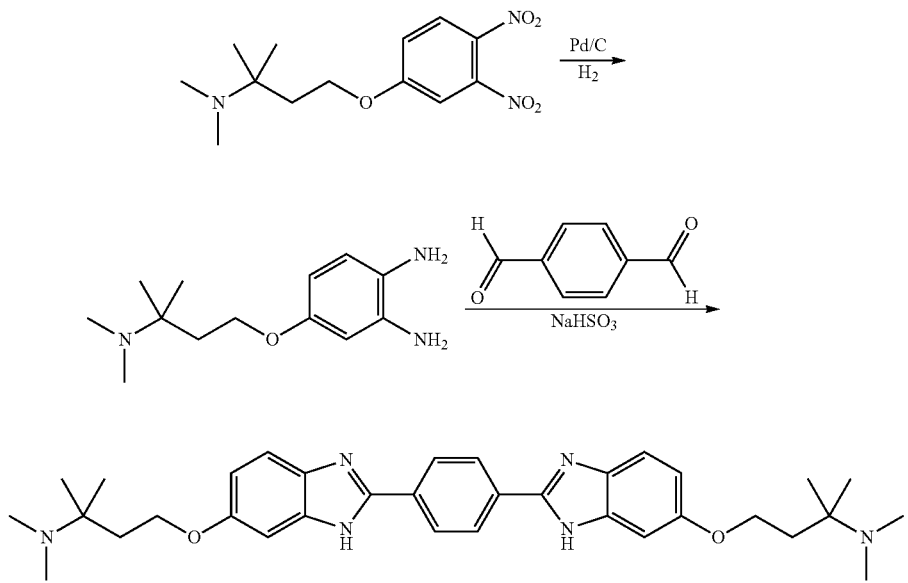

282

Synthesis of tert-butyl (4-hydroxy-2-methylbutan-2-yl) carbamate Into a 200-mL round-bottom flask under a nitrogen atmosphere, was placed a solution of 3-amino-3-methylbutan-1-ol (2.5 g, 24.2 mmol, 1 equiv) and TEA (4.9 g, 48.5 mmol, 2 equiv) in anhydrous DCM (50 mL). The mixture was stirred for 10 minutes at 25° C. Then (Boc)$_2$O (5.3 g, 24.2 mmol, 1 equiv) was added in one portion. The resulting solution was stirred for 6 hours at 25° C. The reaction was then quenched by the addition of water (20 mL). The resulting solution was extracted with dichloromethane (3×30 mL) and the organic layers combined was washed with brine, dried over anhydrous sodium sulfate and concentrated in vacuum. This resulted in tert-butyl N-(4-hydroxy-2-methylbutan-2-yl)carbamate which was used in the next step directly.

Synthesis of tert-butyl (4-(3,4-dinitrophenoxy)-2-methylbutan-2-yl)carbamate Into a 200-mL round-bottom flask under a nitrogen atmosphere, was placed a solution of tert-butyl N-(4-hydroxy-2-methylbutan-2-yl)carbamate (2 g, 9.8 mmol, 1 equiv) in anhydrous THF (50 mL). Then sodium hydride (0.28 g, 11.8 mmol, 1.2 equiv) was added portionwise at 0° C. The mixture was stirred for 30 minutes at 25° C. Then 4-fluoro-1,2-dinitrobenzene (1.83 g, 9.8 mmol, 1.00 equiv) was added in one portion. The resulting solution was stirred for 12 hours at 25° C. The reaction was then quenched by the careful addition of water (20 mL). The resulting solution was extracted with dichloromethane (3×30 mL) and the organic layers combined was washed with brine, dried over Na$_2$SO$_4$ and concentrated in vacuum. The residue was purified by a silica gel column eluting with dichloromethane/methanol (10:1) to afford tert-butyl N-[4-(3,4-dinitrophenoxy)-2-methylbutan-2-yl]carbamate Synthesis of 4-(3,4-dinitrophenoxy)-2-methylbutan-2-amine hydrochloride Into a 200-mL round-bottom flask under a nitrogen atmosphere, was placed a solution of tert-butyl N-[4-(3,4-dinitrophenoxy)-2-methylbutan-2-yl]carbamate (2.3 g, 1 equiv) in 4 mol/L HCl in 1,4-dioxane (50 mL). The mixture was stirred for 6 hours at 25° C. The resulting mixture was concentrated under vacuum. The resulting mixture was washed with EtOAc (50 ml) and the solid was collected by filtration. This resulted in 4-(3,4-dinitrophenoxy)-2-methylbutan-2-amine hydrochloride which was used in the next step directly Synthesis of 4-(3,4-dinitrophenoxy)-N,N,2-trimethylbutan-2-amine Into a 200-mL round-bottom flask under a nitrogen atmosphere, was placed a solution of 4-(3,4-dinitrophenoxy)-2-methylbutan-2-amine (1.7 g, 6.31 mmol, 1 equiv) and HCHO (15 mL, 37% in H$_2$O) in MeOH (100 mL). Then NaBH$_3$CN (1.59 g, 25.3 mmol, 4 equiv) was added portionwise. The mixture was stirred for 2 hours at 25° C. The resulting mixture was concentrated under vacuum and extracted with EtOAc (50 mL×3). The organic layers combined was washed with brine, dried over Na$_2$SO$_4$ and concentrated under vacuum. This resulted in [4-(3,4-dinitrophenoxy)-2-methylbutan-2-yl]dimethylamine Synthesis of 4-(3-(dimethylamino)-3-methylbutoxy)benzene-1,2-diamine Into a 200-mL round-bottom flask maintained in a nitrogen atmosphere, was placed a solution of [4-(3,4-dinitrophenoxy)-2-methylbutan-2-yl]dimethylamine (1.25 g, 4.204 mmol, 1 equiv) in methanol (100 mL). Then 0.5 g Pd/C (10% w/w) was added carefully. The system was backfilled with hydrogen several times and the reaction mixture was stirred for 6 hours at 25°. The catalyst was filtered out and the filtrate was concentrated in vacuo. This resulted in 4-[3-(dimethylamino)-3-methylbutoxy]benzene-1,2-diamine which was used in the next step immediately.

Synthesis of 4,4'-((1,4-phenylenebis(1H-benzo[d]imidazole-2,6-diyl))bis(oxy))bis(N,N,2-trimethylbutan-2-amine) Into a 50-mL round-bottom flask, was placed a solution of benzene-1,4-dicarbaldehyde (110 mg, 0.820 mmol, 1 equiv), 4-[3-(dimethylamino)-3-methylbutoxy]benzene-1,2-diamine (583.93 mg, 2.460 mmol, 3.00 equiv) and NaHSO$_3$ (256.01 mg, 2.460 mmol, 3 equiv) in MeOH (20 mL). The resulting solution was stirred for 12 hours at 80° in an oil bath. The solids were filtered out. The crude product was purified by Prep-HPLC. This resulted in the title compound. MS (ESI): m/z=569 [M+H]$^+$.

Example 189

Synthesis of Compound 283

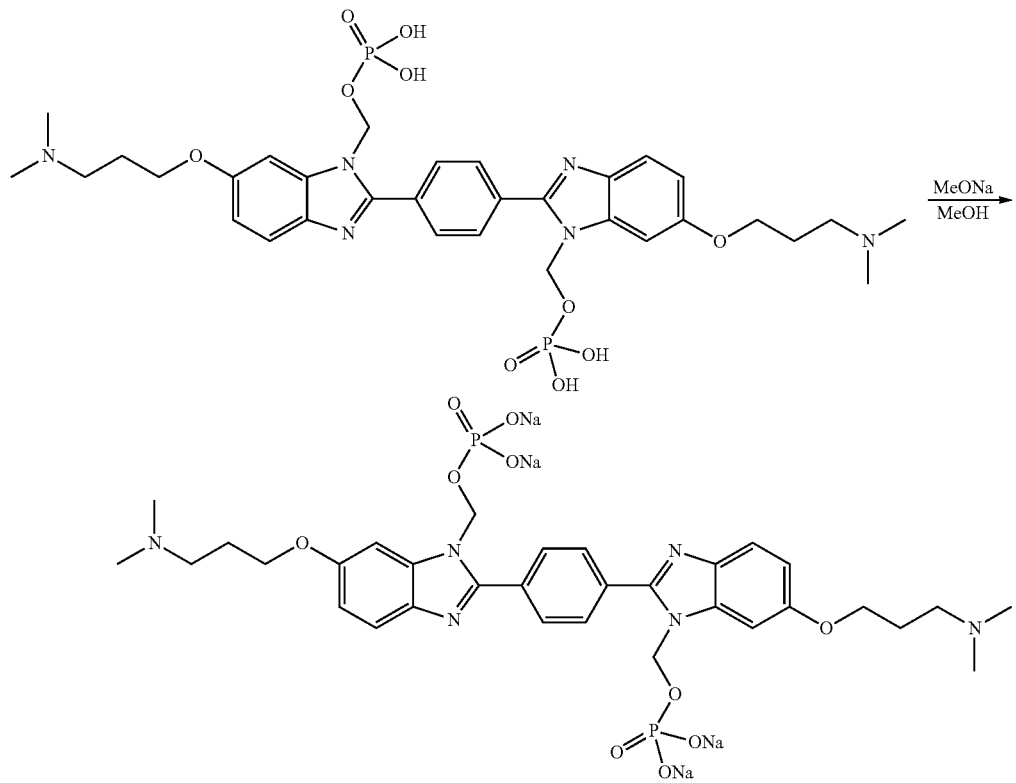

Synthesis of sodium(1,4-phenylenebis(6-(3-(dimethylamino)propoxy)-1H-benzo[d]imidazole-2,1-diyl))bis(methylene)bis(phosphate) Into a 25-mL round-bottom flask, was placed a solution of ([6-[3-(dimethylamino)propoxy]-2-(4-[6-[3-(dimethylamino)propoxy]-1-[(phosphonooxy)methyl]-1H-1,3-benzodiazol-2-yl]phenyl)-1H-1,3-benzodiazol-1-yl]methoxy)phosphonic acid (23 mg, 0.031 mmol, 1 equiv) in methanol (20 mL). Then methoxysodium (6.78 mg, 0.125 mmol, 4.00 equiv) was added in one portion. The resulting solution was stirred for 12 hours at 25°. The resulting mixture was concentrated in vacuo and the residue was dissolved in water which was lyophilized to yield the title compound. MS (ESI): m/z=734 [M+H]+.

Example 190

Synthesis of Compound 284

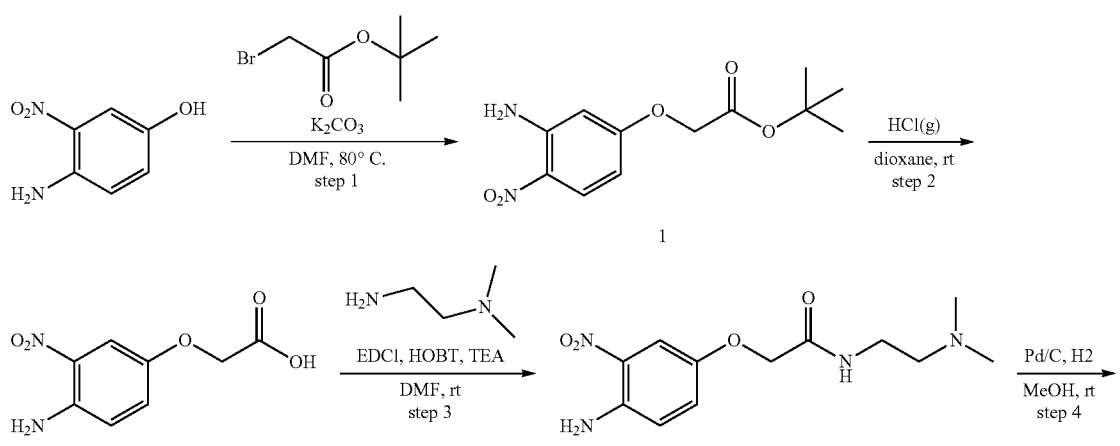

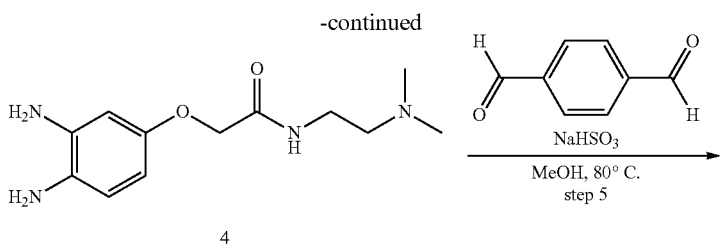

4

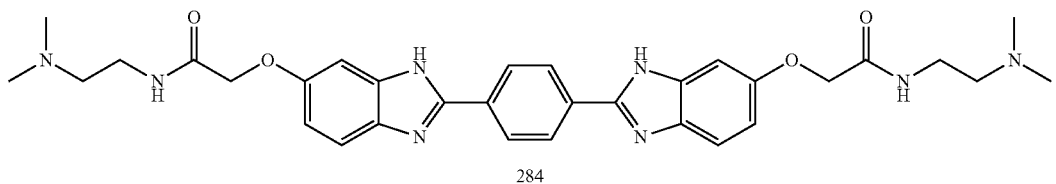

284

Synthesis of tert-butyl 2-(4-amino-3-nitrophenoxy)acetate Into a 250-mL round-bottom flask under a nitrogen atmosphere, was placed a solution of 4-amino-3-nitrophenol (3 g, 19 mmol, 1 equiv), tert-butyl 2-bromoacetate (5.7 g, 29 mmol, 1.5 equiv) and $K_2OC_3$ (5.37 g, 38.9 mmol, 2 equiv) in anhydrous DMF (100 mL). The reaction mixture was stirring at 80° C. for 12 hours. The reaction mixture was diluted with water and extracted with DCM (100 mL×3). The combined organic layer was washed with brine, dried over anhydrous sodium sulphate and concentrated in vacuo. The residue was purified by silica gel column chromatography (100:0 to 5:1 DCM/MeOH) to afford tert-butyl 2-(4-amino-3-nitrophenoxy)acetate Synthesis of 2-(3-amino-4-nitrophenoxy)acetic acid Into a 250-mL round-bottom flask under a nitrogen atmosphere, was placed tert-butyl 2-(4-amino-3-nitrophenoxy)acetate (1.55 g, 5.78 mmol, 1 equiv) in 4 mol/L HCl in 1,4-dioxane (100 mL). The mixture was stirred for 16 hours at room temperature. The resulting mixture was concentrated. The resulting mixture was washed with EtOAc (50 ml). The solids were collected by filtration. This resulted in 2-(3-amino-4-nitrophenoxy)acetic acid.

Synthesis of 2-(3-amino-4-nitrophenoxy)-N-(2-(dimethylamino)ethyl)acetamide To a 50 ml of round-bottomed flask, was placed a solution of 2-(3-amino-4-nitrophenoxy)acetic acid (1.2 g, 5.7 mmol, 1 eq), N1,N1-dimethylethane-1,2-diamine (0.55 g, 6.22 mmol, 1.1 eq), EDC (1.3 g, 6.79 mmol, 1.2 eq), HOBt (0.92 g, 6.79 mmol, 1.2 eq) and TEA (1.72 g, 17 mmol, 3 eq) in anhydrous DMF (15 mL). The reaction mixture was stirring for 12 h at room temperature. After reaction completed, the reaction mixture was concentrated under vacuum and the residue was purified by Combi-Flash (C18 Column; Mobile Phase A: Water, Mobile Phase B: ACN; Flow rate: 60 mL/min; Gradient: 5% B to 50% B in 8 min; 254/220 nm). This afford 2-(3-amino-4-nitrophenoxy)-N-(2-(dimethylamino)ethyl)acetamide.

Synthesis of 2-(3,4-diaminophenoxy)-N-(2-(dimethylamino)ethyl)acetamide Into a 100 mL of round-bottomed flask purged and maintained in a nitrogen atmosphere, was placed a solution of 2-(3-amino-4-nitrophenoxy)-N-(2-(dimethylamino)ethyl)acetamide (1.17 g, 4.1 mmol, 1 equiv) in methanol (50 mL). Then 0.2 g of anhydrous Pd/C (10%) was added. The system was backfilled with hydrogen several times and the reaction mixture was stirred for 16 hours at room temperature under $H_2$. The catalyst was filtered out and the solvent was removed under reduced pressure to result in 2-(3,4-diaminophenoxy)-N-(2-(dimethylamino)ethyl)acetamide which was used in the next step directly.

Synthesis of 2,2'-((1,4-phenylenebis(1H-benzo[d]imidazole-2,6-diyl))bis(oxy))bis(N-(2-(dimethylamino)ethyl)acetamide) In a 40 mL of sealed tube under a nitrogen atmosphere, was placed a solution of terephthalaldehyde (175 mg, 1.3 mmol, 1 equiv), 2,2'-((1,4-phenylenebis(1H-benzo[d]imidazole-2,6-diyl))bis(oxy))bis(N-(2-(dimethylamino)ethyl)acetamide) (989 mg, 1.65 mmol, 3 eq) and $NaHSO_3$ (680.3 mg, 6.54 mmol, 5 eq) in dry MeOH (15 mL). The reaction mixture was 80° C. for 16 h. After reaction completed, the reaction mixture was concentrated under vacuum and the residue was purified by prep-HPLC. This afforded the title compound. MS (ESI): m/z=599 $[M+H]^+$.

Example 191

Synthesis of Compound 285

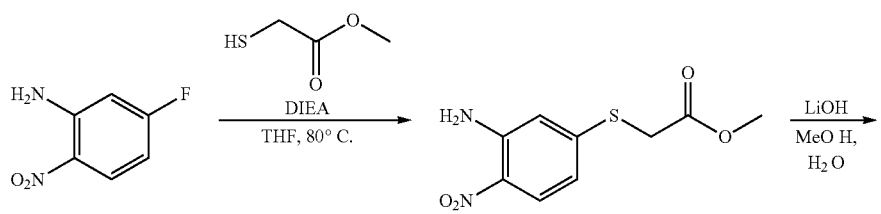

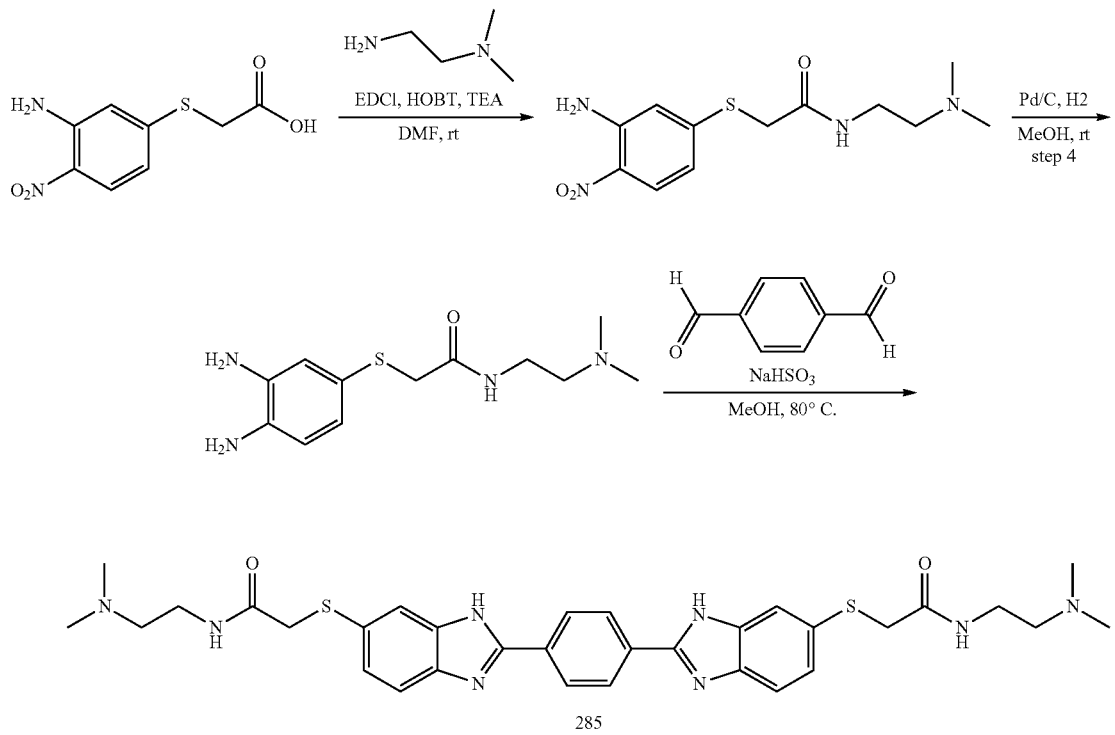

285

Synthesis of methyl 2-[(3-amino-4-nitrophenyl)sulfanyl] acetate Into a 100-mL round-bottom flask purged and maintained with an inert atmosphere of nitrogen, was placed a solution of 5-fluoro-2-nitroaniline (2 g, 12.811 mmol, 1 equiv), DIEA (1.32 g, 10.249 mmol, 0.8 equiv) and methyl 2-sulfanylacetate (1.09 g, 10.249 mmol, 0.8 equiv) in THF (20 mL). The resulting solution was stirred at 65° C. for 16 hours. The crude product was purified by Combi-Flash (Column, C18; Mobile Phase A: Water, Mobile Phase B: ACN; Flow rate: 60 mL/min; 254/220 nm). This resulted in methyl 2-[(3-amino-4-nitrophenyl)sulfanyl]acetate.

Synthesis of 2-[(3-amino-4-nitrophenyl)sulfanyl]acetic acid Into a 100-mL round-bottom flask purged and maintained with an inert atmosphere of nitrogen, was placed a solution of methyl 2-[(3-amino-4-nitrophenyl)sulfanyl]acetate (2 g, 8.256 mmol, 1 equiv) in MeOH (24 mL), then a solution of LiOH (1.98 g, 82.559 mmol, 10 equiv) in $H_2O$ (6 mL) was added dropwise. The resulting solution was stirred at 25° C. for 16 hours. MeOH was removed by reduce pressure and the pH was adjusted to 4-5 by 2N HCl solution. The mixture was extracted by DCM (5×10 ml), the organic layer was washed with saturated NaCl solution and dried with $Na_2SO_4$. The solvent was removed by reduced pressure. This resulted in 2-[(3-amino-4-nitrophenyl)sulfanyl] acetic acid which was used directly without further purification.

Synthesis of 2-[(3-amino-4-nitrophenyl)sulfanyl]-N-[2-(dimethylamino)ethyl]acetamide into a 100-mL round-bottom flask purged and maintained with an inert atmosphere of nitrogen, was placed a solution of 2-[(3-amino-4-nitrophenyl)sulfanyl]acetic acid (1.2 g, 5.258 mmol, 1 equiv), EDCI (1209.58 mg, 6.310 mmol, 1.2 equiv), HOBt (852.59 mg, 6.310 mmol, 1.2 equiv), (2-aminoethyl)dimethylamine (695.28 mg, 7.887 mmol, 1.5 equiv) and TEA (1596.20 mg, 15.774 mmol, 3 equiv) in DMF (50 ml). The resulting solution was stirred at 25° C. for 16 hours and the solvent was removed in vacuo. The crude product was purified by Combi-Flash (Column, C18; Mobile Phase A: Water, Mobile Phase B: ACN; Flow rate: 60 mL/min; 254/220 nm) to afford 2-[(3-amino-4-nitrophenyl)sulfanyl]-N-[2-(dimethylamino) ethyl]acetamide.

Synthesis of 2-[(3,4-diaminophenyl)sulfanyl]-N-[2-(dimethylamino)ethyl]acetamide into a 100-mL round-bottom flask purged and maintained with an inert atmosphere of nitrogen, was placed a solution of 2-[(3-amino-4-nitrophenyl)sulfanyl]-N-[2-(dimethylamino)ethyl]acetamide (574 mg, 1.924 mmol, 1 equiv) in MeOH (20 ml). Then anhydrous Pd/C (500 mg) was added carefully. The reaction system was backfilled with hydrogen several times and the resulting solution was stirred at 25° C. for 16 hours. The catalyst was filtered out and the MeOH was removed by reduce pressure. This resulted in 2-[(3,4-diaminophenyl) sulfanyl]-N-[2-(dimethylamino)ethyl]acetamide which was used directly without further purification.

Synthesis of N-[2-(dimethylamino)ethyl]-2-[[2-(4-[6-[([[2-(dimethylamino)ethyl]carbamoyl]methyl)sulfanyl]-1H-1,3-benzodiazol-2-yl]phenyl)-1H-1,3-benzodiazol-6-yl] sulfanyl]acetamide into a 50-mL of round-bottom flask under a nitrogen atmosphere, was placed a suspension of 2-[(3,4-diaminophenyl)sulfanyl]-N-[2-(dimethylamino) ethyl]acetamide (470.20 mg, 1.752 mmol, 2.5 equiv), benzene-1,4-dicarbaldehyde (94 mg, 0.701 mmol, 1 equiv) and $NaHSO_3$ (364.63 mg, 3.504 mmol, 5 equiv) in MeOH (20 ml). The resulting solution was stirred at 80° C. for 16 hours. The crude product was purified by prep-HPLC. This resulted in the title compound. MS (ESI): m/z=631 [M+H]$^+$ Example 192
Synthesis of Compound 286
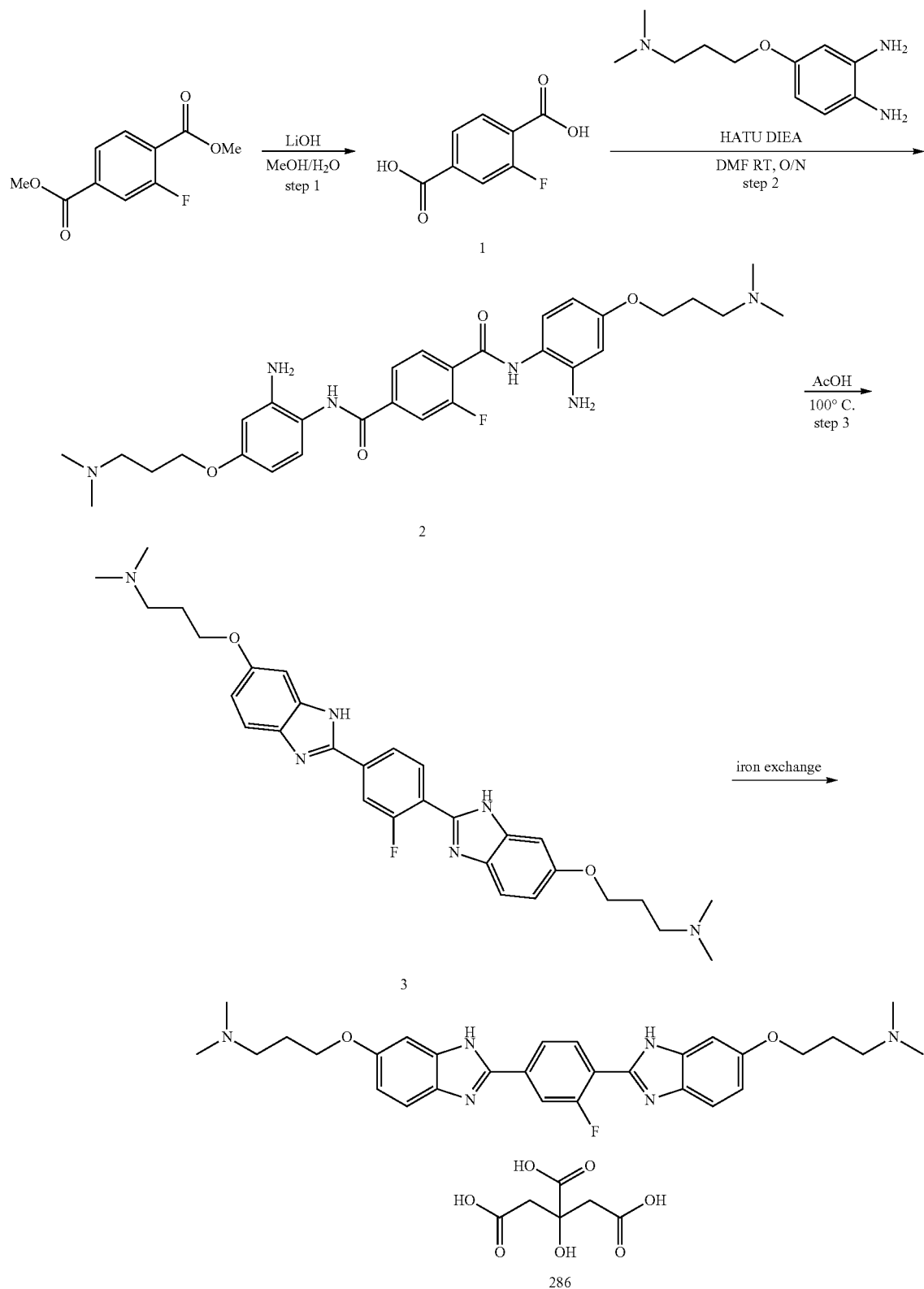

Synthesis of Compound 1: Into a 50-mL of round-bottom flask, was placed a solution of 1,4-dimethyl 2-fluorobenzene-1,4-dicarboxylate (1 g, 4.713 mmol, 1 equiv) in MeOH (20 ml). Then a solution of LiOH (1.13 g, 47.131 mmol, 10 equiv) in H$_2$O (5 ml) was added at RT. The resulting suspension was stirred at room temperature for 12 h. The reaction mixture was acidified with 2M HCl to pH=3-4. The solid was collected by filtration and washed with water, dried in vacuo. This afforded the target product 2-fluorobenzene-1,4-dicarboxylic acid Synthesis of Compound 2: Into a 10-mL round-bottom flask purged and maintained with an inert atmosphere of nitrogen was placed a solution of 2-fluorobenzene-1,4-dicarboxylic acid (200 mg, 1.086 mmol, 1 equiv), 4-[3-(dimethylamino)propoxy]benzene-1,2-diamine (682 mg, 3.258 mmol, 3 equiv) and HATU (1.24 mg, 3.26 mmol, 3 equiv) in anhydrous DMF (5 ml). Then DIEA (702 mg, 5.432 mmol, 5 equiv) was added at rt. The reaction mixture was stirred at room temperature for 12 h. The reaction mixture was purified by pre-TLC (MeOH:TEA=100:1) to afford desired product N1,N4-bis([2-amino-4-[3-(dimethylamino)propoxy]phenyl])-2-fluorobenzene-1,4-dicarboxamide Synthesis of Compound 3: Into a 50 ml round-bottom flask purged and maintained at a nitrogen atmosphere, was placed a solution of N1,N4-bis([2-amino-4-[3-(dimethylamino)propoxy]phenyl])-2-fluorobenzene-1,4-dicarboxamide (420 mg, crude) in AcOH (15 mL). The reaction was heated to 100° C. for 12 h. The reaction mixture was cooled to room temperature and concentrated in vacuo. The residue was purified by preparative prep-HPLC. This afford (3-[[2-(4-[6-[3-(dimethylamino)propoxy]-1H-1,3-benzodiazol-2-yl]-3-fluorophenyl)-1H-1,3-benzodiazol-6-yl]oxy]propyl) dimethylamine.

Synthesis of Compound 286: 103.1 mg of (3-[[2-(4-[6-[3-(dimethylamino)propoxy]-1H-1,3-benzodiazol-2-yl]-3-fluorophenyl)-1H-1,3-benzodiazol-6-yl]oxy]propyl)dimethylamine was dissolved in 5 mL (as less as possible) of MeOH/H$_2$O (1/10=v/v). The solution was applied on an ion-exchange column and eluting with a mixed solvent of MeOH/H2O (1/10: v/v). This resulted in the title compound. MS (ESI): m/z=531 [M+H]$^+$.

Compound 286 was prepared in the same manner as compound 286. MS (ESI): m/z=531 [M+H]$^+$.

Treatment of the resin: 15-20 g of commercial available (Beijing Innochem Science & Technology Co. Ltd) anion-exchange resin (Dowex 1×8 (a), 100-200 mesh) was washed with 100 mL×3 of a mixed solvent of methanol and de-ionized water (1/10 v/v) in a 250-mL beaker and then treated as follows:

The suspension of resin in water was packed in a column (30 mm×400 mm, resin height: ~25 cm) and eluted with 1-2 volume of the column of de-ionized water, then eluted with 2 N NaOH for 2-3 volume of the column. After eluting with de-ionized water to neutral, the resin was eluted with 2-3 volume of the column of 2 N citric acid solution in de-ionized water. Then the column was eluted with mixed solvent of methanol and de-ionized water (1/10 v/v) until the eluent was near neutral.

Example 193

Synthesis of Compound 288

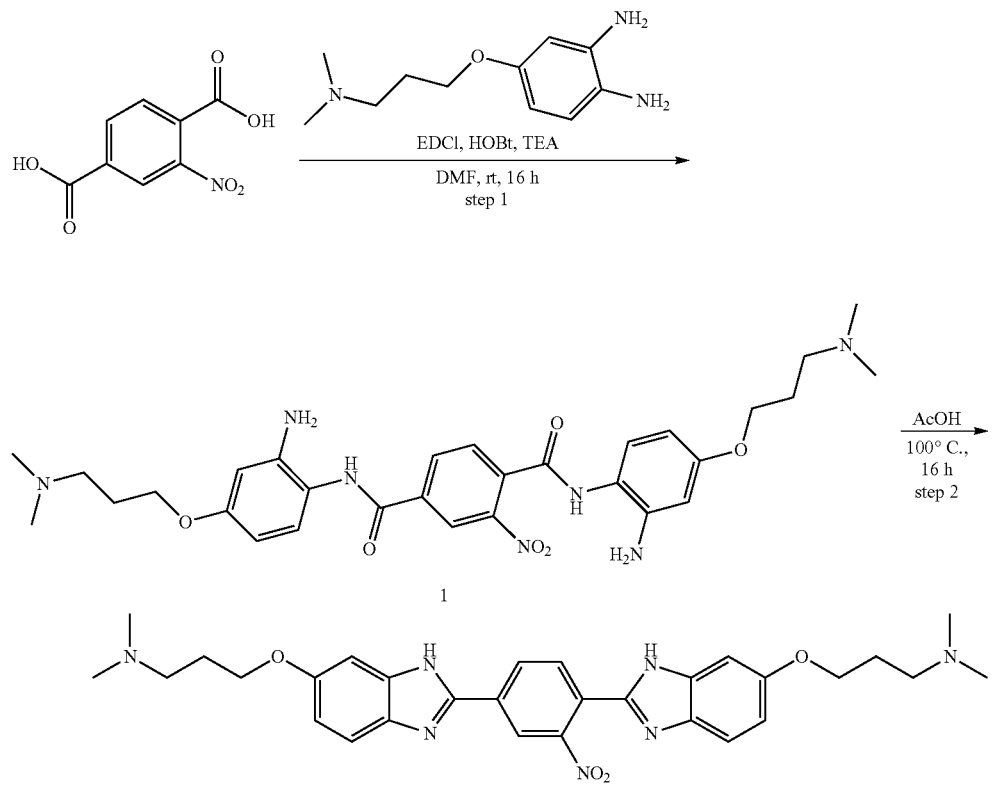

Synthesis of Compound 1: Into a 50 mL of round-bottom flask under a nitrogen atmosphere, was placed a solution of 2-nitroterephthalic acid (600 mg, 2.8 mmol, 1 equiv), 4-(3-(dimethylamino)propoxy)benzene-1,2-diamine (1.5 g, 7 mmol, 2.5 equiv), EDCl (1.3 g, 7 mmol, 2.5 equiv), HOBT (952 mg, 7 mmol, 2.5 equiv) and TEA (1.7 g, 16.8 mmol, 6 equiv) in anhydrous DMF (10 mL). The reaction mixture was stirred at room temperature for 16 hours. Then the solvent was removed under reduced pressure and the residue was purified by Combi-Flash eluting with DCM/MeOH (1:1) to afford N1,N4-bis(2-amino-4-(3-(dimethylamino)propoxy)phenyl)-2-nitroterephthalamide Synthesis of Compound 288: Into a 25 mL of round-bottom flask in a nitrogen atmosphere, was placed a solution of N1,N4-bis(2-amino-4-(3-(dimethylamino)propoxy)phenyl)-2-nitroterephthalamide (160 mg, 0.27 mmol, 1 equiv) in AcOH (5 ml). The reaction mixture was stirred at 100° C. for 16 hours. The solvent was removed under reduced pressure and the residue was purified by prep-HPLC. This resulted in the title compound. MS (ESI): m/z=558 [M+H]$^+$.

Example 194

Synthesis of Compound 291

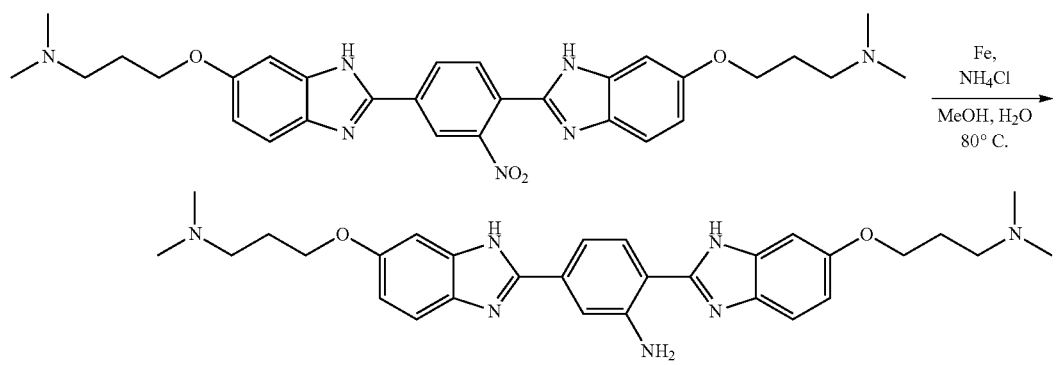

Synthesis of 3,3'-(((2-amino-1,4-phenylene)bis(1H-benzo[d]imidazole-2,6-diyl))bis(oxy))bis(N,N-dimethylpropan-1-amine) In a 50 ml of round-bottom flask, was placed a suspension of 3,3'-(((2-nitro-1,4-phenylene)bis(1H-benzo[d]imidazole-2,6-diyl))bis(oxy))bis(N,N-dimethylpropan-1-amine) (110 mg, 0.2 mmol, 1 eq), Fe powder (33.05 mg, 0.59 mmol, 3 eq) and NH$_4$Cl (31.65 mg, 0.59 mmol, 3 eq) in MeOH (10 mL). The reaction mixture was 80° C. for 16 h. After reaction completed, the solid was filtered out and the residue was concentrated in vacuo. The residue was purified by prep-HPLC to afford the title compound. MS (ESI): m/z=528 [M+H]$^+$.

Example 195

Synthesis of Compound 292

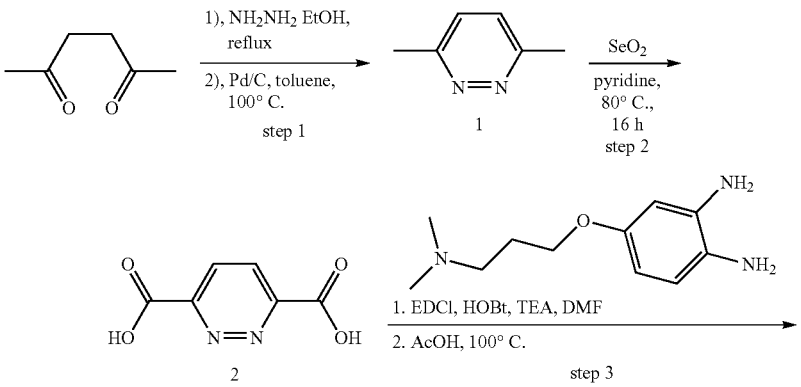

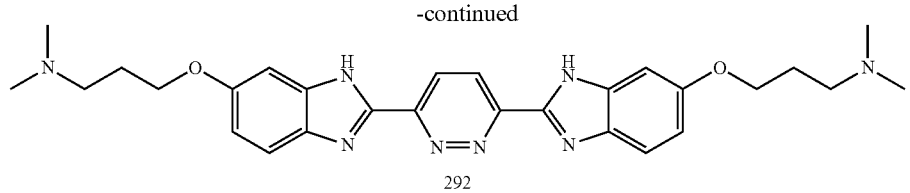

292

Synthesis of Compound 1: Into a 50 mL of round-bottom flask purged and maintained in a nitrogen atmosphere, was placed a suspension of hexane-2,5-dione (1 g, 8.761 mmol, 1 equiv) and hydrazine hydrate (0.56 g, 17.475 mmol, 1.99 equiv) in EtOH (15 mL). The reaction mixture was stirred at 90° C. for 10 h. The solvent was removed under reduced pressure and the crude product was used in the next step directly without further purification. Into above crude product toluene (20 mL) was added in a nitrogen atmosphere, then Pd/C (1.93 g, 18.136 mmol, 2.00 equiv) was added slowly. The resulting mixture was stirred at 100° C. for 10 h. After cooling to room temperature, the solid was filtered out and the filter cake was washed with cold MeOH (3×10 mL). The filtrate was concentrated under reduce pressure. The residue was purified by silica gel column chromatography, eluted with $CH_2Cl_2$/MeOH (30:1) to afford 3,6-dimethylpyridazine Synthesis of Compound 2: Into a 100 mL of round-bottom flask maintained in a nitrogen atmosphere, was placed a mixture of 3,6-dimethylpyridazine (700 mg, 6.473 mmol, 1 equiv) and $SeO_2$ (3591.14 mg, 32.364 mmol, 5.00 equiv) in pyridine (20 mL). The reaction mixture was stirred for 16 h at 120° C. After cooling to room temperature, the resulting mixture was concentrated under reduced pressure. Into above crude product was added water (30 mL) and the resulting mixture was stirred for 2 h at room temperature. The solid was collected by filtration and washed with MeOH (3×10 mL). The filtrate was concentrated under reduced pressure. This resulted in pyridazine-3,6-dicarboxylic acid which was used in the next step directly.

Synthesis of Compound 3: Into a 10 mL of round-bottom flask purged and maintained in a nitrogen atmosphere, was placed a solution of pyridazine-3,6-dicarboxylic acid (50 mg, 0.297 mmol, 1 equiv), 4-[3-(dimethylamino)propoxy]benzene-1,2-diamine (130.72 mg, 0.625 mmol, 2.10 equiv), EDCl (171.05 mg, 0.892 mmol, 3 equiv), HOBT (120.57 mg, 0.892 mmol, 3 equiv) and TEA (180.58 mg, 1.785 mmol, 6 equiv) in anhydrous DMF (2.5 mL). The reaction mixture was stirred at rt for 16 h. The residue was purified by Prep-TLC (MeOH/TEA 100:1) to afford a crude product. Then the crude product was dissolved with AcOH (5 mL) in a 25 mL of round-bottom flask and the solution was stirred at 100° C. for 16 h under a nitrogen atmosphere. After the reaction completed, the solvent was removed under reduced pressure. and the crude product was purified by Prep-HPLC to afford the title compound. MS (ESI): m/z=258/515 $[M+H]^+$.

Example 196

Synthesis of Compound 293

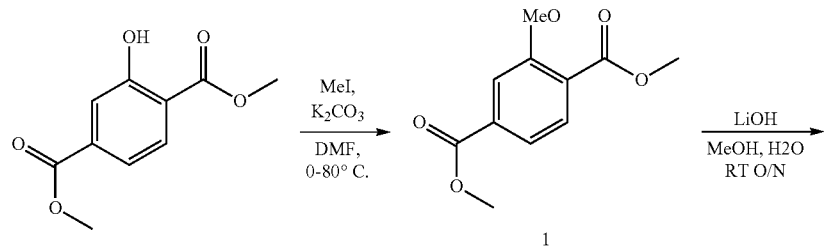

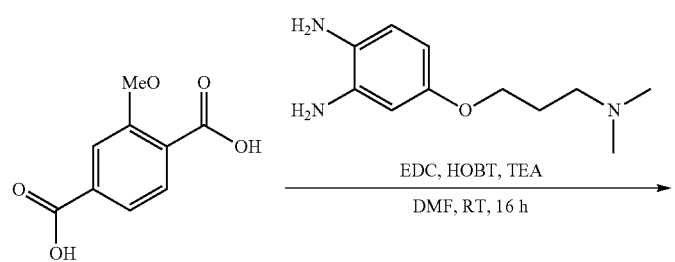

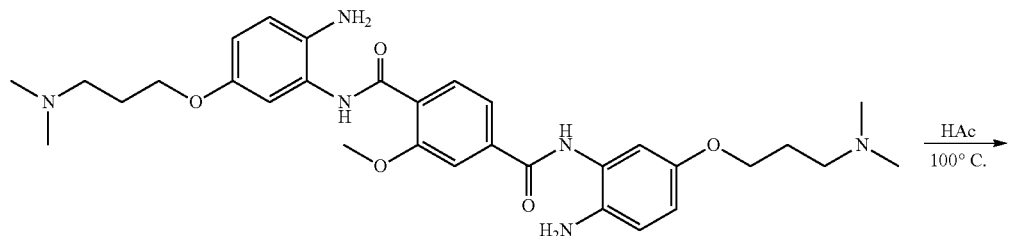

3

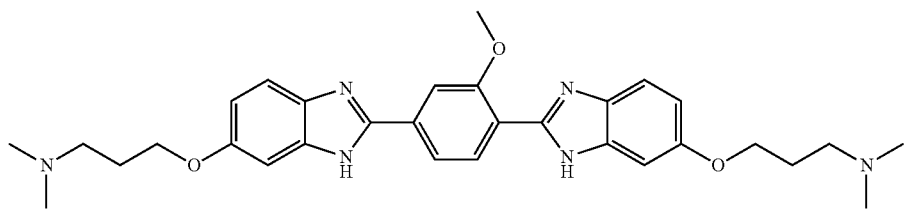

293

Synthesis of Compound 1: Into a 50 ml of round-bottom flask maintained in a nitrogen atmosphere, was placed a suspension of 1,4-dimethyl 2-hydroxybenzene-1,4-dicarboxylate (350 mg, 1.665 mmol, 1 equiv) and $K_2CO_3$ (690.42 mg, 4.996 mmol, 3.00 equiv) in DMF (10 ml). Then MeI (354.5 mg, 2.5 mmol, 1.5 equiv) was added dropwise at 0° C. The resulting mixture was stirred at 80° C. for 16 hours. The resulting was quenched with water (50 ml) and extracted by EtOAc (3×20 mL). The organic layer combined was washed with brine, dried over with anhydrous $Na_2SO_4$ and concentrated under reduced pressure. This resulted in 1,4-dimethyl 2-methoxybenzene-1,4-dicarboxylate Synthesis of Compound 2: Into a 50-mL of round-bottom flask, was placed a solution of 1,4-dimethyl 2-methoxybenzene-1,4-dicarboxylate (357 mg, 1.592 mmol, 1 equiv) in MeOH (5 mL). Then a solution of LiOH (114.40 mg, 4.777 mmol, 3.00 equiv) in H2O (5 mL) was added in one portion at 0° C. The resulting solution was stirred for 2 hr at room temperature. The methanol was removed under reduced pressure and the pH was adjusted to 3-4 by 2N HCl solution. The mixture was extracted with ethyl acetate (3×10 mL) and the organic layer combined was washed with brine solution, dried over with anhydrous $Na_2SO_4$ and concentrated under reduced pressure. This resulted in 2-methoxybenzene-1,4-dicarboxylic acid.

Synthesis of Compound 3: Into a 50-mL of round-bottom flask purged and maintained with an inert atmosphere of nitrogen, was placed a solution of 2-methoxybenzene-1,4-dicarboxylic acid (100 mg, 0.510 mmol, 1 equiv), 4-[3-(dimethylamino)propoxy]benzene-1,2-diamine (234.73 mg, 1.122 mmol, 2.20 equiv), EDC (197.85 mg, 1.274 mmol, 2.50 equiv) HOBT (172.21 mg, 1.274 mmol, 2.50 equiv) and TEA (154.76 mg, 1.529 mmol, 3.00 equiv) in anhydrous DMF (10 ml). The resulting solution was stirred at room temperature for 16 hours. The residue was applied onto a silica gel column with MeOH/TEA (50:1). This resulted in N1,N4-bis([2-amino-5-[3-(dimethylamino)propoxy]phenyl])-2-methoxybenzene-1,4-dicarboxamide Synthesis of 293: Into a 25-mL of round-bottom flask purged and maintained with atmosphere of nitrogen, was placed a solution of N1,N4-bis([2-amino-5-[3-(dimethylamino)propoxy]phenyl])-2-methoxybenzene-1,4-dicarboxamide (200 mg, 0.346 mmol, 1 equiv) in HOAc (8 ml). The resulting solution was stirred at 100° C. overnight. The resulting mixture was cooled to room temperature and concentrated under vacuum. The crude product was purified by Prep-HPLC. This resulted in the title compound. MS (ESI) m/z=543 [M+H]$^+$.

Example 197

Synthesis of Compound 294

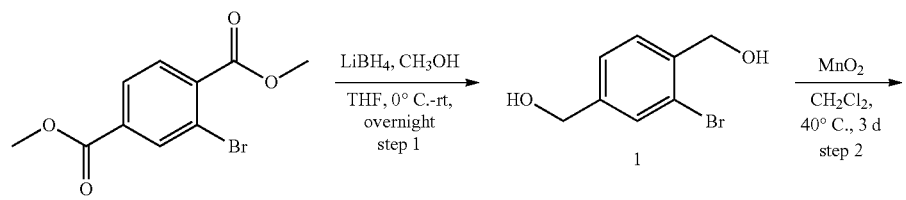

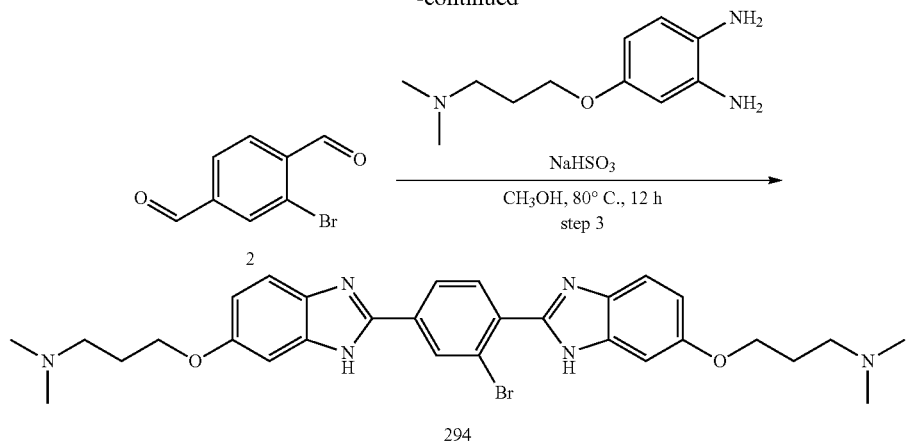

Synthesis of (2-bromo-1,4-phenylene)dimethanol Into a 50-mL of round-bottom flask purged and maintained with an inert atmosphere of nitrogen, was placed a solution of dimethyl 2-bromoterephthalate (2.0 g, 7.4 mmol, 1 equiv) in anhydrous THF (10 mL). Then LiBH4 (360 mg, 16.3 mmol, 2.2 equiv) was added slowly at 0° C. Then 1 mL of MeOH was added to the mixture. The reaction mixture was stirred at room temperature for 16 hours. The reaction mixture was quenched with 1 M HCl solution and the pH was adjusted to 6-7. Then, the mixture was extracted with ethyl acetate (5×10 ml), the organic layer was combined, washed with brine, dried over $Na_2SO_4$, filtered and concentrated in vacuo. The residue was purified by prep-TLC with PE/EA (1:1) to afford (2-bromo-1,4-phenylene)dimethanol.

Synthesis of 2-bromoterephthalaldehyde Into a 50-mL of round-bottom flask, was placed a solution of (2-bromo-1,4-phenylene)dimethanol (400 mg, 1.9 mmol, 1 equiv) in DCM 10 mL). Then MnO2 (1.6 g, 19 mmol, 10 equiv) was added in one portion. The resulting suspension was stirred at 40° C. for 3 days. The solid was filtered out and the filtrate was concentrated under reduced pressure. The crude was purified by prep-TLC with PE/EA (10:1). This result in 2-bromo-terephthalaldehyde.

Synthesis of 3,3'-(2,2'-(2-bromo-1,4-phenylene)bis(3H-benzo[d]imidazole-5,2-diyl))bis(oxy)bis(N,N-dimethylpropan-1-amine) Into a 50-mL of round-bottom flask under a nitrogen atmosphere, was placed a suspension of 2-bromoterephthalaldehyde (200 mg, 0.94 mmol, 1 equiv), $NaHSO_3$ (390 mg, 3.8 mmol, 4 equiv) and 4-(3-(dimethylamino)propoxy)benzene-1,2-diamine (400 mg, 1.9 mmol, 2 equiv) in anhydrous MeOH (10 mL). The resulting solution was stirred at 80° C. for 16 hours. The resulting mixture was concentrated in vacuum. The crude product was purified by Prep-HPLC with the following conditions. This resulted in the title compound. MS (ESI): m/z=593 [M+H]+

Example 198

Synthesis of Compound 296

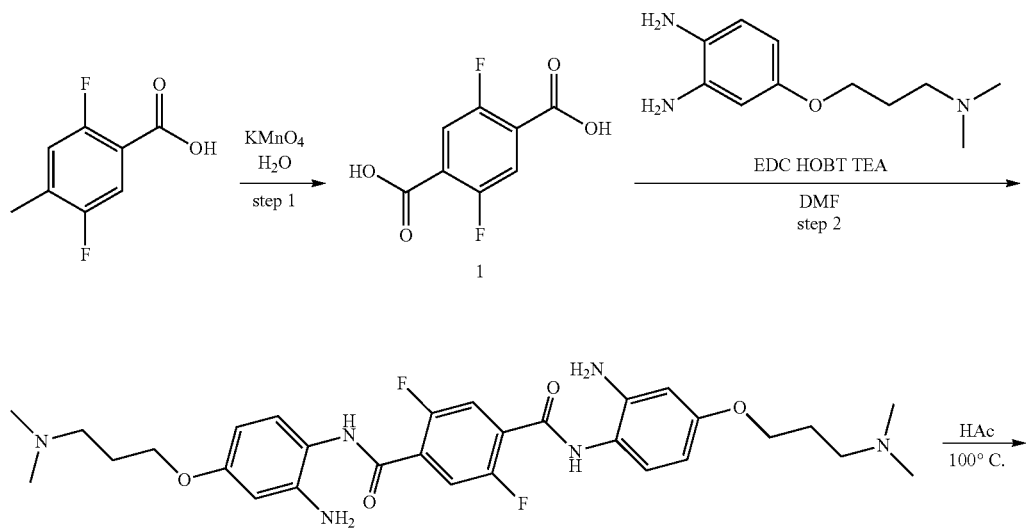

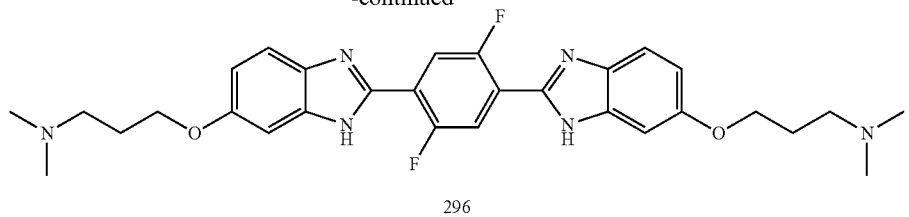

296

Synthesis of Compound 1: Into a 50-mL of round-bottom flask, was placed a solution of 2,5-difluoro-4-methylbenzoic acid (1 g, 5.810 mmol, 1 equiv) and KMnO4 (4.59 g, 29.048 mmol, 5 equiv) in water (20 mL). The resulting solution was stirred overnight at 100° C. The solids were filtered out. The pH of the filtrate was adjusted to 3 with HCl (6 mol/L). The solids were collected by filtration, washed by cool water and dried in vacuo. This resulted in 2,5-difluorobenzene-1,4-dicarboxylic acid.

Synthesis of Compound 2: Into a 50-mL round-bottom flask purged and maintained with an inert atmosphere of nitrogen, was placed a solution of 2,5-difluorobenzene-1,4-dicarboxylic acid (200 mg, 0.990 mmol, 1 equiv), 4-[3-(dimethylamino)propoxy]benzene-1,2-diamine (414.21 mg, 1.979 mmol, 2.00 equiv), HOBT (294.16 mg, 2.177 mmol, 2.2 equiv) and EDC (337.96 mg, 2.177 mmol, 2.2 equiv) in anhydrous N,N-dimethylformamide (10 mL). This was followed by the addition of TEA (300.40 mg, 2.969 mmol, 3 equiv) dropwise with stirring at 0° C. The resulting solution was stirred overnight at room temperature. The residue was applied onto a silica gel column elution with MEOH:TEA (50:1). This resulted in N1,N4-bis([2-amino-4-[3-(dimethylamino)propoxy]phenyl])-2,5-difluorobenzene-1,4-dicarboxamide Synthesis of 296: Into a 50-mL round-bottom flask purged and maintained with an inert atmosphere of nitrogen, was placed a solution of N1,N4-bis([2-amino-4-[3-(dimethylamino)propoxy]phenyl])-2,5-difluorobenzene-1,4-dicarboxamide (200 mg, 0.342 mmol, 1 equiv) in HOAc (10 mL). The resulting solution was stirred at 100° C. for 3 hours. The resulting mixture was cooled to room temperature and concentrated under vacuum. The crude product was purified by Prep-HPLC. This resulted in the title compound. MS (ESI) m/z=549 [M+H]+.

Example 199

Synthesis of Compound 297

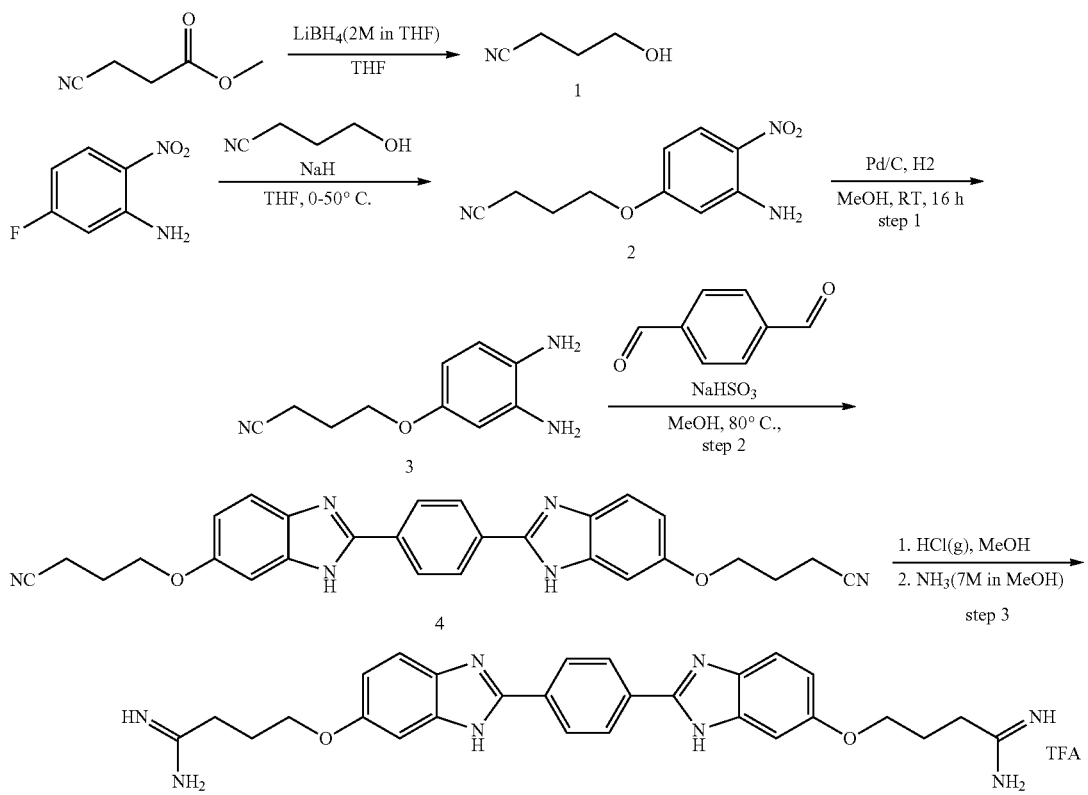

297

Synthesis of Compound 1: Into a 250-mL round-bottom flask purged and maintained with an inert atmosphere of nitrogen, was placed a solution of methyl 3-cyanopropanoate (5 g, 44.202 mmol, 1 equiv) in anhydrous THF (50 mL). Then LiBH4 (50 mL 2M in THF) was added dropwise at 0° C. The resulting solution was stirred at 80° C. for 3 hours. The reaction was then cooled to room temperature and quenched by the addition of water. The mixture was extracted by DCM (3×50 ml) and the organic layer combined was washed with brine, dried over $Na_2SO_4$, filtration and concentrated in vacuo. The residue was applied onto a silica gel column eluting with ethyl acetate/hexane (10:1). This resulted in 4-hydroxybutanenitrile.

Synthesis of Compound 2: Into a 50-mL of round-bottom flask purged and maintained with an inert atmosphere of nitrogen, was placed a solution of 4-hydroxybutanenitrile (0.65 g, 7.687 mmol, 1.2 equiv) in anhydrous THF (10 mL). Then NaH (461.15 mg, 19.216 mmol, 3.00 equiv) was added portionwise at 0° C. The reaction mixture was stirred at rt for 30 min. Then a solution of 5-fluoro-2-nitroaniline (1 g, 6.405 mmol, 1 equiv) in THF (5 mL) was added dropwise at 0° C. The resulting solution was stirred at 50° C. overnight. The resulting solution was cooled to room temperature and quenched by the addition of water (20 mL). The resulting mixture was extracted with ethyl acetate (5×20 ml) and the organic layer combined was washed with brine, dried over anhydrous sodium sulfate and concentrated under vacuum. The residue was applied onto a silica gel column eluting with ethyl acetate/hexane (1:1). This resulted in 4-(3-amino-4-nitrophenoxy)butanenitrile.

Synthesis of Compound 3: Into a 100-mL of round-bottom flask purged and maintained in a nitrogen atmosphere, was placed a solution of 4-(3-amino-4-nitrophenoxy)butanenitrile (400 mg, 1.808 mmol, 1 equiv) in anhydrous MeOH (25 ml). Then Pd/C (300 mg) was added carefully. The reaction system was backfilled with hydrogen several times. The resulting mixture was stirred at rt for 16 hours. The catalyst was filtered out and the filtrate was concentrated under vacuum. This resulted in 4-(3,4-diaminophenoxy)butanenitrile which was used in the next step directly without further purification.

Synthesis of Compound 4: Into a 25-mL of round-bottom flask purged and maintained with an inert atmosphere of nitrogen, was placed a solution of 4-(3,4-diaminophenoxy)butanenitrile (300 mg, 1.569 mmol, 1 equiv), benzene-1,4-dicarbaldehyde (95.74 mg, 0.714 mmol, 0.455 equiv) and NaHSO3 (926 mg, 3.14 mmol, 2 equiv) in MeOH (10 mL). The resulting solution was stirred at 80° C. for 16 hours. The crude product was purified by Combi-Flash (Column, C18; mobile phase, $H_2O$ (0.05% TFA)/ACN=35%; Detector, 254 nm). This resulted in 4-[(2-[4-[6-(3-cyanopropoxy)-1H-1,3-benzodiazol-2-yl]phenyl]-1H-1,3-benzodiazol-6-yl)oxy]butanenitrile.

Synthesis of 297: Into a 250-mL three round flask purged and maintained with an inert atmosphere of nitrogen, was placed a solution of 4-[(2-[4-[6-(3-cyanopropoxy)-1H-1,3-benzodiazol-2-yl]phenyl]-1H-1,3-benzodiazol-6-yl)oxy]butanenitrile (187 mg, 0.392 mmol) in anhydrous MeOH (10 mL). Then dry HCl (g) was bubbled into above solution at 0° C. for 4 hours until the starting material was consumed completely which was confirmed by the LCMS monitor. Then $NH_3$ (7M in MeOH) was added dropwise with stirring at 0° C. until the pH reached 8-9. The resulting solution was stirred at 0° C. for another 2 hours. The solids were filtered out. The filtrate was acidified with HCl (6 mol/L) until the pH of solution=3-4. The crude product was purified by Prep-HPLC. This resulted in the title compound. MS (ESI) m/z=511 [M+H]$^+$.

Example 200

Synthesis of Compound 298

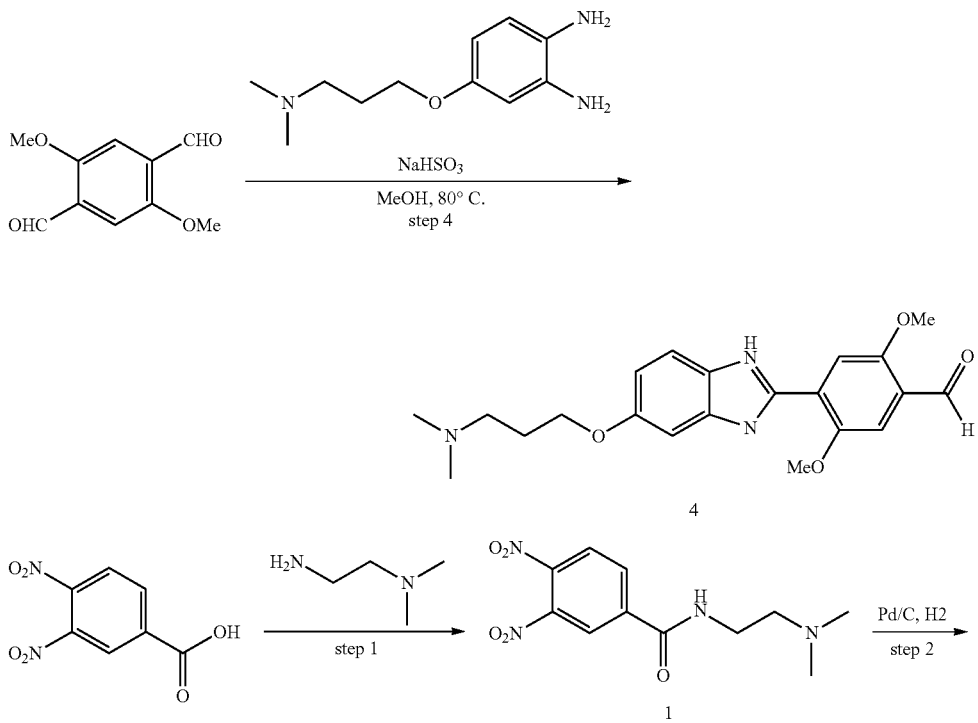

-continued

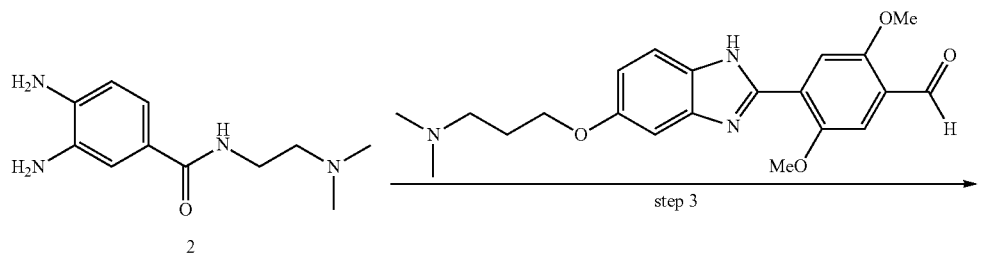

2

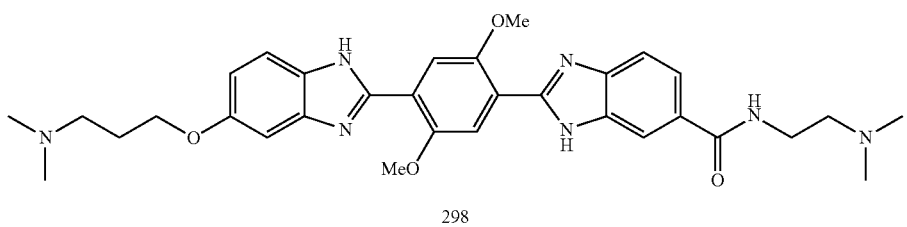

298

Synthesis of Compound 1: in a 50 ml of round-bottom flask purged and maintained in a nitrogen atmosphere, was placed a solution of 3,4-dinitrobenzoic acid (1 g, 4.7 mmol, 1 equiv) in DCM (10 ml). Then oxalyl dichloride (890 mg, 7.05 mmol, 1.5 equiv) was added dropwise at 0° C. followed by the addition of DMF (2 drops). The mixture was stirred at rt for 3 hours. The solvent was removed by reduce pressure to afford the acyl chloride. The crude acyl chloride was dissolved in anhydrous DCM (2 ml) and added dropwise to a solution of N1,N1-dimethylethane-1,2-diamine (620 mg, 7.05 mmol, 1.5 equiv) and TEA (1.4 g, 14.1 mmol, 3 equiv) in DCM (10 ml) at 0° C. and the result mixture was stirred at 0° C. for 3 hours. The mixture was concentrated in vacuo and the residue was purified by prep-TLC (DCM/MeOH=10:1) to afford N-(2-(dimethylamino)ethyl)-3,4-dinitrobenzamide.

Synthesis of Compound 2: Into a 100-mL round-bottom flask purged and maintained at a nitrogen atmosphere, was placed a solution of N-(2-(dimethylamino)ethyl)-3,4-dinitrobenzamide (200 mg, 0.7 mmol) in MeOH (10 mL). Then Pd/C (200 mg) was added carefully. The system was back-filled with hydrogen several times and the resulting solution was stirred for 12 h at room temperature. After the reaction completed, the catalyst was filtered off. The filtrate was concentrated under vacuum to afford 3,4-diamino-N-(2-(dimethylamino)ethyl)benzamide.

Synthesis of Compound 4: in a 50 ml of round-bottom flask in a nitrogen atmosphere, was placed a solution of 2,5-dimethoxyterephthalaldehyde (1 g, 5.14 mmol, 1 equiv), 4-(3-(dimethylamino)propoxy)benzene-1,2-diamine (1.077 g, 5.1 mmol, 1 equiv) and NaHSO$_3$ (1.07 g, 10 mmol, 2 equiv) in dry MeOH (20 mL). The resulting solution was stirred for 16 hours at 80°. After reaction completed, the reaction mixture was cooled to room temperature and concentrated under vacuum. The residue was purified by silica gel column chromatography (100:0 to 5:1 DCM/MeOH) to afford 4-(5-(3-(dimethylamino)propoxy)-1H-benzo[d]imidazol-2-yl)-2,5-dimethoxybenzaldehyde.

Synthesis of 298: in a 50 ml of round-bottom flask in a nitrogen atmosphere, was placed a solution of 4-(5-(3-(dimethylamino)propoxy)-1H-benzo[d]imidazol-2-yl)-2,5-dimethoxybenzaldehyde (80 mg, 0.21 mmol, 1 equiv), 3,4-diamino-N-(2-(dimethylamino)ethyl)benzamide (92.76 mg, 0.42 mmol, 2 equiv) and NaHSO$_3$ (43 mg, 0.42 mmol, 2 equiv) in dry MeOH (15 mL). The resulting solution was stirred for 16 hours at 80° C. After reaction completed, the reaction mixture was concentrated under vacuum and the residue was purified by preparative HPLC. This afforded the title compound. MS (ESI) m/z=586 [M+H]$^+$.

Example 201

Synthesis of Compound 299

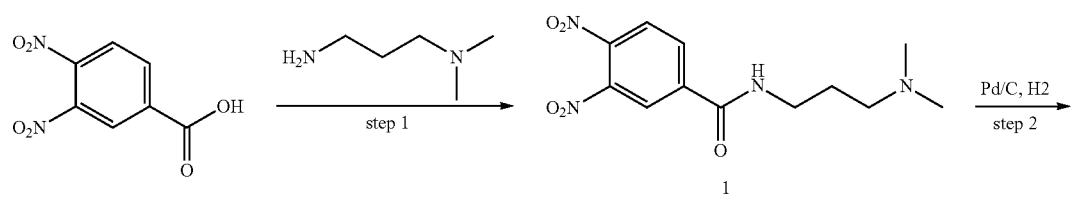

1

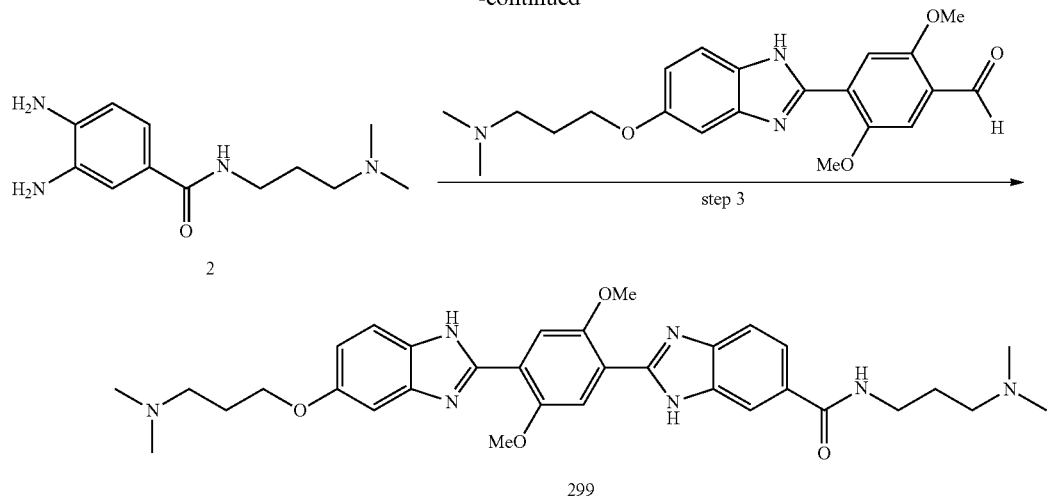

Synthesis of Compound 1: in a 50 ml of round-bottom flask in a nitrogen atmosphere, was placed a solution of 3,4-dinitrobenzoic acid (1 g, 4.7 mmol, 1 equiv) in anhydrous DCM (10 ml), then oxalyl dichloride (890 mg, 7.05 mmol, 1.5 equiv) was added dropwise at 0° C. followed by the addition of DMF (2 drops). The mixture was stirred at rt for 3 hours. The solvent was removed by reduce pressure to afford the acyl chloride. The crude acyl chloride was dissolved in anhydrous DCM (2 ml) and added dropwise to a solution of N1,N1-dimethylpropane-1,3-diamine (720 mg, 7.05 mmol, 1.5 equiv) and TEA (1.4 g, 14.1 mmol, 3 equiv) in DCM (10 ml) at 0° C. The resulting mixture was stirred at 0° C. for 3 hours. The mixture was concentrated in vacuo and purified by prep-TLC (DCM/MeOH=10:1) to afford N-(3-(dimethylamino)propyl)-3,4-dinitrobenzamide.

Synthesis of Compound 2: Into a 100-mL round-bottom flask purged and maintained at a nitrogen atmosphere, was placed a solution of N-(3-(dimethylamino)propyl)-3,4-dinitrobenzamide (350 mg, 1.2 mmol) in MeOH (10 mL). Then Pd/C (200 mg) was added carefully. The system was back-filled with hydrogen several times and the resulting solution was stirred for 12 h at room temperature. After the reaction completed, the catalyst was filtered off. The filtrate was concentrated under vacuum to afford 3,4-diamino-N-(3-(dimethylamino)propyl)benzamide.

Synthesis of 299: in a 50 ml of round-bottom flask in a nitrogen atmosphere, was placed a solution of 4-(5-(3-(dimethylamino)propoxy)-1H-benzo[d]imidazol-2-yl)-2,5-dimethoxybenzaldehyde (90 mg, 0.23 mmol, 1 equiv), 3,4-diamino-N-(3-(dimethylamino)propyl)benzamide (111 mg, 0.47 mmol, 2 equiv), and NaHSO$_3$ (49 mg, 0.47 mmol, 2 equiv) in dry MeOH (15 mL). The resulting solution was stirred for 16 hours at 80° C. After reaction completed, the reaction mixture was concentrated under vacuum and the residue was purified by preparative HPLC. This afforded the title compound. MS (ESI) m/z=600 [M+H]$^+$.

Example 202

Synthesis of Compound 300

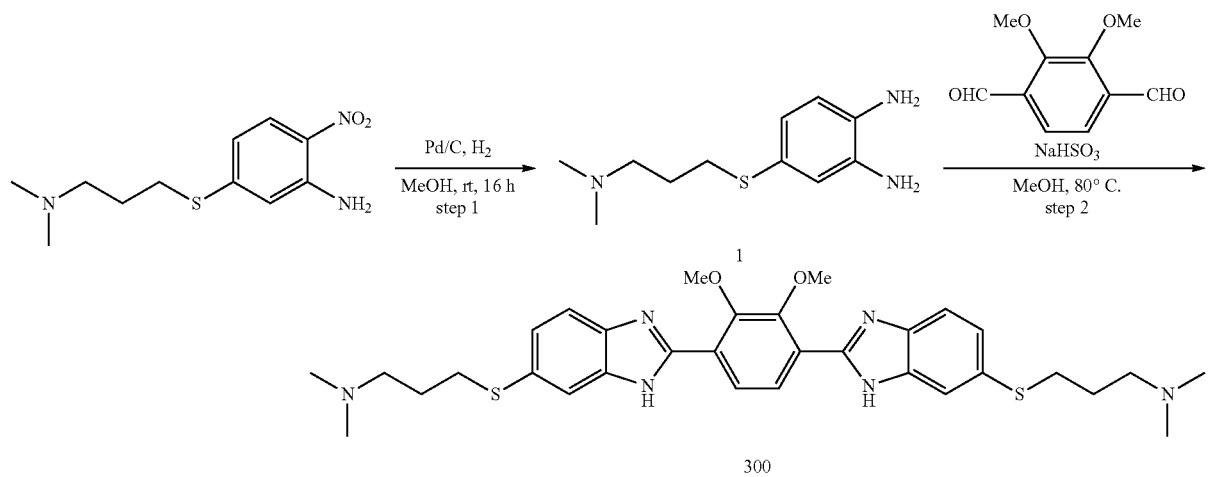

Synthesis of 4-((3-(dimethylamino)propyl)thio)benzene-1,2-diamine into a 50-mL round-bottom flask purged and maintained with an inert atmosphere of nitrogen, was placed a solution of 5-[[3-(methylamino)propyl]sulfanyl]-2-nitroaniline (300 mg, 1.175 mmol, 1 equiv) in MeOH (20 ml). Then Pd/C (10%, 500 mg) was added carefully. The reaction system was backfilled with hydrogen several times and the resulting mixture was stirred at rt for 16 hours. The catalyst was filtered out and the filtrate was concentrated in vacuo. This resulted in a crude residue which was used in the next step directly without further purification.

Synthesis of 3,3'-(((2,3-dimethoxy-1,4-phenylene)bis (1H-benzo[d]imidazole-2,6-diyl))bis(sulfanediyl))bis(N,N-dimethylpropan-1-amine) into a 50-mL round-bottom flask in a nitrogen atmosphere, was placed a solution of 2,3-dimethoxy-4-methylbenzaldehyde (56 mg, 0.288 mmol, 0.5 equiv), 4-((3-(dimethylamino)propyl)thio)benzene-1,2-diamine (130 mg, 0.577 mmol, 1 equiv) and NaHSO3 (120 mg, 1.154 mmol, 2 equiv) in MeOH (10 ml). The resulting solution was stirred at 80° C. for 16 hours. The solid was filtered out and the filtrate was concentrated in vacuo. The residue was purified by Prep-HPLC to afford the title compound. MS (ESI): m/z=605 [M+H]+

Example 203

Synthesis of Compound 301 solution of 4,5-difluoro-2-nitroaniline (500 mg, 2.872 mmol, 1 equiv) in THF (15 ml) was added dropwise at 0° C. The resulting solution was stirred at 50° C. for 16 hours. After reaction completed, the reaction mixture was quenched with ice-water and extracted with DCM (5*10 ml), the organic layer was washed with saturated NaCl solution, dried over Na2SO4 and concentrated in vacuo. The residue was applied onto a silica gel column eluting with dichloromethane/methanol (5:1) to afford 5-[3-(dimethylamino)propoxy]-4-fluoro-2-nitroaniline.

Synthesis of 4-[3-(dimethylamino)propoxy]-5-fluorobenzene-1,2-diamine Into a 50-mL round-bottom flask purged and maintained in a nitrogen atmosphere, was placed a solution of 5-[3-(dimethylamino)propoxy]-4-fluoro-2-nitroaniline (630 mg, 2.449 mmol, 1 equiv) in MeOH (10 mL). Then Pd/C (1 g) was added carefully. The reaction system was backfilled with hydrogen several times. The reaction mixture was stirred at 25° C. for 16 hours. The catalyst was filtered out and the filtrated was concentrated in vacuo. This resulted in 4-[3-(dimethylamino)propoxy]-5-fluorobenzene-1,2-which was used in the next step directly.

Synthesis of N1,N4-bis([2-amino-4-[3-(dimethylamino)propoxy]-5-fluorophenyl])-2-fluorobenzene-1,4-dicarbox-

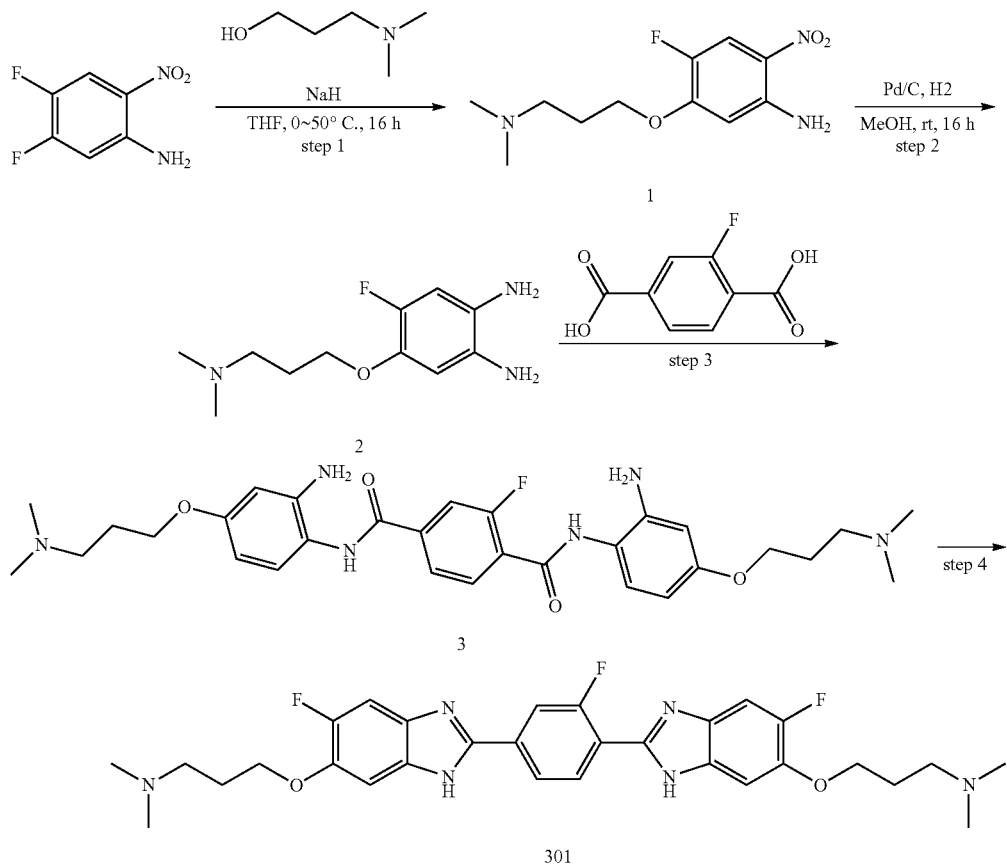

Synthesis of 5-[3-(dimethylamino)propoxy]-4-fluoro-2-nitroaniline Into a 50-mL round-bottom flask purged and maintained with an inert atmosphere of nitrogen, was placed a solution of 3-(dimethylamino)propan-1-ol (444.40 mg, 4.308 mmol, 1.5 equiv) in THF (5 ml). Then NaH (206.75 mg, 8.615 mmol, 3 equiv) was added portionwise at 0° C. The reaction mixture was stirred at rt for 30 min, then a amide Into a 50-mL of round-bottom flask purged and maintained with an inert atmosphere of nitrogen, was placed a solution of 4-[3-(dimethylamino)propoxy]-5-fluorobenzene-1,2-diamine (300 mg, 2.5 equiv), EDCl (304 mg, 3 equiv), HOBT (214 mg, 3 equiv) and 2-fluorobenzene-1,4-dicarboxylic acid (97 mg, 1 equiv) in DMF (10 ml). Then TEA (533 mg, 10 equiv) was added at 0° C. The resulting solution was stirred at 25° C. for 16 hours. The crude product was purified by Prep-HPLC. This resulted in N1,N4-bis([2-amino-4-[3-(dimethylamino)propoxy]-5-fluorophenyl])-2-fluorobenzene-1,4-dicarboxamide.

Synthesis of (3-[[2-(4-[6-[3-(dimethylamino)propoxy]-5-fluoro-1H-1,3-benzodiazol-2-yl]-3-fluorophenyl)-5-fluoro-1H-1,3-benzodiazol-6-yl]oxy]propyl)dimethylamine Into a 50-mL of round-bottom flask purged and maintained with an inert atmosphere of nitrogen, was placed a solution of N1,N4-bis([2-amino-4-[3-(dimethylamino)propoxy]-5-fluorophenyl])-2-fluorobenzene-1,4-dicarboxamide (240 mg, 1 equiv) in AcOH (10 ml). The resulting solution was stirred at 100° C. for 16 hours. The reaction mixture was concentrated under reduced pressure. The residue was purified by Prep-HPLC. This resulted in the title compound. MS (ESI): m/z=567 [M+H]$^+$ Compound 86 was prepared in the same manner as compound 074. MS (ESI): m/z=583 [M+H]$^+$.

Example 204

Synthesis of Compound 302 hours. The mixture was quenched with water (30 ml) and extracted with DCM (3×30 mL), the organic layers combined were dried over $Na_2SO_4$, filtered and concentrated in vacuo. The crude product was purified by prep-TLC with DCM/MeOH=7/1. This resulted in 5-[[3-(dimethylamino)propyl]sulfanyl]-2-nitroaniline.

Synthesis of 4-((3-(dimethylamino)propyl)thio)benzene-1,2-diamine: Into a 50-mL round-bottom flask purged and maintained with an inert atmosphere of nitrogen, was placed a solution of 5-[[3-(methylamino)propyl]sulfanyl]-2-nitroaniline (600 mg, 2.49 mmol, 1 equiv) in MeOH (20 ml). Then Pd/C (10%, 500 mg) was added carefully. The reaction system was backfilled with hydrogen several times and the reaction mixture was stirred at rt for 16 hours. The catalyst was filtered out and the filtrate was concentrated in vacuo. This resulted in a crude residue, which was used in the next step directly without further purification.

Synthesis of 3-((2-(4-(6-((3-(dimethylamino)propyl)thio)-1H-benzo[d]imidazol-2-yl)-2,5-dimethoxyphenyl)-1H-benzo[d]imidazol-5-yl)thio)-N,N-dimethylpropan-1-amine: Into a 50-mL round-bottom flask in a nitrogen atmosphere, was placed a solution of ([3-[(3,4-diaminophe-

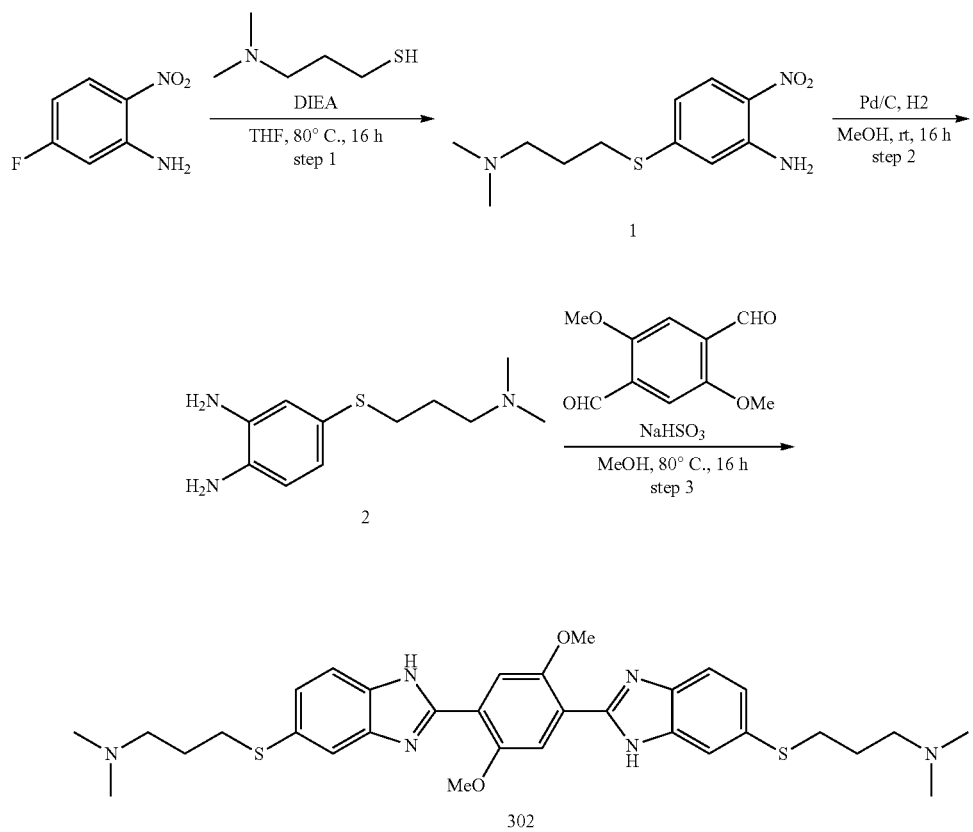

3-(dimethylamino)propane-1-thiol: Into a 50-mL round-bottom flask purged and maintained with an inert atmosphere of nitrogen, was placed a solution of 3-(dimethylamino)propane-1-thiol (1.15 g, 9.608 mmol, 1.5 equiv) in THF (10 mL). Then NaH (536 mg, 12.81 mmol, 2. equiv) was added portionwise at 0° C. The mixture was stirred at rt for 30 min. Then a solution of 5-fluoro-2-nitroaniline (1 g, 6.405 mmol, 1 equiv) in THF (5 mL) was added dropwise at 0° C. The resulting mixture was stirred at 50° C. for 16 nyl)sulfanyl]propyl](methyl)amino)methylium (250 mg, 1.114 mmol, 1 equiv), 2,5-dimethoxybenzene-1,4-dicarbaldehyde (86.6 mg, 0.446 mmol, 0.40 equiv), sulfonylideneoxidane sodium hydride (185.5 mg, 1.783 mmol, 1.60 equiv) in MeOH (10 ml). The resulting solution was stirred for 10 h at 80° C. for 16 hours. The mixture was filtered and the filtrate was concentrated in vacuo. The residue was purified by Prep-HPLC; This resulted in the title compound. MS(ESI): m/z=605 [M+H]$^+$.

Example 205

Synthesis of Compound 303

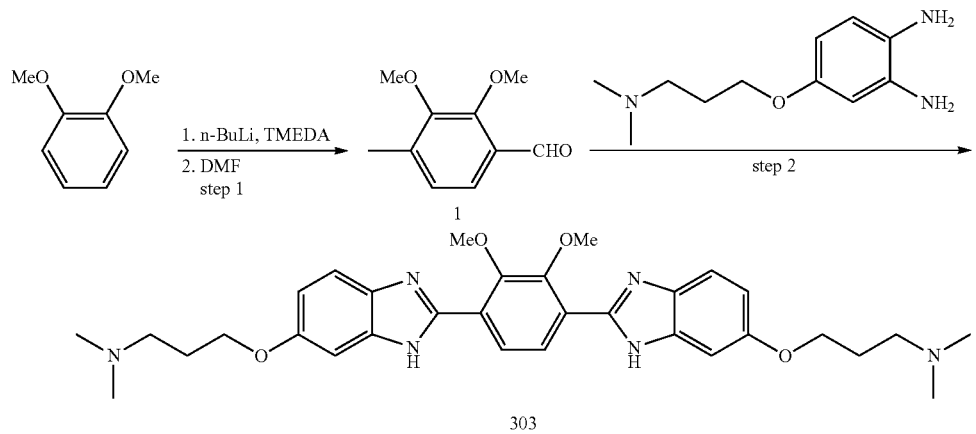

Synthesis of 2,3-dimethoxy-4-methylbenzaldehyde Into a 100-mL three-bound flask purged and maintained in a nitrogen atmosphere, was placed a solution of TMEDA (5 eq, 8.4 g, 72 mmol) and 1,2-dimethoxybenzene (2 g, 14.5 mmol, 1 eq) in dry diethyl ether (29 mL). Then n-Butyllithium 2.5 M in hexane (29 mL, 72 mmol, 5 eq) was added dropwise at 0° C. The lithiation mixture was stirred at reflux for 16 hours. Then DMF (5.8 mL, 72 mmol, 5.1 eq) was added dropwise at 0° C. The reaction was stirred for 2 hours at rt. Then the reaction mixture was quenched by the addition of water (20 ml) and the mixture was extracted with DCM (3×10 ml). The organic layer was combined was washed with brine, dried over with Na2SO4 and concentrated in vacuo. The residue was purified by prep-TLC (PE/EA=10:1) to result in 2,3-dimethoxyterephthalaldehyde.

Synthesis of 3,3'-(((2,3-dimethoxy-1,4-phenylene)bis(1H-benzo[d]imidazole-2,6-diyl))bis(oxy))bis(N,N-dimethylpropan-1-amine) into a 50-mL round-bottom flask in a nitrogen atmosphere, was placed a solution of 2,3-dimethoxy-4-methylbenzaldehyde (120 mg, 0.667 mmol, 1 equiv), 4-(3-(dimethylamino)propoxy)benzene-1,2-diamine (348 mg, 1.6 mmol, 2.5 equiv), sulfonylideneoxidane sodium hydride (277 mg, 2.6 mmol, 4 equiv) in MeOH (10 ml). The resulting solution was stirred at 80° C. for 16 hours. The mixture was filtered and the filtrate was concentrated in vacuo. The residue was purified by Prep-HPLC. This resulted in the title compound. MS (ESI): m/z=573 [M+H]$^+$

Example 206

Synthesis of Compound 304

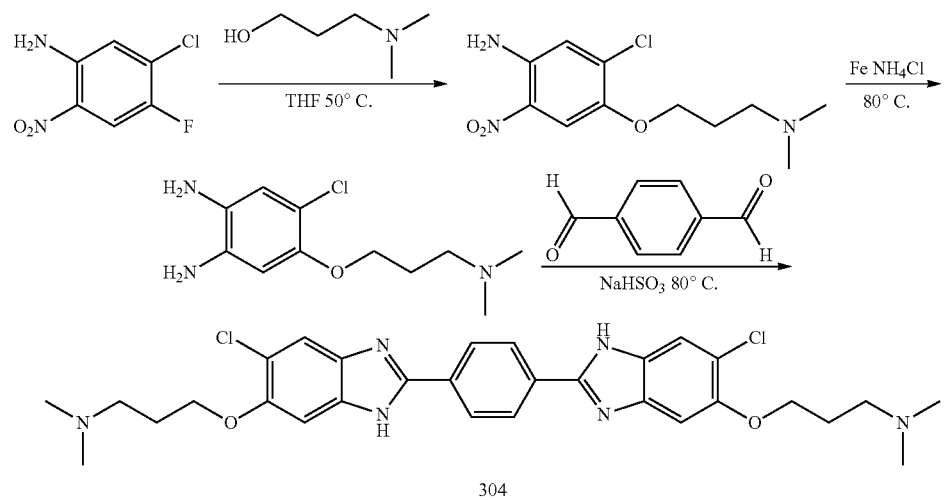

Synthesis of 4-chloro-5-[3-(dimethylamino)propoxy]-2-nitroaniline into a 100-mL of round-bottom flask purged and maintained with an inert atmosphere of nitrogen, was placed a solution of 3-(dimethylamino)propan-1-ol (406.03 mg, 3.936 mmol, 1.5 equiv) in anhydrous THF (15 ml). Then NaH (188.90 mg, 7.872 mmol, 3 equiv) was added portionwise at 0° C. The mixture was stirred at rt for 30 min followed by the addition of a solution of 4-chloro-5-fluoro- 2-nitroaniline (500 mg, 2.624 mmol, 1 equiv) in anhydrous THF (15 ml) at 0° C. The resulting solution was stirred at 50° C. for 16 hours. After reaction completed, the reaction mixture was quenched with ice-water and extracted with DCM (5×10 ml), the organic layer was combined and dried over with $Na_2SO_4$, the solvent was concentrated in vacuo. The residue was applied onto a silica gel column eluting with dichloromethane/methanol (5:1) to afford 4-chloro-5-[3-(dimethylamino)propoxy]-2-nitroaniline.

Synthesis of 4-chloro-5-[3-(dimethylamino)propoxy]benzene-1,2-diamine Into a 50-mL of round-bottom flask purged and maintained with an inert atmosphere of nitrogen, was placed a suspension of 5-chloro-4-[3-(dimethylamino)propoxy]-2-nitroaniline (660 mg, 2.411 mmol, 1 equiv), iron powder (1346.55 mg, 24.112 mmol, 10 equiv) and $NH_4Cl$ (1289.79 mg, 24.112 mmol, 10 equiv) in $MeOH/H_2O$ (5:1 12 ml). The resulting solution was stirred at 80° C. for 16 hours. The solid was filtered out and the filtrate was concentrated in vacuo. The crude product was purified by Combi-FLASH (Column: C18; Mobile Phase A: Water (0.1% $NH_3.H_2O$), Mobile Phase B: ACN; Flow rate: 60 mL/min; Gradient: 0% B to 50% B; 254/220 nm). This resulted in 4-chloro-5-[3-(dimethylamino)propoxy]benzene-1,2-diamine.

Synthesis of (3-[[6-chloro-2-(4-[5-chloro-6-[3-(dimethylamino)propoxy]-1H-1,3-benzodiazol-2-yl]phenyl)-1H-1,3-benzodiazol-5-yl]oxy]propyl)dimethylamine Into a 50-mL of round-bottom flask purged and maintained with an inert atmosphere of nitrogen, was placed a solution of 4-chloro-5-[3-(dimethylamino)benzene-1,2-diamine (500 mg, 2.5 equiv), benzene-1,4-dicarbaldehyde (110 mg, 1 equiv) and $NaHSO_3$ (428 mg, 5 equiv) in MeOH (15 ml). The resulting solution was stirred for at 80° C. 16 hours. The solid was filtered out and the filtrate was concentrated in vacuo. The crude product was purified by Prep-HPLC. This resulted in the title compound. MS (ESI): m/z=581 [M+H]$^+$ Example 207

Synthesis of Compound 305

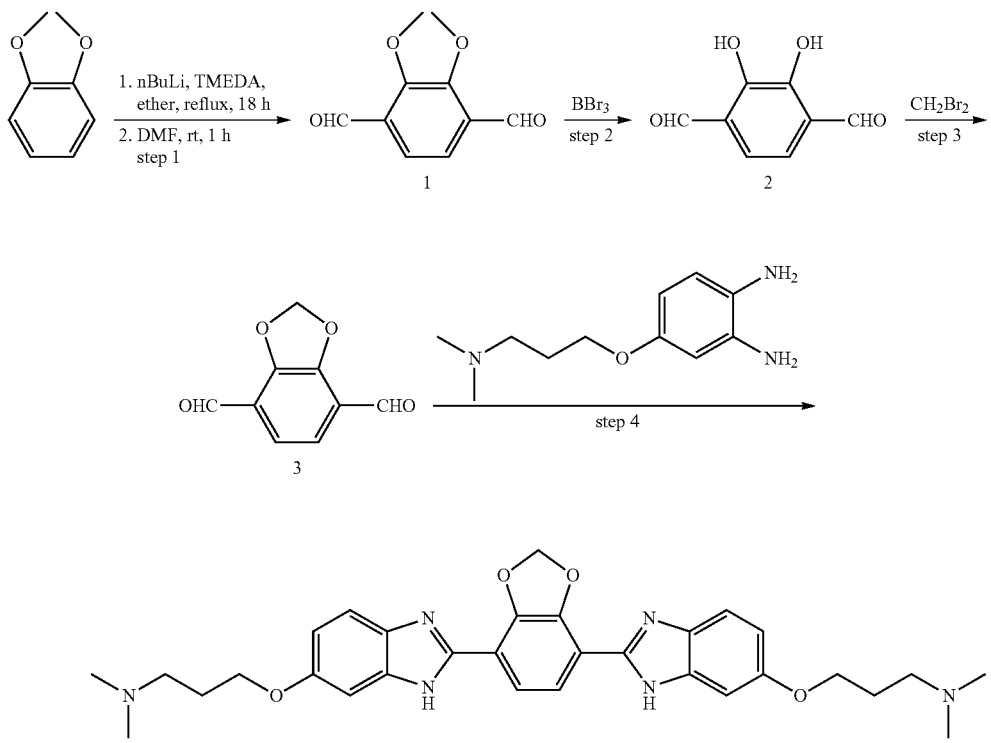

Synthesis of Compound 1: Into a 100-mL three-bound flask purged and maintained in a nitrogen atmosphere, was placed a solution of TMEDA (5 eq, 8.4 g, 72 mmol) and 1,2-dimethoxybenzene (2 g, 14.5 mmol, 1 eq) in anhydrous diethyl ether (29 mL). Then n-Butyllithium 2.5 M in hexane (29 mL, 72 mmol, 5 eq) was added dropwise at 0° C. The reaction mixture was stirred at reflux for 16 hours and then cooled to 0° C. followed by the addition of anhydrous DMF (5.8 mL, 72 mmol, 5.1 eq) dropwise at 0° C. The reaction was stirred for additional 2 hours at room temperature. The reaction was quenched by the addition of water (20 ml) and extracted with DCM (3×10 ml). The organic layer combined was washed with brine, dried over with $Na_2SO_4$ and concentrated in vacuo. The crude was purification by silica gel column (PE/EA=10:1) to afford 2,3-dimethoxyterephthalaldehyde.

Synthesis of Compound 2: Into a 50-mL of round-bottom flask purged and maintained in a nitrogen atmosphere, was placed a solution of 2,3-dimethoxyterephthalaldehyde (300 mg, 1.5 mmol, 1 eq) in DCM (5 mL). Then $BBr_3$ (1 M in DCM) (7.8 mL, 7.5 mmol, 5 eq) was added dropwise at 0° C. The resulting mixture was stirred at 0° C. for 30 min. The reaction mixture was quenched by the addition of water (20 ml) and extracted with EA (3×10 ml). The organic layer combined was washed brine, dried over with Na2SO4 and concentrated in vacuo. This resulting in 2,3-dihydroxyterephthalaldehyde. The crude product was used directly for the next step without further purification.

Synthesis of Compound 3: Into a 10-mL of round-bottom flask purged and maintained in a nitrogen atmosphere was placed a suspension of 2,3-dimethoxyterephthalaldehyde (220 mg, 1.3 mmol, 1 eq) and K2CO3 (538 mg, 3.9 mmol, 3 eq) in DMF (5 mL). The mixture was stirred at room temperature for 10 minutes followed by the addition of dibromomethane (452 mg, 2.6 mmol, 1.5 eq) dropwise at 0° C. The resulting mixture was stirred at 0° C. for 30 min. The reaction mixture was quenched by the addition of water (20 ml) and extracted with EA (3×10 ml). The organic layer combined was washed with brine, dried over with Na2SO4 and concentrated in vacuo. The residue was purification by prep-TLC (PE/EA=10:1) to afford benzo[d][1,3]dioxole-4,7-dicarbaldehyde Synthesis of Compound 305: in a 50 ml of round-bottom flask in a nitrogen atmosphere, was placed a solution of benzo[d][1,3]dioxole-4,7-dicarbaldehyde (50 mg, 0.28 mmol, 1 equiv), 4-(3-(dimethylamino)propoxy)benzene-1,2-diamine (147 mg, 0.70 mmol, 2.5 equiv), and NaHSC3 (117 mg, 1.1 mmol, 4 equiv) in dry MeOH (10 mL). The resulting solution was stirred for 16 hours at 80° C. After reaction completed, the reaction mixture was concentrated under vacuum and the residue was purified by preparative HPLC. This afforded the title compound. MS (ESI) m/z=557 [M+H]$^+$.

Example 208

Synthesis of Compound 307

Synthesis of Compound 1: in a 50 ml of round-bottom flask in a nitrogen atmosphere, was placed a solution of 4-nitrophenol (2 g, 16.1 mmol, 1 equiv) in anhydrous DMF (25 mL). Then anhydrous potassium carbonate (2.69 g, 1.2 equiv, 19.3 mmol) was added and the mixture was stirred at rt for 30 min. Then (bromomethyl)benzene (2.48 g, 0.9 equiv, 14.5 mmol) was added dropwise over a period of 45 minutes. The reaction mixture was stirred at 60° C. for 12 h. The reaction mixture was poured on ice-water (100 mL) and extracted with ethyl acetate (5×30 mL). The organic fractions combined were washed with a saturated solution of sodium chloride (100 mL), dried over anhydrous magnesium sulfate and concentrated in vacuo. The crude was purified by silica gel column eluting with petroleum ether/ethyl acetate (0-10%) to afford 1-(benzyloxy)-4-methoxybenzene.

Synthesis of Compound 2: Into a 100 mL round-bottom flask, was placed a solution of 1-ethoxy-4-methoxybenzene (2.0 g, 1.0 equiv, 9.3 mmol) and anhydrous potassium acetate (1.83 g, 2.0 equiv, 18.7 mmol) in glacial acetic acid (25 ml), was added a solution of bromine (2.98 g, 2.0 equiv, 18.7 mmol) in glacial acetic acid (2 ml) dropwise at 17°. The solution was stirred for 2 h at the same temperature. The mixture was poured into distilled water (150 ml). The precipitate was collected by filtration and dried under reduced pressure. The residue was recrystallised from petroleum ether to give 1-(benzyloxy)-2,5-dibromo-4-methoxybenzene.

Synthesis of Compound 3: Into a 100 mL of round-bottom flask purged and maintained in a nitrogen atmosphere, was placed a solution of 1-(benzyloxy)-2,5-dibromo-4-methoxybenzene (500 mg, 1.0 equiv, 1.3 mmol) in anhydrous THF (50 ml). To this was added n-BuLi (2.70 ml, 2.5 M in hexane, 5.0 equiv, 6.7 mmol) dropwise at −78° C. The solution was stirred for 3 h at the same temperature followed by the addition of anhydrous DMF (491 mg, 5.0 equiv, 6.7 mmol) dropwise at −78° C. The solution was stirred for 1 h at −78° C. and then allowed to warm to room temperature. The reaction mixture was diluted with water and extracted with EA (25 mL×3). The combined organic layer was

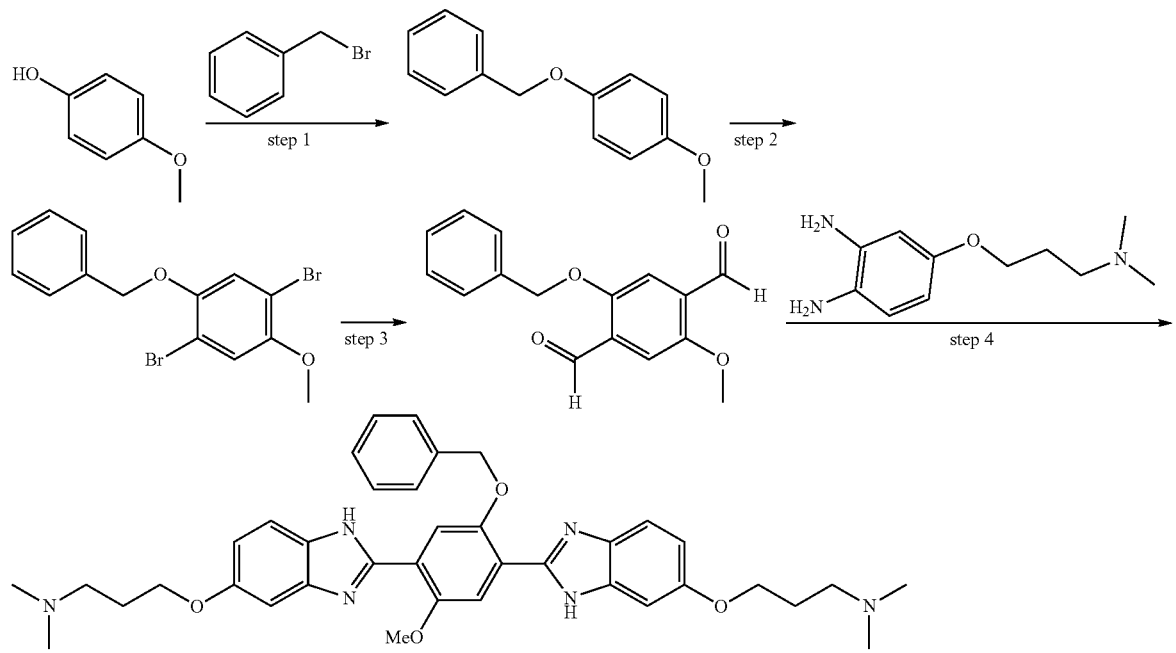

washed with brine, dried over anhydrous sodium sulphate and concentrated in vacuo. The residue was applied onto a silica gel column eluting with petroleum ether/ethyl acetate (5:1) to afford 2-(benzyloxy)-5-methoxyterephthalaldehyde.

Synthesis of Compound 307: Into a 50 ml of round-bottom flask in a nitrogen atmosphere was placed a solution of 2-(benzyloxy)-5-methoxyterephthalaldehyde (70 mg, 0.26 mmol, 1 equiv), 4-(3-(dimethylamino)propoxy)benzene-1,2-diamine (136 mg, 0.65 mmol, 2.5 equiv), and NaHSO₃ (108 mg, 1.0 mmol, 4 equiv) in dry MeOH (15 mL). The resulting solution was stirred for 16 hours at 80° C. After reaction completed, the reaction mixture was concentrated under vacuum and the residue was purified by preparative HPLC. This afforded the title compound. MS (ESI) m/z=649 [M+H]⁺.

Example 209

Synthesis of Compound 308

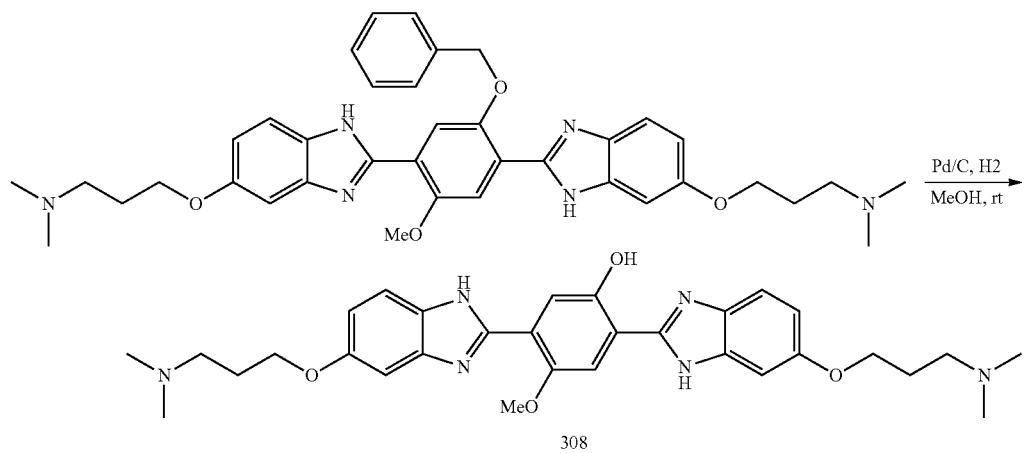

Into a 50 mL of round-bottomed flask purged and maintained in a nitrogen atmosphere, was placed a solution of 3-((2-(2-(benzyloxy)-4-(5-(3-(dimethylamino)propoxy)-1H-benzo[d]imidazol-2-yl)-5-methoxyphenyl)-1H-benzo[d]imidazol-6-yl)oxy)-N,N-dimethylpropan-1-amine (30 mg, 0.046 mmol, 1 equiv) in methanol (10 mL). Then 0.2 g of anhydrous Pd/C was added. The system was backfilled with hydrogen several times and the reaction mixture was stirred for 16 hours at rt. The catalyst was filtered out and the solution was removed under reduced pressure and the crude was purified by prep-HPLC. This resulted in the title compound. MS (ESI) m/z=559 [M+H]⁺.

Example 210

Synthesis of Compound 309

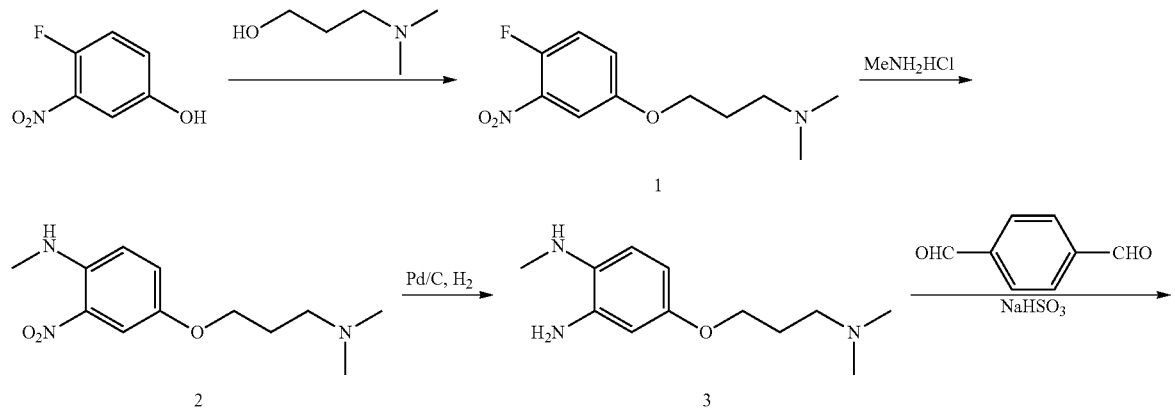

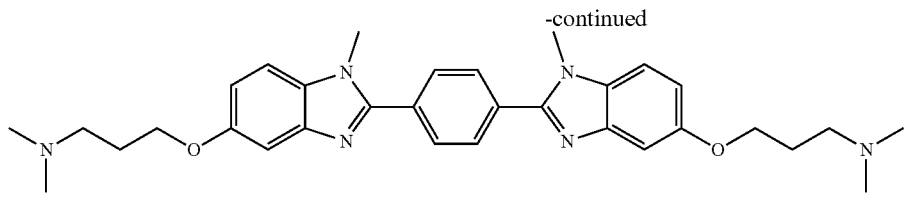

309

Synthesis of 3-(4-fluoro-3-nitrophenoxy)-N,N-dimethyl-propan-1-amine into a 50-mL round-bottom flask purged and maintained with an inert atmosphere of nitrogen was placed a solution of 4-fluoro-3-nitrophenol (1.00 g, 6.365 mmol, 1.00 equiv), triphenylphosphane (2.17 g, 0.008 mmol, 1.30 equiv) and 3-(dimethylamino)propan-1-ol (0.72 g, 0.007 mmol, 1.10 equiv) in anhydrous THF (10 ml), Then DIAD (1.67 g, 0.008 mmol, 1.30 equiv) was added dropwise at 0° C. The resulting solution was stirred for 16 hours at rt. The crude product concentrated in vacuo and the residue was purified by prep-TLC with PE/EA=1:1. This resulted in [3-(4-fluoro-3-nitrophenoxy)propyl]dimethylamine.

Synthesis of 4-(3-(dimethylamino)propoxy)-N-methyl-2-nitroaniline Into a 50-mL round-bottom flask, was placed a solution of [3-(4-fluoro-3-nitrophenoxy)propyl]dimethylamine (500 mg, 2.064 mmol, 1.00 equiv), $CH_3NH_2HCl$ (209 mg, 3.1 mmol, 1.5 equiv) and $K_2CO_3$ (855.76 mg, 6.192 mmol, 3.00 equiv) in DMF (10.00 mL). The resulting solution was stirred for 16 hours at rt. The reaction mixture was diluted with water and extracted with 25 ml×3 of EtOAc. The combined organic layer was washed with brine, dried and concentrated in vacuo. The crude product was purified by prep-TLC with PE/EA=1:1. This resulted in [3-(4-fluoro-3-nitrophenoxy)propyl]dimethylamine.

Synthesis of 4-(3-(dimethylamino)propoxy)-N1-methyl-benzene-1,2-diamine into a 50-mL round-bottom flask purged and maintained with an inert atmosphere of nitrogen was placed a solution of 4-[3-(dimethylamino)propoxy]-N-methyl-2-nitroaniline (460.00 mg, 1.816 mmol, 1.00 equiv) in MeOH (20 ml). Then Pd/C (10%, 500 mg) was added carefully. The reaction system was backfilled with hydrogen several times and the resulting mixture was stirred at rt for 16 hours. The catalyst was filtered out and the filtrate was concentrated in vacuo. This resulted in a crude residue, which was used in the next step directly without further purification.

Synthesis of Compound 309 Into a 50-mL round-bottom flask, was placed a solution of 4-[3-(dimethylamino)propoxy]-N1-methylbenzene-1,2-diamine (200.00 mg, 0.896 mmol, 1.00 equiv), benzene-1,4-dicarbaldehyde (48.05 mg, 0.358 mmol, 0.40 equiv) and NaHSO3 (149.11 mg, 1.433 mmol, 1.60 equiv) in MeOH (10.00 mL). The resulting solution was stirred for 16 h at 80° C. The crude product was concentrated in vacuo and the residue was purified by Prep-HPLC. This resulted in the title compound. MS (ESI): m/z=541 [M+H]+

Compound 310 was prepared in the same manner as compound 309. MS (ESI): m/z=541 [M+H]+.

Example 211

Synthesis of Compound 311

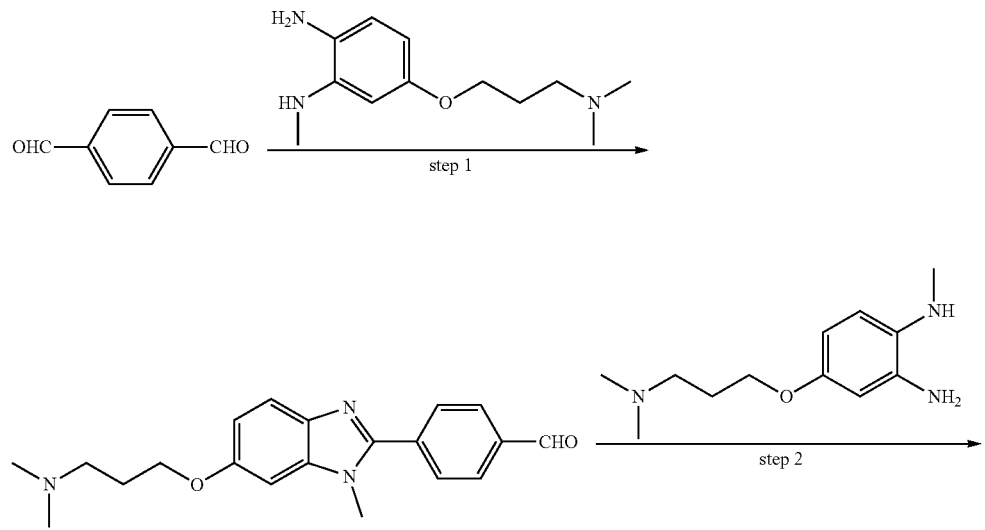

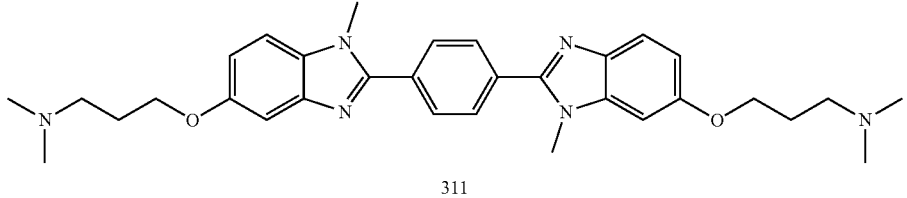

311

Synthesis of Compound 1: in a 50 ml of round-bottom flask was placed a solution of 5-(3-(dimethylamino)propoxy)-N1-methylbenzene-1,2-diamine (300 mg, 1.35 mmol, 0.9 equiv), terephthalaldehyde (200 mg, 1.5 mmol, 1.0 equiv) and NaHSO₃ (310 mg, 3 mmol, 2 equiv) in MeOH (10 mL). The resulting solution was stirred for 16 hours at 80° C. After reaction completed, the reaction mixture was concentrated under vacuum and the residue was purified by preparative Combi-Flash (C18 Column; Mobile Phase A: Water, Mobile Phase B: ACN; Flow rate: 60 mL/min; Gradient: 5% B to 50% B in 15 min; 254/220 nm) to afford 4-(6-(3-(dimethylamino)propoxy)-1-methyl-1H-benzo[d]imidazol-2-yl)benzaldehyde.

Synthesis of Compound 311: in a 50 ml of round-bottom flask, was placed a solution of 4-(6-(3-(dimethylamino)propoxy)-1-methyl-1H-benzo[d]imidazol-2-yl)benzaldehyde (175 mg, 0.52 mmol, 1 equiv), 4-(3-(dimethylamino)propoxy)-N1-methylbenzene-1,2-diamine (232 mg, 1.03 mmol, 2 equiv) and NaHSO₃ (108 mg, 1.03 mmol, 2 equiv) in MeOH (10 mL). The resulting solution was stirred for 16 hours at 80° C. After reaction completed, the reaction mixture was concentrated under vacuum and the residue was purified by prep-HPLC. This resulted in the title compound. MS (ESI) m/z=541 [M+H]⁺.

Example 212

Synthesis of Compound 313

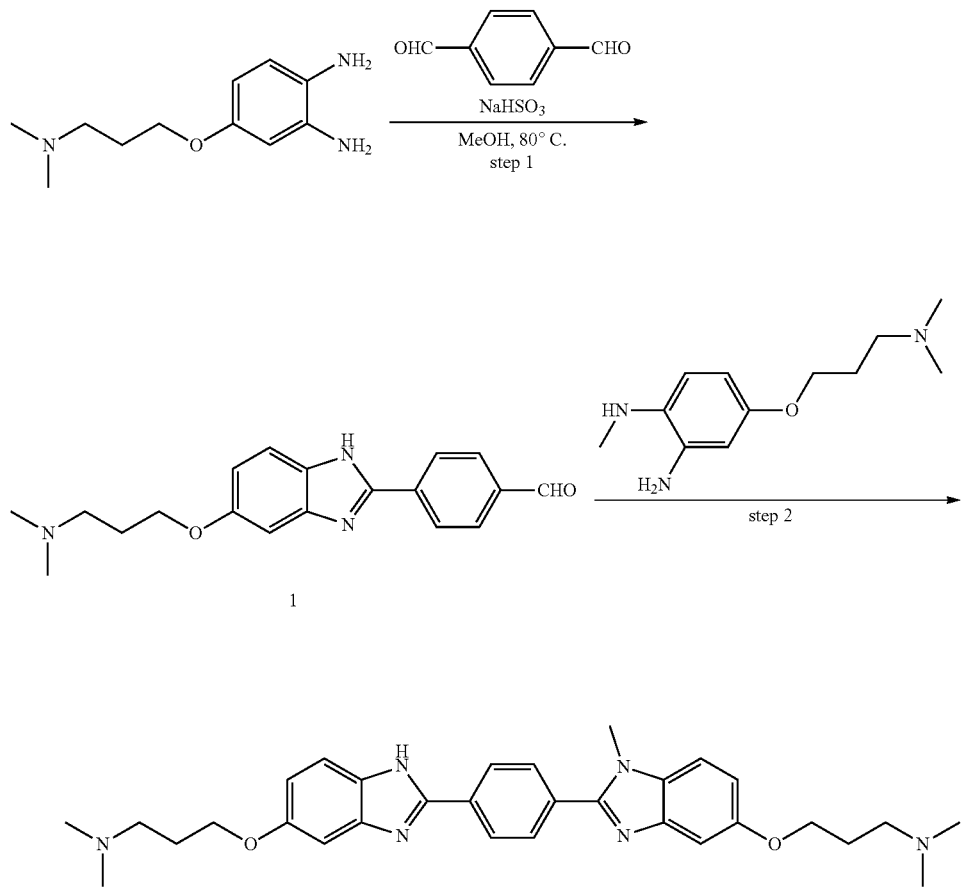

313

Synthesis of Compound 1: in a 50 ml of round-bottom flask was placed a solution of 4-(3-(dimethylamino) propoxy)benzene-1,2-diamine (1.0 g, 4.8 mmol, 1 equiv), terephthalaldehyde (0.7 g, 5.2 mmol, 1.1 equiv) and NaHSC₃ (0.99 g, 9.6 mmol, 2 equiv) in MeOH (20 mL). The resulting solution was stirred for 16 hours at 80° C. After reaction completed, the reaction mixture was concentrated under vacuum and the residue was purified by Combi-Flash (C18 Column; Mobile Phase A: Water, Mobile Phase B: ACN; Flow rate: 60 mL/min; Gradient: 5% B to 50% B in 15 min; 254/220 nm) to afford 4-(5-(3-(dimethylamino) propoxy)-1H-benzo[d]imidazol-2-yl)benzaldehyde.

Synthesis of Compound 313: in a 50 ml of round-bottom flask was placed a solution of 4-(5-(3-(dimethylamino) propoxy)-1H-benzo[d]imidazol-2-yl)benzaldehyde (137 mg, 0.42 mmol, 1 equiv), 4-(3-(dimethylamino)propoxy)-N1-methylbenzene-1,2-diamine (189 mg, 0.85 mmol, 2 equiv) and NaHSO₃ (88 mg, 0.85 mmol, 2 equiv) in MeOH (10 mL). The resulting solution was stirred for 16 hours at 80°. After reaction completed, the reaction mixture was concentrated under vacuum and the residue was purified by prep-HPLC. This resulted in the title compound. MS (ESI) m/z=527 [M+H]⁺.

Example 213

Synthesis of Compound 314

Synthesis of Compound 1: Into a 50-mL round-bottom flask purged and maintained with an inert atmosphere of nitrogen, was placed a solution of 2,5-dihydroxybenzene-1,4-dicarbaldehyde (100.00 mg, 0.602 mmol, 1.00 equiv) and potassium methaneperoxoate potassium (251.39 mg, 1.806 mmol, 3 equiv) in DMF (10 mL). Then iodoethane (234.70 mg, 1.505 mmol, 2.50 equiv) was added dropwise at 0° C. The resulting solution was stirred for 12 hr at 80° C. The reaction was then cooled to room temperature, quenched by the addition of water/ice and extracted with EA (3×10 ml). The organic layer combined was washed with brine, dried over with Na2SO4 and concentrated under reduced pressure. The residue was purified by prep-HPLC. This resulted in 2,5-diethoxybenzene-1,4-dicarbaldehyde Synthesis of 314: Into a 50-mL round-bottom flask purged and maintained with an inert atmosphere of nitrogen, was placed a solution of 2,5-diethoxybenzene-1,4-dicarbaldehyde (85.00 mg, 0.382 mmol, 1.00 equiv), 4-[3-(dimethylamino)propoxy]benzene-1,2-diamine (200.12 mg, 0.956 mmol, 2.5 equiv) and NaHSO3 (119.39 mg, 1.147 mmol, 3 equiv) in methanol (7.00 mL). The resulting solution was stirred for 12 hr at 80° C. The crude product was purified by Prep-HPLC. This resulted in (3-[[2-(4-[5-[3-(dimethylamino)propoxy]-1H-1,3-benzodiazol-2-yl]-2,5-diethoxyphenyl)-1H-1,3-benzodiazol-5-yl]oxy]propyl)dimethylamine the title compound. MS (ESI): m/z=601 [M+H]⁺.

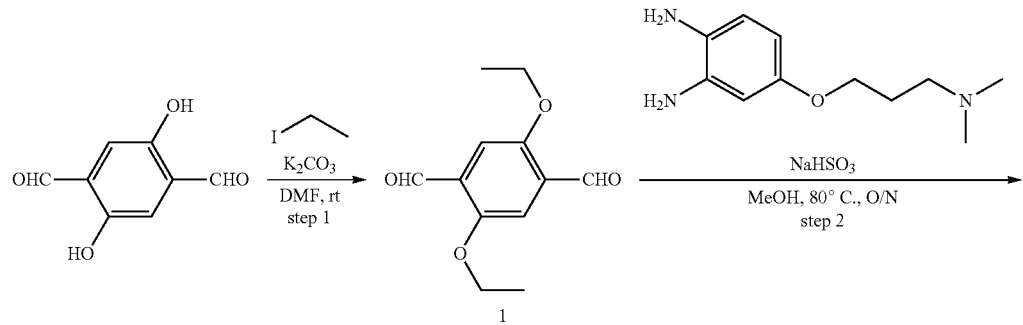

1

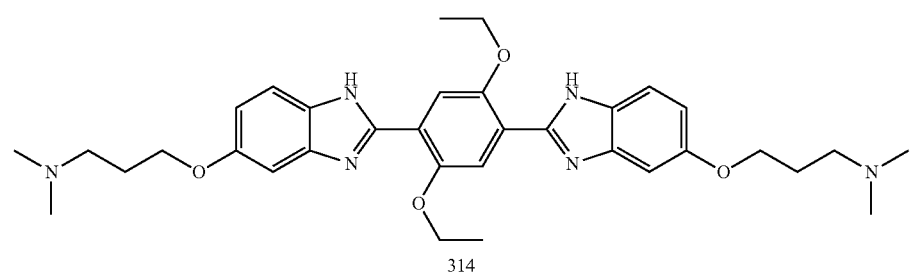

314

Example 214

Synthesis of N-(2-(piperazin-1-yl)ethyl)-2-(4-(6-((2-(piperidin-1-yl)ethyl)carbamoyl)-1H-benzo[d]imidazol-2-yl)phenyl)-1H-benzo[d]imidazole-6-carboxamide

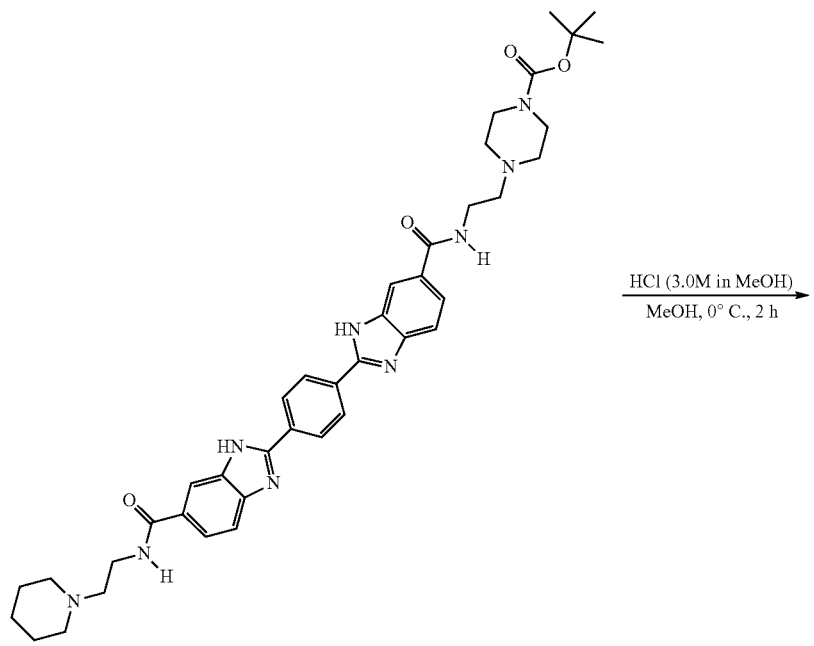

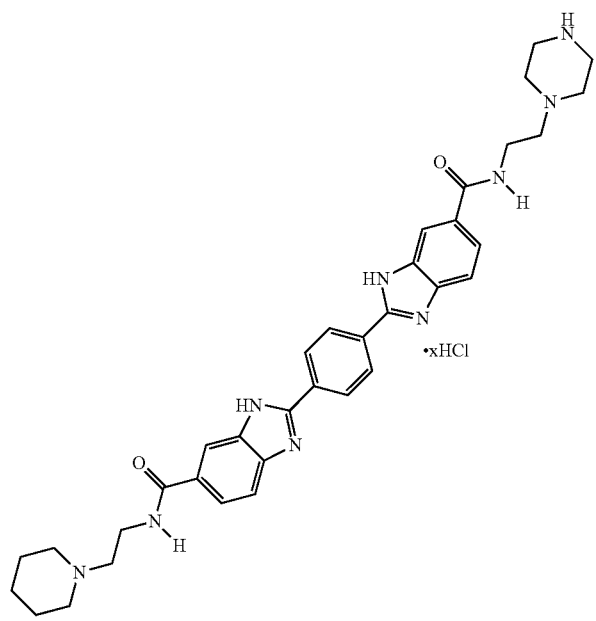

467

To a suspension of tert-butyl 4-(2-(2-(4-(6-((2-(piperidin-1-yl)ethyl)carbamoyl)-1H-benzo[d]imidazol-2-yl)phenyl)-1H-benzo[d]imidazole-6-carboxamido)ethyl)piperazine-1-carboxylate (35 mg, 0.05 mmol) in MeOH (1.0 mL) at 0° C., was added HCl (3.0 M in MeOH, 1.0 mL), and the reaction mixture was stirred for 2 h. The reaction mixture was concentrated under vacuum to obtain the title compound.

MS (ESI+APCI) m/z 620.1 [M+H]$^+$.

Example 215

Synthesis of 4-(2'-(4-((2-(dimethylamino)ethyl)carbamoyl)phenyl)-3H,3'H-[5,5'-bibenzo[d]imidazol]-2-yl)benzoic acid (Compound 390)

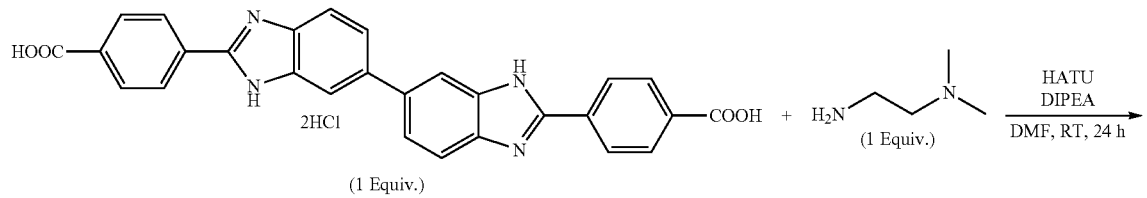

A reaction mixture of 4,4'-(3H,3'H-[5,5'-bibenzo[d]imidazole]-2,2'-diyl)dibenzoic acid (5.0 g, 9.13 mmol), HATU (3.82 g, 10.05 mmol), and dry DMF (100 mL) was taken in a round bottom flask (250 mL) and stirred well under argon. DIPEA (3.9 g, 30.14 mmol) was added dropwise in it. After 15 minutes stirring, $N^1,N^1$-dimethylethane-1,2-diamine (805 mg, 9.13 mmol) was added dropwise. The reaction mixture was stirred at room temperature for 24 h and it was concentrated under vacuum. The residue was triturated with acetone (100 mL), filtered and washed with water (50 mL) and acetone (2×100 mL). The resulting powder was dried under vacuum to give 4.9 g of crude yellow solid. 500 mg of crude product was purified by reverse phase C-18 Biotage column chromatography using a gradient of 0-100% methanol in water, each containing 0.1% TFA to give the title compound and it's bis(N-(2-(dimethylamino)ethyl)benzamide)analog.

LC-MS: (ESI) m/z calculated for $C_{32}H_{29}N_6O_3$ $[M+H^+]$: 545.2, observed: 545.3

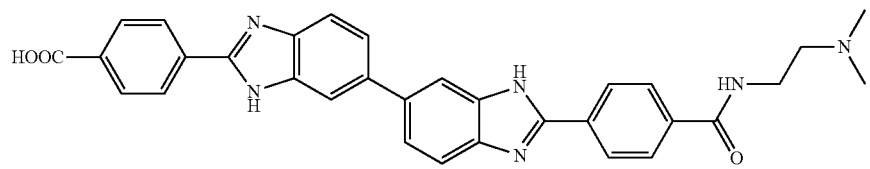

LC-MS: (ESI) m/z calculated for $C_{36}H_{39}N_8O_2$ $[M+H^{30}]$: 615.3, observed: 615.3

Compounds 397, 398, 399, 400, 476, 477, 478, 479 were prepared in the same manner as compound 390.

Compound 397: MALDI: m/z=789.2987 $[M^+]$
Compound 398: MALDI: m/z=701.3327 $[M^+]$
Compound 399: MALDI: m/z=627.3125 $[M^+]$
Compound 400: MALDI: m/z=614.2986 $[M^+]$
Compound 476: LCMS: 565.2 m/z $[M+H]^+$
Compound 477: LCMS: 579.3 m/z $[M+H]^+$
Compound 478: LCMS: 593.3 m/z $[M+H]^+$
Compound 479: LCMS: 551.6 m/z $[M+H]^+$

Example 216

N-(2-(dimethylamino)ethyl)-4-(2'-(4-((3-(1-(3-(4-(2'-(4-(3-(dimethylamino)propoxy)phenyl)-1H,1'H-[5,5'-bibenzo[d]imidazol]-2-yl)benzamido)propyl)-1H-1,2,3-triazol-4-yl)phenyl)carbamoyl)phenyl)-1H,1'H-[5,5'-bibenzo[d]imidazol]-2-yl)benzamide (Compound 468)

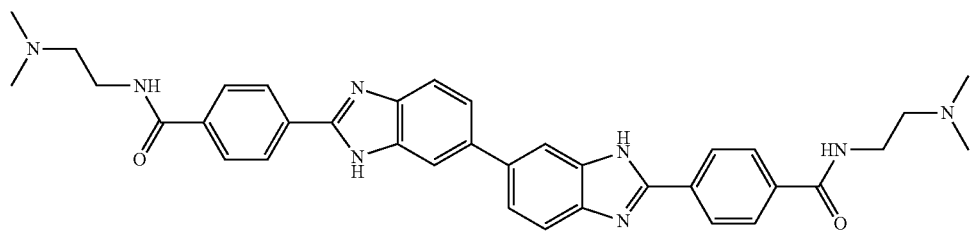

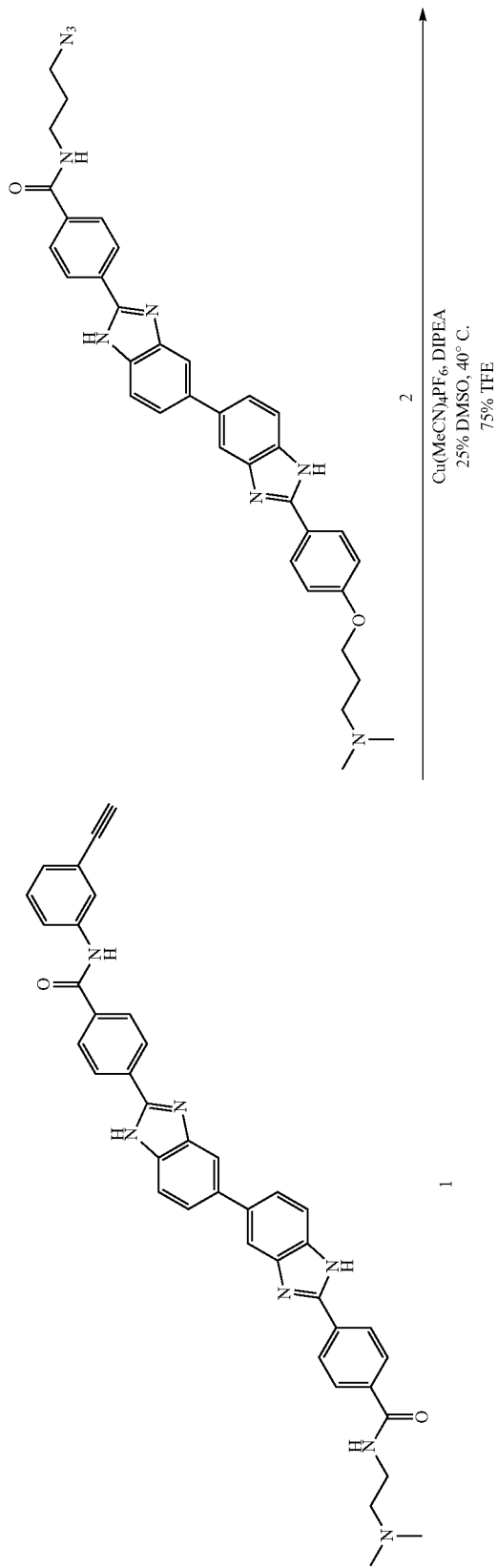

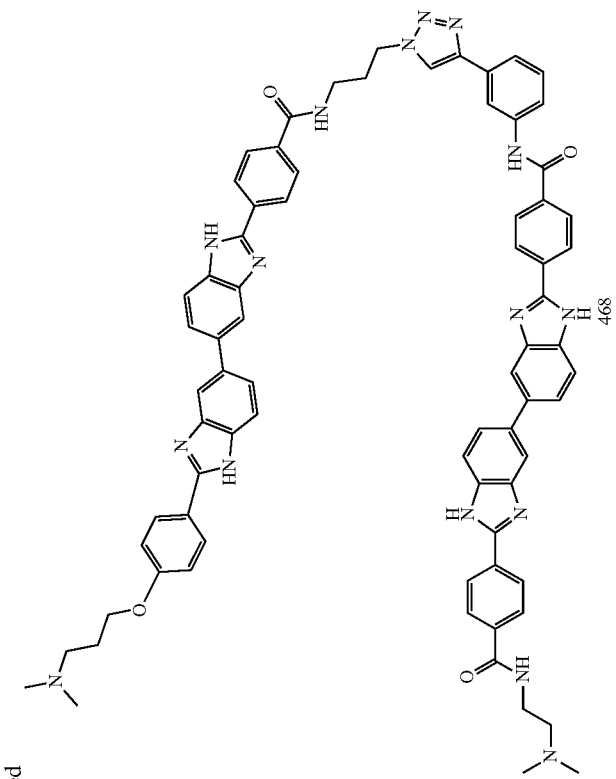
468
-continued

To a stirred solution of N-(2-(dimethylamino)ethyl)-4-(2'-(4-((3-ethynylphenyl)carbamoyl)phenyl)-1H,1'H-[5,5'-bibenzo[d]imidazol]-2-yl)benzamide 1 (100 uL of 0.1 M DMSO solution, 1.0E-05 mol, 1.1 equiv.) was added N-(3-azidopropyl)-4-(2'-(4-(3-(dimethylamino)propoxy)phenyl)-1H,1'H-[5,5'-bibenzo[d]imidazol]-2-yl)benzamide 2 (91 uL of 0.1M DMSO solution, 9.16E-06 mol, 1.0 equiv.) and DIPEA (50 uL, 2.9E-4 mol, 31.3 equiv.). To this mixture was added tetrakis(acetonitrile)copper(I) hexafluorophosphate (1.4 mg, 3.7E-06 mol, 0.4 equiv.) in TFE (500 uL) and the reaction stirred at 40° C. for 24 hours. Water (3 mL) was added and the reaction was purified directly via preparatory reverse-phase HPLC multiple times. Concentration of the fractions containing product afforded title compound 468.

LCMS: 629.6 m/z [M+2H]+/2

Compounds 469, 470, 471, 472, 402, 473, 474, and 404 were prepared in the same manner as compound 468.

Compound 469: LCMS: 612.5 m/z [M+2H]⁺/2
Compound 470: LCMS: 650.5 m/z [M+2H]⁺/2
Compound 471: LCMS: 693.7 m/z [M+2H]⁺/2
Compound 472: LCMS: 648.3 m/z [M+3H]⁺/3; 972.2 m/z [M+2H]⁺/2
Compound 402: LCMS: 823.5 m/z [M+H]+Compound 473: LCMS: 668.5 m/z [M+H]⁺
Compound 474: LCMS: 628.1 m/z [M+3H]⁺/3; 941.6 m/z [M+2H]±/2
Compound 404: LCMS: 625.5 m/z [M+2H]⁺/2

Example 217

N-(2-(dimethylamino)ethyl)-4-(2'-(4-((2-(hex-5-yn-1-yl(methyl)amino)ethyl)carbamoyl)phenyl)-1H,1'H-[5,5'-bibenzo[d]imidazol]-2-yl)benzamide (Compound 401)

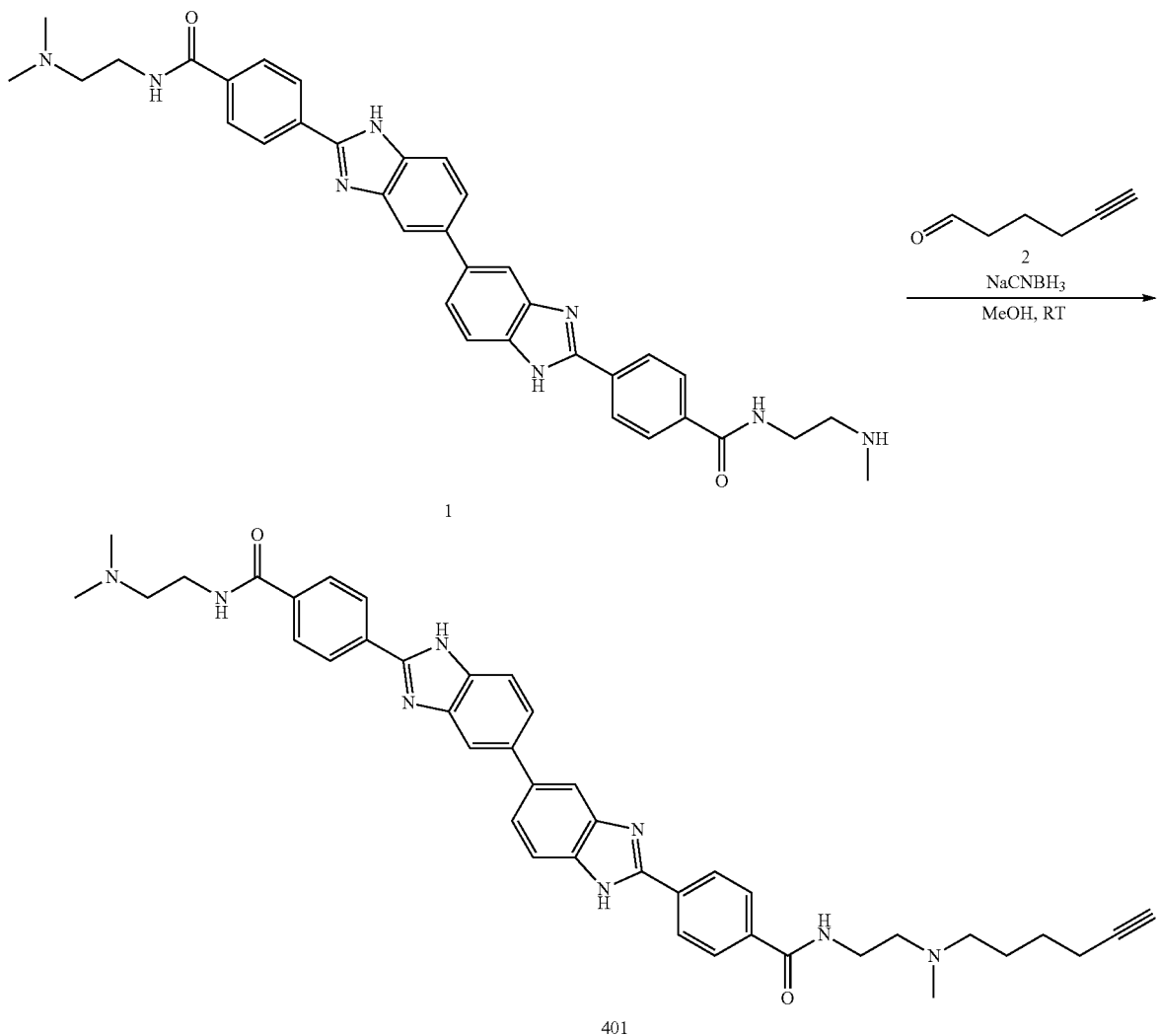

N-(2-(dimethylamino)ethyl)-4-(2'-(4-((2-(methylamino)ethyl)carbamoyl)phenyl)-1H,1'H-[5,5'-bibenzo[d]imidazol]-2-yl)benzamide 1 (66 mg, 1.1E-04 mol, 1.0 equiv.) was dissolved in MeOH (5.5 mL) and hex-5-ynal 2 (21 mg, 2.2E-04 mol, 2.0 equiv.) and sodium cyanoborohydride (35 mg, 5.5E-04, 5.0 equiv.) were added. The reaction was stirred at room temperature for 24 hours, concentrated, dissolved in MeCN/water (3 mL) and purified via preparatory reverse-phase HPLC. Concentration of the fractions containing product afforded title compound 401

LCMS: 681.4 m/z [M+H]⁺

Compounds 403 and 475 were prepared in the same manner as compound 401.

Compound 403: LCMS: 668.5 m/z [M+H]$^+$
Compound 475: LCMS: 650.4 m/z [M+H]+

Example 218

Synthesis of Dimer Library 1

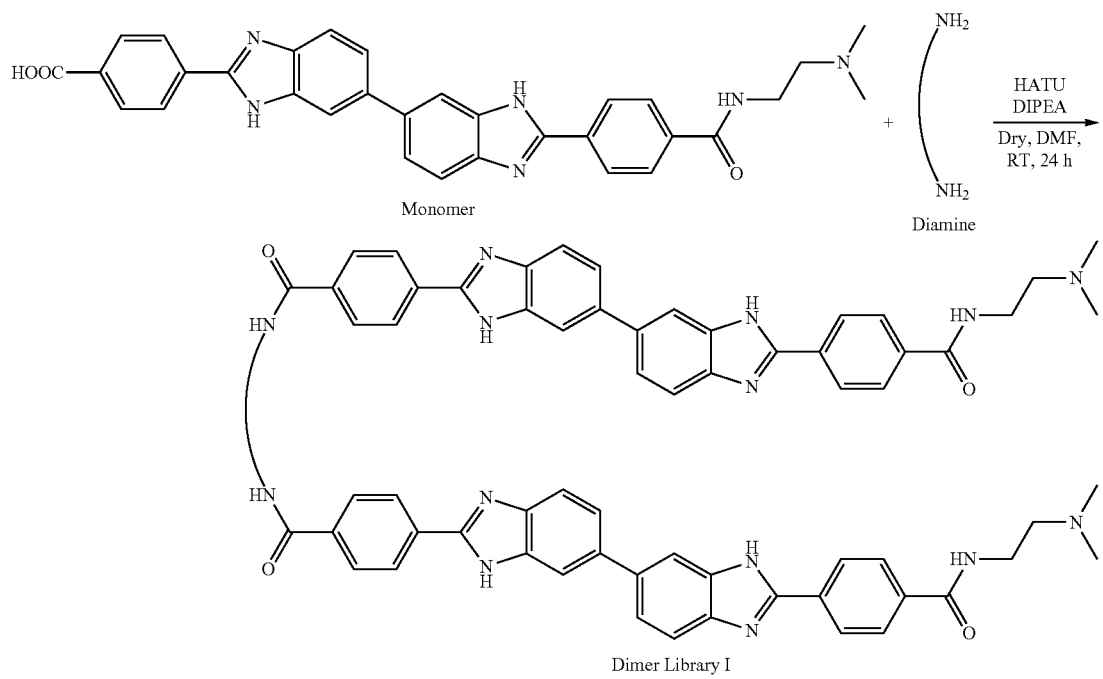

Monomer

Dimer Library I

A reaction mixture of 4-(2'-(4-((2-(dimethylamino)ethyl)carbamoyl)phenyl)-3H,3'H-[5,5'-bibenzo[d]imidazol]-2-yl)benzoic acid (2 equiv.), HATU (2.2 equiv.), and dry DMF (100 μL) was taken in an Eppendorf tube (0.6 mL) and stirred well. DIPEA (6.6 equiv., in 25 μL of dry DMF) was added dropwise in it. After 15 minutes stirring, Diamine (0.9 equiv., in 25 μL of dry DMF) was added dropwise. The reaction mixture was stirred at room temperature for 24 h and analyzed by LCMS. The reaction mixture was dissolved using 2 mL water and 1 mL (1:1) water:methanol solution and purified by reverse phase preparative HPLC using a gradient of 0-100% methanol in water, each containing 0.1% TFA, to give pure dimer. The pure dimer was characterized by using LCMS analysis.

*The reactions were performed using 5 mg or 4 mg or 1 mg amount of 4-(2'-(4-((2-(dimethylamino)ethyl)carbamoyl)phenyl)-3H,3'H-[5,5'-bibenzo[d]imidazol]-2-yl)benzoic acid.

Compounds 409, 410, 411, 412, 413, 414, 419, 420, 421, 422, 423, 424, 425, 426, 427, 428, 429, 439, 440, 441, 442, 449, 450, 451, 452, 453, 454, and 455 were synthesized using this method.

Compound 409: LC-MS: (ESI) m/z calculated for $C_{69}H_{68}N_{14}O_4$ [M+2H$^+$]/2: 578.3, observed: 578.4

Compound 410: LCMS: LC-MS: (ESI) m/z calculated for $C_{70}H_{68}N_{14}O_4$ [M+2H$^+$]/2: 584.3, observed: 584.5

Compound 411: LC-MS: (ESI) m/z calculated for $C_{67}H_{64}N_{14}O_4$ [M+2H$^+$]/2: 564.3, observed: 564.5

Compound 412: LC-MS: (ESI) m/z calculated for $C_{66}H_{62}N_{14}O_4$ [M+2H$^+$]/2=557.3, observed 557.5

Compound 413: LC-MS: (ESI) m/z calculated for $C_{67}H_{64}N_{14}O_4$ [M+2H$^+$]/2=564.3, observed 564.5

Compound 414: LC-MS: (ESI) m/z calculated for $C_{69}H_{68}N_{14}O_4$ [M+2H$^{30}$]/2: 578.3, observed: 578.5

Compound 419: LC-MS: (ESI) m/z calculated for $C_{70}H_{70}N_{14}O_4$ [M+2H$^+$]/2: 585.3, observed: 585.5

Compound 420: LC-MS: (ESI) m/z calculated for $C_{68}H_{66}N_{14}O_4$ [M+2H$^+$]/2=571.3, observed 571.5

Compound 421: LC-MS: (ESI) m/z calculated for $C_{71}H_{72}N_{14}O_4$ [M+2H$^+$]/2: 592.3, observed: 592.5

Compound 422: LC-MS: (ESI) m/z calculated for $C_{72}H_{74}N_{14}O_4$ [M+2H$^+$]/2: 599.3, observed: 599.5

Compound 423: LC-MS: (ESI) m/z calculated for $C_{73}H_{76}N_{14}O_4$ [M+2H$^+$]/2: 606.3, observed: 606.5

Compound 424: LC-MS: (ESI) m/z calculated for $C_{74}H_{78}N_{14}O_4$ [M+2H$^+$]/2: 613.3, observed: 613.5

Compound 425: LC-MS: (ESI) m/z calculated for $C_{69}H_{68}N_{14}O_4$ [M+2H$^+$]/2: 578.3, observed: 578.5

Compound 426: LC-MS: (ESI) m/z calculated for $C_{70}H_{70}N_{14}O_4$ [M+2H$^+$]/2: 585.3, observed: 585.5

Compound 427: LC-MS: (ESI) m/z calculated for $C_{77}H_{80}N_{14}O_4$ [M+2H$^+$]/2: 632.3, observed: 632.6

Compound 428: LC-MS: (ESI) m/z calculated for $C_{77}H_{80}N_{14}O_4$ [M+2H$^+$]/2: 632.3, observed: 632.6

Compound 429: LC-MS: (ESI) m/z calculated for $C_{74}H_{78}N_{14}O_7$ [M+2H$^+$]/2: 637.3, observed: 637.5

Compound 439: LC-MS: (ESI) m/z calculated for $C_{74}H_{74}N_{14}O_4$ [M+2H$^+$]/2: 611.3, observed: 611.6

Compound 440: LC-MS: (ESI) m/z calculated for $C_{70}H_{68}N_{14}O_4$ [M+2H$^+$]/2: 584.3, observed: 584.6

Compound 441: LC-MS: (ESI) m/z calculated for $C_{67}H_{64}N_{14}O_4$ [M+2H$^+$]/2: 564.3, observed: 564.5

Compound 442: LC-MS: (ESI) m/z calculated for $C_{67}H_{64}N_{14}O_4$ [M+2H$^+$]/2: 564.3, observed: 564.5

Compound 449: LC-MS: (ESI) m/z calculated for $C_{73}H_{77}N_{15}O_4$ [M+2H$^+$]/2: 613.8, observed: 614.1

Compound 450: LC-MS: (ESI) m/z calculated for $C_{72}H_{75}N_{15}O_4$ [M+2H$^+$]/2: 606.8, observed: 607.0

Compound 451: LC-MS: (ESI) m/z calculated for $C_{71}H_{73}N_{15}O_4$ [M+2H$^+$]/2: 599.8, observed: 600.0

Compound 452: LC-MS: (ESI) m/z calculated for $C_{76}H_{76}N_{14}O_4$ [M+2H$^+$]/2: 624.3, observed: 624.6

Compound 453: LC-MS: (ESI) m/z calculated for $C_6H_{66}N_{14}O_4$ [M+2H$^+$]/2: 577.3, observed: 577.5

Compound 454: LC-MS: (ESI) m/z calculated for $C_6H_{64}N_{14}O_4$ [M+2H$^+$]/2: 570.3, observed: 570.5

Compound 455: LC-MS: (ESI) m/z calculated for $C_6H_{64}N_{14}O_4$ [M+2H$^+$]/2: 570.3, observed: 570.5

Biological Assay Data

Example 219

Small Molecule Inhibition of the r(CUG)12-MBNL1 Complex Measured by Time Resolved Fluorescence Resonance Energy Transfer (TR-FRET)

The in vitro activity of small molecules were assessed by measuring the inhibition of the r(CUG)$_{12}$-MBNL1 complex using a TR-FRET assay previously reported by Chen et al Analytical and Bioanalytical Chemistry 2012, 402, 1889. Biotinylated r(CUG)$_{12}$ was folded at 60° C. in 1× Folding Buffer (20 mM HEPES, pH 7.5, 100 mM KCl, and 10 mM NaCl) and slowly cooled to room temperature. The buffer was then adjusted to 1× TR-FRET Buffer (1× Folding Buffer supplemented with 2 mM MgCl$_2$, 2 mM CaCl$_2$, 5 mM DTT, 0.1% BSA, 0.05% Tween-20) and MBNL1-His$_6$ was added. The final concentrations of RNA and MBNL1-His$_6$ were 80 nM and 60 nM, respectively. Then dilutions of the small molecule were made in 1× TR-FRET buffer. The samples were equilibrated at room temperature for 15 min, after which 1 μL of antibody solution (1:1 mixture of 8.8 ng/μL Anti-His$_6$-Tb and 800 nM streptavidin XL-665) was added. Samples were incubated at room temperature for 1 h, and then TR-FRET was measured using a Molecular Devices SpectraMax M5 plate reader using an excitation wavelength of 345 nm and a 420 nm cutoff. Controls for maximum TR-FRET (100% complex formation) contained 8 μL of 1×TR-FRET Buffer with RNA and protein and 1 μL water. Controls for minimum TR-FRET (no complex formation) contained 8 μL of 1× Assay Buffer, 1 μL water, and no RNA or protein.

To calculate the percent inhibition of complex formation, the ratio of fluorescence intensity at 545 nm and 665 nm in the presence of compound was compared to the ratio in the absence of small molecule (100% r(CUG)12-MBNL1 complex formation) and in the absence of RNA and protein (no complex formation). The resulting curves were fit to the following equation to determine IC$_{50}$ values:

$$y = B + \frac{A-B}{1+\left(\frac{IC_{50}}{x}\right)^{hillslope}}$$

where y is ratio of fluorescence intensities at 545 nm and 665 nm (F545/F665), x is the concentration of small molecule, B is F545/F665 value at max FRET effect (solution has RNA and protein but no small molecule added); A is F545/F665 value at min FRET effect (solution has antibodies but no RNA, protein, or small molecule); and the IC50 is the concentration of small molecule where half of the protein is displaced by small molecule.

Small Molecule Inhibition of the r(CAG)$_{12}$-MBNL1 Complex Measured by Time Resolved Fluorescence Resonance Energy Transfer (TR-FRET). Same procedure as above except the RNA used is 5' biotinylated r(CAG)$_{12}$.

Small Molecule Inhibition of the r(CUG)$_{12}$-MBNL1 Complex Measured by Time Resolved Fluorescence Resonance Energy Transfer (TR-FRET). Same procedure as above with some minor modifications. 5' biotinylated r(G$_4$C$_2$)$_8$ was folded at 95° C. in 1× Folding Buffer (20 mM HEPES, pH 7.5, and 10 mM NaCl, no KCl) for 2 minutes and slowly cooled to room temperature. Instead of MBNL1-His$_6$, hnRNP h is used as the RNA-binding protein.

Compounds were tested using this protocol and the results are shown in the below Tables L and M.

TABLE L

| Compound # | TR-FRET IC$_{50}$ (μM) |
|---|---|
| 1 | 18 |
| 2 | 197 |
| 3 | 27 |
| 4 | >200 |
| 5 | 76 |
| 6 | 112 |
| 7 | 80 |
| 8 | 150 |
| 9 | 26 |
| 10 | >200 |
| 11 | >200 |
| 12 | >200 |
| 13 | 48 |
| 14 | 11 |
| 15 | 45 |
| 16 | 6.2 |
| 17 | 37 |
| 18 | 35 |
| 19 | 34 |
| 20 | >200 |
| 21 | 150 |
| 22 | 169 |
| 23 | 55 |
| 24 | 35 |
| 25 | 144 |
| 26 | 6.6 |
| 27 | 12.3 |
| 28 | 12.3 |
| 29 | 9.6 |
| 30 | 18.3 |
| 31 | 15.4 |
| 32 | >200 |
| 33 | 8.1 |
| 34 | 14.5 |
| 35 | 6.2 |
| 36 | 7.7 |
| 37 | 7.8 |
| 38 | 2.6 |
| 39 | 4.4 |
| 40 | 7.0 |
| 41 | 6.6 |
| 42 | >200 |
| 43 | >200 |
| 44 | 11.9 |
| 45 | 18.2 |
| 46 | >200 |
| 47 | 6.8 |
| 48 | 10.3 |
| 49 | 22.1 |
| 50 | >200 |
| 51 | >200 |
| 52 | >200 |
| 53 | >200 |
| 54 | 3.6 |
| 55 | 4.2 |

TABLE L-continued

| Compound # | TR-FRET IC$_{50}$ (μM) |
|---|---|
| 56 | 5.0 |
| 57 | 119 |
| 58 | 19.8 |
| 59 | 10.8 |
| 60 | 40 |
| 61 | >200 |
| 62 | >200 |
| 63 | 10.7 |
| 64 | 27 |
| 65 | 3.6 |
| 66 | >200 |
| 67 | >200 |
| 68 | >200 |
| 70 | 144 |
| 72 | 52.1 |
| 73 | 9.5 |
| 74 | 6.7 |
| 75 | 3.2 |
| 76 | 14.5 |
| 77 | 10.8 |
| 78 | >200 |
| 79 | 43.9 |
| 80 | 31.3 |
| 81 | 6.1 |
| 82 | >200 |
| 83 | >200 |
| 84 | >200 |
| 85 | >200 |
| 86 | >200 |
| 87 | >200 |
| 88 | >200 |
| 89 | >200 |
| 90 | >200 |
| 94 | >200 |
| 95 | 106 |
| 96 | 4.6 |
| 97 | 71 |
| 98 | 144 |
| 99 | 15.2 |
| 100 | 6.2 |
| 101 | >200 |
| 102 | ND |
| 103 | ND |
| 104 | >200 |
| 105 | >200 |
| 106 | >200 |
| 107 | >200 |
| 108 | 13 |
| 109 | 15 |
| 110 | 6.9 |
| 111 | 6.9 |
| 112 | 5.0 |
| 113 | 12.6 |
| 114 | 9.5 |
| 115 | 7.1 |
| 116 | 5.3 |
| 117 | 8.9 |
| 120 | >200 |
| 121 | >200 |
| 122 | 24.0 |
| 124 | 170 |
| 125 | 25.6 |
| 126 | 9.5 |
| 127 | 27.8 |
| 128 | 2.6 |
| 129 | 2.3 |
| 130 | 4.6 |
| 131 | 4.5 |
| 132 | 3.0 |
| 133 | 0.48 |
| 134 | 0.31 |
| 135 | 0.26 |
| 136 | 3.6 |
| 146 | 15.8 |
| 148 | 7.4 |
| 149 | 6.1 |
| 150 | 29.6 |
| 152 | 10.7 |

TABLE L-continued

| Compound # | TR-FRET IC$_{50}$ (μM) |
|---|---|
| 153 | 29.0 |
| 160 | 19.2 |
| 166 | 46 |
| 167 | 54.4 |

TABLE M

| Compound # | TR-FRET IC50 (μM) |
|---|---|
| 170 | 6.14 |
| 171 | 9.66 |
| 172 | 28.30 |
| 173 | 22.04 |
| 174 | 4.32 |
| 175 | 49.15 |
| 176 | 5.52 |
| 177 | >200 |
| 178 | 7.90 |
| 179 | 188.80 |
| 180 | 78.87 |
| 181 | 54.38 |
| 182 | 93.58 |
| 183 | 114.40 |
| 184 | >200 |
| 185 | 8.13 |
| 186 | >200 |
| 187 | 58.94 |
| 188 | 46.90 |
| 189 | >200 |
| 190 | 178.90 |
| 191 | 100.10 |
| 192 | 12.94 |
| 193 | 36.70 |
| 194 | 39.01 |
| 195 | 103.70 |
| 196 | 105.60 |
| 197 | 33.65 |
| 198 | 9.67 |
| 199 | 47.81 |
| 200 | 32.09 |
| 201 | 16.42 |
| 202 | 41.96 |
| 203 | 102.70 |
| 204 | 129.00 |
| 205 | 27.31 |
| 206 | 64.36 |
| 207 | 48.56 |
| 208 | 101.30 |
| 209 | 19.35 |
| 210 | 33.34 |
| 211 | 112.30 |
| 212 | 5.30 |
| 213 | 22.77 |
| 214 | 25.22 |
| 215 | 20.46 |
| 216 | 124.90 |
| 217 | 51.87 |
| 218 | 68.71 |
| 219 | 18.14 |
| 220 | >200 |
| 221 | 2.53 |
| 222 | 95.29 |
| 223 | >200 |
| 224 | 63.42 |
| 225 | 153.90 |
| 226 | >200 |
| 227 | 120.30 |
| 228 | 47.10 |
| 229 | >200 |
| 230 | >200 |
| 231 | >200 |
| 232 | 25.00 |
| 233 | 39.50 |
| 234 | 39.80 |
| 235 | 78.20 |

TABLE M-continued

| Compound # | TR-FRET IC50 (μM) |
|---|---|
| 236 | 62.10 |
| 237 | 26.00 |
| 238 | 10.00 |
| 239 | 24.80 |
| 240 | 71.50 |
| 241 | 64.70 |
| 242 | 47.70 |
| 243 | >200 |
| 244 | 23.50 |
| 245 | 83.80 |
| 246 | >200 |
| 247 | 6.80 |
| 248 | >200 |
| 249 | 52.6 |
| 250 | >200 |
| 251 | 112.10 |
| 252 | 18.90 |
| 253 | >200 |
| 254 | >200 |
| 255 | 3.70 |
| 256 | 10.70 |
| 257 | 24.60 |
| 258 | 31.00 |
| 259 | 7.20 |
| 260 | 37.50 |
| 261 | 74.10 |
| 262 | 55.50 |
| 263 | 45.60 |
| 264 | 6.03 |
| 265 | 16.64 |
| 266 | 10.67 |
| 267 | 10.88 |
| 268 | 9.60 |
| 269 | 3.11 |
| 270 | 5.81 |
| 271 | >200 |
| 272 | 95.16 |
| 273 | 6.10 |
| 274 | 12.01 |
| 275 | 24.29 |
| 276 | 9.70 |
| 277 | 8.29 |
| 278 | 38.12 |
| 279 | ND |
| 280 | 31.34 |
| 281 | >200 |
| 282 | 178.60 |
| 283 | 159.50 |
| 284 | 24.14 |
| 285 | >200 |
| 286 | 14.17 |
| 287 | 8.60 |
| 288 | 42.62 |
| 289 | >200 |
| 290 | 11.06 |
| 291 | 61.50 |
| 292 | 14.00 |
| 293 | 18.20 |
| 294 | 18.40 |
| 295 | 69.90 |
| 296 | 8.40 |
| 297 | 9.70 |
| 298 | 23.50 |
| 299 | 10.30 |
| 300 | >200 |
| 301 | 5.30 |
| 302 | 28.00 |
| 303 | >200 |
| 304 | 5.80 |
| 305 | 7.60 |
| 306 | 12.10 |
| 307 | 15.80 |
| 308 | 1.80 |
| 309 | >200 |
| 310 | >200 |
| 311 | >200 |
| 312 | >200 |
| 313 | >200 |

TABLE M-continued

| Compound # | TR-FRET IC50 (μM) |
|---|---|
| 314 | 19.80 |
| 315 | 6.10 |
| 316 | 20.70 |
| 317 | 21.37 |
| 318 | >200 |
| 319 | >200 |
| 320 | 16.70 |
| 321 | 22.45 |
| 322 | 39.80 |
| 323 | 20.29 |
| 329 | >200 |
| 330 | 131.8 |
| 331 | 3.111 |
| 332 | 27.22 |
| 333 | 46.89 |
| 334 | 14.17 |
| 335 | 22.55 |
| 336 | 8.03 |
| 337 | 31.95 |
| 338 | 4.56 |
| 339 | 5.96 |
| 340 | 6.17 |
| 341 | 5.32 |
| 342 | 4.38 |
| 343 | 73.23 |
| 344 | 153.50 |
| 345 | 33.51 |
| 346 | 6.45 |
| 347 | 13.46 |
| 348 | 16.81 |
| 349 | >200 |
| 350 | 16.88 |
| 351 | 200.00 |
| 352 | 25.76 |
| 353 | 13.35 |
| 354 | 16.47 |
| 355 | 11.17 |
| 356 | 30.39 |
| 357 | 15.08 |
| 358 | 19.24 |
| 359 | 65.53 |
| 360 | 21.25 |
| 361 | 9.64 |
| 362 | 29.03 |
| 363 | 18.73 |
| 364 | 7.64 |
| 365 | 9.84 |
| 366 | >200 |
| 367 | 21.54 |
| 368 | 18.04 |
| 369 | >200 |
| 370 | 82.29 |
| 371 | 12.84 |
| 372 | >200 |
| 373 | 29.22 |
| 374 | 12.85 |
| 375 | >200 |
| 376 | 69.53 |
| 378 | 17.31 |
| 379 | 28.79 |
| 380 | 16.68 |
| 381 | 49.87 |
| 382 | 17.39 |
| 383 | 41.58 |
| 384 | 10.12 |
| 385 | 31.23 |
| 386 | 46.41 |
| 387 | 8.86 |
| 388 | 30.15 |
| 389 | 34.18 |
| 390 | >200 |
| 391 | 18.44 |
| 392 | 18.26 |
| 393 | 7.48 |
| 394 | 18.98 |
| 395 | >200 |
| 396 | >200 |
| 397 | 12.20 |

TABLE M-continued

| Compound # | TR-FRET IC50 (μM) |
|---|---|
| 398 | 14.70 |
| 399 | 9.60 |
| 400 | 14.80 |
| 401 | 10.60 |
| 402 | 10.90 |
| 403 | 5.60 |
| 404 | 42.79 |
| 405 | 15.26 |
| 406 | 3.03 |
| 407 | 110.20 |
| 408 | 0.51 |
| 409 | 50.57 |
| 410 | 34.44 |
| 164 | 1.91 |
| 411 | 1.91 |
| 412 | 3.28 |
| 413 | 3.34 |
| 414 | 8.16 |
| 415 | 5.15 |
| 416 | 39.00 |
| 417 | 9.24 |
| 418 | 5.32 |
| 419 | 4.85 |
| 420 | 6.32 |
| 421 | 14.77 |
| 422 | 5.65 |
| 423 | 5.31 |
| 424 | 5.82 |
| 425 | 9.83 |
| 426 | 7.04 |
| 427 | 3.23 |
| 428 | 2.90 |
| 429 | 9.60 |
| 430 | 7.70 |
| 431 | >200 |
| 432 | 11.60 |
| 433 | >200 |
| 434 | 10.50 |
| 435 | 13.30 |
| 436 | 2.60 |
| 437 | 7.50 |
| 438 | >200 |
| 439 | 10.90 |
| 440 | 1.20 |
| 441 | 66.00 |
| 442 | 6.70 |
| 443 | 8.00 |
| 444 | 13.00 |
| 446 | 7.10 |
| 447 | 22.60 |
| 448 | 3.50 |
| 449 | 2.50 |
| 450 | 29.20 |
| 451 | 14.00 |
| 452 | 3.10 |
| 453 | 6.20 |
| 454 | 3.40 |
| 455 | 3.80 |
| 456 | 45.10 |
| 457 | >200 |
| 458 | 20.50 |
| 459 | 27.30 |
| 460 | 1.30 |
| 461 | 2.50 |

Example 220

DM1 Mouse Efficacy Study

HSALR strain 20b mice were used as a model for myotonic dystrophy type I (DM1) experimental studies when testing the efficacy of candidate compounds. To determine the genotype of the mice, the transgene of human skeletal actin (HSA) genomic level was compared to endogenous mouse skeletal actin (MSA) by PCR. Mice with an HSA:MSA ratio of 2:1, homozygous mice were used for the study. Disease phenotype was confirmed in homozygous HSALR by assessing myotonia by pinching the quadriceps of the mouse. Mice positive for "pinch myotonia" exhibit hindlimbs that are unable to release the muscle contraction for ~1-3 seconds. Homozygous HSALR that have been confirmed by PCR genotyping HSA:MSA ratio and are positive for pinch myotonia were selected for candidate compound efficacy studies for DM1.

For each study, a control group of PBS injected mice was included along with mice test groups injected with the compound to be tested. For a statistical power >80%, five mice were used per group (three females and two males). As previously indicated, homozygous HSALR mice were selected aged 8-12 weeks at the beginning of the study. Littermate mice were evenly distributed across groups in the study. Each cage contained mice from a single group. Female mice from different litters were combined into one cage for a single test group. Male mice cannot be combined in cages with non-littermate mice. If any fighting occurred in cages with multiple mice, the mice with minor/superficial fight wounds were be separated and monitored. Mice with severe fight wounds were removed from the study. Mice were monitored throughout the study for weight changes over time, behavioral changes at time of injection, and any other potential health concerns that arose during the study.

Mouse Injections

Mice were injected with approximately ~200 μL solution subcutaneously by 28-gauge syringe. The volume administered was determined by the weight of the mouse where 10 iaL solution is administered per 1 g of the weight of the mouse. The compound was solubilized in DPBS at a concentration of 0.01-3.0 mg compound per 1 mL DPBS, which equated to a dose of 0.1-3.0 mg compound per kg weight of the animal (mpk). Mice were weighed once a week, and the volume of administered compound solution (or DPBS) was adjusted accordingly for correct mpk dosing. Once a compound was tested for acute toxicity in FVB wildtype mice, the compound was typically first tested at 3 mpk, injected every other day (q.o.d.) for five doses, and the mice sacrificed 24 hr after the last injection. Candidate compounds were further tested at different dose regimes to further assess the compound's efficacy in DM1 mice.

Myotonia Assessment By EMG

Mice were anaesthetized by isoflurane in a chamber. Once the mice were fully anaesthetized, they were moved to a nose cone delivery of isoflurane, and the leg where myotonia was ssessed was immobilized by medical tape. Myotonia was assessed by electromyogram (EMG) by inserting a needle into the muscle and recording the electrical signal output from the muscle. For tibialis anterior, gastrocnemius, and quadriceps, 15 EMG signals were assessed for myotonia. Myotonia positive signals have an elongated signal that degrades over the signal while myotonia negative signals have abrupt ends and are typically shorter. Each muscle group was scored for positive myotonia signals calculated by: (number of myotonia positive signals)/(total number of signals scored)×100.

Collecting Tissue for Downstream Efficacy Analysis

For each mouse, blood, brain, heart, liver, kidney, tibialis anterior, gastrocnemius, and quadriceps were dissected and collected. After the mouse was euthanized, blood was collected by cardiac puncture and placed in lithium heparin tubes on ice. Plasma was separated by centrifugation and collected. Brain, heart, half of the liver, tibialis anterior, gastrocnemius, and quadriceps were flash frozen in liquid nitrogen. Half of the liver, kidneys, and subset of heart samples were fixed in 10% formalin. One of the two tibialis anterior muscles was frozen with OCT for cyro-sectioning.

RT-PCR of MBNL1-Dependent Splicing Targets

Gastrocnemius muscle was used for downstream RNA extraction RT-PCR. In the homozygous HSALR mice, gastrocnemius has good expression of the transgene, and gastrocnemius has a mixture of slow and fast fiber type, which is more comparable to human muscle than other mouse muscle groups that have a higher amount of fast fiber type. Half of one gastrocnemius was used for an RNA extraction. The gastrocnemius was homogenized in Trizol reagent and extracted following the protocol of the Zymo Direct-zol RNA Mini Prep Plus kit.

For each RNA sample, 500 ng of RNA was used for a reverse transcription reaction to produce single-stranded cDNA. MBNL1-dependent splicing targets (Clcn1 exon 7a, Mbnl1 exon 5, Serca1 exon 22, and Zasp exon 11) and MBNL1-independent splicing targets (Capzb exon 8, Itgb1 exon 17) were assessed by RT-PCR. For the alternative exons listed, forward and reverse primers were designed to amplify the alternative exon along with the flanking constitutive exons such that one primer may produce two PCR products: one PCR product including the alternative exon and one PCR product excluding the alternative exon. The RT-PCR products were imaged and analyzed by the fragment analyzer. To analyze the data, percent spliced inclusion (PSI) was determined by: (RFU intensity of the inclusion band)/[(RFU intensity of the inclusion band)+(RFU intensity of the exclusion band)]×100. To normalize the data, PSI was converted to percent rescue: [(sample PSI)−(average PSI of control DPBS DM1 control group)]/[(average PSI of wildtype mice)−(average PSI of DPBS DM1 control group)]×100.

Compounds were tested using this protocol and the results are shown in the below Table N.

TABLE N

| Compound # | Dosing | Clcn1 exon 7a splicing rescue % | Mbnl1 exon 5 splicing rescue % | Serca1 exon 22 splicing rescue % | Zasp exon 11 splicing rescue % |
|---|---|---|---|---|---|
| 108 | 30 mg/kg qod 8 doses | 32.5 | 57.4 | 59.1 | 50.1 |
| 75 | 30 mg/kg qd 7 doses | 39.4 | 93.9 | 50.0 | 95.6 |
| 58 | 7.5 mg/kg qod 8 doses | 68.3 | 80.2 | 90.5 | 101.6 |
| 152 | 7.5 mg/kg qod 8 doses | ND | 40.6 | −19.8 | 46.1 |
| 153 | 7.5 mg/kg qod 8 doses | 48.4 | 40.8 | 34.0 | 59.7 |
| 346 | 7.5 mg/kg qod 5 doses | 104.7 | 11.8 | 22.3 | ND |
| 198 | 7.5 mg/kg qod 5 doses | 90.4 | 94.5 | 61.2 | 91.5 |
| 60 | 7.5 mg/kg qod 5 doses | 87.7 | 95.3 | 86.0 | 88.3 |
| 214 | 3 mg/kg qod 5 doses | −31.6 | −17.3 | −5.1 | −12.1 |
| 277 | 3 mq/kg qod 5 doses | 30.3 | 19.9 | 13.2 | 24.2 |
| 286 | 3 mg/kg qod 5 doses | 65.8 | 70.4 | 40.4 | 60.0 |
| 198 | 3 mg/kg qod 5 doses | 55.1 | 49.7 | 22.3 | 35.0 |
| 274 | 3 mq/kg qod 5 doses | 31.6 | 25.2 | 10.7 | 29.8 |
| 354 | 3 mg/kg qod 5 doses | −14.0 | −0.1 | 0.1 | −0.1 |

Example 221

Myotube Splicing Rescue Assays

An assay previously described in Arandel, et al., Dis Model Mech. 2017 Apr. 1; 10(4): 487-497 was used. Primary fibroblasts isolated from DM1 patients were previously immortalized and genetically engineered to carry a doxycycline-inducible MyoD transgene, a prominent muscle transcriptional factor that allows conversion of fibroblasts into myotube-like cells (Arandel et al., 2017). To evaluate the potency of compounds in vitro, one hundred thousand fibroblasts were seeded into each well of a 12-well plate containing fibroblast growth media (DMEM, 10% fetal bovine serum, 1× GlutaMAX, 1× penicillin/streptomycin) and allowed to attach overnight. The following day, growth media was completely removed, cells were briefly washed in PBS and treated in triplicate with 10 µM of compound diluted in differentiation media (DMEM, 100 µg/mL iron-transferrin, 10 µg/mL insulin, 2 µg/mL doxycycline and 1× penicillin/streptomycin). After a 48-hour incubation, cells were washed with PBS and lysed with TRIzol Reagent (ThermoFisher). RNA was extracted using Direct-zol Microprep kit (Zymo) following the manufacturer's instructions and quantified by absorbance measurements. To generate cDNA, 200 ng of RNA was reverse transcribed using SuperScript IV (ThermoFisher). To assess splicing rescue, 50 ng of RNA-equivalent was further amplified by PCR using primers that anneal to constitutive MBNL1 exons 4 and 6, allowing a quantitative analysis of exon 5 inclusion, a characteristic alternative splicing event commonly misregulated in DM1 myotubes. Following capillary electrophoresis, percent inclusion (PSI) was calculated as the fraction of transcripts that include MBNL1 exon 5. For this event, exon inclusion ranged from approximately 5% in unaffected myotubes to 50% in DM1 cells. Based on these reference values, a percent splicing rescue for each compound was determined. Compounds with a myotube splicing rescue superior to 50% were tested for efficacy in a transgenic DM1 mouse model.

Compounds were tested using this protocol and the results are shown in the below Table 0.

TABLE O

| | MBNL1 % splicing rescue at | | |
|---|---|---|---|
| Cpd. # | 10 µM | 5 µM | 1 µM |
| 16 | −4.3 | | |
| 33 | 16.4 | | |
| 34 | | | 20.8 |
| 38 | 0.0 | | |
| 41 | 59.1 | | 43.7 |
| 44 | 16.4 | | 6.1 |
| 47 | 12.8 | | |
| 55 | 12.0 | | |
| 58 | 79.1 | | 11.0 |
| 59 | −17.6 | | |
| 60 | 80.9 | | 18.9 |
| 65 | | | 31.7 |
| 75 | 0.0 | | |
| 77 | 4.2 | | |
| 108 | 63.4 | | 0.0 |
| 112 | 66.5 | | |
| 113 | 45.3 | | 7.9 |
| 115 | 57.5 | | |
| 116 | 74.7 | | |
| 126 | 29.6 | | 16.6 |
| 146 | 7.1 | | 0.8 |
| 148 | 1.7 | | |
| 149 | −1.1 | | |

TABLE O-continued

| Cpd. # | MBNL1 % splicing rescue at 10 µM | 5 µM | 1 µM |
|---|---|---|---|
| 150 | 41.0 | | |
| 152 | 79.8 | | 85.4 |
| 153 | 106.1 | | 82.1 |
| 160 | 63.0 | | |
| 170 | 85.5 | | 24.6 |
| 171 | 7.8 | | 11.5 |
| 172 | 14.2 | | 22.1 |
| 173 | 23.1 | | 1.5 |
| 174 | 1.9 | | 5.2 |
| 176 | −5.0 | | |
| 185 | 39.2 | | |
| 192 | 111.7 | | |
| 198 | 109.8 | | |
| 201 | −13.2 | | |
| 202 | 34.0 | | |
| 205 | −48.4 | | |
| 212 | 77.0 | | |
| 214 | 119.3 | | |
| 221 | −2.5 | | |
| 252 | 13.0 | | |
| 255 | 89.2 | | |
| 256 | 90.6 | | |
| 257 | 92.1 | | |
| 258 | 10.0 | | |
| 259 | −12.7 | | |
| 264 | −23.5 | | |
| 265 | 84.3 | | |
| 266 | −13.1 | | |
| 267 | 1.8 | | |
| 268 | 73.6 | | |
| 269 | 55.6 | | |
| 270 | −19.5 | | |
| 273 | −15.3 | | |
| 274 | 65.3 | | |
| 275 | −6.5 | | |
| 276 | 63.1 | | |
| 277 | 51.0 | | |
| 278 | 48.2 | | 79.7 |
| 286 | 96.4 | | |
| 290 | 97.2 | | |
| 293 | 71.0 | | |
| 297 | −4.4 | | |
| 298 | −41.8 | | |
| 299 | −34.9 | | |
| 301 | 19.4 | | |
| 302 | 32.3 | | |
| 304 | −42.3 | | |
| 305 | 58.8 | | |
| 306 | 11.7 | | |
| 307 | 18.1 | | |
| 308 | −24.4 | | |
| 314 | 22.5 | | |
| 315 | 88.4 | | |
| 316 | 87.1 | | |
| 317 | | | |
| 320 | 88.2 | | |
| 329 | | | |
| 330 | | | |
| 331 | | | |
| 332 | | | |
| 333 | | | |
| 334 | | | 73.1 |
| 336 | 77.0 | | 59.0 |
| 337 | 73.3 | | 57.2 |
| 338 | −5.3 | | 7.8 |
| 339 | 1.8 | | −3.2 |
| 340 | −0.4 | | −3.4 |
| 346 | 74.8 | | 79.9 |
| 347 | 98.1 | | 78.9 |
| 348 | 75.3 | | 75.3 |
| 350 | | | 47.2 |
| 352 | 9.6 | | 3.1 |
| 353 | | | 7.5 |
| 354 | 64.2 | | 66.0 |
| 356 | 59.2 | | 43.7 |
| 357 | 66.0 | | 1.1 |
| 358 | 74.6 | | 12.4 |
| 371 | 72.4 | | 79.7 |
| 384 | 93.9 | | |
| 393 | 17.1 | | |
| 401 | | −11.3 | |
| 402 | | −33.8 | |
| 403 | 90.5 | | |
| 405 | −2.5 | | |
| 406 | 54.3 | | |
| 408 | | | 9.4 |
| 408 | | | 3.9 |
| 458 | | −14.7 | |
| 459 | | −2.6 | |
| 460 | | −21.0 | |
| 461 | −35.5 | | |
| 462 | −2.7 | | |

In view of the many possible embodiments to which the principles of the disclosure may be applied, it should be recognized that the illustrated embodiments are only examples and should not be taken as limiting the scope of the invention.

What is claimed:

1. A compound, or pharmaceutically acceptable salt thereof, having the structure of Formula I:

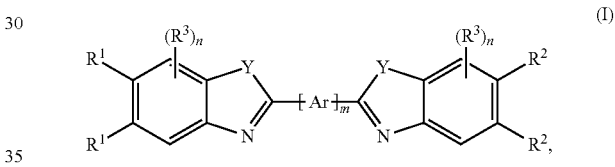

wherein
Ar is $C_{6-10}$ aryl or 5-10 membered heteroaryl having 1-4 heteroatoms selected from N, O, and S, wherein Ar is optionally substituted with 1 to 4 $R^3$;
each $R^1$ and $R^2$ is independently selected from the group consisting of H, $C_{0-3}$ alkylene-halo, $C_{0-3}$ alkylene-CN, $C_{0-3}$ alkylene-NO$_2$, $C_{0-6}$ alkylene-CO$_2R^4$, $C_{0-6}$ alkylene-COR$^4$, $C_{0-6}$ alkylene-CON(R$^4$)$_2$, $C_{0-6}$ alkylene-OR$^4$, $C_{0-6}$ alkylene-N(R$^4$)$_2$, $C_{0-6}$ alkylene-SR$^4$, $C_{0-6}$ alkylene-NH(C=NH)NHR$^4$, $C_{0-6}$ alkylene-NHCONHR$^4$, $C_{0-6}$ alkylene-(C=NR$^4$)NHR$^4$, $C_{0-6}$ alkylene-NHCOR$^4$, $C_{0-6}$ alkylene-R$^4$, $C_{0-6}$ alkylene-NHR$^5$, $C_{0-6}$ alkylene-R$^5$, and $C_{0-6}$ alkylene-Z, and at least one $R^1$ and at least one $R^2$ is other than H;
each $R^3$ is independently selected from the group consisting of H, $C_{0-3}$ alkylene-halo, $C_{0-3}$ alkylene-CN, $C_{0-3}$ alkylene-NH$_2$, $C_{0-6}$ alkylene-NH(C=NH)NHR$^8$, $C_{0-3}$ alkylene-OH, and $C_{0-3}$ alkylene-O—$C_{1-6}$alkyl;
each $R^4$ is independently selected from the group consisting of H, $C_{1-6}$ alkyl, $C_{0-6}$alkylene-N(R$^6$)$_2$, $C_{0-6}$alkylene-N(R$^6$)$_3^+$, $C_{0-6}$alkylene-NR$^7$—$C_{0-6}$alkylene-N(R$^6$)$_2$, CH(OR$^6$)$_2$, $C_{0-6}$alkylene-OR$^6$, $C_{0-6}$alkylene-O—$C_{0-6}$alkylene-N(R$^6$)$_2$, $C_{0-6}$alkylene-NR$^6$(C=NR$^6$)N(R$^6$)$_2$, $C_{0-6}$alkylene-NR$^6$CO$_2R^6$, $C_{0-6}$alkylene-NR$^6$COR$^6$, CH(R$^7$)—$C_{0-6}$alkylene-NR$^6$(C=NR$^6$)N(R$^6$)$_2$, $C_{0-6}$alkylene-NR$^6$, $C_{0-6}$alkylene-NHCO—$C_{0-6}$alkylene-CO$_2R^6$, $C_{0-6}$alkylene-NHR$^5$, and $C_{0-6}$alkylene-Z, or two $R^4$ together with the nitrogen atom to which they are attached form a 4-7 membered heterocycloalkyl ring optionally further including one additional ring heteroatom selected from O and NR';

$R^5$ is selected from the group consisting of 5-10 membered heteroaryl having 1-4 heteroatoms selected from N, O, and S,

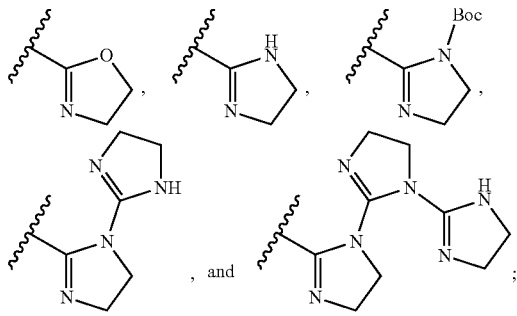

each $R^6$ is independently selected from the group consisting of H, $C_{1-6}$ alkyl, $C_{2-6}$ alkenyl, and $C_{2-6}$ alkynyl, or two $R^6$s taken together with the heteroatom(s) to which they are attached form a 4-10 membered heterocycloalkyl ring, optionally having 1 to 3 additional heteroatom ring atom(s) selected from O and N, and said heterocycloalkyl ring is optionally substituted with one or more $R^7$;

$R^7$ is H, $C_{1-6}$ alkyl, $C_{0-6}$ alkyl-OH, or $CO_2R^8$;

$R^8$ is H or $C_{1-6}$ alkyl;

each Y is independently NH or N—$C_{1-3}$alkyl, and said $C_{1-3}$alkyl is optionally substituted with 1, 2, or 3 groups independently selected from OH, $NH_2$, F, $CO_2H$, $CO_2C_{1-3}$alkyl, $CO_2NH_2$, C(=NH)$NH_2$, NHC(=NH)$NH_2$, and CN;

Z is a bond to a linking moiety;

each n is independently 0-2; and m is 1 or 2, with the proviso that the compound is not 2,2-(1,4-phenylene)bis(1H-benzo[d]imidazol-6-amine),
N,N-[1,4-phenylenebis(1H-benzimidazole-2,6-diyl)]bis-guanidine,
N,N-[1,4-phenylenebis(1H-benzimidazole-2,5-diyl)]bis-guanidine,
2,2-(1,4-phenylene)bis[6-chloro-5-methyl]-1H-benzimidazole,
2,2-(1,4-phenylene)bis[5,7-dimethoxy]-1H-benzimidazole,
2,2-[1,1-biphenyl]-4,4-diylbis[N-(1-methylethyl)]-1H-benzimidazole-6-carboximidamide,
6,6-[1,4-phenylenebis(1H-benzimidazole-2,6-diylimino)]bis-1-hexanol,
2,2-(1,4-phenylene)bis[N-ethyl]-1H-benzimidazole-5-carboximidamide,
2,2-(1,4-phenylene)bis[N-(1,1-dimethylethyl)]-1H-benzimidazole-5-carboximidamide,
2,2-(1,4-phenylene)bis[N-(2-methoxyethyl)]-1H-benzimidazole-5-carboximidamide,
2,2-(1,4-phenylene)bis[N-methyl]-1H-benzimidazole-5-carboximidamide,
2,2-(1,4-phenylene)bis[N-[3-(dimethylamino)propyl]]-1H-benzimidazole-5-carboximidamide,
2,2-(1,4-phenylene)bis[N-pentyl]-1H-benzimidazole-5-carboximidamide,
2,2-(1,4-phenylene)bis[N-(2-methylpropyl)]-1H-benzimidazole-5-carboximidamide,
2,2-(1,4-phenylene)bis[N-propyl]-1H-benzimidazole-5-carboximidamide,
2,2-(1,4-phenylene)bis[N-[2-(4-morpholinyl)ethyl]]-1H-benzimidazole-5-carboximidamide,
2,2-(1,4-phenylene)bis[N-hexyl]-1H-benzimidazole-5-carboximidamide,
N,N-[1,4-phenylenebis(1H-benzimidazole-2,5-diyl)]bis-acetamide,
N,N-[1,4-phenylenebis(1H-benzimidazole-2,5-diyl)]bis[2,2,2-trifluoro]-acetamide,
N,N-[[1,1-biphenyl]-4,4-diylbis(1H-benzimidazole-2,5-diyl)]bis-acetamide,
2,2-(1,4-phenylene)bis[N-[3-(dimethylamino)propyl]-1H-benzimidazole-6-arboxamide,
2,2-(1,4-phenylene)bis[N-(1-methylethyl)-1H-benzimidazole-5-carboximidamide,
2,2-(1,4-phenylene)bis[N-butyl-1H-benzimidazole-5-carboximidamide,
2,2-(pyridine-2,6-diyl)bis(1H-benzo[d]imidazol-5-amine),
2,2-(1,4-phenylene)bis(1H-benzo[d]imidazol-5-amine),
N,N-(pyridine-2,6-diylbis(1H-benzo[d]imidazole-2,6-diyl))bis(2-(piperidin-1-yl)acetamide), or
1,1-(2,6-pyridinediylbis(1H-benz[d]imidazole-2,6-diyl)imino(2-oxo-2,1-ethanediyl)))bis(1-methyl-piperidinium).

2. The compound or salt of claim 1, having the structure of Formula Ia:

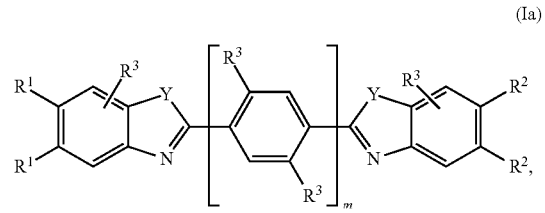

wherein each $R^1$ and $R^2$ is independently selected from the group consisting of H, $C_{0-3}$ alkylene-halo, $C_{0-3}$ alkylene-$NO_2$, $C_{0-6}$ alkylene-$CO_2R^4$, $C_{0-6}$ alkylene-CON$(R^4)_2$, $C_{0-6}$ alkylene-$OR^4$, $C_{0-6}$ alkylene-N$(R^4)_2$, $C_{0-6}$ alkylene-NH(C=NH)NHR$^4$, $C_{0-6}$ alkylene-NH(C=O)NHR$^4$, $C_{0-6}$ alkylene-(C=NH)NHR$^4$, $C_{0-6}$ alkylene-NH(C=O)$R^4$, $C_{0-6}$ alkylene-$R^4$, $C_{0-6}$ alkylene-NHR$^5$, $C_{0-6}$ alkylene-$R^5$, and $C_{0-6}$ alkylene-Z;

each $R^3$ is independently selected from the group consisting of H, F, $NH_2$, NH(C=NH)$NH_2$, OH, and $OCH_3$;

each $R^4$ is independently selected from the group consisting of H, $C_{0-6}$alkylene-N$(R^6)_2$, $C_{0-6}$ alkylene-NR$^7$—$C_{0-6}$ alkylene-N$(R^6)_2$, $C_{0-6}$ alkylene-O—$C_{0-6}$ alkylene-N$(R^6)_2$, $C_{0-6}$alkylene-NR$^6$(C=NH)N$(R^6)_2$, $C_{0-6}$alkylene-NHR$^5$, and $C_{0-6}$ alkylene-Z;

$R^5$ is

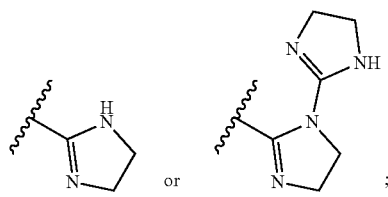 [SMILES: *C1=NCCN1 ; *C1=NCCN1C1=NCCN1]

R$^7$ is H or C$_{1-6}$ alkyl;

each Y is independently NH or N—C$_{1-3}$alkyl, and said C$_{1-3}$alkyl is optionally substituted with 1, 2, or 3 groups independently selected from OH, NH$_2$, F, CO$_2$H, CO$_2$C$_{1-3}$alkyl, CO$_2$NH$_2$, C(=NH)NH$_2$, NHC(=NH)NH$_2$, and CN; and each n is independently 0-2.

3. The compound or salt of claim 1, wherein m is 1.

4. The compound or salt of claim 1, wherein each Y is independently NH or NCH$_3$.

5. The compound or salt of claim 1, wherein one R$^1$ is selected from the group consisting of C$_{0-6}$ alkylene-CO$_2$R$^4$, C$_{0-6}$ alkylene-COR$^4$, C$_{0-6}$ alkylene-CON(R$^4$)$_2$, C$_{0-6}$ alkylene-OR$^4$, C$_{0-6}$ alkylene-N(R$^4$)$_2$, C$_{0-6}$ alkylene-SR$^4$, C$_{0-6}$ alkylene-NH(C=NH)NHR$^4$, C$_{0-6}$ alkylene-NHCONHR$^4$, C$_{0-6}$ alkylene-(C=NR$^4$)NHR$^4$, C$_{0-6}$ alkylene-NHCOR$^4$, C$_{0-6}$ alkylene-R$^4$, C$_{0-6}$ alkylene-NHR$^5$, C$_{0-6}$ alkylene-R$^5$, and C$_{0-6}$ alkylene-Z, and the other R$^1$ is selected from the group consisting of H, C$_{0-3}$alkylene-halo, C$_{0-3}$alkylene-CN, C$_{0-3}$ alkylene-NO$_2$, C$_{0-6}$ alkylene-OR$^4$, and C$_{0-6}$ alkylene-SR$^4$, and C$_{0-6}$ alkylene-Z; and one R$^2$ is selected from the group consisting of C$_{0-6}$ alkylene-CO$_2$R$^4$, C$_{0-6}$ alkylene-COR$^4$, C$_{0-6}$ alkylene-CON(R$^4$)$_2$, C$_{0-6}$ alkylene-OR$^4$, C$_{0-6}$ alkylene-N(R$^4$)$_2$, C$_{0-6}$ alkylene-SR$^4$, C$_{0-6}$ alkylene-NH(C=NH)NHR$^4$, C$_{0-6}$ alkylene-NHCONHR$^4$, C$_{0-6}$ alkylene-(C=NR$^4$)NHR$^4$, C$_{0-6}$ alkylene-NHCOR$^4$, C$_{0-6}$ alkylene-R$^4$, C$_{0-6}$ alkylene-NHR$^5$, C$_{0-6}$ alkylene-R$^5$, and C$_{0-6}$ alkylene-Z, and the other R$^2$ is selected from the group consisting of H, C$_{0-3}$ alkylene-halo, C$_{0-3}$ alkylene-CN, C$_{0-3}$ alkylene-NO$_2$, C$_{0-6}$ alkyl-OR$^4$, C$_{0-6}$ alkyl-SR$^4$, and C$_{0-6}$ alkyl-Z.

6. The compound or salt of claim 1, wherein each R$^1$ and R$^2$ is independently selected from the group consisting of H, C$_{0-3}$ alkylene-NH$_2$, C$_{0-6}$ alkylene-CON(R$^4$)$_2$, C$_{0-6}$ alkylene-N(R$^4$)$_2$, and C$_{0-6}$ alkylene-NH(C=NH)NHR$^4$.

7. The compound or salt of claim 1, wherein R$^4$ is selected from the group consisting of C$_{0-6}$alkylene-N(R$^6$)$_2$, C$_{0-6}$alkylene-N(R$^6$)$_3^+$, C$_{0-6}$alkylene-NR$^7$—C$_{0-6}$alkylene-N(R$^6$)$_2$, C$_{0-6}$alkylene-O—C$_{0-6}$alkylene-N(R$^6$)$_2$, and C$_{0-6}$alkylene-NHR$^5$.

8. The compound or salt of claim 1, wherein one R$^1$ and one R$^2$ each independently comprise C$_{0-6}$ alkylene-CON(R$^4$)$_2$, C$_{0-6}$ alkylene-OR$^4$, C$_{0-6}$ alkylene-N(R$^4$)$_2$, C$_{0-6}$ alkylene-SR$^4$, C$_{0-6}$ alkylene-NHCOR$^4$, C$_{0-6}$ alkylene-R$^4$, and R$^4$ comprises C$_{0-6}$alkylene-N(R$^6$)$_2$, C$_{0-6}$alkylene-N(R$^6$)$_3^+$, C$_{0-6}$alkylene-NR$^7$—C$_{0-6}$alkylene-N(R$^6$)$_2$, or C$_{0-6}$ alkylene-O—C$_{0-6}$ alkylene-N(R$^6$)$_2$.

9. A compound, or pharmaceutically acceptable salt thereof, of structure B$^1$-(L-B$^x$)$_n$-L-B$^2$, wherein each of B$^1$, B$^x$, and B$^2$ independently has a structure of:

(i) Formula I:

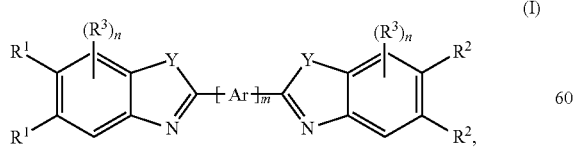

wherein

Ar is C$_{6-10}$ aryl or 5-10 membered heteroaryl having 1-4 heteroatoms selected from N, O, and S, wherein Ar is optionally substituted with 1 to 4 R$^3$;

each R$^1$ and R$^2$ is independently selected from the group consisting of H, C$_{0-3}$ alkylene-halo, C$_{0-3}$ alkylene-CN, C$_{0-3}$ alkylene-NO$_2$, C$_{0-6}$ alkylene-CO$_2$R$^4$, C$_{0-6}$ alkylene-COR$^4$, C$_{0-6}$ alkylene-CON(R$^4$)$_2$, C$_{0-6}$ alkylene-OR$^4$, C$_{0-6}$ alkylene-N(R$^4$)$_2$, C$_{0-6}$ alkylene-SR$^4$, C$_{0-6}$ alkylene-NH(C=NH)NHR$^4$, C$_{0-6}$ alkylene-NHCONHR$^4$, C$_{0-6}$ alkylene-(C=NR$^4$)NHR$^4$, C$_{0-6}$ alkylene-NHCOR$^4$, C$_{0-6}$ alkylene-R$^4$, C$_{0-6}$ alkylene-NHR$^5$, C$_{0-6}$ alkylene-R$^5$, and C$_{0-6}$ alkylene-Z, and at least one R$^1$ and at least one R$^2$ is other than H;

each R$^3$ is independently selected from the group consisting of H, C$_{0-3}$ alkylene-halo, C$_{0-3}$ alkylene-CN, C$_{0-3}$ alkylene-NH$_2$, C$_{0-6}$ alkylene-NH(C=NH)NHR$^8$, C$_{0-3}$ alkylene-OH, and C$_{0-3}$ alkylene-O—C$_{1-6}$alkyl;

each R$^4$ is independently selected from the group consisting of H, C$_{1-6}$ alkyl, C$_{0-6}$alkylene-N(R$^6$)$_2$, C$_{0-6}$alkylene-N(R$^6$)$_3^+$, C$_{0-6}$alkylene-NR'—C$_{0-6}$alkylene-N(R$^6$)$_2$, CH(OR$^6$)$_2$, C$_{0-6}$alkylene-OR$^6$, C$_{0-6}$alkylene-O—C$_{0-6}$alkylene-N(R$^6$)$_2$, C$_{0-6}$alkylene-NR$^6$(C=NR$^6$)N(R$^6$)$_2$, C$_{0-6}$alkylene-NR$^6$CO$_2$R$^6$, C$_{0-6}$alkylene-NR$^6$COR$^6$, CH(R$^7$)—C$_{0-6}$alkylene-NR$^6$(C=NR$^6$)N(R$^6$)$_2$, C$_{0-6}$alkylene-NR$^6$ C$_{0-6}$alkylene-NHCO—C$_{0-6}$alkylene-CO$_2$R$^6$, C$_{0-6}$alkylene-NHR$^5$, and C$_{0-6}$alkylene-Z, or two R$^4$ together with the nitrogen atom to which they are attached form a 4-7 membered heterocycloalkyl ring optionally further including one additional ring heteroatom selected from 0 and NR';

R$^5$ is selected from the group consisting of 5-10 membered heteroaryl having 1-4 heteroatoms selected from N, O, and S,

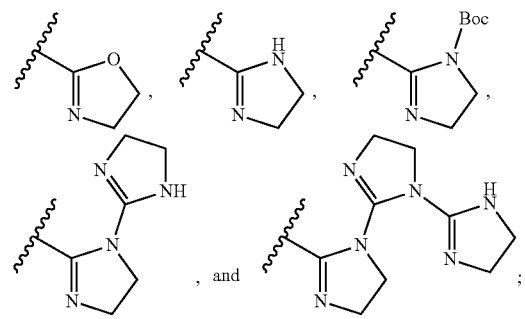

each R$^6$ is independently selected from the group consisting of H, C$_{1-6}$ alkyl, C$_{2-6}$ alkenyl, and C$_{2-6}$ alkynyl, or two R$^6$s taken together with the heteroatom(s) to which they are attached form a 4-10 membered heterocycloalkyl ring, optionally having 1 to 3 additional heteroatom ring atom(s) selected from O and N, and said heterocycloalkyl ring is optionally substituted with one or more R$^7$;

R$^7$ is H, C$_{1-6}$ alkyl, C$_{0-6}$ alkyl-OH, or CO$_2$R$^8$;

R$^8$ is H or C$_{1-6}$ alkyl;

each Y is independently NH or N—C$_{1-3}$alkyl, and said C$_{1-3}$alkyl is optionally substituted with 1, 2, or 3 groups independently selected from OH, NH$_2$, F, CO$_2$H, CO$_2$C$_{1-3}$alkyl, CO$_2$NH$_2$, C(=NH)NH$_2$, NHC(=NH)NH$_2$, and CN;

Z is a bond to a linking moiety;

each n is independently 0-2; and m is 1 or 2;

with the proviso that the compound is not 2,2-(1,4-phenylene)bis(1H-benzo[d]imidazol-6-amine), N,N-[1,4-phenylenebis(1H-benzimidazole-2,6-diyl)]bis-guanidine, N,N-[1,4-phenylenebis(1H-benzimidazole-2,5-diyl)]bis-guanidine, 2,2-(1,4-phenylene)bis[6-chloro-5-methyl]-1H-benzimidazole, 2,2-(1,4-phenylene)bis[5,7-dimethoxy]-1H-benzimidazole, 2,2-[1,1-biphenyl]-4,4-diylbis[N-(1-methylethyl)]-1H-benzimidazole-6-carboximidamide, 6,6-[1,4-phenylenebis(1H-benzimidazole-2,6-diylimino)]bis-1-hexanol, 2,2-(1,4-phenylene)bis[N-ethyl]-1H-benzimidazole-5-carboximidamide, 2,2-(1,4-phenylene)bis[N-(1,1-dimethylethyl)]-1H-benzimidazole-5-carboximidamide, 2,2-(1,4-phenylene)bis[N-(2-methoxyethyl)]-1H-benzimidazole-5-carboximidamide, 2,2-(1,4-phenylene)bis[N-methyl]-1H-benzimidazole-5-carboximidamide, 2,2-(1,4-phenylene)bis[N-[3-(dimethylamino)propyl]]-1H-benzimidazole-5-carboximidamide, 2,2-(1,4-phenylene)bis[N-pentyl]-1H-benzimidazole-5-carboximidamide, 2,2-(1,4-phenylene)bis[N-(2-methylpropyl)]-1H-benzimidazole-5-carboximidamide, 2,2-(1,4-phenylene)bis[N-propyl]-1H-benzimidazole-5-carboximidamide, 2,2-(1,4-phenylene)bis[N-[2-(4-morpholinyl)ethyl]]-1H-benzimidazole-5-carboximidamide, 2,2-(1,4-phenylene)bis[N-hexyl]-1H-benzimidazole-5-carboximidamide, N,N-[1,4-phenylenebis(1H-benzimidazole-2,5-diyl)]bis-acetamide, N,N-[1,4-phenylenebis(1H-benzimidazole-2,5-diyl)]bis[2,2,2-trifluoro]-acetamide, N,N-[[1,1-biphenyl]-4,4-diylbis(1H-benzimidazole-2,5-diyl)]bis-acetamide, 2,2-(1,4-phenylene)bis[N-[3-(dimethylamino)propyl]-1H-benzimidazole-6-arboxamide, 2,2-(1,4-phenylene)bis[N-(1-methylethyl)-1H-benzimidazole-5-carboximidamide, 2,2-(1,4-phenylene)bis[N-butyl-1H-benzimidazole-5-carboximidamide, 2,2-(pyridine-2,6-diyl)bis(1H-benzo[d]imidazol-5-amine), 2,2-(1,4-phenylene)bis(1H-benzo[d]imidazol-5-amine), N,N-(pyridine-2,6-diylbis(1H-benzo[d]imidazole-2,6-diyl))bis(2-(piperidin-1-yl)acetamide), or 1,1-(2,6-pyridinediylbis(1H-benz[d]imidazole-2,6-diyl)imino(2-oxo-2,1-ethanediyl)))bis(1-methyl-piperidinium); or (ii) a compound of Table A1:

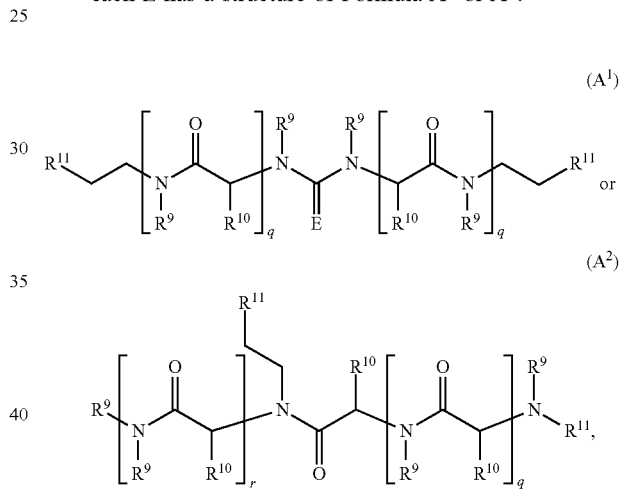

| Compound # | R¹ | R² |
|---|---|---|
| 2 | $NH_2$ | $NH_2$ |
| 3 | $NH(C=NH)NH_2$ | $NH(C=NH)NH_2$ |
| 4 | $NH_2$ | NHAc |
| 6 | NHAc | NHAc |
| 12 | $CONH_2$ | $CONH_2$ |
| 26 | ![H2N-C(=NH)-] | ![H2N-C(=NH)-] | and comprising or further comprising a Z moiety, said Z moiety forming a covalent bond to L;

each L has a structure of Formula $A^1$ or $A^2$:

$$(A^1)$$

$$(A^2)$$

wherein each $R^9$ is independently H or $C_{0-6}$ alkyl;

each $R^{19}$ is independently H, $C_{0-6}$ alkyl, or $C_{0-6}$alkylene-$R^{12}$, and $R^{19}$ is optionally substituted with one to three substituents selected from the group consisting of halo, OH, CN, $NO_2$, $N_3$, $NH_2$, SH, $SCH_3$, COOH, $CONH_2$, $NH(C=NH)NH_2$, $C_{6-10}$ aryl, 5 to 10-membered heteroaryl having 1-4 ring heteroatoms selected from N, O, and S, $C_{6-10}$ cycloalkyl, and 5 to 12-membered heterocycloalkyl having 1-3 ring heteroatoms selected from N, O, and S;

each $R^{11}$ is independently selected from the group consisting of $C_{0-6}$alkylene-(Het)$_s$-$C_{0-6}$alkylene-QZ, CO—$C_{0-6}$alkylene-(Het)$_s$-$C_{0-6}$alkylene-QZ, $C_{0-6}$alkylene-(Het)$_s$-$C_{0-6}$alkylene-(C=O)-QZ, CO—$C_{0-6}$alkylene-(Het)$_s$-$C_{0-6}$alkylene-CO-QZ, $(OCH_2CH_2)_q$-Het-$(CH_2CH_2O)_q$-QZ, $(OCH_2CH_2)_q$-Het-$(CH_2CH_2O)_q$—CO-QZ, $(NR^9CH_2CH_2)_q$-Het-$(CH_2CH_2NR^9)_q$-QZ, and $(NR^9CH_2CH_2)_q$—Het-$(CH_2CH_2NR^9)_q$—CO-QZ;$B^1$ $R^{12}$ is selected from the group consisting of $CO_2H$, $CO_2C_{1-6}$alkyl, SH, $SC_{1-6}$alkyl, OH, $OC_{1-6}$alkyl, $NH_2$, NHC$_{1-6}$alkyl, N(C$_{1-6}$alkyl)$_2$, NH(C=NH)NH$_2$, CONH$_2$, C$_{6-10}$aryl, 5 to 10-membered heteroaryl having 1-4 ring heteroatoms selected from N, O, and S, 5 to 12-membered heterocycloalkyl having 1-3 ring heteroatoms selected from N, O, and S;

E is O or NR$^9$;

Het is 5 to 10-membered heteroaryl having 1-4 ring heteroatoms selected from N, O, and S or 5 to 12-membered heterocycloalkyl having 1-3 ring heteroatoms selected from N, O, and S;

Q is selected from the group consisting of O, NR$^9$, S, C$_{6-10}$ aryl, 5 to 10-membered heteroaryl having 1-4 ring heteroatoms selected from N, O, and S, C$_{6-10}$ cycloalkyl, and 5 to 12-membered heterocycloalkyl having 1-3 ring heteroatoms selected from N, O, and S;

Z is a bond to the B1, B$^x$, or B2 moiety;

each q is independently 1-13;

each r is independently 0 or 1;

each s is independently 0 or 1; and n is 0-2.

10. The compound or salt of claim 9, of structure B$^1$-L-B$^2$ or B$^1$-L-B$^x$-L-B$^2$ or B$^1$-L-B$^x$-L-B$^x$-L-B$^2$.

11. The compound or salt of claim 9, wherein Het comprises triazolyl, imidazolyl, or piperazinyl.

12. The compound of claim 1, selected from compounds 256, 286, 290, 293, and 305:

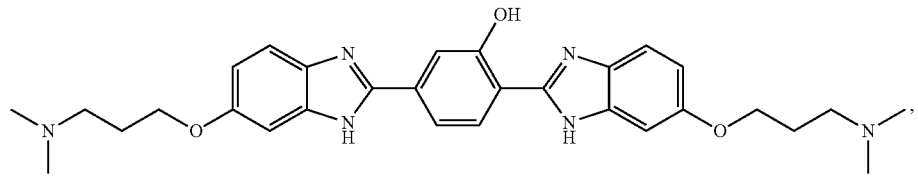

256

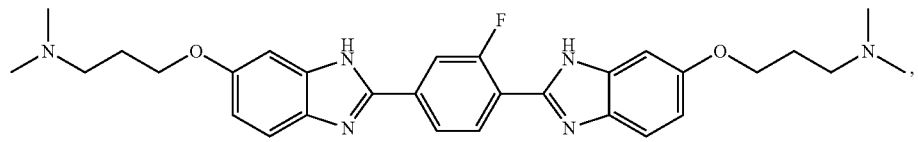

286

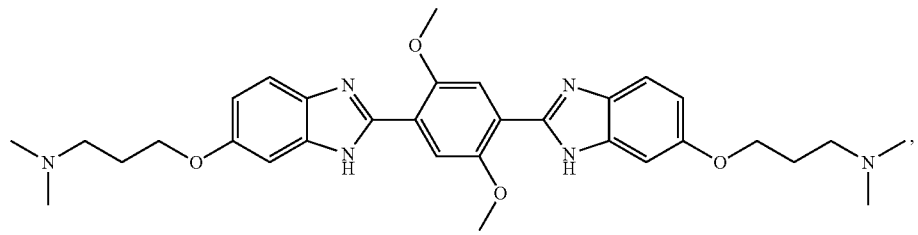

290

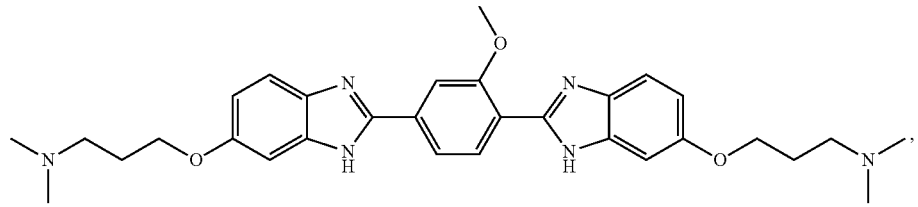

293

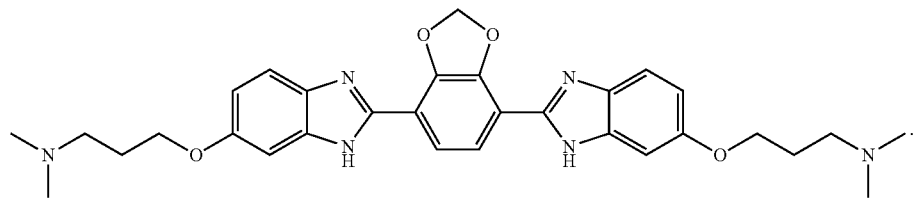

305

* * * * *